US012702682B2

(12) United States Patent
Montgomery et al.

(10) Patent No.: US 12,702,682 B2
(45) Date of Patent: Aug. 11, 2026

(54) PLATELET DERIVATIVE COMPOSITIONS, AND METHODS OF MAKING AND USING SUCH COMPOSITIONS

(71) Applicant: Cellphire, Inc., Rockville, MD (US)

(72) Inventors: Joshua Donald Montgomery, Silver Spring, MD (US); Braden Carl Ishler, Montgomery Village, MD (US); Stephen Edward Amos, Buckeystown, MD (US); Keith Andrew Moskowitz, Westfield, IN (US); Amber Nicole Lee, Montgomery Village, MD (US); Rafael Jorda, Merignac (FR); Glen Michael Fitzpatrick, North Potomac, MD (US); Michael Alexander Mathews, Arlington, VA (US)

(73) Assignee: Cellphire, Inc., Rockville, MD (US)

(*) Notice: Subject to any disclaimer, the term of this patent is extended or adjusted under 35 U.S.C. 154(b) by 665 days.

(21) Appl. No.: 18/052,709

(22) Filed: Nov. 4, 2022

(65) Prior Publication Data

US 2023/0149467 A1 May 18, 2023

Related U.S. Application Data

(60) Provisional application No. 63/376,986, filed on Sep. 23, 2022, provisional application No. 63/371,849, filed on Aug. 18, 2022, provisional application No. 63/364,620, filed on May 12, 2022, provisional application No. 63/264,227, filed on Nov. 17, 2021, provisional application No. 63/264,226, filed on Nov. 17, 2021, provisional application No. 63/276,420, filed on Nov. 5, 2021, provisional application No. 63/275,937, filed on Nov. 4, 2021.

(51) Int. Cl.

| | |
|---|---|
| ***A61K 35/19*** | (2015.01) |
| ***A61K 9/19*** | (2006.01) |
| ***A61K 47/26*** | (2006.01) |

(52) U.S. Cl.
CPC ................ *A61K 35/19* (2013.01); *A61K 9/19* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 3,928,566 | A | 12/1975 | Briggs et al. |
| 3,932,943 | A | 1/1976 | Briggs et al. |
| 4,059,967 | A | 11/1977 | Rowe et al. |
| 4,157,383 | A | 6/1979 | Johannsen et al. |
| 4,455,299 | A | 6/1984 | Grode |
| 4,481,189 | A | 11/1984 | Prince |
| 4,670,013 | A | 6/1987 | Barnes et al. |
| 4,865,871 | A | 9/1989 | Livesey et al. |
| 4,994,367 | A | 2/1991 | Bode et al. |
| 5,059,518 | A | 10/1991 | Kortright et al. |
| 5,213,814 | A | 5/1993 | Goodrich, Jr. et al. |
| 5,332,578 | A | 7/1994 | Chao |
| 5,364,756 | A | 11/1994 | Livesey et al. |
| 5,423,738 | A | 6/1995 | Robinson et al. |
| 5,571,801 | A | 11/1996 | Segall et al. |
| 5,622,867 | A | 4/1997 | Livesey et al. |
| 5,656,498 | A | 8/1997 | Tijima et al. |
| 5,656,598 | A | 8/1997 | Dunstan et al. |
| 5,723,281 | A | 3/1998 | Segall et al. |
| 5,736,313 | A | 4/1998 | Spargo et al. |
| 5,759,542 | A | 6/1998 | Gurewich |
| 5,800,978 | A | 9/1998 | Goodrich, Jr. et al. |
| 5,817,381 | A | 10/1998 | Chen et al. |
| 5,827,741 | A | 10/1998 | Beattie et al. |
| 5,919,614 | A | 7/1999 | Livesey et al. |
| 5,958,670 | A | 9/1999 | Goodrich, Jr. et al. |
| 5,993,804 | A | 11/1999 | Read et al. |
| 6,127,111 | A | 10/2000 | Braun |
| 6,211,575 | B1 | 4/2001 | Hansford |
| 6,221,575 | B1 | 4/2001 | Roser et al. |
| 6,372,423 | B1 | 4/2002 | Braun |
| 6,596,296 | B1 | 7/2003 | Nelson et al. |
| 6,653,062 | B1 | 11/2003 | DePablo et al. |
| 6,723,497 | B2 | 4/2004 | Wolkers et al. |
| 6,770,478 | B2 | 8/2004 | Crowe et al. |
| 6,833,236 | B1 | 12/2004 | Stienstra |
| 6,858,222 | B2 | 2/2005 | Nelson et al. |

(Continued)

FOREIGN PATENT DOCUMENTS

| | | | |
|---|---|---|---|
| CA | 1261259 | A | 9/1989 |
| CA | 2097063 | C | 6/1992 |

(Continued)

OTHER PUBLICATIONS

Bynum et al. (2019) Transfusion, vol. 59, 1490-1498. (Year: 2019).*
Dickerson et al. (2020) Blood 136 (Suppl. 1): 25. (Year: 2020).*
Fitzpatrick et al. (2013) Transfusion, vol. 53, 100S-106S. (Year: 2013).*
Kuhn et al. (2024) J. Thromb. haemost. 22: 686-699. (Year: 2024).*
Montague et al. (2014) Heart 100 (Supplement 3): A91. (Year: 2014).*
Lo et al., "Development of a multi-compartment microfiltration device for particle fractionation" 16th International Conference on Miniaturized Systems for Chemistry and Life Sciences, MicroTAS 2012—Okinawa, Japan, Oct. 28, 2012 -Nov. 1, 2012, 3 pages.
Lucking et. al., "Characterisation and reproducibility of a human ex vivo model of thrombosis", Thrombosis Research, vol. 126, No. 5, Nov. 2010, pp. 431-435, doi: 10.1016/j.thromres.2010.06.030.

(Continued)

*Primary Examiner* — Russell G Fiebig
(74) *Attorney, Agent, or Firm* — Double Helix Law; Emanuel Vacchiano

(57) ABSTRACT

Provided herein are materials and methods for the preparation of blood products. In some aspects, provided herein are compositions that include populations of platelet derivatives, including freeze-dried platelet derivatives, methods of producing the same, as well as methods of using the same to treat a subject. Such platelet derivatives have improved properties, as disclosed herein.

16 Claims, 70 Drawing Sheets

(56) References Cited

U.S. PATENT DOCUMENTS 7,033,603 B2 4/2006 Nelson et al.
7,169,606 B2 1/2007 DePablo et al.
7,514,095 B2 4/2009 Nelson et al.
7,811,558 B2 10/2010 Ho et al.
8,097,403 B2 1/2012 Ho et al.
8,486,617 B2 7/2013 Ho et al.
8,486,619 B2 7/2013 Miller et al.
8,529,961 B2 9/2013 Campbell et al.
8,877,060 B2 11/2014 Sehgal
8,900,209 B2 12/2014 Rosati
9,402,866 B2 8/2016 Radwanski et al.
9,545,379 B2 1/2017 Liu et al.
9,863,699 B2 1/2018 Corbin et al.
9,878,011 B2 1/2018 Landrigan et al.
9,950,035 B2 4/2018 Binder et al.
10,400,017 B2 9/2019 Higgins et al.
10,441,634 B2 10/2019 Landrigan et al.
10,539,367 B2 1/2020 Corbin et al.
10,793,327 B2 10/2020 Weimer et al.
10,843,100 B2 11/2020 Khan et al.
10,969,171 B2 4/2021 Corbin et al.
10,976,105 B2 4/2021 Corbin et al.
11,052,045 B2 7/2021 Liu et al.
11,529,587 B2 12/2022 Montgomery et al.
11,701,388 B2 7/2023 Moskowitz et al.
11,752,468 B2 9/2023 Montgomery et al.
11,767,511 B2 9/2023 Moskowitz et al.
11,813,572 B2 11/2023 Montgomery et al.
12,208,122 B2 1/2025 Moskowitz et al.
12,290,532 B2 5/2025 Moskowitz et al.
12,295,972 B2 5/2025 Moskowitz et al.
12,370,219 B2 7/2025 Moskowitz et al.
12,378,523 B2 8/2025 Moskowitz et al.
12,419,914 B2 9/2025 Moskowitz et al.
2001/0019819 A1 9/2001 Wolkers et al.
2001/0028880 A1 10/2001 Fisher et al.
2001/0046487 A1 11/2001 Roser et al.
2002/0009500 A1 1/2002 Wolkers et al.
2002/0076445 A1 6/2002 Crowe et al.
2003/0022333 A1 1/2003 Bronshtein
2003/0073238 A1 4/2003 Dzekunov et al.
2003/0148449 A1 8/2003 Kuliopulos et al.
2003/0157475 A1 8/2003 Schenk
2004/0136974 A1 7/2004 Crowe et al.
2004/0147024 A1 7/2004 Crowe et al.
2004/0152964 A1 8/2004 Crowe et al.
2004/0185524 A1 9/2004 Crowe et al.
2004/0265293 A1 12/2004 Crowe et al.
2005/0028559 A1 2/2005 Hiromatsu et al.
2005/0048460 A1 3/2005 Crowe et al.
2005/0074402 A1 4/2005 Cagnolini et al.
2005/0181978 A1 8/2005 Rojkjaer et al.
2005/0191286 A1 9/2005 Gandy
2005/0222029 A1 10/2005 Bartel et al.
2006/0034809 A1 2/2006 Ho et al.
2006/0035383 A1 2/2006 Ho et al.
2006/0051731 A1 3/2006 Ho et al.
2006/0223050 A1 10/2006 Crowe et al.
2007/0087061 A1 4/2007 Drake et al.
2007/0166389 A1 7/2007 Bakaltcheva
2007/0178104 A1 8/2007 Awdalla
2007/0243137 A1 10/2007 Hainfeld
2007/0243178 A1 10/2007 Ho et al.
2007/0248612 A1 10/2007 Wilson
2007/0249047 A1 10/2007 McKenna et al.
2008/0064628 A1 3/2008 Goodall et al.
2008/0145834 A1 6/2008 Ho et al.
2008/0286366 A1 11/2008 Fischer et al.
2008/0299212 A1 12/2008 Kim et al.
2009/0035289 A1 2/2009 Wagner et al.
2009/0111118 A1 4/2009 Mylvaganam et al.
2009/0175905 A1 7/2009 Tseng et al.
2009/0299212 A1 12/2009 Principe et al.
2010/0055067 A1 3/2010 Park
2010/0135969 A1 6/2010 Mishra
2010/0159023 A1 6/2010 Bjornstrup et al.
2010/0190717 A1 7/2010 Bevec et al.
2010/0196461 A1 8/2010 Simpkins
2010/0267928 A1 10/2010 Heckl
2010/0273141 A1 10/2010 Bakaltcheva et al.
2011/0008804 A1 1/2011 Kain et al.
2011/0020107 A1 1/2011 Presz, Jr. et al.
2011/0027257 A1 2/2011 Burnouf et al.
2011/0027861 A1 2/2011 Ho et al.
2011/0183311 A1 7/2011 Ho et al.
2011/0189151 A1 8/2011 Stossel et al.
2012/0009221 A1 1/2012 Hoerr et al.
2012/0028236 A1 2/2012 Sehgal
2012/0095085 A1 4/2012 Layzer et al.
2012/0100522 A1 4/2012 Saghbini et al.
2012/0125847 A1 5/2012 Sehgal
2012/0141434 A1 6/2012 Peled et al.
2012/0156306 A1 6/2012 Weissman et al.
2012/0264815 A1 10/2012 Sullenger et al.
2012/0276581 A1 11/2012 Arav et al.
2012/0321722 A1 12/2012 Liu et al.
2013/0059380 A1 3/2013 Ho et al.
2013/0061849 A1 3/2013 Lemper
2013/0122107 A1 5/2013 Bakaltcheva
2013/0195959 A1 8/2013 Patel
2013/0210903 A1 8/2013 Sullenger et al.
2014/0037750 A1 2/2014 Radwanski et al.
2014/0065120 A1 3/2014 Nichols et al.
2014/0329323 A1 11/2014 Nygaard et al.
2014/0330226 A1 11/2014 Coffey
2014/0356948 A1 12/2014 Jeon et al.
2015/0064259 A1 3/2015 Simpkins
2015/0306212 A1 10/2015 Kahvejian et al.
2015/0313943 A1 11/2015 Kishikawa et al.
2015/0313944 A1 11/2015 Feng et al.
2015/0361453 A1 12/2015 Gresele et al.
2016/0082044 A1 3/2016 Liu et al.
2016/0206783 A1 7/2016 Dietz et al.
2016/0219870 A1 8/2016 Wang et al.
2016/0231338 A1 8/2016 Aster et al.
2016/0235781 A1 8/2016 Emanuele
2016/0324897 A1 11/2016 Ingber et al.
2017/0198335 A1 7/2017 Muller et al.
2017/0274012 A1 9/2017 Bode et al.
2017/0333593 A1 11/2017 Willard et al.
2018/0009874 A1 1/2018 Wilcox et al.
2018/0070581 A1 3/2018 Tarrand et al.
2018/0092348 A1 4/2018 She et al.
2018/0169027 A1 6/2018 Zhang et al.
2018/0169139 A1 6/2018 Feuerstein et al.
2018/0235894 A1 8/2018 Gu et al.
2018/0311176 A1 11/2018 Ozsolak et al.
2018/0312903 A1 11/2018 Grölz et al.
2019/0008143 A1 1/2019 Dee et al.
2019/0076478 A1 3/2019 Hale et al.
2019/0192564 A1 6/2019 Hijazi et al.
2020/0046771 A1 2/2020 Kuhn et al.
2020/0060262 A1 2/2020 Stolla
2020/0076455 A1 3/2020 Sharf
2020/0078407 A1 3/2020 Bhattacharya et al.
2020/0093853 A1 3/2020 Feuerstein et al.
2020/0206143 A1 7/2020 Moskowitz et al.
2020/0208109 A1 7/2020 Moskowitz et al.
2020/0208110 A1 7/2020 Lee et al.
2020/0224164 A1 7/2020 Moskowitz et al.
2020/0281980 A1 9/2020 Willard et al.
2020/0291356 A1 9/2020 Jorda et al.
2020/0346167 A1 11/2020 Montgomery et al.
2021/0046120 A1 2/2021 Moskowitz et al.
2021/0046121 A1 2/2021 Moskowitz et al.
2021/0069240 A1 3/2021 Jorda et al.
2021/0100846 A1 4/2021 Lee et al.
2021/0180016 A1 6/2021 Moskowitz et al.
2021/0189341 A1 6/2021 Sheik et al.
2021/0299179 A1 9/2021 Moskowitz et al.
2021/0308066 A1 10/2021 Moskowitz et al.
2021/0308185 A1 10/2021 Moskowitz et al.
2021/0315935 A1 10/2021 Moskowitz et al.
2021/0353680 A1 11/2021 Bhattacharya et al.

(56) References Cited

U.S. PATENT DOCUMENTS

| | | | |
|---|---|---|---|
| 2021/0368782 | A1 | 12/2021 | Dee et al. |
| 2022/0168353 | A1 | 6/2022 | Moskowitz et al. |
| 2022/0211029 | A1 | 7/2022 | Moskowitz et al. |
| 2022/0273724 | A1 | 9/2022 | Moskowitz et al. |
| 2022/0279777 | A1 | 9/2022 | Moskowitz et al. |
| 2023/0112136 | A1 | 4/2023 | Jorda et al. |
| 2023/0149468 | A1 | 5/2023 | Antebi et al. |
| 2023/0158455 | A1 | 5/2023 | Montgomery et al. |
| 2023/0226493 | A1 | 7/2023 | Montgomery et al. |
| 2023/0248771 | A1 | 8/2023 | Moskowitz et al. |
| 2023/0248772 | A1 | 8/2023 | Willard |
| 2023/0285465 | A1 | 9/2023 | Moskowitz et al. |
| 2023/0346839 | A1 | 11/2023 | Bhattacharya et al. |
| 2023/0356150 | A1 | 11/2023 | Montgomery et al. |
| 2023/0383258 | A1 | 11/2023 | Moskowitz et al. |
| 2024/0066065 | A1 | 2/2024 | Moskowitz et al. |
| 2024/0139252 | A1 | 5/2024 | Moskowitz et al. |
| 2024/0254443 | A1 | 8/2024 | Sheik et al. |
| 2024/0277771 | A1 | 8/2024 | Moskowitz et al. |
| 2024/0307453 | A1 | 9/2024 | Moskowitz et al. |
| 2024/0408141 | A1 | 12/2024 | Moskowitz et al. |
| 2025/0000908 | A1 | 1/2025 | Moskowitz et al. |
| 2025/0064856 | A1 | 2/2025 | Moskowitz et al. |
| 2025/0064988 | A1 | 2/2025 | Sheik et al. |
| 2025/0073271 | A1 | 3/2025 | Moskowitz et al. |
| 2025/0177450 | A1 | 6/2025 | Moskowitz et al. |
| 2025/0205284 | A1 | 6/2025 | Moskowitz et al. |
| 2025/0302880 | A1 | 10/2025 | Moskowitz et al. |

FOREIGN PATENT DOCUMENTS

| | | | | |
|---|---|---|---|---|
| CA | 2136848 | A1 | 12/1993 | |
| CA | 2393315 | A1 | 6/2001 | |
| CA | 2840568 | A1 | 1/2013 | |
| CA | 3053041 | A1 | 2/2020 | |
| CN | 101072506 | A | 11/2007 | |
| CN | 103524613 | A | 1/2014 | |
| CN | 103907595 | A | 7/2014 | |
| CN | 108715834 | A | 10/2018 | |
| CN | 109942687 | A | 6/2019 | |
| EP | 0397890 | A1 | 11/1990 | |
| EP | 0815866 | A2 | 1/1998 | |
| EP | 0967862 | B1 | 1/2000 | |
| EP | 1374890 | A2 | 1/2004 | |
| EP | 1652538 | A2 | 5/2006 | |
| EP | 1784639 | A2 | 5/2007 | |
| EP | 3681518 | A1 | 7/2020 | |
| EP | 3307283 | B1 | 9/2020 | |
| EP | 3551198 | B1 | 2/2022 | |
| JP | H08109136 | A | 4/1996 | |
| JP | 2005053841 | A | 3/2005 | |
| JP | 2008509924 | A | 4/2008 | |
| JP | 2012143554 | A | 8/2012 | |
| WO | 1990005461 | A1 | 5/1990 | |
| WO | 9012581 | A1 | 11/1990 | |
| WO | 1991017655 | A1 | 11/1991 | |
| WO | 1992008349 | A1 | 5/1992 | |
| WO | 1993000806 | A1 | 1/1993 | |
| WO | 1993023997 | A1 | 12/1993 | |
| WO | 9428950 | A1 | 12/1994 | |
| WO | 1998034478 | A1 | 8/1998 | |
| WO | 1999055346 | A1 | 11/1999 | |
| WO | 2001007921 | A2 | 2/2001 | |
| WO | 2001058266 | A1 | 8/2001 | |
| WO | 2003014305 | A2 | 2/2003 | |
| WO | 2003039582 | A1 | 5/2003 | |
| WO | 2003090839 | A1 | 11/2003 | |
| WO | 2004050896 | A2 | 6/2004 | |
| WO | 2004078187 | A1 | 9/2004 | |
| WO | 2005002499 | A2 | 1/2005 | |
| WO | 2005020893 | A2 | 3/2005 | |
| WO | 2005021706 | A2 | 3/2005 | |
| WO | 2005077299 | A1 | 8/2005 | |
| WO | 2005002499 | A3 | 11/2005 | |
| WO | 2006020773 | A2 | 2/2006 | |
| WO | 2006059329 | A1 | 6/2006 | |
| WO | 2004050896 | A3 | 12/2006 | |
| WO | 2006020773 | A3 | 7/2007 | |
| WO | 2010046949 | A1 | 4/2010 | |
| WO | 2011020107 | A2 | 2/2011 | |
| WO | 2011020107 | A3 | 10/2011 | |
| WO | 2011149110 | A1 | 12/2011 | |
| WO | 2012018484 | A2 | 4/2012 | |
| WO | 2012074637 | A2 | 6/2012 | |
| WO | 2014051537 | A1 | 4/2014 | |
| WO | 2014055949 | A1 | 4/2014 | |
| WO | 2014066142 | A1 | 5/2014 | |
| WO | 2014084263 | A1 | 6/2014 | |
| WO | 2014118817 | A2 | 8/2014 | |
| WO | 2014118817 | A3 | 10/2014 | |
| WO | 2015073587 | A2 | 5/2015 | |
| WO | 2015191632 | A1 | 12/2015 | |
| WO | 2016014854 | A1 | 1/2016 | |
| WO | 2016057041 | A1 | 4/2016 | |
| WO | 2016077682 | A1 | 5/2016 | |
| WO | 2016141325 | A1 | 9/2016 | |
| WO | 2016201081 | A1 | 12/2016 | |
| WO | 2016205144 | A1 | 12/2016 | |
| WO | 2017040238 | A1 | 3/2017 | |
| WO | 2017123539 | A1 | 7/2017 | |
| WO | 2018084228 | A1 | 5/2018 | |
| WO | 2018106250 | A1 | 6/2018 | |
| WO | 2019055683 | A1 | 3/2019 | |
| WO | 2020023905 | A1 | 1/2020 | |
| WO | 2020056009 | A1 | 3/2020 | |
| WO | 2020112963 | A1 | 6/2020 | |
| WO | 2020113035 | A1 | 6/2020 | |
| WO | 2020113090 | A1 | 6/2020 | |
| WO | 2020113101 | A1 | 6/2020 | |
| WO | 2020165152 | A1 | 8/2020 | |
| WO | 2020186193 | A1 | 9/2020 | |
| WO | 2020219557 | A1 | 10/2020 | |
| WO | WO-2020227149 | A1 * | 11/2020 | ................ A61P 7/02 |
| WO | 2021011857 | A1 | 1/2021 | |
| WO | 2021034716 | A1 | 2/2021 | |
| WO | 2021034719 | A1 | 2/2021 | |
| WO | 2021046409 | A1 | 3/2021 | |
| WO | 2021108538 | A1 | 6/2021 | |
| WO | 2021108539 | A1 | 6/2021 | |
| WO | 2021158622 | A1 | 8/2021 | |
| WO | 2021158625 | A1 | 8/2021 | |
| WO | 2021158641 | A1 | 8/2021 | |
| WO | 2021158645 | A1 | 8/2021 | |
| WO | 2021158646 | A1 | 8/2021 | |
| WO | 2021232015 | A1 | 11/2021 | |
| WO | 2022103861 | A1 | 5/2022 | |
| WO | 2022178177 | A1 | 8/2022 | |
| WO | 2022178191 | A1 | 8/2022 | |
| WO | 2022178177 | A4 | 10/2022 | |
| WO | 2023081804 | A1 | 5/2023 | |
| WO | 2023220694 | A1 | 11/2023 | |
| WO | 2023220739 | A1 | 11/2023 | |
| WO | 2024192173 | A1 | 9/2024 | |
| WO | 2024249704 | A1 | 12/2024 | |

OTHER PUBLICATIONS

Luo et al., "Construction and in vitro studies of magnetic-apoferritin nanocages conjugated with KGDS peptide targeted at activated platelets for the MRI diagnosis of thrombus," Journal of Nanoparticle Research, vol. 21, Issue 8, Aug. 2019, pp. 1-12.

Mailer et al., "Commentary on "Pharmacological profile of asundexian, a novel, orally bioavailable inhibitor of factor Xla": Small molecule factor Xla inhibitor asundexian allows for safer anticoagulation", Journal of Thrombosis and Haemostasis, vol. 20, Issue 6, Jun. 2022, pp. 1309-1311, https://doi.org/10.1111/jth. 15722.

Makielski et al., "Development and implementation of a novel immune thrombocytopenia bleeding score for dogs," J. Vet. Intern. Med., 2018, 32(3):1-10.

Marder, "Bleeding Complications of Thrombolytic Treatment", American Journal of Hospital Pharmacy, vol. 47, Suppl 2, Sep. 1990, pp. S15-S19.

(56) References Cited

OTHER PUBLICATIONS

Marris, "The war against wounds", Nature, Mar. 21, 2007, Issue 446, pp. 369-371.
Mathews et al., "Development of Lyophilized Platelet-Derived Extracellular Vesicles for Multiple Indications", Cellphire, Inc., Oct. 2020, 1 page, Poster.
Mathews et al., "Development of Lyophilized Platelet-Derived Extracellular Vesicles for Multiple Indications", Chellphire, Inc., 2020, 1 page, Abstract.
Mazzucco et al., "The use of autologous platelet gel to treat difficult-to-heal wounds: a pilot study," Transfusion, 2004, 44:1013-1018.
McCarrel, et. al., "Temporal Growth Factor Release from Platelet-Rich Plasma, Trehalose Lyophilized Platelets, and Bone Marrow Aspirate and Their Effect on Tendon and Ligament Gene Expression" Journal of Orthopaedic Research : Official Publication of the Orthopaedic Research Society, vol. 27(8), Aug. 1, 2009, pp. 1033-1042, DOI: 10.1002/jor.20853.
Medwow, "Manufacturer Specifications—CS-2000 Plus, Baxter," Apr. 19, 2011, retrieved on Sep. 26, 2019 from http://www.medwow.com/med/apheresis-machine/baxter/cs-3000-plus/5782.model-spec, 2 pages.
Mehendale, et. al., "Platelet Enrichment From Whole Blood in a Clog-Free Microfluidic Radial Pillar Device (RAPID)", Biomedical Microdevices, bioRxiv, Oct. 4, 2017, DOI: https://doi.org/10.1101/197749.
Mehendale, et. at., "Platelet Enrichment in a Continuous aAnd Clog-Free Microfluidic Filter With Sunflower Head Geometry", 20th International Conference on Miniaturized Systems for Chemistry and Life Sciences, Dublin, Ireland, Oct. 9-13, 2016, pp. 272-273.
Meisel et. al., "A Simplified Direct Lipid Mixing Lipoplex Preparation: Comparison of Liposomal-, Dimethylsulfoxide-, and Ethanol-Based Methods", Scientific Reports, vol. 6, Article 27662, Jun. 21, 2016, 12 pages, doi: 10.1038/srep27662.
Merten et al., "Platelet Microparticles Promote Platelet Interaction with Subendothelial Matrix in a Glycoprotein Iib/Illa Dependent Mechanism", Circulation, 1999, 99:2577-2582.
Miajlovic, et al., "Both complement- and fibrinogen-dependent mechanisms contribute to platelet aggregation mediated by *Staphylococcus aureus* clumping factor B," Infection and Immunity, 2007, 75(7):3335-3343.
Midgett et al., "Combination of freeze-dry microscopy, differential scanning calorimetry, and electron microscopy analysis as a guide for lyophilization cycle optimization to enhance Thrombosomes function", Cryobiology, vol. 63, Issue 3, 2011, p. 320, Abstract, doi:10.1016/j.cryobiol.2011.09.054.
Mihatov, et. al., "Individualizing Dual Antiplatelet Therapy (DAPT) Duration Based on Bleeding Risk, Ischemic Risk, or Both: An Analysis From the DAPT Study", Cardiovascular Revascularization Medicine, vol. 41, Aug. 2022, pp. 105-112, https://doi.org/10.1016/j.carrev.2022.01.006.
Millipore Sigma, "Dulbecco's Modified Eagle's Medium (DMEM)Formulation", Merck KGaA, Sigma-Aldrich Solutions, 2023, 15 pages, retreived from https://www.sigmaaldrich.com/US/en/technical-documents/technical-article/cell-culture-and-cell-culture-analysis/mammalian-cell-culture/dulbecco-modified-eagle-medium-formulation.
Mishra et al., "Cell-penetrating peptides and peptide nucleic acid-coupled MRI contrast agents: evaluation of cellular delivery and target binding." Bioconjugate Chemistry, vol. 20, Issue 10, Oct. 21, 2009, pp. 1860-1868, doi: 10.1021/bc9000454.
Mokobi, "Types of Plant Cell—Definition, Structure, Functions, Diagrams," microbenotes.com [online], Feb. 25, 2020, retrieved May 17, 2021, retrieved from URL, 31 pages.
Montague, "Strategies to Improve Haemostasis in Trauma: Evaluation of Thrombosomes in the Presence of Native Platelet Dysfunction", vol. 100, Issue Suppl 3, 2014, pp. A91-92, DOI: 10.1136/heartjnl-2014-306118.158.
Montecinos et al., "Selective targeting of bioengineered platelets to prostate cancer vasculature: new paradigm for the therapeutic modalities," 2015, 19(7): 1530-1537.
Morris, et al., "A peptide carrier for the delivery of biologically active proteins into mammalian cells," Nature Biotechnoloe:v, 2001, 19:1173-1176.
Morrison et al., "Storage of apheresis platelet concentrates after manual replacement of >95% of plasma with PAS 5", Vox Sanguinis, vol. 107; Issue 3, May 7, 2014, pp. 247-253, XP055759704, doi: 10.1111/vox.12157.
Moskowitz et al., "Freeze Dried Platelet Derivatives (Thrombosomes®) Retain Hemostatic Properties During Heparin Complexation with Protamine", Research and Practice in Thrombosis and Haemostasis, 2022, 2 pages, ISTH 2022 Congress, Abstract PB0880, https://abstracts.isth. org/abstract/freeze-dried-platelet-derivatives-thrombosomes-retain-hemostatic-properties-during-heparin-complexation-with-protamine/.
Moskowitz et al., "Hemostatic Properties of Infusible Trehalose-Stabilized Lyophilized Platelet Derivatives", Blood, vol. 104, Issue 11, Nov. 16, 2004, p. 834, Abstract, doi.org/10.1182/blood.V104.11.834.834.
Moskowitz et al., "Natural History of Bleeding, Transfusion, and Antibody Prevalence in a Subset of Hermansky-Pudlak Syndrom patients: Effects of Freeze-Dried Lyophilized Platelet Derived Hemostat Ex Vivo", Trombosis & Hemostasis Summit 2024, Cellphire Therapeutics, Inc. Apr. 5, 2024, 1 page, Abstract.
Moskowitz et al., "Natural History of Bleeding, Transfusion, and Antibody Prevalence in a Subset of Hermansky-Pudlak Syndrom patients: Effects of Freeze-Dried Lyophilized Platelet Derived Hemostat Ex Vivo", Trombosis & Hemostasis Summit 2024, Cellphire Therapeutics, Inc. Apr. 5, 2024, 1 page, Poster.
Moskowitz et al., "Stabilized Platelets: A Drug Delivery System for Potential Human Hepatocellular Carcinoma Therapy", Research and Practice in Thrombosis and Haemostasis, vol. 7 (Suppl. 2) Oct. 2023, pp. 709-710, Abstract PB0731, doi.org/10.1016/j.rpth.2023.101329.
Moskowitz, "Thrombosomes for the Treatment of Bleeding Associated with Aggressive Anticoagulation", Cellphire, Inc., Dec. 2021, 40 pages, Posters.
Müller et. al., "Factor XI and XII as antithrombotic targets", Current Opinion In Hematology, vol. 15, No. 5, Sep. 2011, pp. 349-355, doi: 10.1097/MOH.0b013e3283497e61.
Mullin, et.al., "Doxorubicin chemotherapy for presumptive cardiac hemangiosarcoma in dogs", Veterinary and Comparative Oncology, vol. 14, Issue 4, Dec. 18, 2014, 13 pages, doi: 10.1111/vco.12131.
Murphy et al., "Platelet transfusions: The problem of refractoriness", Blood Reviews, vol. 4, Issue 1, Mar. 1990, pp. 16-24, doi.org/10.1016/0268-960X(90)90013-I.
NasrEldin, "Effect of cold storage on platelets quality stored in a small containers: Implications for pediatric transfusion", Pediatric Hematology Oncology Journal, vol. 2, Issue 2, Aug. 2017, pp. 29-34, doi.org/10.1016/j.phoj.2017.07.001.
Natan, et al., "Freeze-drying of mononuclear cells derived from umbilical cord blood followed by colony formation", PLoS One, Apr. 21, 2009, vol. 4, Issue 4, e5240, 12 pages, DOI: 10.1371/journal.pone.0005240.
Nieuwland et al., "Cell-Derived Microparticles Generated In Patients During Cardiopulmonary Bypass Are Highly Procoagulant", Circulation, 1997, 96:3534-3541.
Novakowski et al., "Delivery of mRNA to platelets using lipid nanoparticles" Scientific Reports, vol. 9, Article 552, Jan. 24, 2019, 11 pages, doi: 10.1038/s41598-018-36910-2.
O'Brien, et al., "Multiple mechanisms for the activation of human platelet aggregation by *Staphylococcus aureus*: roles for the clumping factors ClfA and ClfB, the serine-aspartate repeat protein SdrE and protein A," Molecular Microbiology, 2002, 44(4):1033-1044.
Ogiwara, et al., "Procoagulant Activity of Antifibrinolytic Agents; A Novel Hemostatic Mechanism of Tranexamic Acid and Epsilon-Aminocaproic Acid", Blood, Nov. 19, 2010, vol. 116, Issue 21, Abstract 1151, 3 pages, https://doi.org/10.1182/blood.V116.21.1151.1151.
Ohanian, et. al., "Freeze-Dried Platelets Are a Promising Alternative in Bleeding Thrombocytopeniatients with Hematological Malignan-

(56) References Cited

OTHER PUBLICATIONS cies", American Journal of Hematology, vol. 97, Issue 3, Mar. 1, 2022, pp. 256-266, doi: 10.1002/ajh.26403.
Oikarinen et al., "Augmentation of the narrow traumatized anterior alveolar ridge to facilitate dental implant placement," Dent. Traumatol., 2003, 19:19-29.
Oliver, "Dry state preservation of nucleated cells: progress and challenge," Cryobiology, Dec. 2011, vol. 63, Issue 3, p. 307, abstract, DOI:10.1016/j.cryobiol.2011.09.007.
Orser et al., "Loading Platelets with Biological Agents for Enhanced Local Delivery", Cellphire, Inc., May 8, 2019, 14 pages, retrieved from https://www.bodevet.com/wp-content/uploads/2019/07/Loading-Platelets-with-Biological-Agents.pdf.
Pan, et al., "Wound healing monitoring using near infrared fluorescent fibrinogen", Biomedical Optics Express, Jul. 27, 2010, vol. 1, Issue 1, pp. 285-294, doi: 10.1364/boe.1.000285.
Pati et al., "Targeting the Endotheliopathy of Trauma in Hemorrhagic Shock and Traumatic Brain Injury with Freeze-Dried Platelets", Defense Technical Information Center, U.S. Army Medical Research and Development Command, Medicine and Medical Research; Biology, Sep. 1, 2020, 22 pages, https://apps.dtic.mil/sti/pdfs/AD1112058.pdf.
Pati et al., "Targeting the Endotheliopathy of Trauma in Hemorrhagic Shock and Traumatic Brain Injury with Freeze-Dried Platelets", Defense Technical Information Center, Sep. 1, 2020, 2 pages, Abstract.
Pemmaraju et al., "Bleeding Risk in Thrombocytopenia Cancer Patients with Venous Thromboembolism (VTE) Receiving Anticoagulation", Blood, vol. 120, Issue 21, Abstract 3408, Nov. 16, 2012, 3 pages, doi.org/10.1182/blood.V120.21.3408.3408.
Pierce, et al., "Platelet-derived growth factor and transforming growth factor-beta enhance tissue repair activities by unique mechanisms", J. Cell Biol., 1989, 109:429-440.
Mathews et al., "Cryopreserved Platelets Can Be Rapidly Thawed in Under 8 Minutes and Are Compatible with Water-Bath and Dry Plasma Thawers", Cellphire Therapeutics, Inc., Military Health System Research Symposium, Jul. 2025, 2 pages, Abstract 14198.
Mathews et al., "Cryopreserved Platelets Can Be Rapidly Thawed in Under 8 Minutes and Are Compatible with Water-Bath and Dry Plasma Thawers", Cellphire Therapeutics, Inc., Military Health System Research Symposium, Jul. 2025, 1 pages, Poster 14198.
Millard et al., "A specific assay for anti-HLA antibodies: application to platelet donor selection", Blood, vol. 70, Issue 5, Nov. 1, 1987, pp. 1495-1499, PMID: 3311206, doi.org/10.1182/blood.V70.5.1495.1495.
Ponomareva et al., "Intracellular origin and ultrastructure of platelet-derived microparticles", Journal of Thrombosis and Haemostasis, vol. 15, Issue 8, Aug. 2017, pp. 1655-1667, doi.org/10.1111/jth.13745.
Ramstrom et al., "Annexin V binding to platelets is agonist, time and temperature dependent", Platelets, vol. 21, Issue 4, Mar. 15, 2010, pp. 289-296, doi.org/10.3109/09537101003660564, abstract.
Trivedi et al., "Lyophilized Platelet Extracellular Vesicles Mitigate TBI Induced Intracranial Hemorrhage via Hemostatic Cargo", Cellphire, Inc. International Society on Thrombosis and Haemostasis Congress, Jul. 22, 2025, 20 pages.
Human Translation of Chinese patent No. CN103907595 A Published Jul. 9, 2014, Trehalose-containing platelet low temperature preservation solution and application thereof, First Inventor Zhao Shuming.
Machine Language Translation of Chinese Patent No. CN108715834 A Titled [En], "A Kind of Platelet Lysates Liquid and Preparation Method There of Rich in CD41+, CD81+ Micro-Capsule", Oct. 30, 2018, 10 pages.
Machine Language Translation of Chinese Patent No. CN109942687 A, Shen et at., Titled [EN], "68Ga Marks EACA Modification c-Met Molecular Imaging Probe And Preparation And Application", Jun. 28, 2019, 10 pages.
Machine Language Translation of Japanese Patent JP2012143554 A2 Titled "[EN] Polysulfone-Based Hollow Fiber Membrane, Hollow Fiber Membrane Module for Cleaning Platelet Suspension, and Cleaning Method of Platelet Suspension.", Aug. 2, 2012, 33 pages.
Machine Language Translation of WO2018084228A1: Nagamura et al., Titled [EN], "Solution for Cryopreservation of Animal Cells or Animal Tissues, Cryopreserved Product, and Cryopreservation Method", May 11, 2018, 16 pages.
Machine Language Translation of Yamamoto, "Appropriate use of platelet preparations", Journal of Thrombosis and Hemostasis, vol. 29, No. 6, 2018, pp. 647-650.
Mbhudutta et al., "Trehalose Stabilized Freeze Dried Human Platelets, Thrombosomes, Persist In Circulation 24 Hours After Infusion and Are Non-Immunogenic in New Zealand White Rabbits", International Society of Blood Transfusion Vox Sanguinis, vol. 99, Suppl. 1, P-0454, 2010, p. 262, Abstract.
Mbhudutta et al., "Trehalose Stabilized Freeze Dried Human Platelets, Thrombosomes, Reduce Blood Loss in Thrombocytopenia Rabbit Ear Bleed Model by as Much as 89.5%", International Society of Blood Transfusion Vox Sanguinis, vol. 99, Suppl. 1, P-0452, 2010, p. 261, Abstract.
Mswanathan et al., "Clopidogrel Alters Thrombus Quantity and Quality in Patients With Type II Diabetes Mellitus and Stable Coronary Artery Disease", Journal of the American College of Cardiology, vol. 61, No. 10, Mar. 2013, E1154, 1 page.
Vlieghe et al., "Synthetic therapeutic peptides: science and market," Drug Discovery Today, 2010, 15:40-56.
Volz et al., "Inhibition of platelet GPVI induces intratumor hemorrhage and increases efficacy of chemotherapy in mice," Blood, 2019, 133(25):2696-2706.
Wajon et al., "Intraoperative Plateletpheresis and Autologous Platelet Gel Do Not Reduce Chest Tube Drainage or Allogeneic Blood Transfusion After Reoperative Coronary Artery Bypass Graft", Anesth. Analg;., 2001, 93:536-542.
Wang et al., "Commonly used dietary supplements on coagulation function during surgery," Medicines, 2015, 2:157-185.
Wang et al., "Solubility and Molecular Interactions of Trimetazidine Hydrochloride in 12 Monosolvents and Solvent Mixtures of Methanol + (Ethanol, N, N-Dimethylformamide or Ethyl Acetate)", Journal of Chemical Engineering Data, Folume 63, Sep. 6, 2018, pp. 3704-3714, doi.org/10.1021/acs.jced.8b00235.
Wei et al., "ICAM-5/Telencephalin Is a Functional Entry Receptor for Enterovirus D68", Cell Host Microbe, vol. 20, Issue 5, Nov. 9, 2016, pp. 631-641, doi: 10.1016/j.chom.2016.09.013.
Whitman et al., "Design of the CRYPTICS Trail: A Randomized Controlled Trial Comparing Cryopreserved to Liquid Stored Platelets in Patients Undergoing Cardiac Surgery", Journal of Thoracic and Cardiovascular Surgery, 2022, doi.org/10.1016/j.xjon.2022.11.003.
Whitney et al. "Ratiometric Activatable Cell-Penetrating Peptides Provide Rapid In Vivo Readout of Thrombin Activation", Angewandte Chemie International Edition, vol. 52, Jan. 2, 2013, Issue 1, pp. 325-330, doi: 10.1002/anie.201205721.
Wickramasinghe, "Washing Cryopreserved Blood Products Using Hollow Fibres", Food and Bioproducts Processing, vol. 77, Issue 4, Dec. 1999, pp. 287-292, DOI:org/10.1205/096030899532574.
Wikström et al., "Viability of freeze dried microencapsulated human retinal pigment epithelial cells", European Journal of Pharmaceutical Sciences, vol. 47, Issue 2, Sep. 29, 2012, pp. 520-526, doi: 10.1016/j.ejps.2012.06.014.
Wilkerson et al., "Platelet size, platelet surface-associated IgG, and reticulated platelets in dogs with immune-mediated thrombocytopenia," Veterinary Clinical Pathology, 2001, 30(3):141-149.
Wilson et al., "A simple rapid method for layering blood on Ficoll-Isopaque gradients," Journal of Immunological Methods, 1975, 9(1): 67-68.
Wolkers et al., "Human Platelets Loaded with Trehalose Survive Freeze-Drying", Cryobiology, vol. 42, 2001, pp. 79-87.
WPI Database No. AN 2014-E98028 / CN103524613, Jan. 22, 2014: 2 pages.
Wright et al., "Doxorubicin delivery via novel lyophilized/reconstituted platelet-product has anti-cancer activity", Hematology & Transfusion International Journal, vol. 9, Issue 3, 2021, pp. 41-51.

(56) References Cited

OTHER PUBLICATIONS

Xu et al., "Doxorubicin-loaded platelets as a smart drug delivery system: An improved therapy for lymphoma", Scientific Reports vol. 7, Article No. 42632, Feb. 15, 2017, 15 pages.
Xu et al., "EACA Loaded Platelets Sustain Clots More Efficiently Than Free EACA", Cellphire, Inc., Jul. 2021, 1 page, Poster.
Xu et al., "EACA Loaded Platelets Sustain Clots More Efficiently Then Free EACA", Cellphire, Inc., 2021. 2 page.
Xu et al., "Human Platelet Derived Lyophilized Hemostatic Retains Hemostatic Properties Heparin Complexation with Protamine", Cellphire, Inc. Jul. 2022, 1 page, Poster.
Xu et al., "Thrombosomes As a Treatment Option for Low-Dose Heparin Reversal", Cellphire Therapeutics, Inc., Rockville, MD, 2020 Annual Meeting, 3 pages.
Yamamoto, "Appropriate use of platelet preparations", Journal of Thrombosis and Hemostasis, vol. 29, No. 6, 2018, pp. 647-650.
Yarovoi et al., "Factor VIII ectopically expressed in platelets: efficacy in hemophilia A treatment", Blood 102(12):4006-4013, 2003.
Zafar et. al., "Badimon Perfusion Chamber: An Ex Vivo Model of Thrombosis", Methods Molecular Biology, vol. 1816, 2018, pp. 161-171, doi: 10.1007/978-1-4939-8597-5_12.
Zhang et al., "Coupling of liquid chromatography with mass spectrometry by desorption electrospray ionization (DESI)", Chemical Communications, Issue 14, Feb. 28, 2011, pp. 4171-4173, doi.org/10.1039/C0CC05736C.
Zhou et al., "Freeze-drying of human platelets: influence of saccharide, freezing rate and cell concentration", Cryoletters, vol. 28, No. 3, May/Jun. 2007, pp. 187-196.
Zhou et al., "Hemostatic and Thrombogenic Properties of Lyophilized Human Platelets", CellPhire, Inc. Jul. 2021, 1 page, Poster.
Zhou et al., "Loading Trehalose into Red Blood Cells by Improved Hypotonic Method," Cell Preservation Technology, 2008, 6(2):119-122.
Zhou et al., "Lyophilized Human Platelets Promote Coagulation in Humanized Mouse VWF Transgenic Models of Hemostasis and Thrombosis", Cellphire, Inc., 2021, 1 page.
Pietramaggiori et al., "Freeze-dried platelet-rich plasma shows beneficial healing properties in chronic wounds", Wound Repair and Regeneration, vol. 14, Issue 5, Sep. 29, 2006, pp. 573-580, doi.org/10.1111/j.1743-6109.2006.00164.x.
Pietramaggiori, et. al., "Trehalose Lyophilized Platelets For Wound Healing", Wound Repair and Regeneration : Official Publication of the Wound Healing Society [and] the European Tissue Repair Society, vol. 15 (2), Mar. 9, 2007, pp. 213-220. doi: 10.1111/j.1524-475X.2007.00207.x.
Powner, et. al., "Counteracting the Effects of Anticoagulants and Antiplatelet Agents During Neurosurgical Emergencies", Neurosurgery, vol. 57, No. 5, Nov. 2005 pp. 823-831.
Prior, et al., "A Sprayable Hemostat Containing Fibrillar Collagen, Bovine Thrombin, and Autologous Plasma", Ann. Thorac. Surg., 1999, 68:479-485.
Read, et. al., "Preservation of hemostatic and structural properties of rehydrated lyophilized platelets: potential for long-term storage of dried platelets for transfusion", Proceedings of the National Academy of Sciences of the USA, vol. 92, Jan. 1995, pp. 397-401, DOI: 10.1073/pnas.92.2.397.
Reddoch et al., "Extended Storage of Refrigerated Platelets in Isoplate and Intersol PAS: An Evaluation of Two FDA-Approved Methods of Collection", Blood, vol. 128, Issue 22, Dec. 2, 2016, 3 pages, doi.org/10.1182/blood.V128.22.2631.2631.
Reuss et al., "Intracellular delivery of carbohydrates into mammalian cells through swelling-activated pathways", The Journal of Membrane Biology, vol. 200, Issue 2, Jul. 15, 2004, pp. 67-81, doi: 10.1007/s00232-004-0694-7.
Robson, et. al., "Coronavirus RNA Proofreading: Molecular Basis and Therapeutic Targeting", Molecular Cell, vol. 79, No. 5, Sep. 3, 2020, pp. 710-727, DOI: 10.1016/j.molcel.2020.07.027, XP055785471.
Rosing et al., "Impaired factor X and prothrombin activation associated with decreased phospholipid exposure in platelets from a patient with a bleeding disorder", Blood, 1985, 65:1557-1561.
Rowley, et. al., "Platelet mRNA: the meaning behind the message," Curr. Opin. Hematol., 2012, 19(5):385-391.
Roytman et al., "Amyloid-Related Imaging Abnormalities: An Update", American Journal of Roentgenol, Issue 220, Issue 4, Nov. 2, 2022, pp. 562-574, doi: 10.2214/AJR.22.28461.
Samanbar et al., "Evaluation of the Hemostatic Ability of the New Device 'Total Thrombus Formation Analysis System' (T-TAS) for Thrombocytopenia Patients. Invitro effect of lyophilized human platelets", Research adn Preactice in Thrombosis and Haemostasis, Jul. 2022, 1 page, Poster.
Samanbar et al., "Evaluation of the hemostatic ability of the new device Total Thrombus Formation Analysis System' (T-TAS) for thrombocytopeniatients. In vitro effect of Thrombosomes®", Research and Practice in Thrombosis and Haemostasis, 2022, 2 pages, ISTH 2022 Congress, Abstract PB0854, https://abstracts.isth.org/abstract/evaluation-of-the-hemostatic-ability-of-the-new-device-total-thrombus-formation-analysis-system-t-tas-for-thrombocytopeniatients-in-vitro-effect-of-thrombosomes/.
Samanbar et al., "Hemostatic Ability of Thrombosomes® in Blood from Thrombocytopeniatients Using the Total Thrombus Formation Analysis System (T-TAS) and Confocal Microscopy in Microfluidic Chambers", Blood, Nov. 15, 2022, 140 (Supplement 1), pp. 11242-11243, doi.org/10.1182/blood-2022-169346.
Sane, et. al., "Bleeding During Thrombolytic Therapy for Acute Myocardial Infarction: Mechanisms and Management", Annals Oo Internal Medicine, vol. 111, No. 12, Dec. 15, 1989, pp. 1010-1022.
Scheinkönig et al., "Adoption of long-term cultures to evaluate the cryoprotective potential of trehalose for freezing hematopoietic stem cells", Bone Marrow Transplantation, September, vol. 34, Issue 6, Sep. 2004, pp. 531-536, doi: 10.1038/sj.bmt.1704631.
Schoug, et.al., "Differential effects of polymers PVP90 and Ficoll400 on storage stability and viability of Lactobacillus coryniformis Si3 freeze-dried in sucrose", Journal of Applied Microbiology, vol. 108, No. 3, pp. 1032-1040, Feb. 8, 2010.
Serebruany, et al., "Crossreactivity of Human versus Swine Platelet Surface Antigens Is Similar for Glycoproteins Ib and IIIa, but Not for the Glycoprotein IIb/IIIa Complex," Journal of Thrombosis And Thrombolysis, vol. 5, Issue 1, 1998, pp. 37-41, doi: 10.1023/a:1008867930862.
Sheik et al., "Stably Loading Human Platelets with Gadolinium Conjugates to Enhance Magnetic Resonance Imaging", Cellphire, Inc., 2020,1 page.
Sheik et al., "Stably Loading Human Platelets with Gadolinium Conjugates to Enhance Magnetic Resonance Imaging", Cellphire, Inc., 2020, 3 pages, poster.
Shi et al., "Impact of Anti-amyloid-B Monoclonal Antibodies on the Pathology and Clinical Profile of Alzheimer's Disease: A Focus on Aducanumab and Lecanemab", Frontiers in Aging Nuroscience, vol. 14, Article 870517, Apr. 12, 2022, 11 pages, doi: 10.3389/fnagi.2022.870517.
Sibbing, et. al., "Antiplatelet effects of clopidogrel and bleeding in patients undergoing coronary stent placement", Journal of Thrombosis and Haemostasis, vol. 8, Issue 2, pp. 250-256, DOI: 10.1111/j.1538-7836.2009.03709.x.
Sims et al., "Complement Proteins C5b-9 Cause Release of Membrane Vesicles from the Platelet Surface That Are Emiched in the Membrane Receptor for Coagulation Factor Va and Express Prothrombinase Activiy", J. Biol Chem., 1988, 263:18205-18212.
Sims et al., "Regulatory control of complement on blood platelets. Modulation of platelet procoagulant responses by a membrane inhibitor of the C5b-9 complex", J Biol. Chem., 1989, 264:19228-19235.
Srivastava, et. al., "The rebirth of the contact pathway: a new therapeutic target", Current Opinion in Hematology, vol. 27, No. 5, Sep. 2020, pp. 311-319, doi: 10.1097/MOH.0000000000000603.
Steed, "The role of growth factors in wound healing," Surg. Clin. North Am., 1997, 77:575-586.
Strober, "Trypan blue exclusion test of cell viability," Current Protocols in Immunology, 1997, A.3B.1-A.3B.2.

(56) References Cited

OTHER PUBLICATIONS

Strong, ed., "Indications for Platelet Transfusion Therapy," Transfusion Medicine Bulletin, Vo. 2, No. 2, Jul. 1999, http://www.scbinfo.org/publications/bulletin_v2_n2.htm, pp. 1-6.
Sum et al., "Wound-healing properties of trehalose-stabilized freeze-dried outdated platelets", Transfusion, vol. 47, Issue 4, Apr. 2007, pp. 672-679, doi: 10.1111/j.1537-2995.2007.01170.x.
Swami, et.al., "von Willebrand Disease: A Concise Review and Update for the Practicing Physician", Clinical and Applied Thrombosis/Hemostasis, vol. 23 (8), Nov. 2017, pp. 900-910, DOI: 10.1177/1076029616675969.
Szekely and Lex, "Antifibrinolytics," Heart, Lung and Vessels, 2014, 6(1):5-7.
Tacar et al., "Doxorubicin: an update on anticancer molecular action, toxicity and novel drug delivery systems," The Journal of Pharmacy and Pharmacolo11:v, 2013, 65(2):157-170.
Tang, et. al., "Targeted repair of heart injury by stem cells fused with platelet nanovesicles", Nature Biomedical Engineering, vol. 2, No. 1, May 30, 2018, pp. 17-26, DOI: 10.1038/s41551-017-0182-x.
Tans et al., "Comparison of anticoagulant and procoagulant activities of stimulated platelets and platelet-derived microparticles", Blood, 1991, 77:2641-2648.
Taune, et al., "Whole blood coagulation assays ROTEM and T-TAS to monitor dabigatran t dabigatran treatment," Thrombosis Research, 2017, 153(30):76-82.
thrombinoscope.com [online], "Thrombin Calibrator," retrieved on Feb. 18, 2021, retrieved from URL , 2 pages.
Török et al., "Preservation of Trehalose-Loaded Red Blood Cells by Lyophilization", Cell Preservation Technology, vol. 3, No. 2, Jul. 11, 2005, pp. 96-11, doi.org/10.1089/cpt.2005.3.96.
Trivedi, et. al., "Freeze-Dried Platelets Promote Clot Formation, Attenuate Endothelial Cell Permeability, and Decrease Pulmonary Vascular Leak in a Murine Model of Hemorrhagic Shock", The Journal of Trauma and Acute Care Surgery, vol. 90, Issue 2, Feb. 1, 2021, pp. 203-214, doi: 10.1097/TA.0000000000002984.
Tsai etal, "Increased risk of bleeding in patients on clopidogrel therapy after drug-eluting stents implantation: insights from the HMO Research Network-Stent Registry (HMORN-stent)", Circulation Cardiovascular Interventions, vol. 3, Issue 3, Jun. 1, 2010, pp. 230-235, DOI: 10.1161/CIRCINTERVENTIONS.109.919001.
Tsegaye et al., "Platelet activation suppresses HIV-1 infection of T cells," Retrovirology, 2013, 10:48:00.
T-TAS.info [online], Publications, 2019, retrieved on Aug. 28, 2019, retrieved from URL, 8 pages.
Ullah et al., "A Review on Malarial Parasite", World Journal of Zoology, vol. 10, No. 4, 2015, pp. 285-290, DOI: 10.5829/idosi.wjz.2015.10.4.95268, XP055785474.
Undas et al., "Antithrombotic properties of aspirin and resistance to aspirin: beyond strictly antiplatelet actions", Blood, vol. 109, No. 6, Mar. 15, 2007, pp. 2285-2292, DOI: 10.1182/blood-2006-01-010645.
Valentini et al., "Use of CD9 and CD61 for the characterization of AML-M7 by flow cytometry in a dog," Veterinary Comparative Oncology, Aug. 31, 2011, vol. 10, No. 4, pp. 312-318, DOI: 10.1111/j.1476-5829.2011.00290.x.
Valeri et al., "Freezing human platelets with 6 percent dimethyl sulfoxide with removal of the supernatant solution before freezing and storage at-80° C. without post thaw processing" Transfusion, vol. 45 (12), Dec. 2005, pp. 1890-1898, DOI: 10.1111/j.1537-2995.2005.00647.x.
Valeri et al., "Survival of baboon biotin-X-N-hydroxysuccinimide and 11 IIn-oxine-labelled autologous fresh and lyophilized reconstituted platelets," Vox Sanguinis, 2005, 88:122-129.
Van Der Meer et al, Platelet preservation: Agitation and containers, Transfusion and Apheresis Science, vol. 44, Issue 3, Jun. 2011, pp. 297-304, //doi.org/10.1016/j.transci.2011.03.005.
Van Der Meijden et al., "Platelet- and erythrocyte-derived microparticles trigger thrombin generation via factor XIIa", Journal of Thrombosis and Haemostasis, vol. 10, Issue 7, Apr. 26, 2012, pp. 1355-1362, doi.org/10.1111/j.1538-7836.2012.04758.x.
Vibhudutta et al., "Trehalose Stabilized Freeze Dried Human Platelets, Thrombosomes, Reduce Blood Loss in Thrombocytopenia Rabbit Ear Bleed Model by as Much as 89.5%", Cellphire, Inc. P-0454, www.bodevet.com, Mar. 2017, 1 page, Poster.
Vibhudutta et al., "Trehalose Stabilized Freeze Dried Human Platelets, Thrombosomes, Persist in Circulation 24 Hours After Infusion and Are Non-Immunogenic In New Zealand White Rabbits", Cellphire, Inc. P-0454, 1 page, Poster.
Alexander et at., "A Prospective, Multicenter, Randomized, Open-Label, Phase 2, Parallel, Dose Ranging Multidose Study of Thrombosomes® vs Liquid Stored Platelets (LSP) in Bleeding Thrombocytopenia Patients", Celphire Therapeutics, Inc., NCT04631211, Statistical Analysis Plan, Apr. 3, 2024, 22 pages.
Anonymous, "Bridging Anticoagulation", Circulation, vol. 125, Issue 12, Mar. 27, 2012, pp. e496-e498, doi.org/10.1161/CIRCULATIONAHA.111.084517.
Arruda, "The search for the origin of factor VIII synthesis and its impact on therapeutic strategies for hemophilia A", Haematologica vol. 100, Issue 7, Jul. 2015, pp. 849-850, doi: 10.3324/haematol.2015.129858.
Baroletti et al., "Heparin-Induced Thrombocytopenia", Circulation, vol. 114, Issue 8, Aug. 22, 2006, pp. e355-e356, doi.org/10.1161/CIRCULATIONAHA.106.632653.
Cid et at., "24-h continuous infusion of platelets for patients with platelet transfusion refractoriness", British Journal of Haematology, vol. 181, No. 3, Mar. 14, 2017, pp. 386-389, doi.org/10.1111/bjh.14572.
Comont et al., "Platelet transfusion refractoriness in patients with acute myeloid leukemia treated by intensive chemotherapy", Leukemia Research, vol. 61, Oct. 2017, pp. 62-67, doi: 10.1016/j.leukres.2017.08.015.
Dumont et al, "Feasibility evaluation of two novel systems for the automated preparation and extended storage of DMSO cryopreserved platelets", Transfusion, vol. 63, No. 8, Jun. 26, 2023, pp. 1554-1562, https://doi.org/10.1111/trf.17464.
Fitzpatrick et al., "A Phase 1, Multi-Center, Open-Label, Dose Escalation Study of Thrombosomes in Bleeding Thrombocytopenia Patients in Three Cohorts", ClinicalTrials.gov ID NCT03394755, updated, Cellphire Therapeutics, Inc, Apr. 13, 2023, 34 pages.
Fitzpatrick et al., "A Phase 1, Multi-Center, Open-Label, Dose Escalation Study of Thrombosomes in Bleeding Thrombocytopenia Patients in Three Cohorts", ClinicalTrials.gov ID NCT03394755, Cellphire Therapeutics, Inc, Jan. 8, 2018, 6 pages.
Fitzpatrick et al., "A Phase 1, Multi-Center, Open-Label, Dose Escalation Study of Thrombosomes in Bleeding Thrombocytopenia Patients in Three Cohorts", Cellphire Therapeutics, Inc., NCT03394755, Statistical Analysis Plan, Jun. 2, 2020, 34 pages.
Fitzpatrick et al., "A Phase I, Multi-Center, Open-Label, Dose Escalation Study of Thrombosomes® in Bleeding Thrombocytopenia Patients in Three Cohorts", Cellphire Therapeutics, Inc., NCT03394755, Study Protocol, Jun. 2, 2020, 55 pages.
Fitzpatrick et al., "A Prospective, Multicenter, Randomized, Open-Label, Phase 2, Parallel, Dose Ranging Multidose Study of Thrombosomes® vs Liquid Stored Platelets (LSP) in Bleeding Thrombocytopeniatients", ClinicalTrials.gov NCT 04631211, Cellphire Therapeutics, Inc., Nov. 10, 2020, 8 pages.
Fitzpatrick et al., "A Prospective, Multicenter, Randomized, Open-Label, Phase 2, Parallel, Dose Ranging Multidose Study of Thrombosomes® vs Liquid Stored Platelets (LSP) in Bleeding Thrombocytopenia Patients", Cellphire Therapeutics, Inc., Clinical Study Protocol, NCT04631211, Mar. 28, 2024, 61 pages.
Fitzpatrick et al., "A Prospective, Multicenter, Randomized, Open-Lavel Phase 2, Parallel, Dose Ranging Multidose Study of Thrombosomes vs Liquid Stored Platelets (LSP) in Bleeding Thrombocytopenia Patients", ClinicalTrials.gov ID NCT04631211, Cellphire Therapeutics, Inc., Apr. 2, 2024, 44 pages.
International Search Report and Written Opinion in International Appln. No. PCT/US2024/027563, mailed Oct. 4, 2024, 15 pages.
International Search Report and Written Opinion in International Appln. No. PCT/US2024/031785, mailed Sep. 24, 2024, 12 pages.
Moskowitz et al., "A Freeze-Dried Platelet-Derived Hemostatic Agent is Partially Resistant to Fibrinolysis In Vitro", Cellphire

(56) References Cited

OTHER PUBLICATIONS

Therapeutics, Military Health System Research Symposium, (MHSRS-24-11499), Aug. 2024, 2 pages, abstract.
Moskowitz et al., "A Freeze-Dried Platelet-Derived Hemostatic Agent is Partially Resistant to Fibrinolysis In Vitro", Cellphire Therapeutics, Military Health System Research Symposium, (MHSRS-24-11499), Aug. 2024, 1 page, poster.
Moskowitz et al., "A Prospective, Multicenter, Randomized, Open-Label, Phase 2, Parallel, Dose Ranging Multidose Study of Thrombosomes@vs Liquid Stored Platelets (LSP) in Bleeding Thrombocytopenia Patients with Hematological Malignancies", Cellphire Therapeutics, Inc., presented at Association for the Advancement of Blood & Biotherapies Oct. 19, 24, 22 pages.
Moskowitz et al., "Cryopreserved Platelets Prepared by Novel Allogenic Pooling and Post-thaw Processes are Stable at Elevated Temperatures", Cellphire, Therapeutics, Military Health System Reserach Symposium, (MHSRS-24-11477), Aug. 2024, 1 page, poster.
Moskowitz et al., "Freeze-Dried Platelets Decrease Bleeding in Refractory Thrombocytopeniatients with Hematological Malignancies", AABB Annual Meeting 2024, abstract submission, 2 pages.
International Search Report and Written Opinion in International Appln. No. PCT/US2020/046525, mail date Nov. 10, 2020, 11 Pages.
International Search Report and Written Opinion in International Appln. No. PCT/US2020/049489, mail date Feb. 16, 2021, 7 Pages.
International Search Report and Written Opinion in International Appln. No. PCT/US2020/062214, mail date Mar. 17, 2021, 8 pages.
International Search Report and Written Opinion in International Appln. No. PCT/US2020/062216, mailed Feb. 9, 2021, 9 pages.
International Search Report and Written Opinion in International Appln. No. PCT/US2021/016360, mailed May 21, 2021, 13 pages.
International Search Report and Written Opinion in International Appln. No. PCT/US2021/016363, mailed May 18, 2021, 15 pages.
International Search Report and Written Opinion in International Appln. No. PCT/US2021/016389, mailed May 18, 2021, 15 pages.
International Search Report and Written Opinion in International Appln. No. PCT/US2021/016390, mailed May 18, 2021, 13 pages.
International Search Report and Written Opinion in International Appln. No. PCT/US2021/032783, mailed Aug. 24, 2021, 13 pages.
International Search Report and Written Opinion in International Appln. No. PCT/US2021/058814, mailed Mar. 17, 2022, 14 pages.
International Search Report and Written Opinion in International Appln. No. PCT/US2022/016866, mailed Jul. 4, 2022, 18 pages.
International Search Report and Written Opinion in International Appln. No. PCT/US2022/016883, mailed May 11, 2022.
International Search Report and Written Opinion in International Appln. No. PCT/US2023/066904, mailed Sep. 12, 2023, 12 pages.
International Search Report and Written Opinion in International Appln. No. PCT/US2023/066965, mailed Aug. 4, 2023, 10 pages.
International Search Report and Written Opinion in International Appln.No. PCT/US2024/019800, mailed Jul. 17, 2024.
Invitation to Pay Additional Fees in PCT Appln. No. PCT/US2020/022705, mailed May 18, 2020, 2 pages.
Ishler et al., "Lyophilized Human Platelets Interact with Fresh Platelets to Promote Hemostasis Under Shear In Vitro", Cellphire, Inc., PB0990, Jul. 2021, 1 page, Poster.
Ishler et al., "Lyophilized Human Platelets Interact with Fresh Platelets to Promote Hemostasis Under Shear In Vitro", Cellphire, Inc., 2021, 2 page, Abstract.
Ishler et al., "Lyophilized Human Platelets Show Hemostatic Function Independent of von Willebrand Factor", Research and Practice in Thrombosis and Haemostasis, 2020; 4 (Suppl 1), 2 pages, ISth 2020 Virtual Congress Presentation, Jul. 2020, Abstract PB1533, https://abstracts.isth.org/abstract/lyophilized-human-platelets-show-hemostatic-function-independent-of-von-willebrand-factor/.
Ishler et al., "Lyophilized Platelets Show Hemostatic Function Independent of von Willebrand Factor", Cellphire, Inc., Department of Discovery and Research, ISth 2020 Virtual Congress, PB1533, Jul. 2020, 1 page, Poster.
Ishler et al., "StablePlate RX Canine Promotes in vitro Thromblin Generation and Thrombus Formation Under High Shear," Journal of Veterinary Internal Medicine, 2019 ACVIM Forum Research Abstract Program, p. 2483, Abstract.
Ishler et al., "StablePlate RX®Canine Promotes In Vitro Thrombin Generation and Thrombus Formation Under High Shear", Cellphire, Inc., 2019, 1 page, Poster1.
Ishler et al., "StablePlate RX® Canine Promotes In Vitro Thrombin Generation and Thrombus Formation Under High Shear", Cellphire, Inc., 2019, 1 page, Poster2.
Ito et al., "Total Thrombus-formation Analysis System (T-TAS) can predict periprocedural bleeding events in patients undergoing catheter ablation for atrial fibrillation," Journal of American Heart Association, 2015, 5(1):e002744, 12 pages.
Jennings et al., "Antiplatelet and anticoagulant agents: Key differences in mechanisms of action, clinical application, and therapeutic benefit in patients with non-ST-segment-elevation acute coronary syndromes", Current Opinion in Cardiology vol. 23, No. 4, Jul. 2008, pp. 302-308, DOI: 10.1097/HCO.0b013e3283021ad9.
Jennings et al., "The pharmacodynamics of parenteral glycoprotein IIb/IIIa inhibitors", Journal of Interventional Cardiology, vol. 15, No. 1, Feb. 2002, pp. 45-60, DOI: 10.1111/j.1540-8183.2002.tb01034.x.
Johnson et al., "Platelet microparticles in cryopreserved platelets: Potential mediators of hemostasis", Transfusion and Apheresis Science, vol. 53, Issue 2, Oct. 2015, pp. 146-152, doi.org/10.1016/j.transci.2015.10.011.
Joshi et al., "Lyophilised Reconstituted Human Platelets Increase Thrombus Formation in a Clinical Ex Vivo Model of Deep Arterial Injury", Thrombosis and Haemostasis, vol. 108, No. 1, 2012, pp. 176-182, DOI: 10.1160/TH12-02-0059.
Joshi et al., "Thrombosomes Show Dose-Dependent Increase in Thrombus Formation in a Model of Deep Arterial Injury", Blood, vol. 118, Issue 21, Nov. 18, 2011, Abstract 2319, 8 pages, doi.org/10.1182/blood.V118.21.2319.2319.
Kariko et al., "Phosphate-enhanced transfection of cationic lipid-complexed mRNA and plasmid DNA," Biochim. Biophys. Acta, 1998, 1369(2):320-334.
Kerrigan, "Platelet interactions with bacteria," The non-thrombotic role of platelets in health and disease; Chapter 4, 2015, 65-84.
Kerrigan, et al., "Molecular basis for *Staphylococcus aureus* mediated platelet aggregate formation under arterial shear in vitro," Arteriosclerosis Thrombosis and Vascular Biology, 2008, 28(2):334-340.
Kessler, "Bleeding after treatment with rivaroxaban or apixaban", Clinical Advances in Hemotology and Oncology, vol. 17, No. 9, Supplement 15, Sep. 2019, pp. 3-19.
Kirby et al., "Preparation of liposomes containing Factor VIII for oral treatment of haemophilia," 1984, J. Microencapsul. 1(1): 33-45.
Kirkley et al., "Use of single donor platelets", Blood Reviews, vol. 8, Issue 3, Sep. 1994, pp. 142-147, doi.org/10.1016/0268-960X(94)90074-R.
Kishbaugh et al., "Intervening with Platelet Therapies", National Elephant Herpesvirus Laboratory at the National Zoo, vol. 4, No. 2, 2017, 4 pages.
Kreuger et al., "HLA-matched platelet transfusions are effective only in refractory patients with positive HLA antibody screening", Transfusion, The Journal of American Association Of Blood Banks, vol. 59, No. 11, Oct. 11, 2019, pp. 3303-3307, doi.org/10.1111/trf.15530.
Kuhn et al., "Assessing Circulation Persistence of Human Platelet Products in a NOD-SCID Mouse Model", Research and Practice in Thrombosis and Haemostasis, 2022, 2 pages, ISTH 2022 Congress, Abstract PB0874, https://abstracts.isth.org/abstract/assessing-circulation-persistence-of-human-platelet-products-in-a-nod-scid-mouse-model/.
Kuhn et al., "Assessing Circulation Persistence of Human Platelet Products in a NOD-SCID Mouse Model", Research and Practice in Thrombosis and Haemostasis, 2022, ISTH 2022 Congress Jul. 2022, 1 page, Poster PB0874.

(56) References Cited

OTHER PUBLICATIONS

Kuhn et al., "Mechanism of Action of a Freeze-dried Platelet-derived Hemostatic Product", Cellphire, Inc. Cellular Therapeutics in Trauma and Critical Care, May 8-11, 2023, 1 page, poster.
Kuhn et al., "Mechanisms of action of an investigational new freeze-dried platelet-derived hemostatic product", Journal of Thrombosis and Haemostasis, Dec. 9, 2023, 4 pages, doi.org/10.1016/j.jtha.2023.11.022.
Lam, et al., "siRNA versus miRNA as therapeutics for gene silencing," Molecular Therapy-Nucleic Acids, 2015, 4:e252.
Lannan, et. al., "Breaking the Mold: Transcription Factors in the Anuceleate Platelet and Platelet-Derived Microparticles," Front Imunnol., 2015, 6:48, 17 pages.
Lassila et. al., "Dynamic Monitoring of Platelet Deposition on Severely Damaged Vessel Wall in Flowing Blood. Effects of Different Stenoses on Thrombus Growth", Arteriosclerosis, vol. 10, No. 2, Mar.-Apr. 1990, pp. 306-315, doi: 10.1161/01.atv.10.2.306.
Lee et al., "High Efficiency Transfection and Preservation of Platelets with Tumor Suppressing Short RNA", Research and Practice in Thrombosis and Haemostasis, Jul. 2020, 1 page, Poster PB1724, ISTH 2020 Congress.
Lee et al., "High Efficiency Transfection and Preservation of Platelets with Tumor Suppressing Short RNA", Research and Practice in Thrombosis and Haemostasis, 2020; 4 (Suppl 1). 2 pages, Abstract PB1724, ISTH 2020 Congress, https://abstracts.isth.org/abstract/high-efficiency-transfection-and-preservation-of-platelets-with-tumor-suppressing-short-rna/.
Lee et al., "Lyophilized Human Platelets Exhibit Adhesive Interactions with Staphylococcus aureus", Research adn Practice in Thrombosis and Haemostasis, 2020; 4 (Suppl 1), 2 pages, Abstract PB1816, ISTH 2020 Congress, https://abstracts.isth.org/abstract/lyophilized-human-platelets-exhibit-adhesive-interactions-with-staphylococcus-aureus/.
Lee et al., "Lyophilized Human Platelets Exhibit Adhesive Interactions with *Staphylococcus aureus*", Research adn Practice in Thrombosis and Haemostasis, 2020, 1 page, Poster PB1816.
Lee et al., "Novel treatment modalities: New platelet preparations and subsititutes," British journal of haematology, Sep. 2001, 114(3):496-505.
Li et al., "Extended antiplatelet therapy with clopidogrel alone versus clopidogrel plus aspirin after completion of 9- to 12-month dual antiplatelet therapy for acute coronary syndrome patients with both high bleeding and ischemic risk. Rationale and design of the OPT-BIRISK double-blinded, placebo-controlled randomized trial", American Hear Journal, vol. 228, Oct. 2020, pp. 1-7, https://doi.org/10.1016/j.ahj.2020.07.005.
"Cryoprotein," The American Heritage® Stedman's Medical Dictionary. Houghton Mifflin Company. Mar. 24, 2010.
"Expose," http://dictionary.reference.com/browse/expose, accessed Jul. 18, 2009.
"Platelet," The American Heritage® Dictionary of the English Language, Fourth Edition. Houghton Mifflin Company, 2004. Mar. 23, 2010.
"Rounding," Dictionary.com. Dictionary.com Unabridged (v 1.1 ). Random House, Inc. http://dictionary.reference.com/browse/rounding (accessed: Oct. 27, 2008).
2. palomar.edu [online], "The Five Kingdoms of Life," Feb. 1998, retrieved on May 17, 2021, retrieved from URL ; 18 pages.
Abdelgawwad, et al., "Transfusion of plateletes loaded with recombinant ADAMTS13 is efficacious for inhibiting arterial thrombosis in mice and in human," Arterioscler. Thromb. Vas. Biol., 2018, 38(11):2731-2743.
Abreu-Blanco et al., "Therapeutic effect of Lyophilized human platelets in an in vitro surrogate model of Bernard-Soulier syndrome and in patient samples", Cellphire, Inc., Oct. 14-17, 2023, 2 pages, abstract.
Abreu-Blanco et al., "Therapeutic effect of Lyophilized human platelets in an in vitro surrogate model of Bernard-Soulier syndrome and in patient samples", Cellphire, Inc., Association for the Advancement of Blood & Biotherapies, Oct. 14-17, 2023, 1 page, poster.
Adams, Ducry et al. ed., "The principles of freeze-drying," DNA Repair Protocols, Methods in Molecular Biology, Humana Press, Clifton, N.J., vol. 368, Chapter 2, 2007, pp. 15-38, doi: 10.1007/978-1-59745-362-2_2.
Agam et al. "Passive Participation of Fixed Platelets in Aggregation Facilitated by Covalently Bound Fibrinogen" Blood 61:1, pp. 186-191, 1983.
Ahmadzada, et al., "Fundamentals of siRNA and miRNA therapeutics and a review of targeted nanoparticle delivery systems in breast cancer," Biophysical Reviews, 2018, 10:69-86.
Al Ghaithi et al., "Evaluation of the Total Thrombus-Formation System (T-TAS): application to human and mouse blood analysis", Platelets, vol. 30, Issue 7, Oct. 26, 2018, pp. 893-900, doi: 10.1080/09537104.2018.1535704.
Alquwaizani, et.al., "Anticoagulants: A Review of the Pharmacology, Dosing, and Complications", Current Emergency and Hospital Medicine Reports, vol. 1, No. 2, Apr. 21, 2013, pp. 83-97, DOI: 10.1007/s40138-013-0014-6.
Appleman et al., "Cryopreservation of canine platelets," Journal of Veterinary Internal Medicine, vol. 23, Issue 1, Jan. 2009, pp. 138-145, doi: 10.1111/j.1939-1676.2008.0225.x.
Arav et. al., "Freeze drying (lyophilization) of red blood cells", Journal Of Trauma, May 2011, vol. 70, No. 5, pages S61-S64, DOI: 10.1097/TA.0b013e31821a6083.
Arnold et al., "The preparation and clinical administration of lyophilized platelet material to children with acute leukemia and aplastic anemia," The Journal of Pediatrics, 1956, 49(5):517-522.
Bannai et al., "The effects of pH and agitation on platelet preservation", The Journal of AABB Transfusion, vol. 25, Jan.-Feb. 1985, pp. 57-59, https://doi.org/10.1046/j.1537-2995.1985.25185116505.x.
Barroso, et. al., "Safety Evaluation of a Lyophilized Platelet Derived Hemostatic Product", Transfusion, vol. 58 (12), Dec. 2018, pp. 2969-2977, DOI: 10.1111/trf.14972.
Böck et al., "Cryopreservation of human platelets with dimethyl sulfoxide: changes in biochemistry and cell function", Transfusion, vol. 35, No. 11, Nov.-Dec. 1995, pp. 921-924, doi: 10.1046/j.1537-2995.1995.351196110896.x.
Bohoněk, Miloš. "Cryopreservation of Platelets: Advances and Current Practice." Cryopreservation Biotechnology in Biomedical and Biological Sciences, Chapter 4. IntechOpen, Dec. 7, 2018, pp. 47-70.
Booth et al., "Lyophilized human platelets are superior to apheresis or fresh-drawn platelets in their ability to accelerate thrombin production", Research and Practice in Thrombosis and Haemostasisc, 2022, ISTH2022 Congress Jul. 2022, 1 page, Poster PB0154.
Booth et al., "Lyophilized human platelets are superior to apheresis or fresh-drawn platelets in their ability to accelerate thrombin production", Research and Practice in Thrombosis and Haemostasis, 2022, 1 page, ISTH 2022 Congress, Abstract PB0154, https://abstracts.isth.org/abstract/lyophilized-human-platelets-are-superior-to-apheresis-or-fresh-drawn-platelets-in-their-ability-to-accelerate-thrombin-production/.
Bullok, et al., "Permeation Peptide Conjugates for In Vivo Molecular Imaging Applications", Molecular Imaging, Jan.-Mar. 2006, vol. 5, Issue 1, pp. 1-15.
Bynum et al., "Evaluation of a lyophilized platelet-derived hemostatic product," Transfusion, 2019, 49: 1490-1498.
Cap, et. al., "Trauma Induced Coagulopathy", Chapter 22: Platelet Transfusion, Springer International Publishing, 2016, pp. 347-376.
Cellphire, Inc. "A Prospective, Multicenter, Randomized, Open-Label Phase 2, Parallel, Dose Ranging Multidose Study of Thrombosomes® vs Liquid Stored Platelets (LSP) in Bleeding Thrombocytopeniatients" Cellphire, Inc, IND 017156, Informed Consent Form and HIPAA Authorization, Protocol Version 1, Jan. 31, 2020, ICF Version 2.0, pp. 1-17.
Charkhkar et al., "Amyloid beta modulation of neuronal network activity in vitro", Brain Research, vol. 1629, Dec. 2015, pp. 1-9, doi: 10.1016/j.brainres.2015.09.036.
Chassot et al., "Perioperative Antiplatelet Therapy", American Family Physician, vol. 82, No. 12, Dec. 15, 2010, pp. 1484-1489.

(56) References Cited

OTHER PUBLICATIONS

Chelliah et. al., "P-selectin antagonism reduces thrombus formation in humans", Journal of Thrombosis and Haemostasis, vol. 7, No. 11, Nov. 2009, pp. 1915-1919. doi: 10.1111/j.1538-7836.2009.03587.x.
Chen et al., "Expanding the Potential of Doxorubicin-Loaded Cryopreserved Platelets for Targeted Cancer Drug Delivery", Cellphire, Inc., 21st International Drug Delivery and Nanomedicines Symposium, Sep. 15-17, 2023, 1 page, poster.
Chen et al., "Modifying murine von Willebrand factor AI domain for in vivo assessment of human platelet therapies," Nature biotechnology, Jan. 2008, 26(1):114-119.
Chen et al., "Stabilized Platelets: A Drug Delivery System for Potential Human Hepatocellular Carcinoma Therapy", Research and Practice in Thrombosis and Haemostasis,2023, ISTH 2023, Montréal, Jun. 24-28, 2023, 1 page, Poster PB0731.
Chen, et al., "Advance of molecular imaging technology and targeted imaging agent in imaging and therapy," Biomed. Res. Int., 2014, 819324, 12 pages.
Chen, et al., "Stabilizaton of peptides against proteolysis through disulfide-bridged conjugation with synthetic aromatics," Org. Biomol. Chem., 2017, 15(8):1921-1929.
Christenson et al., "Autologous fibrin glue reinforced by platelets in surgery of ascending aorta", Thorac. Cardiovasc. Surg., vol. 52, p. 225-229, 2004.
Christopher, et al., "MicroRNA therapeutics: discovering novel targets and developing specific therapy," Perspect. Clin. Res., 2016, 7(2):68-74.
Clemmons et al., "Acquisition and aggregation of canine blood platelets: basic mechanisms of function and differences because of breed origin," Americanjournal of veterinary research, Jan. 1, 1984, 45(1):137-144.
Cogswell et al., "Amyloid-Related Imaging Abnormalities with Emerging Alzheimer Disease Therapeutics: Detection and Reporting Recommendations for Clinical Practice", American Journal Of Neuroradiology, vol. 43, Issue 9, Sep. 2022, pp. E19-E35, doi: 10.3174/ajnr.A7586.
Colman, "Are hemostasis and thrombosis two sides of the same coin?", Journal of Experimental Medicine, Mar. 20, 2006, vol. 203, No. 3, pp. 493-495, doi: 10.1084/jem.20060217.
Cowles, "Anticoagulant effect of aspirin goes beyond platelet aggregation", Hematology/Oncology, May 1, 2007, 3 pages.
Cox, et al., "Platelets and the innate immune system: mechanisms of bacterial-induced platelet activation," Journal of Thrombosis and Haemostasis, 2011, 9:1097-1107.
Crowe et al., "Freeze-dried platelets: Moving towards clinical use", Cryobiology, vol. 66, Issue 3, Jun. 2013, p. 348, Abstract, doi.org/10.1016/j.cryobiol.2013.02.028.
Crowe et. al., "Stabilization of Dry Mammalian Cells: Lessons from Nature", Integrative and Comparative Biology, vol. 45, Issue 5, Nov. 2005, pp. 810-820, https://doi.org/10.1093/icb/45.5.810.
Crowe, et. al., "Stabilization of membranes in human platelets freeze-dried with trehalose", Chemistry and Physics of Lipids, vol. 122, Issues 1-2, Jan. 2003, pp. 41-52, https://doi.org/10.1016/S0009-3084(02)00177-9.
Daidone, "Usefulness of the Total Thrombus-formation Analysis System (T-TAS) in the diagnosis and characterization ofvon Willebrand disease," Haemophillia, 2016, 22:949-956.
Daly et al., "Hemostatic regulators of tumor angiogenesis: a source of antiangiogenic agents for cancer treatment?" Journal of the National Cancer Institute, 2003, 95(22):1660-1673.
Dee et al., "Trehalose Stabilized Freeze Dried Human Platelets, Thrombosomes, Express Surface Markers, Thromboelastogram (TEG) Values And Size Distribution Similar to Two to Three Day Old Stored Platelets", International Society of Blood Transfusion Vox Sanguinis, vol. 99, Suppl. 1, P-0453, 2010, p. 262, Abstract.
Dee et al., "Trehalose Stabilized Freeze Dried Human Platelets, Thrombosomes, Express Surface Markers, Thromboelastogram (TEG) Values And Size Distribution Similar to Two to Three Day Old Stored Platelets", Cellphire, Inc., P-0453, 2019, 1 page, Poster.
Dennison, "A Simple and Universal Method for Making up Buffer Solutions", Biochem Edu., vol. 16, No. 4, 1988, XP023535876, DOI: 10.1016/0307-4412(88)90123-9.
diapharma.com [online], "DiaPhannaProductList," retrieved on Feb. 18, 2021, retrieved from URL, 4 pages.
Gybel-Brask et al., "Freeze-dried platelets (Thrombosomes®) reverses CPB-induced platelet dysfunction ex-vivo", RegionH, Rigshospitalet, The Center of Diagnostic Investigations, 2023, 1 page, poster.
Hagedorn, et. al., "Factor Xlla Inhibitor Recombinant Human Albumin Infestin-4 Abolishes Occlusive Arterial Thrombus Formation Without Affecting Bleeding", Circulation, vol. 121, Issue 13, Apr. 6, 2010, pp. 1510-1517, DOI: 10.1161/CIRCULATIONAHA.109.924761.
Hale et al., "A Novel Use of the Nod Scid Mouse Model for Hemostatic Efficacy", Cellphire, Inc., 2019, 1 page.
Healthline.com [online], "How Many Cells Are in the Human Body? Fast Facts," Jul. 18, 2018, retrieved on May 17, 2021, retrieved from URL, 11 pages.
Heitmeier et al., "Pharmacological profile of asundexian, a novel, orally bioavailable inhibitor of factor XIa", Journal of Thrombosis and Haemostasis, vol. 20, No. 6, Jun. 2022, pp. 1400-1411, https://doi.org/10.1111/jth.15700.
Heitz, et al., "Twenty years of cell-penetrating peptides: from molecular mechanisms to therapeutics," British Journal of Pharmacology, 2009, 157:195-206.
helena.com [online], "Ristocetin Cofactor Assay," retrieved on Feb. 18, 2021, retrieved from URL , 2 pages.
Hemker et al., "Calibrated automated thrombin generation measurement in clotting plasma," Pathophvsiol. Haemost. Thromb., 2003, 33:4-15.
Hoffman et al., "Coagulation Factor IXa Binding to Activated Platelets and Platelet-Derived Microparticles: A Flow Cytometric Study," Thromb. Haemost., 1992, 68:74-78.
Holcomb, et al., "Optimal fluid therapy for traumatic hemorrhagic shock," Crit. Care Clin., 2017, 33(1):15-36.
Holme et al., "Platelet-derived microvesicles and activated platelets express factor Xa activity," Blood Coae:ul. Fibrinolysis, 1995, 6:302-310.
Holmes, et. al., "Combining Antiplatelet and Anticoagulant Therapies", Journal of The American College of Cardiology, vol. 54, No. 2, Jul. 7, 2009, pp. 95-109.
homepage.haemonetics.com [online], "TEG® 5000 Thrombelastograph® Hemostasis Analyzer System," retrieved Feb. 18, 2021, retrieved from 5000>, 3 pagesURL.
Hong et al., "Transfection of human platelets with short interfering RNA", Clinical and Translational Science, vol. 4, Issue 5, Jun. 2011, pp. 180-182, doi: 10.1111/j.1752-8062.2011.00279.x.
Hrachovinova et al., "Interaction of P-selectin and PSGL-1 generates microparticles that correct hemostasis in a mouse model of hemophilia A," Nat Med., 2003, 9(8): 1020-1025.
Huebner et al., "Freeze-dried plasma enhances clot formation and inhibits fibrinolysis in the presence of tissue plasminogen activator similar to pooled liquid plasma", Transfusion, vol. 57, Issue 8, Aug. 2017, pp. 2007-2015, DOI:10.1111/trf.14149.
Inaba et al., "Dried platelets in a swine model of liver injury", Shock, vol. 41, Issue 5, May 2014, pp. 429-434, doi: 10.1097/SHK.0000000000000141.
International Partial Search Report and Provisional Opinion in International Appln No. PCT/US2022/079280, mailed Feb. 20, 2023, 14 pages.
International Partial Search Report in International Appln No. PCT/US2022/016866, mailed May 11, 2022, 13 pages.
International Preliminary Report on Patentability in International Appln. No. PCT/US2005/028559, dated May 8, 2007,5 pages.
International Preliminary Report on Patentability in International Appln. No. PCT/US2015/060533, dated May 16, 2017, 5 pages.
International Preliminary Report on Patentability in International Appln. No. PCT/US2016/036657, dated Dec. 12, 2017, 6 pages.
International Preliminary Report on Patentability in International Appln. No. PCT/US2016/048846, dated Mar. 6, 2018,5 pages.
International Preliminary Report on Patentability in International Appln. No. PCT/US2016/065681, dated Jun. 11, 2019, 7 pages.

(56) References Cited

OTHER PUBLICATIONS

International Preliminary Report on Patentability in International Appln. No. PCT/US2017/012836, dated Jul. 17, 2018, 7 pages.
International Preliminary Report on Patentability in International Appln. No. PCT/US2018/050924, dated Mar. 26, 2020, 17 pages.
International Preliminary Report on Patentability in International Appln. No. PCT/US2019/043723, dated Feb. 11, 2021, 14 pages.
International Preliminary Report on Patentability in International Appln. No. PCT/US2019/050624, dated Mar. 25, 2021, 10 pages.
International Preliminary Report on Patentability in International Appln. No. PCT/US2019/063549, dated Jun. 10, 2021, 9 pages.
International Preliminary Report on Patentability in International Appln. No. PCT/US2019/063650, mailed Jun. 10, 2021, 9 pages.
International Preliminary Report on Patentability in International Appln. No. PCT/US2019/063736, mailed Jun. 10, 2021, 8 pages.
International Preliminary Report on Patentability in International Appln. No. PCT/US2019/063750, mailed Jun. 10, 2021, 8 pages.
International Search Report and Written Opinion in International Appln No. PCT/US2022/079280, mailed date Apr. 21, 2023, 27 pages.
International Search Report and Written Opinion in International Appln. No. PCT/US2005/028559, mailed Mar. 23, 2007,3 pages.
International Search Report and Written Opinion in International Appln. No. PCT/US2015/060553, mailed Jan. 28, 2016, 7 pages.
International Search Report and Written opinion in International Appln. No. PCT/US2016/036657, mailed Aug. 29, 2016,7 pages.
International Search Report and Written Opinion in International Appln. No. PCT/US2016/048846, mailed Nov. 16, 2016, 2 pages.
International Search Report and Written Opinion in International Appln. No. PCT/US2016/065681, mailed Feb. 17, 2017,2 pages.
International Search Report and Written Opinion in International Appln. No. PCT/US2017/012836, mailed Apr. 7, 2017, 8 pages.
International Search Report and Written Opinion in International Appln. No. PCT/US2018/050924, mailed Nov. 20, 2018, 18 pages.
International Search Report and Written Opinion in International Appln. No. PCT/US2019/043723, mailed Oct. 9, 2019, 16 pages.
International Search Report and Written Opinion in International Appln. No. PCT/US2019/050624, mailed Nov. 20, 2019, 23 pages.
International Search Report and Written Opinion in International Appln. No. PCT/US2019/063549, mail date Feb. 4, 2020, 10 pages.
International Search Report and Written Opinion in International Appln. No. PCT/US2019/063650, mail date Feb. 27, 2020, 11 pages.
International Search Report and Written Opinion in International Appln. No. PCT/US2019/063736, mailed Feb. 20, 2020, 10 pages.
International Search Report and Written Opinion in International Appln. No. PCT/US2019/063750, mail date Feb. 19, 2020, 10 pages.
International Search Report and Written Opinion in International Appln. No. PCT/US2020/022705, mailed Jul. 29, 2020, 12 pages.
International Search Report and Written Opinion in International Appln. No. PCT/US2020/031172, mailed Aug. 12, 2020, 8 pages.
International Search Report and Written Opinion in International Appln. No. PCT/US2020/042492, mailed Nov. 24, 2020, 9 pages.
International Search Report and Written Opinion in International Appln. No. PCT/US2020/046522, mailed Nov. 10, 2020, 10 Pages.
Dickerson et al., "Lyophilized Human Platelets Restore Hemostasis in the Presence of the P2Y12 Inhibitors Cangrelor, Ticagrelor and Clopidogrel", Cellphire Therapeutics Inc., Rockville, MD, 7 pages, Poster.
Dickerson et al., "Lyophilized Human Platelets Restore Hemostasis in the Presence of the P2Y12 Inhibitors Cangrelor, Ticagrelor and Clopidogre", American Society of Hematology, Blood, 3.22 Disorders of Coagulation or Fibrinolysis, Nov. 5, 2020, 6 pages.
Dickerson et al., "Lyophilized Human Platelets Restore Hemostasis in the Presence of the P2Y12 Inhibitors Cangrelor, Ticagrelor and Clopidogrel", Cellphire, Inc., 2020, 6 pages, Poster.
Dickerson et al., "Lyophilized human platelets support thrombosis unlike normal platelets in the presence of GPIIb/IIIa antagonists", Cellphire Therapeutics, ISth Virtual Congress, Jul. 2021, 1 page, Poster.
Dickerson et al., "Lyophilized human platelets support thrombosis unlike normal platelets in the presence of GPIIb/IIIa antagonists", Cellphire, Inc., AS-ISTH-2021-01436, 2021. 2 pages, Abstract.
Dickerson et al., "Thrombosomes as a Treatment Option for Low-Dose Heparin Reversal", Cellphire, Inc, Oct. 2020. 1 page, Poster.
Dickson et al., "A scalable, micropore, platelet rich plasma separation device." Biomedical Microdevices, vol. 14(6), Jul. 2012, pp. 1095-1102. DOI: 10.1007/s10544-012-9675-2.
Dielis et al., "Coagulation factors and the protein C system as determinants of thrombin generation in a normal population," J. Thromb. Haemost., 2008, 6:125-131.
Diener, "Antiplatelet agents and randomized trials," Review in Neurological Diseases, 2007, 4(4):177-183.
Dinçer et al., "Effect of taurine on wound healing", Amino Acids, vol. 10, Issue 1, Mar. 1996, pp. 59-71, doi: 10.1007/BF00806093.
Dong, et al., "Ristocetin-dependent, but not botrocetin-dependent, binding of von Willebrand factor to the platelet glycoprotein Ib-IX-V complex correlates with shear-dependent interactions," Blood, 2001, 97:162-+168.
Dumont, et. al, "A randomized controlled trial evaluating recovery and survival of 6% dimethyl sulfoxide-frozen autologous platelets in healthy volunteers", Transfusion vol. 53(1), Jan. 2013, pp. 128-137.
Duquesnoy, "HLAMatchmaker: a molecularly based algorithm for histocompatibility determination. I. Description of the algorithm", Human Immunology, vol. 63, Issue 5, May 2002, pp. 339-352, doi. org/10.1016/S0198-8859(02)00382-8.
Durbin et al., "Platelet Extracellular Vesicles as a Therapeutic Agent in Hemorrhagic Shock", Oregon Health & Science University Department of Surgery, Division of Trauma, Sep. 20, 2023, 23 pages.
Eikelboom, et. al., "Combined antiplatelet and anticoagulant therapy clinical benefits and risks", Journal of Thrombosis and Haemostasis, vol. 5, Suppl 1, Jul. 2007, pp. 255-263, DOI: 10.1111/j.1538-7836. 2007.02499.x.
Etchill, et. al., "Platelet Transfusion in Critical Care and Surgery: Evidence-Based Review of Contemporary Practice and Future Directions", Shock, vol. 47, No. 5, May 1, 2017, pp. 537-549.
Extended European Search Report in EP Appln. No. 05784165.2, date Mar. 26, 2008.
Extended European Search Report in EP Appln. No. 16808270.9, date Nov. 22, 2018.
Extended European Search Report in EP Appln. No. 16842662.5, date Jul. 26, 2019.
Extended European Search Report in EP Appln. No. 16923314.5, date Jun. 18, 2020.
Extended European Search Report in EP Appln. No. 17738796.6, date Jul. 23, 2019.
Extended European Search Report in EP Appln. No. 18856149.2, date May 26, 2021.
Extended European Search Report in EP Appln. No. 19840600.1 date Mar. 25, 2022.
Extended European Search Report in EP Appln. No. 19860896.0 date Jun. 14, 2023.
Extended European Search Report in EP Appln. No. 19888909.9 date Sep. 28, 2022.
Extended European Search Report in EP Appln. No. 19888994.1 date Nov. 7, 2022.
Extended European Search Report in EP Appln. No. 19891082.0 date Sep. 30, 2022.
Extended European Search Report in EP Appln. No. 20769409.2 date Dec. 6, 2022.
Extended European Search Report in EP Appln. No. 20802506.4 date Jan. 4, 2023.
Extended European Search Report in EP Appln. No. 20855485.7 date Sep. 15, 2023.
Extended European Search Report in EP Appln. No. 20855619.1 dated Sep. 15, 2023.

(56) References Cited

OTHER PUBLICATIONS

Extended European Search Report in EP Appln. No. 20894004.9 date Nov. 8, 2023.
Fijnheer et al., "Platelet activation during preparation of platelet concentrates: a comparison of the platelet-rich plasma and the buffy coat methods," Transfusion, 1990, 30(7):634-638.
Fischer et al., "Primary and secondary hemostatic functionalities of rehydrated, lyophilized platelets," 2006, Transfusion, 46:1943-1950.
Fischer et al., "The interaction of factor VIIa with rehydrated, lyophilized platelets", Platelets, vol. 19 (3), May 2008, pp. 182-191, DOI: 10.1080/09537100701493794.
Fischer et. al., "Thrombus Formation with Rehydrated, Lyophilized Platelets", Hematology (Amsterdam, Netherlands), vol. 7 (6), Dec. 2002, pp. 359-369, DOI: 10.1080/1024533021000047954.
Fitzpatrick et al., "A Novel Lyophilized Platelet Derivative Produces Effective Hemostasis in Uncontrolled Bleeding/Shock Model without Systemic Thrombosis", Blood, vol. 118, Issue 21, Nov. 18, 2011, pp. 719-722, doi. org/10.1182/blood.V118.21.719.719.
Fitzpatrick et al., "Freeze-dried platelets: Advancing towards clinical use", Cryobiology, vol. 67, Issue 3, Dec. 2013, p. 420, Abstract, doi.org/10.1016/j.cryobiol.2013.09.086.
Fitzpatrick et al., "Stabilization and preservation of a platelet derived hemostatic agent, Thrombosomes", Cryobiology, vol. 63, Issue 3, Dec. 2011, p. 306, Abstract, doi: 10.1016/j.cryobiol.2011.09.005.
Fitzpatrick et al., "Thrombosomes: a platelet-derived hemostatic agent for control of noncompressible hemorrhage", Transfusion, vol. 53, Jan. 2013 Supplement, pp. 100S-106S, doi: 10.1111/trf.12043.
Fitzpatrick, "Novel platelet products under development for the treatment of thrombocytopenia or acute hemorrhage", Transfusion and Apheresis Science, vol. 58, Issue 1, Feb. 2019, pp. 7-11, doi: 10.1016/j.transci.2018.12.010.
Gaertner et al., "Migrating platelets are mechano-scavengers that collect and bundle bacteria," Cell, Nov. 30, 2017, 171(6):1368-1382.
Gao et al., "Development of Optimal Techniques for Cryopreservation of Human Platelets: I. Platelet activation during cold storage (at 22 and 8° C) and cryopreservation", Cryobiology vol. 38(3), May 1999, pp. 225-235, DOI: 10.1006/cryo.1999.2162.
Ghaithi et al., "Evaluation of the Total Thrombus-Formation System (T-TAS): application to human and mouse blood analysis", Platelets, vol. 30, Issue 7, 2019, pp. 893-900, doi: 10.1080/09537104.2018.1535704.
Gilbert et al., "Platelet-derived microparticles express high affinity receptors for factor VIII.", I.Biol. Chem., 1991, 266:17261-17268.
Giles et al., "A combination of factor Xa and phosphatidylcholine-phosphatidylserine vesicles bypasses factor VIII in vivo", Br. J., Haematol., 1988, 69(4):491-497.
Godier et al., "Management of antiplatelet therapy for non elective invasive procedures of bleeding complications: proposals from the French working group on perioperative haemostasis (GIHP), in collaboration with the French Society of Anaesthesia and Intensive Care Medicine (SFAR)" Anaesthesia, Critical Care and Pain Medicine, vol. 38, Issue 3, Jun. 2019, pp. 289-302, doi: 10.1016/j.accpm.2018.10.004.
Goggs, et. al., "Lyophilized Platelets Versus Cryopreserved Platelets for Management of Bleeding in Thrombocytopenia Dogs: A Multicenter Randomized Clinical Trial", Journal of Veterinary Internal Medicine, Nov. 2020, vol. 34, Issue 6, pp. 2384-2397, doi: 10.1111/jvim.15922.
Greene, et. al., "Chapter 9: Component Preparation and Manufacturing", Transfusion Medicine and Hemostasis, Elsevier Science, 1st edition, 2009, pp. 45-50, doi:10.1016/B978-0-12-374432-6.00009-9, XP009527060.
Grosset et al., "Rapid presymptomatic detection of PrPSc via conformationally responsive palindromic PrP peptides", Peptides, vol. 26, Issue 11, Nov. 2005, pp. 2193-2200, doi: 10.1016/j.peptides.2005.03.006.
Cancelas, "Frozen Activated Pooled Platelets (CLPH-511) Characterization", Association for the Advancement of Blood & Biotherapies (AABB Oct. 25-28, 2025), 17 pages.
De Koning et al., "Comparing thrombin generation in patients with hemophilia A and patients on vitamin K antagonists" Journal of Thrombosis and Haemostasis, vol. 15, Issue 5, May 2017, pp. 868-875, doi.org/10.1111/jth.13674.
Fitzpatrick et al., "Cryopreserved Platelets Promote Hemostatic Clot Formation and Extend Platelet Shelf Life", Cellphire Therapeutics, Association for the Advancement of Blood & Biotherapies, (AABB Oct. 25-28, 2025), 1 page, poster.
Fitzpatrick et al., "Cryopreserved Platelets Promote Hemostatic Clot Formation and Extend Platelet Shelf Life", Cellphire Therapeutics, Association for the Advancement of Blood & Biotherapies, (AABB Oct. 25-28, 2025), 3 pages, abstract.
Gao et al., "Platelet regulates neuroinflammation and restores blood-brain barrier integrity in a mouse model of traumatic brain injury", Journal of Neurochemistry, vol. 154, Issue 2, Feb. 12, 2020, pp. 190-204, doi.org/10.1111/jnc.14983.
Nebie et al., "Human platelet lysate biotherapy for traumatic brain injury: preclinical assessment", Brain, vol. 144, Issue 10, Jun. 4, 2021, pp. 3142-3158, doi.org/10.1093/brain/awab205.
Nebie et al., "Human platelet lysate biotherapy for traumatic brain injury: preclinical assessment", Brain, vol. 144, Issue 10, Jun. 4, 2021, 18 pages, Supplementary Materials, awab205.
Nogami, "Dynamic understanding of blood clotting and advances in hemophilia practice", Japanese Journal of Thrombosis and Hemostasis, vol. 25, No. 3, 2014, pp. 371-379.
Samanbar et al., "A freeze-dried platelet-derived hemostatic agent improves hemostasis in patients with severe thrombocytopenia before and after standard platelet transfusion: Studies ex vivo in the total thrombus-formation analysis system 01" Transfusion, 2026, 11 pages, doi: 10.1111/trf.70153.
Samanbar et al., "A freeze-dried platelet-derived hemostatic agent improves hemostasis in patients with severe thrombocytopenia before and after standard platelet transfusion: Studies ex vivo in the total thrombus-formation analysis system 01" Transfusion, 2026, 1 pages, Supplemental Information.
Schutgens et al. "New concepts for anticoagulant therapy in persons with hemophilia", vol. 28, Issue 20, Nov. 2, 170216, pp. 2471-2474, doi.org/10.1182/blood-2016-07-727032.
Six et al., "Comparison between manufacturing sites shows differential adhesion, activation, and GPIbα expression of cryopreserved platelets", Tansfusion vol. 58. Issue 11, Nov. 2018, pp. 2645-2656, https://doi.org/10.1111/trf.14828.
Swanson et al., Cryopreserved platelets (CPP) enhance thrombin generation and have greater activation than room temperature stored platelets (RTP) and cold-stored platelets (CSP), Cellphire, ISTH, Jun. 6, 2025, 3 pages.
Veale, et al. "Thrombus formation and adhesion of cryopreserved platelets to collagen and endothelial cells under shear stress." Vox Sanguinis, Supplement 107.Suppl 1. (2014): 54-54.
Whitman, "Topline results from the CRYPTICS study", Association for the Advancement of Blood & Biotherapies (AABB Oct. 25-28, 2025), NCT04709705, 19 pages.

* cited by examiner

*Class I Background*

*Class II Background*

*Class I Background*

*Class II Background*

*Class II Gate*

*Class I Gate*

| Batch I (TFF) MFI | | | |
|---|---|---|---|
| Rep | Unstained | 9F9 Isotype | 9F9 Test |
| 1 | 1200 | 1691 | 105960 |
| 2 | 1190 | 2090 | 102894 |
| Average | 1195 | 1891 | 104427 |

| Batch I (TFF) PAC-1 MFI | | |
|---|---|---|
| Rep | Unstained | PAC-1 Test |
| 1 | 1200 | 1792 |
| 2 | 1190 | 1329 |
| Average | 1195 | 1561 |

Apheresis Platelets Were Used to Confirm TRAP Activity

TRAP Does Not Increase AV Binding to TFF-FDPDs

| FDPDs Annexin V MFIs | | |
|---|---|---|
| **Sample Type** | **- TRAP** | **+TRAP** |
| Unstained | 98 | 99 |
| Calcium Free Control | 203 | 198 |
| AV Stained | 68,179 | 68,783 |

Von Willebrand Factor Measured with Flow Cytometry

Thrombospondin-1 Measured with Flow Cytometry

Fibrinogen Measured with Flow Cytometry

Light Scattering Measured with Flow Cytometry

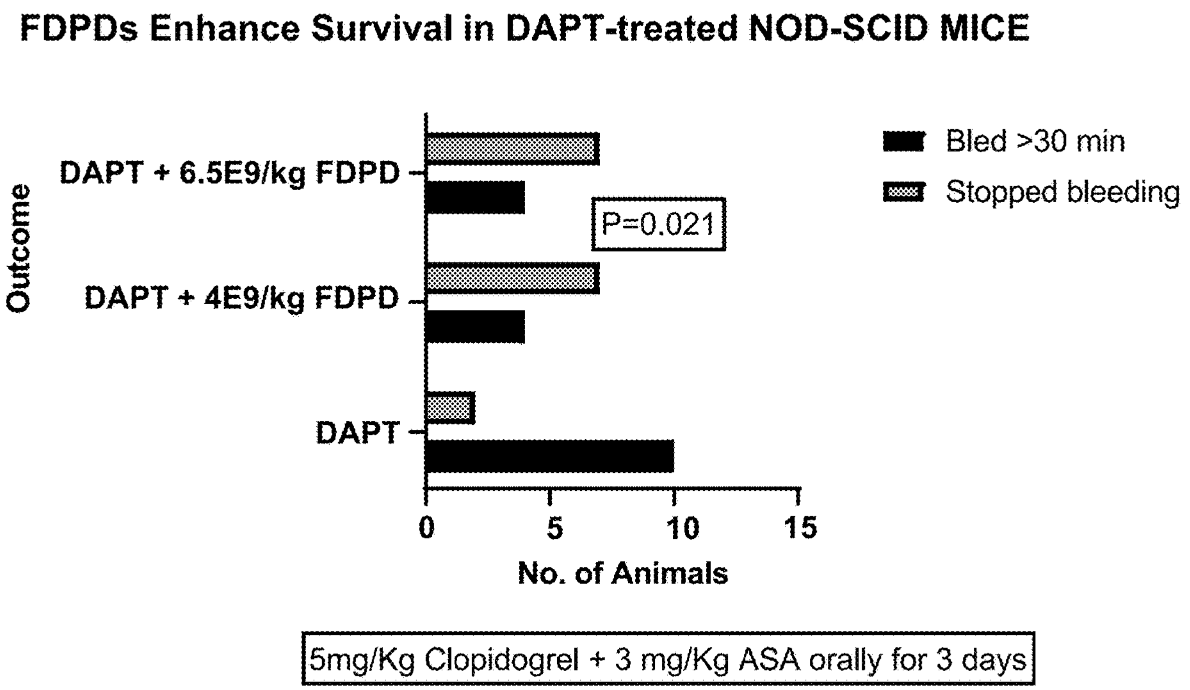
Fig. 40
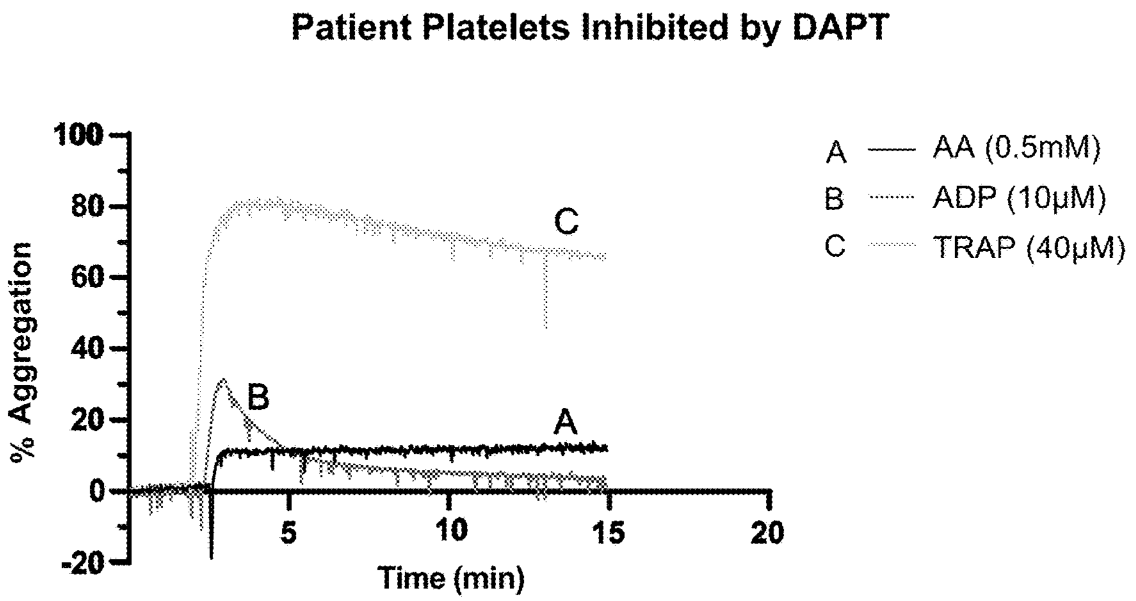
Fig· 41

A: PRP
B: PRP ASA ticagrelor
C: PRP ASA ticagrelor 2K FDPDs
D: PRP ASA ticagrelor 20K FDPDs A: PRP
B: PRP ASA ticagrelor
C: PRP ASA ticagrelor 2K FDPDs
D: PRP ASA ticagrelor 20K FDPDs A: PRP (donor)
B: PRP ASA prasugrel
C: PRP ASA prasugrel 2K FDPDs
D: PRP ASA prasugrel 20K FDPDs A: PRP (donor)
B: PRP ASA prasugrel
C: PRP ASA prasugrel 2K FDPDs
D: PRP ASA prasugrel 20K FDPDs

PLATELET DERIVATIVE COMPOSITIONS, AND METHODS OF MAKING AND USING SUCH COMPOSITIONS

CROSS-REFERENCE TO RELATED APPLICATIONS

This application claims priority to U.S. Provisional Application Ser. No. 63/275,937, filed on Nov. 4, 2021, U.S. Provisional Application Ser. No. 63/276,420, filed on Nov. 5, 2021, U.S. Provisional Application Ser. No. 63/264,226, filed on Nov. 17, 2021, U.S. Provisional Application Ser. No. 63/264,227, filed on Nov. 17, 2021, U.S. Provisional Application Ser. No. 63/364,620, filed on May 12, 2022, U.S. Provisional Application Ser. No. 63/371,849, filed on Aug. 18, 2022, and U.S. Provisional Application Ser. No. 63/376,986, filed on Sep. 23, 2022, each of which is incorporated herein by reference in its entirety.

STATEMENT OF GOVERNMENT INTEREST

This invention was made with government support under Contract No. HHSO100201300021 awarded by the Biomedical Advanced Research and Development Authority (BARDA) of the U.S. Department of Health and Human Services. The government has certain rights in the invention.

TECHNICAL FIELD

The present disclosure generally relates to blood products, including those containing platelet derivatives, methods of producing such blood products, and methods of treating a subject using such blood products.

BACKGROUND

Blood is a complex mixture of numerous components. In general, blood can be described as comprising four main parts: red blood cells, white blood cells, platelets, and plasma. The first three are cellular or cell-like components, whereas the fourth (plasma) is a liquid component comprising a wide and variable mixture of salts, proteins, and other factors necessary for numerous bodily functions. The components of blood can be separated from each other by various methods. In general, differential centrifugation is most commonly used currently to separate the different components of blood based on size and, in some applications, density.

Inactivated platelets, which are also commonly referred to as thrombocytes, are small, often irregularly-shaped (e.g., discoidal or ovoidal) megakaryocyte-derived components of blood that are involved in the clotting process. They aid in protecting the body from excessive blood loss due not only to trauma or injury, but to normal physiological activity as well. Platelets are considered crucial in normal hemostasis, providing the first line of defense against blood escaping from injured blood vessels. Platelets generally function by adhering to the lining of broken blood vessels, in the process becoming activated, changing to an amorphous shape, and interacting with components of the clotting system that are present in plasma or are released by the platelets themselves or other components of the blood. Purified platelets have found use in treating subjects with low platelet count (thrombocytopenia) and abnormal platelet function (thrombasthenia). Concentrated platelets are often used to control bleeding after injury or during acquired platelet function defects or deficiencies, for example those occurring during surgery and those due to the presence of platelet inhibitors.

SUMMARY

Provided herein, at least in part, are blood products (e.g., a composition comprising platelets or platelet derivatives (e.g., thrombosomes)) with reduced levels of free protein (e.g., antibodies (e.g., Human Leukocyte Antigen (HLA) antibodies, or Human Neutrophil Antigen (HNA) antibodies)) and methods of producing and using the same. Accordingly, provided herein are compositions including platelets, and/or, in illustrative embodiments, platelet derivatives.

Implementations can have one or more of the following features. The composition can have a solid, such as a powder form. The composition can be in an aqueous medium. The protein concentration of the aqueous medium can be less than 30% of the protein concentration of donor apheresis plasma. The aqueous medium can have a concentration of human leukocyte antigen (HLA) Class I antibodies that is less than 30% of the human leukocyte antigen (HLA) Class I antibody concentration in donor apheresis plasma. The aqueous medium can have a concentration of human leukocyte antigen (HLA) Class II antibodies that is less than 30% of the human leukocyte antigen (HLA) Class II antibody concentration in donor apheresis plasma. The aqueous medium can have a concentration of human neutrophil antigen (HNA) antibodies that is less than 30% of the HNA antibody concentration in donor apheresis plasma. The protein concentration can be less than 10% of the protein concentration of donor apheresis plasma. The aqueous medium can have a concentration of human HLA Class I antibodies that is less than 10% of the HLA Class I antibody concentration in donor apheresis plasma. The aqueous medium can have a concentration of human HLA Class II antibodies that is less than 10% of the HLA Class II antibody concentration in donor apheresis plasma. The aqueous medium can have a concentration of human HNA antibodies that is less than 10% of the HNA antibody concentration in donor apheresis plasma. The protein concentration can be less than 5% of the protein concentration of donor apheresis plasma. The aqueous medium can have a concentration of human HLA Class I antibodies that is less than 5% of the HLA Class I antibody concentration in donor apheresis plasma. The aqueous medium can have a concentration of human HLA Class II antibodies that is less than 5% of the HLA Class II antibody concentration in donor apheresis plasma. The aqueous medium can have a concentration of human HNA antibodies that is less than 5% of the HNA antibody concentration in donor apheresis plasma. The protein concentration can be less than 3% of the protein concentration of donor apheresis plasma. The aqueous medium can be a concentration of human HLA Class I antibodies that is less than 3% of the HLA Class I antibody concentration in donor apheresis plasma. The aqueous medium can have a concentration of human HLA Class II antibodies that is less than 3% of the HLA Class II antibody concentration in donor apheresis plasma. The aqueous medium can have a concentration of human HNA antibodies that is less than 3% of the HNA antibody concentration in donor apheresis plasma. The protein concentration can be less than 1% of the protein concentration of donor apheresis plasma. The aqueous medium can have a concentration of human HLA Class I antibodies that is less than 1% of the HLA Class I antibody concentration in donor apheresis plasma. The aqueous medium can have a concentration of human HLA Class II antibodies that is less than 1% of the HLA Class II antibody concentration in donor apheresis plasma. The aqueous medium can have a concentration of human HNA antibodies that is less than 1% of the HNA antibody concentration in donor apheresis plasma. The protein concentration can be determined by absorbance at 280 nanometers (nm) with a path length of 0.5 cm. In some embodiments, the absorbance at 280 nm can be less than 1.7 AU. In some embodiments, the absorbance at 280 nm can be less than 1.66 AU. In some embodiments, the absorbance at 280 nm can be less than 1.6 AU. In some embodiments, the platelet count can be at least $200\times10^3$ platelets/μL. In some embodiments, the platelet count can be at least $2250\times10^3$ platelets/μL. In some embodiments, the composition can have an erythrocyte count less than $0.2\times10^6$ erythrocytes/μL. In some embodiments, the composition can further include erythrocytes. In some embodiments, the erythrocyte count can be less than $0.2\times10^6$ erythrocytes/μL. The composition can be negative for HLA Class I antibodies based on a regulatory agency approved test. The composition can be negative for HLA Class II antibodies based on a regulatory agency approved test. The composition can be negative for HNA antibodies based on a regulatory agency approved test. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be less than 5%. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be less than 3%. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be less than 1%. The percentage of beads positive for HLA Class I antibodies, as determined for the composition by flow cytometry using beads coated with Class I HLAs, can be less than 5%. The percentage of beads positive for HLA Class I antibodies, as determined for the composition by flow cytometry using beads coated with Class I HLAs, can be less than 3%. The percentage of beads positive for HLA Class I antibodies, as determined for the composition by flow cytometry using beads coated with Class I HLAs, can be less than 1%. The percentage of beads positive for HLA Class II antibodies, as determined for the composition by flow cytometry using beads coated with Class II HLAs can be less than 5%. The percentage of beads positive for HLA Class II antibodies, as determined for the composition by flow cytometry using beads coated with Class II HLAs, can be less than 3%. The percentage of beads positive for HLA Class II antibodies, as determined for the composition by flow cytometry using beads coated with Class II HLAs, can be less than 1%. The percentage of beads positive for HNA antibodies, as determined for the composition by flow cytometry using beads coated with HNAs can be less than 5%. The percentage of beads positive for HNA antibodies, as determined for the composition by flow cytometry using beads coated with HNAs, can be less than 3%. The percentage of beads positive for HNAs, as determined for the composition by flow cytometry using beads coated with HNAs, can be less than 1%. The aqueous medium can further include a buffering agent, a base, a loading agent, optionally a salt, and optionally at least one organic solvent. The buffering agent can be HEPES (4-(2-hydroxyethyl)-1-piperazineethanesulfonic acid). The base can be sodium bicarbonate. The loading agent can be a monosaccharide, a polysaccharide, or a combination thereof. The monosacchariade can be selected from the group consisting of sucrose, maltose, trehalose, glucose, mannose, and xylose. The monosaccharide can be trehalose. The polysaccharide can be polysucrose. The salt can be sodium chloride, potassium chloride, or a combination thereof. The organic solvent can be selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), and combinations thereof. The composition can be prepared by a process including tangential flow filtration (TFF) of a starting material comprising platelets, centrifugation of a starting material comprising platelets, or a combination thereof. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be reduced by at least 50% as compared to a similar composition not prepared by a process including tangential flow filtration of a blood product composition, centrifugation of a blood product composition, or a combination thereof. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be reduced by at least 75% as compared to a similar composition not prepared by a process including tangential flow filtration of a blood product composition, centrifugation of a blood product composition, or a combination thereof. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be reduced by at least 90% as compared to a similar composition not prepared by a process including tangential flow filtration of a blood product composition, centrifugation of a blood product composition, or a combination thereof. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be reduced by at least 95% as compared to a similar composition not prepared by a process including tangential flow filtration of a blood product composition, centrifugation of a blood product composition, or a combination thereof. The starting material can be (a) positive for HLA Class I antibodies based on a regulatory agency approved test, (b) positive for HLA Class II antibodies based on a regulatory agency approved test, (c) positive for HNA antibodies based on a regulatory agency approved test, or (d) one or more of (a), (b), and (c). The starting material can have a protein concentration of about 60 to about 80 mg/ml. The starting material can include donor blood product. The donor blood product can be pooled donor blood product. The starting material can include donor apheresis material. The TFF can include concentrating. The TFF can include diafiltering. The diafiltering can include diafiltering with at least two diavolumes. The TFF can include buffer exchange. The TFF can be carried out using a membrane with pore size of about 0.2 μm to about 1 μm. The TFF can be carried out using a membrane with pore size of about 0.2 μm to about 0.45 μm. The TFF can be performed at a temperature of about 20° C. to about 37° C. The TFF can be carried out until the absorbance at 280 nm of the aqueous medium is less than 50% of the absorbance at 280 nm of the starting material, using a path length of 0.5 cm. The TFF can be carried out until the absorbance at 280 nm of the aqueous medium is less than 30% of the absorbance at 280 nm of the starting material, using a path length of 0.5 cm. The TFF can be carried out until the absorbance at 280 nm of the aqueous medium is less than 10% of the absorbance at 280 nm of the starting material, using a path length of 0.5 cm. The TFF can be carried out until the absorbance at 280 nm of the aqueous medium is less than 5% of the absorbance at 280 nm of the starting material, using a path length of 0.5 cm. The TFF can be carried out until the absorbance at 280 nm of the aqueous medium is less than 3% of the absorbance at 280 nm of the starting material, using a path length of 0.5 cm. The TFF can be carried out until the absorbance at 280 nm of the aqueous medium is less than 1% of the absorbance at 280 nm of the starting material, using a path length of 0.5 cm. The TFF can be carried out until the absorbance at 280 nm of the aqueous medium is less than 1.70 AU, using a path length of 0.5 cm. The TFF can be carried out until the absorbance at 280 nm of the aqueous medium is less than 1.66 AU, using a path length of 0.5 cm. The TFF can be carried out until the absorbance at 280 nm of the aqueous medium is less than 1.60 AU, using a path length of 0.5 cm. The TFF can be carried out until the platelet concentration is at least about $2000\times10^3$ platelets/μL. The TFF can be carried out until the platelet concentration is at least about $2250\times10^3$ platelets/μL. The TFF can include buffer exchange into a buffer comprising a buffering agent, a base, a loading agent, optionally a salt, and optionally at least one organic solvent. The buffering agent can be HEPES (4-(2-hydroxyethyl)-1-piperazineethanesulfonic acid). The base can be sodium bicarbonate. The loading agent can be a monosaccharide, a polysaccharide, or a combination thereof. The monosaccharide can be selected from the group consisting of sucrose, maltose, trehalose, glucose, mannose, and xylose. The monosaccharide can be trehalose. The polysaccharide can be polysucrose. The salt can be sodium chloride, potassium chloride, or a combination thereof. The organic solvent can be selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), and combinations thereof. The centrifugation can include centrifugation at 1400×g to about 1550×g. The centrifugation can include centrifugation at 1450×g to about 1500×g. The process can lack centrifugation of a composition comprising platelets. The composition can include less than 5.0% (by scattering intensity) microparticles. The composition can include less than 4.5% (by scattering intensity) microparticles. The composition can include less than 4.0% (by scattering intensity) microparticles. The composition can include less than 3.5% (by scattering intensity) microparticles. The platelets or platelet derivatives can have a CD41 percent positivity of at least 55%. The platelets or platelet derivatives can have a CD41 percent positivity of at least 60%. The platelets or platelet derivatives can have a CD41 percent positivity of at least 65%. The platelets or platelet derivatives can have a CD42 percent positivity of at least 80%. The platelets or platelet derivatives can have a CD42 percent positivity of at least 85%. The platelets or platelet derivatives can have a CD42 percent positivity of at least 90%. The platelets or platelet derivatives can retain at least about 10% of the lactate dehydrogenase activity of donor apheresis platelets. The platelets or platelet derivatives can retain at least about 15% of the lactate dehydrogenase activity of donor apheresis platelets. The platelets or platelet derivatives can retain at least about 20% of the lactate dehydrogenase activity of donor apheresis platelets. The platelets or platelet derivatives can have an annexin V percent positivity of at least 70%. The platelets or platelet derivatives can have an annexin V percent positivity of at least 75%. The platelets or platelet derivatives can have an annexin V percent positivity of at least 80%. The platelets or platelet derivatives can have CD47 percent positivity of at least 8%. The platelets or platelet derivatives can have CD47 percent positivity of at least 10%. The platelets or platelet derivatives can have CD47 percent positivity of at least 15%. The platelets or platelet derivatives can have CD47 percent positivity of at least 20%. The platelets or platelet derivatives can have CD62 percent positivity of at least 80%. The platelets or platelet derivatives can have CD62 percent positivity of at least 82%. The platelets or platelet derivatives can have CD62 percent positivity of at least 85%. The platelets or platelet derivatives can have CD62 percent positivity of at least 90%. The platelets or platelet derivatives can have fibrinogen associated with the cell membrane. The aqueous medium can have a lactate concentration of less than 2.0 mmol/L. The aqueous medium can have a lactate concentration of less than 1.5 mmol/L. The aqueous medium can have a lactate concentration of about 0.4 to about 1.3 mmol/L. The aqueous medium can have a lactate concentration of about 0.5 to about 1.0 mmol/L. The platelet derivatives can include thrombosomes.

Also provided herein is a process for preparing a composition comprising platelets, or in illustrative embodiments, platelet derivatives and an aqueous medium, the process including tangential flow filtration (TFF) of a starting material comprising platelets, centrifugation of a starting material comprising platelets, or a combination thereof, wherein the aqueous medium has a protein concentration less than 50% of the protein concentration of donor apheresis plasma.

Implementations can include one or more of the following features. The starting material can be (a) positive for HLA Class I antibodies based on a regulatory agency approved test, (b) positive for HLA Class II antibodies based on a regulatory agency approved test, (c) positive for HNA antibodies based on a regulatory agency approved test, or (d) one or more of a), b), and c). The starting material can have a protein concentration of about 60 to about 80 mg/mL. The starting material can include donor blood product. The donor blood product can be pooled donor blood product. The starting material can include donor apheresis material. The TFF can include concentrating. The TFF can include diafiltering. The diafiltration can include diafiltering with at least two diavolumes. The TFF can include buffer exchange. The TFF can be carried out using a membrane with pore size of about 0.2 μm to about 1 μm. The TFF can be carried out using a membrane with pore size of about 0.2 μm to about 0.45 μm. The TFF can be performed at a temperature of about 20° C. to about 37° C. The TFF can be carried out until the absorbance at 280 nm of the aqueous medium is less than 50% of the absorbance at 280 nm of the starting material, using a path length of 0.5 cm. The TFF is carried out until the absorbance at 280 nm of the aqueous medium is less than 30% of the absorbance at 280 nm of the starting material, using a path length of 0.5 cm. The TFF can be carried out until the absorbance at 280 nm of the aqueous medium is less than 10% of the absorbance at 280 nm of the starting material, using a path length of 0.5 cm. The TFF can be carried out until the absorbance at 280 nm of the aqueous medium is less than 5% of the absorbance at 280 nm of the starting material, using a path length of 0.5 cm. The TFF can be carried out until the absorbance at 280 nm of the aqueous medium is less than 3% of the absorbance at 280 nm of the starting material, using a path length of 0.5 cm. The TFF can be carried out until the absorbance at 280 nm of the aqueous medium is less than 1% of the absorbance at 280 nm of the starting material, using a path length of 0.5 cm. The TFF can be carried out until the absorbance at 280 nm of the aqueous medium is less than 1.70 AU, using a path length of 0.5 cm. The TFF can be carried out until the absorbance at 280 nm of the aqueous medium is less than 1.66 AU, using a path length of 0.5 cm. The TFF can be carried out until the absorbance at 280 nm of the aqueous medium is less than 1.60 AU, using a path length of 0.5 cm. The TFF can be carried out until the platelet concentration is at least about $2000\times10^3$ platelets/μL. The TFF can be carried out until the platelet concentration is at least about $2250\times10^3$ platelets/μL. The TFF can include buffer exchange into a buffer comprising a buffering agent, a base, a loading agent, optionally a salt, and optionally at least one organic solvent. The buffering agent can be HEPES (4-(2-hydroxyethyl)-1-piperazineethanesulfonic acid). The base can be sodium bicarbonate. The loading agent can be a monosaccharide, a polysaccharide, or a combination thereof. The monosaccharide can be selected from the group consisting of sucrose, maltose, trehalose, glucose, mannose, and xylose. The monosaccharide can be trehalose. The polysaccharide can be polysucrose. The salt can be sodium chloride, potassium chloride, or a combination thereof. The organic solvent can be selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), and combinations thereof. The centrifugation can include centrifugation at 1400×g to about 1550×g. The centrifugation can include centrifugation at 1450×g to about 1500×g. The process can lack centrifugation of a composition comprising platelets. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be reduced by at least 50% as compared to a similar composition not prepared by a process including tangential flow filtration of a blood product composition, centrifugation of a blood product composition, or a combination thereof. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be reduced by at least 75% as compared to a similar composition not prepared by a process including tangential flow filtration of a blood product composition, centrifugation of a blood product composition, or a combination thereof. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be reduced by at least 90% as compared to a similar composition not prepared by a process including tangential flow filtration of a blood product composition, centrifugation of a blood product composition, or a combination thereof. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be reduced by at least 95% as compared to a similar composition not prepared by a process including tangential flow filtration of a blood product composition, centrifugation of a blood product composition, or a combination thereof. The protein concentration can be less than 30% of the protein concentration of donor apheresis plasma. The aqueous medium can have a concentration of human leukocyte antigen (HLA) Class I antibodies that is less than 30% of the human leukocyte antigen (HLA) Class I antibody concentration in donor apheresis plasma. The aqueous medium can have a concentration of human leukocyte antigen (HLA) Class II antibodies that is less than 30% of the human leukocyte antigen (HLA) Class II antibody concentration in donor apheresis plasma. The aqueous medium can have a concentration of human neutrophil antigen (HNA) antibodies that is less than 30% of the HNA antibody concentration in donor apheresis plasma. The protein concentration can be less than 10% of the protein concentration of donor apheresis plasma. The aqueous medium can have a concentration of human HLA Class I antibodies that is less than 10% of the HLA Class I antibody concentration in donor apheresis plasma. The aqueous medium can have a concentration of human HLA Class II antibodies that is less than 10% of the HLA Class II antibody concentration in donor apheresis plasma. The aqueous medium can have a concentration of human HNA antibodies that is less than 10% of the HNA antibody concentration in donor apheresis plasma. The protein concentration can be less than 5% of the protein concentration of donor apheresis plasma. The aqueous medium can have a concentration of human HLA Class I antibodies that is less than 5% of the HLA Class I antibody concentration in donor apheresis plasma. The aqueous medium can have a concentration of human HLA Class II antibodies that is less than 5% of the HLA Class II antibody concentration in donor apheresis plasma. The aqueous medium can have a concentration of human HNA antibodies that is less than 5% of the HNA antibody concentration in donor apheresis plasma. The protein concentration can be less than 3% of the protein concentration of donor apheresis plasma. The aqueous medium can have a concentration of human HLA Class I antibodies that is less than 3% of the HLA Class I antibody concentration in donor apheresis plasma. The aqueous medium can have a concentration of human HLA Class II antibodies that is less than 3% of the HLA Class II antibody concentration in donor apheresis plasma. The aqueous medium can have a concentration of human HNA antibodies that is less than 3% of the HNA antibody concentration in donor apheresis plasma. The protein concentration can be less than 1% of the protein concentration of donor apheresis plasma. The aqueous medium can have a concentration of human HLA Class I antibodies that is less than 1% of the HLA Class I antibody concentration in donor apheresis plasma. The aqueous medium can have a concentration of human HLA Class II antibodies that is less than 1% of the HLA Class II antibody concentration in donor apheresis plasma. The aqueous medium can have a concentration of human HNA antibodies that is less than 1% of the HNA antibody concentration in donor apheresis plasma. The composition can be negative for HLA Class I antibodies based on a regulatory agency approved test. The composition can be negative for HLA Class II antibodies based on a regulatory agency approved test. The composition can be negative for HNA antibodies based on a regulatory agency approved test. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be less than 5%. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be less than 3%. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be less than 1%. The percentage of beads positive for HLA Class I antibodies, as determined for the composition by flow cytometry using beads coated with Class I HLAs, can be less than 5%. The percentage of beads positive for HLA Class I antibodies, as determined for the composition by flow cytometry using beads coated with Class I HLAs, can be less than 3%. The percentage of beads positive for HLA Class I antibodies, as determined for the composition by flow cytometry using beads coated with Class I HLAs, can be less than 1%. The percentage of beads positive for HLA Class II antibodies, as determined for the composition by flow cytometry using beads coated with Class II HLAs can be less than 5%. The percentage of beads positive for HLA Class II antibodies, as determined for the composition by flow cytometry using beads coated with Class II HLAs, can be less than 3%. The percentage of beads positive for HLA Class II antibodies, as determined for the composition by flow cytometry using beads coated with Class II HLAs, can be less than 1%. The percentage of beads positive for HNA antibodies, as determined for the composition by flow cytometry using beads coated with HNAs, can be less than 5%. The percentage of beads positive for HNA antibodies, as determined for the composition by flow cytometry using beads coated with HNAs, can be less than 3%. The percentage of beads positive for HNAs, as determined for the composition by flow cytometry using beads coated with HNAs, can be less than 1%. The process of any claims herein, wherein the composition comprises less than 5.0% (by scattering intensity) microparticles. The composition can include less than 4.5% (by scattering intensity) microparticles. The composition can include less than 4.0% (by scattering intensity) microparticles. The composition can include less than 3.5% (by scattering intensity) microparticles. The platelets or platelet derivatives can have a CD41 percent positivity of at least 55%. The platelets or platelet derivatives can have a CD41 percent positivity of at least 60%. The platelets or platelet derivatives can have a CD41 percent positivity of at least 65%. The platelets or platelet derivatives can have a CD42 percent positivity of at least 80%. The platelets or platelet derivatives can have a CD42 percent positivity of at least 85%. The platelets or platelet derivatives can have a CD42 percent positivity of at least 90%. The platelets or platelet derivatives can retain at least about 10% of the lactate dehydrogenase activity of donor apheresis platelets. The platelets or platelet derivatives can retain at least about 15% of the lactate dehydrogenase activity of donor apheresis platelets. The platelets or platelet derivatives can retain at least about 20% of the lactate dehydrogenase activity of donor apheresis platelets. The platelets or platelet derivatives can have an annexin V percent positivity of at least 70%. The platelets or platelet derivatives can have an annexin V percent positivity of at least 75%. The platelets or platelet derivatives can have an annexin V percent positivity of at least 80%. The platelets or platelet derivatives can have CD47 percent positivity of at least 8%. The platelets or platelet derivatives can have CD47 percent positivity of at least 10%. The platelets or platelet derivatives can have CD47 percent positivity of at least 15%. The platelets or platelet derivatives can have CD47 percent positivity of at least 20%. The platelets or platelet derivatives can have CD62 percent positivity of at least 80%. The platelets or platelet derivatives can have CD62 percent positivity of at least 82%. The platelets or platelet derivatives can have CD62 percent positivity of at least 85%. The platelets or platelet derivatives can have CD62 percent positivity of at least 90%. The platelets or platelet derivatives can have fibrinogen associated with the cell membrane. The aqueous medium can have a lactate concentration of less than 2.0 mmol/L. The aqueous medium can have a lactate concentration of less than 1.5 mmol/L. The aqueous medium can have a lactate concentration of about 0.4 to about 1.3 mmol/L. The aqueous medium can have a lactate concentration of about 0.5 to about 1.0 mmol/L. The platelet derivatives can include thrombosomes. The process can further include a pathogen reduction step. The pathogen reduction step can precede TFF. The process can further include lyophilizing the composition comprising platelets or platelet derivatives. The process can further include thermally treating the composition comprising platelets or platelet derivatives.

Also provided herein is a composition including platelets and an aqueous medium prepared by any of the processes described herein.

Also provided herein is a process for preparing freeze-dried platelets, including (a) preparing a composition comprising platelets and an aqueous medium using any of the processes described herein and (b) freeze-drying the composition comprising platelets and the aqueous medium.

Also provided herein is a composition comprising freeze-dried platelets, prepared by any of the processes described herein.

Also provided herein is a method for preparing a composition comprising platelets or platelet derivatives and an aqueous medium, the method including diluting a starting material comprising platelets to form a diluted starting material, concentrating the platelets to about $2250\times10^3$ cells/μL ($\pm250\times10^3$) to form a concentrated platelet composition, and washing the concentrated platelet composition with at least 2 diavolumes (DV) of the preparation agent to form a TFF-treated composition.

Implementations can include one or more of the following features. Diluting can include diluting with an approximately equal weight (±10%) of the preparation agent. The method can further include a pathogen reduction step. The pathogen reduction step can occur before diluting the starting material. The residual plasma percentage can be less than about 15% relative plasma (as determined by plasma protein content). Following washing, if the concentration of the cells in the TFF-treated composition is not about $2000\times10^3$ cells/μL ($\pm300\times10^3$), the method can further include diluting the preparation agent or can be concentrated to fall within this range. The method can further include lyophilizing the TFF-treated composition to form a lyophilized composition. The method can further include treating the lyophilized composition at about 80° C. for about 24 hours.

Also provided herein is a composition comprising platelets or platelet derivatives prepared by any of the methods described herein.

The materials and methods described herein can provide several advantages. For example, they can allow for the collection of otherwise deferred donors and reduce the competition for apheresis materials.

Further details regarding aspects and embodiments of the present disclosure are provided throughout this patent application. The preceding paragraphs in this Summary section is not an exhaustive list of aspects and embodiments disclosed herein. Sections and section headers are for ease of reading and are not intended to limit combinations of disclosure, such as methods, compositions, and kits or functional elements therein across sections.

DESCRIPTION OF THE DRAWINGS

FIG. 40 is a bar plot depicting the tail snip model results for the number of animals (mice) treated with clopidogrel and ASA (aspirin) that stopped bleeding vs those that continued to bleed in the presence of FDPDs varying in the number of cells/kg. The plot shows FDPDs enhanced return to hemostasis in DAPT-treated NOD-SCID mice.

FIG. 41 shows a graph of percent platelet aggregation with time using Dual Antiplatelet Therapy (DAPT) platelets in the presence of an agonist (AA, ADP). The DAPT platelets are obtained from patients treated with prasugrel and aspirin.

Figure 1A:
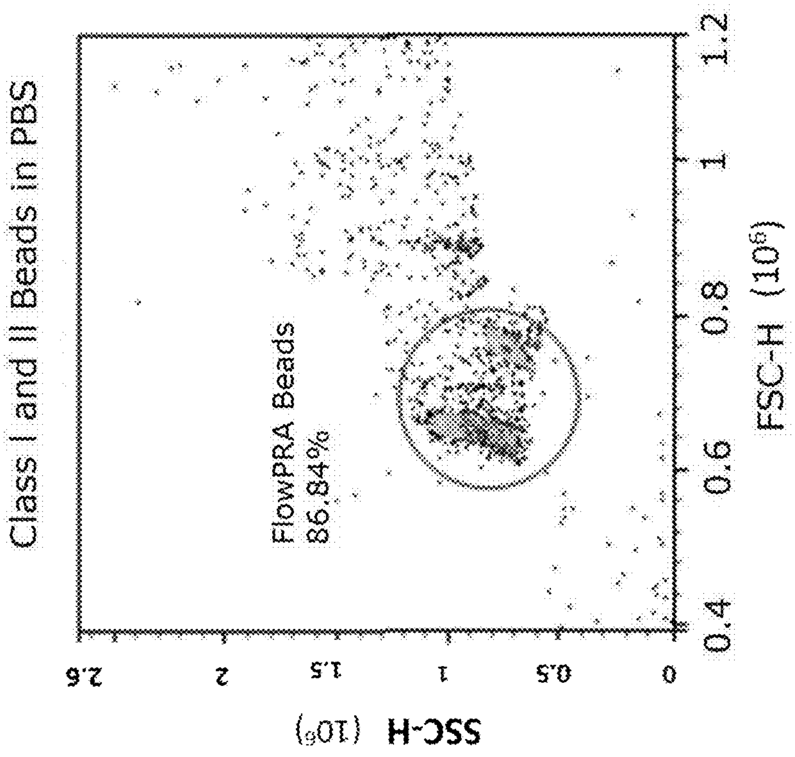
FIG. 1A shows initial gate placement for identification of Class I and Class II HLA FLOWPRA™ beads in PBS using side scattering vs. forward scattering.

As used herein and in the appended claims, the singular forms “a”, “an”, and “the” include plural referents unless the context clearly dictates otherwise. Thus, for example, reference to “a platelet” includes a plurality of such platelets. Furthermore, the use of terms that can be described using equivalent terms include the use of those equivalent terms. Thus, for example, the use of the term “subject” is to be understood to include the terms “patient”, “individual” and other terms used in the art to indicate one who is subject to a treatment.

Unless defined otherwise, all technical and scientific terms used herein have the same meaning as commonly understood by one of ordinary skill in the art to which the term belongs. Although any methods and materials similar or equivalent to those described herein can be used in the practice or testing of the present disclosure, the preferred methods and materials are now described. All publications mentioned herein are incorporated herein by reference to disclose and describe the methods and/or materials in connection with which the publications are cited. The present disclosure is controlling to the extent it conflicts with any incorporated publication. Any Headings herein are for convenience only and are not intended to be limiting, and it will be understood that the disclosure including aspects and embodiments provided within one section herein can be combined with the disclosure includes aspects and embodiments provided within any other section herein.

DETAILED DESCRIPTION

It is to be understood that the terminology used herein is for the purpose of describing particular aspects and embodiments only, and is not intended to be limiting. Further, where a range of values is disclosed, the skilled artisan will understand that all other specific values within the disclosed range are inherently disclosed by these values and the ranges they represent without the need to disclose each specific value or range herein. For example, a disclosed range of 1-10 includes 1-9, 1-5, 2-10, 3.1-6, 1, 2, 3, 4, 5, and so forth. In addition, each disclosed range includes up to 5% lower for the lower value of the range and up to 5% higher for the higher value of the range. For example, a disclosed range of 4-10 includes 3.8-10.5. This concept is captured in this document by the term “about”.

“Platelets” may include, for example, platelets in whole blood, platelets in plasma, platelets in buffer optionally supplemented with select plasma proteins, cold stored platelets. Platelets may be from a mammal(s), such as of humans, or such as non-human mammals.

As used herein, “thrombosomes” (sometimes also called Tsomes) or “thrombosomes platelet derivatives” are platelet derivatives that have been treated with a preparation agent (e.g., any of the preparation agents described herein) and lyopreserved (such as freeze-dried). In some cases, thrombosomes platelet derivatives can be prepared from pooled platelets. Thrombosomes platelet derivatives can have a shelf life of 2-3 years in dry form at ambient temperature and can be rehydrated with sterile water within minutes for immediate infusion. One example of thrombosomes freeze-dried platelet derivatives are THROMBOSOMES® freeze-dried platelet derivatives (Cellphire Inc., Rockville, MD), which are in clinical trials. In non-limiting illustrative embodiments, thrombosome compositions, or illustrative freeze-dried platelet-derivative compositions herein, such as those prepared according to Example 1 herein, are compositions that include platelet derivatives, wherein at least 50% of the platelet derivatives are CD 41-positive platelet derivatives, wherein less than 15%, 10%, or in further, non-limiting illustrative embodiments less than 5% of the CD 41-positive platelet derivatives are microparticles having a diameter of less than 0.5 μm, and wherein the platelet derivatives have a potency of at least 0.5, 1.0 and in further, non-limiting illustrative embodiments 1.5 thrombin generation potency units (TGPU) per $10^6$ platelet derivatives. In certain illustrative embodiments, including non-limiting examples of the illustrative embodiment in the preceding sentence, the platelet derivatives are at least 0.5 μm in diameter, and in some embodiments 0.5 to 2.5 μm in diameter.

Reduced Plasma Protein Content and Antibodies

Transfusion-related acute lung injury (TRALI) is a condition believed to be caused by the presence of antibodies (e.g., Human Leukocyte Antigen (HLA), Human Neutrophil Antigen (HNA), or granulocyte antibodies) in a transfused blood product, which can react with antigens in a transfusion recipient.

The use of plasma-based blood products from donors considered to be high-risk or who test positive for Human Leukocyte Antigen (HLA) Class I, Class II, and neutrophil-specific antibodies are banned from use in transfusion or production of human-derived platelet products (e.g., compositions comprising platelets and/or platelet derivatives (e.g., thrombosomes)) and are therefore omitted from the donor pool.

The use of tangential flow filtration (TFF) or multi-pass centrifugation can reduce the amount of antibody in a blood product, for example, to limits not detectable by current, FDA-approved, testing methods. In some cases, reduction of certain plasma components (e.g., HLA antibodies) can allow for this donor population to be accepted for production of blood products (e.g., compositions comprising platelets and/or platelet derivatives (e.g., thrombosomes)). In some embodiments described herein, a blood product can be a composition that includes platelets and an aqueous medium.

Thrombosomes or cryopreserved platelet production can be limited by the availability of licensed apheresis collections performed at blood donor centers around the United States. Competition for these products can be fierce, and distribution for blood product manufacturing needs is usually prioritized below the needs of patient care. Blood product manufacturing (e.g., scale-up), could be aided by apheresis collections from otherwise deferred donors. One way this could be accomplished is by reducing free antibody levels in donor plasma to meet current, FDA approved, testing thresholds by utilizing tangential flow filtration (TFF) or centrifugation and plasma removal. Centrifugation of the raw materials (e.g., donor plasma), while typically more time consuming than TFF, can have a similar effect on the raw material. In some cases, removal of the donor plasma and replacement with buffer can allow the inventors to manufacture and characterize a final product (e.g., compositions comprising platelets and/or platelet derivatives (e.g., thrombosomes)) with a reduced protein (e.g., antibody (e.g., HLA antibody or HNA antibody)) content (e.g., as measured by absorbance at 280 nm). Such a product can increase the safety for a recipient of the product by reducing the transfusion related cause for TRALI.

In some embodiments, the materials and methods provided herein can allow previously deferred donors (such as those who screen positive for HLA antibodies or whose donor history presents a risk for positive HLA) to be allowed into the donor pool of raw materials used to manufacture blood products (e.g., compositions comprising platelets and/or platelet derivatives (e.g., thrombosomes)). In some embodiments described herein, a blood product can be a composition that includes platelets and an aqueous medium. Additionally, a reduction in HLA antibodies from the raw materials (e.g., donor apheresis material (e.g., platelets or pooled platelets)) can allow for a final product (e.g., compositions comprising platelets and/or platelet derivatives (e.g., thrombosomes)) to be labeled as HLA-reduced, increasing the safety of a product for a recipient.

In some embodiments, a blood product (e.g., compositions comprising platelets and/or platelet derivatives (e.g., thrombosomes)) as provided herein can have no detectable level of HLA antibodies. In some embodiments, a blood product (e.g., compositions comprising platelets and/or platelet derivatives (e.g., thrombosomes)) as provided herein can have no detectable level of an antibody selected from the group consisting of HLA Class I antibodies, HLA Class II antibodies, and HNA antibodies. In some embodiments, a blood product (e.g., compositions comprising platelets and/or platelet derivatives (e.g., thrombosomes)) as provided herein can have no detectable level of HLA Class I antibodies. In some embodiments, a blood product (e.g., compositions comprising platelets and/or platelet derivatives (e.g., thrombosomes)) as provided herein can have no detectable level of HLA Class II antibodies. In some embodiments, a blood product (e.g., compositions comprising platelets and/or platelet derivatives (e.g., thrombosomes)) as provided herein can have no detectable level of HNA antibodies. In some embodiments, detection of antibodies can be carried out using a regulatory agency approved (e.g., FDA cleared) assay. A regulatory agency approved assay can be any appropriate regulatory agency approved assay. In some embodiments, a regulatory agency approved test can be the LABSCREEN™ Mixed by One Lambda. In some implementations, a regulatory agency approved test can be carried out using a LUMINEX® 100/200 or a LUMINEX® XY and the HLA FUSION™ software. In some embodiments described herein, a blood product can be a composition that includes platelets and an aqueous medium.

In some embodiments, a blood product (e.g., compositions comprising platelets and/or platelet derivatives (e.g., thrombosomes)) as provided herein can have a level of an antibody selected from the group consisting of HLA Class I antibodies, HLA Class II antibodies, and HNA antibodies below a reference level. In some embodiments, a blood product (e.g., compositions comprising platelets and/or platelet derivatives (e.g., thrombosomes)) as provided herein can have a level of HLA Class I antibodies below a reference level. In some embodiments, a blood product (e.g., compositions comprising platelets and/or platelet derivatives (e.g., thrombosomes)) as provided herein can have a level of HLA Class II antibodies below a reference level. In some embodiments, a blood product (e.g., a composition comprising platelets and/or platelet derivatives (e.g., thrombosomes)) as provided herein can have a level of HNA antibodies below a reference level. A reference level can be any appropriate reference level. In some embodiments described herein, a blood product can be a composition that includes platelets and an aqueous medium.

In some embodiments, a blood product (e.g., a composition comprising platelets and/or platelet derivatives (e.g., thrombosomes)) as provided herein test negative for an antibody selected from the group consisting of HLA Class I antibodies, HLA Class II antibodies, and HNA antibodies in a regulatory agency approved assay (e.g., an FDA cleared assay). In some embodiments, a blood product (e.g., a composition comprising platelets and/or platelet derivatives (e.g., thrombosomes)) as provided herein can test negative for HLA Class I antibodies in a regulatory agency approved assay (e.g., an FDA cleared assay). In some embodiments, a blood product (e.g., a composition comprising platelets and/or platelet derivatives (e.g., thrombosomes)) as provided herein can test negative for HLA Class II antibodies a in regulatory agency approved assay (e.g., an FDA cleared assay). In some embodiments, a blood product (e.g., a composition comprising platelets and/or platelet derivatives (e.g., thrombosomes)) as provided herein can test negative for HNA antibodies in a regulatory agency approved assay (e.g., an FDA cleared assay). In some embodiments described herein, a blood product can be a composition that includes platelets and an aqueous medium. A regulatory agency approved assay can be any appropriate regulatory agency approved assay. In some embodiments, a regulatory agency approved test can be the LABSCREEN™ Mixed by One Lambda. In some implementations, a regulatory agency approved test can be carried out using a LUMINEX® 100/200 or a LUMINEX® XY and the HLA FUSION™ software.

In some aspects, provided herein are compositions comprising platelets and/or platelet derivatives (e.g., thrombosomes) and an aqueous medium. In some embodiments, the aqueous medium can include a preparation agent (e.g., any of the preparation agents described herein). In some embodiments, an aqueous medium as provided herein can have a level of an antibody selected from the group consisting of HLA Class I antibodies, HLA Class II antibodies, and HNA antibodies below a reference level. In some embodiments, an aqueous medium as provided herein can have a level of HLA Class I antibodies below a reference level. In some embodiments, an aqueous medium as provided herein can have a level of HLA Class II antibodies below a reference level. In some embodiments, an aqueous medium as provided herein can have a level of HNA antibodies below a reference level. A reference level can be any appropriate reference level. In some embodiments, an aqueous medium as provided herein can test negative for an antibody selected from the group consisting of HLA Class I antibodies, HLA Class II antibodies, and HNA antibodies in a regulatory agency approved assay (e.g., an FDA cleared assay). In some embodiments, an aqueous medium as provided herein can test negative for HLA Class I antibodies in a regulatory agency approved assay (e.g., an FDA cleared assay). In some embodiments, an aqueous medium as provided herein can test negative for HLA Class II antibodies in a regulatory agency approved assay (e.g., an FDA cleared assay). In some embodiments, an aqueous medium as provided herein can test negative for HNA antibodies in a regulatory agency approved assay (e.g., an FDA cleared assay). A regulatory agency approved assay can be any appropriate regulatory agency approved assay. In some embodiments, a regulatory agency approved test can be the LABSCREEN™ Mixed by One Lambda. In some implementations, a regulatory agency approved test can be carried out using a LUMINEX® 100/200 or a LUMINEX® XY and the HLA FUSION™ software.

In some embodiments, an aqueous medium can have a reduced amount of residual plasma compared to donor apheresis plasma (e.g., single-donor apheresis plasma or pooled donor apheresis plasma) can be a percentage of residual plasma (e.g., less than or equal to about 50%, 40%, 30%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1% of residual plasma). In some embodiments, an aqueous medium can have a reduced amount of residual plasma compared to donor apheresis plasma (e.g., single-donor apheresis plasma or pooled donor apheresis plasma) can be a percentage range of residual plasma (e.g., about 5% to about 50%, about 5% to about 40%, about 5% to about 30%, about 5% to about 20%, about 5% to about 15%, about 5% to about 10%, about 10% to about 20%, about 7% to about 15%, about 7% to about 10%, about 8% to about 15%, about 8% to about 10%, about 0.1% to about 5%, about 0.1% to about 3%, about 0.1% to about 1%, about 0.5% to about 3%, about 0.5% to about 1%, or about 1% to about 3% of residual plasma). In some embodiments, an aqueous medium can have a protein concentration less than or equal to about 50% (e.g., less than or equal to about 40%, 30%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%) of the protein concentration of donor apheresis plasma (e.g., single-donor apheresis plasma or pooled donor apheresis plasma). In some embodiments, an aqueous medium can have a protein concentration of about 5% to about 50% (e.g., about 5% to about 40%, about 5% to about 30%, about 5% to about 20%, about 5% to about 15%, about 5% to about 10%, about 10% to about 20%, about 7% to about 15%, about 7% to about 10%, about 8% to about 15%, or about 8% to about 10%) of the protein concentration of donor apheresis plasma (e.g., single-donor apheresis plasma or pooled donor apheresis plasma). In some embodiments, an aqueous medium can have a protein concentration of about 0.1% to about 5% (e.g., about 0.1% to about 3%, about 0.1% to about 1%, about 0.5% to about 3%, about 0.5% to about 1%, about 1% to about 2%, or about 1% to about 3%) of the protein concentration of donor apheresis plasma (e.g., single-donor apheresis plasma or pooled donor apheresis plasma). A protein concentration can be measured by any appropriate method. Apart from the relative protein concentration of proteins in the aqueous medium, the protein concentration in the aqueous medium can also be measured in absolute terms. Accordingly, in some embodiments, a protein concentration can be measured by absorbance at 280 nm (A280). In some embodiments, an aqueous medium can have an A280 that is less that is less than 2.0 AU (e.g., less than 1.97, 1.95, 1.93, 1.90, 1.87, 1.85, 1.83, 1.80, 1.77, 1.75, 1.73, 1.70, 1.66, 1.6, 1.5, 1.4, 1.3, 1.2, 1.1, 1.0, 0.9, 0.8, 0.7, 0.6, 0.5, 0.4, 0.3, 0.2, or 0.1 AU) with a path length of 0.5 cm. In some embodiments, the protein concentration in the aqueous medium is less than or equal to 15%, 14%, 13%, 12%, 11%, 10%, 9%, 8%, 7%, 6%, 5%, 4%, 3%, 2%, 1%, 0.1%, or 0.01%. In some illustrative embodiments, the protein concentration is less than 3% or 4%. In some embodiments, the protein concentration is in the range of 0.01-15%, 0.1-15%, 1-15%, 1-10%, 0.1-10%, 0.01-10%, 0.1-5%, 0.1-4%, 0.1-3%, 0.1-2%, 0.1-1%, 1-5%, 1-4%, 1-3%, 1-2%, 3-12%, or 5-10%. In some embodiments, an aqueous medium can have a HLA Class I antibody concentration less than about 70% (e.g., less than about 60%, 50%, 40%, 30%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%) of the HLA Class I antibody concentration of donor apheresis plasma (e.g., single-donor apheresis plasma or pooled donor apheresis plasma). A HLA Class I antibody concentration can be measured by any appropriate method. In some embodiments, the HLA class I antibody concentration in the aqueous medium can be quantitated in absolute terms such that the aqueous medium can have HLA Class I antibody concentration less than about 70% (e.g., less than about or less than exactly 60%, 50%, 40%, 30%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%) in the aqueous medium. In some embodiments, the HLA Class I antibody in the aqueous medium is low enough such that the composition comprising platelet derivatives and aqueous medium is negative for HLA Class I antibodies based on a regulatory agency approved test for HLA Class I antibodies.

In some embodiments, an aqueous medium can have a HLA Class II antibody concentration less than about 50% (e.g., less than about 40%, 30%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%) of the HLA Class II antibody concentration of donor apheresis plasma (e.g., single-donor apheresis plasma or pooled donor apheresis plasma). A HLA Class II antibody concentration can be measured by any appropriate method. In some embodiments, the HLA class II antibody concentration in the aqueous medium can be quantitated in absolute terms such that the aqueous medium can have HLA Class I antibody concentration less than about 50% (e.g., less than about or less than exactly 40%, 30%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%) in the aqueous medium. In some embodiments, the HLA Class II antibody in the aqueous medium is low enough such that the composition comprising platelet derivatives and aqueous medium is negative for HLA Class II antibodies based on a regulatory agency approved test for HLA Class II antibodies.

In some embodiments, an aqueous medium can have a HNA antibody concentration less than about 50% (e.g., less than about 40%, 30%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%) of the HNA antibody concentration of donor apheresis plasma (e.g., single-donor apheresis plasma or pooled donor apheresis plasma). A HNA antibody concentration can be measured by any appropriate method. In some embodiments, the HNA antibody concentration in the aqueous medium can be quantitated in absolute terms such that the aqueous medium can have HNA antibody concentration less than about 50% (e.g., less than about or less than exactly 40%, 30%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%) in the aqueous medium. In some embodiments, the HNA antibody in the aqueous medium is low enough such that the composition comprising platelet derivatives and aqueous medium is negative for HNA antibodies based on a regulatory agency approved test for HNA antibodies.

In some cases, flow cytometry can be used to evaluate compositions as provided herein. In some embodiments, an antibody selected from the group consisting of HLA Class I antibodies, HLA Class II antibodies, and HNA antibodies, as determined for a composition comprising platelets and an aqueous medium by flow cytometry using beads coated with Class I HLAs, Class II HLAs, or HNAs, respectively, is less than 10% (e.g., less than about or less than exactly 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%). In some embodiments, the percentage of beads positive for HLA Class I antibodies, as determined for a composition comprising platelets and an aqueous medium by flow cytometry using beads coated with Class I HLAs, is less than 10% (e.g., less than 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%). In some embodiments, the percentage of beads positive for HLA Class II antibodies, as determined for a composition comprising platelets and an aqueous medium by flow cytometry using beads coated with Class II HLAs is less than 10% (e.g., less than about or less than exactly 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%). In some embodiments, the percentage of beads positive for HNA antibodies, as determined for a composition comprising platelets and an aqueous medium by flow cytometry using beads coated with HNAs is less than 10% (e.g., less than about or less than exactly 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%).

In some embodiments, an antibody selected from the group consisting of HLA Class I antibodies, HLA Class II antibodies, and HNA antibodies, as determined for an aqueous medium by flow cytometry using beads coated with Class I HLAs, Class II HLAs, or HNAs, respectively, is less than 10% (e.g., less than 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%). In some embodiments, the percentage of beads positive for HLA Class I antibodies, as determined for an aqueous medium by flow cytometry using beads coated with Class I HLAs, is less than 10% (e.g., less than 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%). In some embodiments, the percentage of beads positive for HLA Class II antibodies, as determined for an aqueous medium by flow cytometry using beads coated with Class II HLAs is less than 10% (e.g., less than 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%). In some embodiments, the percentage of beads positive for HNA antibodies, as determined for an aqueous medium by flow cytometry using beads coated with HNAs is less than 10% (e.g., less than 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%).

In some embodiments, the protein concentration is low enough to exclude the HLA Class I, HLA Class II, and HNA antibodies from the donor pheresis plasma such that the composition is negative for: a) HLA Class I antibodies based on a regulatory agency approved test for HLA Class I antibodies; b) HLA Class II antibodies based on a regulatory agency approved test for HLA Class II antibodies; and c) HNA antibodies based on a regulatory agency approved test for HNA antibodies. The platelet derivative composition of the present disclosure, and the process for obtaining the same, thus provides the flexibility to utilize the apheresis plasma from different multiple donors, and yet obtain a final product (platelet derivative composition) that is negative for the HLA Class I, HLA Class II, and HNA antibodies.

In some aspects, provided herein are platelet derivative compositions comprising platelet derivatives in the form of a solid, a composition with less than 1% water, and/or a powder. The composition in solid form, in illustrative embodiments dried form, for example with less than 1% water, can be one amongst different kinds in which the composition would be packed and commercialized. Thus, it is contemplated that the composition in the dried form would preserve the characteristics with respect to the low content, or even absence of detectable HLA Class I, HLA Class II, and HNA antibodies as described with respect to the aqueous medium in the embodiments described herein. In some embodiments, the platelet derivative composition in the form of a powder is negative for HLA Class I antibodies based on a regulatory agency approved test for HLA Class I antibodies. In some embodiments, the platelet derivative composition in the form of a powder is negative for HLA Class II antibodies based on a regulatory agency approved test for HLA Class II antibodies. In some embodiments, the platelet derivative composition in the form of a powder is negative for HNA antibodies based on a regulatory agency approved test for HNA antibodies. In some embodiments, the platelet derivative composition in the form of a powder is negative for HLA Class I antibodies, HLA Class II antibodies, and HNA antibodies based on a regulatory agency approved test for HLA Class I antibodies, HLA Class II antibodies, and HNA antibodies, respectively.

Quantity of Platelet or Platelet Derivatives, and Erythrocytes

The composition comprising platelet derivatives and aqueous medium can have varying quantity of platelets and/or platelet derivatives along with erythrocytes. In some embodiments, a composition as described herein can have a platelet count of at least $10^6$ (e.g., at least $5\times10^6$, $10^7$, $5\times10^7$, $10^8$, $5\times10^8$, $10^9$, $5\times10^9$, or $10^{10}$). In some embodiments, a composition as described herein can have a platelet count of at least about $200\times10^3$ platelets/μL (e.g., at least about $300\times10^3$, $400\times10^3$, $500\times10^3$, $750\times10^3$, $1000\times10^3$, $1500\times10^3$, $2000\times10^3$, or $2500\times10^3$ platelets/μL). In some embodiments, a composition as described herein can have a platelet count of at least about $2000\times10^3$ platelets/μL (e.g., at least about $2050\times10^3$, $2100\times10^3$, $2150\times10^3$, $2200\times10^3$, $2250\times10^3$, $2300\times10^3$, $2350\times10^3$, $2400\times10^3$, $2450\times10^3$, or $2500\times10^3$ platelets/μL). In some embodiments, a composition as described herein can have a platelet count less than or equal to $1000\times10^4$ platelets/μL. In some embodiments, the platelets or platelet derivatives in the composition are at least $100\times10^3$ platelets/μL, or $200\times10^3$ platelets/μL, or $400\times10^3$ platelets/μL, or $1000\times10^3$ platelets/μL, or $1250\times10^3$ platelets/μL, or $1500\times10^3$ platelets/μL, or $1750\times10^3$ platelets/μL, $2000\times10^3$ platelets/μL, or $2250\times10^3$ platelets/μL, or $2500\times10^3$ platelets/μL, or $2750\times10^3$ platelets/μL, or $3000\times10^3$ platelets/μL, $3250\times10^3$ platelets/μL, $3500\times10^3$ platelets/μL, $3750\times10^3$ platelets/μL, $4000\times10^3$ platelets/μL, or $4250\times10^3$ platelets/μL, or $4500\times10^3$ platelets/μL, or $4750\times10^3$ platelets/μL, or $5000\times10^3$ platelets/μL, or $5250\times10^3$ platelets/μL, or $5500\times10^3$ platelets/μL, or $5750\times10^3$ platelets/μL, or $6000\times10^3$ platelets/μL, or $7000\times10^3$ platelets/μL, or $8000\times10^3$ platelets/μL, or $9000\times10^3$ platelets/μL, or $10,000\times10^3$ platelets/μL, or $11,000\times10^3$ platelets/μL, or $12,000\times10^3$ platelets/μL, or $13,000\times10^3$ platelets/μL, or $14,000\times10^3$ platelets/μL, or $15,000\times10^3$ platelets/μL, or $16,000\times10^3$ platelets/μL, or $17,000\times10^3$ platelets/μL, or $18,000\times10^3$ platelets/μL, or $19,000\times10^3$ platelets/μL, or $20,000\times10^3$ platelets/μL. In some embodiments, the platelets or platelet derivatives in the composition is in the range of $100\times10^3$-$20,000\times10^3$ platelets/μL, or $1000\times10^3$-$20,000\times10^3$ platelets/μL, or $1000\times10^3$-$10,000\times10^3$ platelets/μL, or $500\times10^3$-$5,000\times10^3$ platelets/μL, or $1000\times10^3$-$5,000\times10^3$ platelets/μL, or $2000\times10^3$-$8,000\times10^3$ platelets/μL, or $10,000\times10^3$-$20,000\times10^3$ platelets/μL, or $15,000\times10^3$-$20,000\times10^3$ platelets/μL.

In some embodiments, a composition as provided herein can include erythrocytes. In some embodiments, a composition as provided herein can have an erythrocyte count of less than about $10^{10}$ (e.g., less than $5\times10^9$, $10^9$, $5\times10^8$, $10^8$, $5\times10^7$, $10^7$, $5\times10^6$, or $10^6$). In some embodiments, the erythrocyte count can be less than $0.2\times10^6$/μL (e.g., less than $0.1\times10^6$/μL, $0.5\times10^5$/μL, or $0.1\times10^5$/μL). In some embodiments, the erythrocytes in the composition is in the range of $0.1\times10^5$ erythrocytes/μL to $0.2\times10^6$ erythrocytes/μL, or $0.5\times10^5$ erythrocytes/μL to $0.1\times10^6$ erythrocytes/μL.

Preparation Agent and Additional Components

In some embodiments, a composition provided herein can include one or more additional components. In some embodiments, a composition provided herein can include a preparation agent (e.g., any of the preparation agents described herein). In some embodiments, the composition can include a buffering agent, a base, a loading agent, optionally a salt, and optionally at least one organic solvent. A buffering agent can be any appropriate buffering agent. In some embodiments, a buffering agent can be HEPES (4-(2-hydroxyethyl)-1-piperazineethanesulfonic acid). A base can be any appropriate base. In some embodiments, a base can be sodium bicarbonate. A loading agent can be any appropriate loading agent. In some embodiments, a loading agent can be a monosaccharide, a polysaccharide, or a combination thereof. In some embodiments, a loading agent can be selected from the group consisting of sucrose, maltose, trehalose, glucose, mannose, and xylose. In some embodiments, a loading agent can be trehalose. In some embodiments, a polysaccharide can be polysucrose. A salt can be any appropriate salt. In some embodiments, a salt can be sodium chloride, potassium chloride, or a combination thereof. An organic solvent can be any appropriate organic solvent. In some embodiments, an organic solvent can be selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), and combinations thereof.

A preparation agent can include any appropriate components. In some embodiments, the preparation agent may comprise a liquid medium. In some embodiments the preparation agent may comprise one or more salts selected from phosphate salts, sodium salts, potassium salts, calcium salts, magnesium salts, and any other salt that can be found in blood or blood products, or that is known to be useful in drying platelets, or any combination of two or more of these.

In some embodiments, the preparation agent comprises one or more salts, such as phosphate salts, sodium salts, potassium salts, calcium salts, magnesium salts, and any other salt that can be found in blood or blood products. Exemplary salts include sodium chloride (NaCl), potassium chloride (KCl), and combinations thereof. In some embodiments, the preparation agent includes from about 0.5 mM to about 100 mM of the one or more salts. In some embodiments, the preparation agent includes from about 0.5 mM to about 100 mM (e.g., about 0.5 to about 2 mM, about 2 mM to about 90 mM, about 2 mM to about 6 mM, about 50 mM to about 100 mM, about 60 mM to about 90 mM, about 70 to about 85 mM) of the one or more salts. In some embodiments, the preparation agent includes about 5 mM, about 75 mM, or about 80 mM of the one or more salts. In some embodiments, the preparation agent comprises one or more salts selected from calcium salts, magnesium salts, and a combination of the two, in a concentration of about 0.5 mM to about 2 mM.

Preferably, these salts are present in the composition comprising platelets or platelet derivatives, such as freeze-dried platelets, at an amount that is about the same as is found in whole blood.

In some embodiments, the preparation agent further comprises a carrier protein. In some embodiments, the carrier protein comprises human serum albumin, bovine serum albumin, or a combination thereof. In some embodiments, the carrier protein is present in an amount of about 0.05% to about 1.0% (w/v).

The preparation agent may be any buffer that is non-toxic to the platelets and provides adequate buffering capacity to the solution at the temperatures at which the solution will be exposed during the process provided herein. Thus, the buffer may comprise any of the known biologically compatible buffers available commercially, such as phosphate buffers, such as phosphate buffered saline (PBS), bicarbonate/carbonic acid, such as sodium-bicarbonate buffer, N-2-hydroxyethylpiperazine-N'-2-ethanesulfonic acid (HEPES), and tris-based buffers, such as tris-buffered saline (TBS). Likewise, it may comprise one or more of the following buffers: propane-1,2,3-tricarboxylic (tricarballylic); benzenepentacarboxylic; maleic; 2,2-dimethylsuccinic; EDTA; 3,3-dimethylglutaric; bis(2-hydroxyethyl)imino-tris(hydroxymethyl)-methane (BIS-TRIS); benzenehexacarboxylic (mellitic); N-(2-acetamido)imino-diacetic acid (ADA); butane-1,2,3,4-tetracarboxylic; pyrophosphoric; 1,1-cyclopentanediacetic (3,3 tetramethylene-glutaric acid); piperazine-1,4-bis-(2-ethanesulfonic acid) (PIPES); N-(2-acetamido)-2-amnoethanesulfonic acid (ACES); 1,1-cyclohexanediacetic; 3,6-endomethylene-1,2,3,6-tetrahydrophthalic acid (EMTA; ENDCA); imidazole; 2-(aminoethyl)trimethylammonium chloride (CHOLAMINE); N,N-bis(2-hydroxyethyl)-2-aminoethanesulfonic acid (BES); 2-methylpropane-1,2,3-triscarboxylic (beta-methyltricarballylic); 2-(N-morpholino)propanesulfonic acid (MOPS); phosphoric; and N-tris(hydroxymethyl)methyl-2-amminoethane sulfonic acid (TES). In some embodiments, the preparation agent includes one or more buffers, e.g., N-2-hydroxyethylpiperazine-N'-2-ethanesulfonic acid (HEPES), or sodium-bicarbonate ($NaHCO_3$) In some embodiments, the preparation agent includes from about 5 to about 100 mM of the one or more buffers. In some embodiments, the preparation agent includes from about 5 to about 50 mM (e.g., from about 5 mM to about 40 mM, from about 8 mM to about 30 mM, about 10 mM to about 25 mM) about of the one or more buffers. In some embodiments, the preparation agent includes about 10 mM, about 20 mM, about 25 mM, or about 30 mM of the one or more buffers.

In some embodiments, the preparation agent includes one or more saccharides, such as monosaccharides and disaccharides, including sucrose, maltose, trehalose, glucose, mannose, dextrose, and xylose. In some embodiments, the saccharide is a monosaccharide. In some embodiments, the saccharide is a disaccharide. In some embodiments, the saccharide is a monosaccharide, a disaccharide, or a combination thereof. In some embodiments, the saccharide is a non-reducing disaccharide. In some embodiments, the saccharide is sucrose, maltose, trehalose, glucose (e.g., dextrose), mannose, or xylose. In some embodiments, the saccharide comprises trehalose. In some embodiments, the preparation agent comprises a starch. In some embodiments, the preparation agent includes polysucrose, a polymer of sucrose and epichlorohydrin. In some embodiments, the preparation agent includes from about 10 mM to about 1,000 mM of the one or more saccharides. In some embodiments, the preparation agent includes from about 50 to about 500 mM of the one or more saccharides. In some embodiments, one or more saccharides is present in an amount of from 10 mM 10 to 500 mM. In some embodiments, one or more saccharides is present in an amount of from 50 mM to 200 mM. In some embodiments, one or more saccharides is present in an amount from 100 mM to 150 mM. In some embodiments, the one or more saccharides are the lyophilizing agent; for example, in some embodiments, the lyophilizing agent comprises trehalose, polysucrose, or a combination thereof. In some embodiments, the preparation agent comprises trehalose in the range of 0.4-35%, or 1-35%, or 2-30%, or 1-10%, or 1-5%, or 0.5-5%. In an exemplary embodiment, the composition comprises 3.5% trehalose. In some embodiments, the preparation agent comprises polysucrose in the range of 2-8%, or 2.25-7.75%, or 2.5-7.5%, or 2.5-6.5%, wherein the composition is in a rehydrated form. In an exemplary embodiment, the composition comprises 3% polysucrose. In another exemplary embodiment, the composition comprises 6% polysucrose. Different ionic forms of polysucrose can be used in the preparation agent that would be used to lyophilize the platelet derivatives. The ionic forms of polysucrose can be exploited to increase the efficiency of the lyophilization process. The ionic forms can be optimized to accommodate higher concentrations of platelet concentrations in the solution for performing lyophilization process. In some embodiments of the composition, wherein the composition comprises polysucrose, the polysucrose is a cationic form of polysucrose. In some embodiments, the cationic form of polysucrose is diethylaminoethyl (DEAE)-polysucrose. In some embodiments, the polysucrose is an anionic form of polysucrose. In some embodiments, the anionic form of polysucrose is carboxymethyl-polysucrose. Polysucrose of different molecular weight can be used to increase the efficiency of the lyophilization process. In some embodiments of the composition, polysucrose has a molecular weight in the range of 70,000 MW to 400,000 MW. In some embodiments, polysucrose has a molecular weight in the range of 80,000 MW to 350,000 MW, or 100,000 MW to 300,00 MW. In some exemplary embodiments, polysucrose has a molecular weight in the range of 120,000 MW to 200,000 MW. In some exemplary embodiments, polysucrose has a molecular weight of 150,000 MW, or 160,000 MW, or 170,000 MW, or 180,000 MW, 190,000 MW, or 200,000 MW.

In some embodiments the composition comprising platelets or platelet derivatives, (e.g., thrombosomes), may comprise one or more of water or a saline solution. In some embodiments the composition comprising platelets or platelet derivatives, such as freeze-dried platelets, may comprise DMSO.

In some embodiments, the preparation agent comprises an organic solvent, such as an alcohol (e.g., ethanol). In such a preparation agent, the amount of solvent can range from 0.1% to 5.0% (v/v). In some embodiments, the organic solvent can range from about 0.1% (v/v) to about 5.0% (v/v), such as from about 0.3% (v/v) to about 3.0% (v/v), or from about 0.5% (v/v) to about 2% (v/v).

In some embodiments, suitable organic solvents include, but are not limited to alcohols, esters, ketones, ethers, halogenated solvents, hydrocarbons, nitriles, glycols, alkyl nitrates, water or mixtures thereof. In some embodiments, suitable organic solvents includes, but are not limited to methanol, ethanol, n-propanol, isopropanol, acetic acid, acetone, methyl ethyl ketone, methyl isobutyl ketone, methyl acetate, ethyl acetate, isopropyl acetate, tetrahydrofuran, isopropyl ether (IPE), tert-butyl methyl ether, dioxane (e.g., 1,4-dioxane), acetonitrile, propionitrile, methylene chloride, chloroform, toluene, anisole, cyclohexane, hexane, heptane, ethylene glycol, nitromethane, dimethylformamide, dimethyl sulfoxide, N-methyl pyrrolidone, dimethylacetamide, and combinations thereof. In some embodiments the organic solvent is selected from the group consisting of ethanol, acetic acid, acetone, acetonitrile, dimethylformamide, dimethyl sulfoxide (DMSO), dioxane, methanol, n-propanol, isopropanol, tetrahydrofuran (THF), N-methyl pyrrolidone, dimethylacetamide (DMAC), or combinations thereof. In some embodiments, the organic solvent comprises ethanol, DMSO, or a combination thereof. The presence of organic solvents, such as ethanol, can be beneficial in the processing of platelets, platelet derivatives, or thrombosomes (e.g., freeze-dried platelet derivatives).

In some embodiments the preparation agent does not include an organic solvent. In some embodiments, the preparation agent comprises an organic solvent. In some embodiments the preparation agent comprises DMSO.

A preparation agent can have any appropriate pH. For example, in some embodiments, a preparation agent can have a pH of about 5.5 to about 8.0 (e.g., about 6.5 to about 6.9, or about 6.6 to about 6.8). In some embodiments, the preparation agent has a pH in the range of 5.5 to 8.0, or 6.0 to 8.0, or 6.0 to 7.5. In an exemplary embodiment, the preparation agent has a pH of 6.5. In another exemplary embodiment, the preparation agent has a pH of 7.4.

In some embodiments, one or more other components may be combined with in the platelets (e.g., as part of a preparation agent). Exemplary components may include Prostaglandin E1 or Prostacyclin and or EDTA/EGTA to prevent platelet aggregation and activation.

In some embodiments, a preparation agent can be Buffer A, as shown in Example 1. In some embodiments, a preparation agent can comprise Buffer A, as shown in Example 1, wherein one or more components (e.g., ethanol) is present in an amount up to three times the amount shown in Example 1. Non-limiting examples of preparation agent compositions that may be used are shown in Tables P1-P6.

TABLE P1

A preparation agent that can be used
Buffer

| Component | Concentration (mM unless otherwise specified) |
|---|---|
| NaCl | 75.0 |
| KCl | 4.8 |
| HEPES | 9.5 |
| $NaHCO_3$ | 12.0 |
| Dextrose | 3 |
| Trehalose | 100 |
| Ethanol | 1% (v/v) |

TABLE P2

A preparation agent that can be used
Buffer

| Component | Concentration (mM unless otherwise specified) |
|---|---|
| NaCl | 75.0 |
| KCl | 4.8 |
| HEPES | 9.5 |
| $NaHCO_3$ | 12.0 |
| Dextrose | 3 |
| Trehalose | 100 |

TABLE P3

A preparation agent that can be used.
Buffer A1 (pH 6.5)

| Component | Concentration (mM unless specified otherwise) |
|---|---|
| $CaCl_2$ | 1.8 |
| $MgCl_2$ | 1.1 |
| KCl | 2.7 |
| NaCl | 137 |
| $NaH_2PO_4$ | 0.4 |

TABLE P3-continued

A preparation agent that can be used.
Buffer A1 (pH 6.5)

| Component | Concentration (mM unless specified otherwise) |
|---|---|
| HEPES | 10 |
| D-glucose | 5.6 |

TABLE P4

Buffer B can used when incubating platelets, e.g., for flow cytometry. Such an incubation can be done at room temperature in the dark. Albumin is an optional component of Buffer B.
Buffer B

| Component | Concentration (mM unless otherwise specified) |
|---|---|
| Buffer and Salts | Table P5 (below) |
| BSA | 0.35% |
| Dextrose | 5 |
| pH | 7.4 |

TABLE P5

Concentration of HEPES and of Salts in Buffer B

| Component | Concentration (mM unless otherwise specified) |
|---|---|
| HEPES | 25 |
| NaCl | 119 |
| KCl | 5 |
| $CaCl_2$ | 2 |
| $MgCl_2$ | 2 |
| glucose | 6 g/l |

Table P5 shows the concentrations of HEPES and salts in Buffer B. The pH can be adjusted to 7.4 with NaOH. Albumin is an optional component of Buffer B.

TABLE P6

Tyrode's HEPES Buffer (plus PGE1)

| Component | Concentration (mM) |
|---|---|
| $CaCl_2$ | 1.8 |
| $MgCl_2$ | 1.1 |
| KCl | 2.7 |
| NaCl | 137 |
| $NaH_2PO_4$ | 0.4 |
| HEPES | 10 |
| D-glucose | 5.6 |
| pH | 6.5 |
| Prostagalandin E1 (PGE1) | 1 μg/ml |

Table P6 is another exemplary preparation agent.

Rehydration of the Composition Comprising Platelet Derivatives

In some aspects, the platelet derivative composition of the present disclosure is in the form of a powder. In some aspects, the process for preparing the platelet derivative composition results in the final product which is in a dry powdered form. The platelet derivative composition in its dry form comprises platelet derivatives. The platelet derivative composition in its dry form comprises platelet derivatives, and/or freeze-dried platelets. It is well-known to a skilled artisan that the platelet derivatives in the dried form shall preserve the characteristics which it is intended to observe once the platelet derivatives are rehydrated for clinical application and/or studying the characteristics such as, the presence of platelet activation markers.

In some embodiments, rehydrating the composition comprising platelets or platelet derivatives comprises adding to the platelets an aqueous liquid. In some embodiments, the aqueous liquid is water. In some embodiments, the aqueous liquid is an aqueous solution (e.g., a buffer). In some embodiments, the aqueous liquid is a saline solution. In some embodiments, the aqueous liquid is a suspension.

In some embodiments, the platelets or platelet derivatives (e.g., thrombosomes) have less than about 10%, such as less than about 8%, such as less than about 6%, such as less than about 4%, such as less than about 2%, such as less than about 0.5% crosslinking of platelet membranes via proteins and/or lipids present on the membranes. In some embodiments, the rehydrated platelets or platelet derivatives (e.g., thrombosomes), have less than about 10%, such as less than about 8%, such as less than about 6%, such as less than about 4%, such as less than about 2%, such as less than about 0.5% crosslinking of platelet membranes via proteins and/or lipids present on the membranes.

In some embodiments, rehydrating the composition comprising platelets or platelet derivatives comprises adding to the platelets or platelet derivatives sterile water (e.g., sterile water for injection) over about 10 minutes at about room temperature. In general, the rehydration volume is about equal to the volume used to fill each vial of platelet derivative composition prior to drying, for example, freeze-drying.

Process for Preparing a Platelet Derivative Composition

In some embodiments, the platelets or pooled platelets can be initially diluted, further diluted (e.g. if initially diluted in an acidified buffer) or suspended in a preparation agent as described herein before being loaded onto a TFF unit to exchange the solution, buffer or diluted preparation agent with a preparation agent in the TFF unit. A skilled artisan would understand that before being loaded onto a TFF unit, the input composition can be initially diluted to a desirable dilution in order to carry out the TFF process in an effective manner. In some embodiments, the platelets or pooled platelets comprised in a composition can be diluted with an acidified washing buffer for example, and/or with a preparation agent as described herein before loading onto a TFF unit. In some embodiments, the platelets or pooled platelets are diluted 1:0.5, 1:1, 1:2, 1:4, 1:5, or 1:10, in a preparation agent, which in illustrative embodiments is the preparation in which the platelets will be freeze dried. In illustrative embodiments, the platelets or the pooled platelets can be diluted or suspended in a preparation agent comprising trehalose and in illustrative embodiments polysucrose before being loaded onto a TFF unit, followed by performing TFF with the preparation agent in the TFF unit. In illustrative embodiments, the platelets or the pooled platelets can be diluted or suspended in a preparation agent comprising 0.4 to 35% trehalose and 2% to 8% polysucrose, before being loaded onto a TFF unit, followed by performing TFF with the preparation agent in the TFF unit. A skilled artisan would understand that performing TFF is a continuous process of fluid exchange between the preparation agent and the platelets or the pooled platelets. The preparation agent that is used to dilute or suspend the platelets or the pooled platelets before being loaded onto a TFF unit can be the same preparation agent that is used for performing the TFF or it can be a different solution (e.g., acidified washing buffer) typically that is compatible with processing viable platelets. In some embodiments, the preparation agent used to dilute or suspend the platelets or the pooled platelets before being loaded onto a TFF unit can have the same ingredients but differ in the concentration of the ingredients than the preparation agent used for performing the TFF. A skilled artisan would understand the extent of the difference, if at all needed, based upon the dilution required to perform the TFF.

In some embodiments, the platelets or pooled platelets may be acidified to a pH of about 5.5 to about 8.0 prior to TFF or being diluted with the preparation agent. In some embodiments, the method comprises acidifying the platelets to a pH of about 6.5 to about 6.9. In some embodiments, the method comprises acidifying the platelets to a pH of about 6.6 to about 6.8. In some embodiments, the method comprises acidifying the platelets to a pH of about 6.6 to 7.5. In some embodiments, the acidifying comprises adding to the pooled platelets a solution comprising Acid Citrate Dextrose (ACD).

In some embodiments, the platelets are isolated prior to the step comprising tangential flow filtration (TFF) or being diluted with the preparation agent. In some embodiments, the method further comprises isolating platelets by using centrifugation. In some embodiments, the centrifugation occurs at a relative centrifugal force (RCF) of about 1000×g to about 2000×g. In some embodiments, the centrifugation occurs at relative centrifugal force (RCF) of about 1300×g to about 1800×g. In some embodiments, the centrifugation occurs at relative centrifugal force (RCF) of about 1500×g. In some embodiments, the centrifugation occurs for about 1 minute to about 60 minutes. In some embodiments, the centrifugation occurs for about 10 minutes to about 30 minutes. In some embodiments, the centrifugation occurs for about 30 minutes.

In some embodiments, platelets are isolated, for example in a liquid medium, prior to treating a subject.

In some embodiments, platelets are donor-derived platelets. In some embodiments, platelets are obtained by a process that comprises an apheresis step. In some embodiments, platelets are pooled platelets.

In some embodiments, platelets are pooled from a plurality of donors. Such platelets pooled from a plurality of donors may be also referred herein to as pooled platelets. In some embodiments, the donors are more than 5, such as more than 10, such as more than 20, such as more than 50, such as up to about 100 donors. In some embodiments, the donors are from about 5 to about 100, such as from about 10 to about 50, such as from about 20 to about 40, such as from about 25 to about 35. Pooled platelets can be used to make any of the compositions described herein. The platelets can be pooled wherein the platelets are donated by human subjects. In some other embodiments, the donor can be a non-human animal. In some embodiments, the donor can be a canine subject. In some embodiments, the donor can be an equine subject. In some embodiments, the donor can be a feline subject.

In some embodiments, platelets are derived in vitro. In some embodiments, platelets are derived or prepared in a culture. In some embodiments, preparing the platelets comprises deriving or growing the platelets from a culture of megakaryocytes. In some embodiments, preparing the platelets comprises deriving or growing the platelets (or megakaryocytes) from a culture of human pluripotent stem cells (PSCs), including embryonic stem cells (ESCs) and/or induced pluripotent stem cells (iPSCs).

Accordingly, in some embodiments, platelets or platelet derivatives (e.g., thrombosomes) are prepared prior to treating a subject as described herein. In some embodiments, the platelets or platelet derivatives (e.g., thrombosomes) are lyophilized. In some embodiments, the platelets or platelet derivatives (e.g., thrombosomes) are cryopreserved. For example, in some embodiments, the platelets or platelet derivatives can be cryopreserved in plasma and DMSO (e.g., 3-9% DMSO (e.g., 6% DMSO)). In some embodiments, the platelets or platelet derivatives are cryopreserved as described in U.S. Patent Application Publication No. 2020/0046771 A1, published on Feb. 13, 2020, incorporated herein by reference in its entirety.

In some embodiments, platelets (e.g., apheresis platelet, platelets isolated from whole blood, pooled platelets, or a combination thereof) form a suspension in a preparation agent comprising a liquid medium at a concentration from 10,000 platelets/μL to 10,000,000 platelets/μL, such as 50,000 platelets/μL to 2,000,000 platelets/μL, such as 100,000 platelets/μL to 500,000 platelets/μL, such as 150,000 platelets/μL to 300,000 platelets/μL, such as 200,000 platelets/μL.

In some embodiments, the method further comprises drying the platelets or platelet derivatives (e.g., thrombosomes). In some embodiments, the drying step comprises lyophilizing the platelets or platelet derivatives (e.g., thrombosomes). In some embodiments, the drying step comprises freeze-drying the platelets or platelet derivatives (e.g., thrombosomes). In some embodiments, the method further comprises rehydrating the platelets or platelet derivatives (e.g., thrombosomes) obtained from the drying step.

In some embodiments, the platelets or platelet derivatives (e.g., thrombosomes) are cold stored, cryopreserved, or lyophilized (e.g., to produce thrombosomes) prior to use in therapy or in functional assays.

Any known technique for drying platelets can be used in accordance with the present disclosure, as long as the technique can achieve a final residual moisture content of less than 5%. Preferably, the technique achieves a final residual moisture content of less than 2%, such as 1%, 0.5%, or 0.1%. Non-limiting examples of suitable techniques are freeze-drying (lyophilization) and spray-drying. A suitable lyophilization method is presented in Table LA. Additional exemplary lyophilization methods can be found in U.S. Pat. Nos. 7,811,558, 8,486,617, and 8,097,403. An exemplary spray-drying method includes: combining nitrogen, as a drying gas, with a preparation agent according to the present disclosure, then introducing the mixture into GEA Mobile Minor spray dryer from GEA Processing Engineering, Inc. (Columbia MD, USA), which has a Two-Fluid Nozzle configuration, spray drying the mixture at an inlet temperature in the range of 150° C. to 190° C., an outlet temperature in the range of 65° C. to 100° C., an atomic rate in the range of 0.5 to 2.0 bars, an atomic rate in the range of 5 to 13 kg/hr, a nitrogen use in the range of 60 to 100 kg/hr, and a run time of 10 to 35 minutes. The final step in spray drying is preferentially collecting the dried mixture. The dried composition in some embodiments is stable for at least six months at temperatures that range from −20° C. or lower to 90° C. or higher.

TABLE LA

Exemplary Lyophilization Protocol

| | Step | Temp. Set | Type | Duration | Pressure Set |
|---|---|---|---|---|---|
| Freezing Step | F1 | −50° C. | Ramp | Var | N/A |
| | F2 | −50° C. | Hold | 3 Hrs | N/A |
| Vacuum Pulldown | F3 | −50° | Hold | Var | N/A |
| Primary Dry | P1 | −40° | Hold | 1.5 Hrs | 0 mT |
| | P | | | | 0 |
| | P2 | −35° | Ramp | 2 Hrs | 0 mT |
| | P3 | −25° | Ramp | 2 Hrs | 0 mT |
| | P4 | −17° C. | Ramp | 2 Hrs | 0 mT |
| | P5 | 0° C. | Ramp | 1.5 Hrs | 0 mT |
| | P6 | 27° C. | Ramp | 1.5 Hrs | 0 mT |
| | P7 | 27° C. | Hold | 16 Hrs | 0 mT |
| Secondary Dry | S1 | 27° C. | Hold | >8 Hrs | 0 mT |

In some embodiments, the step of drying the platelets or platelet derivatives (e.g., thrombosomes) that are obtained as disclosed herein, such as the step of freeze-drying the platelets and/or platelet derivatives that are obtained as disclosed herein, comprises incubating the platelet and/or platelet derivatives with a lyophilizing agent (e.g., a non-reducing disaccharide). Accordingly, in some embodiments, the methods for preparing platelets and/or platelet derivatives further comprises incubating the platelets with a lyophilizing agent. In some embodiments the lyophilizing agent is a saccharide. In some embodiments the saccharide is a disaccharide, such as a non-reducing disaccharide.

In some embodiments, the platelets and/or platelet derivatives are incubated with a lyophilizing agent for a sufficient amount of time and at a suitable temperature to incubate the platelets with the lyophilizing agent. Non-limiting examples of suitable lyophilizing agents are saccharides, such as monosaccharides and disaccharides, including sucrose, maltose, trehalose, glucose (e.g., dextrose), mannose, and xylose. In some embodiments, non-limiting examples of lyophilizing agent include serum albumin, dextran, polyvinyl pyrolidone (PVP), starch, and hydroxyethyl starch (HES). In some embodiments, exemplary lyophilizing agents can include a high molecular weight polymer. By "high molecular weight" it is meant a polymer having an average molecular weight of about or above 70 kDa and up to 1,000,000 kDa. Non-limiting examples are polymers of sucrose and epichlorohydrin (e.g., polysucrose). In some embodiments, the lyophilizing agent is polysucrose. Although any amount of high molecular weight polymer can be used as a lyophilizing agent, it is preferred that an amount be used that achieves a final concentration of about 3% to 10% (w/v), such as 3% to 7%, for example 6%. In some embodiments, polysucrose is used in the range of 2% to 8%%, or 2.25-7.75%, or 2.5-7.5%, or 2.5-6.5%. In an exemplary embodiment, the composition comprises 3% polysucrose. In another exemplary embodiment, the composition comprises 6% polysucrose. In some embodiments of the composition, wherein the composition comprises polysucrose, the polysucrose is a cationic form of polysucrose. In some embodiments, the cationic form of polysucrose is diethylaminoethyl (DEAE)-polysucrose. In some embodiments, the polysucrose is an anionic form of polysucrose. In some embodiments, the anionic form of polysucrose is carboxymethyl-polysucrose. In some embodiments of the composition, polysucrose has a molecular weight in the range of 70,000 Da to 400,000 Da. In some embodiments, polysucrose has a molecular weight in the range of 80,000 Da to 350,000 Da, or 100,000 Da to 300.00 Da. In some exemplary embodiments, polysucrose has a molecular weight in the range of 120,000 Da to 200,000 Da. In some exemplary embodiments, polysucrose has a molecular weight of 150,000 Da, or 160,000 Da, or 170,000 Da, or 180,000 Da, 190,000 Da, or 200,000 Da.

An exemplary saccharide for use in the compositions disclosed herein is trehalose. Regardless of the identity of the saccharide, it can be present in the composition in any suitable amount. For example, it can be present in an amount of 1 mM to 1 M. In embodiments, it is present in an amount of from 10 mM 10 to 500 mM. In some embodiments, it is present in an amount of from 20 mM to 200 mM. In embodiments, it is present in an amount from 40 mM to 100 mM. In some embodiments, the composition comprises trehalose in the range of 0.4-35%, or 1-35%, or 2-30%, or 1-10%, or 1-5%, or 0.5-5%. In an exemplary embodiment, the composition comprises 3.5% trehalose.

In various embodiments, the saccharide is present in different specific concentrations within the ranges recited above, and one of skill in the art can immediately understand the various concentrations without the need to specifically recite each herein. Where more than one saccharide is present in the composition, each saccharide can be present in an amount according to the ranges and particular concentrations recited above.

In some cases, preparation of thrombosomes further comprises one or more of the procedures described in U.S. Pat. No. 8,486,617 (such as, e.g., Examples 1-5) and U.S. Pat. No. 8,097,403 (such as, e.g., Examples 1-3), incorporated herein by reference in their entirety. In some cases, a starting material (e.g., one or more donor platelet units) are initially pooled into a common vessel. In some embodiments, a starting material can comprise one or more donor platelet units. In some embodiments, a starting material can comprise donor plasma. The starting material may or may not be acidified with an anti-coagulation buffer (i.e. ACD-A) before centrifugation. Plasma can be aspirated off of the platelet pellet after centrifugation. Cell compatible buffer containing cryoprotectants (e.g., a loading buffer, which can be similar to or the same as a preparation agent) can be added to the platelet pellet before resuspending the cells into suspension. Platelets may or may not be diluted to a pre-determined concentration (e.g., 2200 k/ul to 2800 k/ul) with buffer if desired. Platelets in buffer may be incubated between 0 minutes and 240 minutes at an incubation temperature from 18° C. to 37° C. A lyoprotectant bulking agent (e.g., polysucrose) can be added to the platelets in buffer to achieve a final bulking agent concentration from 1% to 10% w/v (with preference at 6% w/v). The centrifuged processed platelets can then be filled into vials, lyophilized and thermally treated.

Platelet Derivatives and Microparticles

Platelet derivatives herein have been observed to have numerous surprising properties, as disclosed in further detail herein. It will be understood, as illustrated in the Examples provided herein, that although platelet derivatives in some aspects and embodiments are in a solid, such as a powder form, the properties of such platelet derivatives can be identified, confirmed, and/or measured when a composition comprising such platelet derivatives is in liquid form.

A skilled artisan would be well-versed with different techniques that are available for measuring particle sizes of platelets, platelet derivatives or FDPDs, and microparticles. One such technique, in a non-limiting manner, that can be used for measuring particle sizes is flow cytometry. Flow Cytometry is a technique for quantifying characteristics of cells such as cell number, size and complexity, fluorescence, phenotype, and viability. In general, the forward scatter in a flow cytometry is located in line with the laser intercept and is typically considered a measure of the relative cell size. The side scatter is typically located perpendicular to the laser beam intercept and is used to measure the relative complexity of the cell. Commercially available sizing beads can be used to obtain the forward scatter values to calibrate the instrument in order to measure the sizes of the particles.

Liquid and dried compositions provided herein, in illustrative embodiments those prepared using freeze drying, and more specifically in some embodiments, prepared using methods provided herein, include particles that can be categorized broadly into populations based on at least one physical property, for example, but not limiting to, the size of the particles obtained. In some embodiments, the particles can be categorized into two populations based on size, typically in embodiments where exosomes are not present in detectable quantities, are not resolvable by the instrument analyzing particle size, and/or are not considered particles: For example, a first population comprising larger particles similar, or much more similar in size to in-dated stored platelets, which can be referred to herein as platelet derivatives, FDPDs, platelet-sized particles, a population of platelet derivatives with a size distribution centered around ~1,000 nm radius, or ~1,000 nm radius particles, and a second population comprising relatively smaller particles, which can be referred to herein as microparticles, a population of microparticles with a size distribution centered around ~50 nm radius, or ~50 nm radius particles (See e.g., FIG. 24A, FIG. 27B, or FIG. 28B where the main population of human in-dated stored platelets is centered at around 1,100 or 1,500 nm radius respectively, with a smaller (i.e. microparticle) peak at around 100 nm radius; and the particles in the FDPD composition (i.e. thrombosomes), which have a ~platelet-sized major peak with a radius of approximately 1,100 nm (FIG. 24A) or 1,000 nm (FIG. 27B and FIG. 28B) (i.e. platelet derivatives) and a microparticle radius peak at approximately 50-75 nm).

A skilled artisan would further understand that the sizes determined for such populations of particles may not always be accurate enough to provide an exact cut-off value/range between these two particle size peaks. However, the difference in the sizes of the two populations can be resolved reproducibly using known methods, for example, using flow cytometry, or by using a particle/cell counter. And approximate size values or size range values can be obtained using such techniques optionally with sizing standards. In some embodiments, a composition comprising platelet derivatives or FDPDs as described herein or prepared according to methods described herein. can have a population comprising platelet derivatives or FDPDs that includes between 95.1% to 99.9% of total particles in the composition, and the rest of the measurable particles, for example above 1 nm radius, can be microparticles. In some embodiments, platelet derivatives or FDPDs in such a composition can have a diameter of at least 0.4 μm (i.e., radius of at least 200 nm), and the microparticles in such a composition can have a diameter less than 0.4 μm (i.e., radius less than 200 nm). In other embodiments, platelet derivatives or FDPDs in such a composition can have a diameter of at least 0.5 μm (i.e., radius of at least 250 nm), and the microparticles in such a composition can have a diameter less than 0.5 μm (i.e., radius of less than 250 nm). In some embodiments, the platelet derivatives, or FDPDs can have a diameter of at least 0.4 μm, for example in the range of 0.5 μm to 22 μm (i.e., radius in the range of 200 nm or 250 nm to 11,000 nm), and the microparticles can have a diameter less than 0.5 μm (i.e., less than 250 nm radius), for example in the range of 0.04 μm to 0.350 μm (i.e., radius in the range of 20 nm to 175 nm). In some embodiments, the platelet derivatives, or FDPDs can have a diameter in the range of 1 μm to 18 μm (i.e., radius in the range of 500 nm to 9,000 nm), and the microparticles can have a diameter in the range of 0.06 μm to 0.2 μm (i.e., radius in the range of 30 nm to 100 nm). In some embodiments, the composition comprises platelet derivatives or FDPDs, and microparticles as the only or essentially the only particles present in the composition, optionally or typically other than exosomes, in embodiments where exosomes are not present in detectable quantities, are not resolvable by the instrument analyzing particle size, and/or are not considered particles. Of course, a composition as described herein may comprise any specific percentage number, or fraction thereof, of platelet derivatives, FDPDs or microparticles within the ranges discussed herein.

In some embodiments, the platelets or platelet derivatives (e.g., thrombosomes) have a particle size, for example a diameter, max dimension, or radius of at least about 0.5 μm (e.g., at least about at least about 0.6 μm, at least about 0.7 μm, at least about 0.8 μm, at least about 0.9 μm, at least about 1.0 μm, at least about 1.2 μm, at least about 1.5 μm, at least about 2.0 μm, at least about 2.5 μm, or at least about 5.0 μm). In some embodiments, the particle size, for example the diameter, max dimension, or radius, is less than about 5.0 μm (e.g., less than about 2.5 μm, less than about 2.0 μm, less than about 1.5 μm, less than about 1.0 μm, less than about 0.9 μm, less than about 0.8 μm, less than about 0.7 μm, less than about 0.6 μm, less than about 0.5 μm, less than about 0.4 μm, or less than about 0.3 μm). From this disclosure, it will be apparent that microparticles typically have a size of less than 250 nm radius (i.e. less than 500 nm diameter). In some embodiments, the particle size is from about 0.5 μm to about 5.0 μm (e.g., from about 0.5 μm to about 4.0 μm, from about 0.5 μm to about 2.5 μm, from about 0.6 μm to about 2.0 μm, from about 0.7 μm to about 1.0 μm, from about 0.5 μm to about 0.9 μm, or from about 0.6 μm to about 0.8 μm).

In some embodiments, at least 50% (e.g., at least about 55%, at least about 60%, at least about 65%, at least about 70%, at least about 75%, at least about 80%, at least about 85%, at least about 90%, at least about 95%, or at least about 99%) of platelets or platelet derivatives (e.g., thrombosomes), have a particle size of at least 0.5 μm, for example in the range of about 0.5 μm to about 25.0 μm, 20.0 μm, 15.0 μm, 12.5 μm, 10.0 μm, or 5.0 μm (e.g., from about 0.5 μm to about 4.0 μm, from about 0.5 μm to about 2.5 μm, from about 0.6 μm to about 2.0 μm, from about 0.7 μm to about 1.0 μm, from about 0.5 μm to about 0.9 μm, or from about 0.6 μm to about 0.8 μm). In some embodiments, at most 99% (e.g., at most about 95%, at most about 80%, at most about 75%, at most about 70%, at most about 65%, at most about 60%, at most about 55%, or at most about 50%) of the platelets or platelet derivatives (e.g., thrombosomes), are in the range of about 0.5 μm to about 5.0 μm (e.g., from about 0.5 μm to about 4.0 μm, from about 0.5 μm to about 2.5 μm, from about 0.6 μm to about 2.0 μm, from about 0.7 μm to about 1.0 μm, from about 0.5 μm to about 0.9 μm, or from about 0.6 μm to about 0.8 μm). In some embodiments, about 50% to about 99% (e.g., about 55% to about 95%, about 60% to about 90%, about 65% to about 85, about 70% to about 80%) of the platelets or platelet derivatives (e.g., thrombosomes) are in the range of about 0.5 μm to about 5.0 μm (e.g., from about 0.5 μm to about 4.0 μm, from about 0.5 μm to about 2.5 μm, from about 0.6 μm to about 2.0 μm, from about 0.7 μm to about 1.0 μm, from about 0.5 μm to about 0.9 μm, or from about 0.6 μm to about 0.8 μm).

In some illustrative embodiments, a microparticle can be a particle having a particle size (e.g., diameter, max dimension) of less than about 0.5 μm (less than about 0.45 μm or 0.4 μm) In some cases, a microparticle can be a particle having a particle size of about 0.01 μm to about 0.5 μm (e.g., about 0.02 μm to about 0.5 μm).

Compositions comprising platelets or platelet derivatives (e.g., thrombosomes), such as those prepared according to methods described herein, can have a microparticle content that contributes to less than about 5.0% (e.g., less than about 4.5%, 4.0%, 3.5%, 3.0%, 2.5%, 2.0%, 1.5%, 1.0%, 0.5%, or 0.1%) of the total scattering intensity of all particles from about 1 nm to about 60,000 nm in radius in the composition. In some embodiments, the platelet derivative composition comprises a population of platelet derivatives comprising CD41-positive platelet derivatives, wherein less than 15%, 10%, 7.5%, 5%, 4.5%, 4%, 3.5%, 3%, 2.5%, 2%, 1.5%, 1%, 0.5%, or 0.1% of the CD41-positive platelet derivatives are microparticles having a diameter of less than 1 μm, 0.9 μm, 0.8 μm, 0.7 μm, 0.6 μm, 0.5 μm, 0.4 μm, 0.3 μm, 0.2 μm, or 0.1 μm, which in certain illustrative embodiments are less than 0.5 μm. In some embodiments, the platelet derivative composition comprises a population of platelet derivatives comprising CD42-positive platelet derivatives, wherein less than 15%, 10%, 7.5%, 5%, 4.5%, 4%, 3.5%, 3%, 2.5%, 2%, 1.5%, 1%, 0.5%, or 0.1% of the CD42-positive platelet derivatives are microparticles having a diameter of less than 1 μm, 0.9 μm, 0.8 μm, 0.7 μm, 0.6 μm, 0.5 μm, 0.4 μm, 0.3 μm, 0.2 μm, or 0.1 μm, which in certain illustrative embodiments are less than 0.5 μm. In some embodiments, the platelet derivative composition comprises a population of platelet derivatives comprising CD61-positive platelet derivatives, wherein less than 15%, 10%, 7.5, 5%, 4.5%, 4%, 3.5%, 3%, 2.5%, 2%, 1.5%, 1%, 0.5%, or 0.1% of the CD61-positive platelet derivatives are microparticles having a diameter of less than 1 μm, 0.9 μm, 0.8 μm, 0.7 μm, 0.6 μm, 0.5 μm, 0.4 μm, 0.3 μm, 0.2 μm, or 0.1 μm, which in certain illustrative embodiments are less than 0.5 μm. In some illustrative embodiments, the microparticles have a diameter of less than 0.5 μm. In some embodiments of any of the aspects and embodiments herein that include a platelet derivative composition in a powdered form, the diameter of the microparticles is determined after rehydrating the platelet derivative composition with an appropriate solution. In some embodiments, the amount of solution for rehydrating the platelet derivative composition is equal to the amount of buffer or preparation agent present at the step of freeze-drying. As used herein, a content of microparticles "by scattering intensity" refers to the microparticle content based on the scattering intensity of all particles from about 1 nm to about 60,000 nm in radius in the composition. The microparticle content can be measured by any appropriate method, for example, by dynamic light scattering (DLS). In some cases, the viscosity of a sample used for DLS can be at about 1.060 cP (or adjusted to be so), as this is the approximate viscosity of plasma. In some embodiments, the platelet derivative composition as per any aspects, or embodiments comprises a population of platelet derivatives, and microparticles, wherein the numerical ratio of platelet derivatives to the microparticles is at least 90:1, 91:1, 92:1, 93:1, 94:1, 95:1, 96:1, 97:1, 98:1, or 99:1. In some embodiments, the platelet derivatives have a diameter in the range of 0.5-2.5 μm, and the microparticles have a diameter less than 0.5 μm.

Platelets or platelet derivatives (e.g., thrombosomes) as described herein can have cell surface markers. The presence of cell surface markers can be determined using any appropriate method. In some embodiments, the presence of cell surface markers can be determined using binding proteins (e.g., antibodies) specific for one or more cell surface markers and flow cytometry (e.g., as a percent positivity, e.g., using approximately $2.7\times10^5$ thrombosomes/μL; and about 4.8 μL of an anti-CD41 antibody, about 3.3 μL of an anti-CD42 antibody, about 1.3 μL of annexin V, or about 2.4 μL of an anti-CD62 antibody). Non-limiting examples of cell-surface markers include CD41 (also called glycoprotein IIb or GPIIb, which can be assayed using e.g., an anti-CD41 antibody), CD42 (which can be assayed using, e.g., an anti-CD42 antibody), CD62 (also called CD62P or P-selectin, which can be assayed using, e.g., an anti-CD62 antibody), phosphatidylserine (which can be assayed using, e.g., annexin V (AV)), and CD47 (which is used in self-recognition; absence of this marker, in some cases, can lead to phagocytosis). The percent positivity of any cell surface marker can be any appropriate percent positivity. For example, platelets or platelet derivatives (e.g., thrombosomes), such as those prepared by methods described herein, can have an average CD41 percent positivity of at least 55% (e.g., at least 60%, at least 65%, at least 67%, at least 70%, at least 75%, at least 80%, at least 85%, at least 90%, or at least 95%). In some embodiments, at least 90%, 91%, 92%, 93%, 94%, 95%, 96%, 97%, 98%, 99% platelet derivatives that are positive for CD 41 have a size in the range of 0.5-2.5 μm. In some embodiments, at least 90%, 91%, 92%, 93%, 94%, 95%, 96%, 97%, 98%, or 99% platelet derivatives that are positive for CD 41 have a size in the range of 0.4-2.8 μm. In some embodiments, at least 90%, 91%, 92%, 93%, 94%, 95%, 96%, 97%, 98%, or 99% platelet derivatives that are positive for CD 41 have a size in the range of 0.3-3 μm.

As another example, platelets or platelet derivatives (e.g., thrombosomes), such as those described herein, can have an average CD42 percent positivity of at least 65% (e.g., at least 67%, at least 70%, at least 75%, at least 80%, at least 85%, at least 90%, or at least 95%). In some embodiments, platelets or platelet derivatives can have an average CD42 percent positivity of at least 76%, 77%, 78%, or 79%. In some embodiments, platelets or platelet derivatives can have an average CD42 percent positivity in the range of 76-95%, 76-94%, 77-93%, or 78-90%. In some embodiments, at least 90%, 91%, 92%, 93%, 94%, 95%, 96%, 97%, 98%, or 99% platelet derivatives that are positive for CD 42 have a size in the range of 0.5-2.5 μm. In some embodiments, at least 90%, 91%, 92%, 93%, 94%, 95%, 96%, 97%, 98%, or 99% platelet derivatives that are positive for CD 42 have a size in the range of 0.4-2.8 μm. In some embodiments, at least 90%, 91%, 92%, 93%, 94%, 95%, 96%, 97%, 98%, or 99% platelet derivatives that are positive for CD 42 have a size in the range of 0.3-3 μm.

As another example, platelets or platelet derivatives (e.g., thrombosomes), such as those prepared by methods described herein, can have an average CD62 percent positivity of at least 10% (e.g., at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 83%, at least 84%, at least 85%, at least 90%, or at least 95%). In some embodiments, at least 70%, 75%, 80%, 85%, 90%, 91%, 92%, 93%, 94%, 95%, 96%, 97%, 98%, or 99% platelet derivatives that are positive for CD 62 have a size in the range of 0.5-2.5 μm. In some embodiments, at least 70%, 75%, 80%, 85%, 90%, 91%, 92%, 93%, 94%, 95%, 96%, 97%, 98%, or 99% platelet derivatives that are positive for CD 62 have a size in the range of 0.4-2.8 μm. In some embodiments, at least 70%, 75%, 80%, 85%, 90%, 91%, 92%, 93%, 94%, 95%, 96%, 97%, 98%, or 99% platelet derivatives that are positive for CD 62 have a size in the range of 0.3-3 μm.

As yet another example, platelets or platelet derivatives (e.g., thrombosomes), such as those prepared by methods described herein, can have an average annexin V positivity of at least 25% (e.g., at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, or at least 99%). In some embodiments, at least 90%, 91%, 92%, 93%, 94%, 95%, 96%, 97%, 98%, 99% platelet derivatives that are positive for annexin V have a size in the range of 0.5-2.5 μm. In some embodiments, at least 90%, 91%, 92%, 93%, 94%, 95%, 96%, 97%, 98%, or 99% platelet derivatives that are positive for annexin V have a size in the range of 0.4-2.8 μm. In some embodiments, at least 90%, 91%, 92%, 93%, 94%, 95%, 96%, 97%, 98%, or 99% platelet derivatives that are positive for annexin V have a size in the range of 0.3-3 μm.

In some embodiments, the platelet derivatives as described herein are activated to a maximum extent such that in the presence of an agonist, the platelet derivatives are not able to show an increase in the platelet activation markers on them as compared to the level of the platelet activation markers which were present prior to the exposure with the agonist. In some embodiments, the platelet derivatives as described herein show an inability to increase expression of a platelet activation marker in the presence of an agonist as compared to the expression of the platelet activation marker in the absence of an agonist. In some embodiments, the agonist is selected from the group consisting of collagen, epinephrine, ristocetin, arachidonic acid, adenosine di-phosphate, and thrombin receptor associated protein (TRAP). In some embodiments, the platelet activation marker is selected from the group consisting of Annexin V, and CD 62. In some embodiments, the platelet derivatives as described herein show an inability to increase expression of Annexin V in the presence of TRAP. An increased amount of the platelet activation markers on the platelets indicates the state of activeness of the platelets. However, in some embodiments, the platelet derivatives as described herein are not able to increase the amount of the platelet activation markers on them even in the presence of an agonist. This property indicates that the platelet derivatives as described herein are activated to a maximum extent. In some embodiments, the property can be beneficial where maximum activation of platelets is required, because the platelet derivatives as described herein is able to show a state of maximum activation in the absence of an agonist.

As another example, platelets or platelet derivatives (e.g., thrombosomes), such as those prepared by methods described herein, can have an average CD47 percent positivity of at least about 8% (e.g., at least about 10%, 15%, 20%, 25%, 30%, 35%, 40%, 45%, 50%, or 55%).

Glycoprotein VI (GPVI) is a platelet receptor for collagen, and the binding of collagen to GVPI activates the platelet. Receptor binding can be noticeably reduced in thrombosomes compared to fresh platelets. Without being bound by any particular theory, it is believed that the manufacturing process is blocking or destroying some copies of this receptor in thrombosomes, possibly to a reduction in collagen binding in thrombosomes relative to fresh platelets.

Platelets or platelet derivatives (e.g., thrombosomes) as described herein can have fibrinogen associated with the cell membrane. Aggregation of activated platelets is mediated by the formation of the GPIIb/IIIa complex, which can bind to fibrinogen (also called Factor 1) and form a clot. GPIIb/IIIa is a platelet fibrinogen receptor also known as CD41/CD61 complex. The GPIIb/IIIa clone PAC-1 binds to the active form of the GPIIb/IIIa. Without being bound by any particular theory, it is believed that the presence of fibrinogen on the cell membrane may be indicative of platelets or platelet derivatives (e.g., thrombosomes) capable of forming clots. Similarly, without being bound by any particular theory, it is believed that a lack of binding by anti-PAC1 antibodies to the platelets or platelet derivatives (e.g., thrombosomes), such as those prepared by methods described herein, can be indicative of fibrinogen bound to the active form of GPIIb/GPIIIa, as PAC-1 binds to the same complex. In some cases, platelets or platelets derivatives (e.g., thrombosomes), such as those prepared by methods described herein, can have a greater amount of bound fibrinogen when they retain a higher amount of residual plasma. In some embodiments of a platelet derivative composition as described herein, the platelet derivatives can have an amount of fibrinogen on their surface that is greater than that present on the surface of resting platelets, activated platelets, or lyophilized fixed platelets. In some embodiments, the platelet derivatives have at least 25%, 30%, 35%, 40%, 45%, 50%, 55%, 60%, 65%, 70%, 75%, 80%, 85%, 90%, 95%, or 100% higher fibrinogen on their surface as compared to resting platelets, or activated platelets, or fixed platelets. In some embodiments, the platelet derivatives when analyzed for the binding of anti-fibrinogen antibody to the platelet derivatives using flow cytometry exhibit at least 2 folds higher mean fluorescent intensity (MFI) in the absence of an agonist as compared to the MFI of binding of anti-fibrinogen antibody to the lyophilized fixed platelets. In some embodiments, the platelet derivatives when analyzed for the binding of anti-fibrinogen antibody to the platelet derivatives using flow cytometry exhibit at least 10, 15, 20, 25, 30, 35, or 40 folds higher mean fluorescent intensity (MFI) in the absence of an agonist as compared to the MFI of binding of anti-fibrinogen antibody to the fixed platelets. In some embodiments, the greater amount of fibrinogen present on the surface of the platelet derivatives as described herein as compared to that of lyophilized fixed platelets is beneficial. Without being bound by any particular theory, it is believed that the higher amount of fibrinogen on the cell membrane of the platelet derivatives (e.g., thrombosomes) as compared to that of lyophilized fixed platelets can make the platelet derivatives superior in terms of its ability to form clots as compared to lyophilized fixed platelets.

Von Willebrand factor (vWF) is a multimeric glycoprotein that plays a major role in blood coagulation. vWF serves as a bridging molecule that promotes platelet binding to subendothelium and other platelets, thereby promoting platelet adherence and aggregation. vWF also binds to collagens to facilitate clot formation at sites of injury. In some embodiments, the platelet derivatives as described herein have the presence of von Willebrand factor (vWF) on their surface at a level that is greater than that on the surface of resting platelets, activated platelets, or lyophilized fixed platelets. In some embodiments, the platelet derivatives have the presence of von Willebrand factor (vWF) on their surface at a level that is at least 10%, 20%, 25%, 30%, 50%, 60%, 70%, 80%, 90%, or 100% higher than on the surface of resting platelets, or lyophilized fixed platelets. In some embodiments, the platelet derivatives when analyzed for the binding of anti-von Willebrand factor (vWF) antibody to the platelet derivatives using flow cytometry exhibits at least 1.5 folds, 2 folds, or 3 folds, or 4 folds higher mean fluorescent intensity (MFI) in the absence of an agonist as compared to the MFI of binding of anti-vWF antibody to the resting platelets, or lyophilized fixed platelets. In some embodiments, the platelet derivatives when analyzed for the binding of anti-von Willebrand factor (vWF) antibody to the platelet derivatives using flow cytometry exhibits 2-4 folds, or 2.5-3.5 higher mean fluorescent intensity (MFI) in the absence of an agonist as compared to the MFI of binding of anti-vWF antibody to the resting platelets, or lyophilized fixed platelets.

Thrombospondin is a glycoprotein secreted from the α-granules of platelets upon activation. In the presence of divalent cations, the secreted protein binds to the surface of the activated platelets and is responsible for the endogenous lectin-like activity associated with activated platelets. In some embodiments, the platelet derivatives have the presence of thrombospondin (TSP-1) on their surface at a level that is greater than that presence on the surface of resting platelets, activated platelets, or lyophilized fixed platelets. In some embodiments, the platelet derivatives have the presence of thrombospondin (TSP-1) on their surface at a level that is at least 10%, 20%, 25%, 30%, 50%, 60%, 70%, 80%, 90%, or 100% higher than on the surface of resting platelets, or lyophilized fixed platelets. In some embodiments, the platelet derivatives have the presence of thrombospondin (TSP-1) on their surface at a level that is more than 100% higher than on the surface of resting platelets, or lyophilized fixed platelets. In some embodiments, the platelet derivatives when analyzed for the binding of anti-thrombospondin (TSP) antibody to the platelet derivatives using flow cytometry exhibit at least 2 folds, 5 folds, 7 folds, 10 folds, 20 folds, 30 folds, 40 folds, 50 folds, 60 folds, 70 folds, 80 folds, 90 folds, or 100 folds higher mean fluorescent intensity (MFI) in the absence of an agonist as compared to the MFI of binding of anti-TSP antibody to the resting platelets. In some embodiments, the platelet derivatives when analyzed for the binding of anti-thrombospondin (TSP) antibody to the platelet derivatives using flow cytometry exhibit at least 2 folds, 5 folds, 7 folds, 10 folds, 20 folds, 30 folds, or 40 folds higher mean fluorescent intensity (MFI) in the absence of an agonist as compared to the MFI of binding of anti-TSP antibody to the lyophilized fixed platelets. In some embodiments, the platelet derivatives when analyzed for the binding of anti-thrombospondin (TSP) antibody to the platelet derivatives using flow cytometry exhibit 10-800 folds, 20-800 folds, 100-700 folds, 150-700 folds, 200-700 folds, or 250-500 folds higher mean fluorescent intensity (MFI) in the absence of an agonist as compared to the MFI of binding of anti-TSP antibody to the resting platelets. In some embodiments, the platelet derivatives when analyzed for the binding of anti-thrombospondin (TSP) antibody to the platelet derivatives using flow cytometry exhibit at least 2 folds, 5 folds, 7 folds, 10 folds, 20 folds, 30 folds, or 40 folds higher mean fluorescent intensity (MFI) in the absence of an agonist as compared to the MFI of binding of anti-TSP antibody to the active platelets. In some embodiments, the platelet derivatives when analyzed for the binding of anti-thrombospondin (TSP) antibody to the platelet derivatives using flow cytometry exhibit 2-40 folds, 5-40 folds, 5-35 folds, 10-35 folds, or 10-30 folds higher mean fluorescent intensity (MFI) in the absence of an agonist as compared to the MFI of binding of anti-TSP antibody to the active platelets.

Platelets or platelet derivatives (e.g., thrombosomes) as described herein can be capable of generating thrombin, for example, when in the presence of a reagent containing tissue factor and phospholipids. For example, in some cases, platelets or platelet derivatives (e.g., thrombosomes) (e.g., at a concentration of about $4.8\times10^3$ particles/μL) as described herein can generate a thrombin peak height (TPH) of at least 25 nM (e.g., at least 30 nM, 35 nM, 40 nM, 45 nM, 50 nM, 52 nM, 54 nM, 55 nM, 56 nM, 58 nM, 60 nM, 65 nM, 70 nM, 75 nM, or 80 nM) when in the presence of a reagent containing tissue factor (e.g., at 0.25 pM, 0.5 pM, 1 pM, 2 pM, 5 pM or 10 pM) and optionally phospholipids. For example, in some cases, platelets or platelet derivatives (e.g., thrombosomes) (e.g., at a concentration of about $4.8\times10^3$ particles/μL) as described herein can generate a TPH of about 25 nM to about 100 nM (e.g., about 25 nM to about 50 nM, about 25 to about 75 nM, about 50 to about 100 nM, about 75 to about 100 nM, about 35 nM to about 95 nM, about 45 to about 85 nM, about 55 to about 75 nM, or about 60 to about 70 nM) when in the presence of a reagent containing tissue factor and (e.g., at 0.25 pM, 0.5 pM, 1 pM, 2 pM, 5 pM or 10 pM) and optionally phospholipids. In some cases, platelets or platelet derivatives (e.g., thrombosomes) (e.g., at a concentration of about $4.8\times10^3$ particles/μL) as described herein can generate a TPH of at least 25 nM (e.g., at least 30 nM, 35 nM, 40 nM, 45 nM, 50 nM, 52 nM, 54 nM, 55 nM, 56 nM, 58 nM, 60 nM, 65 nM, 70 nM, 75 nM, or 80 nM) when in the presence of PRP Reagent (cat #TS30.00 from Thrombinoscope), for example, using conditions comprising 20 μL of PRP Reagent and 80 μL of a composition comprising about $4.8\times10^3$ particles/μL of platelets or platelet derivatives (e.g., thrombosomes). In some cases, platelets or platelet derivatives (e.g., thrombosomes) (e.g., at a concentration of about $4.8\times10^3$ particles/μL) as described herein can generate a TPH of about 25 nM to about 100 nM (e.g., about 25 nM to about 50 nM, about 25 to about 75 nM, about 50 to about 100 nM, about 75 to about 100 nM, about 35 nM to about 95 nM, about 45 to about 85 nM, about 55 to about 75 nM, or about 60 to about 70 nM) when in the presence of PRP Reagent (cat #TS30.00 from Thrombinoscope), for example, using conditions comprising 20 μL of PRP Reagent and 80 μL of a composition comprising about $4.8\times10^3$ particles/μL of platelets or platelet derivatives (e.g., thrombosomes).

Platelets or Platelet derivatives (e.g., thrombosomes) as described herein can be capable of generating thrombin, for example, when in the presence of a reagent containing tissue factor and phospholipids. For example, in some cases, platelets or platelet derivatives (e.g., thrombosomes) can have a potency of at least 1.2 (e.g., at least 1.3, 1.4, 1.5, 1.6, 1.7, 1.8, 1.9, 2.0, 2.1, 2.2, 2.3, 2.4, or 2.5) thrombin generation potency units (TGPU) per $10^6$ particles. For example, in some cases, platelets or platelet derivatives (e.g., thrombosomes) can have a potency of between 1.2 and 2.5 TPGU per $10^6$ particles (e.g., between 1.2 and 2.0, between 1.3 and 1.5, between 1.5 and 2.25, between 1.5 and 2.0, between 1.5 and 1.75, between 1.75 and 2.5, between 2.0 and 2.5, or between 2.25 and 2.5 TPGU per $10^6$ particles). TPGU can be calculated as follows: TGPU/million particles=[TPH in nM]*[Potency Coefficient in IU/(nM)]/[0.576 million particles in the well]. Similarly, the Potency Coefficient for a sample of thrombin can be calculated as follows: Potency Coefficient=Calculated Calibrator Activity (IU)/Effective Calibrator Activity (nM). In some cases, the calibrator activity can be based on a WHO international thrombin standard.

Platelets or platelet derivatives (e.g., thrombosomes) as described herein can be capable of clotting, as determined, for example, by using a total thrombus-formation analysis system (T-TAS®). In some cases, platelets or platelet derivatives as described herein, when at a concentration of at least $70\times10^3$ particles/μL (e.g., at least $73\times10^3$, $100\times10^3$, $150\times10^3$, $173\times10^3$, $200\times10^3$, $250\times10^3$, or $255\times10^3$ particles/μL) can result in a T-TAS occlusion time (e.g., time to reach kPa of 80) of less than 14 minutes (e.g., less than 13.5, 13, 12.5, 12, 11.5, or 11 minutes), for example, in platelet-reduced citrated whole blood. In some cases, platelets or platelet derivatives as described herein, when at a concentration of at least $70\times10^3$ particles/μL (e.g., at least $73\times10^3$, $100\times10^3$, $150\times10^3$, $173\times10^3$, $200\times10^3$, $250\times10^3$, or $255\times10^3$ particles/μL) can result in an area under the curve (AUC) of at least 1300 (e.g., at least 1380, 1400, 1500, 1600, or 1700), for example, in platelet-reduced citrated whole blood.

Platelets or platelet derivatives (e.g., thrombosomes) as described herein can be capable of thrombin-induced trapping in the presence of thrombin. In some cases, platelets or platelet derivatives (e.g., thrombosomes) as described herein can have a percent thrombin-induced trapping of at least 5% (e.g., at least 10%, 15%, 20%, 25%, 30%, 35%, 40%, 45%, 50%, 55%, 60%, 65%, 67%, 70%, 75%, 85%, 90%, or 99%) in the presence of thrombin. In some cases, platelets or platelet derivatives (e.g., thrombosomes) as described herein can have a percent thrombin-induced trapping of about 25% to about 100% (e.g., about 25% to about 50%, about 25% to about 75%, about 50% to about 100%, about 75% to about 100%, about 40% to about 95%, about 55% to about 80%, or about 65% to about 75%) in the presence of thrombin. Thrombin-induced trapping can be determined by any appropriate method, for example, light transmission aggregometry. Without being bound by any particular theory, it is believed that the thrombin-induced trapping is a result of the interaction of fibrinogen present on the surface of the platelet derivatives with thrombin.

Platelets or platelet derivatives (e.g., thrombosomes) as described herein can be capable of co-aggregating, for example, in the presence of an aggregation agonist, and fresh platelets. Non-limiting examples of aggregation agonists include, collagen, epinephrine, ristocetin, arachidonic acid, adenosine di-phosphate, and thrombin receptor associated protein (TRAP). In some cases, platelets or platelet derivatives (e.g., thrombosomes) as described herein can have a percent co-aggregation of at least 5% (e.g., at least 10%, 15%, 20%, 25%, 30%, 35%, 40%, 45%, 50%, 55%, 60%, 65%, 67%, 70%, 75%, 85%, 90%, or 99%) in the presence of an aggregation agonist, and fresh platelets. In some cases, platelets or platelet derivatives (e.g., thrombosomes) as described herein can have a percent co-aggregation of about 25% to about 100% (e.g., about 25% to about 50%, about 25% to about 75%, about 50% to about 100%, about 75% to about 100%, about 40% to about 95%, about 55% to about 80%, or about 65% to about 75%) in the presence of an aggregation agonist. Percent co-aggregation can be determined by any appropriate method, for example, light transmission aggregometry.

Platelet derivative compositions in certain illustrative embodiments herein, comprise a population of platelet derivatives having a reduced propensity to aggregate under aggregation conditions comprising an agonist but no fresh platelets, compared to the propensity of fresh platelets and/or activated to aggregate under these conditions. Platelets or platelet derivatives (e.g., thrombosomes) as described herein in illustrative embodiments, display a reduced propensity to aggregate under aggregation conditions comprising an agonist but no fresh platelets, compared to the propensity of fresh platelets and/or activated to aggregate under these conditions. It is noteworthy that aggregation of platelet derivatives is different from co-aggregation in that aggregation conditions typically do not include fresh platelets, whereas co-aggregation conditions include fresh platelets. Exemplary aggregation and co-aggregation conditions are provided in the Examples herein. Thus, in some embodiments, the platelet derivatives as described herein have a higher propensity to co-aggregate in the presence of fresh platelets and presence of an agonist, while having a reduced propensity to aggregate in the absence of fresh platelets and presence of an agonist, compared to the propensity of fresh platelets to aggregate under these conditions. In some embodiments, a platelet derivative composition comprises a population of platelet derivatives having a reduced propensity to aggregate, wherein no more than 1%, 2%, 3%, 4%, 5%, 7.5%, 10%, 12.5%, 15%, 17.5%, 20%, 22.5%, or 25% of the platelet derivatives in the population aggregate under aggregation conditions comprising an agonist but no platelets, in illustrative embodiments no fresh platelets. In some embodiments, the population of platelet derivatives aggregate in the range of 0-1%, 0-2%, 0-3%, 0-4%, 0-5%, 0-7.5%, 0-10%, 2-30%, 5-25%, 10-30%, 10-25%, or 12.5-25%, and in illustrative embodiments 0-1% or 0 to about 1%, of the platelet derivatives under aggregation conditions comprising an agonist but no platelets, in illustrative embodiments no fresh platelets. In these and other illustrative embodiments the agonist is other than arachidonic acid. It will be understood that if an aggregation reaction control sample produces a background aggregation above 0% then aggregation values/ranges for FDPDs disclosed herein would be increased by the background value obtained with the control sample. Thus, if a background aggregation produced using a control sample was 1%, then the above ranges would be increased by 1% (e.g., 1-2%, 1-3%, 1-4%, 1-5%, 1-6%, 1-8.5%, and 1-11% etc.). Accordingly, in some embodiments, the values and ranges provided herein for aggregation are values above background values, for example obtained using a control sample or no sample, and thus can be referred to control-corrected, or control-adjusted aggregation values. In some embodiments, a platelet derivative composition comprises a population of platelet derivatives having a reduced propensity to aggregate, such that less than ⅕, 1/10, or 1/20 of the platelet derivatives in the population aggregate under aggregation conditions comprising an agonist but no platelets, compared to platelet rich plasma, in illustrative embodiments prepared from fresh platelets.

Compositions comprising platelets or platelet derivatives (e.g., thrombosomes) as described herein can have appropriate conditions and amounts of cellular substrates and/or metabolites, such as pH, $pCO_2$, $pO_2$, $HCO_3$ concentration, total carbon dioxide ($TCO_2$), $sO_2$, and lactate concentration. Lactate can be the products of glycolysis. Without being bound by any particular theory, a starting material can have high lactate concentration because it has been stored ex vivo, respirating and performing glycolysis, for a period of time (e.g., about 3 days) by the time of manufacturing. For example, in some cases, the pH can be about 5.5 to about 8.0 (e.g., about 6.0 to about 7.4, about 6.9 to about 7.5, or about 7.0 to about 7.3). As another example, the $pCO_2$ can be about 10 to about 20 mmHg (e.g., about 10 to about 15 mmHg, about 15 to about 20 mmHg, or about 17 to about 19 mmHg). The $pO_2$ can be about 140 to about 165 mmHg (e.g., about 140 to about 150 mmHg, about 150 to about 160 mmgH, or about 160 to about 165 mmHg). The $HCO_3$ concentration can be about 4.5 to about 6.5 mmol/L (e.g., about 5.0 to about 6.0 mmol/L). The total carbon dioxide can be about 4 to about 8 mmol/L (e.g., about 5 to about 7 mmol/L). The s02 can be at least about 98% (e.g., at least about 99%). The lactate concentration can be less than about 2.0 mmol/L (e.g., less than 1.5 mmol/L or 1.0 mmol/L). The lactate concentration can be about 0.4 to about 1.3 mmol/L (e.g., about 0.5 to about 0.6 mmol/L, about 0.5 to about 1.0 mmol/L, or about 0.8 to about 1.3 mmol/L).

Membrane Integrity of the Platelet Derivatives

Platelet derivatives in certain illustrative aspects and embodiments herein are surrounded by a compromised plasma membrane. In these illustrative aspects and embodiments, the platelet derivatives lack an integrated membrane around them. Instead, the membrane has pores on them that are larger than pores observed on living cells. Not to be limited by theory, it is believed that in embodiments where platelet derivatives have a compromised membrane, such platelet derivatives have a reduced ability to, or are unable to transduce signals from the external environment into a response inside the particle that are typically transduced in living platelets. A compromised membrane can be identified through a platelet derivative's inability to retain more than 50% of lactate dehydrogenase (LDH) as compared to fresh platelets, or cold stored platelets, or cryopreserved platelets. In some embodiments, the platelet derivatives are incapable of retaining more than 35%, 40%, 45%, 50%, 55%, 60%, 65%, 70%, or 75% of lactate dehydrogenase as compared to lactate dehydrogenase retained in fresh platelets, or cold stored platelets, or cryopreserved platelets. In some embodiments, the platelet derivatives exhibit an increased permeability to antibodies. In some embodiments, the antibodies can be IgG antibodies. The increased permeability can be identified by targeting IgG antibodies against a stable intracellular antigen. One non-limiting type of stable intracellular antigen is tubulin. The compromised membrane of the platelet derivatives can also be determined by flow cytometry studies.

Platelet or platelet derivatives (e.g., thrombosomes) as described herein can retain some metabolic activity, for example, as evidenced by lactate dehydrogenase (LDH) activity. In some cases, platelets or platelet derivatives (e.g., thrombosomes) as described herein can retain at least about 10% (e.g., at least about 12%, 15%, 20%, 25%, 30%, 35%, 40%, or 45%) of the LDH activity of donor apheresis platelets. Without being bound by any particular theory, it is believed that the addition of increasing amounts of polysucrose increases the amount of LDH activity remained (e.g., products of a preparation agent with 8% polysucrose have more retained LDH activity than products of a preparation agent with 4% polysucrose). Similarly unbound by any particular theory, it is believed that thermal treatment of a lyophilized composition comprising platelets or platelet derivatives (e.g., thrombosomes) increases the amount of LDH activity retained. As another example, metabolic activity can be evidenced by retained esterase activity, such as the ability of the cells to cleave the acetate groups on carboxyfluorescein diacetate succinimidyl ester (CFDASE) to unmask a fluorophore.

Pathogen Reduction

The reduction of pathogens is generally desirable in blood products. Without being bound by any particular theory, it is believed that some methods of pathogen reduction can cause the formation of microparticles in the treated blood product. One method of pathogen reduction involves the use of a photosensitive nucleic acid-intercalating compound to alter the nucleic acids of pathogens upon illumination with an appropriate wavelength. The INTERCEPT® system (made by Cerus) uses amotosalen, a nucleic acid intercalating compound that forms cross-links in nucleic acid upon illumination with UVA.

Starting Material Comprising Platelets or a Platelet Composition

A final blood product (e.g., platelets, cryopreserved platelets, freeze-dried platelets (e.g., thrombosomes)) as described herein can be prepared by any appropriate method. A final blood product (e.g., platelets, cryopreserved platelets, freeze-dried platelets (e.g., thrombosomes)) as described herein can be prepared by a method as disclosed herein. In some embodiments described herein, a final blood product can be a composition that includes platelets and an aqueous medium. In some embodiments, a final blood product can be the result of freeze-drying a composition that includes platelets and an aqueous medium, as described herein. In some embodiments, a final blood product can be prepared using tangential flow filtration (TFF) of a starting material (e.g., an unprocessed blood product (e.g., donor apheresis material (e.g., pooled donor apheresis material)), or a partially processed blood product (e.g., a blood product that has undergone filtration)). In some embodiments, a final blood product can be prepared using centrifugation of a starting material (e.g., an unprocessed blood product (e.g., donor apheresis material (e.g., pooled donor apheresis material)), or a partially processed blood product (e.g., a blood product that has undergone filtration)). It will be appreciated that while the methods described herein are generally described in the context of a starting material being apheresis material, other materials, such as platelets cultured in vitro, or whole blood, may be used. In some cases, platelets may be isolated from whole blood (e.g. pooled whole blood).

A starting material can be any appropriate starting material. In some embodiments, a starting material can have a protein concentration of about 60 to about 80 mg/mL. In some embodiments, a protein concentration can be based on the protein concentration in the plasma of whole blood. In some embodiments, a protein concentration can be based on the protein concentration of donor apheresis plasma. In some embodiments, a starting material can be donor blood product (e.g., whole blood or fractionated blood). In some embodiments, the starting material can be pooled donor blood product (e.g., pooled whole blood or pooled fractionated blood). In some embodiments, a starting material can include donor apheresis plasma. In some embodiments, a starting material can be derived from donor apheresis plasma. As used herein, "donor apheresis plasma" can refer to the plasma component of apheresis material, whether or not the material contains platelets or other blood cells.

In some embodiments, a starting material can be donor apheresis material (e.g., donor platelets or a pool of donor platelets). In some embodiments, a starting material is positive for one or more of: HLA Class I antibodies, HLA Class II antibodies, and HNA antibodies based on a regulatory agency-approved assay (e.g., an FDA cleared assay). In some embodiments, starting material can test positive for HLA Class I antibodies in a regulatory agency approved assay (e.g., an FDA cleared assay). In some embodiments, a starting material can test positive for HLA Class II antibodies in a regulatory agency approved assay (e.g., an FDA cleared assay). In some embodiments, starting material can test positive for HNA antibodies in a regulatory agency approved assay (e.g., an FDA cleared assay). A regulatory agency approved assay can be any appropriate regulatory agency approved assay. In some embodiments, a regulatory agency approved test can be the LABSCREEN™ Mixed by One Lambda. In some implementations, a regulatory agency approved test can be carried out using a LUMINEX® 100/200 or a LUMINEX® XY and the HLA FUSION™ software.

In some embodiments, a starting material can undergo a pathogen reduction step, for example, a nucleic acid intercalating compound that forms cross-links in nucleic acid upon illumination with UVA.

In some embodiments, a starting material (e.g., one or more units of donor platelets) can be initially pooled into a common vessel. The starting material may or may not be initially diluted with an acidified washing buffer (e.g., a control buffer). Without being bound by any particular theory, it is believed that washing with an acidified washing buffer can reduce platelet activation during processing. In some cases, a starting material can undergo two general processing pathways; either washed with control buffer (e.g. using TFF) until a desired residual component is reached (e.g., a percentage of residual donor plasma) before being concentrated to a final concentration; or the starting material can be concentrated to a final concentration before being washed with control buffer (e.g., using TFF) until a desired residual component is reached (e.g., a percentage of residual donor plasma). TFF processed material can then be filled into vials, lyophilized and thermally treated.

Different Steps in Processing of a Starting Material, and TFF

In some embodiments, the method can include an initial dilution step, for example, a starting material (e.g., an unprocessed blood product (e.g., donor apheresis material (e.g., pooled donor apheresis material)) can be diluted with a preparation agent (e.g., any of the preparation agents described herein) to form a diluted starting material. In some cases, the initial dilution step can include dilution with a preparation agent with a mass of preparation agent equal to at least about 10% of the mass of the starting material (e.g., at least about 15%, 25%, 50%, 75%, 100%, 150%, or 200% of the mass of the starting material. In some embodiments, an initial dilution step can be carried out using the TFF apparatus.

In some embodiments, the method can include concentrating (e.g., concentrating platelets) (e.g., concentrating a starting material or a diluted starting material) to form a concentrated platelet composition. For example, concentrated can include concentrating to a about $1000\times10^3$ to about $4000\times10^3$ platelets/μL (e.g., about $1000\times10^3$ to about $2000\times10^3$, about $2000\times10^3$ to about $3000\times10^3$, or about $4000\times10^3$ platelets/μL). In some embodiments, a concentration step can be carried out using the TFF apparatus.

The concentration of platelets or platelet derivatives (e.g., thrombosomes) can be determined by any appropriate method. For example, a counter can be used to quantitate concentration of blood cells in suspension using impedance (e.g., a Beckman Coulter AcT 10 or an AcT diff 2).

In some embodiments, TFF can include diafiltering (sometimes called "washing") of a starting material, a diluted starting material, a concentrated platelet composition, or a combination thereof. In some embodiments, diafiltering can include washing with at least 2 (e.g., at least 3, 4, 5, 6, 7, 8, 9, 10, or more) diavolumes. In some embodiments, TFF can include buffer exchange. In some embodiments, a buffer can be used in TFF. A buffer can be any appropriate buffer. In some embodiments, the buffer can be a preparation agent (e.g., any of the preparation agents described herein). In some embodiments, the buffer can be the same preparation agent as was used for dilution. In some embodiments, the buffer can be a different preparation than was used for dilution. In some embodiments, a buffer can include a lyophilizing agent, including a buffering agent, a base, a loading agent, optionally a salt, and optionally at least one organic solvent such as an organic solvent selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof. A buffering agent can be any appropriate buffering agent. In some embodiments, a buffering agent can be HEPES ((4-(2-hydroxyethyl)-1-piperazineethanesulfonic acid). A base can be any appropriate base. In some embodiments, a base can be sodium bicarbonate. In some embodiments, a saccharide can be a monosaccharide. In some embodiments, a loading agent can be a saccharide. In some embodiments, a saccharide can include sucrose, maltose, trehalose, glucose (e.g., dextrose), mannose, or xylose. In some embodiments, a monosaccharide can be trehalose. In some embodiments, the loading agent can include polysucrose. A salt can be any appropriate salt. In some embodiments, a salt can be selected from the group consisting of sodium chloride (NaCl), potassium chloride (KCl), or a combination thereof.

In some embodiments, a membrane with a pore size of about 0.1 μm to about 1 μm (e.g., about 0.1 μm to about 1 μm, about 0.1 μm to about 0.5 μm, about 0.2 to about 0.45 μm, about 0.45 to about 1 μm, about 0.1 μm, about 0.2 μm, about 0.45 μm, about 0.65 μm, or about 1 μm) can be used in TFF. A membrane can be made from any appropriate material. In some cases, a membrane can be a hydrophilic membrane. In some embodiments, a membrane can be a hydrophobic membrane. In some embodiments, a membrane with a nominal molecular weight cutoff (NMWCO) of at least about 100 kDa (e.g., at least about 200 kDa, 300 kDa, 500 kDa, or 1000 kDa) can be used in TFF. The TFF can be performed with any appropriate pore size within the range of 0.1 μm to 1.0 μm with the aim of reducing the microparticles content in the composition and increasing the content of platelet derivatives in the composition. A skilled artisan can appreciate the required optimization of the pore size in order to retain the platelet derivatives and allow the microparticles to pass through the membrane. The pore size in illustrative embodiments, is such that the microparticles pass through the membrane allowing the TFF-treated composition to have less than 5% microparticles. The pore size in illustrative embodiments is such that a maximum of platelet derivatives gets retained in the process allowing the TFF-treated composition to have a concentration of the platelet derivatives in the range of $100\times10^3$ to $20{,}000\times10^3$. The pore size during the TFF process can be exploited to obtain a higher concentration of platelet derivatives in the platelet derivative composition such that a person administering the platelet derivatives to a subject in need has to rehydrate/reconstitute fewer vials, therefore, being efficient with respect to time and effort during the process of preparing such platelet derivatives for a downstream procedure, for example a method of treating provided herein. TFF can be performed at any appropriate temperature. In some embodiments, TFF can be performed at a temperature of about 20° C. to about 37° C. (e.g., about 20° C. to about 25° C., about 20° C. to about 30° C., about 25° C. to about 30° C., about 30° C. to about 35° C., about 30° C. to about 37° C., about 25° C. to about 35° C., or about 25° C. to about 37° C.). In some embodiments, TFF can be carried out at a flow rate (e.g., a circulating flow rate) of about 100 ml/min to about 800 ml/min (e.g., about 100 to about 200 ml/min, about 100 to about 400 ml/min, about 100 to about 600 ml/min, about 200 to about 400 ml/min, about 200 to about 600 ml/min, about 200 to about 800 ml/min, about 400 to about 600 ml/min, about 400 to about 800 ml/min, about 600 to about 800 ml/min, about 100 ml/min, about 200 ml/min, about 300 ml/min, about 400 ml/min, about 500 ml/min, about 600 ml/min, about 700 ml/min, or about 800 ml/min).

In some embodiments, TFF can be performed until a particular endpoint is reached, forming a TFF-treated composition. An endpoint can be any appropriate endpoint. In some embodiments, an endpoint can be a percentage of residual plasma (e.g., less than or equal to about 50%, 40%, 30%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1% of residual plasma). In some embodiments, an endpoint can be a relative absorbance at 280 nm (A280). For example, an endpoint can be an A280 (e.g., using a path length of 0.5 cm) that is less than or equal to about 50% (e.g., less than or equal to about 40%, 30%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%) of the A280 (e.g., using a path length of 0.5 cm) prior to TFF (e.g., of a starting material or of a diluted starting material). In some embodiments, an A280 can be relative to a system that measures 7.5% plasma=1.66 AU. In some embodiments, an instrument to measure A280 can be configured as follows: a 0.5 cm gap flow cell can be attached to the filtrate line of the TFF system. The flow cell can be connected to a photometer with fiber optics cables attached to each side of the flow cell (light source cable and light detector cable). The flow cell can be made with a silica glass lens on each side of the fiber optic cables. Apart from the relative protein concentration of proteins in the aqueous medium, the protein concentration in the aqueous medium can also be measured in absolute terms. In some embodiments, the protein concentration in the aqueous medium is less than or equal to 15%, or 14%, or 13%, or 12%, or 11%, or 10%, or 9%, or 8%, or 7%, or 6%, or 5%, or 4%, or 3%, or 2%, or 1%, or 0.1%, or 0.01%. In some exemplary embodiments, the protein concentration is less than 3% or 4%. In some embodiments, the protein concentration is in the range of 0.01-15%, or 0.1-15%, or 1-15%, or 1-10%, or 0.01-10%, or 3-12%, or 5-10% in the TFF-treated composition. In some embodiments, an endpoint can be an absolute A280 (e.g., using a path length of 0.5 cm). For example, an endpoint can be an A280 that is less than or equal to 2.50 AU, 2.40 AU, 2.30 AU, 2.20 AU, 2.10 AU, 2.0 AU, 1.90 AU, 1.80 AU, or 1.70 AU (e.g., less than or equal to 1.66, 1.6, 1.5, 1.4, 1.3, 1.2, 1.1, 1.0, 0.9, 0.8, 0.7, 0.6, 0.5, 0.4, 0.3, 0.2, or 0.1 AU) (e.g., using a path length of 0.5 cm). In some embodiments, a percentage of residual plasma, a relative A280, or an A280 can be determined based on the aqueous medium of a composition comprising platelets and an aqueous medium. In some embodiments, a percentage of residual plasma can be determined based on a known correlation to an A280. In some embodiments, an endpoint can be a platelet concentration, as TFF can include concentration or dilution of a sample (e.g., using a preparation agent). For example, an endpoint can be a platelet concentration of at least about $2000\times10^3$ platelets/μL (e.g., at least about $2050\times10^3$, $2100\times10^3$, $2150\times10^3$, $2200\times10^3$, $2250\times10^3$, $2300\times10^3$, $2350\times10^3$, $2400\times10^3$, $2450\times10^3$, or $2500\times10^3$ platelets/μL). As another example, an endpoint can be a platelet concentration of about $1000\times10^3$ to about 2500 platelets/μL (e.g., about $1000\times10^3$ to about $2000\times10^3$, about $1500\times10^3$ to about $2300\times10^3$, or about $1700\times10^3$ to about $2300\times10^3$ platelets/μL). In some embodiments, an endpoint can be a concentration of platelets in the TFF-treated composition are at least $100\times10^3$ platelets/μL, $200\times10^3$ platelets/μL, $400\times10^3$ platelets/μL, $1000\times10^3$ platelets/μL, $1250\times10^3$ platelets/μL, $1500\times10^3$ platelets/μL, $1750\times10^3$ platelets/µL, $2000\times10^3$ platelets/µL, $2250\times10^3$ platelets/µL, $2500\times10^3$ platelets/µL, $2750\times10^3$ platelets/µL, $3000\times10^3$ platelets/µL, $3250\times10^3$ platelets/µL, $3500\times10^3$ platelets/µL, $3750\times10^3$ platelets/µL, $4000\times10^3$ platelets/µL, $4250\times10^3$ platelets/µL, $4500\times10^3$ platelets/µL, $4750\times10^3$ platelets/µL, $5000\times10^3$ platelets/µL, $5250\times10^3$ platelets/µL, $5500\times10^3$ platelets/µL, $5750\times10^3$ platelets/µL, $6000\times10^3$ platelets/µL, $7000\times10^3$ platelets/µL, $8000\times10^3$ platelets/µL, $9000\times10^3$ platelets/µL, $10,000\times10^3$ platelets/µL, $11,000\times10^3$ platelets/µL, $12,000\times10^3$ platelets/µL, $13,000\times10^3$ platelets/µL, $14,000\times10^3$ platelets/µL, $15,000\times10^3$ platelets/µL, $16,000\times10^3$ platelets/µL, $17,000\times10^3$ platelets/µL, $18,000\times10^3$ platelets/µL, $19,000\times10^3$ platelets/µL, $20,000\times10^3$ platelets/µL. In some embodiments, the platelets or platelet derivatives in the TFF-treated composition is in the range of $100\times10^3$-$20,000\times10^3$ platelets/µL, or $1000\times10^3$-$20,000\times10^3$ platelets/µL, or $1000\times10^3$-$10,000\times10^3$ platelets/µL, or $500\times10^3$-$5,000\times10^3$ platelets/µL, or $1000\times10^3$-$5,000\times10^3$ platelets/µL, or $2000\times10^3$-$8,000\times10^3$ platelets/µL, or $10,000\times10^3$-$20,000\times10^3$ platelets/µL, or $15,000\times10^3$-$20,000\times10^3$ platelets/µL.

In some embodiments, an endpoint can include more than one criterion (e.g., a percentage of residual plasma and a platelet concentration, a relative A280 and a platelet concentration, or an absolute A280 and a platelet concentration).

Typically, a TFF-treated composition is subsequently lyophilized, optionally with a thermal treatment step, to form a final blood product (e.g., platelets, cryopreserved platelets, freeze-dried platelets (e.g., thrombosomes)). However, in some cases, a TFF-treated composition can be considered to be a final blood product.

In some embodiments, a blood product can be prepared using centrifugation of a blood product (e.g., an unprocessed blood product (e.g., donor apheresis material (e.g., pooled donor apheresis material)), or a partially processed blood product (e.g., a blood product that has undergone TFF)). In some embodiments, a blood product can be prepared without centrifugation of a blood product (e.g., an unprocessed blood product (e.g., donor apheresis material), or a partially processed blood product (e.g., a blood product that has undergone TFF)). Centrifugation can include any appropriate steps. In some embodiments, centrifugation can include a slow acceleration, a slow deceleration, or a combination thereof. In some embodiments, centrifugation can include centrifugation at about 1400×g to about 1550×g (e.g., about 1400 to about 1450×g, about 1450 to about 1500×g, or 1500 to about 1550×g, about 1400×g, about 1410×g, about 1430×g, about 1450×g, about 1470×g, about 1490×g, about 1500×g, about 1510×g, about 1530×g, or about 1550×g). In some embodiments, the duration of centrifugation can be about 10 min to about 30 min (e.g., about 10 to about 20 min, about 20 to about 30 min, about 10 min, about 20 min, or about 30 min).

In some embodiments, a final blood product can be prepared using both TFF and centrifugation (e.g., TFF followed by centrifugation or centrifugation followed by TFF).

Also provided herein are compositions prepared by any of the methods described herein.

In some embodiments, a composition as described herein can be analyzed at multiple points during processing. In some embodiments, a starting material (e.g., donor apheresis material (e.g., pooled donor apheresis material)) can be analyzed for antibody content (e.g., HLA or HNA antibody content). In some embodiments, a starting material (e.g., donor apheresis material (e.g., pooled donor apheresis material)) can be analyzed for protein concentration (e.g., by absorbance at 280 nm (e.g., using a path length of 0.5 cm)). In some embodiments, a composition in an intermediate step of processing (e.g., when protein concentration reduced to less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less) of the protein concentration of an unprocessed blood product) can be analyzed for antibody content (e.g., HLA or HNA antibody content). In some embodiments, the antibody content (e.g., HLA or HNA antibody content) of a blood product in an intermediate step of processing can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the antibody content of the starting material. In some embodiments, a final blood product (e.g., (e.g., platelets, cryopreserved platelets, freeze-dried platelets (e.g., thrombosomes)) can be analyzed for antibody content (e.g., HLA or HNA antibody content). In some embodiments described herein, a final blood product can be a composition that includes platelets and an aqueous medium. In some embodiments, the antibody content (e.g., HLA or HNA antibody content) of a final blood product (e.g., (e.g., platelets, cryopreserved platelets, freeze-dried platelets (e.g., thrombosomes)) can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the antibody content of the starting material. In some embodiments, a final blood product can have no detectable level of an antibody selected from the group consisting of HLA Class I antibodies, HLA Class II antibodies, and HNA antibodies. In some embodiments, the aqueous medium of a composition as described herein can be analyzed as described herein.

In some embodiments, a composition as described herein can be analyzed at multiple points during processing. In some embodiments, donor apheresis plasma can be analyzed for antibody content (e.g., HLA or HNA antibody content). In some embodiments, donor apheresis plasma can be analyzed for protein concentration (e.g., by absorbance at 280 nm). In some embodiments, a composition in an intermediate step of processing (e.g., when protein concentration reduced to less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less) of the protein concentration of an unprocessed blood product) can be analyzed for antibody content (e.g., HLA or HNA antibody content). In some embodiments, the antibody content (e.g., HLA or HNA antibody content) of a blood product in an intermediate step of processing can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the antibody content of donor apheresis plasma. In some embodiments, a final blood product (e.g., (e.g., platelets, cryopreserved platelets, freeze-dried platelets (e.g., thrombosomes)) can be analyzed for antibody content (e.g., HLA or HNA antibody content). In some embodiments described herein, a final blood product can be a composition that includes platelets and an aqueous medium. In some embodiments, the antibody content (e.g., HLA or HNA antibody content) of a final blood product (e.g., (e.g., platelets, cryopreserved platelets, freeze-dried platelets (e.g., thrombosomes)) can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the antibody content of donor apheresis plasma. In some embodiments, a final blood product can have no detectable level of an antibody selected from the group consisting of HLA Class I antibodies, HLA Class II antibodies, and HNA antibodies. In some embodiments, the aqueous medium of a composition as described herein can be analyzed as described herein.

The protein concentration of a blood product can be measured by any appropriate method. In some embodiments, the protein concentration of a blood product can be measured using absorbance at 280 nm.

The antibody content (e.g., HLA or HNA antibody content) of a blood product can be measured by any appropriate method.

In some embodiments, a FLOWPRA™ Screening or a LABScreen Multi test kits from One Lambda, Thermo Fisher Scientific can be used as a method of HLA detection. Raw materials can be tested prior to the TFF or centrifugation processes to determine a baseline level of class I and II antibodies for Human Leukocyte Antigen (HLA) and Human Neutrophil Antigens (HNA). Testing can be repeated after processing by centrifugation or TFF to measure the removal of HLA and HNA. Additional testing points can be performed throughout the TFF procedure to maintain in-process control. Post-lyophilization and annealing, random samples can be selected from a batch and qualitative HLA/HNA antibody testing can be performed to ensure reduction and compliance with current FDA testing and acceptance requirements.

In some embodiments, the antibody content (e.g., HLA or HNA antibody content) of two blood products can be compared by determining the percentage of beads positive for a marker (e.g., HLA or HNA coated beads bound to HLA or HNA antibodies, respectively). Any appropriate comparative method can be used. In some embodiments, the antibody content of two blood products can be compared using a method as described herein. In some embodiments, such a method can be carried out as follows. An aliquot of plasma (e.g., about 1 mL) platelet-poor plasma can be obtained. In some embodiments, an aliquot of filtered (e.g., using a 0.2 μm filter) platelet-poor plasma (PPP) (e.g., about 1 mL) can be obtained. Beads coated with Class I HLA and/or beads coated with Class II HLA can be added to the plasma (e.g., about 5 μL of each type of bead to about 20 μL of PPP) to form a mixture of PPP and beads. The mixture of PPP and beads can be vortexed. The mixture of PPP and beads can be incubated to form an incubated mixture. Any appropriate incubation conditions can be used. For example, in some embodiments, incubation can occur for a time (e.g., for about 30 minutes) at a temperature (e.g., at room temperature) with other conditions (e.g., in the dark) to form an incubated mixture. In some embodiments, incubation can include agitation (e.g., gentle rocking). The beads in the incubated mixture can be washed using any appropriate conditions. In some embodiments, the beads in the incubated mixture can be washed with a wash buffer. Washed beads can be separated from the incubated mixture by any appropriate method. In some embodiments, the washed beads can be separated by centrifugation (e.g., at 9,000×g for 2 minutes) to obtain pelleted beads. In some embodiments, the washing step can be repeated. The beads can be resuspended to form a bead solution. An antibody (e.g., an antibody that will bind to the assayed antibody content (e.g., HLA or HNA antibody content)) conjugated to a detectable moiety can be added to the bead solution (e.g., an αIgG conjugated to a fluorescent reporter, such as FITC). The antibody can be incubated with the bead solution under any appropriate conditions. In some embodiments, the antibody can be incubated for a time (e.g., for about 30 minutes) at a temperature (e.g., at room temperature) with other conditions (e.g., in the dark) to form labeled beads. Labeled beads can be washed to remove unbound antibody conjugated to a detectable moiety. The labeled beads can be washed using any appropriate conditions. In some embodiments, the labeled beads can be washed with a wash buffer. Washed labeled beads can be separated by any appropriate method. In some embodiments, the washed labeled beads can be separated by centrifugation (e.g., at 9,000 g for 2 minutes) to obtain pelleted labeled beads. In some embodiments, the washing step can be repeated. Labeled beads can be detected by any appropriate method. In some embodiments, labeled beads can be detected by flow cytometry. In some embodiments, detection can include measurement of the percentage of beads that are positive for the detectable moiety as compared to a negative control. In some embodiments, a negative control can be prepared as above, using a PPP sample that is known to be negative for antibodies (e.g. HLA Class I, HLA Class II, or HNA antibodies).

In some embodiments, a blood product (e.g., platelets, cryopreserved platelets, freeze-dried platelets (e.g., thrombosomes)) can be analyzed at multiple points during processing. In some embodiments, a starting material (e.g., donor apheresis material) can be analyzed to determine the percent of positive beads (e.g., HLA or HNA coated beads). In some embodiments, a starting material (e.g., donor apheresis material) can be analyzed for protein concentration (e.g., by absorbance at 280 nm). In some embodiments, a blood product in an intermediate step of processing (e.g., when protein concentration reduced to less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less) of the protein concentration of a starting material) can be analyzed to determine the percent of positive beads (e.g., HLA or HNA coated beads). In some embodiments, a blood product in an intermediate step of processing (e.g., when protein concentration reduced to less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less) of the protein concentration of a starting material) can be analyzed to determine the percent of positive beads (e.g., HLA or HNA coated beads). In some embodiments, the percent of positive beads (e.g., HLA or HNA coated beads) from a blood product in an intermediate step of processing can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the percent of positive beads from a starting material. In some embodiments, the percent of positive beads (e.g., HLA or HNA coated beads) from a blood product in an intermediate step of processing can be less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less) of the total amount of beads. In some embodiments, a final blood product (e.g., (e.g., platelets, cryopreserved platelets, freeze-dried platelets (e.g., thrombosomes)) can be analyzed to determine the percent of positive beads (e.g., HLA or HNA coated beads). In some embodiments, the percent of positive beads (e.g., HLA or HNA coated beads) from a final blood product (e.g., (e.g., platelets, cryopreserved platelets, freeze-dried platelets (e.g., thrombosomes)) can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the percent of positive beads from a starting material. In some embodiments, the percent of positive beads (e.g., HLA or HNA coated beads) from a final blood product can be less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less) of the total amount of beads. In some embodiments, the aqueous medium of a composition as described herein can be analyzed as described herein.

In some embodiments, a blood product (e.g., platelets, cryopreserved platelets, freeze-dried platelets (e.g., thrombosomes)) can be analyzed at multiple points during processing. In some embodiments, donor apheresis plasma can be analyzed to determine the percent of positive beads (e.g., HLA or HNA coated beads). In some embodiments, donor apheresis plasma can be analyzed for protein concentration (e.g., by absorbance at 280 nm). In some embodiments, a blood product in an intermediate step of processing (e.g., when protein concentration reduced to less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less) of the protein concentration of a starting material) can be analyzed to determine the percent of positive beads (e.g., HLA or HNA coated beads). In some embodiments, a blood product in an intermediate step of processing (e.g., when protein concentration reduced to less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less) of the protein concentration of a starting material) can be analyzed to determine the percent of positive beads (e.g., HLA or HNA coated beads). In some embodiments, the percent of positive beads (e.g., HLA or HNA coated beads) from a blood product in an intermediate step of processing can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the percent of positive beads from donor apheresis plasma. In some embodiments, the percent of positive beads (e.g., HLA or HNA coated beads) from a blood product in an intermediate step of processing can be less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less) of the total amount of beads. In some embodiments, a final blood product (e.g., (e.g., platelets, cryopreserved platelets, freeze-dried platelets (e.g., thrombosomes)) can be analyzed to determine the percent of positive beads (e.g., HLA or HNA coated beads). In some embodiments, the percent of positive beads (e.g., HLA or HNA coated beads) from a final blood product (e.g., (e.g., platelets, cryopreserved platelets, freeze-dried platelets (e.g., thrombosomes)) can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the percent of positive beads from donor apheresis material. In some embodiments, the percent of positive beads (e.g., HLA or HNA coated beads) from a final blood product can be less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less) of the total amount of beads. In some embodiments, the aqueous medium of a composition as described herein can be analyzed as described herein.

A percentage of positive beads can be determined using any appropriate method. In some embodiments, positive beads can be determined compared to a negative control sample. A negative control sample can be any appropriate negative control sample. In some embodiments, a negative control sample can be used to determine positivity gating such that less than a certain percentage (e.g., between about 0.01% and about 1% (e.g., about 0.01% to about 0.05%, about 0.05% to about 0.1%, about 0.1% to about 0.5%, about 0.5% to about 1%, about 0.01%, about 0.05%, about 0.1%, about 0.5%, or about 1%)) of the negative control sample is present within the positivity gate. In some embodiments, a negative control sample can be a buffer (e.g., PBS). In some embodiments, a negative control sample can be a synthetic plasma composition. In some embodiments, a negative control sample can be a blood product known to be negative for the assayed antibodies (e.g., HLA or HNA antibodies).

Also provided herein is a method of reducing the percentage of an antibody (e.g., a HLA antibody (e.g., a HLA Class I antibody or a HLA Class II antibody) or a HNA antibody) in a composition (e.g., a blood product) comprising platelets, the method comprising filtering the composition by tangential flow filtration. Also provided herein is a method of reducing the amount of an antibody (e.g., a HLA antibody (e.g., a HLA Class I antibody or a HLA Class II antibody) or a HNA antibody) in a composition (e.g., a blood product) comprising platelets, the method comprising filtering the composition by tangential flow filtration. Also provided herein is a method of reducing the percentage of beads positive for an antibody (e.g., a HLA antibody (e.g., a HLA Class I antibody or a HLA Class II antibody) or a HNA antibody) in a composition (e.g., a blood product) comprising platelets, the method comprising filtering the composition by tangential flow filtration.

Also provided herein is a method of reducing the percentage of an antibody (e.g., a HLA antibody (e.g., a HLA Class I antibody or a HLA Class II antibody) or a HNA antibody) in a composition (e.g., a blood product) comprising platelets, the method comprising filtering the composition by centrifugation. Also provided herein is a method of reducing the amount of an antibody (e.g., a HLA antibody (e.g., a HLA Class I antibody or a HLA Class II antibody) or a HNA antibody) in a composition (e.g., a blood product) comprising platelets, the method comprising filtering the composition by centrifugation. Also provided herein is a method of reducing the percentage of beads positive for an antibody (e.g., a HLA antibody (e.g., a HLA Class I antibody or a HLA Class II antibody) or a HNA antibody) in a composition (e.g., a blood product) comprising platelets, the method comprising filtering the composition by centrifugation.

In some embodiments of any of the methods described herein, the amount of an antibody (e.g., a HLA antibody (e.g., a HLA Class I antibody or a HLA Class II antibody) or a HNA antibody) in a composition (e.g., a blood product) can be reduced to below a reference level. A reference level can be any appropriate reference level. In some embodiments of any of the methods described herein, the percentage of beads positive an antibody (e.g., a HLA antibody (e.g., a HLA Class I antibody or a HLA Class II antibody) or a HNA antibody) in a composition (e.g., a blood product) can be reduced as compared to the blood product before undergoing the methods described herein. A percentage of beads positive for an antibody can be reduced by any appropriate amount. In some embodiments, a percentage of beads positive for an antibody can be reduced by at least 5% (e.g., reduced by at least 10%, 20%, 30%, 40%, 50%, 60%, 70%, 75%, 80%, 85%, 90%, 95%, 96%, 97%, 98%, 99%, or more) compared to the blood product before undergoing any of the methods described herein.

In some embodiments, a composition as described herein can undergo any appropriate additional processing steps. In some embodiments, a composition as described herein can be freeze-dried. In some embodiments, freeze-dried platelets can be thermally treated (e.g., at about 80° C. for about 24 hours).

For example, in some embodiments, a composition can be cryopreserved or freeze-dried. In some embodiments, a first composition (e.g., a composition comprising platelets and an aqueous medium as described herein) can be treated with a mixture. In some embodiments, a mixture can include a lyophilizing agent, including a base, a loading agent, and optionally at least one organic solvent such as an organic solvent selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof, to form a second composition comprising platelets. In some embodiments, a loading agent can be a saccharide. In some embodiments, a saccharide can be a monosaccharide. In some embodiments, a saccharide can be sucrose, maltose, trehalose, glucose (e.g., dextrose), mannose, or xylose. In some embodiments, the loading agent can be polysucrose.

In some embodiments, a first composition or a second composition can be dried. In some embodiments, a first composition or a second composition can be dried with a cryoprotectant. In some embodiments, a cryoprotectant can include a saccharide, optionally a base, and optionally at least one organic solvent such as an organic solvent selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof to form a third composition. In some embodiments, a cryoprotectant can be polysucrose.

In some embodiments, a first composition or a second composition can be freeze-dried. In some embodiments, a first composition or a second composition can be freeze-dried with a cryoprotectant. In some embodiments, a cryoprotectant can include a saccharide, optionally a base, and optionally at least one organic solvent such as an organic solvent selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof to form a fourth composition. In some embodiments freeze-drying can occur at a temperature of about −40° C. to about 5° C. In some embodiments, freeze-drying can occur over a gradient (e.g., about −40° C. to about 5° C.). In some embodiments, a secondary drying step can be carried out (e.g., at about 20° C. to about 40° C.).

Also provided herein are blood products (e.g., platelets, cryopreserved platelets, freeze-dried platelets (e.g., thrombosomes)) produced by any of the methods described herein.

In some embodiments, the percentage of beads positive for an antibody selected from the group consisting of HLA Class I antibodies, HLA Class II antibodies, and HNA antibodies, as determined for a composition as described herein by flow cytometry using beads coated with Class I HLAs, Class II HLAs, or HNAs, respectively, is reduced by at least 10% (e.g., at least 20%, 30%, 40%, 50%, 60%, 70%, 75%, 80%, 85%, 90%, 95%, or 99%) as compared to a similar composition not prepared by a process comprising tangential flow filtration of a composition comprising platelets, centrifugation of a composition comprising platelets, or a combination thereof.

In some embodiments, the percentage of beads positive for HLA Class I antibodies, as determined for a composition as described herein by flow cytometry using beads coated with Class I HLAs, is reduced by at least 10% (e.g., at least 20%, 30%, 40%, 50%, 60%, 70%, 75%, 80%, 85%, 90%, 95%, or 99%) as compared to a similar composition not prepared by a process comprising tangential flow filtration of a composition comprising platelets, centrifugation of a composition comprising platelets, or a combination thereof.

In some embodiments, the percentage of beads positive for HLA Class II antibodies, as determined for a composition as described herein by flow cytometry using beads coated with Class II HLAs, is reduced by at least 10% (e.g., at least 20%, 30%, 40%, 50%, 60%, 70%, 75%, 80%, 85%, 90%, 95%, or 99%) as compared to a similar composition not prepared by a process comprising tangential flow filtration of a composition comprising platelets, centrifugation of a composition comprising platelets, or a combination thereof.

In some embodiments, the percentage of beads positive for HNA antibodies, as determined for a composition as described herein by flow cytometry using beads coated with HNAs, is reduced by at least 10% (e.g., at least 20%, 30%, 40%, 50%, 60%, 70%, 75%, 80%, 85%, 90%, 95%, or 99%) as compared to a similar composition not prepared by a process comprising tangential flow filtration of a composition comprising platelets, centrifugation of a composition comprising platelets, or a combination thereof.

Within the process provided herein for making the compositions provided herein, optional addition of a lyophilizing agent can be the last step prior to drying. However, in some embodiments, the lyophilizing agent can be added at the same time or before other components of the composition, such as a salt, a buffer, optionally a cryoprotectant, or other components. In some embodiments, the lyophilizing agent is added to a preparation agent, thoroughly mixed to form a drying solution, dispensed into a drying vessel (e.g., a glass or plastic serum vial, a lyophilization bag), and subjected to conditions that allow for drying of a TFF-treated composition to form a dried composition.

In various embodiments, the lyophilization bag is a gas-permeable bag configured to allow gases to pass through at least a portion or all portions of the bag during the processing. The gas-permeable bag can allow for the exchange of gas within the interior of the bag with atmospheric gas present in the surrounding environment. The gas-permeable bag can be permeable to gases, such as oxygen, nitrogen, water, air, hydrogen, and carbon dioxide, allowing gas exchange to occur in the compositions provided herein. In some embodiments, the gas-permeable bag allows for the removal of some of the carbon dioxide present within an interior of the bag by allowing the carbon dioxide to permeate through its wall. In some embodiments, the release of carbon dioxide from the bag can be advantageous to maintaining a desired pH level of the composition contained within the bag.

In some embodiments, the container of the process herein is a gas-permeable container that is closed or sealed. In some embodiments, the container is a container that is closed or sealed and a portion of which is gas-permeable. In some embodiments, the surface area of a gas-permeable portion of a closed or sealed container (e.g., bag) relative to the volume of the product being contained in the container (hereinafter referred to as the "SA/V ratio") can be adjusted to improve pH maintenance of the compositions provided herein. For example, in some embodiments, the SAN ratio of the container can be at least about 2.0 $cm^2/mL$ (e.g., at least about 2.1 $cm^2/mL$, at least about 2.2 $cm^2/mL$, at least about 2.3 $cm^2/mL$, at least about 2.4 $cm^2/mL$, at least about 2.5 $cm^2/mL$, at least about 2.6 $cm^2/mL$, at least about 2.7 $cm^2/mL$, at least about 2.8 $cm^2/mL$, at least about 2.9 $cm^2/mL$, at least about 3.0 $cm^2/mL$, at least about 3.1 $cm^2/mL$, at least about 3.2 $cm^2/mL$, at least about 3.3 $cm^2/mL$, at least about 3.4 $cm^2/mL$, at least about 3.5 $cm^2/mL$, at least about 3.6 $cm^2/mL$, at least about 3.7 $cm^2/mL$, at least about 3.8 $cm^2/mL$, at least about 3.9 $cm^2/mL$, at least about 4.0 $cm^2/mL$, at least about 4.1 $cm^2/mL$, at least about 4.2 $cm^2/mL$, at least about 4.3 $cm^2/mL$, at least about 4.4 $cm^2/mL$, at least about 4.5 $cm^2/mL$, at least about 4.6 $cm^2/mL$, at least about 4.7 $cm^2/mL$, at least about 4.8 $cm^2/mL$, at least about 4.9 $cm^2/mL$, or at least about 5.0 $cm^2/mL$. In some embodiments, the SAN ratio of the container can be at most about 10.0 $cm^2/mL$ (e.g., at most about 9.9 $cm^2/mL$, at most about 9.8 $cm^2/mL$, at most about 9.7 $cm^2/mL$, at most about 9.6 $cm^2/mL$, at most about 9.5 $cm^2/mL$, at most about 9.4 $cm^2/mL$, at most about 9.3 $cm^2/mL$, at most about 9.2 $cm^2/mL$, at most about 9.1 $cm^2/mL$, at most about 9.0 $cm^2/mL$, at most about 8.9 $cm^2/mL$, at most about 8.8 $cm^2/mL$, at most about 8.7 $cm^2/mL$, at most about 8.6, $cm^2/mL$ at most about 8.5 $cm^2/mL$, at most about 8.4 $cm^2/mL$, at most about 8.3 $cm^2/mL$, at most about 8.2 $cm^2/mL$, at most about 8.1 $cm^2/mL$, at most about 8.0 $cm^2/mL$, at most about 7.9 $cm^2/mL$, at most about 7.8 $cm^2/mL$, at most about 7.7 $cm^2/mL$, at most about 7.6 $cm^2/mL$, at most about 7.5 $cm^2/mL$, at most about 7.4 $cm^2/mL$, at most about 7.3 $cm^2/mL$, at most about 7.2 $cm^2/mL$, at most about 7.1 $cm^2/mL$, at most about 6.9 $cm^2/mL$, at most about 6.8 $cm^2/mL$, at most about 6.7 $cm^2/mL$, at most about 6.6 $cm^2/mL$, at most about 6.5 $cm^2/mL$, at most about 6.4 $cm^2/mL$, at most about 6.3 $cm^2/mL$, at most about 6.2 $cm^2/mL$, at most about 6.1 $cm^2/mL$, at most about 6.0 $cm^2/mL$, at most about 5.9 $cm^2/mL$, at most about 5.8 $cm^2/mL$, at most about 5.7 $cm^2/mL$, at most about 5.6 $cm^2/mL$, at most about 5.5 $cm^2/ML$, at most about 5.4 $cm^2/mL$, at most about 5.3 $cm^2/mL$, at most about 5.2 $cm^2/mL$, at most about 5.1 $cm^2/mL$, at most about 5.0 $cm^2/mL$, at most about 4.9 $cm^2/mL$, at most about 4.8 $cm^2/mL$, at most about 4.7 $cm^2/mL$, at most about 4.6 $cm^2/mL$, at most about 4.5 $cm^2/mL$, at most about 4.4 $cm^2/ML$, at most about 4.3 $cm^2/mL$, at most about 4.2 $cm^2/mL$, at most about 4.1 $cm^2/mL$, or at most about 4.0 $cm^2/mL$. In some embodiments, the SAN ratio of the container can range from about 2.0 to about 10.0 $cm^2/mL$ (e.g., from about 2.1 $cm^2/mL$ to about 9.9 $cm^2/mL$, from about 2.2 $cm^2/mL$ to about 9.8 $cm^2/mL$, from about 2.3 $cm^2/mL$ to about 9.7 $cm^2/mL$, from about 2.4 $cm^2/mL$ to about 9.6 $cm^2/mL$, from about 2.5 $cm^2/mL$ to about 9.5 $cm^2/mL$, from about 2.6 $cm^2/mL$ to about 9.4 $cm^2/mL$, from about 2.7 $cm^2/mL$ to about 9.3 $cm^2/mL$, from about 2.8 $cm^2/mL$ to about 9.2 $cm^2/mL$, from about 2.9 $cm^2/mL$ to about 9.1 $cm^2/mL$, from about 3.0 $cm^2/mL$ to about 9.0 $cm^2/mL$, from about 3.1 $cm^2/mL$ to about 8.9 $cm^2/mL$, from about 3.2 $cm^2/mL$ to about 8.8 $cm^2/mL$, from about 3.3 $cm^2/mL$ to about 8.7 $cm^2/mL$, from about 3.4 $cm^2/mL$ to about 8.6 $cm^2/mL$, from about 3.5 $cm^2/mL$ to about 8.5 $cm^2/mL$, from about 3.6 $cm^2/mL$ to about 8.4 $cm^2/mL$, from about 3.7 $cm^2/mL$ to about 8.3 $cm^2/mL$, from about 3.8 $cm^2/mL$ to about 8.2 $cm^2/mL$, from about 3.9 $cm^2/mL$ to about 8.1 $cm^2/mL$, from about 4.0 $cm^2/mL$ to about 8.0 $cm^2/mL$, from about 4.1 $cm^2/mL$ to about 7.9 $cm^2/mL$, from about 4.2 $cm^2/mL$ to about 7.8 $cm^2/mL$, from about 4.3 $cm^2/mL$ to about 7.7 $cm^2/mL$, from about 4.4 $cm^2/mL$ to about 7.6 $cm^2/mL$, from about 4.5 $cm^2/mL$ to about 7.5 $cm^2/mL$, from about 4.6 $cm^2/mL$ to about 7.4 $cm^2/mL$, from about 4.7 $cm^2/mL$ to about 7.3 $cm^2/mL$, from about 4.8 $cm^2/mL$ to about 7.2 $cm^2/mL$, from about 4.9 $cm^2/mL$ to about 7.1 $cm^2/mL$, from about 5.0 $cm^2/mL$ to about 6.9 $cm^2/mL$, from about 5.1 $cm^2/mL$ to about 6.8 $cm^2/mL$, from about 5.2 $cm^2/mL$ to about 6.7 $cm^2/mL$, from about 5.3 $cm^2/mL$ to about 6.6 $cm^2/mL$, from about 5.4 $cm^2/mL$ to about 6.5 $cm^2/mL$, from about 5.5 $cm^2/mL$ to about 6.4 $cm^2/mL$, from about 5.6 $cm^2/mL$ to about 6.3 $cm^2/mL$, from about 5.7 $cm^2/mL$ to about 6.2 $cm^2/mL$, or from about 5.8 $cm^2/mL$ to about 6.1 $cm^2/mL$.

Gas-permeable closed containers (e.g., bags) or portions thereof can be made of one or more various gas-permeable materials. In some embodiments, the gas-permeable bag can be made of one or more polymers including fluoropolymers (such as polytetrafluoroethylene (PTFE) and perfluoroalkoxy (PFA) polymers), polyolefins (such as low-density polyethylene (LDPE), high-density polyethylene (HDPE)), fluorinated ethylene propylene (FEP), polystyrene, polyvinylchloride (PVC), silicone, and any combinations thereof.

In some embodiments, dried platelets or platelet derivatives (e.g., thrombosomes) can undergo heat treatment. Heating can be performed at a temperature above about 25° C. (e.g., greater than about 40° C., 50° C., 60° C., 70° C., 80° C. or higher). In some embodiments, heating is conducted between about 70° C. and about 85° C. (e.g., between about 75° C. and about 85° C., or at about 75° C. or 80° C.). The temperature for heating can be selected in conjunction with the length of time that heating is to be performed. Although any suitable time can be used, typically, the lyophilized platelets are heated for at least 1 hour, but not more than 36 hours. Thus, in embodiments, heating is performed for at least 2 hours, at least 6 hours, at least 12 hours, at least 18 hours, at least 20 hours, at least 24 hours, or at least 30 hours. For example, the lyophilized platelets can be heated for 18 hours, 19 hours, 20 hours, 21 hours, 22 hours, 23 hours, 24 hours, 25 hours, 26 hours, 27 hours, 28 hours, 29 hours, or 30 hours. Non-limiting exemplary combinations include: heating the dried platelets or platelet derivatives (e.g., thrombosomes) for at least 30 minutes at a temperature higher than 30° C.; heating the dried platelets or platelet derivatives (e.g., thrombosomes) for at least 10 hours at a temperature higher than 50° C.; heating the dried platelets or platelet derivatives (e.g., thrombosomes) for at least 18 hours at a temperature higher than 75° C.; and heating the dried platelets or platelet derivatives (e.g., thrombosomes) for 24 hours at 80° C. In some embodiments, heating can be performed in sealed container, such as a capped vial. In some embodiments, a sealed container be subjected to a vacuum prior to heating. The heat treatment step, particularly in the presence of a cryoprotectant such as albumin or polysucrose, has been found to improve the stability and shelf-life of the freeze-dried platelets. Indeed, advantageous results have been obtained with the particular combination of serum albumin or polysucrose and a post-lyophilization heat treatment step, as compared to those cryoprotectants without a heat treatment step. A cryoprotectant (e.g., sucrose) can be present in any appropriate amount (e.g. about 3% to about 10% by mass or by volume of the platelets or platelet derivatives (e.g., thrombosomes).

In some cases, compositions comprising platelets or platelet derivatives (e.g., thrombosomes) can be rehydrated with water (e.g., sterile water for injection) over about 10 minutes at about room temperature. In general, the rehydration volume is about equal to the volume used to fill each vial of thrombosomes prior to drying.

In some embodiments, the platelets or platelet derivatives (e.g., thrombosomes) prepared as disclosed herein have a storage stability that is at least about equal to that of the platelets prior to the preparation.

In some embodiments, the method further comprises cryopreserving the platelets or platelet derivatives prior to administering the platelets or platelet derivatives (e.g., with a preparation agent, e.g., a preparation agent described herein).

In some embodiments, the method further comprises drying a composition comprising platelets or platelet derivatives, (e.g., with a preparation agent e.g., a preparation agent described herein) prior to administering the platelets or platelet derivatives (e.g., thrombosomes). In some embodiments, the method may further comprise heating the composition following the drying step. In some embodiments, the method may further comprise rehydrating the composition following the freeze-drying step or the heating step.

In some embodiments, the method further comprises freeze-drying a composition comprising platelets or platelet derivatives (e.g., with a preparation agent e.g., a preparation agent described herein) prior to administering the platelets or platelet derivatives (e.g., thrombosomes) In some embodiments, the method may further comprise heating the composition following the freeze-drying step. In some embodiments, the method may further comprise rehydrating the composition following the freeze-drying step or the heating step.

In some embodiments, the method further comprises cold storing the platelets, platelet derivatives, or the thrombosomes prior to administering the platelets, platelet derivatives, or thrombosomes (e.g., with a preparation agent, e.g., a preparation agent described herein).

Storing conditions include, for example, standard room temperature storing (e.g., storing at a temperature ranging from about 20 to about 30° C.) or cold storing (e.g., storing at a temperature ranging from about 1 to about 10° C.). In some embodiments, the method further comprises cryopreserving, freeze-drying, thawing, rehydrating, and combinations thereof, a composition comprising platelets or platelet derivatives (e.g., thrombosomes) (e.g., with a preparation agent e.g., a preparation agent described herein) prior to administering the platelets or platelet derivatives (e.g., thrombosomes). For example, in some embodiments, the method further comprises drying (e.g., freeze-drying) a composition comprising platelets or platelet derivatives (e.g., with a preparation agent e.g., a preparation agent described herein) (e.g., to form thrombosomes) prior to administering the platelets or platelet derivatives (e.g., thrombosomes). In some embodiments, the method may further comprise rehydrating the composition obtained from the drying step.

In some embodiments, provided herein is a method for preparing a composition comprising platelets or platelet derivatives (e.g., thrombosomes). The method can include diluting a starting material comprising platelets with an approximately equal weight (±10%) of a preparation agent (e.g., Buffer A, as provided in Example 1), concentrating the platelets to about $2250\times10^3$ cells/μL ($\pm250\times10^3$) and then washed with 2-4 diavolumes (DV) (e.g., about 2 diavolumes) of the preparation agent to form a TFF-treated composition. The residual plasma percentage can be less than about 15% relative plasma (as determined by plasma protein content). Following washing, if the concentration of the cells in the TFF-treated composition is not about $2000\times10^3$ cells/μL ($\pm300\times10^3$), the cells can be diluted with the preparation agent or can be concentrated to fall within this range. The method can further include lyophilizing the TFF-treated composition and subsequently treating the lyophilized composition comprising platelets or platelet derivatives (e.g., thrombosomes) at about 80° C. for about 24 hours. In some embodiments, the method can further include a pathogen reduction step, for example, before diluting the starting material.

Plurality of Containers Containing Platelet Derivative Composition

The platelet derivative composition as described herein can be contained in containers/vials, which further can be packed into a plurality of containers for shipping to a customer, which can be part of a commercialization process to fulfill an order for such platelet derivative composition. The containers, in certain embodiments, are 5 ml vials, 10 ml vials, 20 ml vials, 25 ml vs, 30 ml vials, 40 ml vials, 50 ml vials, 60 ml vials, 75 ml vials, 100 ml vials, 125 ml vials, 150 ml vials, 200 ml vials, or 250 ml vials. The vial(s) can be a cryovial, or a cryotube especially in illustrative embodiments where the TFF-treated composition that includes platelets is lyophilized to obtain the platelet derivative composition in the form of a powder, which further can be baked or not baked after it is lyophilized. In some embodiments, the volume of the containers in a plurality of containers (e.g. vials or tubes), which for example can be all from one lot, or from more than one lot (e.g. 2, 3, 4, 5, 6, 7, 8, 9 or 10 lots), can vary from one or more than one size between 10-100 ml. Typically, the volume of the vial/container in embodiments where the platelet derivative is a freeze-dried solid/powder, is 1× the volume of, or 1.10, 1.25, 1.5, 2, 2.5, 3, 4 or 5 times the volume of a composition that was filled in the vial before lyophilization, and/or the volume in which the powder in the vials will be rehydrated, which is an illustrative embodiment. Thus, the maximum volume of such vials can be the same or more than the volume of the composition that was filled inside prior to lyophilization or the volume in which the platelet derivative composition in the form of a powder can be rehydrated. For example, in one non-limiting embodiment, a vial with a maximum capacity of 100 ml, can be used to fill 10 ml of a TFF-treated composition that includes platelets for lyophilization. In certain embodiments, the capacity of a vial in which a TFF-treated composition that includes platelets is lyophilized, is 1-2.5 times and in other embodiments, 1-2 times, 1-3 times, 1-4 times, 1-5 times, and in certain illustrative embodiments, 1.1 to 2 times or 1.25 to 2 times the volume of a TFF-treated composition that is lyophilized therein.

The TFF-treated platelet composition before lyophilization, or in some embodiments, the platelet derivative composition obtained after the lyophilization step, with or without post-lyophilization heat treatment (baking), can be filled into a plurality of vessels or other powder and liquid-holding containers, such as vials, in a sterile manner. In some embodiments, the containers can vary in volume from 5-100 ml, 10-90 ml, 25-75 ml, or 5-40 ml. In some embodiments, the volume of containers can be 5 ml, 10 ml, 15 ml, 20 ml, 25 ml, 30 ml, 35 ml, 40 ml, 45 ml, 50 ml, 55 ml, 60 ml, 65 ml, 70 ml, 75 ml, 80 ml, 85 ml, 90 ml, 95 ml, or 100 ml. In some embodiments, the volume of containers can be above 100 ml, for example, 125 ml, 150 ml, 175 ml, or 200 ml. The platelet derivative composition as described herein can be filled in vials of different volumes as per the commercialization requirements. A plurality (or collection) of containers having the platelet derivative composition as per any of the embodiments herein, obtained by lyophilizing the composition that includes platelets during one process (e.g. TFF or other process) for preparing a platelet derivative, can be referred to as a "batch" or a "lot". In some embodiments, a batch/lot can have 10-500 vials, 25-450 vials, 50-350 vials, 100-300 vials, or 150-250 vials. In some embodiments, a batch/lot can have 10, 20, 30, 40, 50, 60, 70, 80, 90, 100, 110, 120, 130, 140, 150, 160, 170, 180, 190, 200, 250, 300, 350, 400, 450, or 500 vials. In some embodiments, the number of vials per batch/lot can be increased to more than 500 as per the requirements, for example, 600, 700, 800, 900, or 1000 vials. In some embodiments, the number of vials can be 10-1000, 50-1000, 100-900, 200-800, 100-500, 100-400, 150-700, or 150-500 vials. The containers in a batch/lot can have a volume in the range of 5-100 ml, for example, such that a lot has several containers with the same volume or containers with different volumes. For example, 200 vials/containers in a batch/lot can have a volume of 10 ml each, 100 vials/containers in the same or a separate batch/lot can have a volume of 20 ml each, 100 vials/containers in the same or another batch/lot can have a volume of 30 ml each, or 300 vials/containers in the same or a different batch/lot can have a volume of 10 ml each. The number of containers (e.g. vials) in which a platelet derivative composition as per one of the embodiments or aspects described herein can be packed in a batch/lot can vary with manufacturing requirements, the requirements of downstream processes, for example clinical processes, and the amount of starting material comprising platelet composition.

The quantity of platelet derivatives that is present in a batch/lot can vary based on the units of starting material comprising platelets that is used to produce the platelet derivatives. Certain methods provided herein, such as the TFF methods provided herein, allow more platelet units to be used to make platelet derivatives with the characteristics provided herein than prior methods. This is the result, for example, of the ability to reduce the level of certain components in a platelet composition starting material, such as HLA antibodies, HNA antibodies, and/or microparticles, to very low levels, as provided herein. Accordingly, the starting material comprising platelets, the corresponding composition (e.g. TFF-treated composition) that is lyophilized in illustrative embodiments, and the resulting platelet derivative composition powder, can vary, such that for example, in some embodiments, the starting material, the TFF-treated composition, and/or the resulting platelet derivative composition powder can include 10-500 units of platelets or platelet derivatives (e.g. 0.5 to 2.5 μm in diameter), with one unit being $3\times10^{11}$ platelets or platelet derivatives. In some embodiments, the starting platelet material, the composition to be lyophilized, and/or the platelet derivative (e.g. 0.5 to 2.5 μm in diameter) composition can include, for example, 20-500 units, 30-400 units, 40-350 units, or 50-200 units of platelets or platelet derivatives, respectively. In some embodiments, the platelet units in the starting platelet composition can be a pooled platelet product from multiple donors as described herein, or multiple batches of processed platelet compositions, such as TFF-treated compositions comprising platelets, can be pooled before lyophilization. In some embodiments, there can be $1\times10^9$ to $1\times10^{16}$ platelets in a starting platelet composition for processing, in a platelet composition that is lyophilized, and/or of platelet derivatives in a platelet derivative composition that is produced after lyophilization, per batch/lot. In some embodiments, the platelet-containing starting composition, the platelet composition that is lyophilized, and/or the platelet derivatives that are produced, typically after lyophilization per batch/lot can vary from $1\times10^{10}$ to $1\times10^{15}$, $1\times10^{11}$ to $1\times10^{15}$, $1\times10^{12}$ to $1\times10^{16}$, $1\times10^{13}$ to $1\times10^{15}$ or $1\times10^{13}$ to $1\times10^{14}$.

In certain illustrative embodiments, platelet derivative compositions that are present in a liquid, or in illustrative embodiments, a solid form such as a dried powder in the plurality of containers (e.g. vials), in illustrative embodiments of a 1 or more lots, are compositions that include platelet derivatives, wherein at least 50% of the platelet derivatives are CD 41-positive platelet derivatives, wherein less than 15%, 10%, or in further, non-limiting illustrative embodiments less than 5% of the CD 41-positive platelet derivatives are microparticles having a diameter of less than 0.5 μm, and wherein the platelet derivatives have a potency of at least 0.5, 1.0 and in further, non-limiting illustrative embodiments 1.5 thrombin generation potency units (TGPU) per $10^6$ platelet derivatives. In certain illustrative embodiments, including non-limiting examples of the illustrative embodiment in the preceding sentence, the platelet derivatives are 0.5 to 2.5 μm in diameter. Such platelet derivatives and platelet derivative compositions comprising the same, can have additional characteristics disclosed herein for such derivatives and compositions.

Processes provided herein for producing platelet derivative compositions, provide better lot to lot consistency than prior processes. For example, TFF methods provided herein provide improved lot to lot variability with respect to the components of compositions that include platelet derivatives prepared therein, in illustrative embodiments, compositions that include freeze-dried platelet derivates. Such freeze-dried platelet derivatives can be one of, or the main active ingredient(s). In some embodiments, a plurality of containers provided herein comprise the platelet derivative composition from at least 2 different lots in separate containers. In some embodiments, the amount of plasma protein in the powder of any two containers chosen from different lots, differs by less than 50%, 40%, 30%, 25%, or 20%, and in illustrative embodiments less than 10%, 5%, 2%, 1%, or 0.5%. The TFF process is highly controllable and can be stopped at a certain A280 for example, from 2.0 AU to 0.01 AU, or when it reaches 15% to 0.01% protein concentration in the composition that is to be lyophilized (e.g. TFF-treated composition), therefore, the plasma protein content can be very consistent not only within the containers/vials of a lot, but even between lots as well. Since different lots of platelet derivative compositions provided herein are typically prepared from platelets from different subjects or different combinations of subjects (e.g. pooled platelets from 2, 3, 4, 5, 6, 7, 8, 9, 10, 15, 20, 25, 30, 40, 50, 60, 70, 75, 80, or 100 subjects), different lots in illustrative embodiments differ in amino acid sequence of at least one (e.g., 1, 2, 3, 4, 5, 6, 7, 8, 9, 10, 1-100, or 1-10) of the proteins in, on, and/or associated with platelet derivatives of the compositions therein between the lots. In illustrative embodiments, these one or more amino acid differences occur at one or more (e.g., 1, 2, 3, 4, 5, 6, 7, 8, 9, 10, 1-100, or 1-10) of the site(s) of SNPs, in illustrative embodiments non-synonymous SNPs. In certain embodiments, such SNPs or non-synonymous SNPs have a minor allele frequency of less than or equal to 5%. In some embodiments, such pooled platelets are provided by processes provided herein, for example because HLA or HNA antibody levels can be reduced to very low or non-existent levels. Thus, not only can platelets be pooled from more subjects, before processing to form platelet derivatives, but those subjects can be males or females. As a result, platelet derivatives, in illustrative embodiments, FDPDs, of compositions herein, for example liquid or dried compositions, in some embodiments have different amino acid sequences for at least 1 or a plurality of FDPD proteins. Furthermore, as a result, in certain embodiments, within a lot or between lots, greater than 10%, 20%, 25%, 30%, or 40%, and in illustrative embodiments greater than 50%, 60%, 70%, 75%, 80%, 90%, or 95% of amino acids encoded by SNPs, in illustrative embodiments encoded by non-synonymous SNPs in one or more proteins that are bound to or otherwise associated with or part of a platelet derivative, are present for SNPs, for example with a minor allele frequency of greater than 5%, in certain embodiments including in proteins that result from expression of coding sequences comprising SNPs, in illustrative embodiments non-synonymous SNPs on a mammalian X and Y chromosome.

In some embodiments, the amount of microparticles that are less than 0.5 μm in the powder of any two containers chosen from different lots, differs in amount by less than 10%, 5%, 2%, or 1%. Since, for example, a TFF process disclosed herein is very controllable, the concentration of microparticles to be obtained in the platelet derivative composition can be optimized, for example, by performing scattering intensity studies at different time points. Once the desired level is achieved, the TFF-treated composition can be lyophilized and packed in the vials with or without the baking step.

In some embodiments, the percentage by weight of platelet derivative in the powder of any two containers chosen from different lots, differs by less than 10%, 5%, 2%, or 1%. The TFF process can be optimized to achieve a pre-determined level of platelet derivatives in the TFF-treated composition. Such a TFF-treated composition when lyophilized gives a platelet composition in the form of a powder having a certain weight percentage of platelet derivatives. Since, the TFF process is controllable, in some embodiments, there can be a minimum or a negligible variation in the weight percentages of the platelet derivatives in any two containers chosen from different lots.

In some embodiments, at least one container comprises a first lot of platelet derivatives and the one or more other containers comprise a second lot of platelet derivatives. In some embodiments, plurality of containers comprises the platelet derivative composition from at least 2, 3, 4, 5, 6, 7, 8, 9, or 10 different lots, wherein the platelet derivative composition in at least 2 of the lots have a different amino acid sequences for at least one protein of a collection of protein gene products from a corresponding collection of encoding genes. In illustrative embodiments all, of the lots have a different amino acid sequences for at least one protein of a collection of protein gene products from a corresponding collection of encoding genes. In some embodiments, the amino acid difference(s) is at one or more residues corresponding to amino acid residues encoded by a non-synonymous single nucleotide polymorphism (SNP).

As per one of the embodiments, a platelet derivative composition as described herein can be prepared from multiple donors of a single species, for example, mammals, such as for example canine, equine, porcine and in illustrative embodiments humans that are genetically different, in order to obtain a platelet derivative composition to prepare allogenic platelet derivatives, an allogenic platelet derivative product, and/or a composition comprising allogenic platelet derivatives. Such a platelet derivative composition can be filled in vials and a plurality of such vials can be packaged in containers, for example boxes for commercialization as described herein, to obtain a commercial product that is a composition comprising allogeneic platelet derivatives, in illustrative embodiments allogeneic freeze-dried platelet derivatives. The allogenic platelet derivatives as described herein, in some embodiments, can be a U.S. FDA-approved product comprising an allogenic platelet derivative composition. In some embodiments, a platelet derivative composition as described herein can be a European EMA-approved product comprising an allogenic platelet derivative composition. In some other embodiments, a platelet derivative composition as described herein can be a China FDA-approved product comprising an allogenic platelet derivative composition.

In some embodiments, platelets are pooled from a plurality of donors before they are used as starting material for a process for producing a platelet derivative as provided herein. Such platelets pooled from a plurality of donors can be also referred herein to as pooled platelets. In some embodiments, the donors are more than 5, such as more than 10, such as more than 20, such as more than 50, such as up to about 100 donors. In some embodiments, the donors are from 5 to 100, such as from 10 to 50, such as from 20 to 40, such as from 25 to 35. Pooled platelets can be used to make any of the platelet derivative compositions as described herein. The platelets can be pooled wherein the platelets are donated by mammalian (e.g. bovine, feline, porcine, canine, and in illustrative embodiments, human) subjects. In some embodiments, the gender of the subjects can be male or female. In some embodiments, the donor can vary from any number of male to any number of female subjects, for example, from a total of 100 donors, any number can be female donors, ranging from 0-100, 5-95, 10-90, 20-80, 30-70, or 40-60, and the rest can be male donors. In some other embodiments, the donor can be a non-human animal. In some embodiments, the donor can be a canine, equine, porcine, bovine, or feline subject.

In some embodiments of any of the aspects and embodiments herein that include a composition, or in some compositions used in or formed by a process that includes a plurality of containers each filled with a platelet derivative composition in the form of a powder, each of the plurality of containers are purged with at least one inert gas. In some embodiments, the inert gas can be argon, or nitrogen.

Platelet Derivatives for Treating Disorders

In some embodiments, a platelet derivative composition, in illustrative embodiment a freeze-dried platelet derivative, including, but not limited to, those of any of the aspects or embodiments herein, or the platelet derivative composition prepared by any of the process described in the aspects or embodiments herein, can be administered, or delivered to a subject having an indication and thus afflicted with a disorder or disease that could benefit from delivery of such platelet derivative compositions. In some embodiments, such indication can be any one or a combination of Von Willebrand disease, immune thrombocytopenia (ITP), intracranial hemorrhage (ICH), traumatic brain injury (TBI), Hermansky Pudlak Syndrome (HPS), chemotherapy induced thrombocytopenia (CIT), Scott syndrome, Evans syndrome, hematopoietic stem cell transplantation, fetal and neonatal alloimmune thrombocytopenia, Bernard Soulier syndrome, acute myeloid leukemia, Glanzmann thrombasthenia, myelodysplastic syndrome, hemorrhagic shock, coronary thrombosis (myocardial infarction), ischemic stroke, arterial thromboembolism, Wiskott Aldrich syndrome, venous thromboembolism, MYH9 related disease, acute lymphoblastic lymphoma (ALL), acute coronary syndrome, chronic lymphocytic leukemia (CLL), acute promyelocytic leukemia, cerebral venous sinus thrombosis (CVST), liver cirrhosis, factor v deficiency (Owren Parahemophilia), thrombocytopenia absent radius syndrome, Kasabach Merritt syndrome, Gray platelet syndrome, aplastic anemia, chronic liver disease, acute radiation syndrome, Dengue hemorrhagic fever, pre-eclampsia, snakebite envenomation, HELLP syndrome, haemorrhagic cystitis, multiple myeloma, disseminated intravascular coagulation, heparin induced thrombocytopenia, pre-eclampsia, labor and delivery, hemophilia, cerebral (fatal) malaria, Alexander's disease (Factor VII Deficiency), hemophilia C (Factor XI Deficiency), familial hemophagocytic lymphohistiocytosis, acute lung injury, hemolytic uremic syndrome, menorrhagia, chronic myeloid leukemia. In illustrative embodiments, a platelet derivative composition of any of the aspects or embodiments herein, or the platelet derivative composition prepared by any of the process described in the aspects or embodiments herein can be administered, or delivered to a subject afflicted by Immune thrombocytopenia. In certain illustrative embodiments, a platelet derivative composition of any of the aspects or embodiments herein, or the platelet derivative composition prepared by any of the process described in the aspects or embodiments herein can be administered, or delivered to a subject afflicted by Von Willebrand disease. In some embodiments, a method of treating of any of the aspects or embodiments herein, can include a method of treating a subject afflicted with any of the indications as described herein. In any of the methods herein wherein platelet derivatives are administered to a subject having any of the listed indications/disorders, the subject can have an anti-coagulant or antiplatelet agent in their body, such as in their blood, and can be, or have been within 1 month, 1 week, 5 days, 4 days, 3, days, 2 days, 1 day, 12 hours, 8 hours, or 4 hours, taking or administered an anti-coagulant and/or an anti-platelet agent.

In some embodiments, a platelet derivative composition of any of the aspects or embodiments herein, or the platelet derivative composition prepared by any of the process described in the aspects or embodiments can be used to treat a subject having any one or a combination of any of the indications as described herein. In certain embodiments, a platelet derivative composition as described herein can be used, for example as a medicament or in the manufacture of a kit, for treating a subject having any one or a combination of indication as disclosed herein.

In some embodiments, an indication or indications can include those type of indications which require a much higher dose of the platelet derivatives herein, or would require an unsafe dose of, or cannot be treated with, unmodified, cold stored, naturally-occurring, endogenous, autologous, allogeneic, or normal platelets, platelets having the characteristics of in-vivo platelets, or conventional platelets (e.g. platelets collected by a conventional method for collecting platelets such as, for example, a platelet-rich plasma-method, a buff coat-method, or by apheresis), but are treatable using a platelet derivative composition of any of the aspects or embodiments herein, or the platelet derivative composition prepared by any of the processes disclosed herein, in illustrative embodiments freeze-dried platelet derivatives. In some embodiments, such an indication can be an indication that is associated with defective platelet production in a subject. In some embodiments, such an indication can be an indication that is associated with a defective platelet activity in a subject. In some embodiments, such an indication can be any of the indication as described herein. In some embodiments, indications that are typically cannot be treated with conventional platelets, but are treatable with a platelet derivative composition as disclosed herein are Von Willebrand disease, immune thrombocytopenia (ITP), intracranial hemorrhage (ICH), traumatic brain injury (TBI), Hermansky Pudlak Syndrome (HPS), Chemotherapy induced thrombocytopenia (CIT), Scott syndrome, Evans syndrome, Hematopoietic Stem Cell Transplantation, Fetal and neonatal alloimmune thrombocytopenia, Bernard Soulier syndrome, Acute myeloid leukemia, or combinations thereof. In some embodiments, such an indication can be Von Willebrand disease. In some embodiments, such an indication can be Immune thrombocytopenia. In some embodiments, such an indication can be Chemotherapy induced thrombocytopenia (CIT). In some embodiments, such an indication can be fetal and neonatal alloimmune thrombocytopenia.

In some embodiments, an indication or indications can include those type of indications which typically, can be well-suited for treatment using a platelet derivative composition as described herein. In some embodiments, such an indication or indications can include Von Willebrand disease, immune thrombocytopenia, intracranial hemorrhage (ICH), traumatic brain injury (TBI), Hermansky Pudlak Syndrome (HPS), Scott syndrome, Evans syndrome, Bernard Soulier syndrome, Glanzmann thrombasthenia, coronary thrombosis (myocardial infarction), arterial thromboembolism, Wiskott Aldrich syndrome, venous thromboembolism, and acute coronary syndrome.

In some embodiments, platelet derivatives as described herein can have several applications in terms of treating a subject suffering with a disorder selected from the group consisting of alopecia areata, Von Willebrand Disease, hemophilia, thrombasthenia, thrombocytopenia, thrombocytopenic purpura, trauma, or a combination thereof. In some embodiments, the platelet derivatives can be used to treat clotting-related disorders. The platelet derivatives as disclosed herein can be used both as a topical application and systemic administration. In some embodiments, there is provided a method for treating a clotting-related disorder in a subject, said method comprising administering to the subject a therapeutically effective amount of the platelet derivative composition of any of the aspects or embodiments herein, or the platelet derivative composition prepared by any of the process described in the aspects or embodiments herein. In some embodiments, the clotting-related disorder is selected from the group consisting of Von Willebrand Disease, hemophilia, thrombasthenia, thrombocytopenia, thrombocytopenic purpura, trauma, or a combination thereof. In some embodiments, a platelet derivative composition is passed through a filter of 18 μm before administering to the subject. A skilled artisan would be able to appreciate that the platelet derivative composition in the form of a powder which would be commercialized in vials would be rehydrated with an appropriate amount of a solution before administering to a subject. In some embodiments, such a rehydrated platelet derivative composition is passed through a filter of 18 μm before administering to the subject. In some embodiments, the platelet derivative composition as disclosed herein can be used in treating a coagulopathy in a subject that has been administered or is being administered an antiplatelet agent. In some embodiments, the platelet derivative composition of any of the aspects or embodiments herein is provided for use an anti-platelet reversal agent. In some embodiments, the platelet derivative composition of any of the aspects or embodiments herein can be used in treating a coagulopathy in a subject that has been administered or is being administered an anticoagulant agent.

In some embodiments, the platelet derivatives disclosed herein can be used for healing wounds in a subject. In some embodiments, there is provided a method for healing a wound in a subject, comprising administering a therapeutically effective amount of a platelet derivative composition of any of the aspects or embodiments herein, or the platelet derivative composition prepared by any of the process described in the aspects or embodiments herein, to the subject and/or a wound of the subject.

In some embodiments, the administering can include administering topically. Administering can include administering parenterally. Administering can include administering intravenously. Administering can include administering intramuscularly. Administering can include administering intrathecally. Administering can include administering subcutaneously. Administering can include administering intraperitoneally.

Platelet derivative compositions comprising platelet derivatives as described herein can be used as a medicament for treating a subject. Further, there is also provided herein, methods of treating a subject by administering to a subject a therapeutically effective amount or dose of a platelet derivative composition comprising platelet derivatives as described herein. In some embodiments, the subject is suffering from a condition, or a disease selected from the group consisting of thrombocytopenia, hematologic malignancy, bone marrow aplasia, myeloproliferative disorders, myelodysplastic syndromes, and platelet refractoriness. In some embodiments, the subject is suffering from one or more diseases or condition as described herein. In some embodiments, a therapeutically effective dose of platelet derivatives is based on units of thrombin generation activity administered per kilogram of body weight of the subject and/or the number of platelet derivatives delivered to the subject. In some embodiments of any aspect or embodiment herein the effective dose is based on the weight of the subject. It can be contemplated by a person of skill in the art that the effective dose can be based on any criteria that suits the requirement of the medical intervention of the subject.

A person of skill in the art can contemplate the effective dose of platelet derivatives that can be required to treat a subject in need thereof. The need may differ based on the condition of the subject. The effective dosage can be categorized into a) low dosage; b) medium dosage; and c) high dosage. In some embodiments, a medicament or a method of treating a subject can have the effective dose as low, medium, or high dosage of platelet derivatives that can broadly range from $1.0\times10^{7}$ on the low end of the range to $1.0\times10^{10}$/kg, $1.0\times10^{11}$/kg or $1.0\times10^{12}$/kg of the subject on the high end of the range.

In some embodiments, a platelet derivative composition as described herein can be administered or delivered to a subject, such as a subject afflicted with any one or combination of indications as described herein, and the dose of a platelet derivative composition can be in the range of $1.0\times10^{7}$ to $1.0\times10^{12}$ particles/kg of the subject. For example, in some embodiments, a dose of a composition comprising platelets or platelet derivatives (e.g., FDPDs) can include between about or exactly $1.0\times10^{7}$ on the low end of the range to $1.0\times10^{12}$ particles (e.g. FDPDs)/kg of a subject on the high end of the range, $1.0\times10^{7}$ to $1.0\times10^{11}$ particles (e.g. FDPDs)/kg of a subject, $1.0\times10^{7}$ to $1.0\times10^{10}$ particles (e.g. FDPDs)/kg of a subject, $1.6\times10^{7}$ to $1.0\times10^{11}$ particles (e.g. FDPDs)/kg of a subject, $1.6\times10^{7}$ to $1.0\times10^{10}$ particles (e.g. FDPDs/kg of subject, $1.6\times10^{7}$ to $5.1\times10^{9}$ particles (e.g. FDPDs/kg of a subject, $1.6\times10^{7}$ to $3.0\times10^{9}$ particles (e.g. FDPDs)/kg of a subject, $1.6\times10^{7}$ to $1.0\times10^{9}$ particles (e.g. FDPDs)/kg of a subject, $1.6\times10^{7}$ to $5.0\times10^{8}$ particles (e.g. FDPDs)/kg of a subject, $1.6\times10^{7}$ to $1.0\times10^{8}$ particles (e.g. FDPDs)/kg of a subject, $1.6\times10^{7}$ to $5.0\times10^{7}$ particles (e.g. FDPDs)/kg of a subject, $5.0\times10^{7}$ to $1.0\times10^{8}$ particles (e.g. FDPDs)/kg of a subject, $1.0\times10^{8}$ to $5.0\times10^{8}$ particles (e.g. FDPDs)/kg of a subject, $5.0\times10^{8}$ to $1.0\times10^{9}$ particles (e.g. FDPDs)/kg of a subject, $1.0\times10^{9}$ to $5.0\times10^{9}$ particles (e.g. FDPDs)/kg of a subject, $5.0\times10^{7}$ to $1.0\times10^{11}$ particles (e.g. FDPDs)/kg of a subject, $5.0\times10^{9}$ to $1.0\times10^{10}$ particles (e.g. FDPDs)/kg of a subject), or $1.0\times10^{10}$ to $1.0\times10^{11}$ or $1.0\times10^{12}$ particles (e.g. FDPDs)/kg of a subject on the high end of the range. In some embodiments, the dose can be in the range of 250 and 5000 TGPU per kg of the subject.

In some embodiments, a platelet derivative composition, such as that provided in any aspect or embodiment herein, can be administered or delivered to a subject afflicted with any one or combination of indications/diseases as disclosed herein, and the dose of a platelet derivative composition can be in the range of $1.0\times10^{7}$ on the low end of the range to $1.0\times10^{12}$ particles/kg of the subject. For example, in some embodiments, a dose of a composition comprising platelets or platelet derivatives (e.g., FDPDs) can include between about or exactly $1.0\times10^{7}$ on the low end of the range to $1.0\times10^{12}$ particles (e.g. FDPDs)/kg of a subject, $1.0\times10^{7}$ to $1.0\times10^{11}$ particles (e.g. FDPDs)/kg of a subject, $1.0\times10^{7}$ to $1.0\times10^{10}$ particles (e.g. FDPDs)/kg of a subject, $1.6\times10^{7}$ to $1.0\times10^{10}$ particles (e.g. FDPDs/kg of subject, $1.6\times10^{7}$ to $5.1\times10^{9}$ particles (e.g. FDPDs/kg of a subject, $1.6\times10^{7}$ to $3.0\times10^{9}$ particles (e.g. FDPDs)/kg of a subject, $1.6\times10^{7}$ to $1.0\times10^{9}$ particles (e.g. FDPDs)/kg of a subject, $1.6\times10^{7}$ to $5.0\times10^{8}$ particles (e.g. FDPDs)/kg of a subject, $1.6\times10^{7}$ to $1.0\times10^{8}$ particles (e.g. FDPDs)/kg of a subject, $1.6\times10^{7}$ to $5.0\times10^{7}$ particles (e.g. FDPDs)/kg of a subject, $5.0\times10^{7}$ to $1.0\times10^{8}$ particles (e.g. FDPDs)/kg of a subject, $1.0\times10^{8}$ to $5.0\times10^{8}$ particles (e.g. FDPDs)/kg of a subject, $5.0\times10^{8}$ to $1.0\times10^{9}$ particles (e.g. FDPDs)/kg of a subject, $1.0\times10^{9}$ to $5.0\times10^{9}$ particles (e.g. FDPDs)/kg of a subject, or $5.0\times10^{9}$ to $1.0\times10^{10}$ particles (e.g. FDPDs)/kg of a subject). In some embodiments, a dose of a composition comprising platelets or platelet derivatives (e.g., FDPDs) can be a range of between about or exactly $1.0\times10^{8}$, $5.0\times10^{8}$, $1.0\times10^{9}$, $3.0\times10^{9}$, $4.0\times10^{9}$, $5.0\times10^{9}$, $1.0\times10^{10}$, $2.5\times10^{10}$, or $5.0\times10^{10}$ on the low end of the range to $1.0\times10^{12}$ particles (e.g. FDPDs)/kg of a subject on the high end of the range. In some embodiments, and in illustrative embodiments wherein a subject has indications as described herein, a dose of a composition comprising platelets or platelet derivatives (e.g., FDPDs) can be a range of between about or exactly $3.0\times10^{9}$, $4.0\times10^{9}$, $5.0\times10^{9}$, $1.0\times10^{10}$, $2.5\times10^{10}$, or $5.0\times10^{10}$ on the low end of the range to $1.0\times10^{12}$ particles (e.g. FDPDs)/kg of a subject on the high end of the range. In some embodiments, and in illustrative embodiments wherein a subject has indications as described herein, a dose of a composition comprising platelets or platelet derivatives (e.g., FDPDs) can be a range of between about or exactly $3.0\times10^{9}$, $4.0\times10^{9}$, $5.0\times10^{9}$, $1.0\times10^{10}$, $2.5\times10^{10}$, or $5.0\times10^{10}$ on the low end of the range to $5.0\times10^{11}$ particles or $1.0\times10^{12}$ (e.g. FDPDs)/kg of a subject on the high end of the range. In some embodiments, and in illustrative embodiments wherein a subject has indications as described herein, a dose of a composition comprising platelets or platelet derivatives (e.g., FDPDs) can be a range of between about or exactly $3.0\times10^{9}$, $4.0\times10^{9}$, $5.0\times10^{9}$, $1.0\times10^{10}$, $2.5\times10^{10}$, or $5.0\times10^{10}$ on the low end of the range to $1.0\times10^{11}$ particles or $1.0\times10^{12}$ (e.g. FDPDs)/kg of a subject on the high end of the range. In some embodiments, and in illustrative embodiments wherein a subject has indications as described herein, a dose of a composition comprising platelets or platelet derivatives (e.g., FDPDs) can be a range of between about or exactly $3.0\times10^{9}$, $4.0\times10^{9}$, or $5.0\times10^{9}$ on the low end of the range to $1.0\times10^{10}$ particles (e.g. FDPDs)/kg of a subject on the high end of the range. In some embodiments, and in illustrative embodiments wherein a subject has indications as described herein, a dose of a composition comprising platelets or platelet derivatives (e.g., FDPDs) can be in a range of greater than $1.5\times10^9$ FDPDs/kg of the subject on the low end of the range and $1.5\times10^{10}$, $1.4\times10^{10}$, $1.3\times10^{10}$, $1.2\times10^{10}$, or $1.1\times10^{10}$ FDPDs/kg of the subject on the high end; or greater than $1.0\times10^{10}$ FDPDs/kg of the subject on the low end of the range and $1.5\times10^{10}$, $1.4\times10^{10}$, $1.3\times10^{10}$, $1.2\times10^{10}$, or $1.1\times10^{10}$ FDPDs/kg of the subject on the high end; or $1.1\times10^{10}$ FDPDs/kg of the subject on the low end of the range and $1.5\times10^{10}$, $1.4\times10^{10}$, $1.3\times10^{10}$, or $1.2\times10^{10}$ FDPDs/kg of the subject on the high end; or $1.1\times10^{10}$ FDPDs/kg of the subject on the low end and less than $1.5\times10^{10}$, $1.4\times10^{10}$, $1.3\times10^{10}$, or $1.2\times10^{10}$ FDPDs/kg of the subject on the high end of the range.

In some embodiments of any aspect or embodiment herein a therapeutically effective dose or effective dose or amount of the platelet derivatives in a platelet derivative composition is in the range of $1.5\times10^7$ to $5.0\times10^{10}$/kg, $2.0\times10^7$ to $1.0\times10^{10}$/kg, $2.5\times10^7$ to $5.0\times10^9$/kg, $2.75\times10^7$ to $3.0\times10^9$/kg, $2.8\times10^7$ to $4.0\times10^9$/kg, $3.0\times10^7$ to $4.0\times10^9$/kg, $5\times10^7$ to $4.0\times10^9$/kg, $6\times10^7$ to $3.0\times10^9$/kg, $9\times10^7$ to $3.0\times10^9$/kg, $1.0\times10^8$ to $2.0\times10^9$/kg, or $1.3\times10^8$ to $1.8\times10^9$/kg of the subject. In some embodiments, a therapeutically effective dose or effective dose or amount of the platelet derivatives in a platelet derivative composition is in the range of $5.0\times10^7$ to $1.0\times10^9$/kg, $1.0\times10^8$ to $5.0\times10^8$/kg, $1.2\times10^8$ to $2.5\times10^8$/kg, $1.6\times10^8$ to $2.2\times10^8$/kg, or $1.7\times10^8$ to $2.0\times10^8$/kg of the subject. In some embodiments, the platelet derivatives in a platelet derivative composition is $1.1\times10^8$/kg, $1.2\times10^8$/kg, $1.3\times10^8$/kg, $1.4\times10^8$/kg, $1.5\times10^8$/kg, $1.6\times10^8$/kg, $1.7\times10^8$/kg, $1.8\times10^8$/kg, $1.9\times10^8$/kg, $2.0\times10^8$/kg, $2.1\times10^8$/kg, $2.2\times10^8$/kg. $2.3\times10^8$/kg, $2.4\times10^8$/kg, or $2.5\times10^8$/kg of the subject.

In some embodiments of any aspect or embodiment herein a therapeutically effective dose or effective dose or amount of the platelet derivatives in a platelet derivative composition is in the range of $5.1\times10^8$ to $9.9\times10^8$/kg, $5.5\times10^8$ to $9.5\times10^8$/kg, $5.8\times10^8$ to $9.3\times10^8$/kg, $6.1\times10^8$ to $9.0\times10^8$/kg, $6.5\times10^8$ to $8.8\times10^8$/kg, $6.8\times10^8$ to $8.5\times10^8$/kg, $7.0\times10^8$ to $8.4\times10^8$/kg, $7.5\times10^8$ to $8.3\times10^8$/kg, $7.8\times10^8$ to $8.2\times10^8$/kg, or $7.9\times10^8$ to $8.1\times10^8$/kg of the subject. In some embodiments, a therapeutically effective dose or effective dose or amount of the platelet derivatives in a platelet derivative composition is $7.5\times10^8$/kg, $7.6\times10^8$/kg, $7.7\times10^8$/kg, $7.8\times10^8$/kg, $7.9\times10^8$/kg, $8.0\times10^8$/kg, $8.1\times10^8$/kg, $8.2\times10^8$/kg, $8.3\times10^8$/kg, $8.4\times10^8$/kg, or $8.5\times10^8$/kg of the subject.

In some embodiments of any aspect or embodiment herein a therapeutically effective dose or effective dose or amount of the platelet derivatives in a platelet derivative composition is in the range of $1.0\times10^9$ to $1.0\times10^{10}$/kg, $1.1\times10^9$ to $8.0\times10^9$/kg, $1.2\times10^9$ to $7.0\times10^9$/kg, $1.2\times10^9$ to $6.0\times10^9$/kg, $1.2\times10^9$ to $5.0\times10^9$/kg, $1.3\times10^9$ to $4.0\times10^9$/kg, $1.3\times10^9$ to $3.0\times10^9$/kg, $1.3\times10^9$ to $2.5\times10^9$/kg, $1.4\times10^9$ to $1.9\times10^9$/kg, $1.50\times10^9$ to $1.75\times10^9$/kg, or $1.55\times10^9$ to $1.70\times10^9$/kg of the subject. In some embodiments, a therapeutically effective dose or effective dose or amount of the platelet derivatives in a platelet derivative composition is $1.1\times10^9$/kg, $1.2\times10^9$/kg, $1.3\times10^9$/kg, $1.4\times10^9$/kg $1.5\times10^9$/kg, $1.55\times10^9$/kg, $1.56\times10^9$/kg, $1.57\times10^9$/kg, $1.58\times10^9$/kg, $1.59\times10^9$/kg, $1.6\times10^9$/kg, $1.61\times10^9$/kg, $1.62\times10^9$/kg, $1.63\times10^9$/kg, $1.64\times10^9$/kg, $1.65\times10^9$/kg, $1.66\times10^9$/kg, $1.7\times10^9$/kg, $1.8\times10^9$/kg, $1.9\times10^9$/kg, or $2.0\times10^9$/kg of the subject.

In some embodiments, a medicament or a method of treating a subject can have a low, medium, or high dosage of platelet derivatives that has a potency in the range of 250 to 5000 TGPU per kg of the subject.

In some embodiments of any aspect or embodiment herein a therapeutically effective dose or an effective dose or amount of the platelet derivatives is an amount that has a potency in the range of 250 to 5000 TGPU per kg, 270 to 4500 TGPU per kg, 280 to 4300 TGPU per kg, 290 to 4100 TGPU per kg, 300 to 3800 TGPU per kg, 310 to 3500 TGPU per kg, or 320 to 3000 TGPU per kg of the subject. In some embodiments, a therapeutically effective dose or effective dose or amount of the platelet derivatives is an amount that has a potency in the range of 275 to 500 TGPU per kg, 280 to 450 TGPU per kg, 290 to 400 TGPU per kg, 300 to 375 TGPU per kg, 310 to 350 TGPU per kg, or 320 to 340 TGPU per kg of the subject. In some embodiments of any aspect or embodiment herein a therapeutically effective dose or effective dose or amount of the platelet derivatives is an amount that has a potency of 270 TGPU per kg, 280 TGPU per kg, 290 TGPU per kg, 300 TGPU per kg, 310 TGPU per kg, 320 TGPU per kg, 330 TGPU per kg, 340 TGPU per kg, or 350 TGPU per kg of the subject.

In some embodiments of any aspect or embodiment herein a therapeutically effective dose or effective dose or amount of the platelet derivatives is an amount that has a potency in the range of 1001 to 2000 TGPU per kg, 1200 to 2000 TGPU per kg, 1300 to 1950 TGPU per kg, 1400 to 1900 TGPU per kg, 1500 to 1900 TGPU per kg, 1600 to 1900 TGPU per kg, 1700 to 1900 TGPU per kg, 1750 to 1875 TGPU per kg, or 1800 to 1850 TGPU per kg of the subject. In some embodiments, a therapeutically effective dose or effective dose or amount of the platelet derivatives is an amount that has a potency of 1780 TGPU per kg, 1790 TGPU per kg, 1800 TGPU per kg, 1810 TGPU per kg, 1820 TGPU per kg, 1830 TGPU per kg, 1840 TGPU per kg, or 1850 TGPU per kg of the subject.

In some embodiments of any aspect or embodiment herein a therapeutically effective dose or effective dose or amount of the platelet derivatives is an amount that has a potency in the range of 2001 to 3500 TGPU per kg, 2300 to 3300 TGPU per kg, 2500 to 3100 TGPU per kg, 2600 to 3100 TGPU per kg, 2700 to 3100 TGPU per kg, 2800 to 3100 TGPU per kg, 2850 to 3050 TGPU per kg, 2900 to 3000 TGPU per kg, or 2940 to 2990 TGPU per kg of the subject. In some embodiments, a therapeutically effective dose or effective dose or amount of the platelet derivatives is an amount that has a potency of 2910 TGPU per kg, 2920 TGPU per kg, 2930 TGPU per kg, 2940 TGPU per kg, 2950 TGPU per kg, 2960 TGPU per kg, 2970 TGPU per kg, 2980 TGPU per kg, 2990 TGPU per kg, 3000 TGPU per kg, or 3100 TGPU per kg of the subject.

In certain embodiments, any of the dose ranges provided above, and in illustrative embodiments those that include less than $1\times10^{11}$ particles/kg, or any of the ranges provided herein, for example those provided in the paragraph immediately above, can be administered more than 1 time to a subject. For example, a dose range of between $1.0\times10^7$ particles to about $1.0\times10^{10}$ particles, can be administered between 2 and 10 times, or between 2 and 8 times, or between 2 and 6 times, or between 3 and 8 times, or between 3 and 6 times, or between 4 and 6 times in a timeframe between within 1, 2, 3, 4, 5, or 7 days from the first dose.

In a method of treating a subject with platelet derivatives as described herein, there can be several endpoints that determine if the subject is treated. A method of treating can have one or more primary endpoints. A method can additionally have one or more secondary endpoints. In some embodiments, in a method of treatment or a composition for use as a medicament as described herein, a method or a medicament leads to cessation or decrease in bleeding at a primary bleeding site at 12 hours, 24 hours, 48 hours, 72 hours, 4 days, 5 days, 6 days, and/or 7 days after administering the platelet derivative composition. In illustrative embodiments, a method or a medicament as described herein leads to cessation or decrease in bleeding at bleeding sites other than primary bleeding site at 24 hours after administering the platelet derivative composition. In some embodiments, the primary bleeding site is based upon the most severe bleeding location of the subject within 12 hours prior to administering the platelet derivative composition. In some embodiments, the administering involves infusing a platelet derivative composition. In some embodiments, a platelet derivative composition is administered on Day 1 of the treatment. In some embodiments, the cessation or decrease is evidenced by an ordinal change in WHO bleeding score of the subject evaluated at 24 hours after administering the platelet derivative composition to the subject. In some embodiments, a method or a medicament as described herein leads to cessation or decrease in bleeding at bleeding sites other than primary bleeding site at 12 hours, 24 hours, 48 hours, 72 hours, 4 days, 5 days, 6 days, and 7 days after administering the platelet derivative composition. In some embodiments, the bleeding in a subject is a non-compressible bleeding or a non-compressible hemorrhage. A non-compressible hemorrhage is a type of hemorrhage that is inaccessible to a tourniquet or pressure dressing. In some embodiments, a method or a medicament leads to an increase in platelet count in the subject at 12 hours, 24 hours, 48 hours, 72 hours, 4 days, 5 days, 6 days, and 7 days after administering the platelet derivative composition. In some embodiments, the increase is at least 500 platelets/μl, 1000 platelets/μl, 2000 platelets/μl, 3000 platelets/μl, 4000 platelets/μl, 5000 platelets/0, 6000 platelets/μl, 7000 platelets/μl, 8000 platelets/μl, 9000 platelets/μl, or 10000 platelets/μl in the subject. In some embodiments, the increase is in the range of 500 to 10000 platelets/μl, 1000 to 10000 platelets/μl, 2000 to 8000 platelets/μl, or 3000 to 7000 platelets/μl in the subject. In some illustrative embodiments, the increase can be at least 5000 platelets/0.

In some embodiments, a method or a medicament leads to changes, or in other embodiments, does not lead to changes, in one or more markers of endothelial cell injury in the subject from a pre-administration time through 12 hours to 35 days, 24 hours to 32 days, 24 hours to 30 days, or 48 hours to 28 days after administering the platelet derivative composition. In illustrative embodiments, a method or a medicament leads to changes, or in other embodiments, does not lead to changes, in one or more markers of endothelial cell injury in the subject from a pre-administration time through baseline to 72 hours after administering the platelet derivative composition. In some embodiments, the method or the medicament leads to changes in two or more markers, three or markers, four or more markers, five or more markers, or all of the markers selected from the group consisting of Syndecan-1, hyaluronan, thrombomodulin, vascular endothelial growth factor (VEGF), interleukin 6, and sVE cadherin. In some embodiments, the changes can be an increase or a decrease in the markers of endothelial cell injury in the subject as compared to a control.

In some embodiments, a method or a medicament leads to acceptable measures of coagulation in the subject at between 12 hours to 35 days, 24 hours to 32 days, 24 hours to 30 days, or 24 hours to 28 days after administering the platelet derivative composition. In illustrative embodiments, a method or a medicament leads to acceptable measures of coagulation in the subject at 72 hours after administering the platelet derivative composition. In some embodiments, the acceptable measure of coagulation includes one or more, two or more, three or more, four or more, five or more, or all of prothrombin time (PT), international normalized ratio (INR), fibrinogen, D-dimer, activated partial thromboplastin time (aPTT), and thromboelastography (TEG) or rotational thromboelastometry (ROTEM). In some embodiments, a method or a medicament leads to an increase or a decrease in the acceptable measure of coagulation in the subject as compared to a control.

In some embodiments, a method or a medicament leads to acceptable measures of hematology in the subject from a pre-administration time through 12 hours to 35 days, 24 hours to 32 days, 24 hours to 30 days, or 48 hours to 28 days after administering the platelet derivative composition. In some embodiments, the acceptable measures of hematology are one or more, two or more, three or more, four or more, five or more, or all selected from the group consisting of Prothrombin Fragment 1+2, thrombin generation assay (TGA), Thrombopoietin, activated Protein C, tissue plasminogen activator (TPA), and/or plasminogen activator inhibitor (PAI). In some embodiments, the acceptable measures of hematology can be an increase or a decrease in the subject as compared to a control.

In some embodiments, a method of treatment or a composition for use as a medicament as described herein, a method or a medicament leads to survival of the subject without WHO Grade 2A or greater bleeding during the first 3, 4, 5, 6, 7, 8, 9, or 10 days after administering of a platelet derivative composition.

In some embodiments, administering confers an improved survival at 10, 15, 20, 25, 30, 35, 40, 45, or 50 days after administering the platelet derivatives. In some embodiments, administering leads to a decrease in administration of secondary blood products, platelets, or platelet derivatives to the subject for the first 5, 6, 7, 8, 9, or 10 days after the administering of the platelet derivatives.

A person of skill in the art can contemplate treating a subject or using platelet derivatives as described herein as a medicament in several doses in a span of time for treating the subject. In some embodiments, administering of platelet derivatives as described herein is performed in a maximum of 2, 3, 4, 5, 6, 7, 8, 9, or 10 doses in a 72-hour period of treatment. Further, in some embodiments, the subject involved in the treatment or a medication process satisfies certain criteria involving one or more of: minimum age; minimum weight; total circulating platelets (TCP); confirmed diagnosis of hematologic malignancy, myeloproliferative disorder, myelodysplastic syndrome or aplasia; undergoing chemotherapy, immunotherapy, radiation therapy or hematopoietic stem cell transplantation; refractory to platelet transfusion defined as two 1-hour CCI of <5000 on consecutive transfusions of liquid stored platelets; and WHO Bleeding Score of 2 excluding cutaneous bleeding. In some embodiments, the subject has a count of total circulating platelets (TCP) between 5,000 to 100,000 platelets/μl, 10,000 to 90,000 platelets/μl, 10,000 to 80,000 platelets/μl, or 10,000 to 70,000 platelets/μl of blood at the time of administering. In some embodiments, the subject is undergoing one or more, two or more, three or more, or all of chemotherapy, immunotherapy, radiation therapy or hematopoietic stem cell transplantation at the time of administering. In some embodiments, the subject is refractory to platelet transfusion, wherein refractory is a two 1-hour CCI [corrected count increment] of <5000 on consecutive transfusions of liquid stored platelets. In some embodiments, the subject has a WHO bleeding score of 2 excluding cutaneous bleeding. In some embodiments, the subject at the time of administering has one, two or more, or all of: confirmed diagnosis of hematologic malignancy, myeloproliferative disorder, myelodysplastic syndrome, or aplasia; undergoing chemotherapy, immunotherapy, radiation therapy or hematopoietic stem cell transplantation; or refractory to platelet transfusion wherein refractory is a two 1-hour CCI of <5000 on consecutive transfusions of liquid stored platelets.

Delivery to a Subject being Treated with an Anti-Platelet or Anti-Coagulant Agent In some aspects and embodiments, platelet derivatives provided herein can be used to treat a coagulopathy in a subject that has been administered or is being administered an antiplatelet agent or an anticoagulant agent. Accordingly, in related aspects and embodiments platelet derivatives as provided herein can be used as an anti-platelet reversal agent, or an anti-coagulant reversal agent. The antiplatelet class of drugs, which an illustrative class of antiplatelet agents, is widely used to prevent unwanted clotting episodes that lead to heart failure, stroke, and the like. In many cases, an antiplatelet drug may need to be reversed or stopped. In the case of advanced notice, as in a pre-planned surgery situation, the antiplatelet drug dose can sometimes be stopped before the surgery, preventing unwanted bleeding during surgery. In the case where an antiplatelet agent needs reversing quickly, reversal agents are typically not readily available, are expensive, or carry significant risk to the patient. In the case of need for rapid antiplatelet reversal, a platelet transfusion is typically administered, though the response to this is often only partial reversal. The caveat of this course of reversal is that the newly-infused platelets themselves are susceptible to circulating drug antiplatelet activity whereas, in some embodiments, compositions as described herein (e.g., including thrombosomes) are not. In some embodiments, compositions as described herein (e.g., including thrombosomes) are an active reversal agent. In some embodiments, the hemostatic activity of compositions as described herein (e.g., including thrombosomes) does not succumb to antiplatelet drugs. In some embodiments, an antiplatelet agent can be selected from the group consisting of aspirin, cangrelor, ticagrelor, clopidogrel, prasugrel, eptifibatide, tirofiban, abciximab, and combinations thereof.

In some embodiments of any of the methods for treating or methods of administering aspects herein, the subject is being treated or was treated with an anti-coagulant. In certain embodiments, the anticoagulant is dabigatran, argatroban, hirudin, rivaroxaban, apixaban, edoxaban, fondaparinux, warfarin, heparin, a low molecular weight heparin, a supplement, or a combination thereof. In some embodiments of any of the methods for administering or for treating aspects herein, wherein the subject is being treated with an anticoagulant, the anticoagulant is dabigatran, argatroban, hirudin, rivaroxaban, apixaban, edoxaban, fondaparinux, warfarin, heparin, low molecular weight heparins, tifacogin, Factor VIIai, SB249417, pegnivacogin (with or without anivamersen), TTP889, idraparinux, idrabiotaparinux, SR23781A, apixaban, betrixaban, lepirudin, bivalirudin, ximelagatran, phenprocoumon, acenocoumarol, indandiones, fluindione, a health and wellness supplement with anti-coagulant properties, or a combination thereof.

In some embodiments, there is provided a method of administering to a subject, or a method of treating coagulopathy in a subject, wherein the subject has been treated or is being treated with an antiplatelet agent or an anti-coagulant, the method comprising administering to the subject in need thereof an effective amount of a composition comprising platelet derivatives as described herein and an incubating agent comprising one or more salts, a buffer, optionally a cryoprotectant, and optionally an organic solvent. In some embodiments, there is provided a method of restoring normal hemostasis in a subject, the method comprising administering to the subject in need thereof an effective amount of a composition comprising platelet derivatives as described herein and an incubating agent comprising one or more salts, a buffer, optionally a cryoprotectant, and optionally an organic solvent. In some embodiments, there is provided a method of preparing a subject for surgery, the method comprising administering to the subject in need thereof an effective amount of a composition comprising platelet derivative composition as described herein and an incubating agent comprising one or more salts, a buffer, optionally a cryoprotectant, and optionally an organic solvent.

In some embodiments, the subject that has been administered or is being administered an antiplatelet agent or an anticoagulant agent in a subject having an indication and thus afflicted with a disorder or disease, that is any one or a combination of Von Willebrand disease, immune thrombocytopenia, intracranial hemorrhage (ICH), traumatic brain injury (TBI), Hermansky Pudlak Syndrome (HPS), chemotherapy induced thrombocytopenia (CIT), Scott syndrome, Evans syndrome, Hematopoietic Stem Cell Transplantation, fetal and neonatal alloimmune thrombocytopenia, Bernard Soulier syndrome, acute myeloid leukemia, Glanzmann thrombasthenia, myelodysplastic syndrome, hemorrhagic shock, coronary thrombosis (myocardial infarction), ischemic stroke, arterial thromboembolism, Wiskott Aldrich Syndrome, venous thromboembolism, MYH9 related disease, Acute Lymphoblastic Lymphoma (ALL), Acute Coronary Syndrome, Chronic Lymphocytic Leukemia (CLL), Acute Promyelocytic Leukemia, Cerebral Venous Sinus Thrombosis (CVST), Liver Cirrhosis, Factor V Deficiency (Owren Parahemophilia), Thrombocytopenia absent radius syndrome, Kasabach Merritt syndrome, Gray platelet syndrome, aplastic anemia, chronic liver disease, acute radiation syndrome, Dengue hemorrhagic fever, pre-eclampsia, snakebite envenomation, HELLP syndrome, haemorrhagic cystitis, multiple myeloma, disseminated intravascular coagulation, heparin induced thrombocytopenia, pre-eclampsia, labor and delivery, hemophilia, cerebral (fatal) malaria, Alexander's Disease (Factor VII deficiency), hemophilia c (factor xi deficiency), familial hemophagocytic lymphohistiocytosis, acute lung injury, hemolytic uremic syndrome, menorrhagia, chronic myeloid leukemia.

Provided herein in one aspect is a method of treating a coagulopathy in a subject, the method including administering to the subject in need thereof an effective amount of a composition including platelets, or in illustrative embodiments platelet derivatives, and in further illustrative embodiments FDPDs, thereby treating the coagulopathy. In illustrative embodiments, the composition comprising the platelet derivatives is administered such that the bleeding potential of the subject is reduced, and in illustrative embodiments such that normal hemostasis is restored in the subject.

In one aspect, provided herein is a method of treating a coagulopathy in a subject, the method including administering to the subject in need thereof an effective amount of a composition prepared by a process including incubating platelets with an incubating agent including one or more salts, a buffer, optionally a cryoprotectant, and optionally an organic solvent, and in illustrative embodiments freeze-drying the incubated platelets, to form the composition, wherein the composition includes platelet derivatives, and in illustrative embodiments FDPDs, thereby treating the coagulopathy. In illustrative embodiments, the composition comprising the platelet derivatives is administered such that the bleeding potential of the subject is reduced, and in illustrative embodiments such that normal hemostasis is restored in the subject.

In one aspect, provided herein is a method of restoring normal hemostasis in a subject, the method including administering to the subject in need thereof an effective amount of a composition including platelets, or in illustrative embodiments platelet derivatives, and in further illustrative embodiments FDPDs, thereby treating the coagulopathy. In illustrative embodiments, the composition comprising the platelet derivatives is administered such that the bleeding potential of the subject is reduced, and in illustrative embodiments such that normal hemostasis is restored in the subject.

In one aspect, provided herein is a method of restoring normal hemostasis in a subject, the method including administering to the subject in need thereof an effective amount of a composition prepared by a process including incubating platelets with an incubating agent including one or more salts, a buffer, optionally a cryoprotectant, and optionally an organic solvent, and in illustrative embodiments freeze-drying the incubated platelets, to form the composition, wherein the composition comprises platelet derivatives, and in further illustrative embodiments FDPDs, thereby treating the coagulopathy. In illustrative embodiments, the composition comprising the platelet derivatives is administered such that the bleeding potential of the subject is reduced, and in illustrative embodiments such that normal hemostasis is restored in the subject.

In one aspect, provided herein is a method of preparing a subject for surgery, the method including administering to the subject in need thereof an effective amount of a composition including platelets, or in illustrative embodiments platelet derivatives, and in further illustrative embodiments FDPDs. Various properties of exemplary embodiments of such FDPDs are provided herein, thereby treating the coagulopathy. In illustrative embodiments, the composition comprising the platelet derivatives is administered such that the bleeding potential of the subject is reduced, and in illustrative embodiments such that normal hemostasis is restored in the subject. Implementations can include one or more of the following features. The surgery can be an emergency surgery. The surgery can be a scheduled surgery.

In one aspect, provided herein is a method of preparing a subject for surgery, the method including administering to the subject in need thereof an effective amount of a composition prepared by a process including incubating platelets with an incubating agent including one or more salts, a buffer, optionally a cryoprotectant, and optionally an organic solvent, and in illustrative embodiments freeze-drying the incubated platelets, to form the composition, wherein the composition includes platelet derivatives, and in further illustrative embodiments FDPDs, thereby treating the coagulopathy. In illustrative embodiments, the composition comprising the platelet derivatives is administered such that the bleeding potential of the subject is reduced, and in illustrative embodiments such that normal hemostasis is restored in the subject. Various properties of exemplary embodiments of such FDPDs are provided herein. Implementations can include one or more of the following features. The surgery can be an emergency surgery. The surgery can be a scheduled surgery.

In one aspect, provided herein is a method of ameliorating the effects of an antiplatelet agent in a subject, the method including administering to the subject in need thereof an effective amount of a composition platelets, or in illustrative embodiments platelet derivatives, and in further illustrative embodiments FDPDs, thereby treating the coagulopathy. In illustrative embodiments, the composition comprising the platelet derivatives is administered such that the bleeding potential of the subject is reduced, and in illustrative embodiments such that normal hemostasis is restored in the subject.

In one aspect, provided herein is a method of ameliorating the effects of an antiplatelet agent in a subject, the method including administering to the subject in need thereof an effective amount of a composition prepared by a process including incubating platelets with an incubating agent including one or more salts, a buffer, optionally a cryoprotectant, and optionally an organic solvent, to form the composition, wherein the composition includes platelet derivatives, and in further illustrative embodiments FDPDs, thereby treating the coagulopathy. In illustrative embodiments, the composition comprising the platelet derivatives is administered such that the bleeding potential of the subject is reduced, and in illustrative embodiments such that normal hemostasis is restored in the subject.

In one aspect, provided herein is a method of treating a coagulopathy in a subject, or of restoring hemostasis in a subject, or of reducing bleeding potential of a subject that is being administered, or has been administered, an antiplatelet agent, the method comprising: administering to the subject in need thereof an effective amount of a composition comprising platelet derivatives, thereby treating the coagulopathy. In illustrative embodiments, the platelet derivatives are freeze-dried platelet derivatives (FDPDs). In further illustrative embodiments, the composition comprising the platelet derivatives is administered such that the bleeding potential of the subject is reduced, and in illustrative embodiments such that normal hemostasis is restored in the subject.

In another aspect, provided herein is a method of treating a coagulopathy in a subject, or of restoring hemostasis in a subject, or of reducing bleeding potential of a subject, wherein the subject is being administered, or has been administered, an antiplatelet agent, the method comprising administering to the subject in need thereof an effective amount of the composition comprising FDPDs, wherein the composition comprising FDPDs comprises a population of FDPDs having a reduced propensity to aggregate such that no more than 10% of the FDPDs in the population aggregate under aggregation conditions comprising an agonist but no platelets, thereby treating the coagulopathy. In further illustrative embodiments, the composition comprising the FDPDs is administered such that the bleeding potential of the subject is reduced, and in illustrative embodiments such that normal hemostasis is restored in the subject.

In another aspect, provided herein is a method of preventing or mitigating the potential for a coagulopathy in a subject, the method comprises: (a) determining that information regarding whether the subject was administered an antiplatelet agent is unavailable; and (b) administering to the subject an effective amount of a composition comprising freeze-dried platelet derivatives (FDPDs). In some embodiments of such a method, information regarding whether the subject was administered an antiplatelet agent is unavailable for a reason comprising that the subject cannot be identified. In some embodiments of the method, information regarding whether the subject was administered an antiplatelet agent is unavailable for a reason comprising that the medical history of the subject is unavailable. In further embodiments information regarding whether the subject was administered an antiplatelet agent is unavailable for a reason comprising that the subject is in need of emergency treatment.

In another aspect, provided herein is a method of treating a coagulopathy in a subject or of reducing the bleeding potential of a subject, or of restoring hemostasis in a subject, wherein the method comprises: administering to the subject in need thereof an effective amount of a composition comprising platelet derivatives, in illustrative embodiments, FDPDs, wherein the subject before the administering the composition comprising platelet derivatives, was administered an antiplatelet agent and a second agent that decreases platelet function, thereby treating the coagulopathy. In further illustrative embodiments, the composition comprising the platelet derivatives is administered such that the bleeding potential of the subject is reduced, and in illustrative embodiments such that normal hemostasis is restored in the subject. In illustrative embodiments, before the administering of the composition comprising FDPDs the subject was in need thereof because of an increased risk of bleeding due to, or as a result of being administered the anti-platelet agent and the second agent.

In another aspect, provided herein is a composition comprising freeze-dried platelet derivatives (FDPDs) for treating a coagulopathy in a subject, wherein the treating comprises: administering to the subject in need thereof, an effective amount of the composition comprising FDPDs such that the bleeding potential, or risk of bleeding of the subject is reduced, wherein the subject was administered an antiplatelet agent and a second agent that decreases platelet function, and wherein the subject is in need thereof because of an increased potential for, or risk of bleeding due to, or as a result of being administered the antiplatelet agent and the second agent, thereby treating the coagulopathy.

In another aspect, provided herein is a composition comprising freeze-dried platelet derivatives (FDPDs) for treating a coagulopathy in a subject having an increased potential for, or risk of bleeding as a result of being administered or having been administered an anticoagulant, wherein the treating comprises: administering to the subject having the increased potential for, or risk of bleeding, an effective amount of the composition comprising FDPDs such that the bleeding potential or risk of bleeding of the subject is reduced, wherein the composition comprising FDPDs comprises a population of FDPDs having a reduced propensity to aggregate such that no more than 10% of the FDPDs in the population aggregate under aggregation conditions comprising an agonist but no platelets, thereby treating the coagulopathy.

In some embodiments of any of the method or use embodiments herein, a dose, and in illustrative embodiments an effective amount of a composition comprising platelets or platelet derivatives (e.g., FDPDs) administered to a subject or patient, can be a range of between about or exactly $1.0\times10^{8}$, $5.0\times10^{8}$, $1.0\times10^{9}$, $3.0\times10^{9}$, $4.0\times10^{9}$, $5.0\times10^{9}$, $1.0\times10^{10}$, or $5.0\times10^{10}$ to $1.0\times10^{12}$ particles (e.g. FDPDs)/kg of a subject. In some embodiments, and in illustrative embodiments wherein a subject has blood comprising two anti-platelet agents and/or has been administered dual anti-platelet therapy, a dose of a composition comprising platelets or platelet derivatives (e.g., FDPDs) can be a range of between about or exactly $3.0\times10^{9}$, $4.0\times10^{9}$, $5.0\times10^{9}$, $1.0\times10^{10}$, $2.5\times10^{10}$, or $5.0\times10^{10}$ to $5.0\times10^{11}$ particles (e.g. FDPDs)/kg of a subject. In some embodiments, and in illustrative embodiments wherein a subject has blood comprising two anti-platelet agents and/or has been administered dual anti-platelet therapy, a dose of a composition comprising platelets or platelet derivatives (e.g., FDPDs) can be a range of between about or exactly $3.0\times10^{9}$, $4.0\times10^{9}$, $5.0\times10^{9}$, $1.0\times10^{10}$, $2.5\times10^{10}$, or $5.0\times10^{10}$ to $1.0\times10^{11}$ particles (e.g. FDPDs)/kg of a subject. In some embodiments, and in illustrative embodiments wherein a subject has blood comprising two anti-platelet agents and/or has been administered dual anti-platelet therapy, a dose of a composition comprising platelets or platelet derivatives (e.g., FDPDs) can be a range of between about or exactly $3.0\times10^{9}$, $4.0\times10^{9}$, or $5.0\times10^{9}$ to $1.0\times10^{10}$ particles (e.g. FDPDs)/kg of a subject. In one illustrative embodiment, and in illustrative embodiments wherein a subject has blood comprising i) an anti-platelet agent and a second agent that decreases platelet function; ii) two anti-platelet agents; and/or iii) has been administered dual anti-platelet therapy, a dose or an effective amount of a composition comprising FDPDs is between $5.0\times10^{10}$ to $1.0\times10^{12}$/kg of the subject, $5.0\times10^{10}$ to $5.0\times10^{11}$/kg of the subject, $5.0\times10^{10}$ to $1.0\times10^{11}$/kg of the subject, $5.0\times10^{9}$ to $1.0\times10^{11}$/kg of the subject, $5.0\times10^{9}$ to $5.0\times10^{10}$/kg of the subject, or $5.0\times10^{9}$ to $1.0\times10^{10}$/kg of the subject. In some embodiments, and in illustrative embodiments wherein a subject has blood comprising two anti-platelet agents and/or has been administered dual anti-platelet therapy, a dose of a composition comprising platelets or platelet derivatives (e.g., FDPDs) can be in a range of greater than $L5\times10^{9}$ FDPDs/kg of the subject on the low end of the range and $1.5\times10^{10}$, $1.4\times10^{10}$, $1.3\times10^{10}$, $1.2\times10^{10}$, or $1.1\times10^{10}$ FDPDs/kg of the subject on the high end; or greater than $1.0\times10^{10}$ FDPDs/kg of the subject on the low end of the range and $1.5\times10^{10}$, $1.4\times10^{10}$, $1.3\times10^{10}$, $1.2\times10^{10}$, or $1.1\times10^{10}$ FDPDs/kg of the subject on the high end; or $1.1\times10^{10}$ FDPDs/kg of the subject on the low end of the range and $1.5\times10^{10}$, $1.4\times10^{10}$, $1.3\times10^{10}$, $1.2\times10^{10}$, or $1.1\times10^{10}$ FDPDs/kg of the subject on the high end; or $1.1\times10^{10}$ FDPDs/kg of the subject on the low end and less than $1.5\times10^{10}$, $1.4\times10^{10}$, $1.3\times10^{10}$, or $1.2\times10^{10}$ FDPDs/kg of the subject on the high end.

In some embodiments, for example of aspects wherein a subject was administered the antiplatelet agent and the second agent that decreases platelet function, such a method further comprises before the administering the composition comprising FDPDs, determining that the subject was administered the antiplatelet agent and the second agent that decreases platelet function. In some embodiments, the antiplatelet agent is a first antiplatelet agent and the second agent is a second antiplatelet agent. In some embodiments, the first antiplatelet agent and the second anti-platelet agent are each different antiplatelet agents selected from aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, cilostazol, prostaglandin E1, epoprostenol, dipyridamole, treprostinil sodium, and sarpogrelate. In some embodiments, the first antiplatelet agent and the second anti-platelet agent have different mechanisms of action. In some embodiments, the first antiplatelet agent and the second anti-platelet agent are each different antiplatelet agents selected from aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, cilostazol, prostaglandin E1, epoprostenol, dipyridamole, treprostinil sodium, and sarpogrelate.

In some embodiments of any of the aspects herein, before, immediately before, at the moment before, at the moment of, and/or at an initial time of, the administering of the composition comprising platelet derivatives, for example FDPDs, the subject was or is at an increased risk of bleeding due to being administered or having been administered the anti-platelet agent. Furthermore, the subject can be at an increased risk of bleeding at 7, 6, 5, 4, 3, 2, or 1 day, 12 hours, 8 hours, 4 hours, 2 hours, 1 hour or 45, 30, 15, 10, 5, 4, 3, 2, or 1 minute before the administering of the composition comprising the platelet derivatives. In some optional embodiments, this is confirmed by laboratory testing. However, in some embodiments no laboratory testing of bleeding risk or any clotting parameter is performed 7, 6, 5, 4, 3, 2, or 1 day or sooner before and/or after the administering of the composition comprising the platelet derivatives. Bleeding risk is typically decreased after administration of an effective dose of the composition comprising platelet derivatives, in illustrative embodiments FDPDs. Furthermore, the subject may remain at an increased risk of bleeding even after the administering of the composition comprising platelet derivatives (e.g. FDPDs), for example for 1, 2, 3, 4, 5, 10, 15, 20, 30, or 45 minutes, or 1, 2, 3, 4, 5, or 8 hours, or longer after the administering, depending on how long it takes for the FDPDs to decrease the risk in the subject after they are administered. Furthermore, in some embodiments, the administration of the composition comprising the platelet derivatives (e.g. FDPDs) decreases but does not completely resolve the increased risk of bleeding in the subject.

In some embodiments, for example of aspects wherein a subject was administered the antiplatelet agent and the second agent that decreases platelet function, administration of the second agent is stopped, for example before administrating the composition comprising the platelet derivatives. In other embodiments of such aspects, administration of the second agent is continued, for example after administering the composition comprising the platelet derivatives.

In certain embodiments of any of the aspects provided herein, the method further comprises before administering the composition comprising platelet derivatives, determining in a pre-administering evaluation, that the subject has an abnormal value for one or more clotting parameters. The pre-administration evaluation, in illustrative embodiments, is an in vitro laboratory test.

In certain embodiments of any of the aspects provided herein, the antiplatelet agent is selected from aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, cilostazol, prostaglandin E1, epoprostenol, dipyridamole, treprostinil sodium, and sarpogrelate. In other embodiments, the antiplatelet agent is selected from cangrelor, ticagrelor, abciximab, terutroban, picotamide, elinogrel, ibuprofen, vorapaxar, atopaxar, cilostazol, prostaglandin E1, epoprostenol, dipyridamole, treprostinil sodium, and sarpogrelate.

Platelet Derivatives Comprising an Imaging Agent

In some embodiments, provided herein is a platelet derivative composition, wherein the platelet derivatives can include an imaging agent. In some embodiments, platelets can include/be loaded with an imaging agent, for example before being dried or after being dried. In some embodiments, platelet derivatives that include an imaging agent, such as imaging agent-loaded platelet derivatives can retain the ability or properties of platelet derivatives that are not loaded with imaging agents. Loading of platelet derivatives with an agent typically facilitates imaging of the platelet derivatives in vivo. Thus, a step of detecting an imaging agent, for example an MRI agent, in a subject can be included in any method herein that includes administering or otherwise delivering platelet derivatives to the subject. The imaging agent that can be used to load the platelet derivatives as described herein can include a radioactive metal ion, a paramagnetic metal ion, a gamma-emitting radioactive halogen, a positron-emitting radioactive non-metal, a hyperpolarized NMR-active nucleus, a reporter suitable for in vivo optical imaging, or a beta-emitter suitable for intravascular detection. For example, a radioactive metal ion can include, but is not limited to, positron emitters such as $^{54}Cu$, $^{48}V$, $^{52}Fe$, $^{55}Co$, $^{94}Tc$ or $^{68}Ga$; or gamma-emitters such as $^{171}Tc$, $^{111}In$, $^{113}In$, or $^{67}Ga$. For example, a paramagnetic metal ion can include, but is not limited to Gd(III), a Mn(II), a Cu(II), a Cr(III), a Fe(III), a Co(II), a Er(II), a Ni(II), a Eu(III) or a Dy(III), an element comprising an Fe element, a neodymium iron oxide (NdFeO3) or a dysprosium iron oxide (DyFeO3). For example, a paramagnetic metal ion can be chelated to a polypeptide or a monocrystalline nanoparticle. For example, a gamma-emitting radioactive halogen can include, but is not limited to 123I, $^{131}I$ or $^{77}Br$. For example, a positron-emitting radioactive non-metal can include, but is not limited to $^{11}C$, $^{13}N$, $^{15}O$, $^{17}F$, $^{75}Br$, $^{76}Br$ or $^{124}I$. For example, a hyperpolarized NMR-active nucleus can include, but is not limited to $^{13}C$, $^{15}N$, $^{19}F$, $^{29}Si$ and $^{31}P$. For example, a reporter suitable for in vivo optical imaging can include, but is not limited to any moiety capable of detection either directly or indirectly in an optical imaging procedure. For example, the reporter suitable for in vivo optical imaging can be a light scatterer (e.g., a colored or uncolored particle), a light absorber or a light emitter. For example, the reporter can be any reporter that interacts with light in the electromagnetic spectrum with wavelengths from the ultraviolet to the near infrared. For example, organic chromophoric and fluorophoric reporters include groups having an extensive delocalized electron system, e.g. cyanines, merocyanines, indocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, b/s(dithiolene) complexes, $b_{is}$(benzene-dithiolate) complexes, iodoaniline dyes, b/stS.O-dithiolene) complexes. For example, the reporter can be, but is not limited to a fluorescent, a bioluminescent, or chemiluminescent polypeptide. For example, a fluorescent or chemiluminescent polypeptide is a green florescent protein (GFP), a modified GFP to have different absorption/emission properties, a luciferase, an aequorin, an obelin, a mnemiopsin, a berovin, or a phenanthridinium ester. For example, a reporter can be, but is not limited to rare earth metals (e.g., europium, samarium, terbium, or dysprosium), or fluorescent nanocrystals (e.g., quantum dots). For example, a reporter may be a chromophore that can include, but is not limited to fluorescein, sulforhodamine 101 (Texas Red), rhodamine B, rhodamine 6G, rhodamine 19, indocyanine green, Cy2, Cy3, Cy3.5, Cy5, Cy5.5, Cy7, Marina Blue, Pacific Blue, Oregon Green 88, Oregon Green 514, tetramethylrhodamine, and Alexa Fluor 350, Alexa Fluor 430, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, and Alexa Fluor 750. For example, a beta-emitter can include, but is not limited to radio metals $^{67}Cu$, $^{89}Sr$, $^{90}Y$, $^{153}Sm$, $^{185}Re$, $^{188}Re$ or $^{192}Ir$, and non-metals $^{32}P$, $^{33}P$, $^{38}S$, $^{38}Cl$, $^{39}Cl$, $^{82}Br$ and $^{83}Br$. In some embodiments, an MRI agent loaded into platelets can be associated with gold or other equivalent metal particles (such as nanoparticles). For example, a metal particle system can include, but is not limited to gold nanoparticles (e.g., Nanogold™).

In some embodiments, an MRI agent loaded into platelets that is modified with an imaging agent is imaged using an imaging unit. The imaging unit can be configured to image the MRI agent loaded platelets in vivo based on an expected property (e.g., optical property from the imaging agent) to be characterized. For example, imaging techniques (in vivo imaging using an imaging unit) that can be used, but are not limited to are: computer assisted tomography (CAT), magnetic resonance spectroscopy (MRS), magnetic resonance imaging (MRI), positron emission tomography (PET), single-photon emission computed tomography (SPECT), or bioluminescence imaging (BLI). Chen, Z., et. al., Advance of Molecular Imaging Technology and Targeted Imaging Agent in Imaging and Therapy, *Biomed Res Int.,* 819324, doi: 10.1155/2014/819324 (2014) have described various imaging techniques and which is incorporated by reference herein in its entirety. In some embodiments, an imaging agent is an MRI agent. In other embodiments, the MRI agent can be gadolinium-based compounds. In some embodiments, platelet derivatives that include an MRI agent, such as, MRI agent-loaded platelet derivatives can retain the ability or properties of platelet derivatives that are not loaded with MRI agents.

In some embodiments, an imaging agent as provided herein is loaded on platelets or platelet derivatives using a cell penetrating peptide (CPP). In some embodiments, an imaging agent can be conjugated to a CPP and further can be incubated with platelets or platelet derivatives to form imaging agent-loaded platelets or platelet derivatives. In some embodiments, an imaging agent can be an MRI agent to form MRI agent-loaded platelets or platelet derivatives. In some embodiments, a CPP can be any of the CPP well known in the art that can cross the cytoplasmic membrane efficiently. In some embodiments, CPP can be any peptide having 10 to 30 amino acids and are capable of crossing the cytoplasmic membrane. In some embodiments, CPP can be any of the peptides that are described in Kersemans et al 2008 (Kersemans, Veerle et al. "Cell penetrating peptides for in vivo molecular imaging applications." *Current pharmaceutical design* vol. 14, 24 (2008): 2415-47). In some embodiments, CPP can be a protein-derived CPP, a synthetic CPP, or a mixed CPP. In some embodiments, a protein-derived CPP are derived from naturally occurring protein such as, but not limiting to, TAT protein, and penetratin. In some embodiments, a synthetic CPP such as, but not limiting to polyarginines can be a CPP that is developed by known techniques, such as, phage display method. In some embodiments, a mixed CPP can be a CPP which are a combination of naturally occurring (protein derived) CPP, and synthetic CPP, such as transportan CPP, a combination of the N-terminal fragment of the neuropeptide gelanin and the membrane-interacting wasp venom peptide, mastoparan. In some embodiments, a protein-derived CPPs is selected from the group consisting of penetratin, TAT peptide (49-57 amino acids), TAT peptide (48-60 amino acids), calcitonin-derived CPP, nuclear localization sequences, new polybasic CPPs, N-terminal repetitive domain of maize gamma-zein, peptides from gp41 fusion sequence, preS2-TLM, signal-sequence hydrophobic region (SSHR), pVEC, Vpr, VP22, Human integrin b3 signal sequence, gp41 fusion sequence, *Caiman crocodylus* Ig(v) light chain, hCT derived peptide, Kaposi FGF signal sequences, CPP from pestivirus envelope glycoprotein, CPP derived from the prion protein, Yeast PRP6 (129-144), Phi21 N (12-29), Delta N (1-22), FHV coat (35-49), BMV Gag (7-25), HTLV-II Rex (4-16), HIV-1 Rev (9-20), RSG-1.2, Lambda-N (48-62), SV40 NLS, Bipartite, Nucleoplasmin (155-170), NLS, Herpesvirus, 8 k8 protein (124-135), Buforin-II (20-36), Magainin, PDX-1-PTD, crotamine, pIsl, SynB1, Fushi-tarazu (254-313), and Engrailed (454-513). In certain illustrative embodiments, a protein-derived CPP is penetratin. In certain illustrative embodiments, a protein-derived CPP is TAT peptide (49-57 amino acids). In certain illustrative embodiments, a protein-derived CPP is TAT peptide (48-60 amino acids). In certain illustrative embodiments, a protein-derived CPP can be any peptide described in the publication Kersemans et al 2008.

In some embodiments, a synthetic and/or mixed CPP is selected from the group consisting of transportan, polyarginine CPPs, poly-d-arginine, KLAL peptide/model amphipathic peptide (MAP), KALA model amphipathic peptide, modeled Tat peptide, Loligomer, b-sheet-forming peptide, retro-inverso forms of established CPPs, W/R penetratin, MPG, Pep-1, Signal-sequence-based peptides (I), Signal-sequence-based peptides (II), Carbamate 9, PTD-4, PTD-5, RSV-A9, CTP-512, and U2AF. In certain illustrative embodiments, a synthetic and/or mixed CPP can be any peptide described in the publication Kersemans et al 2008.

Exemplary Embodiments

Provided in this Exemplary Embodiments section are non-limiting exemplary aspects and embodiments provided herein and further discussed throughout this specification. For the sake of brevity and convenience, all of the aspects and embodiments disclosed herein, and all of the possible combinations of the disclosed aspects and embodiments are not listed in this section. Additional embodiments and aspects are provided in other sections herein. Furthermore, it will be understood that embodiments are provided that are specific embodiments for many aspects and that can be combined with any other embodiment, for example as discussed in this entire disclosure. It is intended in view of the full disclosure herein, that any individual embodiment recited below or in this full disclosure can be combined with any aspect recited below or in this full disclosure where it is an additional element that can be added to an aspect or because it is a narrower element for an element already present in an aspect. Such combinations are sometimes provided as non-limiting exemplary combinations and/or are discussed more specifically in other sections of this detailed description.

In one aspect, provided herein is a composition comprising platelets or platelet derivatives and an aqueous medium, wherein the aqueous medium has a protein concentration less than or equal to 50% of the protein concentration of donor apheresis plasma.

In one aspect, provided herein is a platelet derivative composition in the form of a powder, comprising a population of platelet derivatives having a reduced propensity to aggregate, such that no more than 25%, 10%, 5%, 4%, 3%, or in illustrative embodiments, no more than 2%, of the platelet derivatives in the population aggregate under aggregation conditions comprising an agonist but no platelets, and wherein the platelet derivatives are capable of generating thrombin, and in certain embodiments have a potency of at least 0.5, 1.0, and in non-limiting illustrative embodiments 1.5 thrombin generation potency units (TGPU) per $10^6$ platelet derivatives.

In one aspect, provided herein is a platelet derivative composition in the form of a powder, comprising a population of platelet derivatives having a reduced propensity to aggregate, wherein no more than 25%, 10%, 5%, 4%, 3%, or in illustrative embodiments, no more than 2% no more than 25%, 10%, 5%, 4%, 3%, or in illustrative embodiments, no more than 2%, of the platelet derivatives in the population aggregate under aggregation conditions comprising an agonist but no platelets; and having one or more, two or more, or all of the following characteristics of a super-activated platelet selected from: a. the presence of thrombospondin (TSP) on their surface at a level that is greater than on the surface of resting platelets; b. the presence of von Willebrand factor (vWF) on their surface at a level that is greater than on the surface of resting platelets; c. an inability to increase expression of a platelet activation marker in the presence of an agonist as compared to the expression of the platelet activation marker in the absence of an agonist.

In one aspect, provided herein is a platelet derivative composition in the form of a powder, comprising platelet derivatives, wherein less than 15%, and in certain non-limiting illustrative embodiments less than 5% of the CD 41-positive platelet derivatives are microparticles, in non-limiting illustrative embodiments having a diameter of less than 1 μm, and in certain non-limiting illustrative embodiments less than 0.5 μm, and wherein the platelet derivatives are capable of generating thrombin, such that, for example, the platelet derivatives have a potency of at least 0.5, 1.0, or in non-limiting illustrative embodiments 1.5 thrombin generation potency units (TGPU) per $10^6$ platelet derivatives.

In one aspect, provided herein is a platelet derivative composition in the form of a powder, comprising a population of platelet derivatives comprising CD 41-positive platelet derivatives, wherein the population comprises platelet derivatives having a reduced propensity to aggregate such that no more than 25%, 10%, 5%, 4%, 3%, or in illustrative embodiments, no more than 2% no more than 25%, 10%, 5%, 4%, 3%, or in illustrative embodiments, no more than 2%, of the platelet derivatives in the population aggregate under aggregation conditions comprising an agonist but no platelets, wherein the platelet derivatives have an inability to increase expression of a platelet activation marker in the presence of an agonist as compared to the expression of the platelet activation marker in the absence of the agonist, wherein the platelet derivatives are capable of generating thrombin, such that, for example, in illustrative embodiments the platelet derivatives are capable of generating thrombin, such that, for example, the platelet derivatives have a potency of at least 0.5, 1.0, or in non-limiting illustrative embodiments 1.5 thrombin generation potency units (TGPU) per $10^6$ platelet derivatives; and wherein less than 15%, and in certain non-limiting illustrative embodiments less than 5% of the CD 41-positive platelet derivatives are microparticles having a diameter of less than 1 μm, and in certain non-limiting illustrative embodiments less than 0.5 μm.

In one aspect, provided herein is a platelet derivative composition in the form of a powder, comprising a population of platelet derivatives having a reduced propensity to aggregate, such that no more than 25%, 10%, 5%, 4%, 3%, or in illustrative embodiments, no more than 2% no more than 25%, 10%, 5%, 4%, 3%, or in illustrative embodiments, no more than 2%, of the platelet derivatives in the population aggregate under aggregation conditions comprising an agonist but no platelets, and further having one or both of: the presence of thrombospondin (TSP) on their surface at a level that is greater than on the surface of resting platelets; and the presence of von Willebrand factor (vWF) on their surface at a level that is greater than on the surface of resting platelets.

In one aspect, provided herein is a platelet derivative composition in the form of a powder, comprising a population of platelet derivatives comprising CD41-positive platelet derivatives, wherein less than 15%, and in certain non-limiting illustrative embodiments less than 5% of the CD41-positive platelet derivatives are microparticles having a diameter of less than 1 μm, and in certain non-limiting illustrative embodiments less than 0.5 μm, and comprising platelet derivatives having one or more of, two or more of, three or more of, and in illustrative embodiments all of the following: a reduced propensity to aggregate, in certain embodiments such that no more than 25%, 10%, 5%, 4%, 3%, and in illustrative embodiments no more than 2% of the platelet derivatives in the population aggregate under aggregation conditions comprising an agonist but no platelets; an inability to increase expression of a platelet activation marker in the presence of an agonist as compared to the expression of the platelet activation marker in the absence of the agonist; the presence of thrombospondin (TSP) on their surface at a level that is greater than on the surface of resting platelets; the presence of von Willebrand factor (vWF) on their surface at a level that is greater than on the surface of resting platelets; and are capable of generating thrombin, such that, for example, in illustrative embodiments the platelet derivatives are capable of generating thrombin, such that, for example, the platelet derivatives have a potency of at least 0.5, 1.0, or in non-limiting illustrative embodiments 1.5 thrombin generation potency units (TGPU) per $10^6$ platelet derivatives.

In one aspect, provided herein is a platelet derivative composition in the form of a powder, comprising trehalose in the range of 20-35% by weight, polysucrose in the range of 45-60% by weight, and platelet derivatives in the range of 0.5-20% by weight, wherein the platelet derivatives to microparticles have a numerical ratio of at least 95:1 in the platelet derivative composition, and wherein the platelet derivatives are capable of generating thrombin, such that, for example, in illustrative embodiments the platelet derivatives are capable of generating thrombin, such that, for example, the platelet derivatives have a potency of at least 0.5, 1.0, or in non-limiting illustrative embodiments 1.5 thrombin generation potency units (TGPU) per $10^6$ platelet derivatives.

In one aspect, provided herein is a platelet derivative composition in the form of a powder, comprising trehalose in the range of 20-35% by weight, polysucrose in the range of 45-60% by weight, and platelet derivatives in the range of 0.5-20% by weight, wherein the platelet derivative composition comprises a population of platelet derivatives having a reduced propensity to aggregate such that no more than 25%, 10%, 5%, 4%, 3%, or in illustrative embodiments, no more than 2%, of the platelet derivatives in the population aggregate under aggregation conditions comprising an agonist but no platelets, and further having one or both of: the presence of thrombospondin (TSP) on their surface at a level that is greater than on the surface of resting platelets; and the presence of von Willebrand factor (vWF) on their surface at a level that is greater than on the surface of resting platelets.

In one aspect, provided herein is a plurality of containers each containing a platelet derivative composition in the form of a powder, wherein the platelet derivative composition in each container comprises a population of platelet derivatives having a reduced propensity to aggregate such that no more than 25%, 10%, 5%, 4%, 3%, or in illustrative embodiments, no more than 2% of the platelet derivatives in the population aggregate under aggregation conditions comprising an agonist but no platelets, wherein the platelet derivative compositions in each container are capable of generating thrombin, such that, for example, in illustrative embodiments the platelet derivatives are capable of generating thrombin, such that, for example, the platelet derivatives have a potency of at least 0.5, 1.0, or in non-limiting illustrative embodiments 1.5 thrombin generation potency units (TGPU) per $10^6$ platelet derivatives, wherein the platelet derivatives have an inability to increase expression of a platelet activation marker in the presence of an agonist as compared to the expression of the platelet activation marker in the absence of the agonist, wherein the plurality of containers comprise the platelet derivative composition from at least 2 different lots in separate containers, and wherein one or more of: the amount of plasma protein in the powder of any two containers chosen from different lots, differs by less than 10%, 5%, 2%, or 1%, and the amount of microparticles that are less than 1 μm, and in certain non-limiting illustrative embodiments less than 0.5 μm in the powder of any two containers chosen from different lots, differs by less than 10%, 5%, 2%, or 1%.

In one aspect, provided herein is a plurality of containers each filled with a platelet derivative composition in the form of a powder, wherein the platelet derivative composition comprises trehalose in the range of 20-35% by weight; polysucrose in the range of 45-60% by weight; and platelet derivatives in the range of 0.5-20% by weight, wherein the platelet derivatives are capable of generating thrombin, such that, for example, in illustrative embodiments the platelet derivatives are capable of generating thrombin, such that, for example, the platelet derivatives have a potency of at least 0.5, 1.0, or in non-limiting illustrative embodiments 1.5 thrombin generation potency units (TGPU) per $10^6$ platelet derivatives, and a population of platelet derivatives comprising CD41-positive platelet derivatives, wherein less than 15%, and in certain non-limiting illustrative embodiments less than 5% of the CD41-positive platelet derivatives are microparticles having a diameter of less than 1 μm, and in certain non-limiting illustrative embodiments less than 0.5 μm.

In one aspect, provided herein is a process for preparing a composition comprising platelets or platelet derivatives and an aqueous medium, the process comprising: tangential flow filtration (TFF) of a starting material comprising platelets, a diluted starting material comprising platelets, a concentrated platelet composition, or a combination thereof, thereby preparing a composition comprising platelets or platelet derivatives and aqueous medium, wherein the aqueous medium has a protein concentration less than or equal to 50% of the protein concentration of donor apheresis plasma.

In one aspect, provided herein is a process for preparing freeze-dried platelets, comprising: a) preparing a composition comprising platelets and an aqueous medium using the process comprising: tangential flow filtration (TFF) of a starting material comprising platelets, a diluted starting material comprising platelets, a concentrated platelet composition, or a combination thereof, thereby preparing a composition comprising platelets or platelet derivatives and aqueous medium, wherein the aqueous medium has a protein concentration less than or equal to 50% of the protein concentration of donor apheresis plasma; and b) freeze-drying the composition comprising platelets and the aqueous medium.

In one aspect, provided herein is a process for preparing a composition comprising platelets or platelet derivatives and an aqueous medium, the process comprising: diluting a starting material comprising platelets to form a diluted starting material; concentrating the diluted starting material such that the platelets have a concentration of about $2250\times10^3$ cells/μL ($\pm250\times10^3$) to form a concentrated platelet composition; and washing the concentrated platelet composition with at least 2 diavolumes (DV) of a preparation agent to form a TFF-treated composition.

In one aspect, provided herein is a process for preparing a platelet derivative composition, comprising performing tangential flow filtration (TFF) of a platelet composition with a preparation agent, in a preparation agent, or in a solution that optionally can have components of the preparation agent or can be a different solution, wherein the TFF is performed to at least partially exchange the solution with the preparation agent having a pH in the range of 5.5 to 8.0 and comprising 0.4 to 35% trehalose and 2% to 8% polysucrose, wherein said TFF is performed using a 0.3 to 1 micron filter, to at least partially or fully exchange the platelets into the preparation agent, thereby preparing a TFF-treated composition comprising $100\times10^3$ to $20,000\times10^3$ platelets/μl, in certain illustrative embodiments between $10,000\times10^3$ to $20,000\times10^3$ platelets/μL, in an aqueous medium having less than or equal to 15% plasma protein, and having less than 15%, and in certain non-limiting illustrative embodiments less than 5.0% microparticles by scattering intensity having a diameter of less than 1 μm, and in certain non-limiting illustrative embodiments less than 0.5 μm; freeze drying the TFF-treated composition comprising platelets in the aqueous medium to form a freeze-dried composition comprising platelet derivatives; and heating the freeze-dried composition at a temperature in the range of 60° C. to 90° C. for at least 1 hour to not more than 36 hours to thermally treat the platelet derivatives in the freeze-dried composition to form the platelet derivative composition, wherein the platelet derivatives in the platelet derivative composition are capable of generating thrombin, such that, for example, in illustrative embodiments the platelet derivatives are capable of generating thrombin, such that, for example, the platelet derivatives have a potency of at least 0.5, 1.0, or in non-limiting illustrative embodiments 1.5 thrombin generation potency units (TGPU) per $10^6$ platelet derivatives, and a reduced propensity to aggregate, wherein no more than 25%, 10%, 5%, 4%, 3%, or in illustrative embodiments, no more than 2%, of the platelet derivatives in the population aggregate under aggregation conditions comprising an agonist but no platelets. The platelets can be diluted 1:0.5, 1:1, 1:2, 1:5, or 1:10 in a solution or in the preparation agent before performing the TFF.

In one aspect, provided herein is a process for preparing a platelet derivative composition, comprising performing tangential flow filtration (TFF) of a platelet composition with a preparation agent, in a preparation agent, or in a solution that optionally can have components of the preparation agent or can be a different solution, wherein the TFF is performed to at least partially exchange the solution with the preparation agent having a pH in the range of 5.5 to 8.0 and comprising 0.4 to 35% trehalose and 2% to 8% polysucrose, wherein the TFF is performed using a 0.3 to 1 micron filter, to at least partially or fully exchange the platelets into the preparation agent, thereby preparing a TFF-treated composition comprising $100\times10^3$ to $20,000\times10^3$ platelets/μl, in certain illustrative embodiments between $10,000\times10^3$ to $20,000\times10^3$ platelets/μl, in an aqueous medium having less than or equal to 15% plasma protein, and having less than 15%, and in certain non-limiting illustrative embodiments less than 5.0% microparticles by scattering intensity having a diameter of less than 1 μm, and in certain non-limiting illustrative embodiments less than 0.5 μm, freeze drying the TFF-treated composition comprising platelets in the aqueous medium to form a freeze-dried composition comprising platelet derivatives; and heating the freeze-dried composition at a temperature in the range of 60° C. to 90° C. for at least 1 hour to not more than 36 hours to thermally treat the platelet derivatives in the freeze-dried platelet composition to form the platelet derivative composition, wherein the platelet derivative composition is: a)

negative for HLA Class I antibodies based on a regulatory agency approved test for HLA Class I antibodies; b) negative for HLA Class II antibodies based on a regulatory agency approved test for HLA Class II antibodies; and c) negative for HNA antibodies based on a regulatory agency approved test for HNA antibodies. The platelets can be diluted 1:0.5, 1:1, 1:2, 1:5, or 1:10 in a solution or in the preparation agent before performing the TFF.

In one aspect, provided herein is a process for preparing a platelet derivative composition, comprising performing tangential flow filtration (TFF) of a platelet composition with a preparation agent, in a preparation agent, or in a solution that optionally can have components of the preparation agent or can be a different solution, wherein the TFF is performed to at least partially exchange the solution with the preparation agent having a pH in the range of 5.5 to 8.0 and comprising 0.4 to 35% trehalose and 2% to 8% polysucrose, wherein said TFF is performed using a 0.3 to 1 micron filter, to at least partially or fully exchange the platelets into the preparation agent, thereby preparing a TFF-treated composition comprising $100\times10^3$ to $20,000\times10^3$ platelets/μl, in certain illustrative embodiments between $10,000\times10^3$ to $20,000\times10^3$ platelets/μl in an aqueous medium having less than or equal to 15% plasma protein, and having less than 15%, and in certain non-limiting illustrative embodiments less than 5.0% microparticles by scattering intensity having a diameter of less than 1 μm, and in certain non-limiting illustrative embodiments less than 0.5 μm; freeze drying the TFF-treated composition comprising platelets in the aqueous medium to form a freeze-dried composition comprising platelet derivatives; and heating the freeze-dried composition at a temperature in the range of 60° C. to 90° C. for at least 1 hour to not more than 36 hours to thermally treat the platelet derivatives in the freeze-dried composition to form the platelet derivative composition, wherein the platelet derivative composition comprising a population of platelet derivatives having a reduced propensity to aggregate, such that no more than 25%, 10%, 5%, 4%, 3%, or in illustrative embodiments, no more than 2%, of the platelet derivatives in the population aggregate under aggregation conditions comprising an agonist but no platelets and having one or both of: the presence of thrombospondin (TSP) on their surface at a level that is greater than on the surface of resting platelets; and the presence of von Willebrand factor (vWF) on their surface at a level that is greater than on the surface of resting platelets. The platelets can be diluted 1:0.5, 1:1, 1:2, 1:5, or 1:10 in a solution or in the preparation agent before performing the TFF.

In one aspect, provided herein is a process for preparing a process for preparing a platelet derivative composition, comprising performing tangential flow filtration (TFF) of a platelet composition with a preparation agent, in a preparation agent, or in a solution that optionally can have components of the preparation agent or can be a different solution, wherein the TFF is performed to at least partially exchange the solution with the preparation agent having a pH in the range of 5.5 to 8.0 and comprising 0.4 to 35% trehalose and 2% to 8% polysucrose, wherein said TFF is performed using a 0.3 to 1 micron filter, to at least partially or fully exchange the platelets into the preparation agent, thereby preparing a TFF-treated composition comprising $100\times10^3$ to $20,000\times10^3$ platelets/μl, in certain illustrative embodiments between $10,000\times10^3$ to $20,000\times10^3$ platelets/μl in an aqueous medium having less than or equal to 15% plasma protein, and having less than 15%, and in certain non-limiting illustrative embodiments less than 5.0% microparticles by scattering intensity having a diameter of less than 1 μm, and in certain non-limiting illustrative embodiments less than 0.5 μm; freeze drying the TFF-treated composition comprising platelets in the aqueous medium to form a freeze-dried composition comprising platelet derivatives; and heating the freeze-dried composition at a temperature in the range of 60° C. to 90° C. for at least 1 hour to not more than 36 hours to thermally treat the platelet derivatives in the freeze-dried composition to form the platelet derivative composition, wherein the platelet derivatives in the platelet derivative composition display one or more of, two or more of, three or more of, four or more of, or all of the following properties: a reduced propensity to aggregate, wherein no more than 25%, 10%, 5%, 4%, 3%, or in illustrative embodiments, no more than 2%, of the platelet derivatives in the population aggregate under aggregation conditions comprising an agonist but no platelets; an inability to increase expression of a platelet activation marker in the presence of an agonist as compared to the expression of the platelet activation marker in the absence of the agonist; the presence of thrombospondin (TSP) on their surface at a level that is greater than on the surface of resting platelets; the presence of von Willebrand factor (vWF) on their surface at a level that is greater than on the surface of resting platelets; and are capable of generating thrombin, such that in illustrative embodiments, the platelet derivatives are capable of generating thrombin, such that, for example, the platelet derivatives have a potency of at least 0.5, 1.0, or in non-limiting illustrative embodiments 1.5 thrombin generation potency units (TGPU) per $10^6$ platelet derivatives. The platelets can be diluted 1:0.5, 1:1, 1:2, 1:5, or 1:10 in a solution or in the preparation agent before performing the TFF.

In one aspect, provided herein is a method for treating a subject, said method comprising administering to the subject, a therapeutically effective amount of platelet derivatives in a platelet derivative composition of any aspect or embodiment herein or the platelet derivative composition prepared by a process of any method of preparing or making provided herein.

In one aspect, provided herein is a platelet derivative composition comprising platelet derivatives of any aspect provided herein, or a platelet derivative composition prepared by the process of any method for preparing or making provided herein, for use as a medicament in treating a subject.

In one aspect, provided herein is a platelet derivative composition comprising platelet derivatives of any aspect provided herein, or a platelet derivative composition prepared by the process of any method for preparing or making provided herein, wherein the platelet derivatives comprise an imaging agent.

In one aspect, provided herein is a method of delivering an imaging agent to a subject, comprising: (a) rehydrating platelet derivative composition comprising platelet derivatives of any aspect provided herein, or a platelet derivative composition prepared by the process of any method for preparing or making provided herein to form rehydrated platelet derivative composition; (b) contacting the rehydrated platelet derivative composition with an imaging agent, to form imaging agent loaded-platelet derivatives; and (c) administrating an effective dose of the imaging agent-loaded platelet derivatives to the subject.

In one aspect, provided herein is a platelet derivative composition for use in the treatment of a subject having an indication selected from the group consisting of intracranial hemorrhage (ICH), traumatic brain Injury (TBI), and Hermansky Pudlak Syndrome (HPS), wherein the treatment comprises rehydrating platelet derivatives in the platelet derivative composition to form a rehydrated platelet derivative composition and administering an effective dose of the platelet derivatives in the rehydrated platelet derivative composition to the subject, wherein the platelet derivative composition comprises a population of platelet derivatives: comprising CD 41-positive platelet derivatives, wherein less than 10%, 8%, in illustrative embodiments, less than 5% of the CD 41-positive platelet derivatives are microparticles; having a reduced propensity to aggregate such that no more than 2%, 3%, 4%, 5%, 6%, 7%, 8%, 9%, 10%, or 25% of the platelet derivatives in the population aggregate under aggregation conditions comprising an agonist but no platelets; and having a potency of at least 0.5, 1.0, and in illustrative embodiments, 1.5 thrombin generation potency units (TGPU) per $10^6$ platelet derivatives.

In one aspect, provided herein is a platelet derivative composition for use in the treatment of a subject having an indication of immune thrombocytopenia (ITC), or Bernard Soulier syndrome, wherein the treatment comprises rehydrating platelet derivatives in the platelet derivative composition to form a rehydrated platelet derivative composition, and administering an effective dose of the platelet derivatives in the rehydrated platelet derivative composition to the subject, wherein the platelet derivative composition comprises a population of platelet derivatives: comprising CD 41-positive platelet derivatives, wherein less than 10%, 8%, in illustrative embodiments, less than 5% of the CD 41-positive platelet derivatives are microparticles; having a reduced propensity to aggregate such that no more than 2%, 3%, 4%, 5%, 6%, 7%, 8%, 9%, 10%, or 25% of the platelet derivatives in the population aggregate under aggregation conditions comprising an agonist but no platelets; and having a potency of at least 0.5, 1.0, and in illustrative embodiments, 1.5 thrombin generation potency units (TGPU) per $10^6$ platelet derivatives.

In one aspect, provided herein is a platelet derivative composition for use in the treatment of a subject having an indication selected from the group consisting of Von Willebrand disease, immune thrombocytopenia, intracranial hemorrhage (ICH), traumatic brain Injury (TBI), Hermansky Pudlak Syndrome (HPS), Chemotherapy induced thrombocytopenia (CIT), Scott syndrome, Evans syndrome, Hematopoietic Stem Cell Transplantation, Fetal and neonatal alloimmune thrombocytopenia, Bernard Soulier syndrome, Acute myeloid leukemia, Glanzmann thrombasthenia, Myelodysplastic syndrome, Hemorrhagic Shock, Coronary thrombosis (myocardial infarction), Ischemic Stroke, Arterial Thromboembolism, Wiskott Aldrich Syndrome, Venous Thromboembolism, MYH9 related disease, Acute Lymphoblastic Lymphoma (ALL), Acute Coronary Syndrome, Chronic Lymphocytic Leukemia (CLL), Acute Promyelocytic Leukemia, Cerebral Venous Sinus Thrombosis (CVST), Liver Cirrhosis, Factor V Deficiency (Owren Parahemophilia), Thrombocytopenia absent radius syndrome, Kasabach Merritt syndrome, Gray platelet syndrome, Aplastic anemia, Chronic Liver Disease, Acute radiation syndrome, Dengue Hemorrhagic Fever, Pre-Eclampsia, Snakebite envenomation, HELLP syndrome, Haemorrhagic Cystitis, Multiple Myeloma, Disseminated Intravascular Coagulation, Heparin Induced Thrombocytopenia, Pre-Eclampsia, Labor And Delivery, Hemophilia, Cerebral (Fatal) Malaria, Alexander's Disease (Factor VII Deficiency), Hemophilia C (Factor XI Deficiency), Familial hemophagocytic lymphohistiocytosis, Acute lung injury, Hemolytic Uremic Syndrome, Menorrhagia, Chronic myeloid leukemia, or any combinations thereof, wherein the treatment comprises rehydrating platelet derivatives in the platelet derivative composition to form a rehydrated platelet derivative composition and administering an effective dose of the platelet derivatives in the rehydrated platelet derivative composition to the subject, and wherein the platelet derivative composition comprises a population of platelet derivatives: comprising CD 41-positive platelet derivatives, wherein less than 10%, 8%, in illustrative embodiments, less than 5% of the CD 41-positive platelet derivatives are microparticles; having a reduced propensity to aggregate such that no more than 2%, 3%, 4%, 5%, 6%, 7%, 8%, 9%, 10%, or 25% of the platelet derivatives in the population aggregate under aggregation conditions comprising an agonist but no platelets; and having a potency of at least 0.5, 1.0, and in illustrative embodiments 1.5, thrombin generation potency units (TGPU) per $10^6$ platelet derivatives.

In one aspect, provided herein is a plurality of containers each containing a platelet derivative composition in the form of a powder, wherein the platelet derivative composition comprises a population of platelet derivatives comprising CD 41-positive platelet derivatives, wherein less than 10%, 8%, in illustrative embodiments, less than 5% of the CD 41-positive platelet derivatives are microparticles having a diameter of less than 0.3 μm, 0.4 μm, 0.5 μm, 0.6 μm, 0.7 μm, 0.8 μm, 0.9 μm, or 1 μm having a reduced propensity to aggregate such that no more than 2%, 3%, 4%, 5%, 6%, 7%, 8%, 9%, 10%, or 25% of the platelet derivatives in the population aggregate under aggregation conditions comprising an agonist but no platelets, and having a potency of at least 0.5, 1.0, and in illustrative embodiments, 1.5 thrombin generation potency units (TGPU) per $10^6$ platelet derivatives.

In one aspect, provided herein is a process for preparing a platelet derivative composition comprising a population of platelet derivatives, the process comprising performing tangential flow filtration (TFF) of a platelet composition in a solution to at least partially exchange the solution with a preparation agent having a pH in the range of 5.5 to 8.0 and comprising 0.4 to 35% trehalose and 2% to 8% polysucrose, wherein said TFF is performed using a 0.3 to 1 micron filter, thereby preparing a TFF-treated composition comprising $100\times10^3$-$20{,}000\times10^3$ platelets/μL, $1000\times10^3$-$20{,}000\times10^3$ platelets/μL, $1000\times10^3$-$10{,}000\times10^3$ platelets/μL, $500\times10^3$-$5{,}000\times10^3$ platelets/μL, $1000\times10^3$-$5{,}000\times10^3$ platelets/μL, $2000\times10^3$-$8{,}000\times10^3$ platelets/μL, or $15{,}000\times10^3$-$20{,}000\times10^3$ platelets/μL, in illustrative embodiments, $10{,}000\times10^3$ to $20{,}000\times10^3$ platelets/μl in an aqueous medium having less than or equal to 5%, 10%, or 15% plasma protein, and having less than 10%, 8%, in illustrative embodiments, less than 5.0% microparticles having a radius less than 0.1 μm, 0.2 μm, 0.25 μm, or 0.5 μm, by scattering intensity; and freeze drying the TFF-treated composition comprising platelets in the aqueous medium to form a freeze-dried composition comprising platelet derivatives to form the platelet derivative composition, wherein the platelet derivatives in the platelet derivative composition display a potency of at least 0.5, 1.0, and in illustrative embodiments, 1.5 thrombin generation potency units (TGPU) per $10^6$ platelet derivatives, and a reduced propensity to aggregate such that no more than 2%, 3%, 4%, 5%, 6%, 7%, 8%, 9%, 10%, or 25% of the platelet derivatives in the population aggregate under aggregation conditions comprising an agonist but no platelets.

In one aspect, provided herein is a platelet derivative composition in the form of a powder, comprising a population of platelet derivatives having a compromised plasma membrane and a reduced propensity to aggregate such that no more than 2%, 3%, 4%, 5%, 6%, 7%, 8%, 9%, 10%, or 25% of the platelet derivatives in the population aggregate under aggregation conditions comprising an agonist but no platelets, wherein at least 30%, 40%, 50%, 60%, 70%, or 80% of the platelet derivatives are CD 41-positive platelet derivatives, wherein less than 1%, 2%, 3%, 4%, or 5% of the CD 41-positive platelet derivatives are microparticles having a diameter or radius of less than 0.3 μm, 0.4 μm, 0.5 μm, 0.7 μm, or 1 μm and wherein the platelet derivatives have a potency of at least 0.5, 1.0, and in illustrative embodiments, 1.5 thrombin generation potency units (TGPU) per $10^6$ platelet derivatives.

To reiterate, any embodiments herein in this section and in this specification and associated claims, can be combined and/or used in any of the aspects herein and in combination with any of the other embodiments herein. Furthermore, a "powder" recited in any aspect or embodiment can alternatively be a solid, or a composition comprising less than 1% water content in such aspect or embodiment.

In certain illustrative embodiments of a composition, or in some compositions used in or formed by a process, the platelet derivatives in a composition, as a non-limited example a powder, and/or formed by a process disclosed herein, are surrounded by a compromised plasma membrane, are positive for CD 41, and/or are 0.5 to 25.0 μm, 20.0 μm, 15.0 μm, 12.5 μm, 10.0 μm, or 2.5 μm in radius or diameter. In some embodiments, the composition comprises platelet derivatives such that at least 95% platelet derivatives positive for CD 41 have a radius or diameter in the range of 0.5 to 25.0 μm, 20.0 μm, 15.0 μm, 12.5 μm, 10.0 μm, or 2.5 μm. Such radius or diameter can be measured, for example by flow cytometry technique as known to a skilled artisan in the art.

In some embodiments of any of the aspects and embodiments herein that include platelet derivatives in a hydrated or rehydrated form, the protein concentration, or plasma protein concentration, is in the range of 0.01%-50%, 5%-50%, 5%-30%, 5-15%, 8%-10%, 7%-10%, or 3-7% of the protein concentration of donor apheresis plasma. In some embodiments of a composition or in some compositions used in or formed by a process herein, the protein concentration, or plasma protein concentration is less than or equal to 30%, 25%, 20%, 15%, 10%, 5%, 4%, 3%, 2%, or 1% of the protein concentration of donor apheresis plasma. In some embodiments of a composition or a process herein, the protein concentration, or plasma protein concentration is less than or equal to 15%, 14%, 13%, 12%, 11%, 10%, 9%, 8%, 7%, 6%, 5%, 4%, 3%, 2%, 1%, 0.1%, or 0.01%. In some exemplary embodiments, the protein concentration, or plasma protein concentration is less than 3% or 4%. In some embodiments, the protein concentration, or plasma protein concentration is between 0.01% and 20%, 0.01% and 15%, 0.01% and 10%, 0.01% and 5%, 0.1% and 20%, 0.1% and 15%, 0.1% and 10%, 0.1% and 5%, 1% and 20%, 1% and 15%, 1% and 10%, 1% and 5%, 2% and 10%, 2% and 5%, 2.5% and 5%, 2.5% and 7.5%, or between 3% and 5%. In some embodiments of a composition or a process herein, the protein concentration is in the range of 0.01-15%, 0.1-15%, 1-15%, 1-10%, 0.01-10%, 3-12%, or 5-10%. In some embodiments, the absorbance at 280 nm is less than or equal to 2.0 AU, or 1.90 AU, or 1.80 AU, or 1.7 AU, or 1.66 AU, or 1.6 AU when measured using a path length of 0.5 cm.

In some embodiments of any of the aspects and embodiments herein that include platelet derivatives in a powdered form, the protein concentration is in the range of 0.01-15%, 0.1-15%, 1-15%, 1-10%, 0.01-10%, 3-12%, or 5-10%. In some embodiments, the protein concentration is less than or equal to 25%, 20%, 15%, 10%, 7.5%, 5%, 2.5%, 1%, or 0.1%.

In some embodiments of any of the aspects and embodiments herein that include a process for preparing a platelet derivative composition, the process comprises performing TFF of a platelet composition in a solution to at least partially exchange the solution with a preparation agent having a pH in the range of 5.5 to 8.0 and comprising trehalose and polysucrose, wherein said TFF is performed using a 0.3 to 1 micron filter, thereby preparing a TFF-treated composition.

In some embodiments of any of the aspects and embodiments herein that include a composition or in some compositions used in or formed by a process that includes a population of platelet derivatives in a hydrated or rehydrated form, the composition comprises less than 10%, 7.5%, 7%, 6%, 5%, 4.5%, 4%, 3.5%, 3%, 2.5%, 2%, 1.5%, 1.0%, 0.75%, 0.5%, 0.25%, or 0.1% (by scattering intensity) microparticles. In some embodiments, the composition comprises microparticles (by scattering intensity) in the range of 0.01%-10%, 0.01%-7.5%, 0.01%-5%, 0.1%-10%, 0.1%-5%, 0.1%-4.9%, 0.5%-4.5%, 1%-10%, 1%-5%, 0.01%-4%, −0.1%-4%, 1%-4%, 1.5%-3%, 0.1%-3%, or 1%-3%. In some embodiments, the microparticles have a diameter less than 1 μm. In illustrative embodiments, the microparticles have a radius or diameter less than 0.5 μm. In some embodiments, the microparticles have a radius or diameter in the range of 0.01-0.5 μm, 0.1-0.5 μm, or 0.1-0.49 μm, 0.1-0.47 μm, or 0.1-0.45 μm, or 0.1-0.4 μm, or 0.2-0.49 μm, or 0.25-0.49 μm, or 0.3-0.47 μm. In some embodiments, the radius or diameter of the microparticles is measured using flow cytometry.

In some embodiments of any of the aspects and embodiments herein that include a platelet derivative composition in a powdered form, the platelet derivative composition comprises a population of platelet derivatives comprising CD41-positive platelet derivatives, wherein less than 5%, 4.5%, 4%, 3.5%, 3%, 2.5%, 2%, 1.5%, 1%, 0.5%, or 0.1% of the CD41-positive platelet derivatives are microparticles having a diameter of less than 1 μm, 0.9 μm, 0.8 μm, 0.7 μm, 0.6 μm, 0.5 μm 0.4 μm, 0.3 μm, 0.2 μm, or 0.1 μm. In some embodiments, 0.01%-4.9%, 0.1%-4.9%, 0.5%-4.5%, 0.01%-4%, 0.1%-4%, 1%-4%, 1.5%-3%, 0.1%-3%, or 1%-3% of the CD-41-positive platelet derivatives are microparticles. In some embodiments, the platelet derivative composition comprises a population of platelet derivatives comprising CD42-positive platelet derivatives, wherein less than 5%, 4.5%, 4%, 3.5%, 3%, 2.5%, 2%, 1.5%, 1%, 0.5%, or 0.1% of the CD42-positive platelet derivatives are microparticles having a diameter of less than 1 μm, 0.9 μm, 0.8 μm, 0.7 μm, 0.6 μm, 0.5 μm, 0.4 μm, 0.3 μm, 0.2 μm, or 0.1 μm. In some embodiments, 0.01%-4.9%, 0.1%-4.9%, 0.5%-4.5%, 0.01%-4%, 0.1%-4%, 1%-4%, 1.5%-3%, 0.1%-3%, or 1%-3% of the CD-42-positive platelet derivatives are microparticles. In some embodiments, the platelet derivative composition comprises a population of platelet derivatives comprising CD61-positive platelet derivatives, wherein less than 5%, 4.5%, 4%, 3.5%, 3%, 2.5%, 2%, 1.5%, 1%, 0.5%, or 0.1% of the CD61-positive platelet derivatives are microparticles having a diameter of less than 1 μm, 0.9 μm, 0.8 μm, 0.7 μm, 0.6 μm, 0.5 μm, 0.4 μm, 0.3 μm, 0.2 μm, or 0.1 μm. In some embodiments, 0.01%-4.9%, 0.1%-4.9%, 0.5%-4.5%, 0.01%-4%, 0.1%-4%, 1%-4%, 1.5%-3%, 0.1%-3%, or 1%-3% of the CD positive platelet derivatives are microparticles. In some illustrative embodiments, the microparticles are having a diameter of less than 0.5 μm. In some embodiments of any of the aspects and embodiments herein that include a platelet derivative composition in a powdered form, the diameter of the microparticles is determined after rehydrating the platelet derivative composition with an appropriate solution. In some embodiments, the amount of solution for rehydrating the platelet derivative composition is equal to the amount of buffer or preparation agent present at the step of freeze-drying. In some embodiments, the diameter of the microparticles is determined by flow cytometry.

In some embodiments of any of the aspects and embodiments herein that include a composition or in some compositions used in or formed by a process, the platelet derivatives have a radius or diameter greater than 0.25 μm, greater than 0.3 μm, greater than 0.4 μm, or in illustrative embodiments, greater than 0.5 μm. In some embodiments, the platelet derivatives have a radius or diameter greater than 0.75 μm. In some embodiments, the platelet derivatives have a radius or diameter in the range of 0.25-4 μm, 0.27-3.5 μm, 0.3-3.25 μm, 0.35-3.50 μm, or 0.4-3 μm. In illustrative embodiments, the platelet derivatives have a radius or diameter of at least 0.5 μm, for example in the range of 0.5 μm on the low end of the range to 25.0 μm, 20.0 μm, 15.0 μm, 12.5 μm, 10.0 μm, 5.0 μm or 2.5 μm on the high end of the range. In some embodiments, the diameter of the platelet derivatives is measured using flow cytometry.

In some embodiments of any of the aspects and embodiments herein that include a composition or in some compositions used in or formed by a process, the platelet derivatives are CD-41 positive. In some embodiments, at least 40%, 45%, 50%, 55%, 60%, 65%, 70%, or 75% of the platelet derivatives are CD-41 positive. In some embodiments, the platelet derivatives in the range of 35-97%, 40-97%, 50-97%, 60-97%, 40-95%, 45-90%, 50-95%, 60-90%, or 75-95% are positive for CD-41. In some embodiments, at least 50% of the platelet derivatives are CD 41-positive platelet derivatives, wherein less than 5% of the CD 41-positive platelet derivatives are microparticles having a diameter of less than 0.5 μm, and wherein the platelet derivatives have a potency of at least 1.5 thrombin generation potency units (TGPU) per $10^6$ platelet derivatives.

In some embodiments of any of the aspects and embodiments herein that include a platelet derivative composition in a powdered form, the platelet derivatives in the platelet derivative composition have a weight percentage of at least 0.5%, 0.75%, 1%, 1.5%, 2%, 2.5% 3%, 3.5%, 4%, 4.5%, 5%, 5.5%, 6%, 6.5%, 7%, 7.5%, 8%, 8.5%, 9%, 9.5%, or 10%. In some embodiments, the platelet derivatives in the platelet derivative composition have a weight percentage in the range of 0.5 to 25%, 0.5% to 20%, 1% to 20%, 2.5% to 20%, 5% to 20%, 5% to 10%, 2.5% to 20%, 2.5% to 15%, 2.5% to 10%, or 2.5% to 7.5%.

In some embodiments of the aspects and embodiments herein that include a platelet derivative composition in a powdered form, a platelet derivative composition is devoid of plasma protein. In some embodiments, the plasma protein is in the range of 0.01-15%, 0.1-15%, 1-10%, 2-15%, 3-9%, 1-5%, 1-3%, 0.1-3%, 0.5-2%, or 0.25-2%.

In some embodiments of the aspects and embodiments herein that include a platelet derivative composition in a powdered form, a platelet derivative composition comprises a buffering agent in the range of 0.5-3%, 0.75-2.75%, 1-2.5%, or 1.5-2.5%. In some embodiments, the buffering agent is HEPES.

In some embodiments of any of the aspects and embodiments herein that include a composition or in some compositions used in or formed by a process, the platelet derivatives have an inability to increase expression of a platelet activation marker in the presence of an agonist as compared to the expression of the platelet activation marker in the absence of the agonist. In some embodiments, the platelet activation marker is selected from the group consisting of Annexin V, and CD 62. In some embodiments, the platelet activation marker is Annexin V. In some embodiments, the platelet activation marker is CD 62. In some embodiments, the agonist is selected from the group consisting of collagen, epinephrine, ristocetin, arachidonic acid, adenosine di-phosphate, and thrombin receptor associated protein (TRAP).

In some embodiments of any of the aspects and embodiments herein that include a composition, or in some compositions used in or formed by a process, the aqueous medium has a concentration of human leukocyte antigen (HLA) Class I antibodies that is less than 30%, 10%, 5%, 3%, or 1% of the human leukocyte antigen (HLA) Class I antibody concentration in donor apheresis plasma. In some embodiments, the aqueous medium has a concentration of human leukocyte antigen (HLA) Class II antibodies that is less than 30%, 10%, 5%, 3%, or 1% of the human leukocyte antigen (HLA) Class II antibody concentration in donor apheresis plasma. In some embodiments, the composition is negative for HLA Class I antibodies based on a regulatory agency approved test. In some embodiments, the composition is negative for HLA Class II antibodies based on a regulatory agency approved test. In some embodiments of the composition, a percentage of beads positive for HLA Class I antibodies, as determined for the composition by flow cytometry using beads coated with Class I HLAs, is less than 5%, 3%, or 1%. In some embodiments of the composition, a percentage of beads positive for HLA Class II antibodies, as determined for the composition by flow cytometry using beads coated with Class II HLAs is less than 5%, 3%, or 1%.

In some embodiments of any of the aspects and embodiments herein that include a composition, or in some compositions used in or formed by a process, the aqueous medium has a concentration of human neutrophil antigen (HNA) antibodies that is less than 30%, 10%, 5%, 3%, or 1% of the HNA antibody concentration in donor apheresis plasma. In some embodiments, the composition is negative for HNA antibodies based on a regulatory agency approved test. In some embodiments of the composition, a percentage of beads positive for HNA antibodies, as determined for the composition by flow cytometry using beads coated with HNAs is less than 5%, 3%, or 1%.

In some embodiments of any of the aspects and embodiments herein that include a composition, or in some compositions used in or formed by a process, a percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, is less than 5%, 3%, or 1%. In some embodiments of the composition, a percentage of beads positive for HLA Class I antibodies, HLA Class II antibodies, and HNA antibodies, as determined for the composition by flow cytometry using beads coated with Class I HLAs, Class II HLAs, or HNAs, respectively, is less than 5%, 3%, or 1%. In some embodiments, the composition is negative for the antibodies selected from the group consisting of HLA Class I antibodies, HLA Class II antibodies, and HNA antibodies based on a regulatory agency approved test for the respective antibodies. In some embodiments, the composition is negative for HLA Class I antibodies, HLA Class II antibodies, and HNA antibodies based on a regulatory agency approved test for the respective antibodies.

In some embodiments of any of the aspects and embodiments herein that include a composition, or in some compositions used in or formed by a process that includes a population of platelet derivatives in a hydrated or rehydrated form, the platelets or platelet derivatives in a composition are at least $100\times10^3$ platelets/μL, or $200\times10^3$ platelets/μL, or $400\times10^3$ platelets/μL, or $1000\times10^3$ platelets/μL, or $1250\times10^3$ platelets/μL, or $1500\times10^3$ platelets/μL, or $1750\times10^3$ platelets/μL, $2000\times10^3$ platelets/μL, or $2250\times10^3$ platelets/μL, or $2500\times10^3$ platelets/μL, or $2750\times10^3$ platelets/μL, or $3000\times10^3$ platelets/μL, $3250\times10^3$ platelets/μL, $3500\times10^3$ platelets/μL, $3750\times10^3$ platelets/μL, $4000\times10^3$ platelets/μL, or $4250\times10^3$ platelets/μL, or $4500\times10^3$ platelets/μL, or $4750\times10^3$ platelets/μL, or $5000\times10^3$ platelets/μL, or $5250\times10^3$ platelets/μL, or $5500\times10^3$ platelets/μL, or $5750\times10^3$ platelets/μL, or $6000\times10^3$ platelets/μL, or $7000\times10^3$ platelets/μL, or $8000\times10^3$ platelets/μL, or $9000\times10^3$ platelets/μL, or $10{,}000\times10^3$ platelets/μL, or $11{,}000\times10^3$ platelets/μL, or $12{,}000\times10^3$ platelets/μL, or $13{,}000\times10^3$ platelets/μL, or $14{,}000\times10^3$ platelets/μL, or $15{,}000\times10^3$ platelets/μL, or $16{,}000\times10^3$ platelets/μL, or $17{,}000\times10^3$ platelets/μL, or $18{,}000\times10^3$ platelets/μL, or $19{,}000\times10^3$ platelets/μL, or $20{,}000\times10^3$ platelets/μL. In some embodiments of the composition, the platelets or platelet derivatives in the composition is in the range of $100\times10^3$-$20{,}000\times10^3$ platelets/μL, $1000\times10^3$-$20{,}000\times10^3$ platelets/μL, $1000\times10^3$-$10{,}000\times10^3$ platelets/μL, $500\times10^3$-$5{,}000\times10^3$ platelets/μL, $1000\times10^3$-$5{,}000\times10^3$ platelets/μL, $2000\times10^3$-$8{,}000\times10^3$ platelets/μL, $10{,}000\times10^3$-$20{,}000\times10^3$ platelets/4, $15{,}000\times10^3$-$20{,}000\times10^3$ platelets/μL, $5000\times10^3$ to $20{,}000\times10^3$ platelets/μl, $6000\times10^3$ to $18{,}000\times10^3$ platelets/μl or $6000\times10^3$ to $15{,}000\times10^3$ platelets/0.

In some embodiments, the above concentrations are at any point in a process herein, such as in the volume that is freeze dried. In some embodiments, the above concentrations are for platelet-derivatives herein. It is contemplated that the platelet derivative composition in the form of a powder has to be rehydrated with a solution to determine the platelet-derivative concentration, typically in the intended volume for rehydration of a powder, e.g. freeze-dried, composition, which in illustrative embodiments is a recommended volume of a container containing the powder and/or a same volume as the composition was in before it was dried to form the powder. In some embodiments, the solution for rehydrating can be water. In some embodiments, the solution for rehydrating can be a well-known buffer. In some embodiments, the amount of solution for rehydrating the platelet derivative composition is equal to the amount of buffer or preparation agent present at the step of freeze-drying. In some embodiments, the platelet concentration is in In some embodiments of any of the aspects and embodiments herein that include a composition, or in some compositions used in or formed by a process, the composition(s) comprises a population of platelet derivatives having a reduced propensity to aggregate. In certain embodiments, no more than 25%, 22.5%, 20%, 17.5%, 12.5%, 10%, 7.5%, 5%, 4%, 3%, 2%, or 1% of the platelet derivatives in the population aggregate under aggregation conditions. In an illustrative embodiment no more than 10% of the platelet derivatives in the population aggregate under aggregation conditions. Illustrative embodiments of exemplary aggregation conditions are provided herein. For example, in illustrative embodiments such aggregation conditions comprise an agonist but no platelets are present in the aggregation conditions. In some embodiments, the agonist is selected from the group consisting of collagen, epinephrine, ristocetin, arachidonic acid, adenosine di-phosphate, and thrombin receptor associated protein (TRAP). In some embodiments, the population of platelet derivatives aggregate in the range of 2-30%, 5-25%, 10-30%, 10-25%, 12.5-25%, 2-10%, 2-8%, 2-7.5%, 2-5%, 2-4%, 0-1%, 0- 2%, 0-3%, 0-4%, 0-5%, 0-7.5%, or 0-10%, or in illustrative embodiments 0 to about 1% of the platelet derivatives under aggregation conditions comprising an agonist but no platelets. It can be contemplated that aggregation conditions involve rehydrating the platelet derivative composition in an appropriate amount of water or an appropriate buffer.

In some embodiments of any of the aspects and embodiments herein that include a composition, or in some compositions used in or formed by a process, comprises erythrocytes in an amount lesser than $0.2\times10^6$ erythrocytes/μL, or $0.1\times10^6$ erythrocytes/μL, or $0.5\times10^5$ erythrocytes/μL, or $0.1\times10^5$ erythrocytes/μL. In some embodiments, the erythrocytes in the composition is in the range of $0.1\times10^5$ erythrocytes/μL to $0.2\times10^6$ erythrocytes/μL, or $0.5\times10^5$ erythrocytes/μL to $0.1\times10^6$ erythrocytes/μL.

In some embodiments of any of the aspects and embodiments herein that include a composition, or in some compositions used in or formed by a process, the aqueous medium further comprises a buffering agent, a base, a loading agent, optionally a salt, and optionally at least one organic solvent. In some embodiments, the buffering agent is HEPES (4-(2-hydroxyethyl)-1-piperazineethanesulfonic acid). In some embodiments, the base is sodium bicarbonate. In some embodiments, the loading agent is a monosaccharide, a polysaccharide, or a combination thereof. In some embodiments, the monosacchariade is selected from the group consisting of sucrose, maltose, trehalose, glucose, mannose, and xylose. In some embodiments, the monosaccharide is trehalose. In some embodiments, the polysaccharide is polysucrose. In some embodiments, the salt is sodium chloride, potassium chloride, or a combination thereof. In some embodiments, the organic solvent is selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), and combinations thereof.

In some embodiments of any of the aspects and embodiments herein that include a composition, or in some compositions used in or formed by a process that includes a population of platelet derivatives in a hydrated or rehydrated form, comprises trehalose in the range of 0.4-35%, or 1-35%, or 2-30%, 1-20%, or 1-10%, or 1-5%, or 0.5-5%. In an exemplary embodiment, the composition comprises 3.5% trehalose.

In some embodiments of any of the aspects and embodiments herein that include a composition, or in some compositions used in or formed by a process that includes a platelet composition in a powdered form, comprises trehalose having a weight percentage in the range of 10-60%, 15-55%, 20-60%, 20-50%, 25-60%, 25-50%, 10-50%, 20-40%, 20-35%, or 1-20%. In some embodiments, the weight percentage of trehalose can vary on the weight percentage of other components in the composition like, polysucrose, platelet derivatives, plasma protein, and buffering agents.

In some embodiments of any of the aspects and embodiments herein that include a composition, or in some compositions used in or formed by a process that includes a population of platelet derivatives in a hydrated or rehydrated form, comprises polysucrose in the range of 2-8%, 2.25-7.75%, 2.5-7.5%, or 2.5-6.5%. In an exemplary embodiment, the composition comprises 3% polysucrose. In another exemplary embodiment, the composition comprises 6% polysucrose.

In some embodiments of any of the aspects and embodiments herein that include a composition, or in some compositions used in or formed by a process that includes a platelet composition in a powdered form, comprises polysucrose having a weight percentage in the range of 20-80%, 25-75%, 30-70%, 35-65%, 30-80%, or 45-60%. In some embodiments, the weight percentage of trehalose can vary on the weight percentage of other components in the composition like, trehalose, platelet derivatives, plasma protein, and buffering agents.

In some embodiments of any of the aspects and embodiments herein that include a composition, or in some compositions used in or formed by a process that includes a platelet composition in a powdered form, comprises trehalose and polysucrose having a combined weight percentage in the range of 30-95%, 35-95%, 40-90%, 40-90%, 45-90%, or 60-95%.

In some embodiments of any of the aspects and embodiments herein that include a composition or in some compositions used in or formed by a process herein, comprises polysucrose, the polysucrose is a cationic form of polysucrose. In some embodiments, the cationic form of polysucrose is diethylaminoethyl (DEAE)-polysucrose. In some embodiments, the polysucrose is an anionic form of polysucrose. In some embodiments, the anionic form of polysucrose is carboxymethyl-polysucrose. In some embodiments of the composition, polysucrose has a molecular weight in the range of 70,000 MW to 400,000 MW, 100,000 MW to 400,000 MW, 200,00 MW to 400,000 MW, 80,000 MW to 350,000 MW, 100,000 MW to 300,00 MW, 100,000 MW to 200,000 MW, 120,000 MW to 200,000 MW. In some exemplary embodiments, polysucrose has a molecular weight of 150,000 MW, 160,000 MW, 170,000 MW, 180,000 MW, 190,000 MW, or 200,000 MW.

In some embodiments of any of the aspects and embodiments herein that include a composition or in some compositions used in or formed by a process herein, comprises platelet derivatives that are positive for at least one platelet activation marker selected from the group consisting of Annexin V, and CD 62. In some embodiments, the platelet derivatives are positive for at least one platelet marker selected from the group consisting of CD 41, CD 42, and CD 61. In some embodiments, the platelet derivatives are positive for CD 47. In some embodiments, the platelet derivatives are positive for Annexin V. In some embodiments, the platelet derivatives are positive for Annexin V. In some embodiments, at least 25%, 50%, or 75% of the platelet derivatives in the platelet derivative composition are Annexin V positive. In some embodiments, the platelet derivatives are positive for CD 41. In some embodiments, at least 30%, 35%, 40%, 45%, 50%, 55%, 60%, or 65% of the platelet derivatives in the platelet derivative composition are CD41 positive. In some embodiments, at least 90%, 91%, 92%, 93%, 94%, 95% 96%, 97%, 98%, or 99% platelet derivatives that are positive for CD 41 have a size in the range of 0.5-2.5 μm. In some exemplary embodiments, at least 95% platelet derivatives that are positive for CD 41 have a size in the range of 0.5-2.5 μm. In some embodiments, the platelet derivatives are positive for CD 42. In some embodiments, at least 65%, 80%, or 90% of the platelet derivatives in the platelet derivative composition are CD42 positive. In some embodiments, the platelet derivatives are positive for CD 47. In some embodiments, at least 8%, 10%, 15%, or 20% of the platelet derivatives in the platelet derivative composition are CD47 positive. In some embodiments, the platelet derivatives are positive for CD 62. In some embodiments, at least 10%, 50%, 65%, 80%, or 90% of the platelet derivatives in the platelet derivative composition are CD62 positive. In some embodiments, the platelet derivatives in the platelet derivative composition are positive for CD41, CD62, and Annexin V. In some embodiments, the platelet derivatives in the platelet derivative composition are at least 50% platelet derivatives are positive for CD41, at least 70% platelet derivatives are positive for CD62, and at least 70% platelet derivatives are positive for Annexin V.

In some embodiments of any of the aspects and embodiments herein that include a composition or in some compositions used in or formed by a process herein, the platelet derivatives have fibrinogen associated with their cell membrane. In some embodiments, the platelet derivatives have at least 25%, 30%, 35%, 40%, 45%, 50%, 55%, 60%, 65%, 70%, 75%, 80%, 85%, 90%, 95%, or 100% higher fibrinogen on their surface as compared to resting platelets, or activated platelets, or fixed platelets. In some embodiments, the platelet derivatives when analyzed for the binding of anti-fibrinogen antibody to the platelet derivatives using flow cytometry exhibit at least 10, 15, 20, 25, 30, 35, or 40 folds higher mean fluorescent intensity (MFI) in the absence of an agonist as compared to the MFI of binding of anti-fibrinogen antibody to the fixed platelets.

In some embodiments of any of the aspects and embodiments herein that include a composition or in some compositions used in or formed by a process herein that includes a population of platelet derivatives in a hydrated or rehydrated form, the platelet derivatives in the platelet derivative composition retain at least 10%, or 15%, or 20% of the lactate dehydrogenase activity of donor apheresis platelets. In some embodiments, the aqueous medium has a lactate concentration of less than 2.0 mmol/L, or 1.5 mmol/L. In some embodiments, the lactate concentration is in the range of 0.4 to 1.3 mmol/L, or 0.5 to 1.0 mmol/L.

In some embodiments of any of the aspects and embodiments herein that include a composition or in some compositions used in or formed by a process herein that includes a population of platelet derivatives in a hydrated or rehydrated form, the platelet derivatives, when at a concentration of about $4.8\times10^3$ particles/μL generate a thrombin peak height (TPH) of at least 25 nM, at least 50 nM, at least 75 nM, or at least 100 nM when in the presence of a reagent containing tissue factor and phospholipids. In some embodiments, the platelet derivatives, when at a concentration of about $4.8\times10^3$ particles/μL generate a thrombin peak height (TPH) in the range of 25-100 nM, 30-80 nM, or 25-75 nM.

In some embodiments of any of the aspects and embodiments herein that include a composition or in some compositions used in or formed by a process, the platelet derivatives, have a potency of at least 1.25, at least 1.5, at least 1.75, at least 2.0, at least 2.25, at least 2.5 thrombin generation potency units (TGPU) per $10^6$ particles. In some embodiments, the platelet derivatives have a potency in the range of 1.2 to 2.5, 1.2 to 2.0, 1.3 to 1.5, 1.5 to 2.25, 2 to 2.5, or 2.25 to 2.5 TGPU per $10^6$ particles.

In some embodiments of any of the aspects and embodiments herein that include a composition or in some compositions used in or formed by a process, the platelet derivatives have the presence of thrombospondin (TSP-1) on their surface at a level that is at least 10%. 20%, 25%, 30%, 50%, 60%, 70%, 80%, 90%, or 100% higher than on the surface of resting platelets, or lyophilized fixed platelets. In some embodiments, the platelet derivatives have the presence of thrombospondin (TSP-1) on their surface at a level that is more than 100% higher than on the surface of resting platelets, or lyophilized fixed platelets. In some embodiments, the platelet derivatives have the presence of thrombospondin (TSP-1) on their surface at a level that is at least 50%, 60%, 70%, 80%, 90%, or 100% higher than on the surface of activated platelets, or lyophilized fixed platelets. In some embodiments, the platelet derivatives have the presence of thrombospondin (TSP-1) on their surface at a level that is more than 100% higher than on the surface of activated platelets, or lyophilized fixed platelets. In some embodiments, the platelet derivatives when analyzed for the binding of anti-thrombospondin (TSP) antibody to the platelet derivatives using flow cytometry exhibit at least 2 folds, 5 folds, 7 folds, 10 folds, 20 folds, 30 folds, 40 folds, 50 folds, 60 folds, 70 folds, 80 folds, 90 folds, or 100 folds higher mean fluorescent intensity (MFI) in the absence of an agonist as compared to the MFI of binding of anti-TSP antibody to the resting platelets. In some embodiments, the platelet derivatives when analyzed for the binding of anti-thrombospondin (TSP) antibody to the platelet derivatives using flow cytometry exhibit at least 2 folds, 5 folds, 7 folds, 10 folds, 20 folds, 30 folds, or 40 folds higher mean fluorescent intensity (MFI) in the absence of an agonist as compared to the MFI of binding of anti-TSP antibody to the lyophilized fixed platelets. In some embodiments, the platelet derivatives when analyzed for the binding of anti-thrombospondin (TSP) antibody to the platelet derivatives using flow cytometry exhibit 10-800 folds, 20-800 folds, 100-700 folds, 150-700 folds, 200-700 folds, or 250-500 folds higher mean fluorescent intensity (MFI) in the absence of an agonist as compared to the MFI of binding of anti-TSP antibody to the resting platelets. In some embodiments, the platelet derivatives when analyzed for the binding of anti-thrombospondin (TSP) antibody to the platelet derivatives using flow cytometry exhibit at least 2 folds, 5 folds, 7 folds, 10 folds, 20 folds, 30 folds, or 40 folds higher mean fluorescent intensity (MFI) in the absence of an agonist as compared to the MFI of binding of anti-TSP antibody to the active platelets. In some embodiments, the platelet derivatives when analyzed for the binding of anti-thrombospondin (TSP) antibody to the platelet derivatives using flow cytometry exhibit 2-40 folds, 5-40 folds, 5-35 folds, 10-35 folds, or 10-30 folds higher mean fluorescent intensity (MFI) in the absence of an agonist as compared to the MFI of binding of anti-TSP antibody to the active platelets.

In some embodiments of any of the aspects and embodiments herein that include a composition or in some compositions used in or formed by a process, the platelet derivatives have the presence of von Willebrand factor (vWF) on their surface at a level that is at least 10%, 20%, 25%, 30%, 50%, 60%, 70%, 80%, 90%, or 100% higher than on the surface of resting platelets, or lyophilized fixed platelets. In some embodiments, the platelet derivatives have the presence of von Willebrand factor (vWF) on their surface at a level that is more than 100% higher than on the surface of resting platelets, or lyophilized fixed platelets. In some embodiments, the platelet derivatives when analyzed for the binding of anti-von Willebrand factor (vWF) antibody to the platelet derivatives using flow cytometry exhibits at least 1.5 folds, 2 folds, or 3 folds, or 4 folds higher mean fluorescent intensity (MFI) in the absence of an agonist as compared to the MFI of binding of anti-vWF antibody to the resting platelets, or lyophilized fixed platelets. In some embodiments, the platelet derivatives when analyzed for the binding of anti-von Willebrand factor (vWF) antibody to the platelet derivatives using flow cytometry exhibits 2-4 folds, or 2.5-3.5 higher mean fluorescent intensity (MFI) in the absence of an agonist as compared to the MFI of binding of anti-vWF antibody to the resting platelets, or lyophilized fixed platelets.

In some embodiments of any of the aspects and embodiments herein that include a composition or in some compositions used in or formed by a process, the platelet derivatives lack an integrated membrane as compared to platelets. In some embodiments, the platelet derivatives are surrounded by a compromised plasma membrane. In some embodiments, the platelet derivatives are incapable of retaining more than 35%, 40%, 45%, 50%, 55%, 60%, 65%, 70%, or 75% of lactate dehydrogenase as compared to lactate dehydrogenase retained in fresh platelets, or cold stored platelets, or cryopreserved platelets. In some embodiments, the platelet derivatives can retain 35%-75%, 40-70%, 45-65%, or 35-50% lactate dehydrogenase as compared to fresh platelets, or cold stored platelets, or cryopreserved platelets. In some embodiments, the platelet derivatives exhibit an increased permeability to antibodies. In some embodiments, the antibodies can be IgG antibodies.

In some embodiments of any of the aspects and embodiments herein that include a composition or in some compositions used in or formed by a process, the platelet derivatives, when at a concentration of at least about $70\times10^3$ particles/4, produce an occlusion time of less than 14 minutes, or less than 12 minutes in a total thrombus-formation analysis system (T-TAS) assay. In some embodiments, the occlusion time is in the range of 1 to 13 minutes, 1 to 11 minutes, 1 to 10 minutes, or 1 to 7 minutes.

In some embodiments of any of the aspects and embodiments herein that include a composition or in some compositions used in or formed by a process, the platelet derivatives in the platelet derivative composition comprise thrombosomes. In some embodiments, the platelet derivatives comprise freeze-dried platelets. In some embodiments, the platelet derivatives comprise thermally-treated freeze-dried platelets.

In some embodiments of any of the aspects and embodiments herein that include a process, comprises tangential flow filtration (TFF), centrifugation of a starting material comprising platelet composition, or a combination thereof. In some embodiments of the process, the starting material comprising platelet composition is: a) positive for HLA Class I antibodies based on a regulatory agency approved test; or b) positive for HLA Class II antibodies based on a regulatory agency approved test; or c) positive for HNA antibodies based on a regulatory agency approved test; or two or more of a), b), and c). In some embodiments, the starting material comprising platelet composition has a protein concentration in the range of 60 to 80 mg/mL, or 65 to 75 mg/mL. In some embodiments, the starting material comprising platelet composition comprises donor blood product. In some embodiments, the donor blood product is pooled donor blood product. In some embodiments, the starting material comprising platelet composition comprises donor apheresis material.

In some embodiments of any of the aspects and embodiments herein that include a process, that does not comprise centrifugation of the starting material comprising platelets or platelet composition, the diluted starting material comprising platelets or platelet composition, the concentrated platelet composition, the TFF-treated composition, or the combination thereof. In some embodiments, the process does not comprise centrifugation of a composition comprising platelets or platelet derivatives.

In some embodiments of any of the aspects and embodiments herein that include a process, the TFF comprises concentrating. In some embodiments, the TFF comprises diafiltering. In some embodiments, the diafiltering comprises diafiltering with at least two diavolumes. In some embodiments, the diafiltering is done with at least three diavolumes, or four diavolumes, or five diavolumes, or six diavolumes. In some embodiments, the diafiltering is done with diavolumes in the range of two to ten. In some embodiments, the TFF comprises buffer exchange.

In some embodiments of any of the aspects and embodiments herein that include a process, diluting comprises diluting with an approximately equal weight (±10%) of the preparation agent.

In some embodiments of the process of any of the aspects and embodiments herein that include a process, further comprises a pathogen reduction step. In some embodiments, the pathogen reduction step occurs before the diluting of the starting material. In some embodiments, the pathogen reduction step precedes TFF.

In some embodiments of any of the aspects and embodiments herein that include a process, wherein following washing if the concentration of the platelets or cells in the TFF-treated composition is not $2000\times10^3$ cells/μL ($\pm300\times10^3$), $3000\times10^3$ cells/μL ($\pm300\times10^3$), $4000\times10^3$ cells/μL ($\pm300\times10^3$), $5000\times10^3$ cells/μL ($\pm300\times10^3$), $6000\times10^3$ cells/μL ($\pm300\times10^3$), $7000\times10^3$ cells/μL ($\pm300\times10^3$), $8000\times10^3$ cells/μL ($\pm300\times10^3$), $10000\times10^3$ cells/μL ($\pm300\times10^3$), $12000\times10^3$ cells/μL ($\pm300\times10^3$), $14000\times10^3$ cells/μL ($\pm300\times10^3$), $16000\times10^3$ cells/μL ($\pm300\times10^3$), $18000\times10^3$ cells/μL ($\pm300\times10^3$), or $20000\times10^3$ cells/μL ($\pm300\times10^3$), diluting the preparation agent or concentrating the platelets or the cells to fall within this range.

In some embodiments of any of the aspects and embodiments herein that include a process, further comprises lyophilizing or freeze-drying the TFF-treated composition to form a lyophilized composition. In some embodiments, a process further comprises treating the lyophilized composition at a temperature in the range of 60-90° C., or 65-85° C., or 70-90° C. for a time period in the range of 1-36 hours, or 5-30 hours, or 10-25 hours.

In some embodiments of any of the aspects and embodiments herein that include a process, the TFF is carried out using a membrane with a pore size in the range of 0.2 μm to 1 μm. In some embodiments the TFF is carried out using a membrane with pore size in the range of 0.3 μm to 1 μm, or 0.4 μm to 1 μm, or 0.4 μm to 0.8 μm, or 0.4 μm to 0.7 μm. In illustrative embodiments, the TFF is carried out using a membrane with a pore size of 0.45 μm, or 0.65 μm.

In some embodiments of any of the aspects and embodiments herein that include a process, the TFF is carried out until the absorbance at 280 nm of the aqueous medium is less than or equal to 50%, or 30%, or 10%, or 5%, or 3%, or 1% of the absorbance at 280 nm of the starting material comprising platelet composition, using a path length of 0.5 cm. In some embodiments, the TFF is carried out until the protein concentration or plasma protein concentration in the aqueous medium is less than or equal to 20%, 15%, 12.5%, 10%, 7.5%, 5%, 2.5%, or 1%. In some embodiments, the TFF is carried out until the protein concentration or plasma protein concentration is in between 0.01% and 20%, 0.01% and 15%, 0.01% and 10%, 0.01% and 5%, 0.1% and 20%, 0.1% and 15%, 0.1% and 10%, 0.1% and 5%, 1% and 20%, 1% and 15%, 1% and 10%, 1% and 5%, 2% and 10%, 2% and 5%, 2.5% and 5%, 2.5% and 7.5%, or between 3% and 5%. In some embodiments, the TFF is carried out until the absorbance at 280 nm of the aqueous medium is less than or equal to 2.0 AU, or 1.90 AU, or 1.80 AU, or 1.70 AU, or 1.66 AU, or 1.60 AU, using a path length of 0.5 cm. In some embodiments, the TFF is carried out until the platelet concentration is at least $2000\times10^3$ platelets/μL, $2250\times10^3$ platelets/μL, $3000\times10^3$ platelets/μL, $3250\times10^3$ platelets/μL, $3500\times10^3$ platelets/μL, $4000\times10^3$ platelets/μL, $4250\times10^3$ platelets/μL, $4500\times10^3$ platelets/μL, $4750\times10^3$ platelets/μL, $5000\times10^3$ platelets/μL, $5250\times10^3$ platelets/μL, $5500\times10^3$ platelets/μL, $5750\times10^3$ platelets/μL, $6000\times10^3$ platelets/μL, $7000\times10^3$ platelets/μL, $8000\times10^3$ platelets/μL, $9000\times10^3$ platelets/μL, $10,000\times10^3$ platelets/μL, $11,000\times10^3$ platelets/μL, $12,000\times10^3$ platelets/μL, $13,000\times10^3$ platelets/μL, $14,000\times10^3$ platelets/μL, $15,000\times10^3$ platelets/μL, $16,000\times10^3$ platelets/μL, $17,000\times10^3$ platelets/μL, $18,000\times10^3$ platelets/μL, $19,000\times10^3$ platelets/μL, or $20,000\times10^3$ platelets/μL.

In some embodiments of any of the aspects and embodiments herein that include a process, the TFF-treated composition comprises at least $1000\times10^3$ platelets/μL, $2000\times10^3$ platelets/μL, $2250\times10^3$ platelets/μL, $3000\times10^3$ platelets/μL, $3250\times10^3$ platelets/μL, $3500\times10^3$ platelets/μL, $4000\times10^3$ platelets/μL, $4250\times10^3$ platelets/μL, $4500\times10^3$ platelets/μL, $4750\times10^3$ platelets/μL, $5000\times10^3$ platelets/μL, $5250\times10^3$ platelets/μL, $5500\times10^3$ platelets/μL, $5750\times10^3$ platelets/μL, $6000\times10^3$ platelets/μL, $7000\times10^3$ platelets/μL, $8000\times10^3$ platelets/μL, $9000\times10^3$ platelets/μL, $10,000\times10^3$ platelets/μL, $11,000\times10^3$ platelets/μL, $12,000\times10^3$ platelets/μL, $13,000\times10^3$ platelets/μL, $14,000\times10^3$ platelets/μL, $15,000\times10^3$ platelets/μL, $16,000\times10^3$ platelets/μL, $17,000\times10^3$ platelets/μL, $18,000\times10^3$ platelets/μL, $19,000\times10^3$ platelets/μL, or $20,000\times10^3$ platelets/μL. In some embodiments, the TFF-treated composition comprises $1000\times10^3$ platelets/μL to $20,000\times10^3$ platelets/μL, $10,000\times10^3$ platelets/μL to $20,000\times10^3$ platelets/μL, $5000\times10^3$ platelets/μL to $20,000\times10^3$ platelets/μL, or $5000\times10^3$ platelets/μL to $10,000\times10^3$ platelets/μL.

In some embodiments of any of the aspects and embodiments herein that include a process, the TFF comprises diafiltering with a preparation agent comprising a buffering agent, a base, a loading agent, optionally a salt, and optionally at least one organic solvent. In some embodiments of the process, the TFF comprises buffer exchange into a preparation agent comprising a buffering agent, a base, a loading agent, optionally a salt, and optionally at least one organic solvent. In some embodiments, the buffering agent is HEPES (4-(2-hydroxyethyl)-1-piperazineethanesulfonic acid). In some embodiments, the base is sodium bicarbonate. In some embodiments, the loading agent is a monosaccharide, a polysaccharide, or a combination thereof. In some embodiments, the monosaccharide is selected from the group consisting of sucrose, maltose, trehalose, glucose, mannose, xylose, and combinations thereof. In some embodiments, the monosaccharide is trehalose. In some embodiments, the polysaccharide is polysucrose. In some embodiments, the salt is sodium chloride, potassium chloride, or a combination thereof. In some embodiments, the organic solvent is selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), and combinations thereof.

In some embodiments of any of the aspects and embodiments herein that include a process, the preparation agent has a pH in the range of 5.5 to 8.0, or 6.0 to 8.0, or 6.0 to 7.5. In an illustrative embodiment, the preparation agent has a pH of 6.5. In another illustrative embodiment, the preparation agent has a pH of 7.4.

In some embodiments of any of the aspects and embodiments herein that include a process, that does not comprise a step for fixing the platelets, or platelet derivatives. In some embodiments, the process does not comprise fixing the platelets, or platelet derivatives using a fixative agent known in the art for fixing the platelets or platelet derivatives. In some embodiments, the process does not comprise contacting the platelets, or platelet derivatives with at least one fixative agent. In some embodiments, the fixative agent is an aldehyde. In some embodiments, the fixative agent is an alcohol. In illustrative embodiments, the fixative agent is selected from the group consisting of formaldehyde, paraformaldehyde, glutaraldehyde, and isopropanol.

In some embodiments of any of the aspects and embodiments herein that include a process, further comprises lyophilizing the composition comprising platelets or platelet derivatives.

In some embodiments of any of the aspects and embodiments herein that include a process, further comprises cryopreserving the composition comprising platelets or platelet derivatives.

In some embodiments of any of the aspects and embodiments herein that include a process, further comprises thermally treating the composition comprising platelets or platelet derivatives.

In some of the embodiments of any of the aspects and embodiments herein that include a process, the TFF is performed at a temperature in the range of 20° C. to 37° C., or 25° C. to 37° C., or 20° C. to 35° C., or 25° C. to 35° C.

In some embodiments of any of the aspects and embodiments herein that include a process, a percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, is reduced by at least 50%, or by at least 75%, or by at least 90%, or by at least 95%, as compared to a similar composition not prepared by a process comprising tangential flow filtration of a blood product composition, centrifugation of a blood product composition, or a combination thereof.

In some embodiments of any of the aspects and embodiments herein that include a composition, or in some compositions used in or formed by a process, the platelet derivatives are derived from human platelets and are positive for at least one marker selected from the group consisting of CD 41, CD 42, and CD 61. In some embodiments, the platelet derivatives are derived from human platelets that are positive for CD 41. In some embodiments, embodiments, the platelet derivatives are derived from human platelets that are positive for CD 42. In some embodiments, embodiments, the platelet derivatives are derived from human platelets that are positive for CD 61. In some illustrative embodiments, the platelet derivatives are derived from human platelets that are positive for CD 41, CD 42, and CD 61.

In some embodiments of any of the aspects and embodiments herein that include a composition, or in some compositions used in or formed by a process, the platelet derivatives are derived from a non-human animal. In some embodiments, the non-human animal is selected from the group consisting of canines, equines, and felines. In some exemplary embodiments, the platelet derivatives are derived from canines.

In some embodiments of any of the aspects and embodiments herein that include a composition, or in some compositions used in or formed by a process that includes a population of platelet derivatives a powdered form, the platelet derivative composition comprises no more than 0.1%, 0.2%, 0.3%, 0.4%, 0.5%, 0.6%, 0.7%, 0.8%, 0.9%, 1%, 1.5%, 2%, 2.5%, 3%, 3.5%, 4.0%, 4.5%, or 4.9% residual moisture. In some embodiments, wherein the platelet derivative composition is in a powdered form, the platelet derivative composition comprises residual moisture in the range of 0.1-2%, 0.2-1.5%, 0.5-1.5%, 0.75-1.25%, 2-3%, 2.5-4.9%, 3-4.5%, 1.5-3%, or 1-2% residual moisture. In some illustrative embodiments, the platelet derivative composition comprises no more than 0.5% residual moisture.

In some embodiments of any of the aspects and embodiments herein that include a composition, or in some compositions used in or formed by a process that includes a plurality of containers each filled with a platelet derivative composition in the form of a powder, the platelet derivative composition in at least one of the plurality of containers comprises or is associated with a first protein from a first gene that has a different amino acid sequence than found in all the versions of the first protein from the first gene in the platelet derivative composition in one or more other containers of the plurality.

In some embodiments of any of the aspects and embodiments herein that include a composition, or in some compositions used in or formed by a process that includes a plurality of containers each filled with a platelet derivative composition in the form of a powder, the at least one container comprises a first lot of platelet derivatives and the one or more other containers comprise a second lot of platelet derivatives. In some embodiments, plurality of containers comprises the platelet derivative composition from at least 2, 3, 4, 5, 6, 7, 8, 9, or 10 different lots, wherein the platelet derivative composition in at least 2 of the lots have a different amino acid sequences for at least one protein of a collection of protein gene products from a corresponding collection of encoding genes. In illustrative embodiments all, of the lots have a different amino acid sequences for at least one protein of a collection of protein gene products from a corresponding collection of encoding genes. In some embodiments, the amino acid difference(s) is at one or more residues corresponding to amino acid residues encoded by a non-synonymous single nucleotide polymorphism (SNP).

In some embodiments of any of the aspects and embodiments herein that include a composition, or in some compositions used in or formed by a process that includes a plurality of containers each filled with a platelet derivative composition in the form of a powder, each of the plurality of containers are purged with at least one inert gas. In some embodiments, the inert gas can be argon, or nitrogen.

In some embodiments of any of the aspects and embodiments herein that include a composition, or in some compositions used in or formed by a process that includes a plurality of containers each filled with a platelet derivative composition in the form of a powder, the platelet derivative composition from the at least 2 lots have different amino acid sequences for at least one protein of a collection of protein gene products from a corresponding collection of encoding genes. In some embodiments, the different amino acid sequences differ at one or more residues corresponding to amino acid residues encoded by a non-synonymous single nucleotide polymorphism (SNP). In some embodiments, the platelet derivative composition is in a container, and wherein the container is filled with at least one inert gas.

In some embodiments of any of the aspects and embodiments herein that include a composition, or in some compositions used in or formed by a process that includes a plurality of containers each filled with a platelet derivative composition in the form of a powder, the amount of plasma protein in the powder of any two containers chosen from different lots, differs by less than 50%, 40%, 30%, 20%, 10%, 5%, 2%, 1%, or 0.5%.

In some embodiments of any of the aspects and embodiments herein that include a composition, or in some compositions used in or formed by a process that includes a plurality of containers each filled with a platelet derivative composition in the form of a powder, the amount of microparticles that are less than 0.5 μm in the powder of any two containers chosen from different lots, differs by less than 50%, 40%, 30%, 20%, 10%, 5%, 2%, 1%, or 0.5%.

In some embodiments of any of the aspects and embodiments herein that include a composition, or in some compositions used in or formed by a process that includes a plurality of containers each filled with a platelet derivative composition in the form of a powder, the platelet derivative composition from the at least 2 lots have different amino acid sequences for at least one, two, three, four, or five protein of a collection of protein gene products from a corresponding collection of encoding genes. In some embodiments, the different amino acid sequences differ at one or more residues corresponding to amino acid residues encoded by a non-synonymous single nucleotide polymorphism (SNP).

In some embodiments of any of the aspects and embodiments herein that includes a plurality of containers each filled with a platelet derivative composition in the form of a powder, the containers can vary in volume from 5-100 ml, 10-90 ml, 25-75 ml, or 5-40 ml. In some embodiments, the volume of containers can be 5 ml, 10 ml, 15 ml, 20 ml, 25 ml, 30 ml, 35 ml, 40 ml, 45 ml, 50 ml, 55 ml, 60 ml, 65 ml, 70 ml, 75 ml, 80 ml, 85 ml, 90 ml, 95 ml, or 100 ml. In some embodiments, the volume of containers can be above 100 ml, for example, 125 ml, 150 ml, 175 ml, or 200 ml. In some illustrative embodiments, the volume of vials is 30 ml. In some other illustrative embodiments, the volume of vials is 10 ml. In some embodiments, the plurality of containers can have 10-500 vials, 25-450 vials, 50-350 vials, 100-300 vials, or 150-250 vials. In some embodiments, the plurality of containers can have 10, 20, 30, 40, 50, 60, 70, 80, 90, 100, 110, 120, 130, 140, 150, 160, 170, 180, 190, 200, 250, 300, 350, 400, 450, or 500 vials. In some embodiments, the plurality of containers can be increased to more than 500 as per the requirements, for example, 600, 700, 800, 900, or 1000 vials. In some embodiments, the number of vials can be 10-1000, 50-1000, 100-900, 200-800, or 150-700, or 150-500 vials. The number of vials in which a platelet derivative composition as per one of the embodiments, or aspects described herein can be filled and/or present can vary with the manufacturing requirements and the amount of starting material comprising platelets.

In some embodiments of any of the aspects and embodiments herein that includes a plurality of containers each filled with a platelet derivative composition in the form of a powder, the amount of platelet derivatives when the plurality of containers is taken as a whole can be $1\times10^{9}$ to $1\times10^{16}$, $1\times10^{10}$ to $1\times10^{15}$, $1\times10^{11}$ to $1\times10^{15}$, $1\times10^{12}$ to $1\times10^{16}$, or $1\times10^{13}$ to $1\times10^{15}$.

In some embodiments of any of the aspects and embodiments herein that include a composition, or in some compositions used in or formed by a process, the platelet derivatives are allogenic platelet derivatives. In some embodiments, the platelet derivatives are allogenic platelet derivative product. In some embodiments, a platelet derivative composition as per any of the embodiments or aspects herein, is a composition comprising allogenic platelet derivatives. In some embodiments, a platelet derivative composition as described herein is a U.S. FDA-approved product comprising allogenic platelet derivative composition. In some embodiments, a platelet derivative composition as described herein is a European EMA-approved product comprising allogenic platelet derivative composition. In some embodiments, a platelet derivative composition as described herein is a China FDA-approved product comprising an allogenic platelet derivative composition.

In some embodiments of the aspects and embodiments herein that include a composition, or in some compositions used in or formed by a process, or a process for preparing a platelet derivative composition, the platelets in the starting material can be donated from a human subject. In some embodiments, the human subject can be a male, or a female. In some embodiments, the platelets can be a pooled product from a number of male and female donors. In some embodiments, from a total of 100 donors, any number can be female donors, ranging from 0-100, 5-95, 10-90, 20-80, 30-70, or 40-60, and the rest can be male donors.

In some embodiments of the aspects and embodiments herein that include a composition, or in some compositions used in or formed by a process, or a process for preparing a platelet derivative composition, a starting material can comprise 10-500 units of platelets. In some embodiments, the starting material can comprise 20-500 units, 30-400 units, 40-350 units, or 50-200 units. In some embodiments, the units can be a pooled platelet product from multiple donors as described herein.

In some embodiments of any of the aspects and embodiments herein that include a method for treating a clotting-related disorder in a subject, said method comprising administering to the subject a therapeutically effective amount of the platelet derivative composition of any of the aspects or embodiments herein, or the platelet derivative composition prepared by any of the process described in the aspects or embodiments herein. In some embodiments, the clotting-related disorder is selected from the group consisting of Von Willebrand Disease, hemophilia, thrombasthenia, thrombocytopenia, thrombocytopenic purpura, trauma, or a combination thereof. In some embodiments, the composition is passed through a filter of 18 μm before administering to the subject.

In some embodiments, the platelet derivative composition of any of the aspects or embodiments herein is provided for use in the treatment of a disorder selected from the group consisting of alopecia areata, Von Willebrand Disease, hemophilia, thrombasthenia, thrombocytopenia, thrombocytopenic purpura, trauma, or a combination thereof.

In some embodiments, the platelet derivatives as described herein can be used for healing wounds in a subject. In some embodiments, there is provided a method for healing a wound in a subject, comprising administering a therapeutically effective amount of a platelet derivative composition of any of the aspects or embodiments herein, or the platelet derivative composition prepared by any of the process described in the aspects or embodiments herein, to the subject. In some embodiments, the platelet derivative composition of any of the aspects or embodiments herein is provided for use in wound healing in a subject.

In some embodiments, the platelet derivative composition of any of the aspects or embodiments herein can be used in treating a coagulopathy in a subject that has been administered or is being administered an antiplatelet agent. In some embodiments, the platelet derivative composition of any of the aspects or embodiments herein is provided for use an anti-platelet reversal agent. In some embodiments, the platelet derivative composition of any of the aspects or embodiments herein can be used in treating a coagulopathy in a subject that has been administered or is being administered an anticoagulant agent. In some embodiments, the platelet derivative composition of any of the aspects or embodiments herein is provided for use an anti-coagulant reversal agent.

In some embodiments, there is provided a method of treating a subject, the method comprising administering to the subject in need thereof, an effective amount of any of the platelet derivative compositions disclosed herein, or the platelet derivative composition prepared by any of the methods disclosed herein, wherein the subject has been treated or is being treated with an antiplatelet agent and/or an anti-coagulant, and wherein the method for treating is a) a method for restoring normal hemostasis in the subject; b) for treating a coagulopathy in the subject; or c) for preparing the subject for surgery. In some embodiments, the method of treating is the method of restoring normal hemostasis in the subject. In some embodiments, the method of treating is the method for treating the coagulopathy in the subject. In some embodiments, the method of treating is the method for preparing the subject for surgery. In some embodiments of any of the methods for treating aspects herein, wherein the subject is being treated with an antiplatelet agent, the antiplatelet agent is selected from the group consisting of aspirin, cangrelor, ticagrelor, clopidogrel, prasugrel, eptifibatide, tirofiban, abciximab, a supplement, and a combination thereof. In some embodiments of any of the methods for treating aspects herein, wherein the subject is being treated with an antiplatelet agent, the antiplatelet agent is selected from the group consisting of aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, and a combination thereof. In some embodiments of any of the methods for treating aspects herein, wherein the subject is being treated with an antiplatelet agent, the antiplatelet agent is selected from the group consisting of aspirin, cangrelor, ticagrelor, clopidogrel, prasugrel, eptifibatide, tirofiban, abciximab, terutroban, picotamide, elinogrel, ticlopidine, ibuprofen, vorapaxar, atopaxar, cilostazol, prostaglandin E1, epoprostenol, dipyridamole, treprostinil sodium, sarpogrelate, and a combination thereof.

In some embodiments of any of the methods for treating aspects herein, wherein the subject is being treated with an anticoagulant, the anticoagulant is selected from the group consisting of dabigatran, argatroban, hirudin, rivaroxaban, apixaban, edoxaban, fondaparinux, warfarin, heparin, a low molecular weight heparin, a supplement, and a combination thereof. In some embodiments of any of the methods for treating aspects herein, wherein the subject is being treated with an anticoagulant, the anticoagulant is selected from the group consisting of dabigatran, argatroban, hirudin, rivaroxaban, apixaban, edoxaban, fondaparinux, warfarin, heparin, low molecular weight heparins, tifacogin, Factor VIIai, SB249417, pegnivacogin (with or without anivamersen), TTP889, idraparinux, idrabiotaparinux, SR23781A, apixaban, betrixaban, lepirudin, bivalirudin, ximelagatran, phenprocoumon, acenocoumarol, indandiones, fluindione, a supplement, and a combination thereof. In some embodiments of any of the methods for treating aspects herein, the administering comprises administering topically, parenterally, intravenously, intramuscularly, intrathecally, subcutaneously or intraperitoneally. In some embodiments of any of the methods for treating aspects herein, where the composition is in the form of a powder, the method further includes, before the administering, rehydrating the composition. In some embodiments provided herein is use of any of the platelet derivative compositions herein, in the manufacture of a kit for performing any of the methods of treating provided herein.

In some embodiments, there is provided a composition comprising platelets or platelet derivatives prepared by any of the process described in any of the aspects or embodiments herein. In some embodiments, there is provided a composition comprising platelets or platelet derivatives and an aqueous medium prepared by any of the process described in any of the aspects or embodiments herein. In some of the embodiments, there is provided a composition comprising freeze-dried platelets prepared by any of the process described in any of the aspects or embodiments herein. In some of the embodiments, there is provided a composition comprising thrombosomes prepared by any of the aspects or embodiments herein. In some of the embodiments of any of the aspects and embodiments herein that include a composition, or in some compositions used in or formed by a process, a composition prepared by a process comprising tangential flow filtration (TFF) of a starting material comprising platelets, centrifugation of a starting material comprising platelets, or a combination thereof. In some embodiments, the centrifugation comprises centrifugation at 1400×g to 1550×g, or 1450×g to 1500×g. In some embodiments, the composition is prepared by a process that does not comprise centrifugation.

In some embodiments of the aspects and embodiments herein that include a platelet derivative composition, or in some compositions used in or formed by a process, or a process for preparing a platelet derivative composition, or a method for treating a subject, or a platelet derivative composition comprising platelet derivatives for use as a medicament in treating a subject, a therapeutically effective dose of platelet derivatives is based on units of thrombin generation activity administered per kilogram of body weight of the subject. In further embodiments of these embodiments the effective dose is not based on the number of platelet derivatives delivered to the subject. In some embodiments of any aspect or embodiment herein the effective dose is based on both A) units of thrombin generation activity administered per kilogram of body weight of the subject; and B) the number of platelet derivatives administered to the subject. In some embodiments of any aspect or embodiment herein the effective dose is based on the weight of the subject.

In some embodiments of any aspect or embodiment herein the subject is suffering from a condition, or a disease selected from the group including only thrombocytopenia, hematologic malignancy, bone marrow aplasia, myeloproliferative disorders, myelodysplastic syndromes, and platelet refractoriness. In some embodiments, the subject is suffering from thrombocytopenia. In some embodiments, the subject is suffering from hematologic malignancy. In some embodiments, the subject is suffering from bone marrow aplasia. In some embodiments, the subject is suffering from myeloproliferative disorders. In some embodiments, the subject is suffering from myelodysplastic syndromes. In some embodiments, the subject is suffering from platelet refractoriness. In some embodiments, the subject is suffering from two or more of the disease or condition selected from the group consisting of thrombocytopenia, hematologic malignancy, bone marrow aplasia, myeloproliferative disorders, myelodysplastic syndromes, and platelet refractoriness.

In some embodiments of any aspect or embodiment herein a therapeutically effective dose or amount of the platelet derivatives in a platelet derivative composition is in the range of $1.0\times10^7$ to $1.0\times10^{12}$/kg of the subject.

In some embodiments of any aspect or embodiment herein a therapeutically effective dose or amount of the platelet derivatives is an amount that has a potency in the range of 250 to 5000 TGPU per kg of the subject.

In some embodiments of any aspect or embodiment herein, a method of treatment or a composition for use as a medicament as described herein, a method or a medicament leads to cessation or decrease in bleeding at a primary bleeding site at 12 hours, 24 hours, 48 hours, 72 hours, 4 days, 5 days, 6 days, and/or 7 days after administering the platelet derivative composition. In some embodiments, the primary bleeding site is based upon the most severe bleeding location of the subject within 12 hours prior to administering the platelet derivative composition. In some embodiments, the administering involves infusing a platelet derivative composition. In some embodiments, a platelet derivative composition is administered on Day 1 of the treatment. In some embodiments, the cessation or decrease is evidenced by an ordinal change in WHO bleeding score of the subject evaluated at 24 hours after administering the platelet derivative composition to the subject. In some embodiments, a method or a medicament as described herein leads to cessation or decrease in bleeding at bleeding sites other than primary bleeding site at 12 hours, 24 hours, 48 hours, 72 hours, 4 days, 5 days, 6 days, and 7 days after administering the platelet derivative composition.

In some embodiments of any aspect or embodiment herein, a method of treatment or a composition for use as a medicament as described herein, a method or a medicament leads to an increase in platelet count in the subject at 12 hours, 24 hours, 48 hours, 72 hours, 4 days, 5 days, 6 days, and 7 days after administering the platelet derivative composition. In some embodiments, the increase is at least 500 platelets/μl, 1000 platelets/μl, 2000 platelets/μl, 3000 platelets/μl, 4000 platelets/μl, 5000 platelets/μl, 6000 platelets/μl, 7000 platelets/μl, 8000 platelets/μl, 9000 platelets/μl, or 10000 platelets/μl in the subject. In some embodiments, the increase is in the range of 500 to 10000 platelets/μl, 1000 to 10000 platelets/μl, 2000 to 8000 platelets/μl, or 3000 to 7000 platelets/μl in the subject.

In some embodiments of any aspect or embodiment herein, a method of treatment or a composition for use as a medicament as described herein, a method or a medicament leads to changes, or in some embodiments, does not lead to changes, in one or more markers of endothelial cell injury in the subject from a pre-administration time through 12 hours to 35 days, 24 hours to 32 days, 24 hours to 30 days, or 48 hours to 28 days after administering the platelet derivative composition. In some embodiments, the method or the medicament leads to changes, or in some embodiments, does not lead to changes, in one or more markers of endothelial cell injury in the subject at 72 hours after administering the platelet derivative composition. In some embodiments, the one or more markers of endothelial cell injury is selected from the group consisting of Syndecan-1, hyaluronan, thrombomodulin, vascular endothelial growth factor (VEGF), interleukin 6, and sVE cadherin. In some embodiments, the method or the medicament leads to changes in two or more markers, three or markers, four or more markers, five or more markers, or all of the markers selected from the group consisting of Syndecan-1, hyaluronan, thrombomodulin, vascular endothelial growth factor (VEGF), interleukin 6, and sVE cadherin. In some embodiments, the changes can be an increase or a decrease in the markers of endothelial cell injury in the subject as compared to a control.

In some embodiments of any aspect or embodiment herein, a method of treatment or a composition for use as a medicament as described herein, a method or a medicament leads to acceptable measures of coagulation in the subject at 12 hours to 35, 24 hours to 32 days, 24 hours to 30 days, or 48 hours to 28 days after administering the platelet derivative composition. In some embodiments, a method or a medicament leads to acceptable measures of coagulation in the subject at 72 hours after administering the platelet derivative composition. In some embodiments, the acceptable measure of coagulation includes one or more, two or more, three or more, four or more, five or more, or all of prothrombin time (PT), international normalized ratio (INR), fibrinogen, D-dimer, activated partial thromboplastin time (aPTT), and thromboelastography (TEG) or rotational thromboelastometry (ROTEM). In some embodiments, a method or a medicament leads to an increase or a decrease in the acceptable measure of coagulation in the subject as compared to a control.

In some embodiments of any aspect or embodiment herein, a method of treatment or a composition for use as a medicament as described herein, a method or a medicament leads to acceptable measures of hematology in the subject from a pre-administration time through 12 hours to 35 days, 24 hours to 32 days, 24 hours to 30 days, or 48 hours to 28 days after administering the platelet derivative composition. In some embodiments, the acceptable measures of hematology are one or more, two or more, three or more, four or more, five or more, or all selected from the group consisting of Prothrombin Fragment 1+2, thrombin generation assay (TGA), Thrombopoietin, activated Protein C, tissue plasminogen activator (TPA), and/or plasminogen activator inhibitor (PAI). In some embodiments, the acceptable measures of hematology can be an increase or a decrease in the subject as compared to a control.

In some embodiments of any aspect or embodiment herein, a method of treatment or a composition for use as a medicament as described herein, a method or a medicament leads to survival of the subject without WHO Grade 2A or greater bleeding during the first 3, 4, 5, 6, 7, 8, 9, or 10 days after administering of a platelet derivative composition.

In some embodiments of any aspect or embodiment herein, a method of treatment or a composition for use as a medicament as described herein, administering is performed in a maximum of 2, 3, 4, 5, 6, 7, 8, 9, or 10 doses in a 72-hour period of treatment. In some embodiments, the subject has a count of total circulating platelets (TCP) between 5,000 to 100,000 platelets/μl, 10,000 to 90,000 platelets/μl, 10,000 to 80,000 platelets/μl, or 10,000 to 70,000 platelets/μl of blood at the time of administering. In some embodiments, the subject is undergoing one or more, two or more, three or more, or all of chemotherapy, immunotherapy, radiation therapy or hematopoietic stem cell transplantation at the time of administering. In some embodiments, the subject is refractory to platelet transfusion, wherein refractory is a two 1-hour CCI [corrected count increment] of <5000 on consecutive transfusions of liquid stored platelets. In some embodiments, the subject has a WHO bleeding score of 2 excluding cutaneous bleeding.

In some embodiments of any aspect or embodiment herein the subject at the time of administering has two or more, or all of: confirmed diagnosis of hematologic malignancy, myeloproliferative disorder, myelodysplastic syndrome, or aplasia; undergoing chemotherapy, immunotherapy, radiation therapy or hematopoietic stem cell transplantation; or refractory to platelet transfusion wherein refractory is a two 1-hour CCI of <5000 on consecutive transfusions of liquid stored platelets.

In some embodiments of any aspect or embodiment herein the administering confers an improved survival at 10, 15, 20, 25, 30, 35, 40, 45, or 50 days after administering the platelet derivatives. In some embodiments of any aspect or embodiment herein the administering leads to a decrease in administration of secondary blood products, platelets, or platelet derivatives to the subject for the first 5, 6, 7, 8, 9, or 10 days after the administering of the platelet derivatives.

In some embodiments of any aspect or embodiment herein that include delivering platelet derivatives to a subject, or administering platelet derivatives to a subject, or treating a subject, or use of platelet derivative composition or platelet derivatives as described in any of the aspects or embodiments, the subject is having an indication selected from the group consisting of Von Willebrand disease, immune thrombocytopenia, Intracranial hemorrhage (ICH), Traumatic brain injury (TBI), Hermansky Pudlak Syndrome (HPS), Chemotherapy induced thrombocytopenia (CIT), Scott syndrome, Evans syndrome, Hematopoietic Stem Cell Transplantation, Fetal and neonatal alloimmune thrombocytopenia, Bernard Soulier syndrome, Acute myeloid leukemia, Glanzmann thrombasthenia, Myelodysplastic syndrome, Hemorrhagic Shock, Coronary thrombosis (myocardial infarction), Ischemic Stroke, Arterial Thromboembolism, Wiskott Aldrich Syndrome, Venous Thromboembolism, MYH9 related disease, acute lymphoblastic lymphoma (ALL), Acute Coronary Syndrome, Chronic Lymphocytic Leukemia (CLL), Acute Promyelocytic Leukemia, Cerebral Venous Sinus Thrombosis (CVST), Liver Cirrhosis, Factor V Deficiency (Owren Parahemophilia), Thrombocytopenia absent radius syndrome, Kasabach Merritt syndrome, Gray platelet syndrome, Aplastic anemia, Chronic Liver Disease, Acute radiation syndrome, Dengue Hemorrhagic Fever, Pre-Eclampsia, Snakebite envenomation, HELLP syndrome, Haemorrhagic Cystitis, Multiple Myeloma, Disseminated Intravascular Coagulation, Heparin Induced Thrombocytopenia, Pre-Eclampsia, Labor And Delivery, Hemophilia, Cerebral (Fatal) Malaria, Alexander's Disease (Factor VII Deficiency), Hemophilia C (Factor XI Deficiency), Familial hemophagocytic lymphohistiocytosis, Acute lung injury, Hemolytic Uremic Syndrome, Menorrhagia, Chronic myeloid leukemia, or any combinations thereof. In some embodiments, an indication is Von Willebrand disease. In some embodiments, an indication is Immune thrombocytopenia. In some embodiments, an indication is Chemotherapy induced thrombocytopenia (CIT). In some embodiments, an indication is Fetal and neonatal alloimmune thrombocytopenia.

In some embodiments of any aspect or embodiments herein that include an indication, the indication is selected from the group consisting of Von Willebrand disease, Immune thrombocytopenia, Intracranial hemorrhage (ICH), Traumatic brain injury (TBI), Hermansky Pudlak Syndrome (HPS), Chemotherapy induced thrombocytopenia (CIT), Scott syndrome, Evans syndrome, Hematopoietic Stem Cell Transplantation, Fetal and neonatal alloimmune thrombocytopenia, Bernard Soulier syndrome, Acute myeloid leukemia, Glanzmann thrombasthenia, Myelodysplastic syndrome, Hemorrhagic Shock, Coronary thrombosis (myocardial infarction), Ischemic Stroke, Arterial Thromboembolism, Wiskott Aldrich Syndrome, Venous Thromboembolism, MYH9 related disease, Acute Lymphoblastic Lymphoma (ALL), Acute Coronary Syndrome, Chronic Lymphocytic Leukemia (CLL), Acute Promyelocytic Leukemia, Cerebral Venous Sinus Thrombosis (CVST), Liver Cirrhosis, Factor V Deficiency (Owren Parahemophilia), Thrombocytopenia absent radius syndrome, Kasabach Merritt syndrome, Gray platelet syndrome, Aplastic anemia, or combinations thereof.

In some embodiments of any aspect or embodiments herein that include an indication, the indication is selected from the group consisting of Chronic Liver Disease, Acute radiation syndrome, Dengue Hemorrhagic Fever, Pre-Eclampsia, Snakebite envenomation, HELLP syndrome, Haemorrhagic Cystitis, Multiple Myeloma, Disseminated Intravascular Coagulation, Heparin Induced Thrombocytopenia, Pre-Eclampsia, Labor And Delivery, Hemophilia, Cerebral (Fatal) Malaria, Alexander's Disease (Factor VII Deficiency), Hemophilia C (Factor XI Deficiency), Familial hemophagocytic lymphohistiocytosis, Acute lung injury, Hemolytic Uremic Syndrome, Menorrhagia, Chronic myeloid leukemia, or any combinations thereof.

In some embodiments of any aspect or embodiments herein that include an indication, the indication is selected from the group consisting of Fetal and neonatal alloimmune thrombocytopenia, intracranial hemorrhage (ICH), traumatic brain injury (TBI), Von Willebrand disease, Immune thrombocytopenia, and the indication is not treatable by administering unmodified platelets. In some embodiments, the indication is Von Willebrand disease, and wherein the indication is not treatable by administering unmodified platelets. In some embodiments, the indication is Immune thrombocytopenia, and wherein the indication is not treatable by administering unmodified platelets. In some embodiments, the indication is Fetal and neonatal alloimmune thrombocytopenia, wherein the indication is not treatable by administering unmodified platelets. In some embodiments, the indication is intracranial hemorrhage (ICH), and wherein the indication is not treatable by administering unmodified platelets. In some embodiments, the indication is traumatic brain injury (TBI), and wherein the indication is not treatable by administering unmodified platelets.

In some embodiments of any aspect or embodiment herein that include delivering platelet derivatives to a subject, or administering platelet derivatives to a subject, or treating a subject, or use of platelet derivative composition or platelet derivatives as described in any of the aspects or embodiments, the subject is having an indication that, typically cannot be treated with unmodified platelet preparation but can be treated with a platelet derivative composition as described herein. In some embodiments, such type of indication is Von Willebrand disease, Immune thrombocytopenia, Intracranial hemorrhage (ICH), Traumatic brain injury (TBI), Hermansky Pudlak Syndrome (HPS), Chemotherapy induced thrombocytopenia (CIT), Scott syndrome, Evans syndrome, Hematopoietic Stem Cell Transplantation, Fetal and neonatal alloimmune thrombocytopenia, Bernard Soulier syndrome, Acute myeloid leukemia, or combinations thereof.

In some aspects, provided herein is a method of treating immune thrombocytopenia in a subject, the method comprises administering an effective dose of freeze-dried platelet derivatives, in a platelet derivative composition, to the subject. In some aspects, provided herein is a method of treating intracranial hemorrhage (ICH) in a subject, the method comprises administering an effective dose of freeze-dried platelet derivatives, in a platelet derivative composition, to the subject. In some aspects, provided herein is a method of treating traumatic brain injury (TBI) in a subject, the method comprises administering an effective dose of freeze-dried platelet derivatives, in a platelet derivative composition, to the subject.

In some embodiments of any aspect or embodiment herein that include delivering platelet derivatives to a subject, or administering platelet derivatives to a subject, or treating a subject, or use of platelet derivative composition or platelet derivatives as described in any of the aspects or embodiments, platelet derivatives can have an effective dose or a therapeutically effective dose in the range of $1.0\times10^7$ to $1.0\times10^{11}$ particles/kg of the subject. In some embodiments, platelet derivatives can have an effective dose or a therapeutically effective dose in the range 250 and 5000 TGPU per kg of the subject.

In some embodiments, provided herein is a platelet derivative composition comprising platelet derivatives of any aspect provided herein, or a platelet derivative composition prepared by the process of any method for preparing or making provided herein, wherein the platelet derivatives comprise an imaging agent, to form imaging agent-loaded platelet derivatives. In some embodiments, the platelet derivatives in imaging agent-loaded platelet derivatives are freeze-dried platelet derivatives (FDPDs) that retain one, two, three, or more properties of FDPDs that are not loaded as described herein. In some embodiments, the imaging agent can be an MRI agent, such as gadolinium. In some embodiments, platelet derivatives comprise an MRI agent, termed as MRI agent-loaded platelet derivatives. In some embodiments, MRI agent-loaded platelet derivatives are freeze-dried platelet derivatives (FDPDs) that retain one, two, three, or more properties of FDPDs that are not loaded as described herein.

In some embodiments, provided herein is imaging agent-loaded platelets, cryopreserved platelets, or platelet derivatives. In some embodiments, provided herein is MRI agent-loaded platelets, cryopreserved platelets, or platelet derivatives. In some embodiments, imaging agent-loaded or MRI agent-loaded platelets, cryopreserved platelets, or platelet derivatives comprise a cell penetrating peptide (CPP). A CPP is coupled to an imaging agent or an MRI agent that facilitates the imaging agent or MRI agent to load onto platelets, cryopreserved platelets, or platelet derivatives. In illustrative embodiments, a CPP is a TAT peptide.

In some embodiments, provided herein is a method of delivering an imaging agent to a subject. In some embodiments, platelet derivatives or platelets as described herein are loaded with an imaging agent to form imaging agent-loaded platelet derivatives or platelets, such imaging agent-loaded platelet derivatives or platelets are administered to a subject. In some embodiments, platelet derivatives or platelets as described herein are loaded with an MRI agent to form MRI agent-loaded platelet derivatives or platelets, such MRI agent-loaded platelet derivatives or platelets are administered to a subject.

Also provided herein are compositions produced by any of the methods described herein. In some embodiments, any of the compositions provided herein can be made by the methods described herein. Specific embodiments disclosed herein may be further limited in the claims using "consisting of" or "consisting essentially of" language.

EXAMPLES

Example 1. Tangential Flow Filtration (TFF) Method of Platelet Derivative Preparation Apheresis platelets underwent tangential flow filtration in accordance with a standard operating procedure, including the following process steps: platelet dilution, platelet concentration and platelet washing.

The platelet donor units were initially pooled into a common vessel. The platelets may or may not be initially diluted with an acidified washing buffer (e.g., a control buffer) to reduce platelet activation during processing. The platelets can undergo two processing pathways; either washed with control buffer until a desired residual component is reached (e.g., donor plasma) before being concentrated to a final product concentration or the platelets are concentrated to a final product concentration before being washed with control buffer until a desired residual component is reached (e.g., donor plasma). In both the processing pathways, the platelet donor units were initially diluted or further diluted 1:1 in Buffer A before being loaded onto a TFF machine for further processing. TFF processed platelets are then filled into vials, lyophilized and thermally treated.

One particular protocol follows.

For all steps of the TFF process in this Example, Buffer A was used. The process was carried out at a temperature of 18-24° C.

Buffer A

| Component | Value (±1%) |
|---|---|
| HEPES | 7.6 mM |
| NaCl | 60 mM |
| KCl | 3.84 mM |
| Dextrose | 2.4 mM |
| $NaHCO_3$ | 9.6 mM |
| Trehalose | 80 mM |
| Ethanol | 0.8% |
| Polysucrose | 6% (w/v) |
| pH | 6.6-6.8 |

Platelets were initially diluted in Buffer A (1:1) and loaded onto the TFF (PendoTECH controller system), which was prepared with a Repligen TFF Cassette (XPM45L01E). The TFF process was performed using a membrane with a pore size of 0.45 μm. The platelets were diluted with an equal weight (±10%) of Buffer A. The platelets were concentrated to about $2250\times10^3$ cells/μL ($\pm250\times10^3$) and then washed with approximately 2 diavolumes (DV) of Buffer A. The target plasma percentage was typically less than 15% relative plasma (as determined by plasma protein content). Removal of plasma proteins was monitored through 280 nm UV absorbance against known correlations. Following washing, if the concentration of the cells was not $2000\times10^3$ cells/μL ($\pm300\times10^3$), the cells were either diluted with Buffer A or were concentrated to fall within this range. Under all circumstances whenever the cells are contacted with the buffer A, it was done at a temperature in the range of 18-24° C. For a better clarity, the cells were loaded with the reagents of the buffer A at a temperature in the range of 18-24° C. The cells were typically then freeze-dried (lyophilized) and subsequently heated (thermally treated) at 80° C. for 24 hours, thereby forming thrombosomes, but sometimes the cells were used before lyophilization (sometimes called thrombosomes 'pre-lyo').

In order to perform studies related to the quantification of microparticles, quantification of expression or presence of various surface markers (like Annexin V, CD 41, CD 42, CD 47, CD 62, thrombospondin, von-Willebrand factor), thrombin generation studies (TGPU), aggregation studies, the thrombosomes were typically rehydrated with water over 10 minutes at room temperature. In general, the rehydration volume is equal to the volume used to fill each vial of thrombosomes prior to drying. The thrombosomes which were heated (thermally treated) after lyophilization are also referred to as baked thrombosomes. Whereas the thrombosomes which were not heated (thermally treated) after lyophilization are referred to as unbaked thrombosomes.

Platelet derivatives are also referred to herein as thrombosomes. In the following examples, the platelet derivatives/thrombosomes prepared in accordance with the procedure described in Example 1 is referred to as freeze-dried platelet derivative composition. The freeze-dried platelet derivative composition comprises freeze-dried platelet derivatives (also known as thrombosomes freeze-dried platelet derivatives). It would be clear to a skilled artisan that the thrombosomes which are obtained after lyophilization in the form of a powder can be used for commercial application, like providing the platelet derivative composition (thrombosomes) in dried form in vials to, for example, a medical practitioner who can rehydrate the vials with an appropriate amount of a liquid.

In some cases, samples were drawn at UV readings correlating to about 51% relative plasma volume, about 8.1% relative plasma volume, about 6.0% relative plasma volume, and about 1.3% relative plasma volume. Low volume aliquots were sampled throughout each processing step with the about 6.0% and under samples.

Example 2. Testing Plan and Assay Protocol

Testing Plan:

Freeze-dried platelet derivative composition Batch A was produced by the TFF method described in Example 1 using apheresis platelets collected from high-αHLA titer donors as reported by a platelet supplier.

Individual donor units, the donor pool, and timepoints along the TFF process were collected for αHLA testing. Plasma was added to HLA beads (One Lambda FLOWPRA™ Screen Test), stained with an αIgG secondary antibody, and evaluated for αHLA-IgG binding by flow cytometry (Novocyte 3005 configuration)

Two bead types were evaluated: one coated with HLA Class I antigens and the other coated with HLA Class II antigens. Bead gating was performed as described in the FLOWPRA™ Screen Test instructions. "αHLA Positive" populations are gated on the basis of a George King (GK) PPP (platelet-poor plasma) negative control and a single-donor fresh-drawn negative control. Additional negative controls are collected following production to confirm ideal placement of these positivity gates.

Compensation settings were established using FITC- and PE-conjugated mouse IgG on Spherotech COMPtrol compensation beads. The HLA Class II beads fluoresce in PE and the secondary antibody used for IgG detection is FITC-conjugated.

Assay Protocol:

1. Thaw the One Lambda FLOWPRA™ Screen Test kit components to 4° C.
2. Obtain approximately 1 mL aliquots of 0.2 μm filtered PPP from each desired sample point.
3. To a 1.7 mL microcentrifuge tube, pipet 5 μL Class I HLA beads and 5 μL Class II HLA beads. Add 20 μL filtered test plasma. Vortex to mix.
4. Incubate plasma with HLA-coated beads for 30 minutes at room temperature in the dark with gentle rocking/agitation.
5. Dilute 10× wash buffer to the appropriate volume of 1× working stock with deionized water.
6. Wash the beads with 1 mL wash buffer. Vortex and centrifuge at 9,000 g×2 minutes to pellet the beads. Aspirate the supernatant.
7. Repeat step 6.
8. Dilute 100×αIgG-FITC to the appropriate volume of 1× working stock with wash buffer.
9. Add 100 μL 1×αIgG-FITC to the tube containing washed HLA beads. Vortex to mix.
10. Incubate HLA beads with αIgG-FITC for 30 minutes at room temperature in the dark with gentle rocking/agitation.
11. Repeat steps 6 and 7 to wash away unbound αIgG-FITC.
12. Resuspend the washed HLA beads in 200 μL PBS. Vortex to mix.
13. Pipet approximately 100 μL of the HLA bead suspension to the appropriate well(s) of a 96-well U-bottom microplate and dock onto the NovoSampler.
14. Use the NovoCyte to collect events by flow cytometry.
    a. Slow collection of 10,000 events in the previously determined FLOWPRA™ Beads gate with FSC-H threshold 10,000.
    b. Secondary stop conditions were 2 minutes run time and 40 μL total sample volume.
    c. The SIP is washed between each sample to minimize carryover between wells. A well of PBS is run between each triplicate set to minimize carryover between testing points.

Results

Example 3. Gate Placement and Negative Controls

Figure 1B:
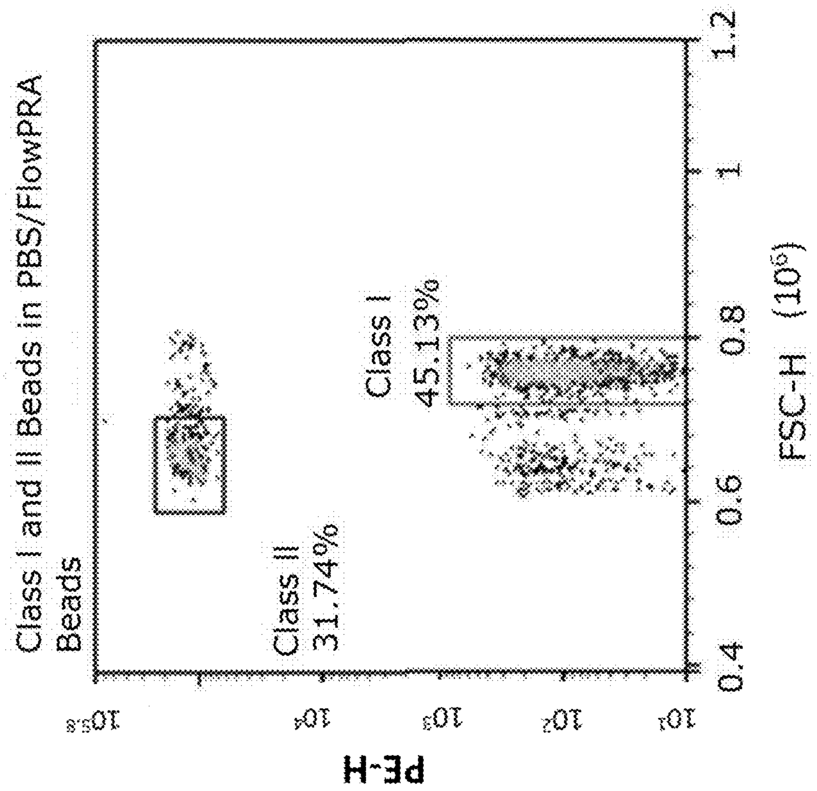
FIG. 1B shows initial gate placement for identification of Class I and Class II HLA FLOWPRA™ beads in PBS using phycoerythrin fluorescence vs. forward scattering.
Figure 2A:
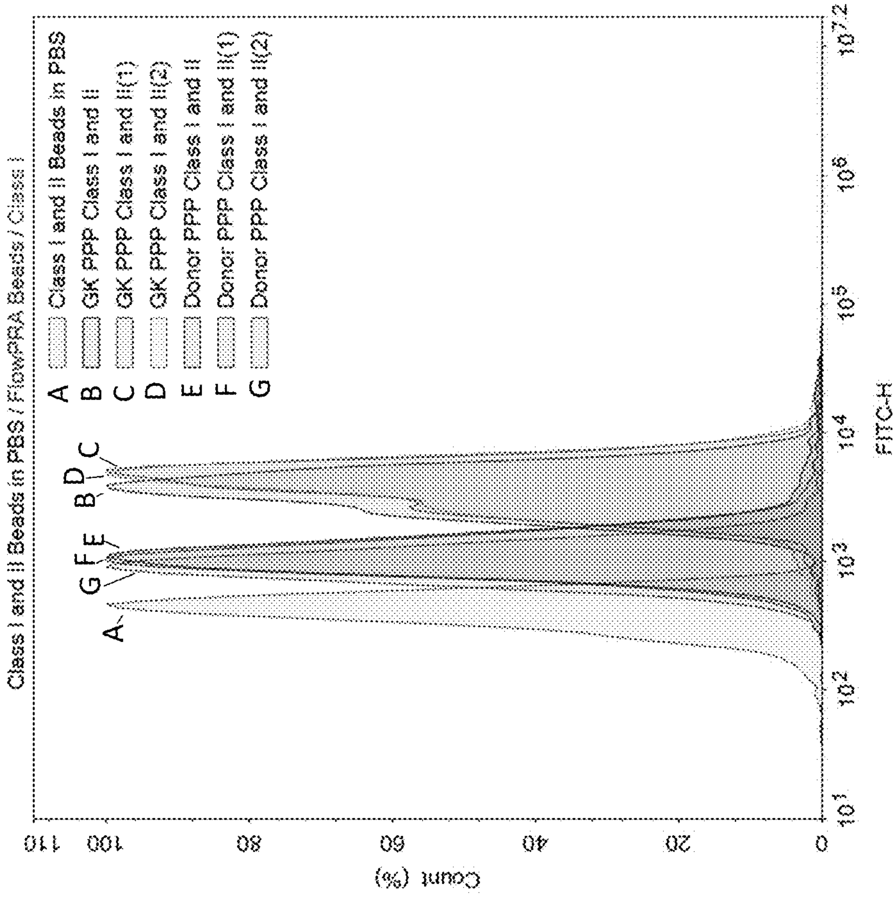
FIG. 2A shows an exemplary FITC-H histogram of FLOWPRA™ beads in PBS, supplier platelet-poor plasma (PPP) (in triplicate), and donor platelet-poor plasma gated on Class I HLA (in triplicate).
Figure 2B:
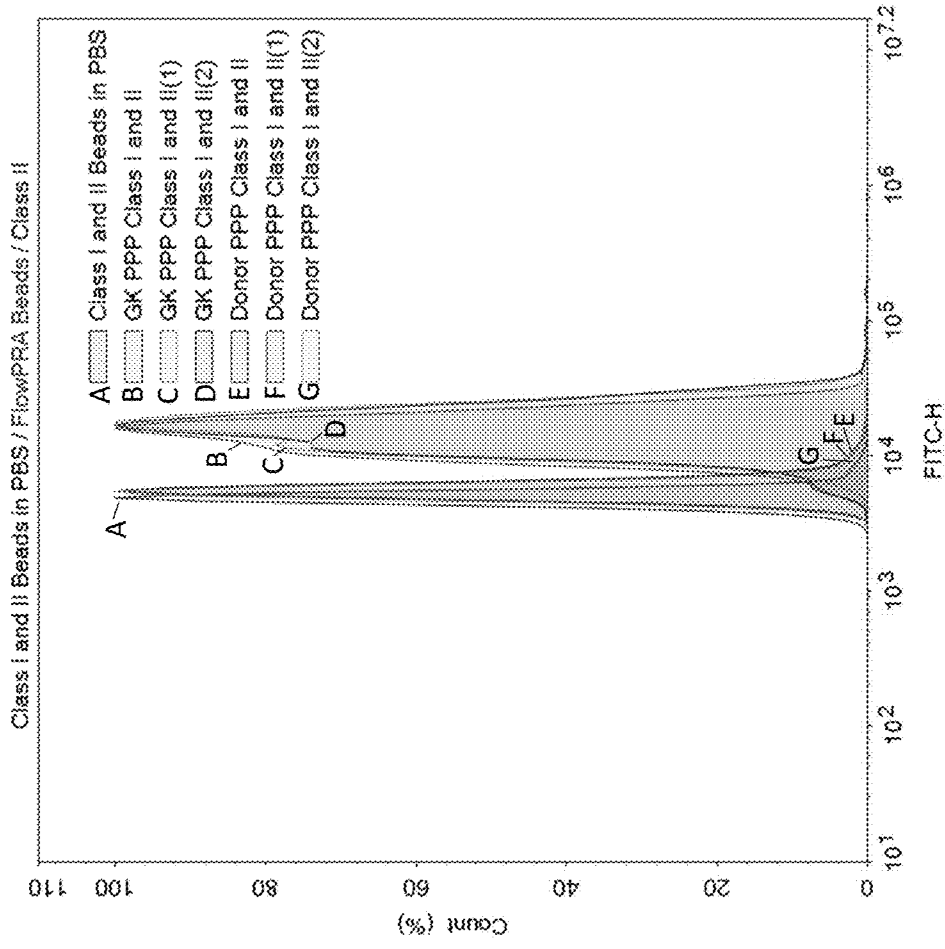
FIG. 2B shows an exemplary FITC-H histogram of FLOWPRA™ beads in PBS, supplier platelet-poor plasma (PPP) (in triplicate), and donor platelet-poor plasma gated on Class II HLA (in triplicate).
Figure 2C:
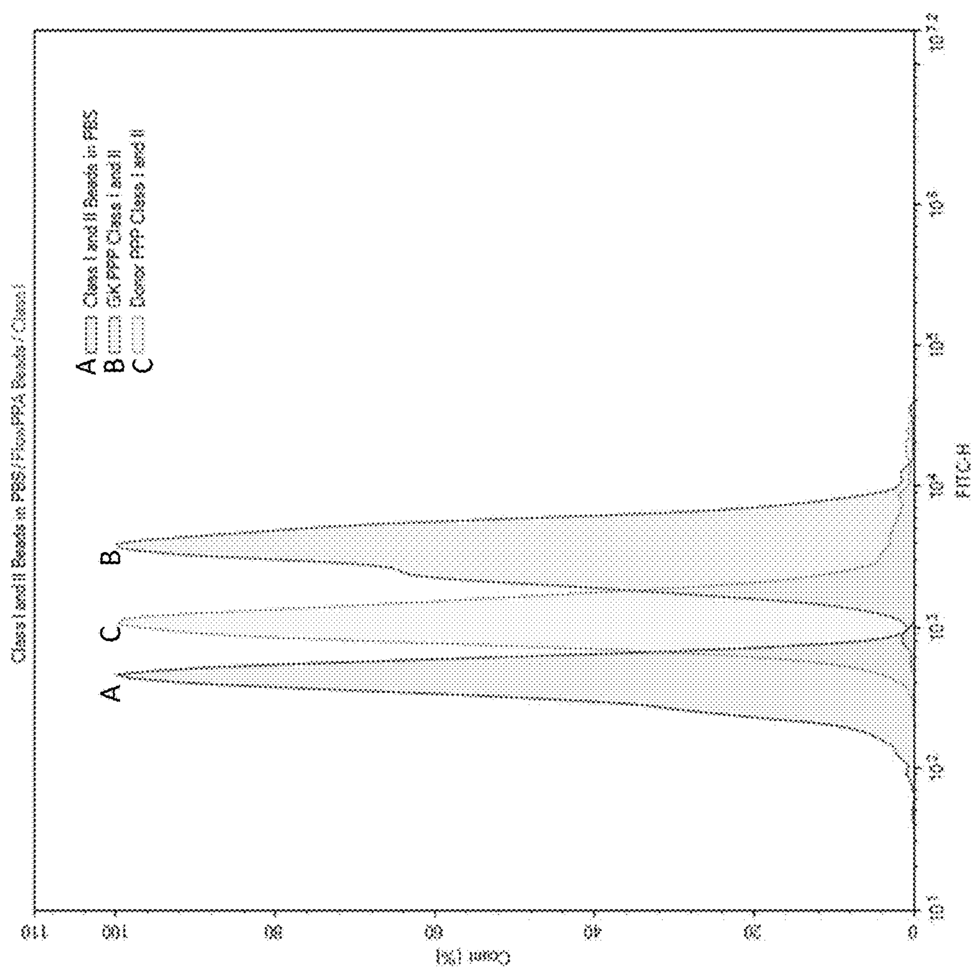
FIG. 2C shows an exemplary FITC-H histogram of FLOWPRA™ beads in PBS, supplier platelet-poor plasma (PPP) (single data set), and donor platelet-poor plasma gated on Class I HLA (single data set).
Figure 2D:
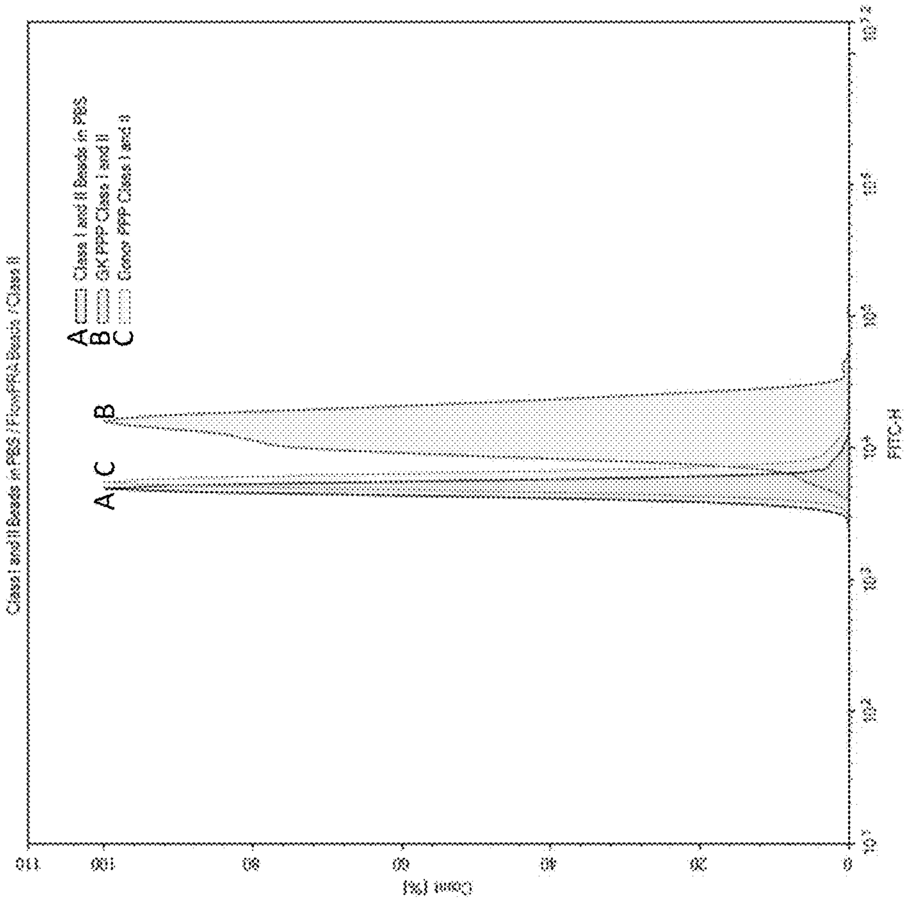
FIG. 2D shows an exemplary FITC-H histogram of FLOWPRA™ beads in PBS, supplier platelet-poor plasma (PPP) (single data set), and donor platelet-poor plasma gated on Class II HLA (single data set).
Figure 3B:
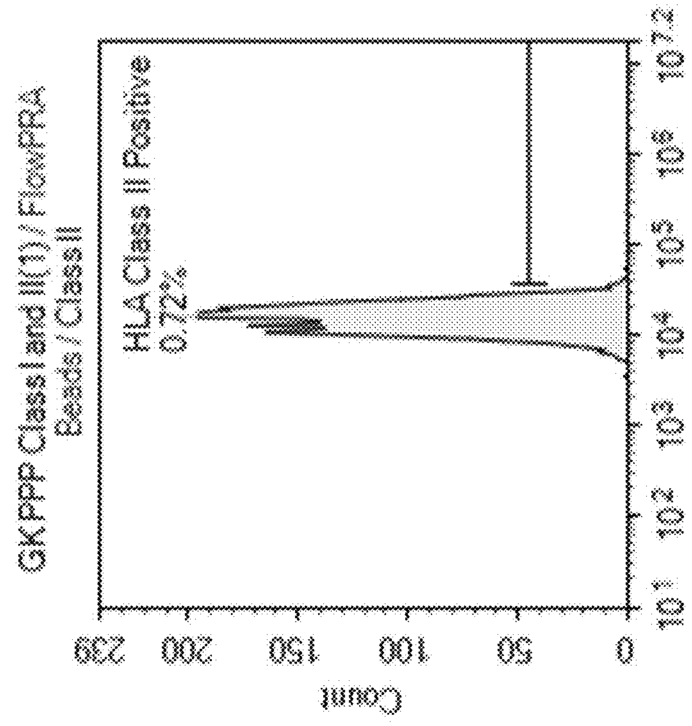
FIG. 3B shows an exemplary FITC-H histogram of FLOWPRA™ beads in George King PPP gated on Class II HLA.
Figure 3A:
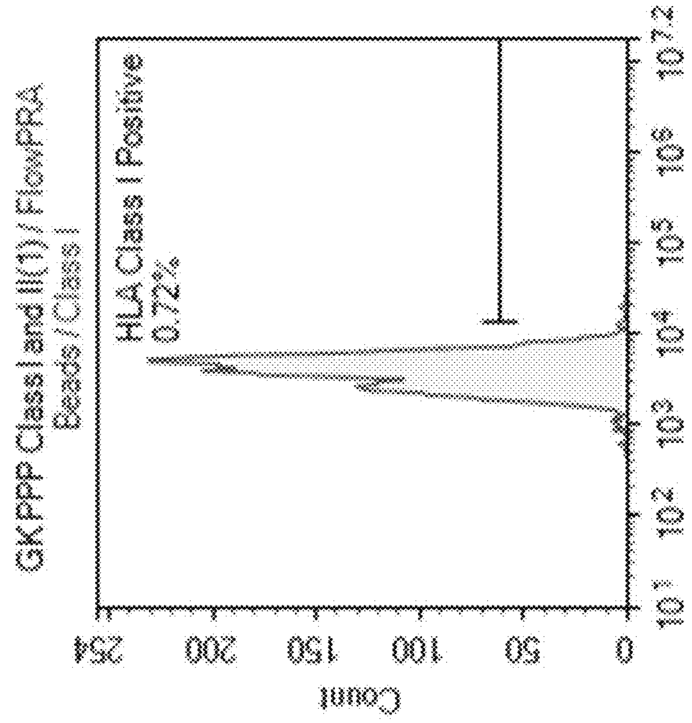
FIG. 3A shows an exemplary FITC-H histogram of FLOWPRA™ beads in George King PPP gated on Class I HLA.

Initial gate placement for identification of Class I and Class II HLA beads is determined using FLOWPRA™ beads in PBS. (FIG. 1A and FIG. 1B)

Background/nonspecific binding is established using GK PPP and fresh donor PPP in triplicate. (Exemplary data is shown in FIG. 2A, FIG. 2B, FIG. 3A, and FIG. 3B) Note that GK PPP is shifted higher on FITC-H than the fresh donor plasma. This may be due to donor variability or freeze/thaw effects on the GK plasma. Additional sampling is necessary. Positivity gates are placed such that <1% of GK PPP returns FITC-positive.

Example 4. Single Donor Results

Representative FITC-H histograms from each HLA class are given for each sample. Positivity >1% is positive. Fluorescence ratios are reported against the GK PPP negative control (Class I and Class II bead FITC-H intensity). Fluorescence ratios >1.0 are positive. As additional negative controls are collected these positivity gates and fluorescence ratios will be updated.

Populations are negative for HLA Class I or Class II antibodies if both percent positivity and fluorescence ratio are ≤1 for that bead type.

Figure 4B:
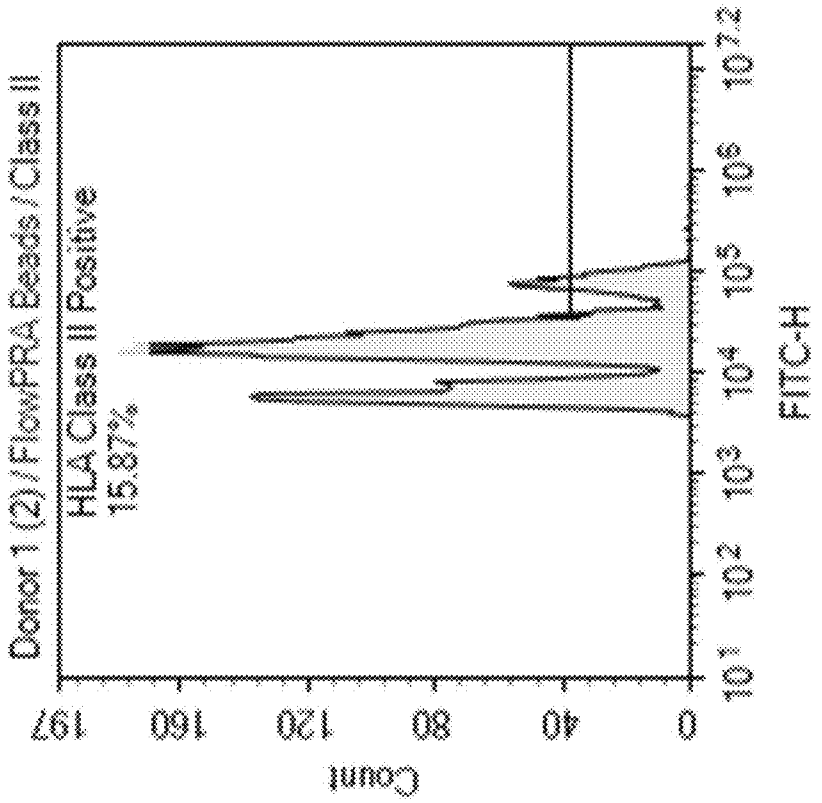
FIG. 4B shows an exemplary FITC-H histogram of FLOWPRA™ beads in Donor 1 PPP gated on Class II HLA.
Figure 4A:
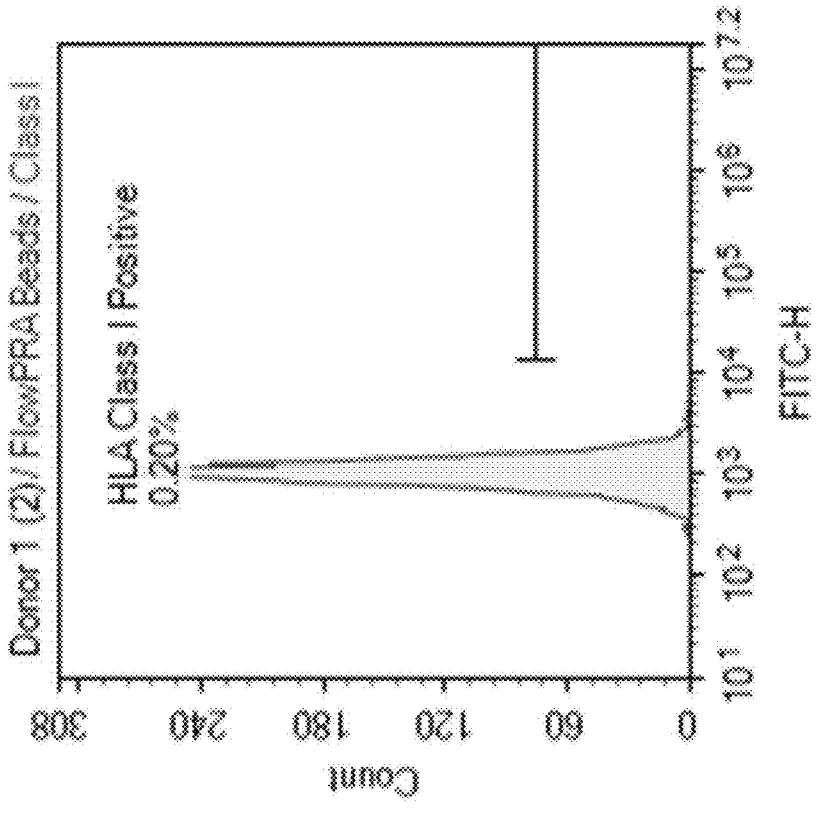
FIG. 4A shows an exemplary FITC-H histogram of FLOWPRA™ beads in Donor 1 PPP gated on Class I HLA.

Donor #1: HLA Class II Positive. Average positivity from triplicate data for Class I is 0.2% with fluorescence ratio 0.3; average positivity for Class II is 16.5% with fluorescence ratio 1.6. (Exemplary data is shown FIG. 4A and FIG. 4B).

Figure 5A:
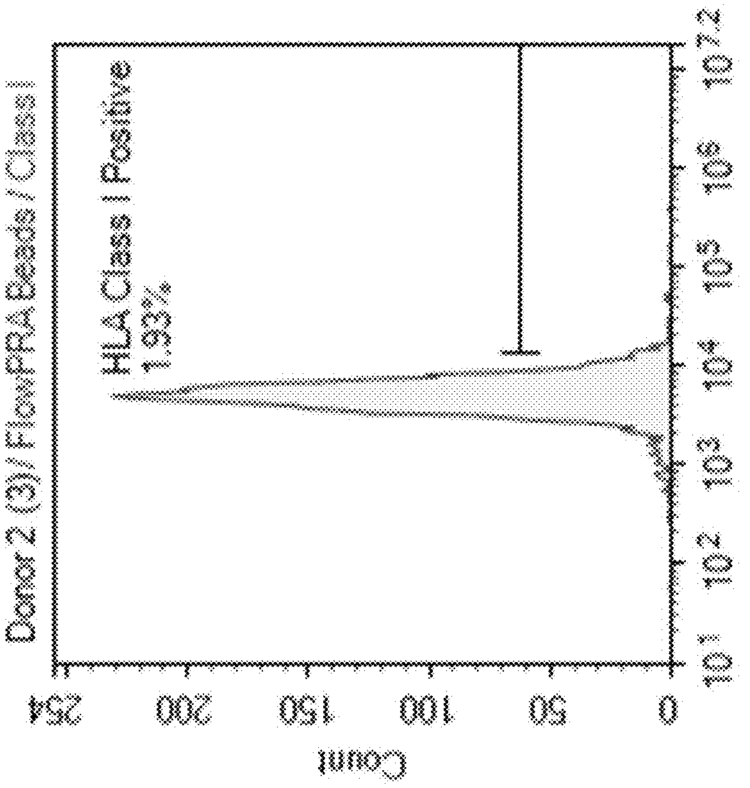
FIG. 5A shows an exemplary FITC-H histogram of FLOWPRA™ beads in Donor 2 PPP gated on Class I HLA.
Figure 5B:
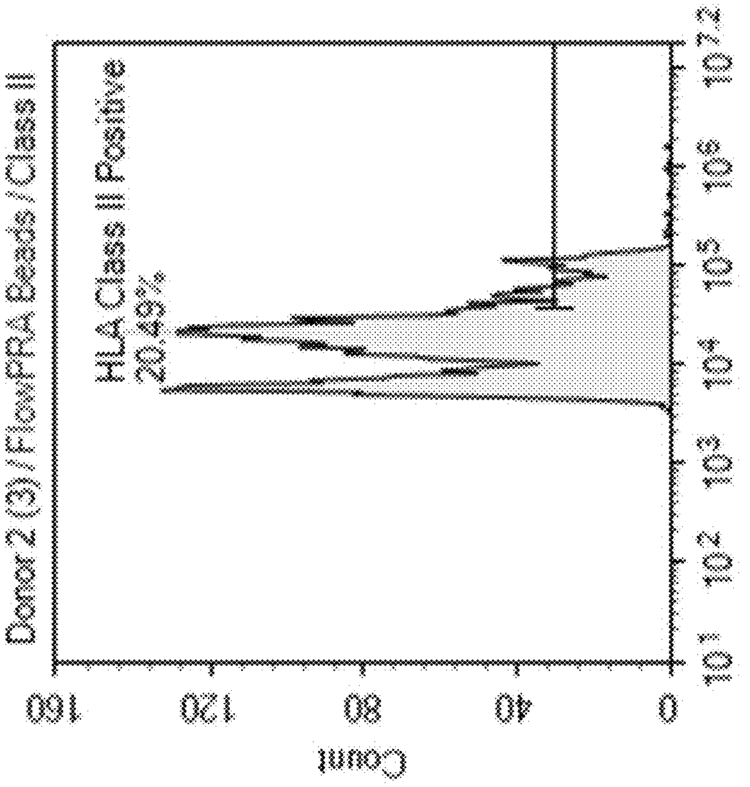
FIG. 5B shows an exemplary FITC-H histogram of FLOWPRA™ beads in Donor 2 PPP gated on Class II HLA.

Donor #2: HLA Class I and Class II Positive. Average positivity from triplicate data for Class I is 1.3% with fluorescence ratio 1.4; average positivity for Class II is 20.3% with fluorescence ratio 1.9. (Exemplary data is shown FIG. 5A and FIG. 5B).

Figure 6B:
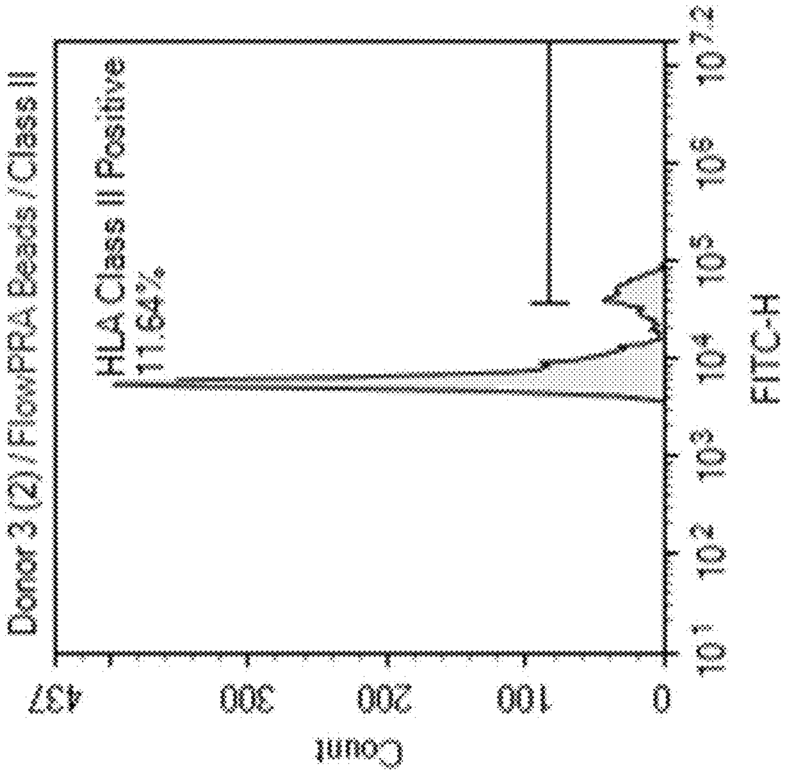
FIG. 6B shows an exemplary FITC-H histogram of FLOWPRA™ beads in Donor 3 PPP gated on Class II HLA.
Figure 6A:
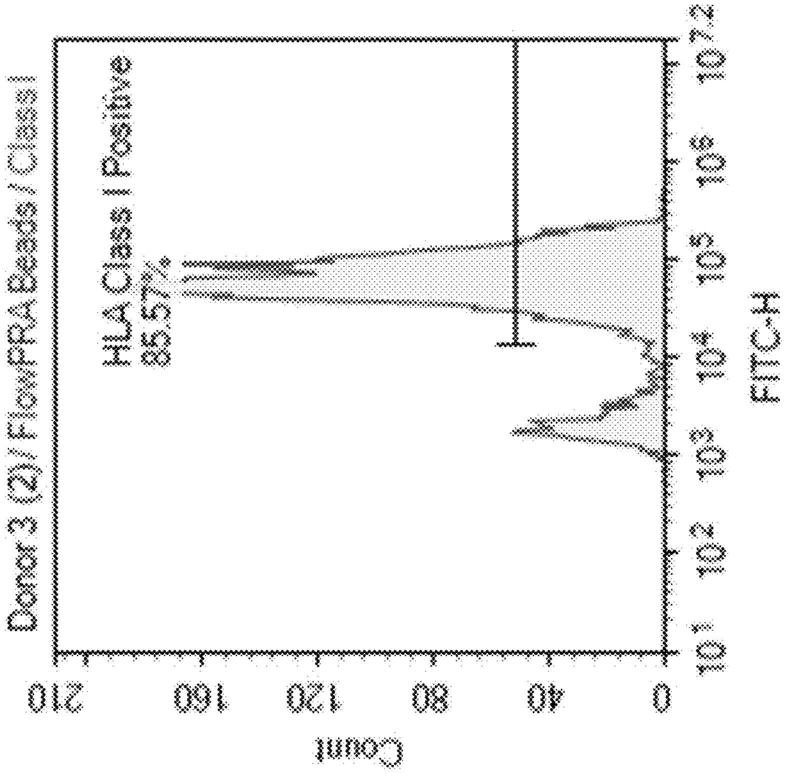
FIG. 6A shows an exemplary FITC-H histogram of FLOWPRA™ beads in Donor 3 PPP gated on Class I HLA.

Donor #3: HLA Class I and Class II Positive. Average positivity from triplicate data for Class I is 85.2% with fluorescence ratio 14.4. Average positivity for Class II is 12.0% with fluorescence ratio 0.8. (Exemplary data is shown FIG. 6A and FIG. 6B).

Figure 7B:
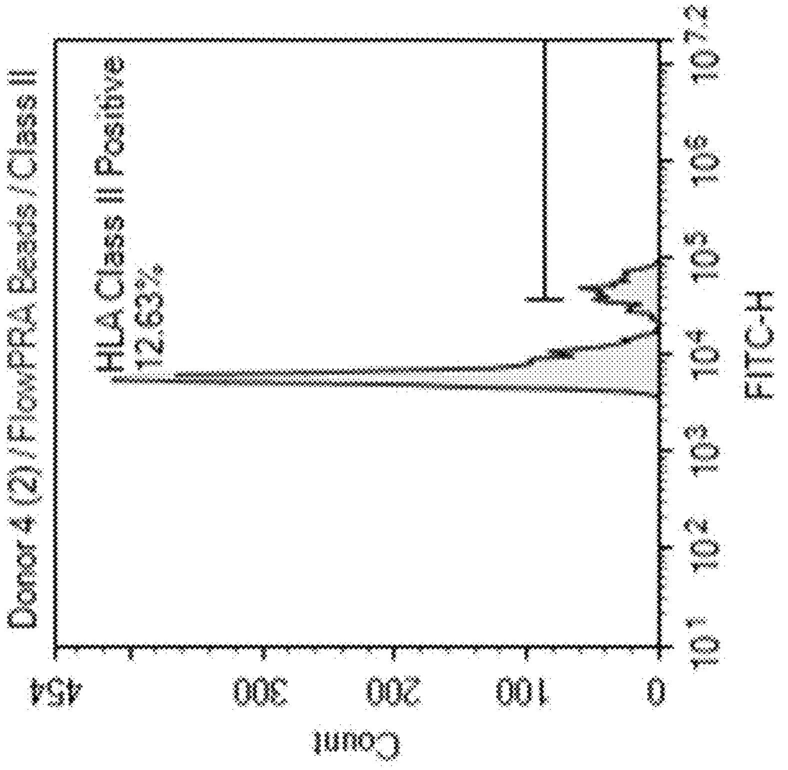
FIG. 7B shows an exemplary FITC-H histogram of FLOWPRA™ beads in Donor 4 PPP gated on Class II HLA.
Figure 7A:
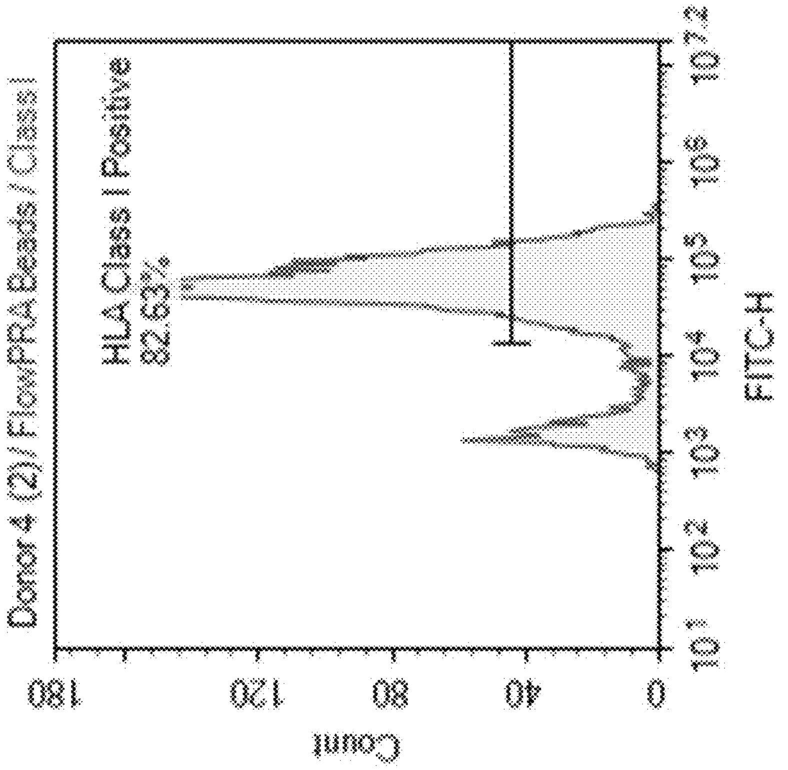
FIG. 7A shows an exemplary FITC-H histogram of FLOWPRA™ beads in Donor 4 PPP gated on Class I HLA.

Donor #4: HLA Class I and Class II Positive. Average positivity from triplicate data for Class I is 83.5% with fluorescence ratio 14.5. Average positivity for Class II is 12.6% with fluorescence ratio 0.8. (Exemplary data is shown FIG. 7A and FIG. 7B).

Figure 8B:
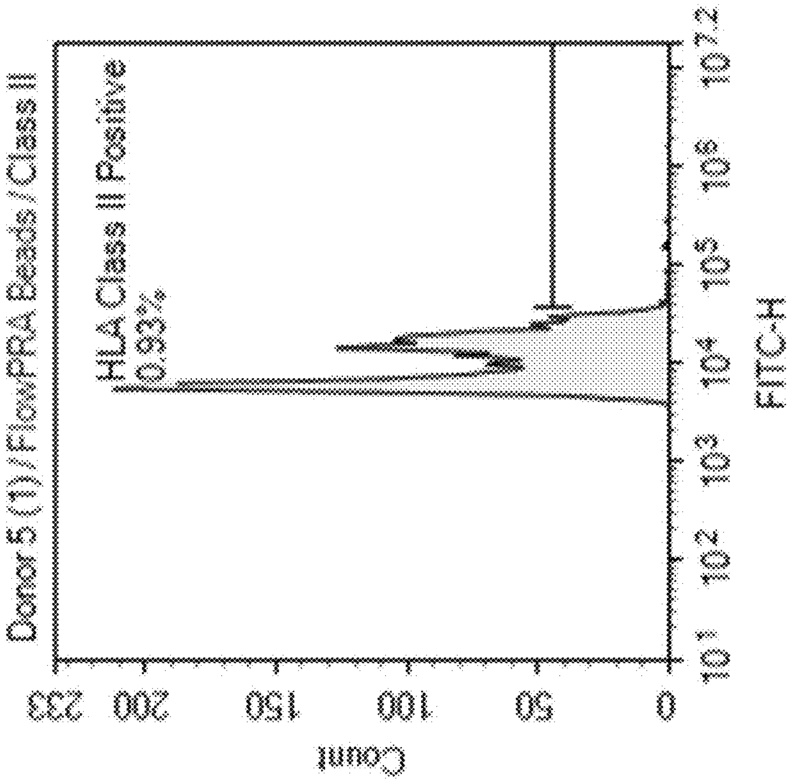
FIG. 8B shows an exemplary FITC-H histogram of FLOWPRA™ beads in Donor 5 PPP gated on Class II HLA.
Figure 8A:
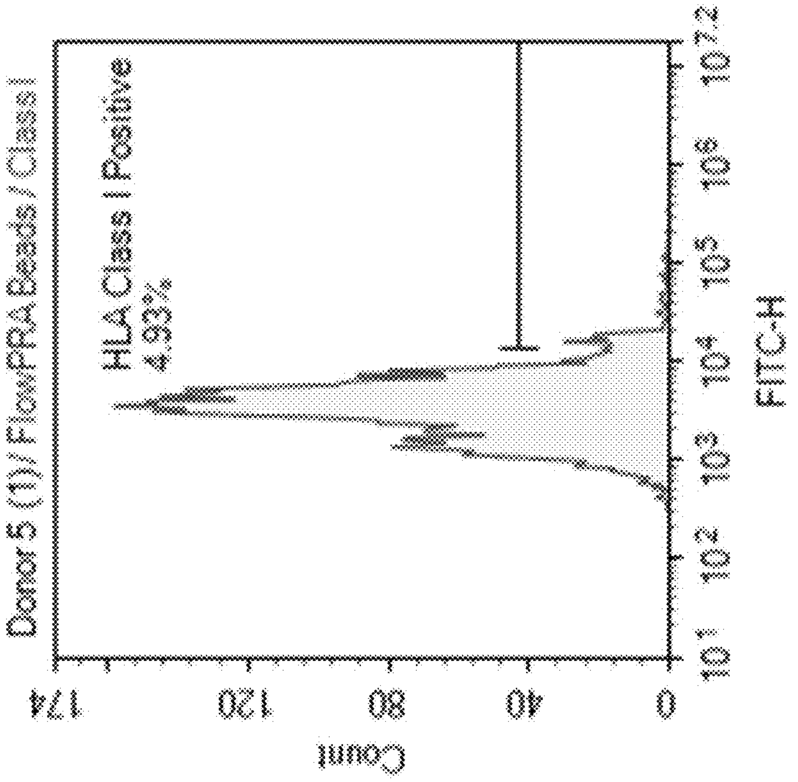
FIG. 8A shows an exemplary FITC-H histogram of FLOWPRA™ beads in Donor 5 PPP gated on Class I HLA.

Donor #5: HLA Class I and Class II Positive. Average positivity from triplicate data for Class I is 4.9% with fluorescence ratio 1.2. Average positivity for Class II is 1.3% with fluorescence ratio 0.8. (Exemplary data is shown FIG. 8A and FIG. 8B).

Figure 9A:
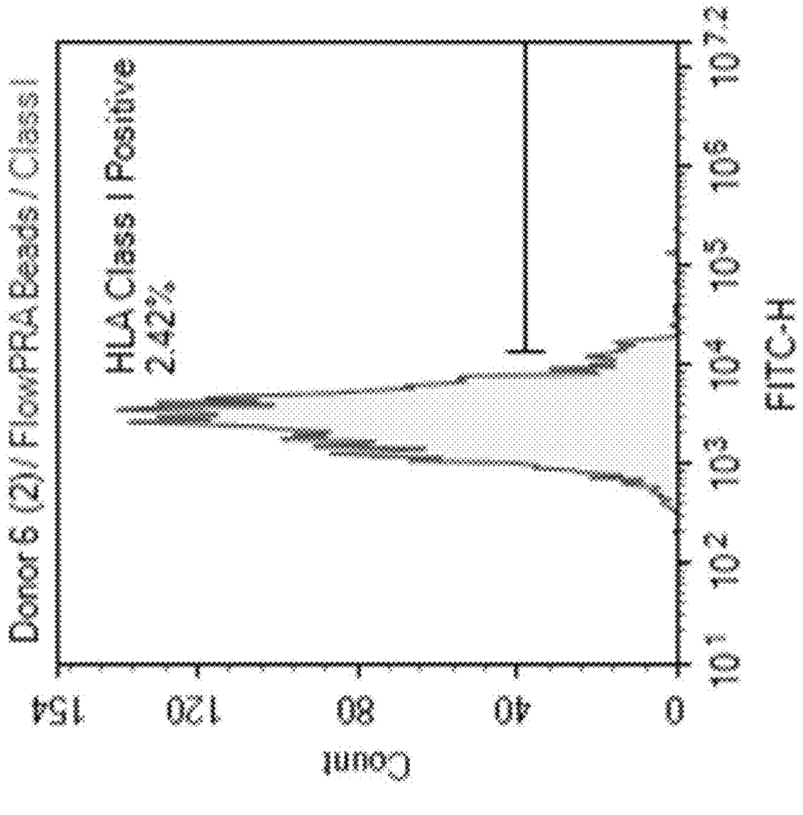
FIG. 9A shows an exemplary FITC-H histogram of FLOWPRA™ beads in Donor 6 PPP gated on Class I HLA.
Figure 9B:
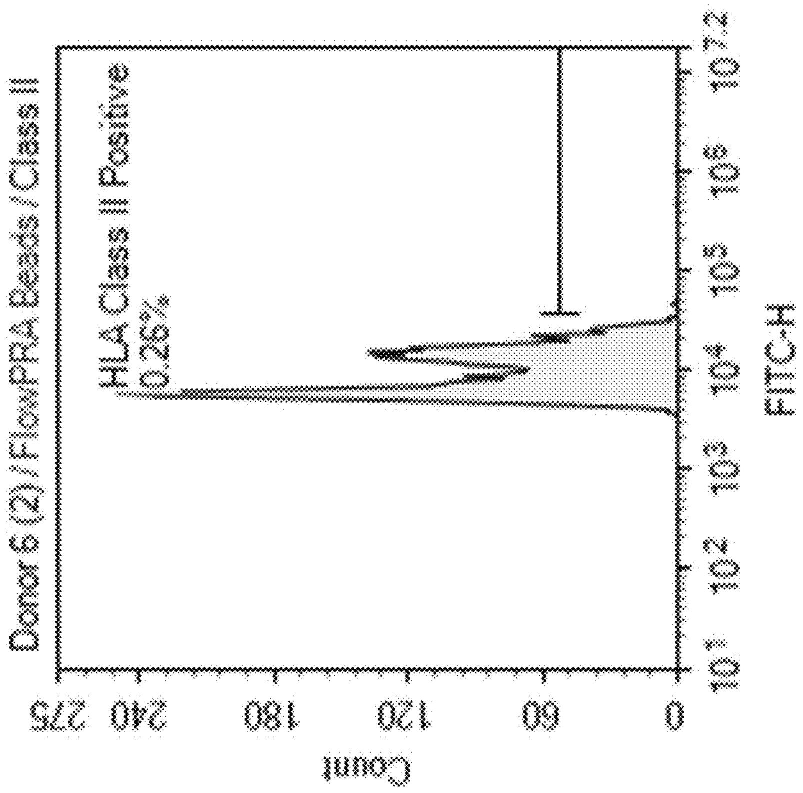
FIG. 9B shows an exemplary FITC-H histogram of FLOWPRA™ beads in Donor 6 PPP gated on Class II HLA.

Donor #6: HLA Class I Positive. Average positivity from triplicate data for Class I is 2.7% with fluorescence ratio 0.9. Average positivity for Class II is 0.3% with fluorescence ratio 0.7. (Exemplary data is shown FIG. 9A and FIG. 9B).

Figure 10A:
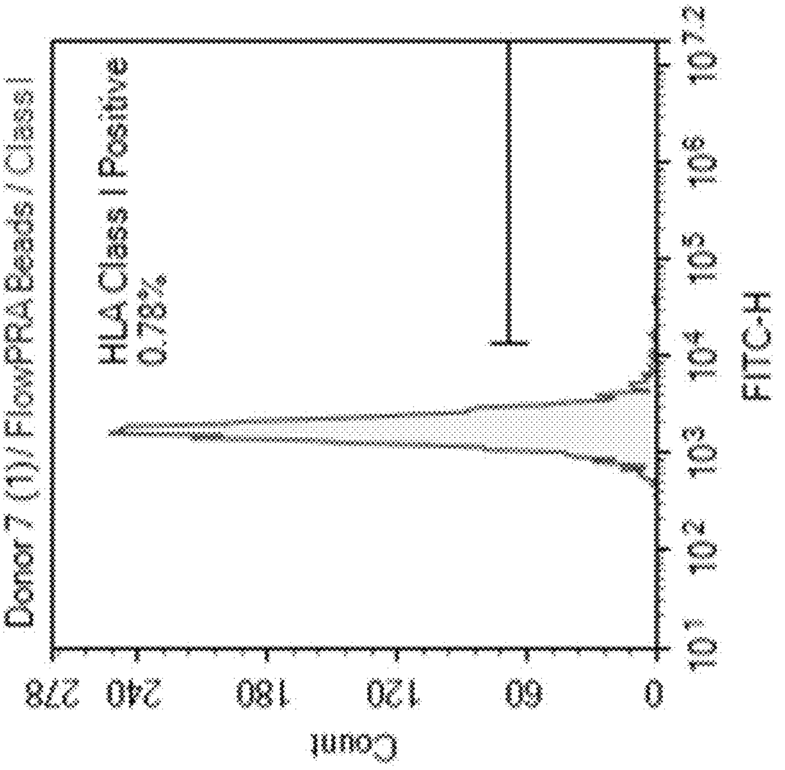
FIG. 10A shows an exemplary FITC-H histogram of FLOWPRA™ beads in Donor 7 PPP gated on Class I HLA.
Figure 10B:
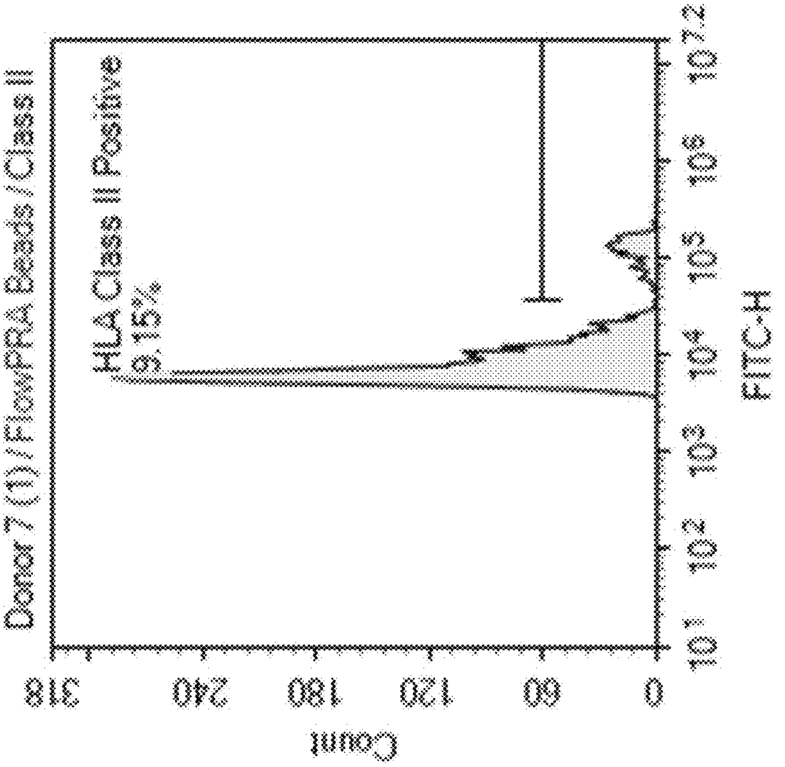
FIG. 10B shows an exemplary FITC-H histogram of FLOWPRA™ beads in Donor 7 PPP gated on Class II HLA.

Donor #7: HLA Class II Positive. Average positivity for from triplicate data Class I is 0.7% with fluorescence ratio 0.5. Average positivity for Class II is 9.0% with fluorescence ratio 1.3. (Exemplary data is shown FIG. 10A and FIG. 10B).

The results for Donors 1-7 are also shown in Table 1.

TABLE 1

| | Donor 1 | Donor 2 | Donor 3 | Donor 4 | Donor 5 | Donor 6 | Donor 7 |
|---|---|---|---|---|---|---|---|
| Average Percent Positivity Class I | 0.2 | 1.3 | 85.2 | 83.5 | 4.9 | 2.7 | 0.7 |
| Average Percent Positivity Class II | 16.5 | 20.3 | 12.0 | 12.6 | 1.3 | 0.3 | 9.0 |
| Average Fluorescence Ratio Class I | 0.3 | 1.4 | 14.4 | 14.5 | 1.2 | 0.9 | 0.5 |
| Average Fluorescence Ratio Class II | 1.6 | 1.9 | 0.8 | 0.8 | 0.8 | 0.7 | 1.3 |

Because there might be HLA-positive donors in the GK PNP pool, Table 2 displays results against an N=1 HLA-negative donor.

TABLE 2

| | Donor 1 | Donor 2 | Donor 3 | Donor 4 | Donor 5 | Donor 6 | Donor 7 |
|---|---|---|---|---|---|---|---|
| AVERAGE PERCENT POSITIVITY CLASS I | 0.3 | 12.3 | 86.1 | 84.8 | 12.4 | 7.6 | 1.1 |
| AVERAGE PERCENT POSITIVITY CLASS II | 66.6 | 67.0 | 19.1 | 19.5 | 43.1 | 36.3 | 22.6 |
| AVERAGE FLUORESCENCE RATIO CLASS I | 0.9 | 4.2 | 44.4 | 44.6 | 3.8 | 2.9 | 1.6 |
| AVERAGE FLUORESCENCE RATIO CLASS II | 4.4 | 5.4 | 2.3 | 2.3 | 2.3 | 2.0 | 3.5 |

Example 5. Filtration Results

Figure 11A:
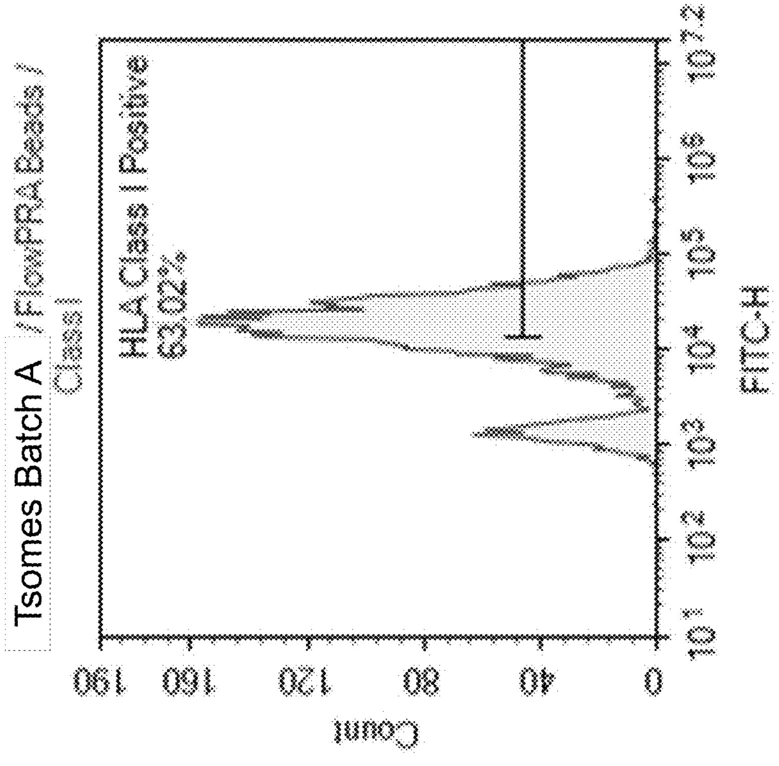
FIG. 11A shows an exemplary FITC-H histogram of FLOWPRA™ beads pooled Donor PPP gated on Class I HLA.
Figure 11B:
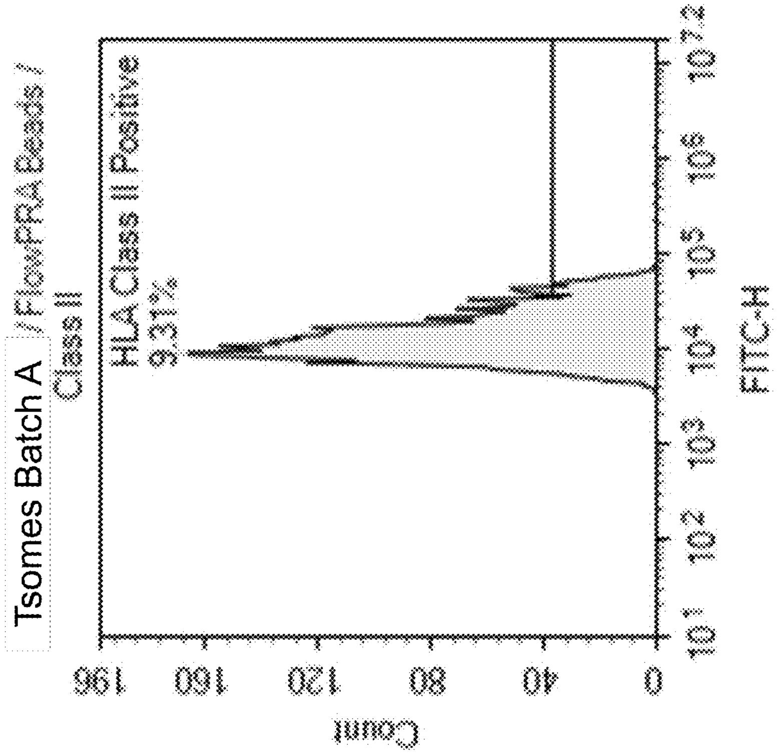
FIG. 11B shows an exemplary FITC-H histogram of FLOWPRA™ beads pooled Donor PPP gated on Class II HLA.

Pool: HLA Class I and Class II Positive. Average positivity from triplicate data for Class I is 61.1% with fluorescence ratio 4.6. Average positivity for Class II is 9.0% with fluorescence ratio 1.1. (Exemplary data is shown FIG. 11A and FIG. 11B).

Figure 12A:
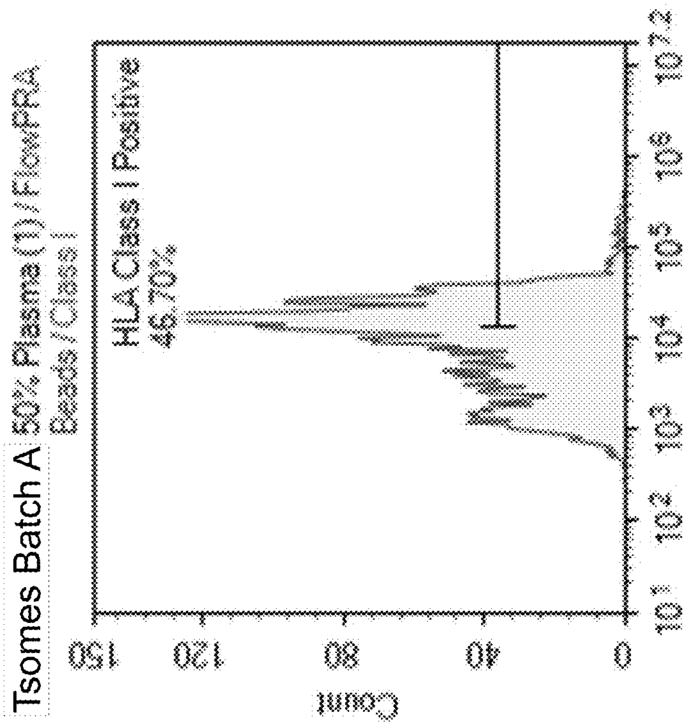
FIG. 12A shows an exemplary FITC-H histogram of FLOWPRA™ beads pooled Donor PPP gated on Class I HLA following tangential flow filtration (TFF) to 50% (by absorbance at 280 nm) retained plasma protein.
Figure 12B:
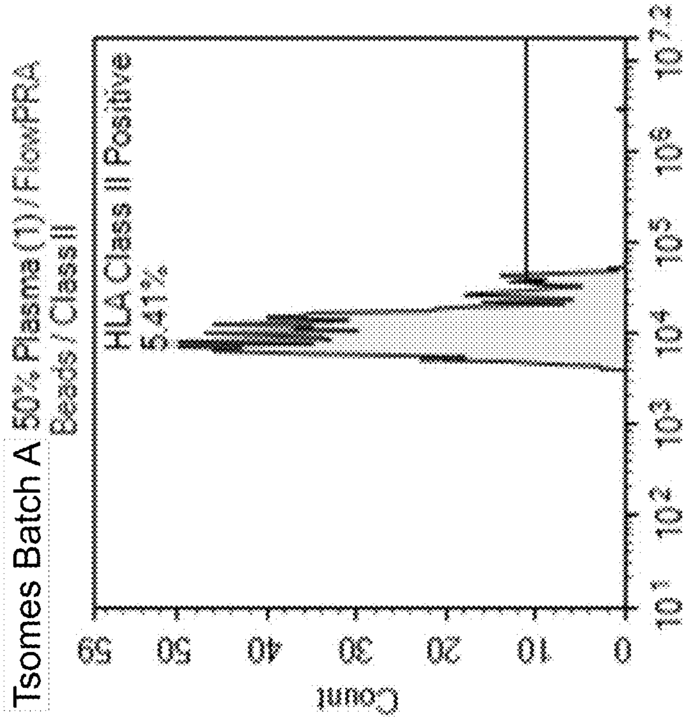
FIG. 12B shows an exemplary FITC-H histogram of FLOWPRA™ beads pooled Donor PPP gated on Class II HLA following tangential flow filtration (TFF) to 50% (by absorbance at 280 nm) retained plasma protein.

Initial Dilution (51%): HLA Class I and Class II Positive. Average positivity from triplicate data for Class I is 48.2% with fluorescence ratio 4.2. Average positivity for Class II is 5.9% with fluorescence ratio 0.9. (Exemplary data is shown FIG. 12A and FIG. 12B).

Figure 13A:
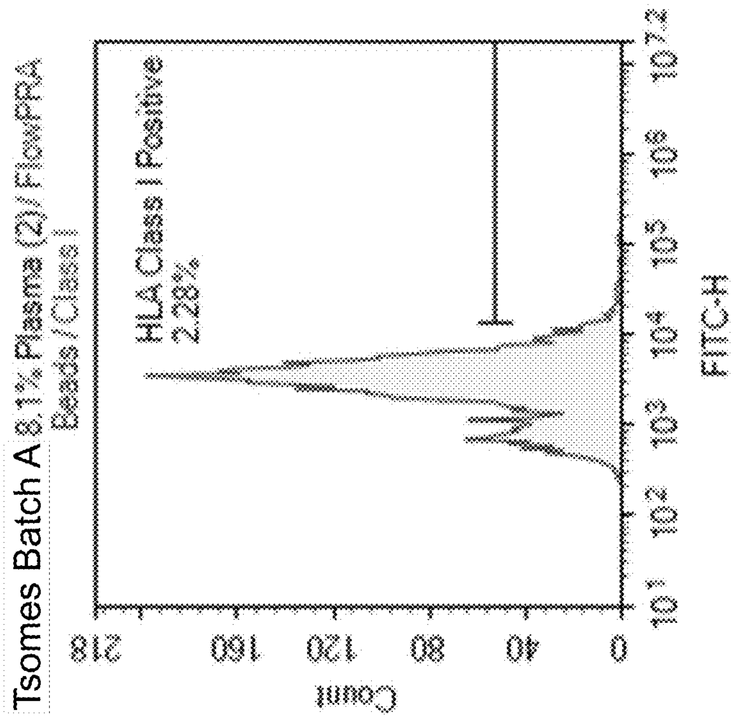
FIG. 13A shows an exemplary FITC-H histogram of FLOWPRA™ beads pooled Donor PPP gated on Class I HLA following tangential flow filtration (TFF) to about 8% (by absorbance at 280 nm) retained plasma protein.
Figure 13B:
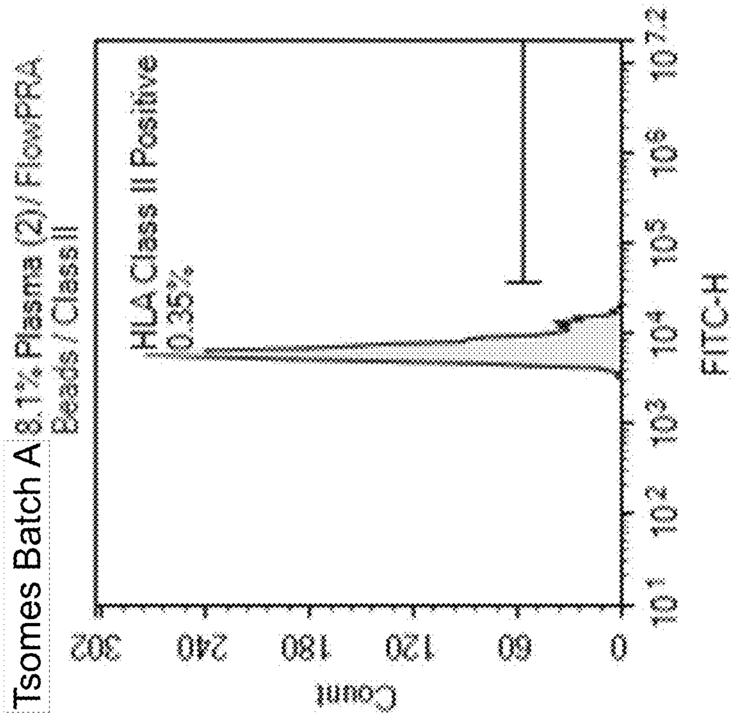
FIG. 13B shows an exemplary FITC-H histogram of FLOWPRA™ beads pooled Donor PPP gated on Class II HLA following tangential flow filtration (TFF) to about 8% (by absorbance at 280 nm) retained plasma protein.

"20%" Plasma (8.1%): HLA Class I Positive. Average positivity from triplicate data for Class I is 2.4% with fluorescence ratio 1.0. Average positivity for Class II is 0.2% with fluorescence ratio 0.5. (Exemplary data is shown FIG. 13A and FIG. 13B).

Figure 14A:
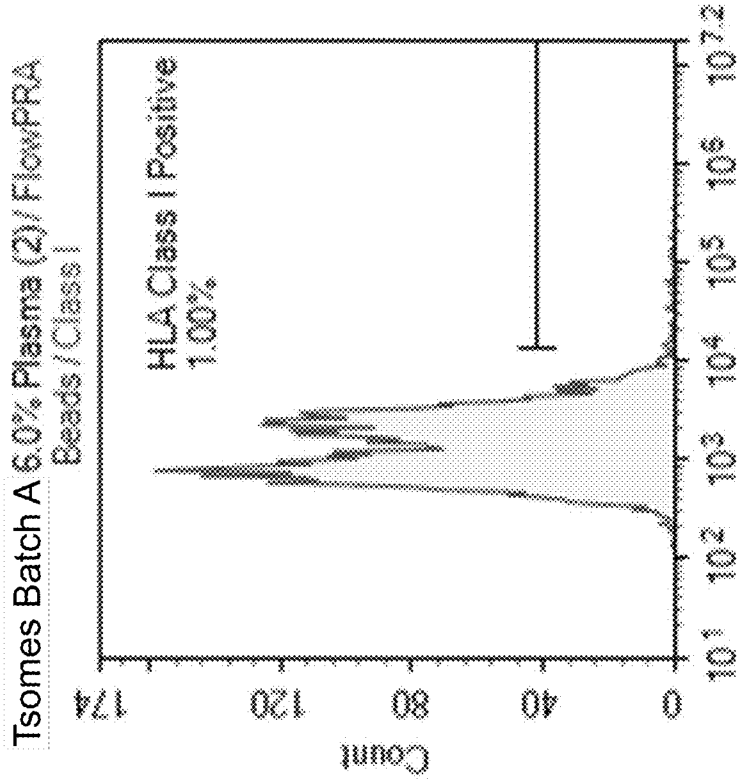
FIG. 14A shows an exemplary FITC-H histogram of FLOWPRA™ beads pooled Donor PPP gated on Class I HLA following tangential flow filtration (TFF) to about 6% (by absorbance at 280 nm) retained plasma protein.
Figure 14B:
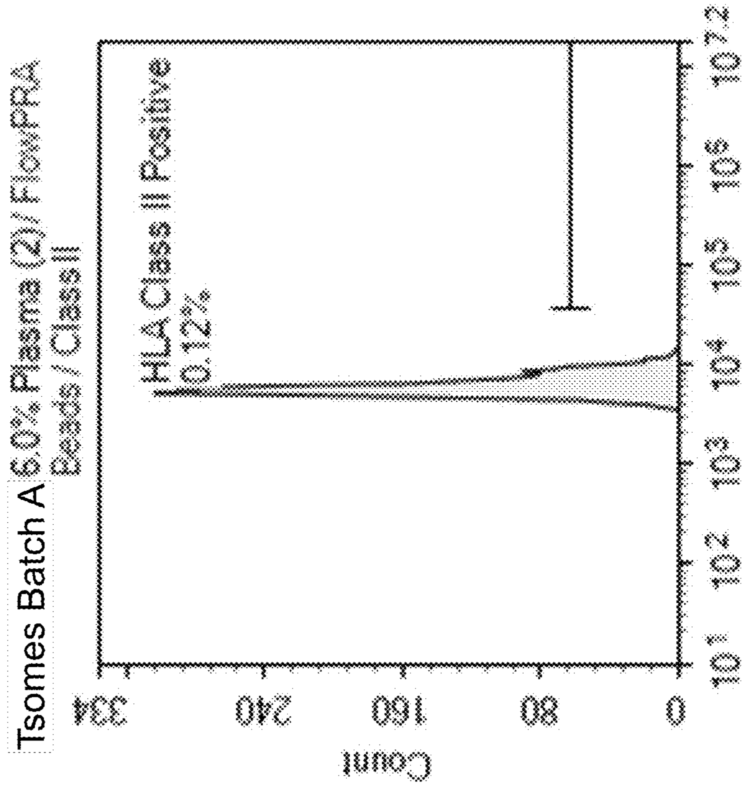
FIG. 14B shows an exemplary FITC-H histogram of FLOWPRA™ beads pooled Donor PPP gated on Class II HLA following tangential flow filtration (TFF) to about 6% (by absorbance at 280 nm) retained plasma protein.

"<10%" Plasma (6.0%): Borderline HLA Class I Positive. Average positivity from triplicate data for Class I is 1.1% with fluorescence ratio 1.0. Average positivity for Class II is 0.2% with fluorescence ratio 0.5. (Exemplary data is shown FIG. 14A and FIG. 14B).

Figure 15A:
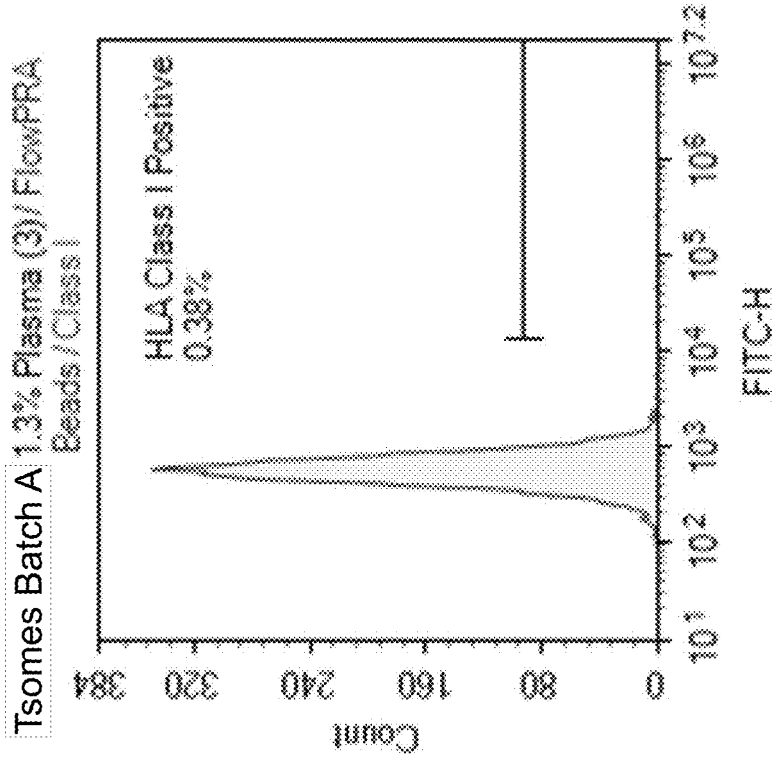
FIG. 15A shows an exemplary FITC-H histogram of FLOWPRA™ beads pooled Donor PPP gated on Class I HLA following tangential flow filtration (TFF) to about 1% (by absorbance at 280 nm) retained plasma protein.
Figure 15B:
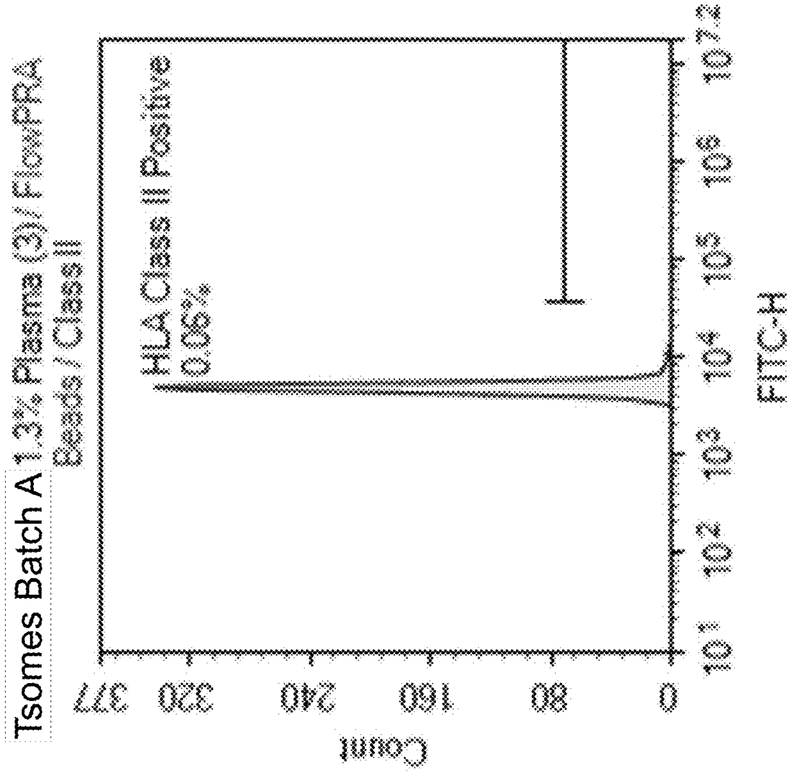
FIG. 15B shows an exemplary FITC-H histogram of FLOWPRA™ beads pooled Donor PPP gated on Class II HLA following tangential flow filtration (TFF) to about 1% (by absorbance at 280 nm) retained plasma protein.

"<3%" Plasma (1.3%): HLA Negative. Average positivity from triplicate data for Class I is 0.4% with fluorescence ratio 0.2. Average positivity for Class II is 0.1% with fluorescence ratio 0.4. (Exemplary data is shown FIG. 15A and FIG. 15B).

The filtration results are also shown in Tables 3A and 3B.

TABLE 3A

| | Pool | 51% Plasma | 8.1% Plasma | 6.0% Plasma | 1.3% Plasma |
|---|---|---|---|---|---|
| Average Percent Positivity Class I | 61.1 | 48.2 | 2.4 | 1.1 | 0.4 |
| Average Percent Positivity Class II | 9.0 | 5.9 | 0.2 | 0.2 | 0.1 |
| Average Fluorescence Ratio Class I | 4.6 | 4.2 | 1.0 | 0.7 | 0.2 |
| Average Fluorescence Ratio Class II | 1.1 | 0.9 | 0.5 | 0.5 | 0.4 |

TABLE 3B

Background fluorescence determined using HLA beads in PBS was subtracted from sample fluorescence prior to calculation of percent reduction in mean fluorescence intensity (a measure of reduction in antibody binding).

| Percent Reduction in Fluorescence Intensity | Class I HLA Beads With background subtraction from beads in PBS | Class II HLA Beads With background subtraction from beads in PBS |
|---|---|---|
| Pool | 0.0% | 0.0% |
| 51% Residual Plasma | 9.6% | 18.7% |
| 8.1% Residual Plasma | 80.8% | 74.8% |
| 6.0% Residual Plasma | 87.4% | 72.0% |
| 1.3% Residual Plasma | 97.3% | 83.8% |
| freeze-dried platelet derivative composition 4.9% Residual Plasma Unbaked | 95.8% | 91.4% |
| freeze-dried platelet derivative composition 4.9% Residual Plasma Baked | 100.0% | 100.6% |
| freeze-dried platelet derivative composition 1.3% Residual Plasma Unbaked | 100.0% | 100.9% |
| freeze-dried platelet derivative composition 1.3% Residual Plasma Baked | 99.6% | 100.8% |

Values ≥100% indicate complete reduction in detectable HLA antibody binding to the indicated beads.

Because there might be HLA-positive donors in the GK PNP pool, Table 4 displays results against an N=1 HLA-negative donor.

TABLE 4

| | Pool | 51% Plasma | 8% Plasma | 6% Plasma | <3% Plasma |
|---|---|---|---|---|---|
| AVERAGE PERCENT POSITIVITY CLASS I | 77.9 | 64.7 | 7.6 | 2.2 | 0.4 |
| AVERAGE PERCENT POSITIVITY CLASS II | 52.8 | 42.7 | 4.9 | 0.7 | 0.2 |
| AVERAGE FLUORESCENCE RATIO CLASS I | 14.3 | 12.9 | 3.0 | 2.1 | 0.7 |
| AVERAGE FLUORESCENCE RATIO CLASS II | 2.9 | 2.6 | 1.4 | 1.4 | 1.2 |

Example 6. Surface Markers and Thrombin Generation

Freeze-dried platelet derivative composition batch were produced by the TFF method described in Example 1 and assayed for cell surface marker expression or presence or absence using flow cytometry.

Flow cytometry was used to assess freeze-dried platelet derivative composition for expression or presence or presence of CD41, CD62, and phosphatidylserine (PS). Samples included approximately 270,000/μL freeze-dried platelet derivatives during staining and were diluted approximately 1:34 before the sample was analyzed in the cytometer. Freeze-dried platelet derivative samples were rehydrated and diluted 1:2 in deionized water. A stock of anti-CD41 was diluted by adding 47.6 μL of antibody to 52.4 μL of HMTA. Samples stained with anti-CD41 were made by adding 10 μL of diluted freeze-dried platelet derivatives to 10 μL HMTA and 10 μL of diluted CD41 antibody. An anti-CD62 master mix was prepared by combining 12 μL anti-CD62 with 23.8 μL anti-CD41 and 64.2 μL of HMTA. An isotype control mix was made in the same manner. Samples stained with anti-CD62 were made by adding 10 μL of diluted freeze-dried platelet derivatives to 20 μL of the anti-CD62 master. The isotype master mix was used to make isotype control samples in the same manner. An annexin V (AV) master mix was prepared by combining 11.7 μL of AV with 83.3 μL of anti-CD41 and 80 μL of HMTA. Sample stained with AV were made by adding 20 μL of diluted freeze-dried platelet derivatives containing 50 mM GPRP to 20 μL of HMTA containing 15 mM $CaCl_2$ and 20 μL of the AV master mix. Negative gating control samples were made in the same manner using HMTA without calcium to prevent AV binding to PS. All samples were incubated at room temperature for 20 minutes. After incubation 1 mL HBS was added to all samples. HBS used to dilute AV test samples contained 5 mM $CaCl_2$ Anti-CD41 binding was used to identify the population of interest. CD62 and PS expression or presence was assessed by anti-CD62 and AV binding within the CD41 positive population.

Figure 16:
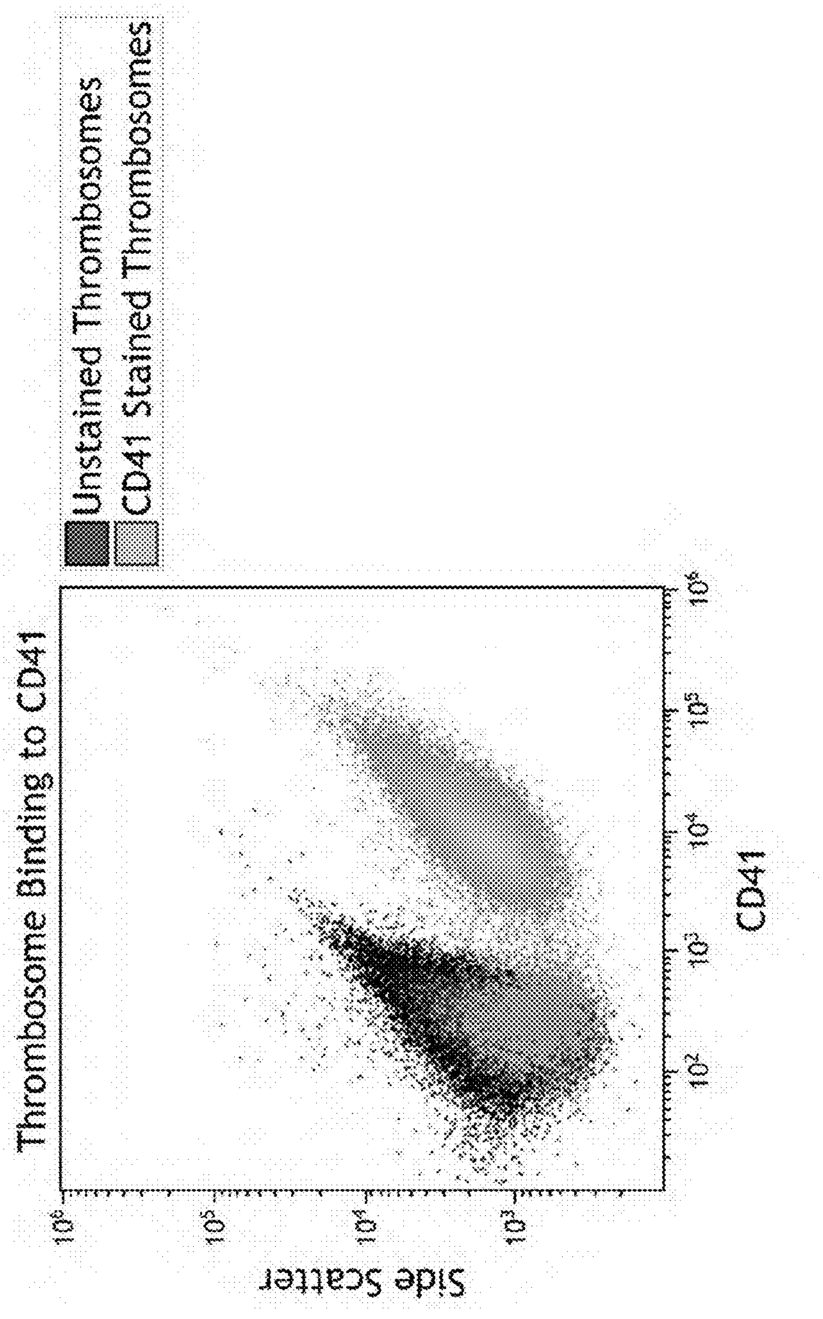
FIG. 16 shows exemplary flow cytometry data of thrombosomes unstained (dark data points) or stained (light data points) with an anti-CD-41 antibody.

Glycoprotein IIb (GPIIb, also known as antigen CD41) expression or presence was assayed using an anti-CD41 antibody (4.8 μL, Beckman Coulter part #IM1416U). The assayed freeze-dried platelet derivatives demonstrated CD41 positivity (Table 5; FIG. 16)

TABLE 5

| Batch | CD41 Positivity (%) |
|---|---|
| 1 | 81.5 |
| 2 | 79.4 |
| 3 | 85.7 |
| 4 | 78.2 |
| 5 | 81.5 |
| 6 | 84.0 |
| 7 | 78.5 |
| Mean | 81.3 |

Figure 17:
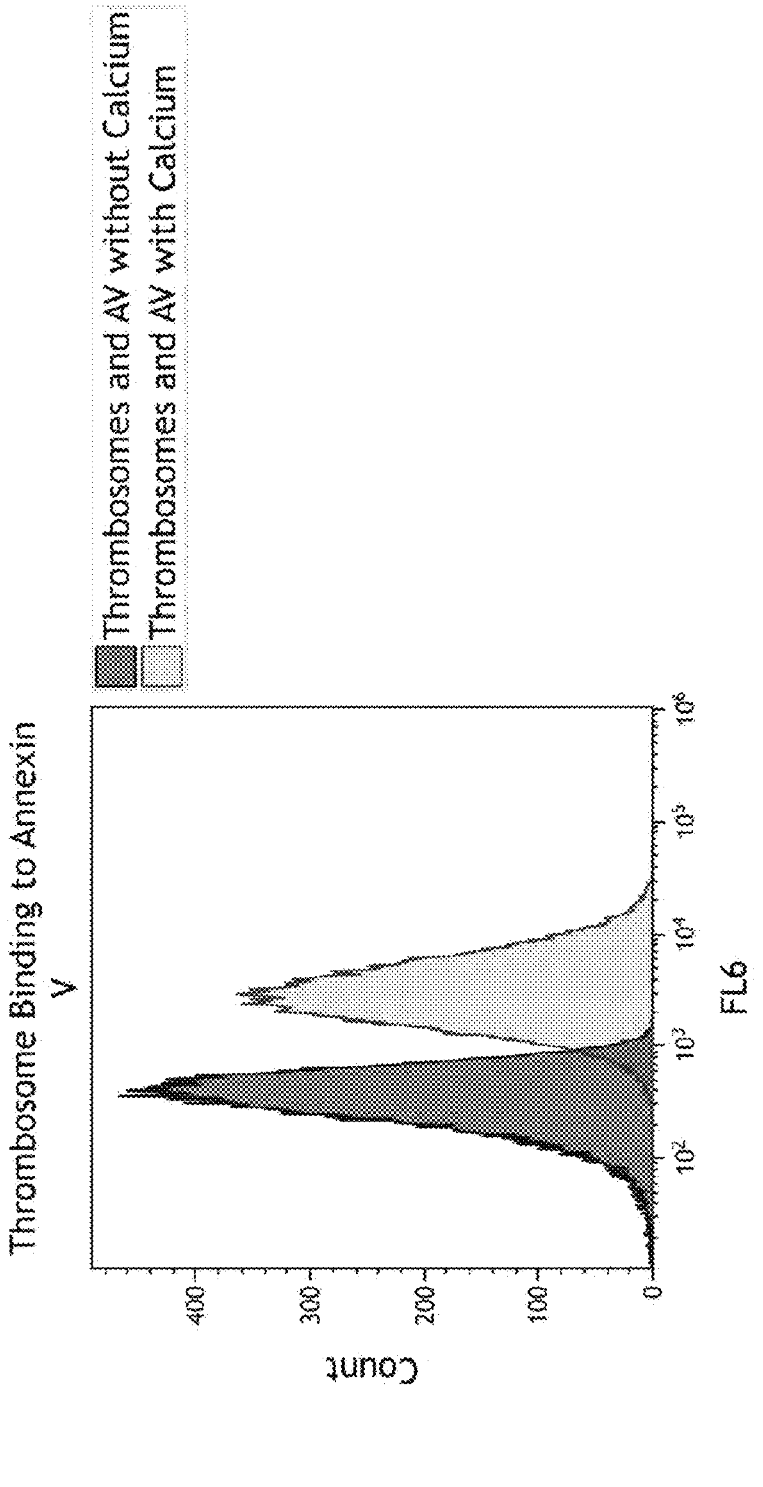
FIG. 17 shows an exemplary histogram of thrombosomes incubated with annexin V with (light data points) and without (dark data points) calcium.

Phosphatidylserine (PS) expression or presence was assayed using annexin V (AV) (1.3 μL, BD Biosciences Cat. No. 550475). AV is a calcium-dependent phospholipid binding protein. The assayed freeze-dried platelet derivatives demonstrated AV positivity (Table 6; FIG. 17).

TABLE 6

| Batch | AV Positivity (%) |
|---|---|
| 1 | 96.7 |
| 2 | 89.9 |
| 3 | 95.3 |
| 4 | 95.4 |
| 5 | 95.9 |
| 6 | 96.2 |
| 7 | 93.5 |
| Mean | 94.7 |

Figure 18:
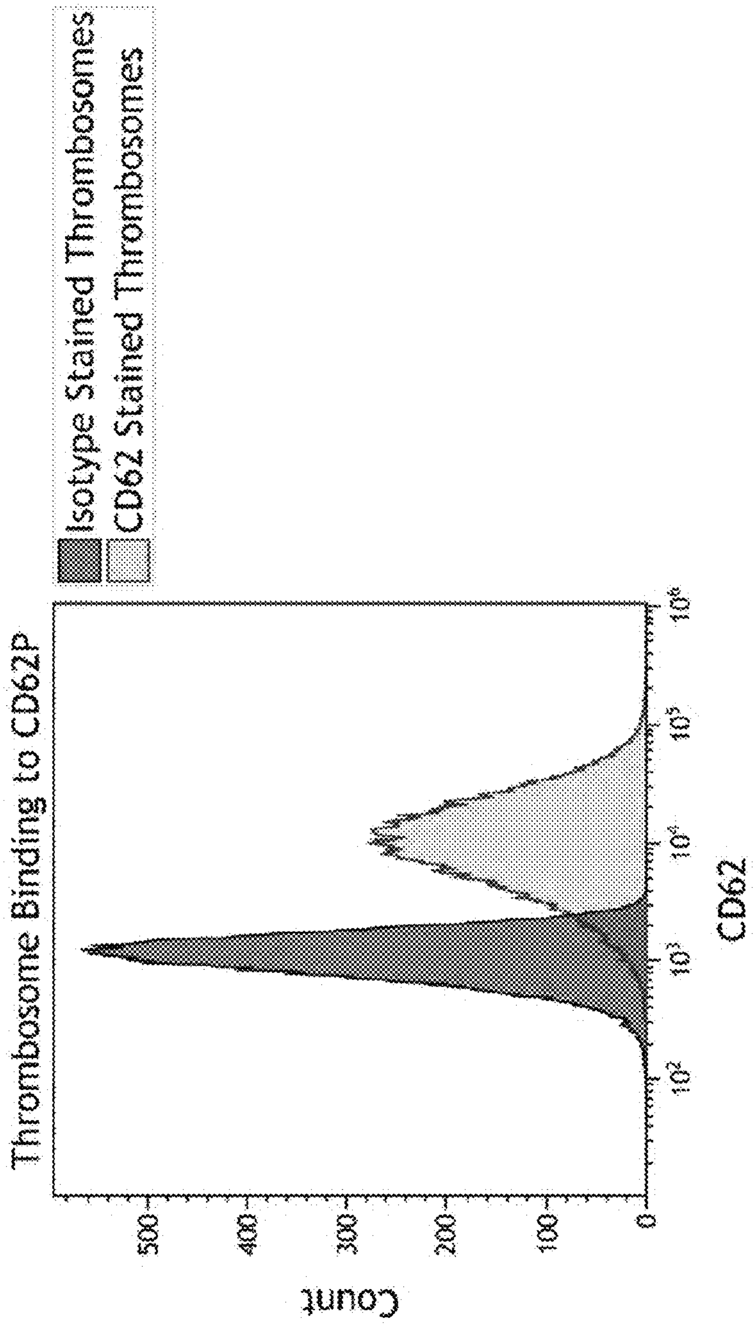
FIG. 18 shows an exemplary histogram of thrombosomes incubated with an anti-CD62 antibody (light data points) or with an isotype control (dark data points).

P-selectin (also called CD62P) expression or presence was assayed using an anti-CD62P antibody (2.4 μL, BD Biosciences Cat. No. 550888). The assayed freeze-dried platelet derivatives demonstrated CD62 positivity (Table 7, FIG. 18)

TABLE 7

| Batch | CD62 Positivity (%) |
|---|---|
| 1 | 94.2 |
| 2 | 93.1 |
| 3 | 89.8 |
| 4 | 92.4 |
| 5 | 92.5 |
| 6 | 87.3 |
| 7 | 90.7 |
| Mean | 91.4 |

Figure 19:
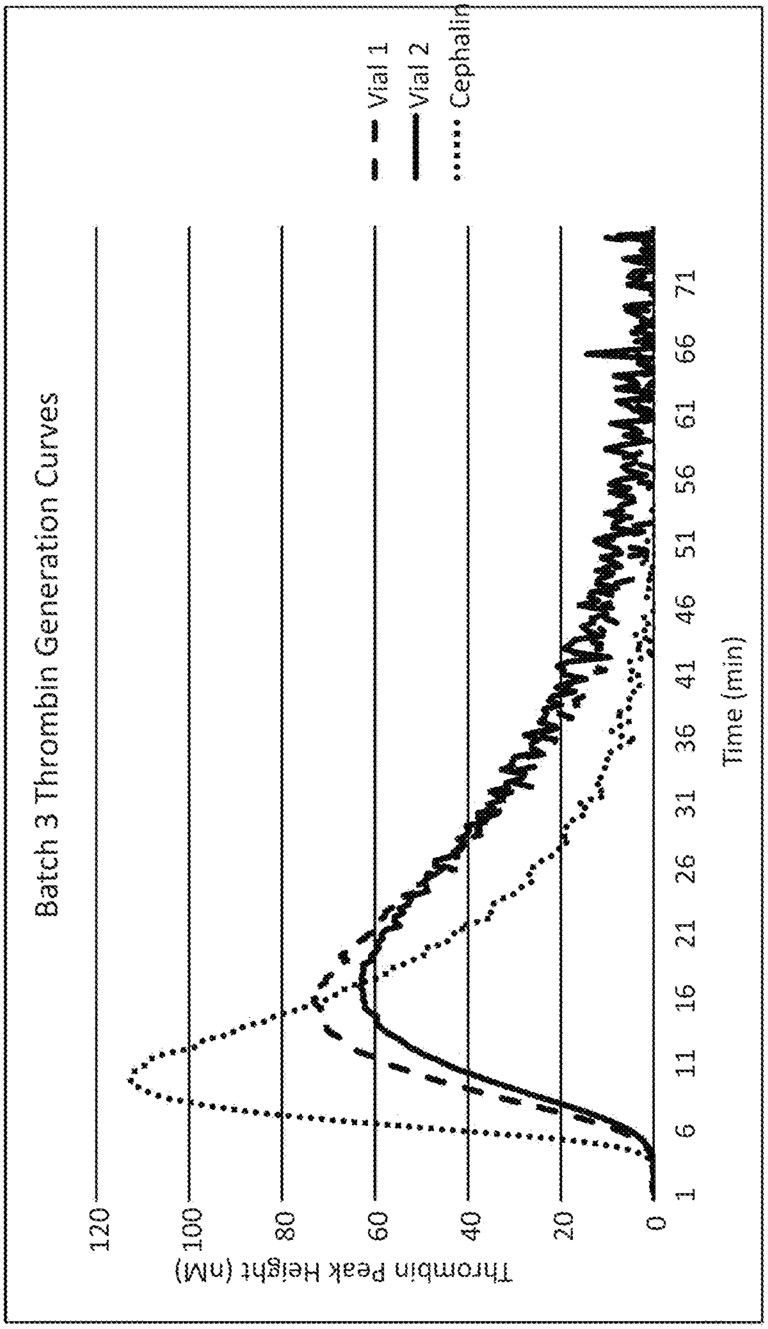
FIG. 19 shows a plot of thrombin peak height for thrombosomes in the presence of PRP Reagent containing tissue factor and phospholipids (solid line and long dashes) and control cephalin (dots).

Thrombin generation was measured at $4.8\times10^3$ freeze-dried platelet derivatives/μl in the presence of PRP Reagent containing tissue factor and phospholipids using the below protocol. On average, the Thrombin Peak Height (TPH) for a freeze-dried platelet derivatives sample was 60.3 nM. Cephalin was used as a positive control. (Table 8; FIG. 19)

For each vial tested, a rehydrated sample of freeze-dried platelet derivatives was diluted to 7,200 particles per μL based on the flow cytometry particle count using 30% solution of Octaplas in control buffer. In a 96 well plate, sample wells were generated by adding 20 μL of PRP reagent (Diagnostica Stago Catalog No. 86196) and 80 μL of diluted freeze-dried platelet derivatives. Calibrator wells were generated by adding 20 μL of Thrombin Calibrator reagent (Diagnostica Stago Catalog No. 86197) to 80 μL of diluted freeze-dried platelet derivatives. The plate was loaded into the plate reader and incubated in the dark at 40° C. for 10 minutes. During sample incubation, FluCa solution was prepared by adding 40 μL of FluCa substrate (Diagnostica Stago Catalog No. 86197) to 1.6 mL of Fluo-Buffer (Diagnostica Stago Catalog No. 86197) warmed to 37° C. and vortexed to mix. The FluCa solution was aspirated in to the dispensing syringe and 20 μL was mechanically dispensed in to each reaction well, bringing the final freeze-dried platelet derivatives concentration in each well to 4,800 particles per μL and starting the thrombin generation reaction. Thrombin generation was measured via fluorescence in each well over the course of 75 minutes.

An exemplary step-by-step protocol follows:

1. Open CAT software; set up instrument; and prepare PRP reagent (including Tissue Factor and some phospholipids), calibrator, and fluo-buffer and fluo-substrate according to manufacturer guidelines.
2. Thaw Octaplas and TGA dilution buffer in 37° C. water bath for 10 minutes.
3. Add thawed Octaplas to TGA dilution buffer to create a buffer containing 30% Octaplas.
4. Use the 30% Octaplas mix to dilute reconstituted cephalin 1:50 to be used as a positive control.
5. Rehydrate freeze-dried platelet derivative composition with cell culture grade water for 10 minutes then dilute with 30% Octaplas to 7,200 freeze-dried platelet derivatives/μL.
6. Using a multichannel pipette, add 20 μL of PRP reagent to each test well. Add 20 μL of Calibrator to each calibration well.
7. Add 80 μL of sample to each test and calibration well. Add 80 μL of 30% Octaplas to negative control wells and 1:50 cephalin to positive control wells.
8. Insert plate into tray and incubate for 10 minutes at 40° C. After incubation, dispense fluo-buffer and fluo-substrate mixture (including a fluorescent-labeled peptide, that when cleaved by thrombin, generates a fluorescent signal) into active wells.
9. Read plate for 75 minutes at 20 s intervals to capture full thrombin generation profile.

TABLE 8

| Batch | TPH (nM) |
|---|---|
| 1 | 61.5 |
| 2 | 71.4 |
| 3 | 67.8 |
| 4 | 52.0 |
| 5 | 60.2 |
| 6 | 54.7 |
| 7 | 54.4 |
| Mean | 60.3 |

Data from these assays is summarized in Table 9.

TABLE 9

| | TFF Batches | | | |
|---|---|---|---|---|
| Batch | Average TPH (nM) | Average CD41 Positivity | Average AV Positivity (0.5 μm-2.5 μm)[1] | Average CD62 Positivity (0.5 μm-2.5 μm)[1] |
| Batch B | 61.5 | 81.5 | 96.7 | 94.2 |
| Batch C | 71.4 | 79.4 | 89.9 | 93.1 |
| Batch D | 67.8 | 85.7 | 95.3 | 89.8 |
| Batch E | 52.0 | 78.2 | 95.4 | 92.4 |
| Batch F | 60.2 | 81.5 | 95.9 | 92.5 |
| Batch G | 54.7 | 84.0 | 96.2 | 87.3 |
| Batch H | 54.4 | 78.5 | 93.5 | 90.7 |
| Mean | 60.3 | 81.3 | 94.7 | 91.4 |

[1]Particle diameter as assessed using sizing beats on the flow cytometry forward scatter.

Example 7. 9F9 and PAC-1 Binding

Aggregation of activated platelets is mediated by the formation of the GPIIb/IIIa complex, which can bind to fibrinogen (also called Factor 1) and form a clot. GPIIb/IIIa is a platelet fibrinogen receptor also known as CD41/CD61 complex. In this process, ADP promotes the active form of the GPIIb/IIIa complex. Antibody 9F9 binds to fibrinogen associated with the cell membrane. The presence of fibrinogen on the cell membrane is thus indicative of freeze-dried platelet derivatives capable of forming clots.

A vial of freeze-dried platelet derivative composition prepared according to Example 1 was rehydrated using 10 mL of deionized water. An aliquot of freeze-dried platelet derivatives was diluted to a final concentration of $1\times10^5$ particles/μL using HMTA (HEPES Modified Tyrode's Albumin). Samples were prepared as shown in Table 11. Unstained samples were prepared by adding 10 μL of diluted freeze-dried platelet derivatives to 20 μL of HMTA. FITC isotype control samples were prepared by adding 10 μL of diluted freeze-dried platelet derivatives to 10 μL of the isotype control antibody (BD Biosciences Cat. No. 555748) and 10 μL of HMTA. Samples stained with 9F9 were prepared by adding 10 μL of diluted freeze-dried platelet derivatives to 10 μL of the 9F9 antibody (BD Biosciences Cat. No. 340507 and 10 μL of HMTA. Samples stained with PAC-1 were prepared by adding 10 μL of diluted freeze-dried platelet derivatives to 5 μL of the isotype control antibody and 15 μL of HMTA. All samples were prepared in duplicated using a total of $1\times10^6$ particles per reaction mixture. Samples were incubated at room temperature for 20 minutes away from open light. After incubation, all samples were diluted with 1 mL of FIBS and analyzed using the ACEA NovoCyte flow cytometer. The fluorescent signal generated by PAC-1 was used to determine the expression or presence of activated GPIIb/IIIa receptors without bound fibrinogen. The fluorescent signal from 9F9 was used to determine binding of fibrinogen to the surface receptors on freeze-dried platelet derivatives.

HTMA (HEPES modified Tyrode's albumin).

| Component | Concentration (mM, except where otherwise indicated) |
|---|---|
| HEPES | 9.5 |
| NaCl | 145.0 |
| KCl | 4.8 |
| $NaHCO_3$ | 12.0 |
| Dextrose | 5.0 |
| Bovine Serum Albumin | 0.35% w/v |

TABLE 10

| | Unstained | FITC Iso | 9F9 | PAC-1 |
|---|---|---|---|---|
| Cells (uL) | 10 | 10 | 10 | 10 |
| HMTA (uL) | 20 | 10 | 10 | 15 |
| Antibody (uL) | 0 | 10 | 10 | 5 |

Figure 20:
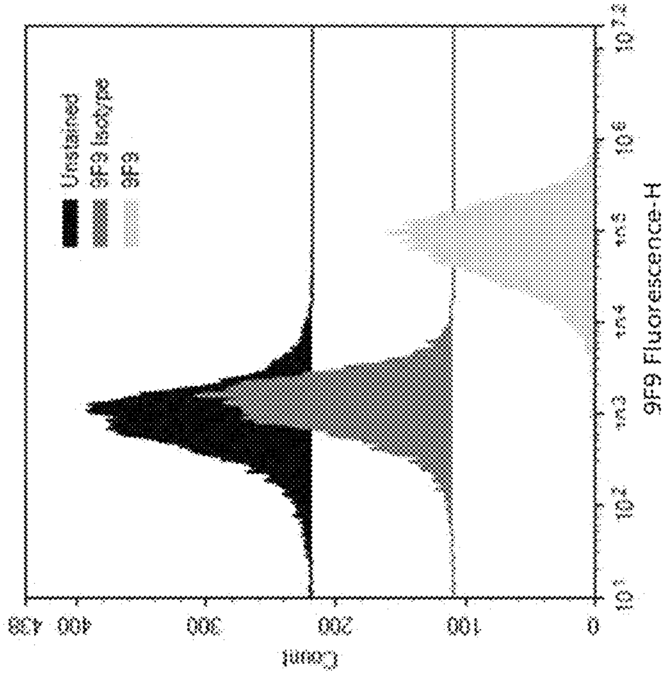
FIG. 20 is an exemplary histogram comparison of low-plasma thrombosomes unstained (black) or stained with an isotype control antibody (dark gray) or a FITC-labeled 9F9 antibody (light gray), and a table showing the mean fluorescence intensity for two replicates.
Figure 21:
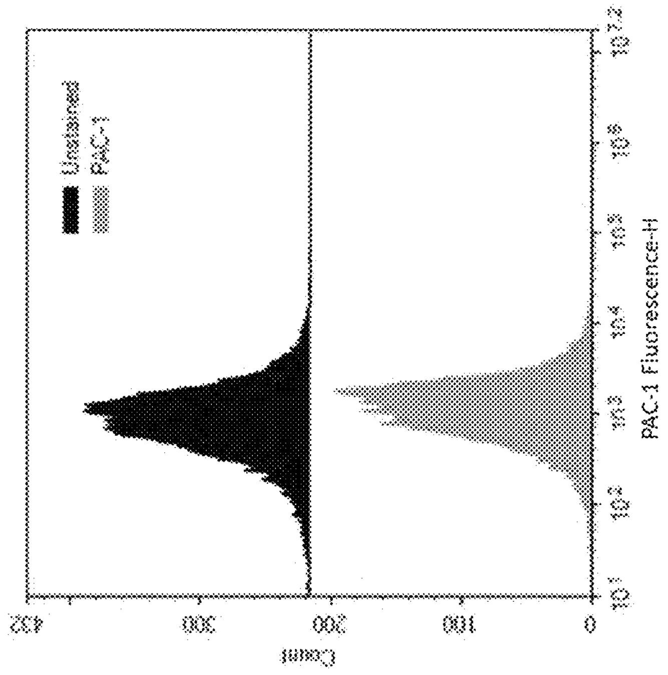
FIG. 21 is an exemplary histogram comparison of low-plasma thrombosomes unstained (black) or stained with an anti-PAC-1 antibody (light gray), and a table showing the mean fluorescence intensity for two replicates.

The samples were assayed by flow cytometry, and it was demonstrated that there is surface-bound fibrinogen post rehydration (FIG. 20), while the anti-PAC-1 antibody shows no significant binding (FIG. 21). This is further evidence that the freeze-dried platelet derivatives prepared by TFF include fibrinogen bound to the active form of GPIIb/GPIIIa, as PAC-1 binds to the same complex.

Example 8. Evaluation of CD47 Binding

CD47 is a cell-surface marker used in self-recognition. Absence of this marker can, in some cases, lead to phagocytosis.

Figure 22A:
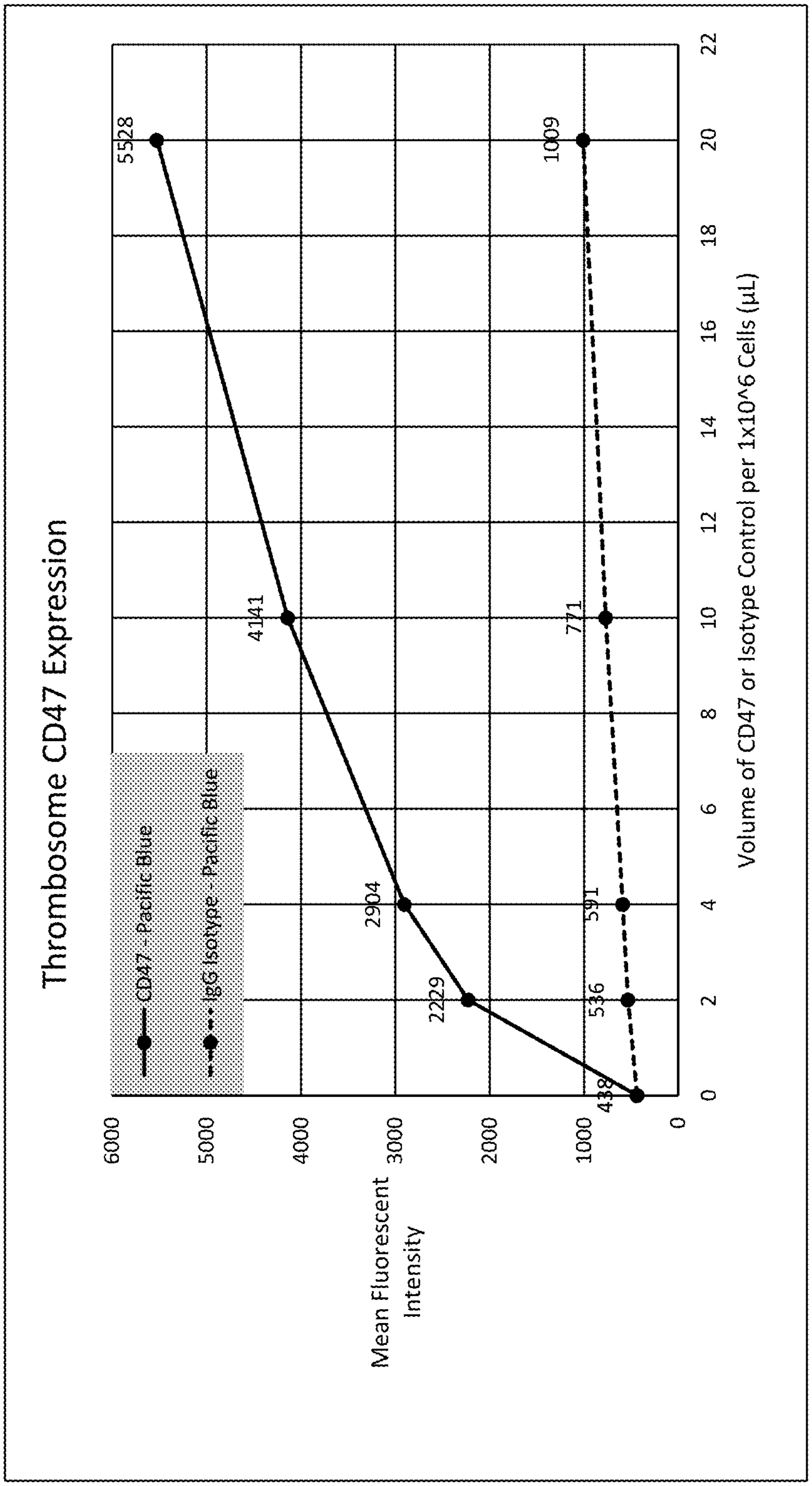
FIG. 22A is a plot of the mean fluorescence intensity of thrombosomes ($1\times10^6$ cells) treated with various concentrations of a labeled anti-CD47 antibody or an isotype control.
Figure 22B:
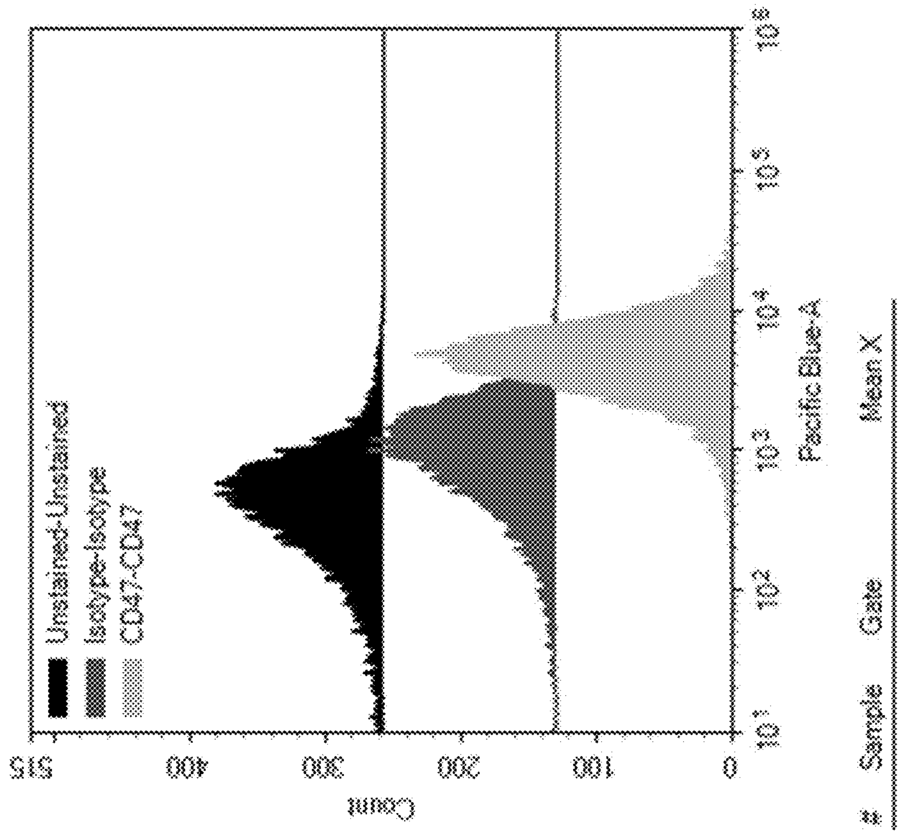
FIG. 22B is an exemplary histogram of thrombosomes that were unstained (black), stained with an isotype control antibody (dark gray), or stained with an anti-CD47 antibody (light gray).

One vial of freeze-dried platelet derivative composition prepared as described in Example 1 was rehydrated with 10 mL sterile water for injection and stained with increasing volumes of anti-CD47 antibody conjugated to Pacific Blue (BD Biosciences Cat. No. 561564) or a corresponding isotype control (BD Biosciences Cat. No. 560373). All samples contained 1 million cells. This titration resulted in a maximum fluorescent signal that was ~5× over background (FIG. 22A) and an overall CD47 positivity of ~40% (Table 12). An exemplary histogram is shown in FIG. 22B.

Aliquots of CD47 antibody conjugated to V450 were prepared at a 1:10, 1:5, and 1:2 dilution with HMTA. The initial concentration of a freeze-dried platelet derivative sample was determined using the AcT diff 2 and the concentration of a 1 mL aliquot was adjusted to $100\times10^3$ per μL using HMTA. TFF freeze-dried platelet derivatives were stained in duplicate at each antibody dilution by adding 10 μL of antibody to 10 μL of diluted freeze-dried platelet derivatives. Samples stained with undiluted antibody were generated in the same manner. Unstained control samples were made by adding 10 μL of HMTA to 10 μL of diluted freeze-dried platelet derivatives. This sample preparation was repeated using an isotype control antibody in place of the anti-CD47. All samples were incubated at room temperature away from light for 20 minutes. After incubation samples were diluted with 500 μL of HBS and 15,000 events were acquired for each sample using the ACEA NovoCyte flow cytometer. V450 fluorescence in the test samples was used to assess antibody binding to CD47 on the freeze-dried platelet derivatives surface. V450 fluorescence of the isotype control samples was used to monitor nonspecific binding.

Table 11 shows the mean fluorescence intensity of samples with various amounts of antibody (anti-CD47 or isotype control).

TABLE 11

| Mean CD47 MFI (Batch C) | | | | | |
|---|---|---|---|---|---|
| Volume Antibody (μL) | 0 | 2 | 4 | 10 | 20 |
| CD47-Pacific Blue | 438 | 2229 | 2904 | 4141 | 5528 |
| IgG Isotype-Pacific Blue | 438 | 536 | 591 | 771 | 1009 |

Table 12 shows the CD47 percent positivity at various concentrations of anti-CD47 antibody.

TABLE 12

| CD47 Percent Positive (Batch C) | | | | | |
|---|---|---|---|---|---|
| Volume Antibody (μL) | 0 (Unstained) | 2 | 4 | 10 | 20 (Undiluted) |
| Rep 1 | 0.00% | 11.89% | 23.07% | 36.51% | 40.18% |
| Rep 2 | 0.00% | 9.39% | 18.24% | 33.28% | 38.43% |
| Average | 0.00% | 10.64% | 20.66% | 34.90% | 39.31% |

Figure 22C:
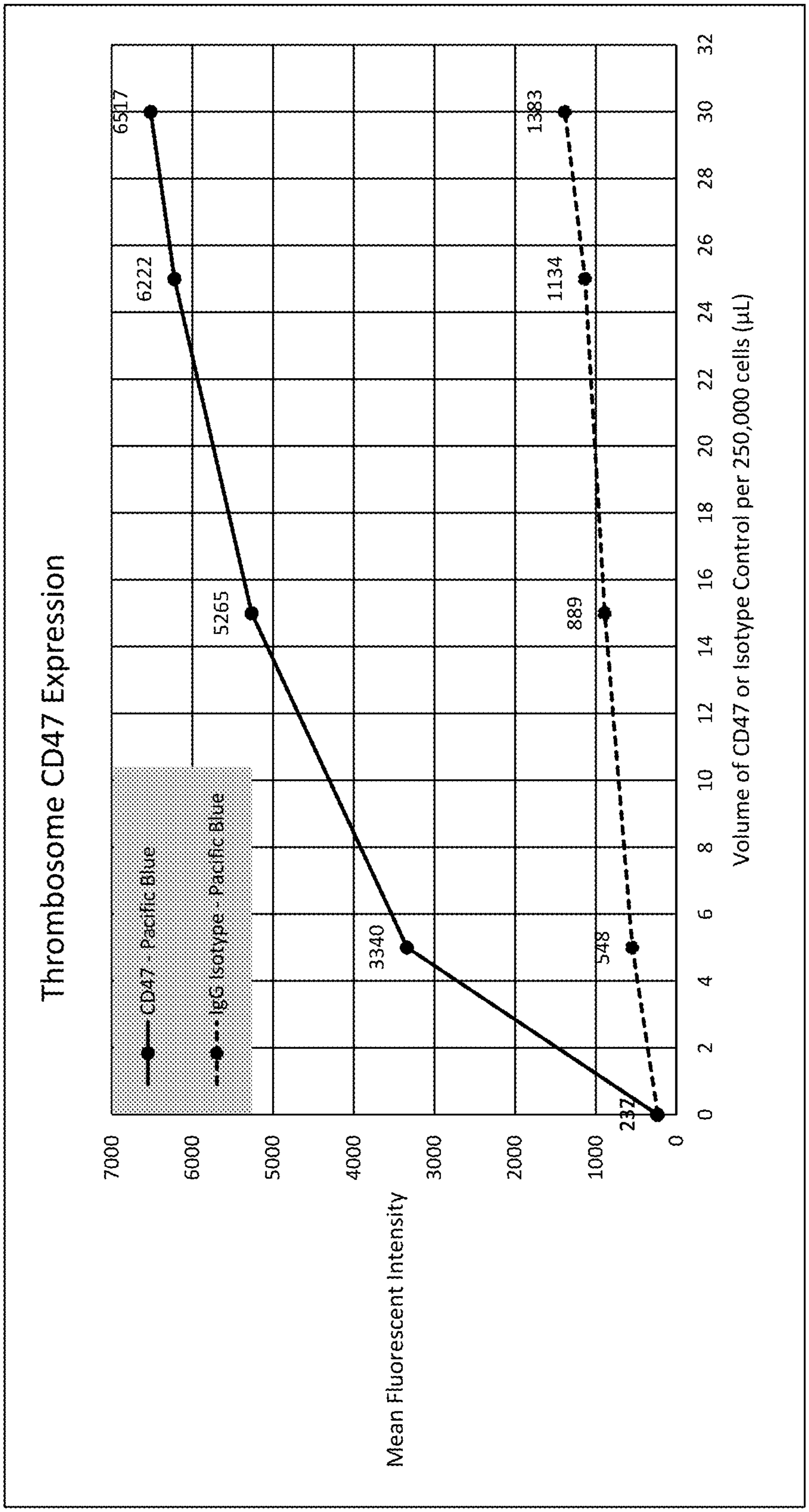
FIG. 22C is a plot of the mean fluorescence intensity of thrombosomes (250,000 cells) treated with various concentrations of a labeled anti-CD47 antibody or an isotype control.
Figure 22D:
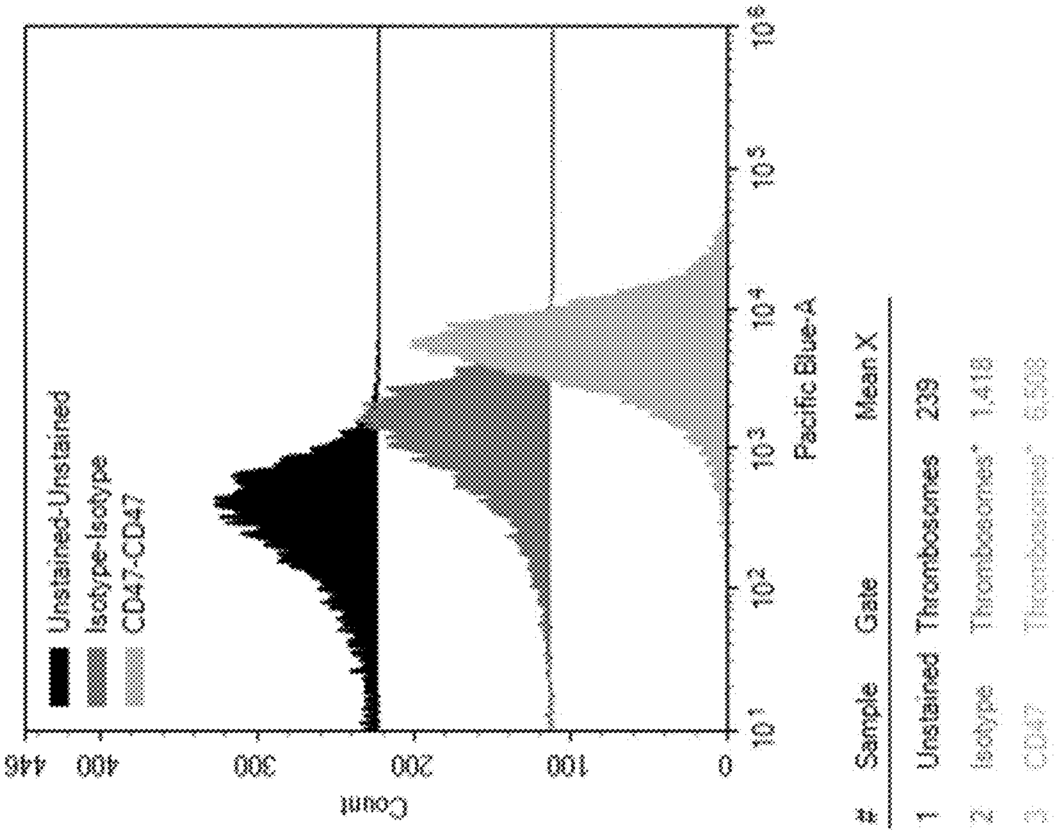
FIG. 22D is an exemplary histogram of thrombosomes that were unstained (black), stained with an isotype control antibody (dark gray), or stained with an anti-CD47 antibody (light gray).

A second vial of TFF freeze-dried platelet derivatives from a different lot was rehydrated and stained with increasing volumes of anti-CD47 conjugated to Pacific Blue or a corresponding isotype control. All sampled contained 250,000 cells. Again, fluorescent signal that was ~5× to 6× over background (FIG. 22C) and an overall CD47 positivity of ~50% (Table 15). An exemplary histogram is shown in FIG. 22D.

A second round of testing was performed on a new TFF freeze-dried platelet derivatives sample using an increased amount of antibody and decreased number of freeze-dried platelet derivatives per sample in order to improve the intensity of the signal caused by anti-CD47 binding to the freeze-dried platelet derivatives. The initial concentration of a freeze-dried platelet derivatives sample was determined using the AcT diff 2 and the concentration of a 1 mL aliquot was adjusted to $25\times10^3$ per μL using HMTA. Samples were stained in duplicate with increasing amounts of antibody according to Table 13 below. The final volume for each sample was held constant at 40 μL. The total number of freeze-dried platelet derivatives in each sample was help constant at $250\times10^3$ per μL. This sample preparation was repeated using an isotype control antibody in place of the anti-CD47.

TABLE 13

| Volume Tsomes | Volume AB (μL) | Volume HMTA (μL) | Total |
|---|---|---|---|
| 10 | 0 | 30 | 40 |
| 10 | 5 | 25 | 40 |
| 10 | 15 | 15 | 40 |
| 10 | 25 | 5 | 40 |
| 10 | 30 | 0 | 40 |

All samples were incubated at room temperature away from light for 20 minutes. After incubation samples were diluted with 500 μL of HBS 15,000 events were acquired for each sample using the ACEA NovoCyte flow cytometer. V450 fluorescence in the test samples was used to assess antibody binding to CD47 on the freeze-dried platelet derivatives surface. V450 fluorescence of the isotype control samples was used to monitor nonspecific binding.

Table 14 shows the mean fluorescence intensity of samples with various amounts of antibody (anti-CD47 or isotype control).

TABLE 14

| Mean CD47 MFI (Batch D) | | | | | |
|---|---|---|---|---|---|
| Volume Antibody (μL) | 0 | 5 | 15 | 25 | 30 |
| Anti-CD47-Pacific Blue | 237 | 3340 | 5265 | 6222 | 6517 |
| IgG Isotype-Pacific Blue | 232 | 548 | 889 | 1134 | 1383 |

Table 15 shows the CD47 percent positivity at various concentrations of anti-CD47 antibody.

TABLE 15

| CD47 Percent Positivity (Batch D) | | | | | |
|---|---|---|---|---|---|
| Sample | Unstained | 5 uL | 15 uL | 25 uL | 30 uL |
| Rep 1 | 0.00% | 48.79% | 49.73% | 41.23% | 38.21% |
| Rep 2 | 0.00% | 42.29% | 51.75% | 38.64% | 33.48% |
| Average | 0.00% | 45.54% | 50.74% | 39.94% | 35.85% |

Example 9. Microparticle Content Reduction

Figure 23A:
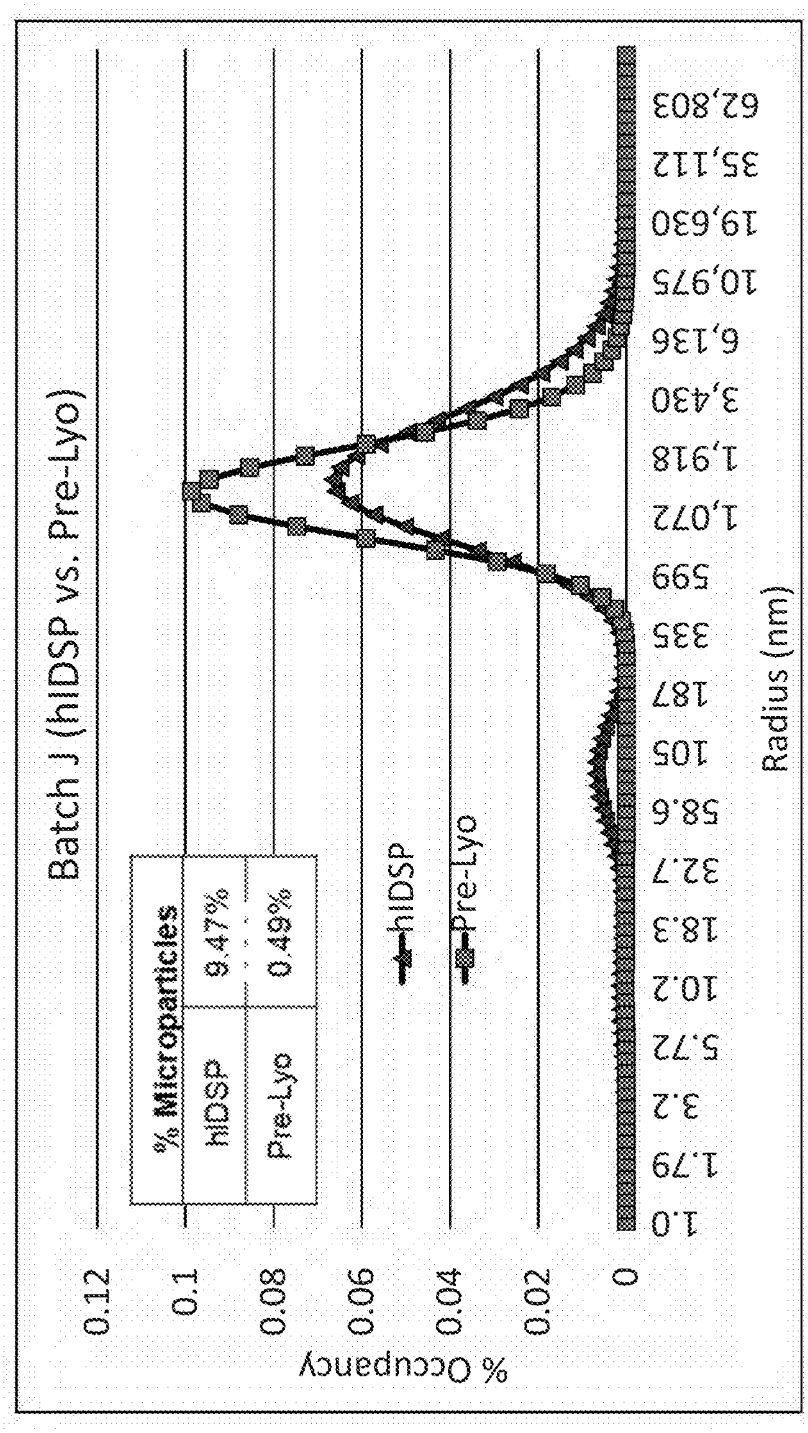
FIG. 23A is a plot of the percent occupancy of particles of different radii in human in-date stored platelets (Batch J) and platelet derivatives (pre-lyophilization) derived therefrom as determined by dynamic light scattering (DLS).
Figure 23B:
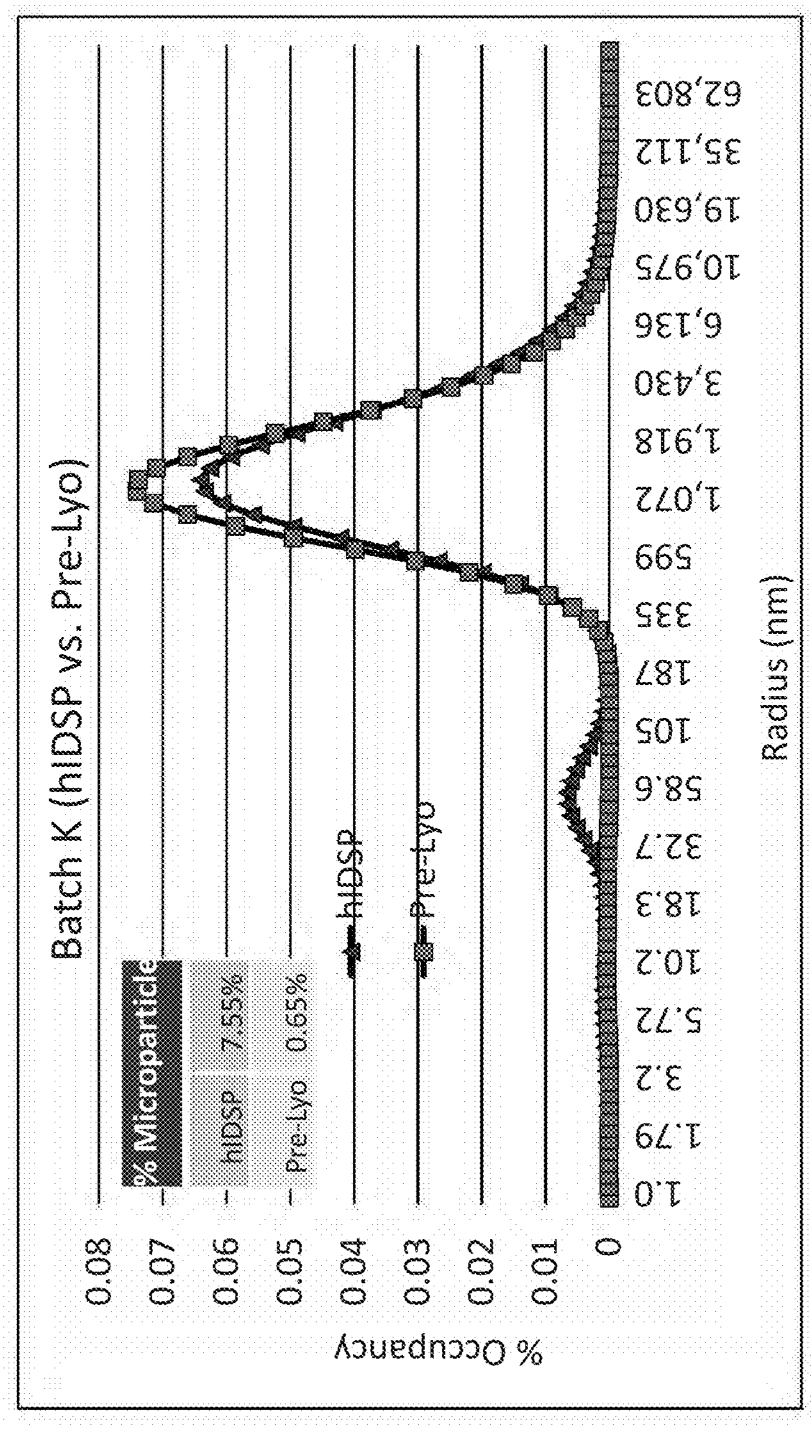
FIG. 23B is a plot of the percent occupancy of particles of different radii in human in-date stored platelets (Batch K) and platelet derivatives (pre-lyophilization) derived therefrom as determined by DLS.
Figure 23C:
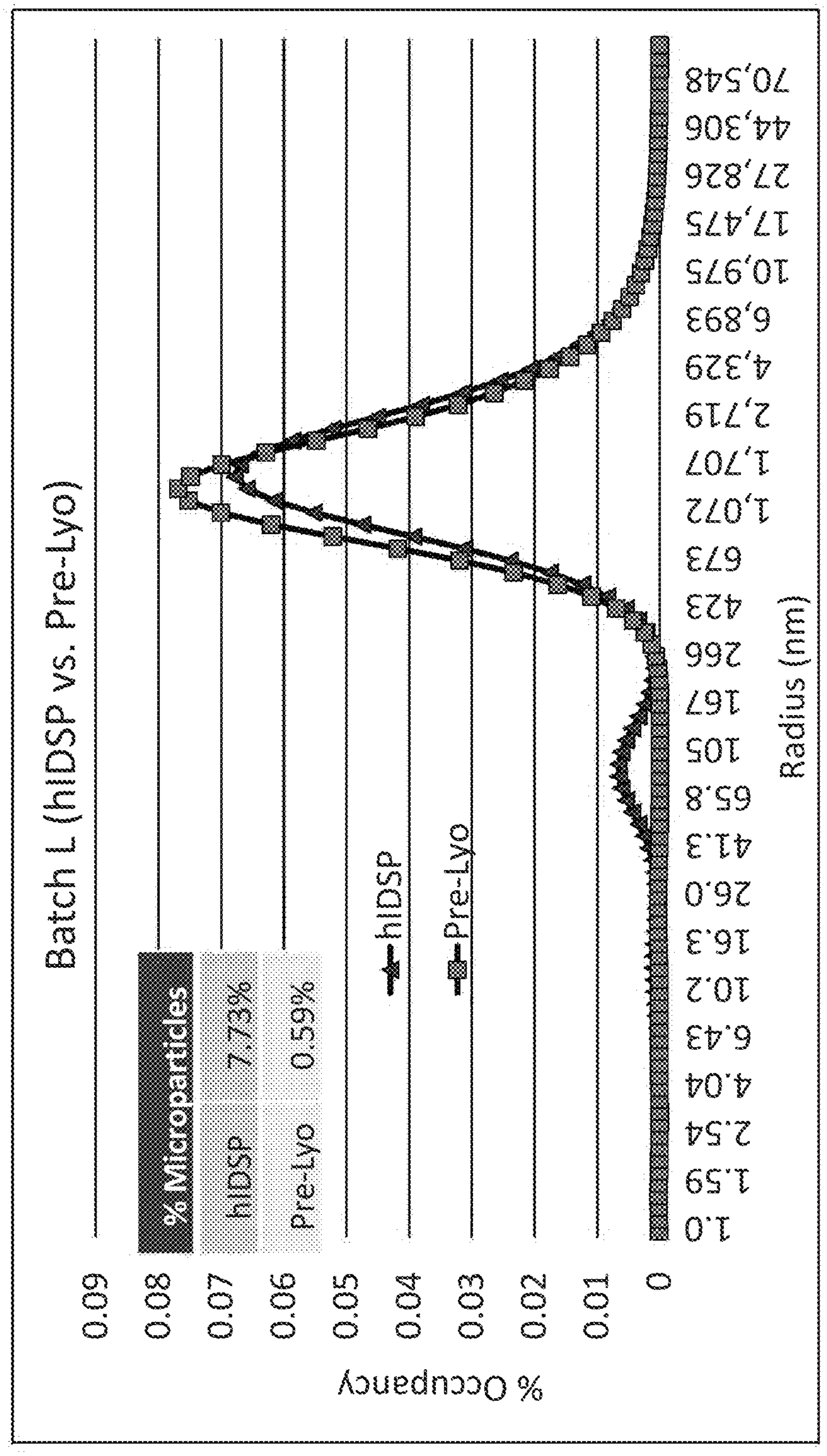
FIG. 23C is a plot of the percent occupancy of particles of different radii in human in-date stored platelets (Batch L) and platelet derivatives (pre-lyophilization) derived therefrom as determined by DLS.

The microparticle content of human in-date stored platelets (hIDSP) compared to freeze-dried platelet derivative composition prepared according to Example 1 (but not lyophilized) were compared using dynamic light scattering. The results are shown in FIGS. 23A-C and Table 16. FIGS. 23A-C are histograms that are normalized to a relative intensity so that the sum of the intensity of each data point equals 1.0. For example, if a particular data point has a y-axis value of 0.1 then it can be typically interpreted that the data point makes up 10% of the scattering intensity of the sample.

A pool of the apheresis units used to manufacture a batch of freeze-dried platelet derivative composition was made for analysis. This sample type is denoted as "hIDSP." A 1 mL aliquot of this hIDSP (human In-Date Stored Platelets) pool was taken for dynamic light scattering (DLS; Thrombolux—Light Integra) analysis. A sample from this aliquot was then drawn into a capillary and inserted into the DLS instrument. The capillary sat in the instrument for 1 minute to allow the temperature and movement to equilibrate. The internal temperature of the machine is 37° C. After 1 minute of equilibration, the viscosity setting for the sample was chosen. The DLS instrument has a built-in viscosity setting for samples that are in plasma, such as apheresis units. This viscosity setting was used for hIDSP samples. The viscosity of this setting is 1.060 cP (centipoise). After the plasma viscosity setting was selected, the sample was analyzed. From the same hIDSP aliquot, a $2^{nd}$ and $3^{rd}$ sample were drawn into a capillary and analyzed with this hIDSP protocol, for triplicate analysis. Microparticle percentage was then determined from the data.

"Pre-Lyo" samples are an in-process sample from the freeze-dried platelet derivatives manufacturing process. This sample type is the material taken right before lyophilization. A viscosity measurement of the sample was taken in order to analysis these samples with DLS. The viscometer (Rheosense μVISC) has a built-in oven that is used to bring the sample to the temperature of the DLS instrument (37° C.). Prior to viscosity analysis of the sample the oven must be heated to 37° C. To determine the viscosity of the pre-lyo sample a 400-350 μL sample was drawn into a syringe and inserted into the viscometer. After inserting the sample into the viscometer, the instrument temperature needs to reach 37° C. again. After the oven reaches 37° C. the sample was analyzed with all settings on AUTO except for "Measurement Volume" which was set to 400 μL. This viscosity was used for the DLS measurement of the same sample. A 1 mL aliquot of this pre-lyo sample was taken for dynamic light scattering (DLS; Thrombolux—LightIntegra) analysis. A sample from this aliquot was then drawn into a capillary and inserted into the DLS instrument. The capillary sat in the instrument for 1 minute to allow the temperature and movement to equilibrate. The internal temperature of the machine is 37° C. After 1 minute of equilibration, the previously measured viscosity was put into the viscosity setting of the DLS instrument. After the viscosity was entered, the sample was analyzed. From the same pre-lyo aliquot, a $2^{nd}$ and $3^{rd}$ sample were drawn into a capillary and analyzed with this Pre-Lyo Protocol, for triplicate analysis. Microparticle percentage was then determined from the data.

Freeze-dried platelet derivatives were rehydrated according to standard protocol and diluted 1:5 in a mixture of SeraSub (CST Technologies, Inc.) and ACD. The SeraSub/ACD diluent consists of a 1:9 dilution of ACD in SeraSub. 1 mL of the 1:5 dilution of freeze-dried platelet derivatives was prepared for analysis by DLS. A sample of the freeze-dried platelet derivatives dilution was drawn into the capillary and inserted into the DLS instrument. The capillary sat in the instrument for 1 minute to allow the temperature and movement to equilibrate. The internal temperature of the machine is 37° C. After 1 minute of equilibration, the viscosity setting for the sample was chosen. The viscosity used for the sample was 1.200 cP. After the viscosity was entered, the sample was analyzed. A $2^{nd}$, $3^{rd}$, and $4^{th}$ sample were drawn into a capillary and analyzed with this freeze-dried platelet derivatives protocol, for quadruplicate analysis. Microparticle percentage was then determined from the data (and platelet radius where applicable).

TABLE 16

| Batch Number | hIDSP % MP | Pre-Lyo % MP |
|---|---|---|
| Batch J | 9.47% | 0.49% |
| Batch K | 7.55% | 0.65% |
| Batch L | 7.73% | 0.59% |
| Average | 8.25% | 0.58% |

Figure 24A:
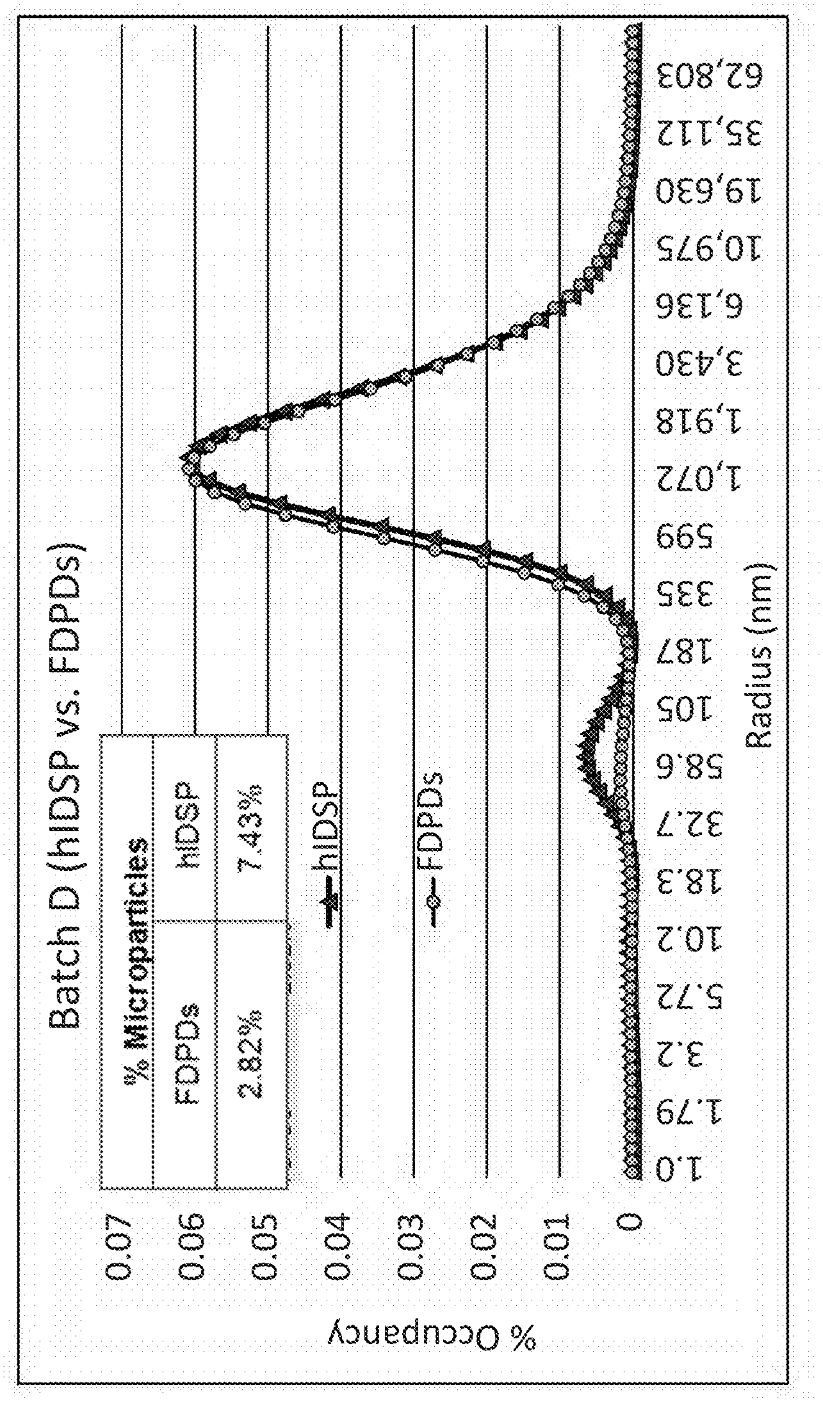
FIG. 24A is a plot of the percent occupancy of particles of different radii in human in-date stored platelets (Batch D) and platelet derivatives (pre-lyophilization) derived therefrom as determined by DLS.
Figure 24B:
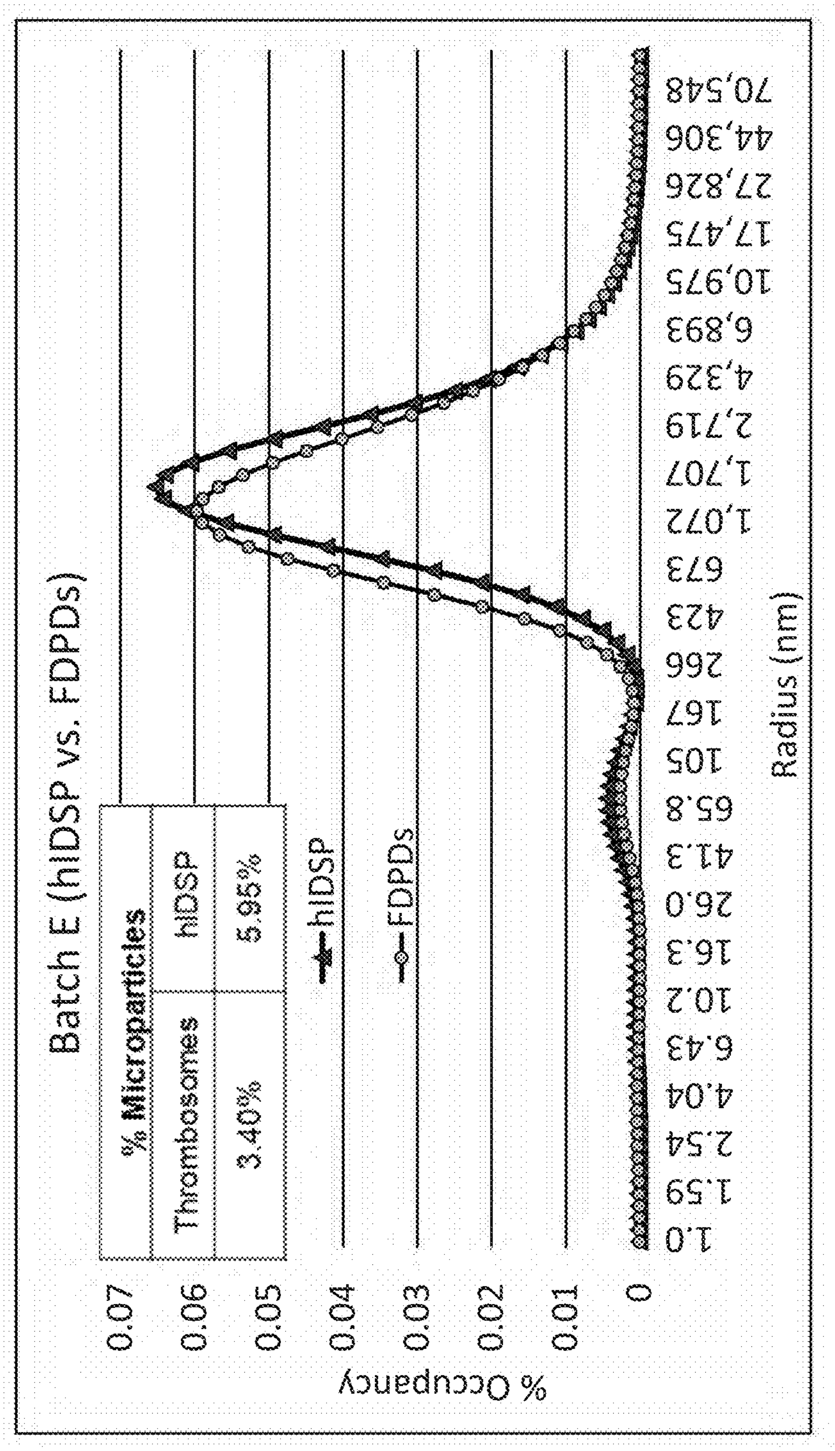
FIG. 24B is a plot of the percent occupancy of particles of different radii in human in-date stored platelets (Batch E) and platelet derivatives (pre-lyophilization) derived therefrom as determined by DLS.
Figure 24C:
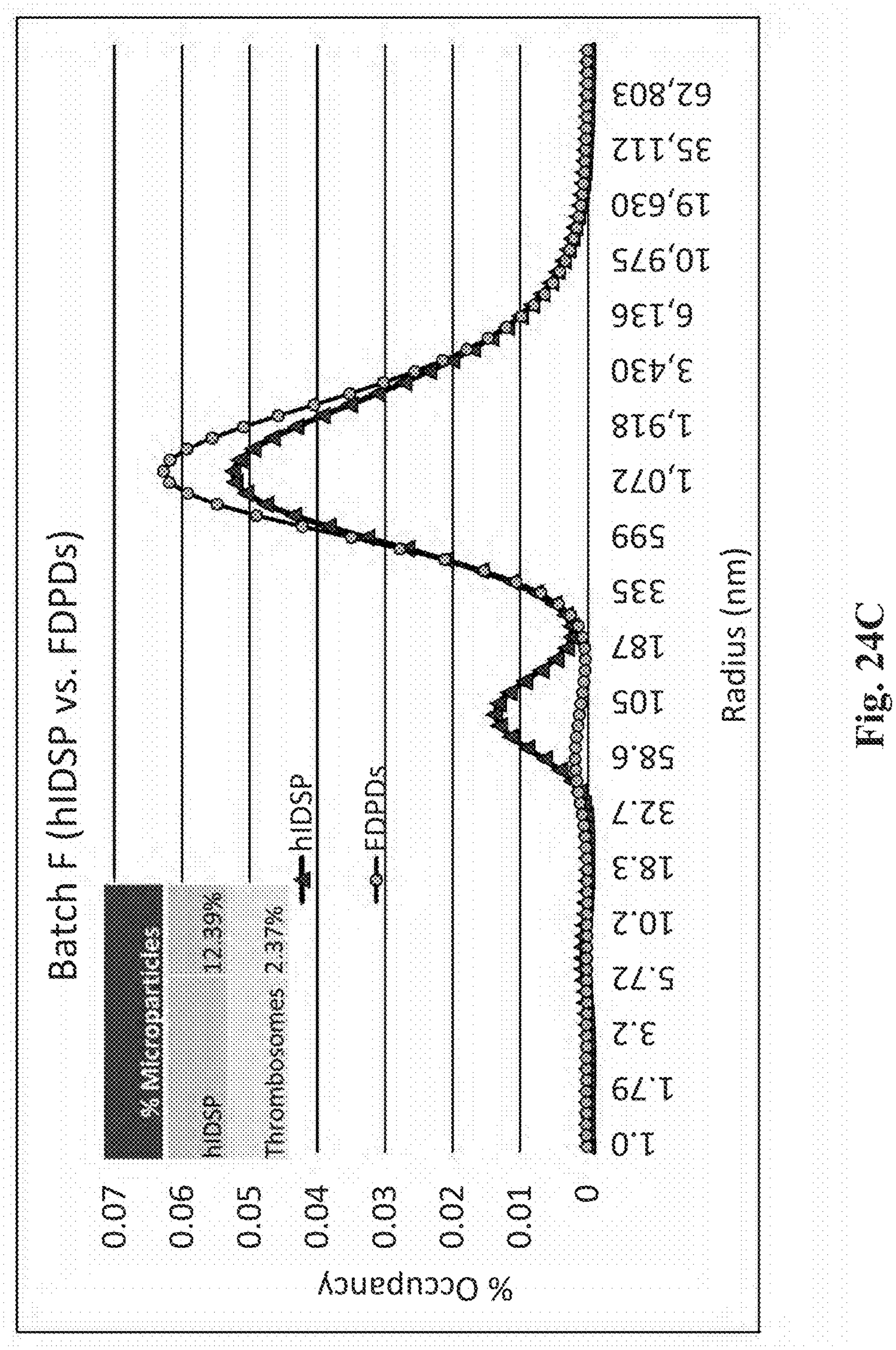
FIG. 24C is a plot of the percent occupancy of particles of different radii in human in-date stored platelets (Batch F) and platelet derivatives (pre-lyophilization) derived therefrom as determined by DLS.

In additional experiments, the microparticle content of human in-date stored platelets (hIDSP) compared to rehydrated freeze-dried platelet derivatives prepared according to Example 1 were compared using dynamic light scattering (DLS). The results are shown in FIGS. 24A-C and Table 17.

TABLE 17

| Batch Number | hIDSP % MP | Freeze-dried platelet derivatives % MP |
|---|---|---|
| Batch D | 7.43% | 2.82% |
| Batch E | 5.95% | 3.40% |
| Batch F | 12.39% | 2.37% |
| Average | 8.59% | 2.86% |

Example 10. Metabolite Analysis

Table 18 shows an analysis of pH and metabolites present in the preparation of freeze-dried platelet derivative composition as described in Example 1, including analyses of the raw platelet material, after an initial dilution, after the platelet derivatives were concentrated, and after the end of the diafiltration process, as determined using an i-STAT handheld blood analyzer and CG4+ cartridges.

Platelet samples for iStat analysis were collected at different processing steps in small volumes (1 ml). The initial sample for iStat analysis named "Raw Material" was collected after the platelet donor units were pooled together but before any processing had occurred. Named "Initial Dilution", The pooled platelet units were 1:1 diluted with Control Buffer before subjecting the platelets to TFF processing. At the end of the concentration phase of TFF, the "End of Conc" sample was drawn from the platelet product. After washing the cells, the "End of DV (Pre-Lyo)" sample was drawn as a representation of the product as it enters the lyophilizer.

TABLE 18

| | Batch P | | | |
|---|---|---|---|---|
| iStat CG4+ | Raw Material | Initial Dilution | End of Conc | End of DV (Pre-Lyo) |
| pH | 7.6 | 7.5 | 7.4 | 7.1 |
| $pCO_2$ (mmHg) | 14.9 | 12.5 | 14.7 | 18 |
| $pO_2$ (mmHg) | 147 | 176 | 160 | 163 |
| $HCO_3$ (mmol/L) | 14.7 | 10 | 9.3 | 5.9 |
| $TCO_2$ (mmol/L) | 15 | 10 | 10 | 6 |
| $sO_2$ (%) | 100 | 100 | 100 | 99 |
| Lac (mmol/L) | 6.14 | 2.97 | 2.6 | 0.55 |

Example 11. Pathogen Reduction

The reduction of pathogens is generally desirable in blood products. One method of pathogen reduction involves the use of a photosensitive nucleic acid-intercalating compound to alter the nucleic acids of pathogens upon illumination with an appropriate wavelength.

Figure 25A:
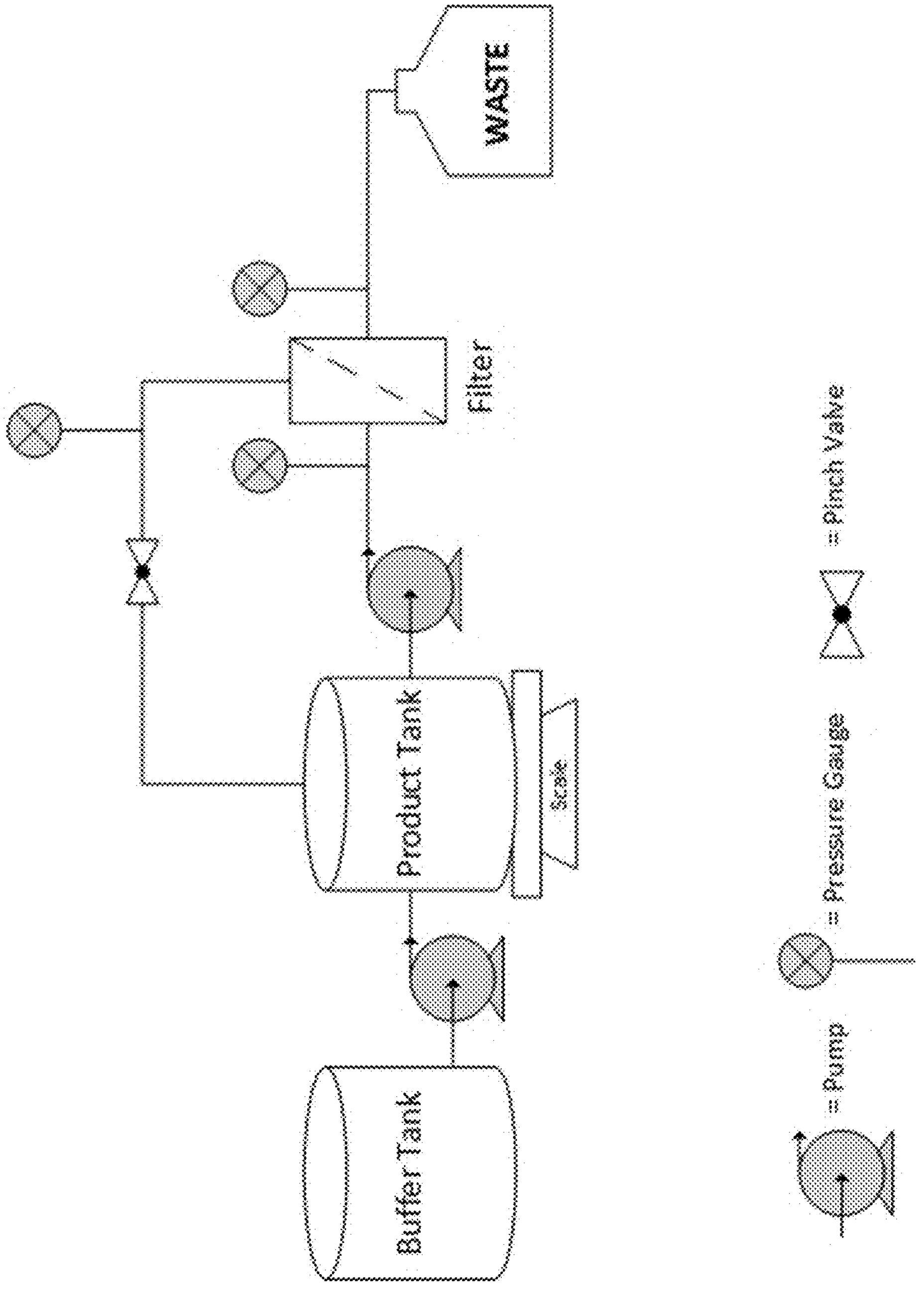
FIG. 25A is an exemplary schematic of a pathogen reduction system.
Figure 25B:
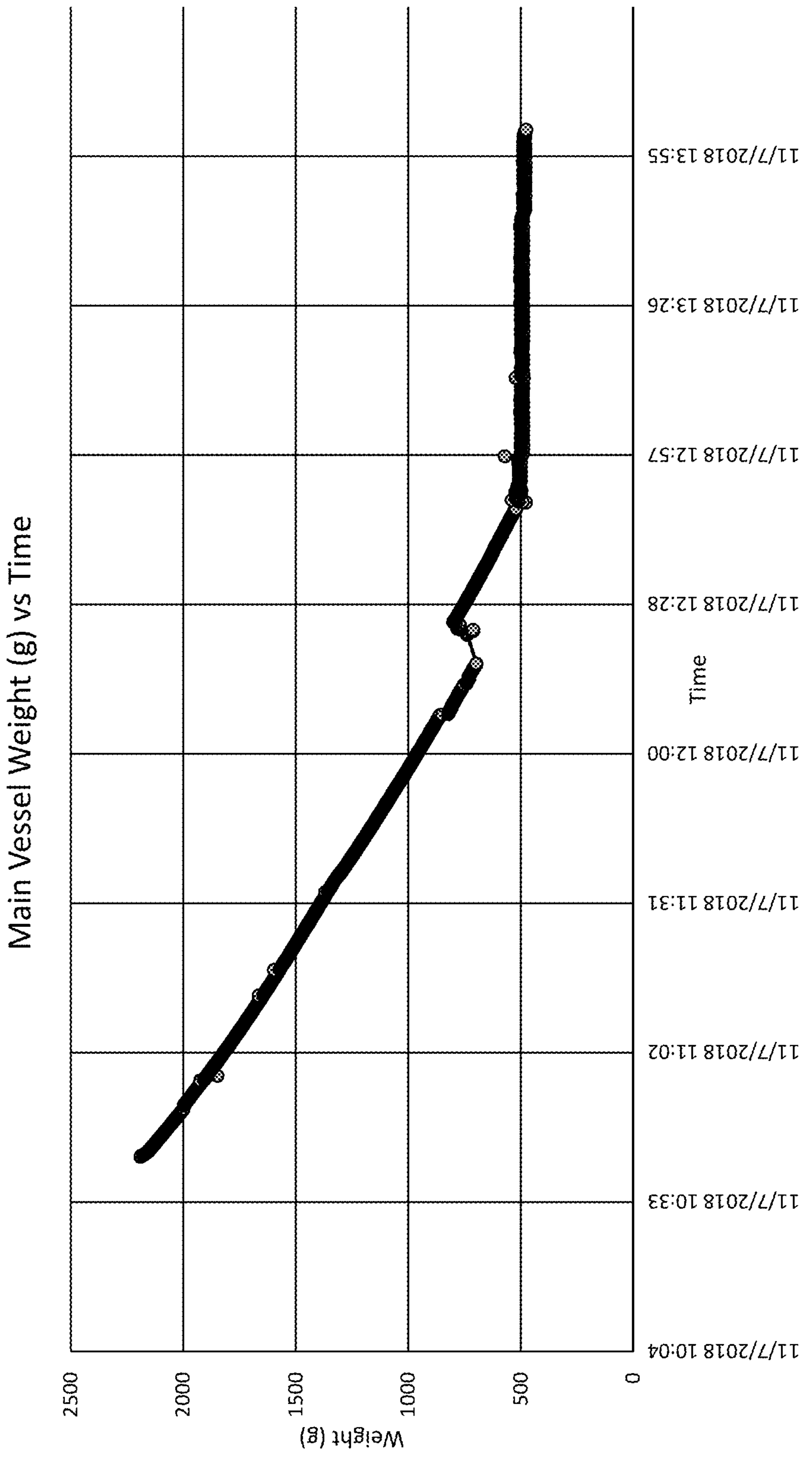
FIG. 25B is a plot of the weight of a reaction vessel over time.
Figure 25C:
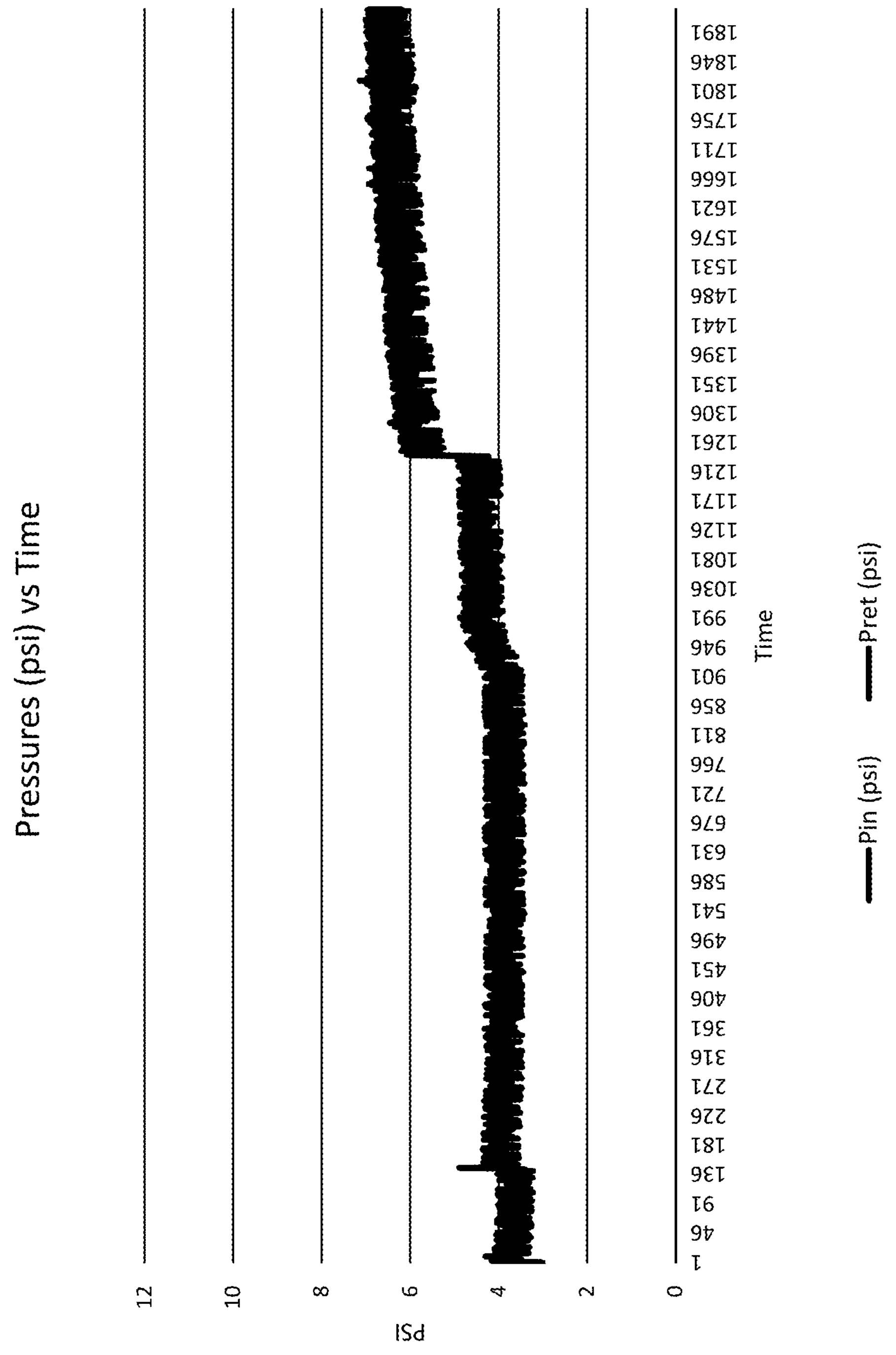
FIG. 25C is a plot of pressure in a reaction vessel over time.

The INTERCEPT® system (made by Cerus) uses amotosalen, a nucleic acid intercalating compound that forms cross-links in nucleic acid upon illumination with UVA. Exemplary parameters for use of this system are shown in Table 19, and a schematic of the system is shown in FIG. 25A, while exemplary process data are shown in FIGS. 25B-C for 2.6 L of processed material in 198 minutes (approx. 14/min average).

DLS was performed as described in Example 9.

TABLE 19

| Process Parameter | Specification |
|---|---|
| Feed Pump | 600 ml/min (3/8" Tube) |
| Retentate Pressure | Target = 4 to 6 PSI<br>Criteria = 2 to 8 PSI |
| Buffer Pump | 100 ml/min (noncritical) |
| DiaVolumes | X2 DVs |
| Concentration Factor | ~4 (from initial dilution) |

Exemplary comparative data of pH and metabolites of freeze-dried platelet derivative composition prepared as in Example 1, with or without treatment with the INTERCEPT® system is shown in Table 20.

TABLE 20

| iSTAT | Raw Material | | Initial Dilution | | End of Con | | End of DV (Pre-Lyo) | |
|---|---|---|---|---|---|---|---|---|
| CG4+ | Control | Treated | Control | Treated | Control | Treated | Control | Treated |
| pH | 7.2 | 7.2 | 7.3 | 7.1 | 7.3 | 7.3 | 7.3 | 7.2 |
| pCO2 (mmHg) | 32.9 | 25.7 | 16.5 | 29.1 | 16.1 | 14.4 | 11.3 | 12.4 |
| pO2 (mmHg) | 67 | 149 | 167 | 150 | 142 | 155 | 145 | 153 |
| HCO3 (mmol/L) | 12.7 | 10.2 | 8.5 | 8.1 | 7.8 | 6.7 | 5.8 | 5.1 |
| TCO2 (mmol/L) | 14 | 11 | 9 | 9 | 8 | 7 | 6 | 5 |

TABLE 20-continued

| iSTAT | Raw Material | | Initial Dilution | | End of Con | | End of DV (Pre-Lyo) | |
|---|---|---|---|---|---|---|---|---|
| CG4+ | Control | Treated | Control | Treated | Control | Treated | Control | Treated |
| sO2 (%) | 89 | 99 | 99 | 98 | 99 | 99 | 99 | 99 |
| Lac (mmol/L) | 6.56 | 6.75 | 3.26 | 3.33 | 2.80 | 2.50 | 0.91 | 1.19 |

Exemplary comparative data of functional characterization (AcT count and aggregation parameters) and cell-surface markers are shown in Tables 21 (hIDSPs), 22 (prior to lyophilization) and Table 23 (following lyophilization and rehydration in 10 mL sterile water for injection to a concentration of approximately $1.8\times10^6/\mu L$ (individual sample counts are shown in Table 23).

TABLE 21

| | | Raw Material (hIDSP) | |
|---|---|---|---|
| | | Batch M "Control" | Batch N "Treated" |
| AcT Counts | AVG (x10^3) | 1212 | 1120 |
| Aggregation (%) or thrombin-induced trapping (%) | Collagen AVG (aggregation) | 22 | 21 |
| | Plasma—A. Acid AVG (aggregation) | 75 | 84 |
| | 250k Thrombin AVG (thrombin-induced trapping) | 97 | 97 |
| | Buffer—A. Acid AVG (aggregation) | 94 | 92 |
| Flow (percent positivity) | CD41 | 93.5 | 97.6 |
| | CD42 | 91.4 | 95.8 |
| | Double Positive % | 92.0 | 95.6 |
| | CD62 | 23.9 | 42.5 |
| | Annexin V (AV5) | 3.8 | 8.4 |

TABLE 22

| | | Pre-Lyophilization | |
|---|---|---|---|
| | | Batch M "Control" | Batch N "Treated" |
| AcT Counts | AVG (x10^3) | 1787 | 2057 |
| Aggregation (%) or thrombin-induced trapping (%) | Collagen AVG (aggregation) | 81 | 82 |
| | Plasma—A. Acid AVG (aggregation) | 93 | 84 |
| | 250k Thrombin AVG (thrombin-induced trapping) | 97 | 90 |
| | Buffer—A. Acid AVG (aggregation) | 89 | 95 |
| Flow (percent positivity) | CD41 | 98.4 | 97.0 |
| | CD42 | 98.2 | 95.4 |
| | Double Positive % | 97.5 | 94.3 |
| | CD62 | 26.7 | 41.6 |
| | AV5 | 10.6 | 13.7 |

TABLE 23

| | | Final Product QC | | |
|---|---|---|---|---|
| | | Batch M "Control" | | Batch N |
| | | V1 | V2 | V1 |
| AcT Counts | AVG (x10^3) | 1765 | 1767 | 1720 |
| thrombin-induced trapping (%) | 375K Thrombin | 84 | 66 | 74 |
| Flow (percent positivity) | CD41 | 85.5 | 79.5 | 91.2 |
| | CD42 | 85.1 | 79.2 | 90.6 |
| | Double Positive % | 84.6 | 78.8 | 90.1 |
| | CD62 | 87.0 | 93.2 | 87.1 |
| | AV5 | 95.4 | 95.0 | 92.6 |
| TGA | 4.8K TPH | 72.3 | 71.5 | 74.8 |
| Residual Plasma % | | 7.0% | | 8.4% |

Figure 26A:
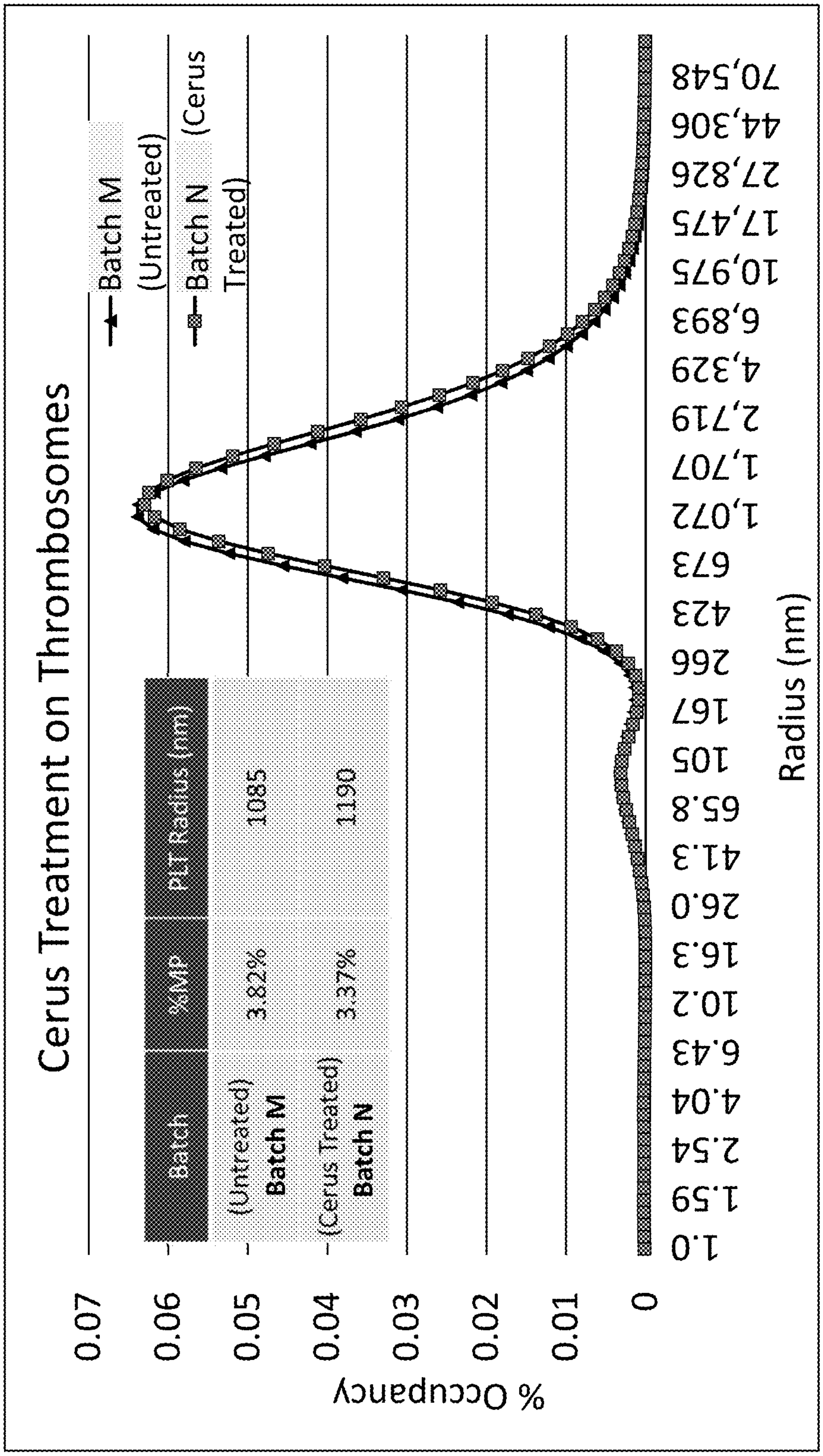
FIG. 26A is a plot of the percent occupancy of particles of different radii in rehydrated thrombosomes that were (Batch N) or were not (Batch M) treated to remove pathogens, as determined by DLS.
Figure 26B:
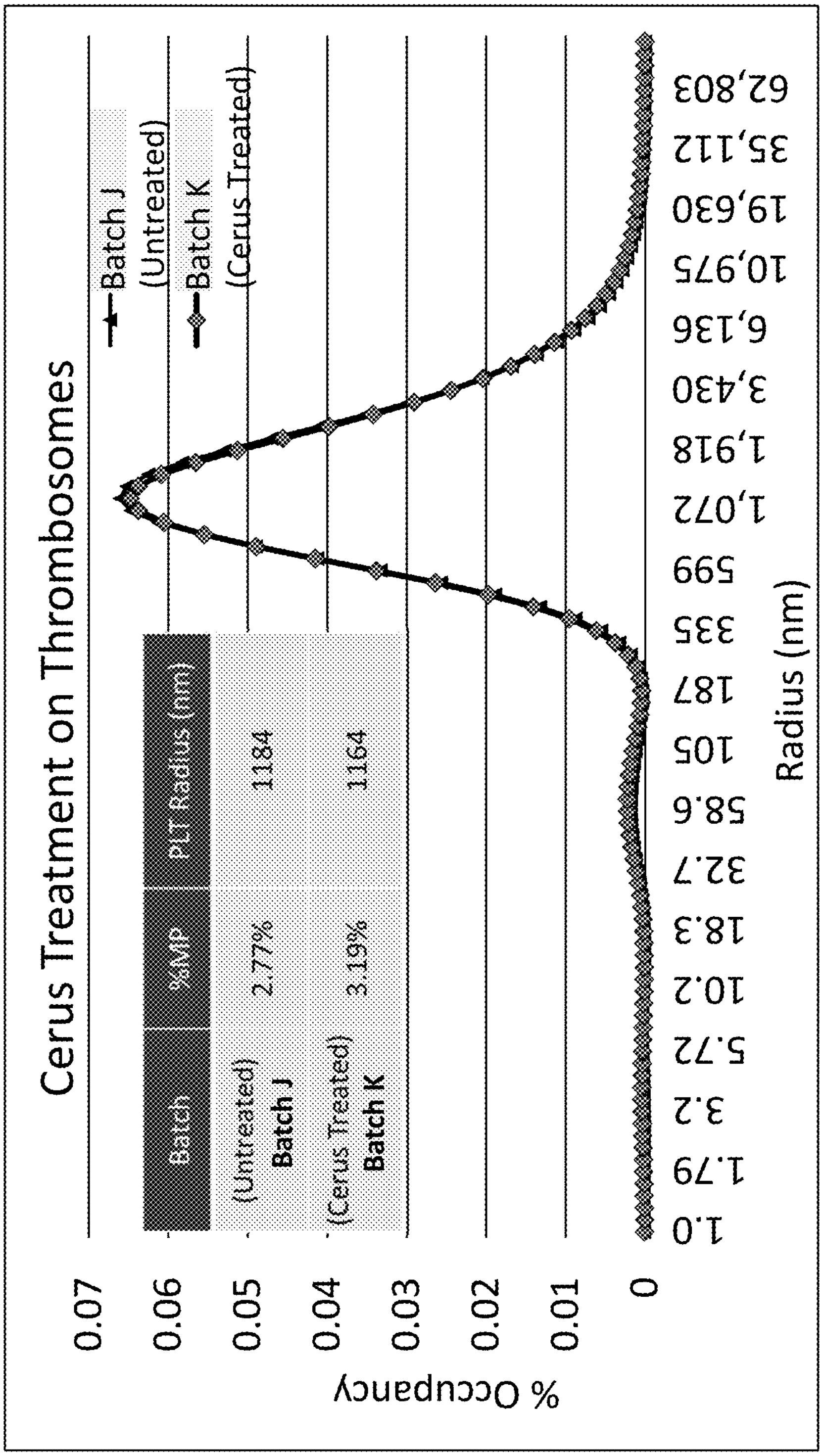
FIG. 26B is a plot of the percent occupancy of particles of different radii in rehydrated thrombosomes that were (Batch K) or were not (Batch J) treated to remove pathogens, as determined by DLS.
Figure 27A:
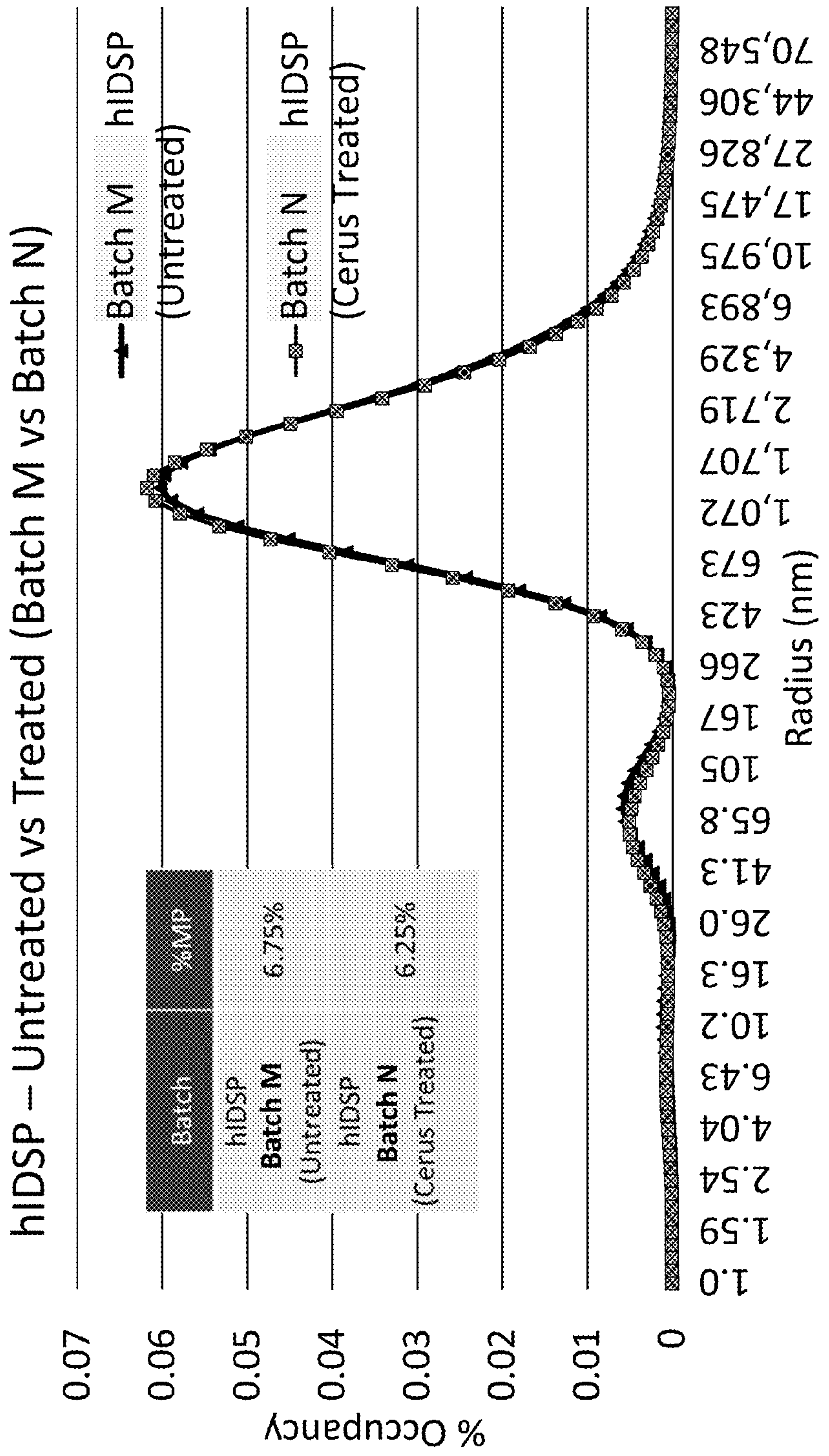
FIG. 27A is a plot of the percent occupancy of particles of different radii in hIDSPs that were (Batch N) or were not (Batch M) treated to remove pathogens, as determined by DLS.
Figure 27B:
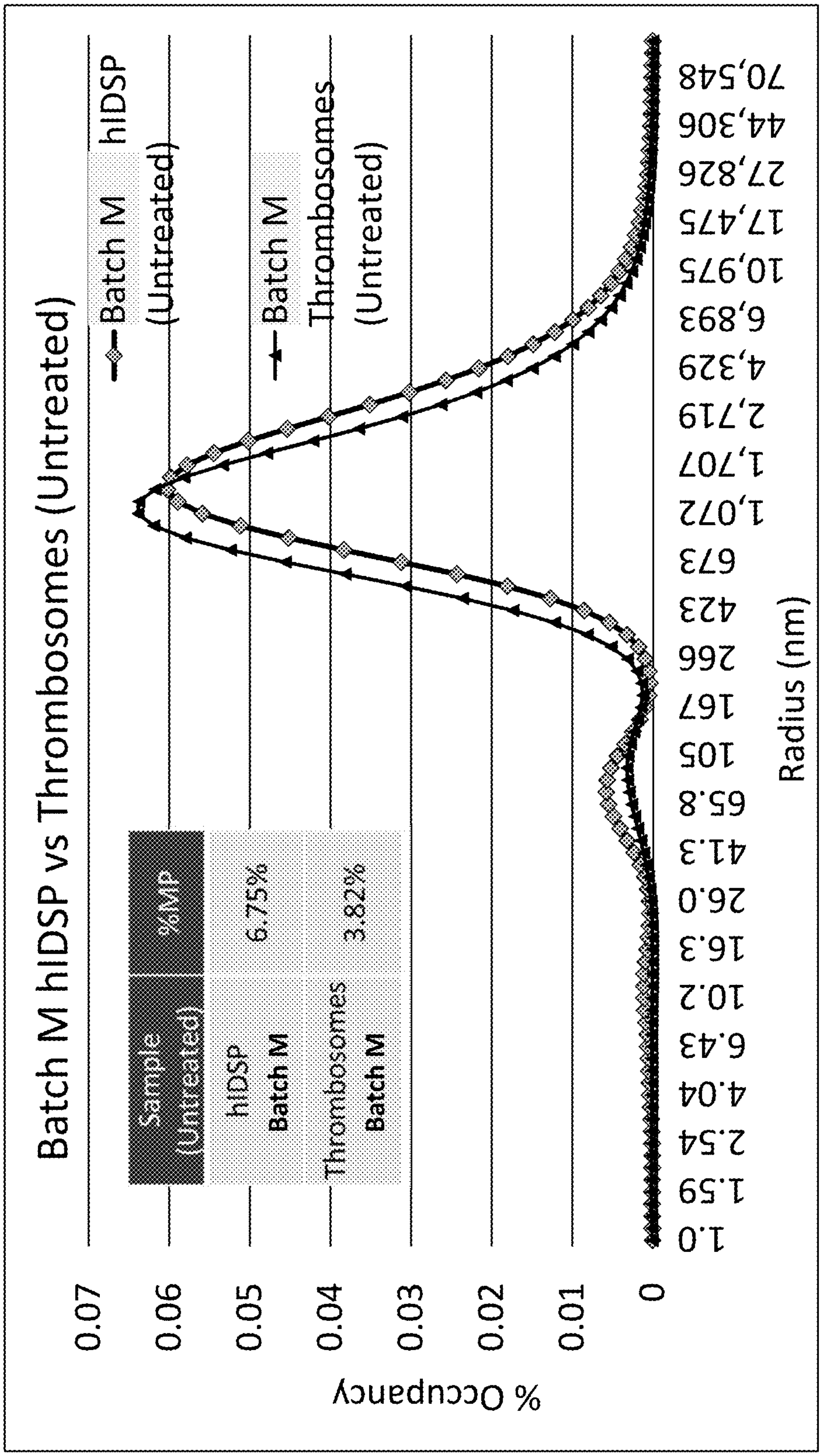
FIG. 27B is a plot of the percent occupancy of particles of different radii in hIDSPs and thrombosomes derived therefrom (Batch M) that were not treated to remove pathogens, as determined by DLS.
Figure 27C:
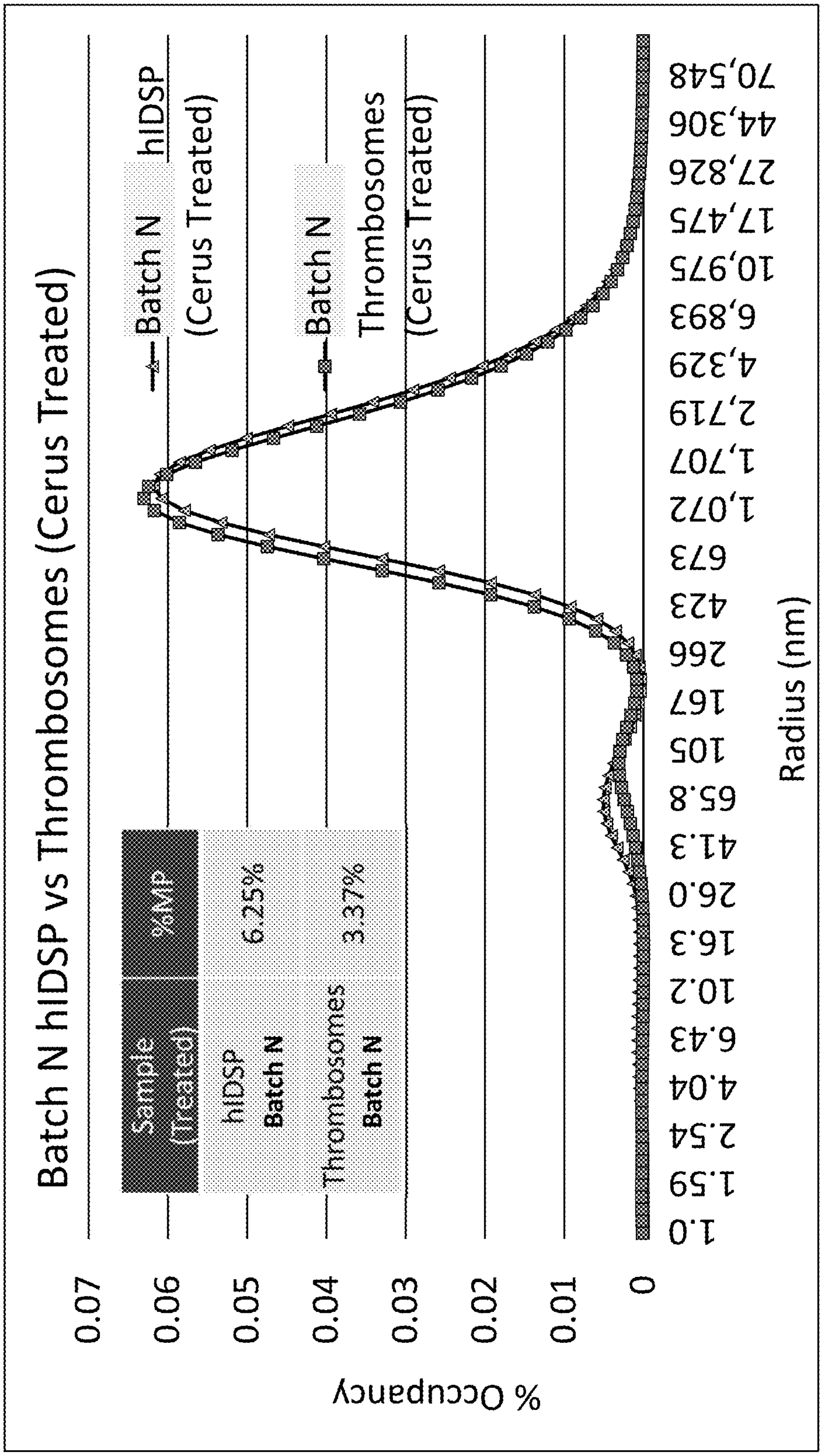
FIG. 27C is a plot of the percent occupancy of particles of different radii in hIDSPs and thrombosomes derived therefrom (Batch N) that were treated to remove pathogens, as determined by DLS.
Figure 28A:
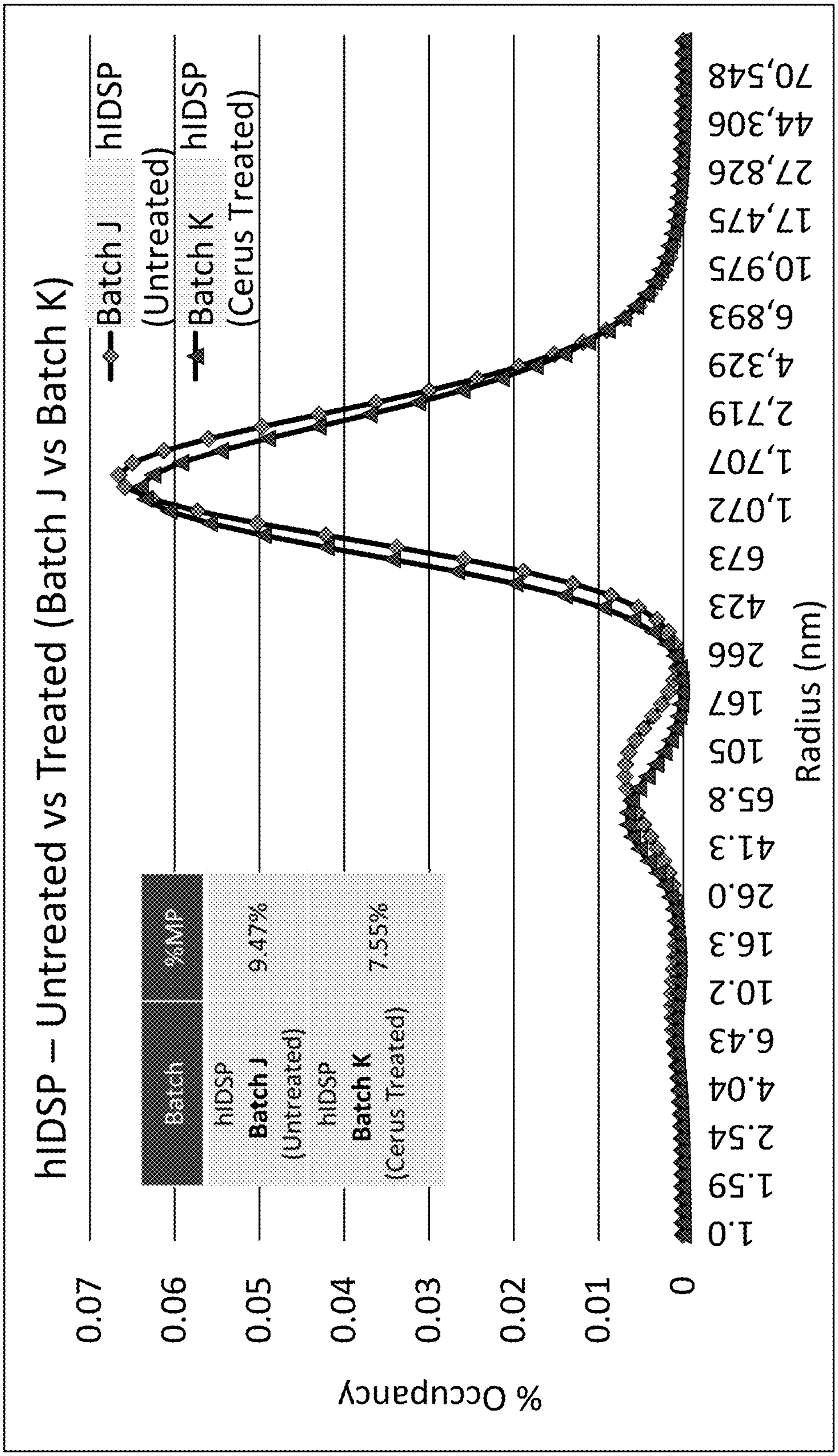
FIG. 28A is a plot of the percent occupancy of particles of different radii in hIDSPs that were (Batch K) or were not (Batch J) treated to remove pathogens, as determined by DLS.
Figure 28B:
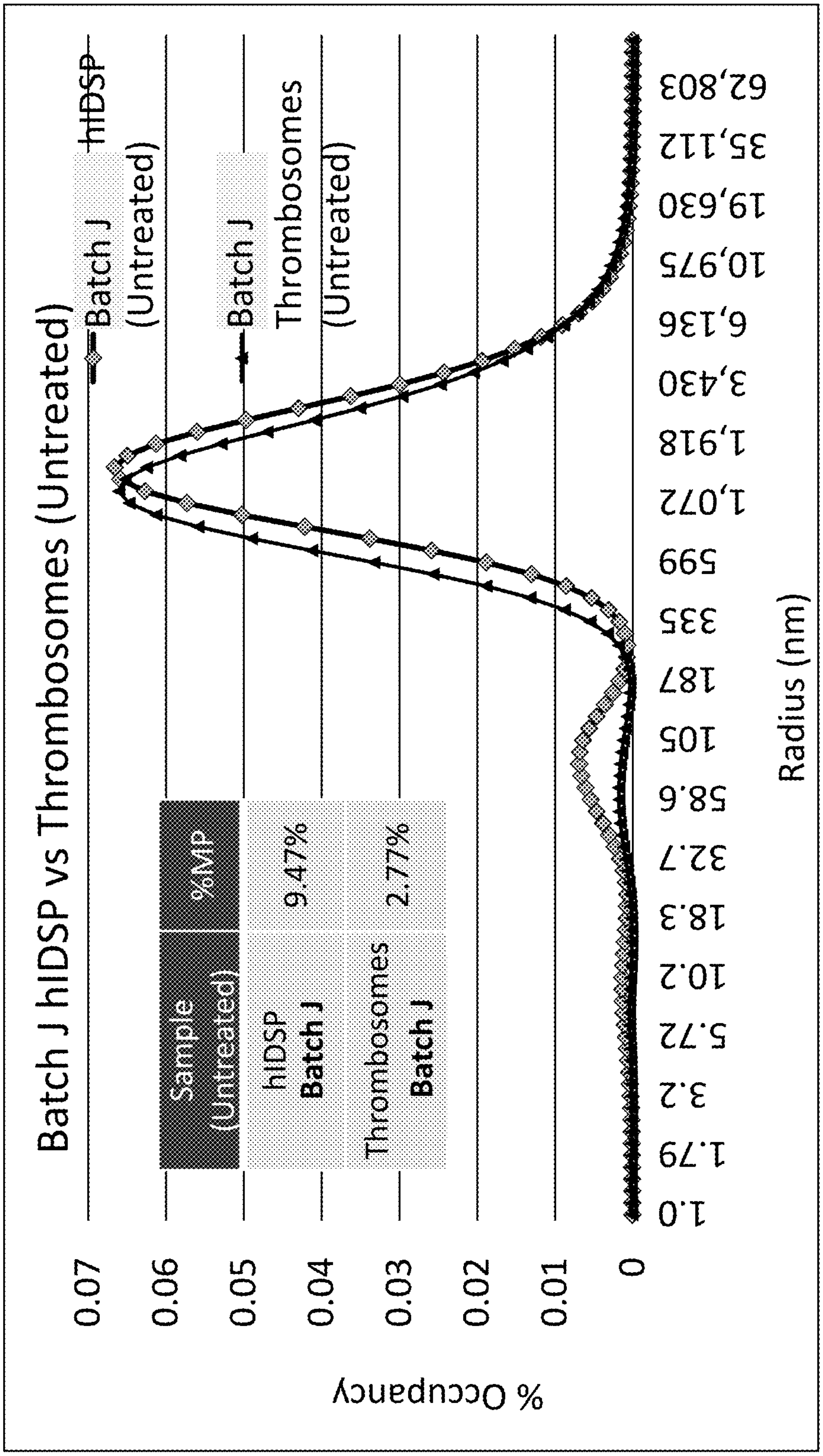
FIG. 28B is a plot of the percent occupancy of particles of different radii in hIDSPs and thrombosomes derived therefrom (Batch J) that were not treated to remove pathogens, as determined by DLS.
Figure 28C:
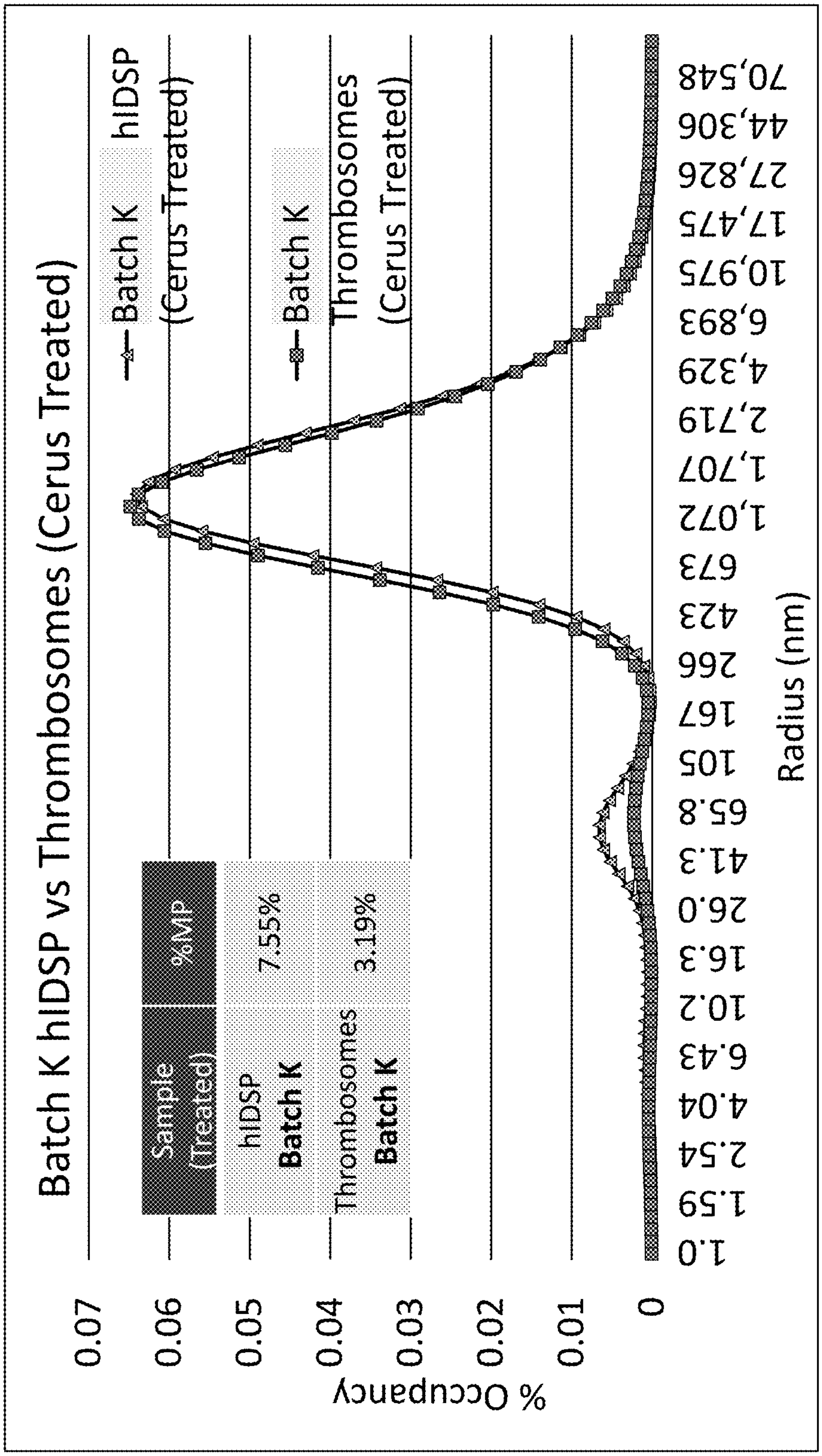
FIG. 28C is a plot of the percent occupancy of particles of different radii in hIDSPs and thrombosomes derived therefrom (Batch K) that were treated to remove pathogens, as determined by DLS.

The microparticle content at various stages of the preparation of freeze-dried platelet derivatives was also determined as described in Example 9. FIGS. 26A-B show the similarity of rehydrated freeze-dried platelet derivatives prepared with and without pathogen reduction treatment. A summary of these data is shown in Table 24. FIG. 27A shows the microparticle content of hiDSPs with or without pathogen reduction treatment. FIGS. 27B-C compare the microparticle content of the hiDSPs shown in FIG. 29A and rehydrated freeze-dried platelet derivatives prepared therefrom. A summary of these data is shown in Table 25. FIG. 28A shows the microparticle content of hiDSPs with or without pathogen reduction treatment. FIGS. 28B-C compare the microparticle content of the hiDSPs shown in FIG. 28A and rehydrated freeze-dried platelet derivatives prepared therefrom. A summary of these data is shown in Table 26.

TABLE 24

| Batch | % MP | Particle Radius (nm) |
|---|---|---|
| (Untreated) Batch M | 3.82% | 1085 |
| (Cerus Treated) Batch N | 3.37% | 1190 |
| (Untreated) Batch J | 2.77% | 1184 |
| (Cerus Treated) Batch K | 3.19% | 1164 |

TABLE 25

| Batch | % MP |
|---|---|
| hIDSP Batch M (Untreated) | 6.75% |

TABLE 25-continued

| Batch | % MP |
|---|---|
| Freeze-dried platelet derivative composition Batch M (Untreated) | 3.82% |
| hIDSP Batch N (Treated) | 6.25% |
| Freeze-dried platelet derivative composition Batch N (Treated) | 3.37% |

TABLE 26

| Batch | % MP |
|---|---|
| hIDSP Batch J (Untreated) | 9.47% |
| Freeze-dried platelet derivative composition Batch J (Untreated) | 2.77% |
| hIDSP Batch K (Treated) | 7.55% |
| Freeze-dried platelet derivative composition Batch K (Treated) | 3.19% |

Example 12. Interactions Between Platelets and Freeze-Dried Platelet Derivatives In this Example, 'platelets' are platelets isolated from citrated whole blood approximately 3 hours post-collection. The freeze-dried platelet derivatives are Batch D, prepared by the method described in Example 1. Table 27 is a sample layout for the experiments in this Example.

TABLE 27

| | Volume Platelets (μL) | Volume Tsomes (μL) | Portion of Count Platelets ($*10^3/\mu L$) | Portion of Count Tsomes ($*10^3/\mu L$) | Total Count ($*10^3/\mu L$) |
|---|---|---|---|---|---|
| Platelets Only | 600 | 0 | 237 | 0 | 237 |
| Tsomes Only | 0 | 600 | 0 | 204 | 204 |
| 9:1 | 540 | 60 | 213 | 20 | 233 |
| 4:1 | 480 | 120 | 190 | 41 | 231 |
| 2:1 | 400 | 200 | 158 | 68 | 226 |
| 1:1 | 300 | 300 | 119 | 102 | 221 |
| 1:2 | 200 | 400 | 79 | 136 | 215 |
| 1:4 | 120 | 480 | 47 | 163 | 210 |

Platelet and freeze-dried platelet derivatives co-aggregation was evaluated by light transmission aggregrometry. Platelets and freeze-dried platelet derivatives were coincubated and evaluated by aggregometry+/−platelet activation with 4β-Phorbol-12-myristate-13-acetate (PMA). For fresh-drawn platelets isolated from whole blood, 100 ng/mL PMA was used. For stored platelets (i.e. apheresis platelets) 1000 ng/mL PMA was used.

Fresh platelets were isolated from ACD anticoagulated whole blood, washed, and diluted to 250,000 cells/μL in HMTA. Freeze-dried platelet derivatives were rehydrated according to standard protocol and diluted to 250,000 cells/μL in HMTA. An aliquot each of platelets in HMTA and freeze-dried platelet derivatives in HMTA were mixed in equal proportions. Platelets, freeze-dried platelet derivatives, and the mixed sample were evaluated by light transmission aggregometry (Helena AggRAM) in response to phorbol-myristate-acetate (PMA; 100 ng/mL) activation. The mixed samples were evaluated with and without a stir bar to assess the effect of stirring-induced shear on observed platelet-Freeze-dried platelet derivatives coaggregation.

Figure 29B:
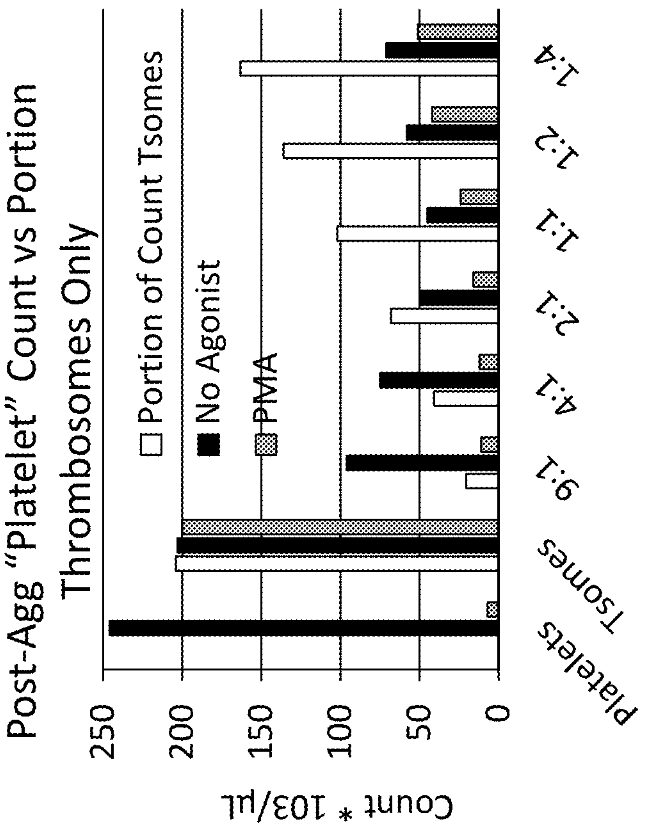
FIG. 29B is a bar plot of the platelet (and/or thrombosome) count of platelets, thrombosomes, and combinations thereof following aggregation.
Figure 29A:
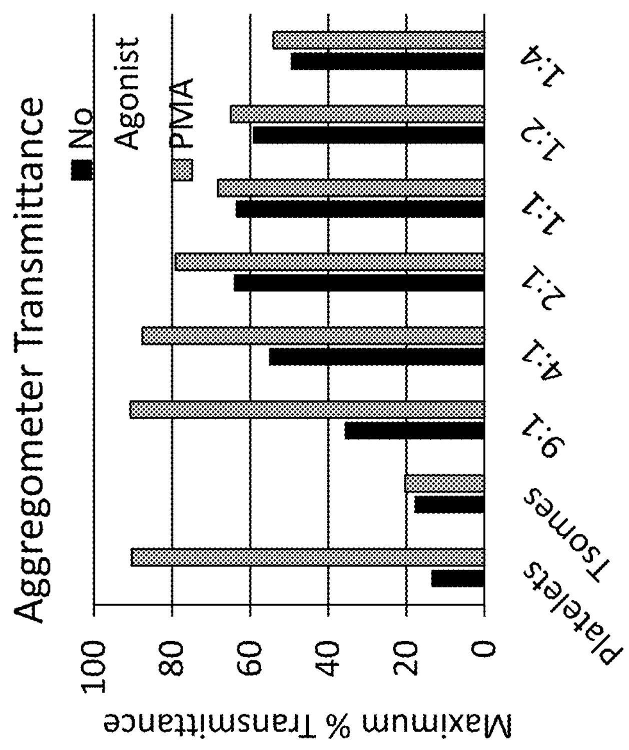
FIG. 29A is a bar plot of the transmittance of platelets, thrombosomes, and combinations thereof using light transmission aggregometry.

FIG. 29A shows the transmittance of the samples in Table 30, with and without agonist. Plus shear and minus agonist (black) mixing, freeze-dried platelet derivatives and fresh-drawn platelets induced platelet activation and aggregation. PMA (gray) activated platelets and the magnitude of % transmittance suggests mixed aggregation with freeze-dried platelet derivatives. Without shear there is either no activation or co-aggregation to less than the magnitude observed in FIG. 29A.

The platelet and freeze-dried platelet derivatives AcT counts pre- and post-aggregrometry were also evaluated. FIG. 29B shows the post-aggregation counts. Cases for which the white bar is greater than the other(s) suggest incorporation of freeze-dried platelet derivatives into platelet aggregates. The absolute decrease in particle count for the no agonist cases (black) is especially dramatic and unexpected.

Figure 29C:
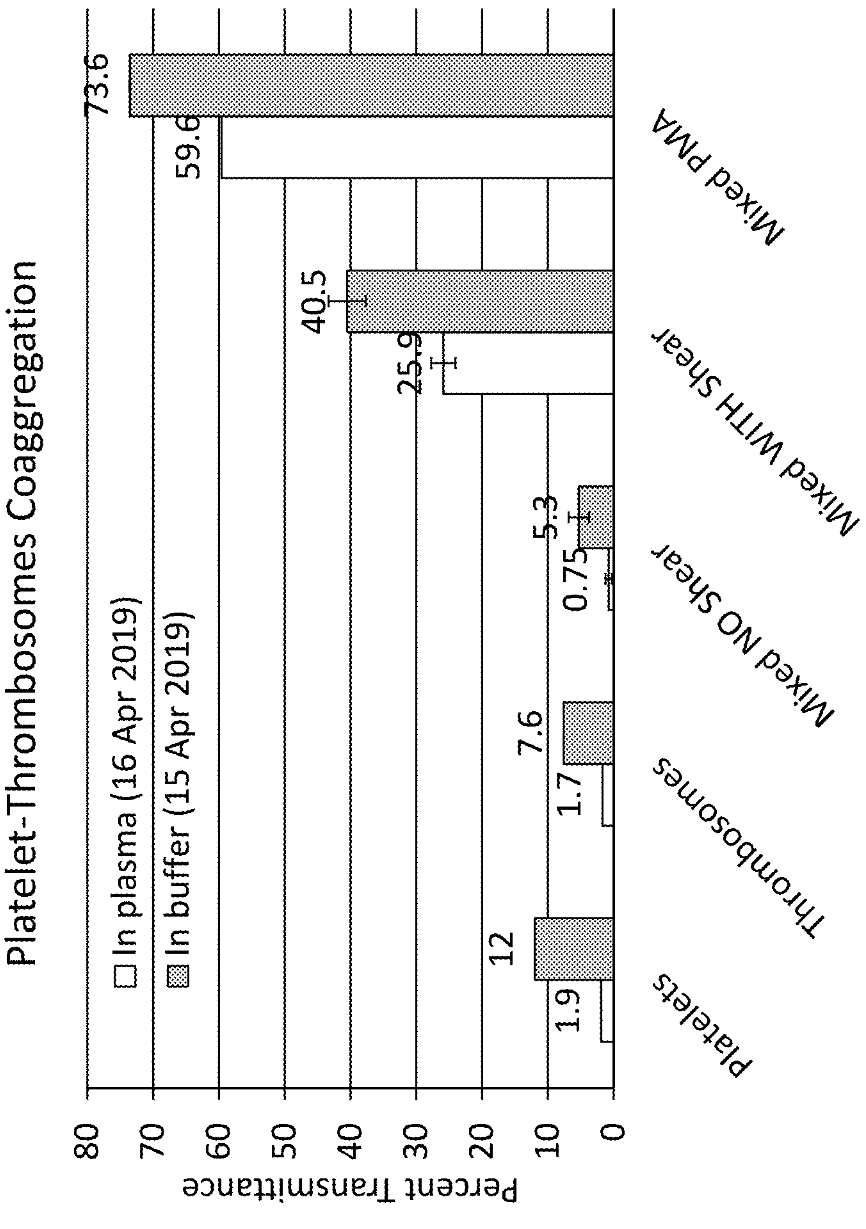
FIG. 29C is a bar plot of the transmittance of platelets, thrombosomes, and combinations thereof in light transmission aggregometry.

The effect of shear on aggregation was also evaluated. Mixed aggregometry (1:1 platelets: freeze-dried platelet derivatives by count) was repeated with and without stir bars. Results are shown in FIG. 29C. These results show that shear is necessary for observable coaggregation in the absence of a platelet agonist. The magnitude of measured counts and co-aggregation+/−agonist is slightly decreased in plasma vs buffer.

Example 13. Inhibition of Fibrin Trapping with GPRP

In this Example, 'platelets' are isolated from whole blood approximately 1 hour post-collection. The freeze-dried platelet derivatives are Batch H, prepared by the method described in Example 1.

Fresh platelets were isolated from ACD anticoagulated whole blood, washed, and diluted to 250,000 cells/μL in HMTA. Freeze-dried platelet derivatives were rehydrated according to standard protocol and diluted to 250,000 cells/μL in HMTA. An aliquot each of platelets in HMTA and freeze-dried platelet derivatives in HMTA were mixed in equal proportions. Each group of platelets, freeze-dried platelet derivatives, or mixed suspensions were divided equally; one group was treated with 1 mM GPRP to inhibit fibrin polymerization and one group remained untreated. The peptide Gly-Pro-Arg-Pro (GPRP; Sigma-Aldrich item G1895) is a peptide that prevents fibrin polymerization. Platelets, freeze-dried platelet derivatives, and the mixed samples were evaluated by light transmission aggregometry (Helena AggRAM) in response to thrombin (2.5 U/mL) activation.

Figure 30:
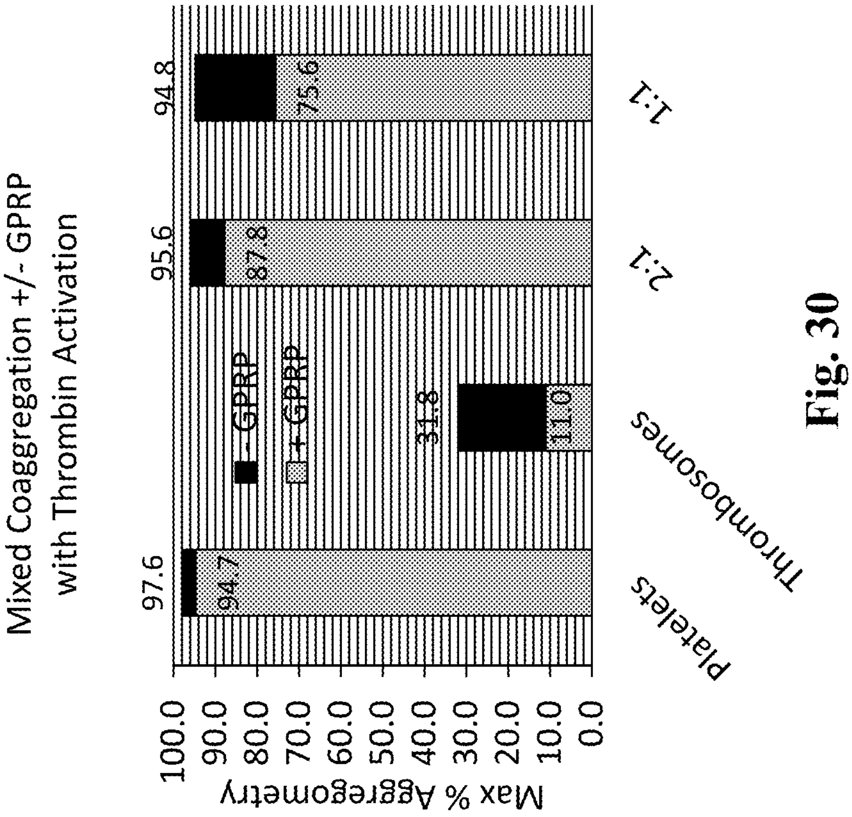
FIG. 30 is a bar plot of the transmittance of thrombin-activated platelets, thrombosomes, and combinations thereof in the presence and absence of GPRP.

FIG. 30 shows the results of co-aggregation experiments using platelets, freeze-dried platelet derivatives, and 2:1 and 1:1 mixtures of platelets and freeze-dried platelet derivatives, all activated with thrombin, either in the presence or absence of GPRP (1 mM). In the mixed cases, total measured aggregation decreased as the freeze-dried platelet derivatives population increased, suggesting that the interaction of platelets and freeze-dried platelet derivatives is partly caused by fibrin trapping. However, the bulk of the co-aggregation interaction was platelet-mediated, and not reliant on fibrin trapping as evidenced by high measured aggregation even with GPRP.

Examples 12-13 show that platelets and freeze-dried platelet derivatives co-aggregated under shear with (and to a lesser extent, without) platelet activation. The fibrin polymerization inhibitor GPRP only slightly inhibited platelet-freeze-dried platelet derivatives co-aggregation following thrombin activation.

Example 14. RGDS Inhibition of Co-Aggregation

In this Example, 'platelets' are isolated from whole blood approximately 1 hour post-collection. The freeze-dried platelet derivatives are Batch H, prepared by the method described in Example 1.

Fresh platelets were isolated from ACD anticoagulated whole blood, washed, and diluted to 250,000 cells/μL in HMTA. Freeze-dried platelet derivatives were rehydrated according to standard protocol and diluted to 250,000 cells/μL in HMTA. An aliquot each of platelets in HMTA and freeze-dried platelet derivatives in HMTA were mixed in equal proportions. Each group of platelets, freeze-dried platelet derivatives, or mixed suspensions were divided equally; one group was treated with 100 μM RGDS to inhibit fibrinogen binding to platelets and one group remained untreated. RGDS (Arg-Gly-Asp-Ser; Cayman Chemical item 15359) is a peptide sequence that binds platelet surface integrins, particularly GPIIb/IIIa. It inhibits platelet binding to fibrinogen and other adhesive proteins. Platelets, freeze-dried platelet derivatives, and the mixed samples were evaluated by light transmission aggregometry in response to phorbol myristate-acetate (PMA; 100 ng/mL) activation.

Figure 31:
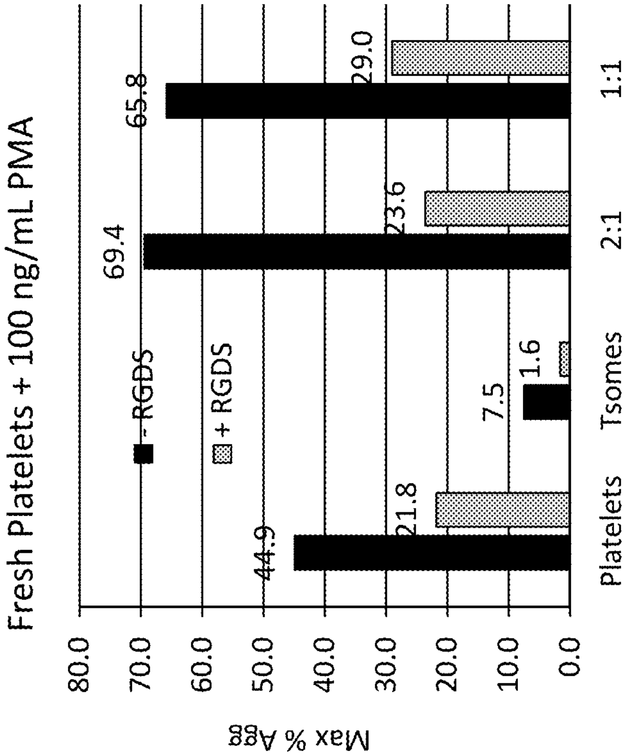
FIG. 31 is a bar plot of the percent aggregation of PMA-activated platelets, thrombosomes, and combinations thereof in the presence and absence of RGDS.

Co-aggregation experiments were performed with 100 μM RGDS and activation with PMA to investigate whether the interaction is caused by fibrinogen bridging between platelets and freeze-dried platelet derivatives. Results are shown in FIG. 31. RGDS blocks >50% of measured co-aggregation, suggesting the interaction between platelets and freeze-dried platelet derivatives may be caused in a large part by fibrinogen binding.

Examples 12-14 show that freeze-dried platelet derivatives readily co-aggregate with activated platelets (e.g., as evidenced by light transmission aggregometry). Spontaneous co-aggregation is induced by shear. Platelet-freeze-dried platelet derivatives interactions are apparent in both buffer and plasma. While co-aggregation is not substantially inhibited by GPRP, co-aggregation is substantially inhibited by RGDS. This suggests a key role for active platelet-fibrinogen binding in the co-aggregation mechanism and that co-aggregation is not caused only by passive fibrin trapping.

Example 15. Scanning Electron Microscopy (SEM)

A 10 mL aliquot of rehydrated freeze-dried platelet derivatives were centrifuged at 2000 RPM for 30 minutes. The supernatant of the centrifuges sample was removed down to 1 mL and discarded. The sample was gently agitated to resuspend the freeze-dried platelet derivatives. The concentrated freeze-dried platelet derivatives were treated with 3% glutaraldehyde in 0.1 M cacodylate buffer at a pH of 7.4 for 2 hours with agitation every 15 minutes. The freeze-dried platelet derivatives were rinsed with sterile water three times and transferred to a 1% solution of osmium tetroxide for 1 hour with agitation every 15 minutes. The sample was then rinsed three more times with sterile water and a 0.5 mL droplet was transferred to a polysulfone filter membrane. The mounted sample was frozen with liquid nitrogen and dried under vacuum before being gold sputtered and imaged using scanning electron microscopy.

Figure 32A:
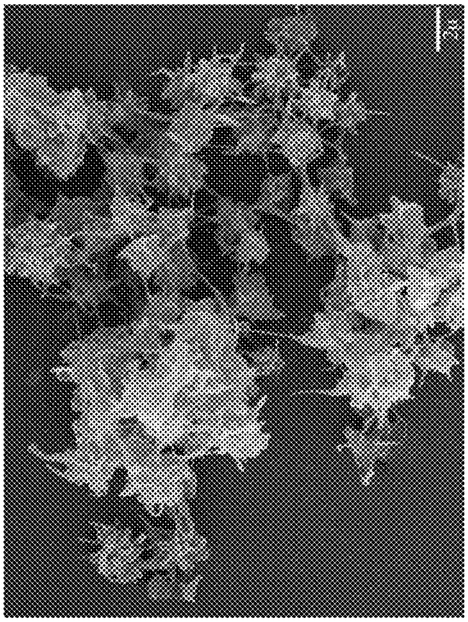
FIG. 32A shows SEM of activated platelets (scale bar=2 μm).
Figure 32B:
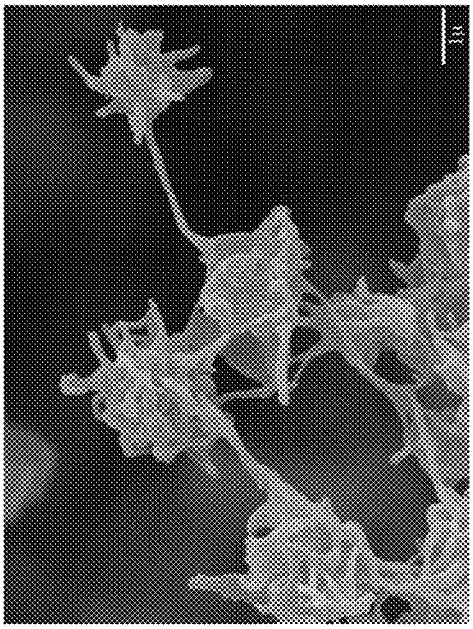
FIG. 32B shows SEM of activated platelets (scale bar=1 μm).
Figure 32C:
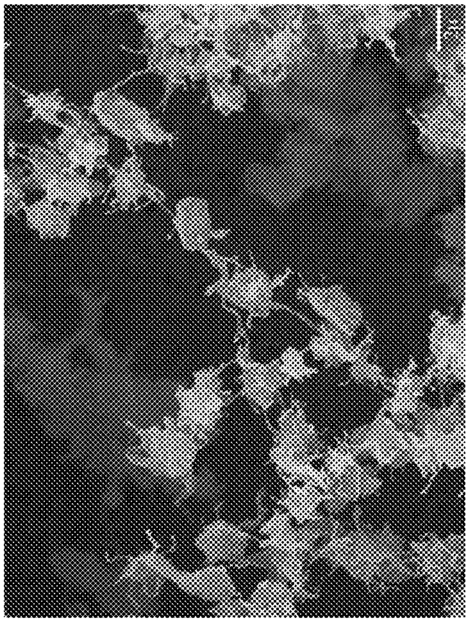
FIG. 32C shows SEM of rehydrated human thrombosomes (scale bar=2 μm).
Figure 32D:
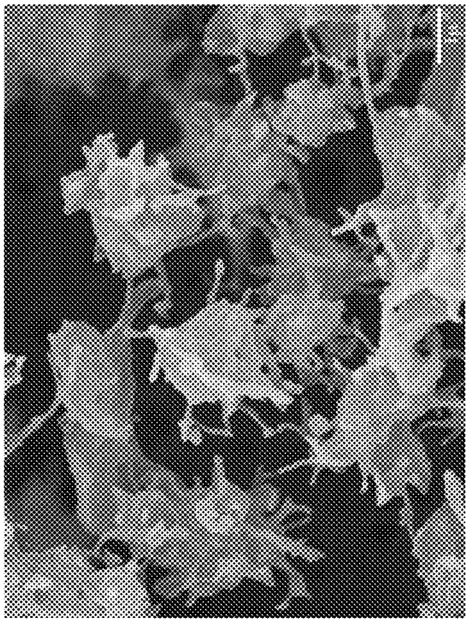
FIG. 32D shows SEM of rehydrated human thrombosomes (scale bar=1 μm).

FIGS. 32A-D show SEM of platelets and human freeze-dried platelet derivatives. Fresh activated platelets are shown in FIG. 32A (scale bar=2 μm) and FIG. 32B (scale bar=1 μm). Rehydrated human freeze-dried platelet derivatives prepared as in Example 1 are shown in FIG. 32C (scale bar=2 μm) and FIG. 32D (scale bar=1 μm).

Example 16. T-TAS® Freeze-Dried Platelet Derivatives Data

In the Total Thrombus-formation Analysis System (T-TAS®, FUJIMORI KOGYO CO., LTD), the sample is forced through collagen-coated microchannels using mineral oil. Changes in pressure are used to assess thrombus formation. The Occlusion Start Time is time it takes to reach Δ10 kPa, and the Occlusion Time=time it takes to each 480 kPa using an AR chip (Zacros Item No, TC0101).

According to FUJIMORI KOGYO CO., LTD, an AR chip can be used for analyzing the formation of a mixed white thrombus consisting chiefly of fibrin and activated platelets. It has a flow path (300 μm wide by 50 μm high) coated with collagen and tissue factors and can be used to analyze the clotting function and platelet function. In comparison, a PL chip can be used for analyzing the formation of a platelet thrombus consisting chiefly of activated platelets. A PL chip has a flow path coated with collagen only and can be used to analyze the platelet function.

T-TAS® reagents (CaCTI, AR Chip) were warmed to 37° C. and freeze-dried platelet derivatives were rehydrated according to standard protocol. An aliquot of the rehydrated freeze-dried platelet derivatives was washed by centrifugation at 3900 g×10 minutes and resuspended to approximately 300,000 cells/μL in sodium citrate anticoagulated platelet-poor plasma (PPP). CaCTI (20 μL) was mixed with freeze-dried platelet derivatives in PPP (480 μL) and run through the T-TAS AR Chip under high shear. Pressure in the system was monitored over 30 minutes or until the maximum backpressure in the channel was achieved.

The T-TAS® instrument was prepared for use according to the manufacturer's instructions. AR Chips (Diapharma Cat. #TC0101) and AR Chip Calcium Corn Trypsin Inhibitor (CaCTI; Diapharma Cat. #TR0101) were warmed to room temperature. 300 μL of rehydrated freeze-dried platelet derivatives were transferred to a 1.7 mL microcentrifuge tube and centrifuged at 3900 g×10 minutes to pellet. The freeze-dried platelet derivatives pellet was resuspended in George King (GK) pooled normal human plasma or autologous plasma with or without autologous platelets to a concentration of approximately 100,000-450,000/μL, as determined by AcT counts (Beckman Coulter AcT Diff 2 Cell Counter). 20 μL of CaCTI with 480 μL of freeze-dried platelet derivatives sample in GK plasma were mixed with gentle pipetting. The sample was loaded and run on the T-TAS® according to the manufacturer's instructions.

Table 28 shows T-TAS® results from citrated whole blood, platelet-reduced citrated whole blood supplemented with varying concentrations of freeze-dried platelet derivatives as prepared in Example 1, and George King Platelet Poor Plasma (GK PPP) supplemented with varying concentrations of freeze-dried platelet derivatives as prepared in Example 1 in experiments run according to the manufacturer's instructions using the AR chip and High Shear instrument settings.

TABLE 28

| T-TAS AR Chip Results | | | | | | |
|---|---|---|---|---|---|---|
| Sample Type | Actual Tsome Concentration (×10^3/μL) | Base Pressure (kPa) | Occlusion Start Time (hh:mm:ss) | Occlusion Time (hh:mm:ss) | Occlusion Speed (kPa/min) | Area Under Curve |
| Citrated Whole Blood | 0 | 3.2 | 0:11:19 | 0:14:03 | 25.6 | 1393.9 |
| Platelet | 0 | 3.3 | 0:12:41 | 0:16:57 | 16.4 | 1180.6 |
| Reduced | 73 | 3.2 | 0:11:11 | 0:13:47 | 26.9 | 1380.9 |
| Citrated | 173 | 3.4 | 0:09:37 | 0:13:22 | 18.7 | 1498.5 |
| Whole Blood | 255 | 3.4 | 0:08:36 | 0:10:40 | 33.9 | 1653.1 |
| GK PPP | 0 | 2.7 | 0:25:34 | 0:00:00† | 0 | 138.8 |
| | 45 | 2.8 | 0:27:22 | 0:28:48 | 48.8 | 190.6 |
| | 193* | 2.9 | 0:12:41 | 0:00:00† | 0 | 775.3 |
| | 384 | 2.8 | 0:10:54 | 0:12:20 | 48.8 | 1479.8 |

*Test peaked at ~75 kPa before rapidly dropping off. Possible erroneous result.
†Test timed out.

Figure 33A:
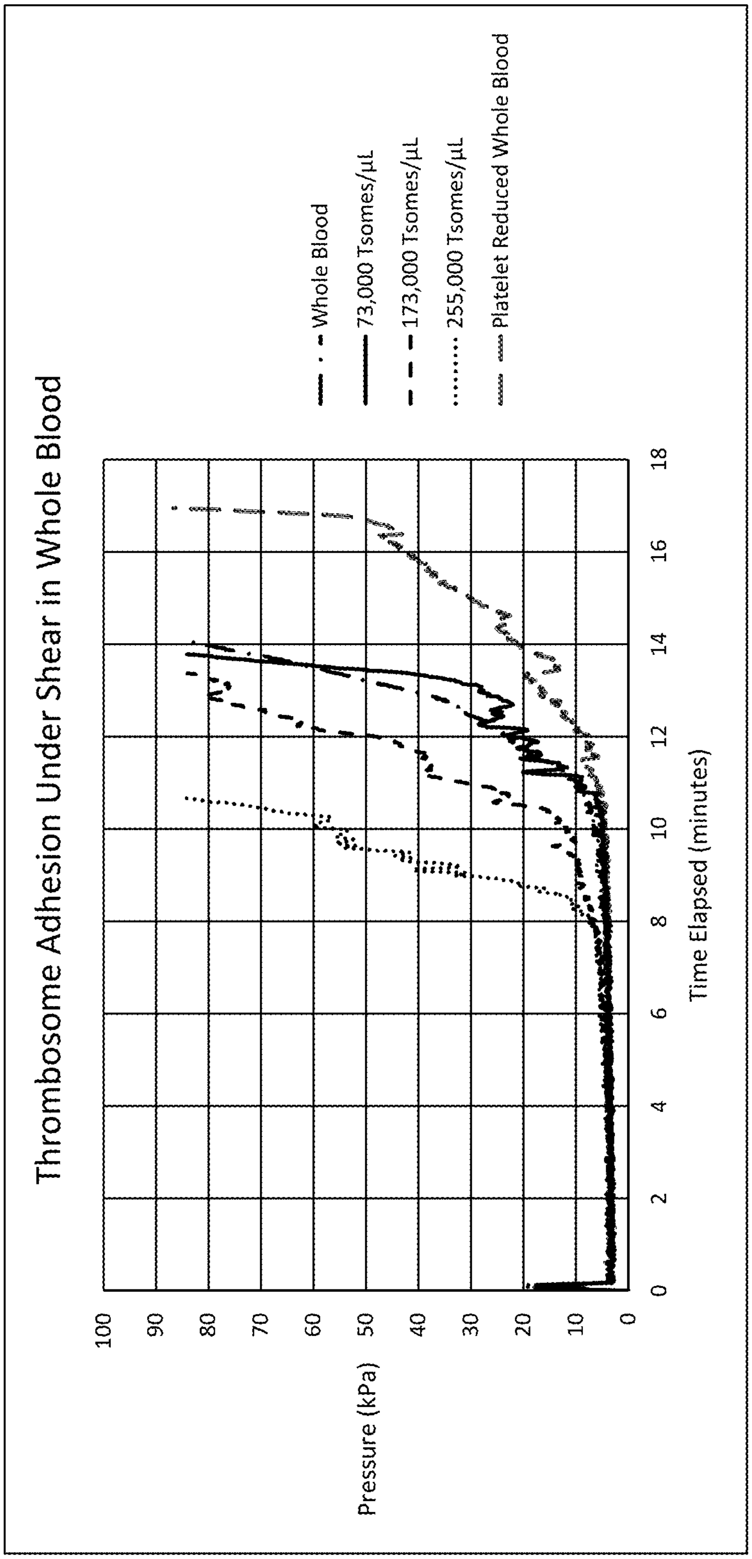
FIG. 33A is a plot of thrombosome adhesion under shear in whole blood.
Figure 33B:
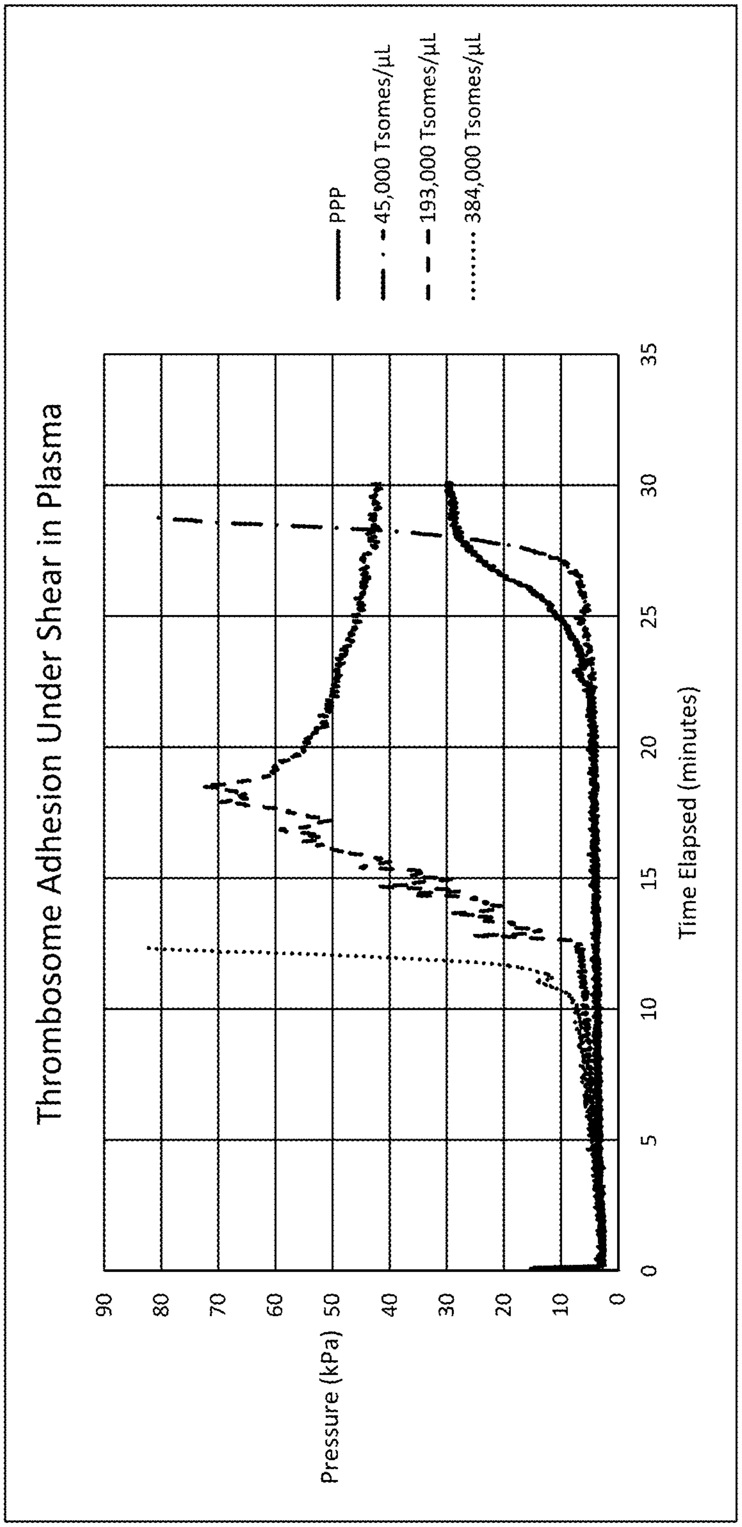
FIG. 33B is a plot of thrombosome adhesion under shear in plasma.

Time-elapsed results are shown in FIGS. 33A-B. Increasing the concentration of freeze-dried platelet derivatives in platelet-reduced whole blood promoted more robust thrombus formation as measured by shortened occlusion times (FIG. 33A). Increasing the concentration of freeze-dried platelet derivatives in platelet poor plasma (PPP) promoted more robust thrombus formation as measured by shortened occlusion times (FIG. 33B).

Figure 33C:
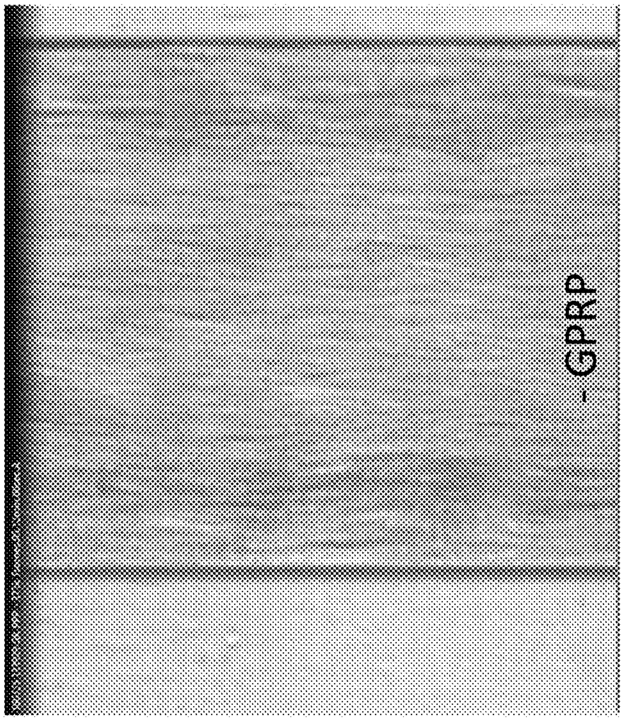
FIG. 33C shows formation of fibrin in a microcapillary channel in the whole absence of GPRP.
Figure 33D:
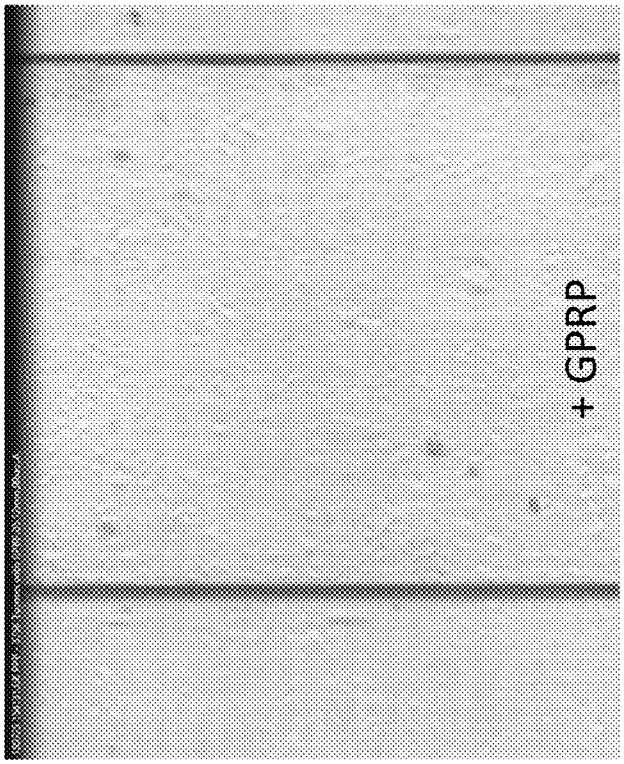
FIG. 33D shows a lack of formation of fibrin in a microcapillary channel in the presence of GPRP.
Figure 33E:
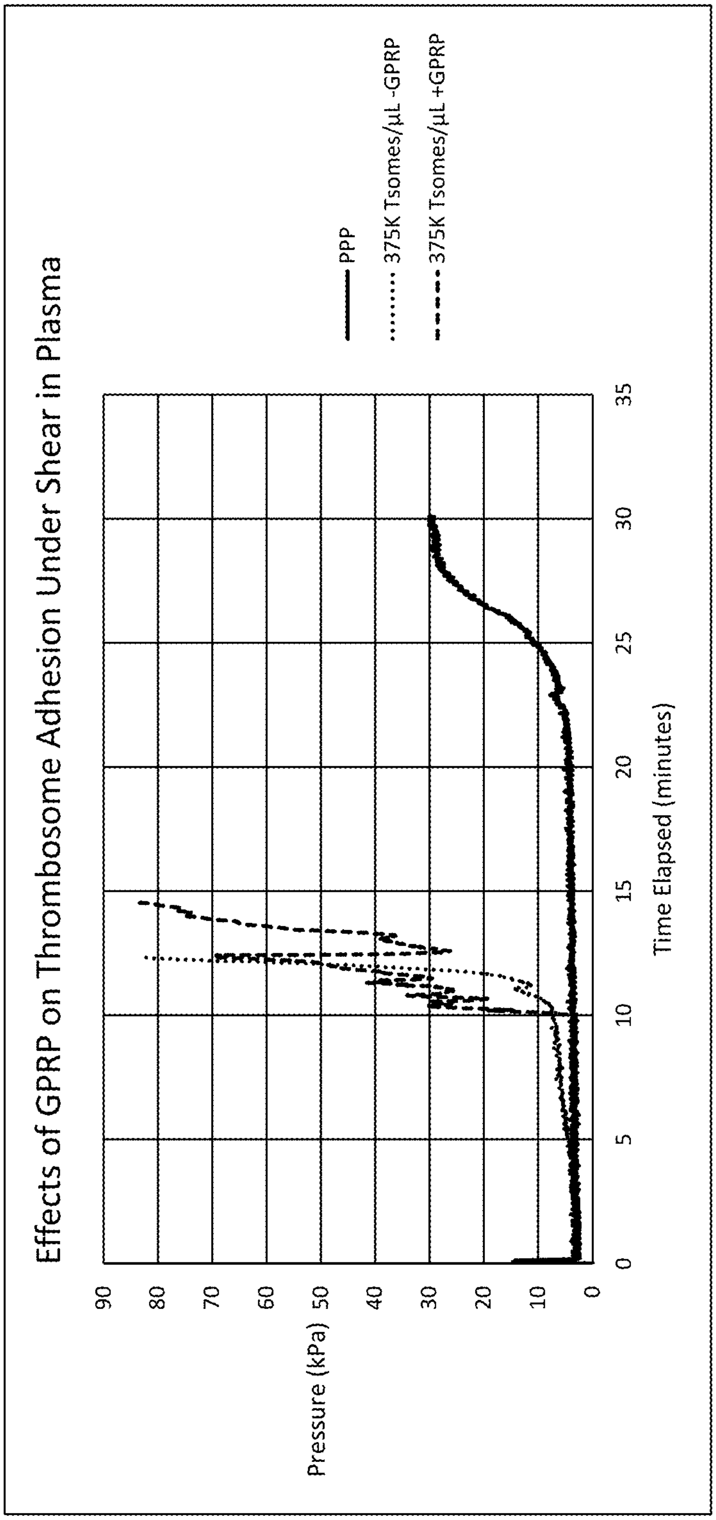
FIG. 33E is a plot of the effect of GPRP on thrombosome adhesion under shear in plasma.

The effect of GPRP (1 mM) on occlusion activity was also assayed. Table 29 shows T-TAS® results for platelet-poor plasma, with and without freeze-dried platelet derivatives in the presence and absence of GPRP. Adding GPRP to prevent fibrinogen formation did not prevent the freeze-dried platelet derivatives-containing sample from reaching occlusion pressure. While the addition of GPRP to freeze-dried platelet derivatives samples in plasma prevents the formation of fibrin in the microcapillary channel (FIGS. 33C (no GPRP) and 33D (GPRP), both in GK PPP), the addition of GPRP to freeze-dried platelet derivatives (PPP) did not prevent thrombus formation (FIG. 33E).

TABLE 29

| AR Chip: GPRP Comparison | | | | | | |
|---|---|---|---|---|---|---|
| Sample Type | Actual Tsome Concentration (×10^3/μL) | Base Pressure (kPa) | Occlusion Start Time (hh:mm:ss) | Occlusion Time (hh:mm:ss) | Occlusion Speed (kPa/min) | Area Under Curve |
| GK PPP (No Tsomes) | 0 | 2.7 | 0:25:34 | 0:00:00† | 0 | 138.8 |
| GK PPP + 1 mM GPRP (No Tsomes) | 0 | 3.5 | 0:00:00 | 0:00:00† | 0 | 52.43 |
| GK PPP + 375k Tsomes | 384 | 2.8 | 0:10:54 | 0:12:20 | 48.8 | 1479.8 |
| GK PPP + 375k Tsomes with 1 mM GPRP | 380 | 3.2 | 0:10:09 | 0:14:32 | 16 | 1426.9 |

†Test timed out

Freeze-dried platelet derivatives, also referred as "TFF thrombosomes", were produced by the TFF method described in Example 1. Fresh platelets in Platelet Rich Plasma (PRP) were prepared from whole blood collected in acid-citrate-dextrose (ACD) collection tubes (BD Vacutainer ACD Solution A Blood Collection Tubes ref #364606). Platelet rich plasma (PRP) was prepared by centrifugation of ACD-whole-blood at 180 g for 15 minutes at 22° C. using a Beckman Coulter Avanti J-15R centrifuge. Platelet poor plasma (PPP) was prepared by centrifugation of ACD-whole-blood at 2000 g for 20 minutes at 22° C.

For sample preparation for aggregometry studies, PRP was diluted with PPP to a platelet concentration (plt count) of 250,000 plts/uL. Platelet count was determined using a Coulter Ac·T diff2 Hematology Analyzer.

Freeze-dried platelet derivatives, lyophilized and thermally treated, were prepared using tangential flow filtration (TFF) as described in Example 1. A 30 mL vial of freeze-dried platelet derivatives was rehydrated using 30 mL of cell culture grade water (Corning Cat #25-055-CI). The vial was incubated at room temperature for a total of 10 minutes. During the 10-minute rehydration period, the vial was gently swirled at 0, 5, and 10 minutes to promote dissolution of the lyophilizate. The aggregometry studies as per the present Example was carried out in the absence of fresh platelets. Therefore, the aggregometry studies supported only aggregation ability of the freeze-dried platelet derivatives, but not the co-aggregation ability.

For sample preparation for aggregometry studies, rehydrated freeze-dried platelet derivatives were diluted in a

Example 17. Inability of Freeze-Dried Platelet Derivatives to Aggregate in the Presence of Agonists and Absence of Fresh Platelets Light transmission aggregometry (LTA) was used to observe freeze-dried platelet derivatives aggregation in the presence of known platelet aggregation agonists. The freeze-dried platelet derivatives aggregation data was compared to aggregation data of fresh platelets.

buffer to a platelet count of 250,000/4. Freeze-dried platelet derivatives sample preparations used for ristocetin aggregation studies were composed of 20% citrated plasma (George King Bio-Medical, Inc. Pooled Normal Plasma product #0010-1) and buffer.

Figure 34A:
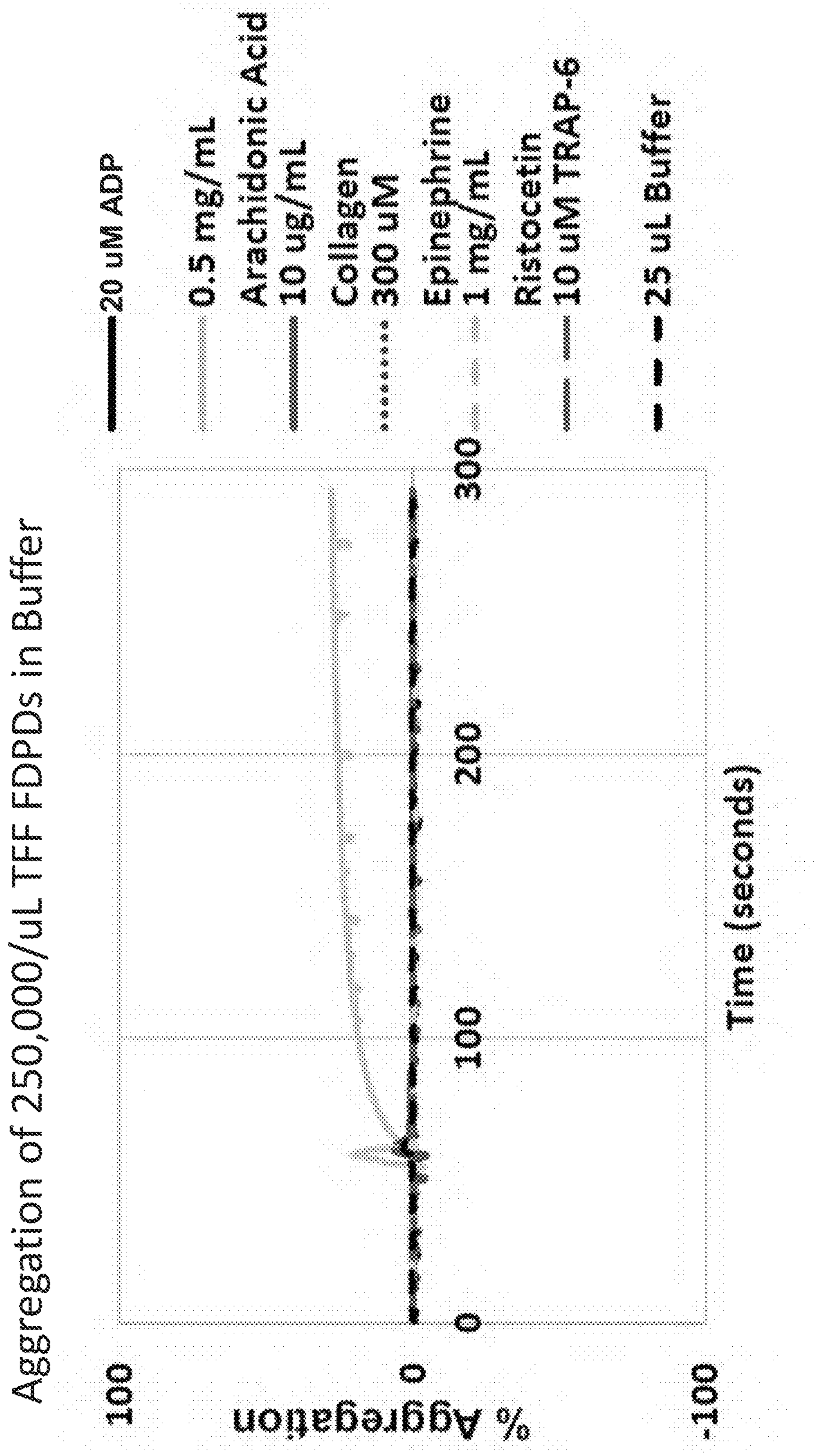
FIG. 34A shows the aggregation response of thrombosomes in the presence of agonists, but in the absence of fresh platelets.

Light transmission aggregometry (LTA) (Bio/Data PAP-8E Platelet Aggregometer catalog #106075) at 37° C. was used to observe the aggregation response of freeze-dried platelet derivatives (FIG. 34A) and PRP samples (FIG. 34B) from a final concentration of 20 μM ADP, 10 μg/mL collagen, 200 μM epinephrine (ADP, collagen, and epinephrine reagents from Helena Laboratories Platelet Aggregation Kit cat. #5369), 0.5 mg/mL arachidonic acid (Helena Arachidonic Acid Reagent cat.), 1 mg/mL ristocetin (Helena Ristocetin for Aggregation Assays cat.), and 10 μM thrombin receptor activator peptide 6 (TRAP-6) (Sigma Aldrich Cat #T1573-5MG). PPP, buffer, or buffer with 20% citrated plasma were used as blanks for the PRP, freeze-dried platelet derivatives, and freeze-dried platelet derivatives with 20% citrated plasma samples, respectively. Prior to agonist treatment, 225 μL of freeze-dried platelet derivatives or PRP sample was reverse pipetted in a test tube containing a stir bar. The test tube was then placed into the aggregometer's non-stirred incubation well for 1 minute. The sample was then placed into a stirred incubation well for 1 minute. The sample was then placed into the stirred test well and the aggregation test was initiated. After 1-minute of baseline observation the sample was treated with agonist and the aggregation response was recorded. Using the same procedure as the test runs, a negative control of 25 μL buffer was included simultaneously with all runs to determine spontaneous baseline-aggregation responses of all sample groups.

Freeze-dried platelet derivative composition in 1.7 mL microcentrifuge tubes, at room temperature, were treated with an agonist at a final agonist concentration of 20 μM ADP, 0.5 mg/mL arachidonic acid, 10 μg/mL collagen, 200 μM epinephrine, 1 mg/mL ristocetin, and 10 μM TRAP-6 or 254 buffer. Freeze-dried platelet derivative counts were determined prior to and 5-minutes after agonist treatment.

ADP (FIG. 34C), collagen (FIG. 34D), epinephrine (FIG. 34E), ristocetin (FIG. 34F), and TRAP-6 (FIG. 34G) did not cause an aggregation response in freeze-dried platelet derivatives when measured by LTA. Freeze-dried platelet derivatives' response from the aforementioned agonists was equivalent to baseline aggregation values that would be obtained from no agonist or a negative control of buffer. When freeze-dried platelet derivatives were treated with arachidonic acid (AA) and observed by LTA (FIG. 34H) there was an apparent aggregation response, however after visual inspection of the aggregometry cuvette it was observed that the solution had become visibly clear and aggregates were not observed, indicating that the apparent aggregation response was from lysis of freeze-dried platelet derivatives and not AA induced aggregation. Determining aggregation by cell count for freeze-dried platelet derivatives produced similar results to the LTA results for all agonists.

Figure 34B:
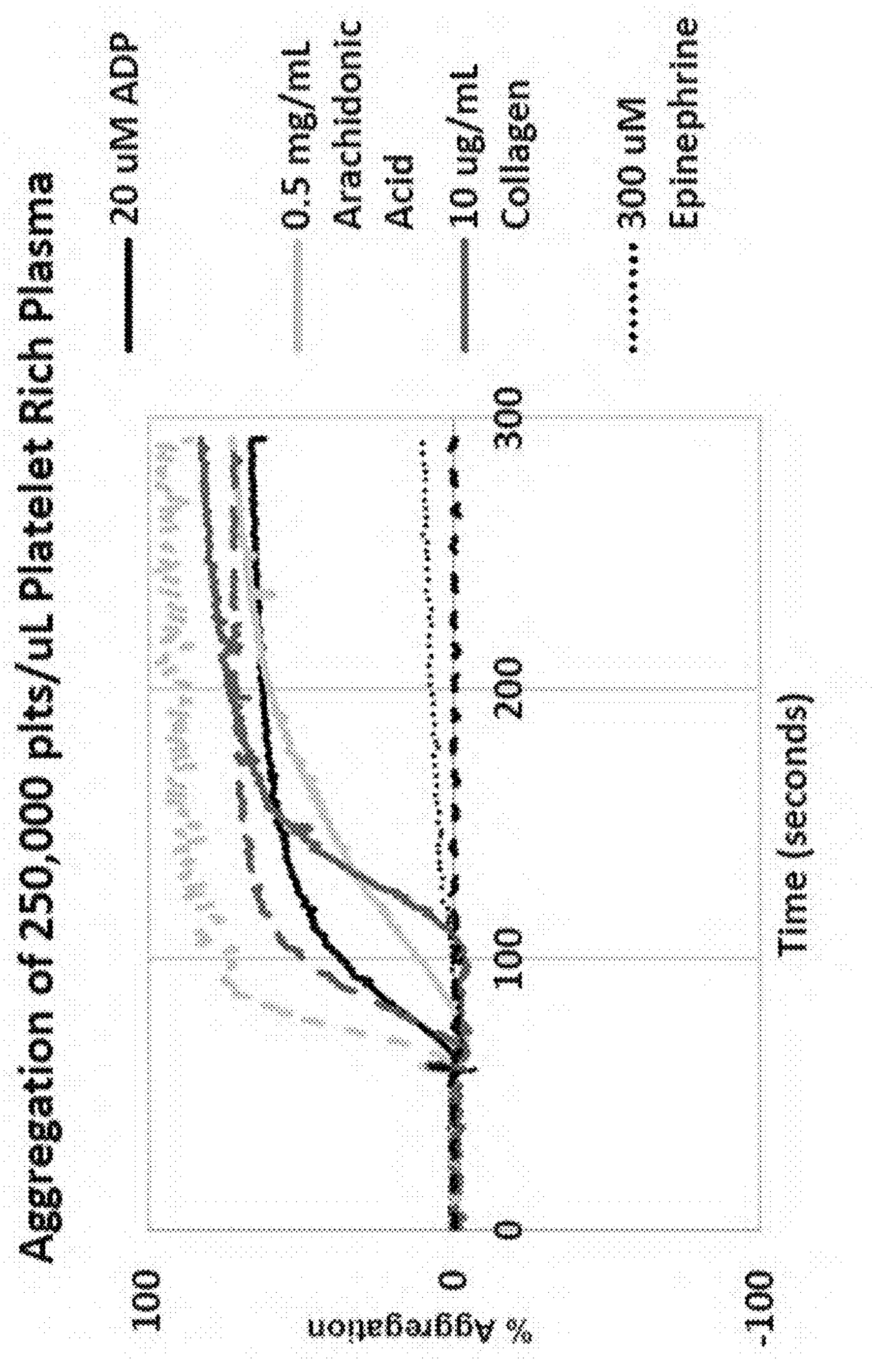
FIG. 34B shows the aggregation response of platelet-rich plasma (PRP) in the presence of agonists, but in the absence of fresh platelets.
Figure 34C:
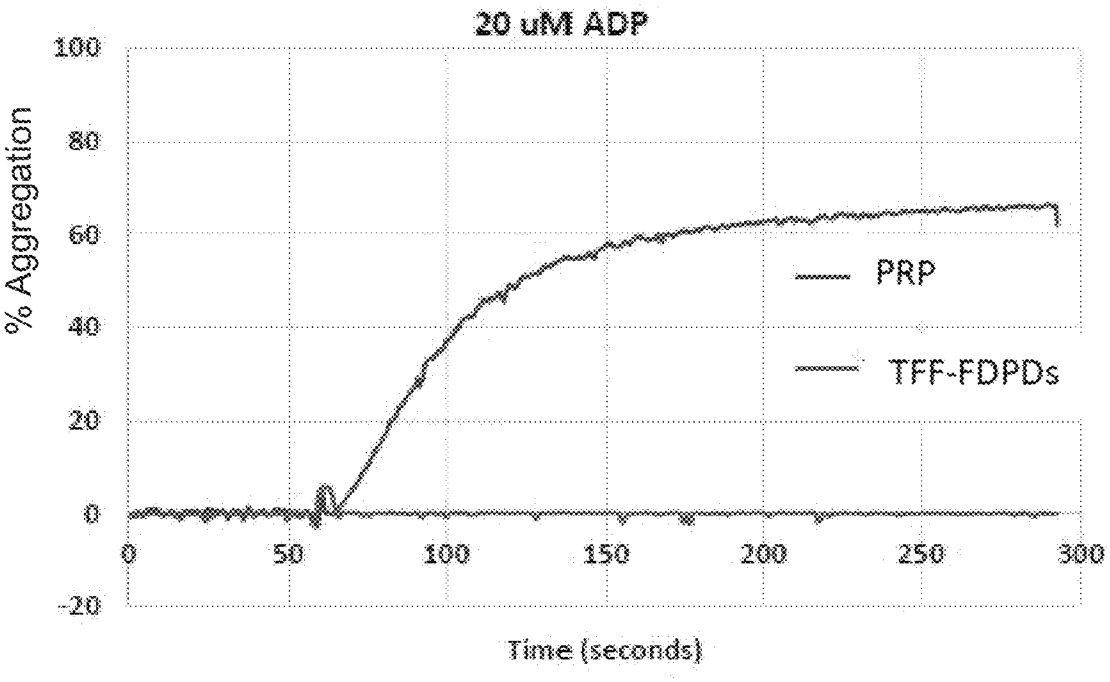
FIG. 34C shows the comparison of aggregation of thrombosomes and PRP in the presence of 20 μM ADP.
Figure 34D:
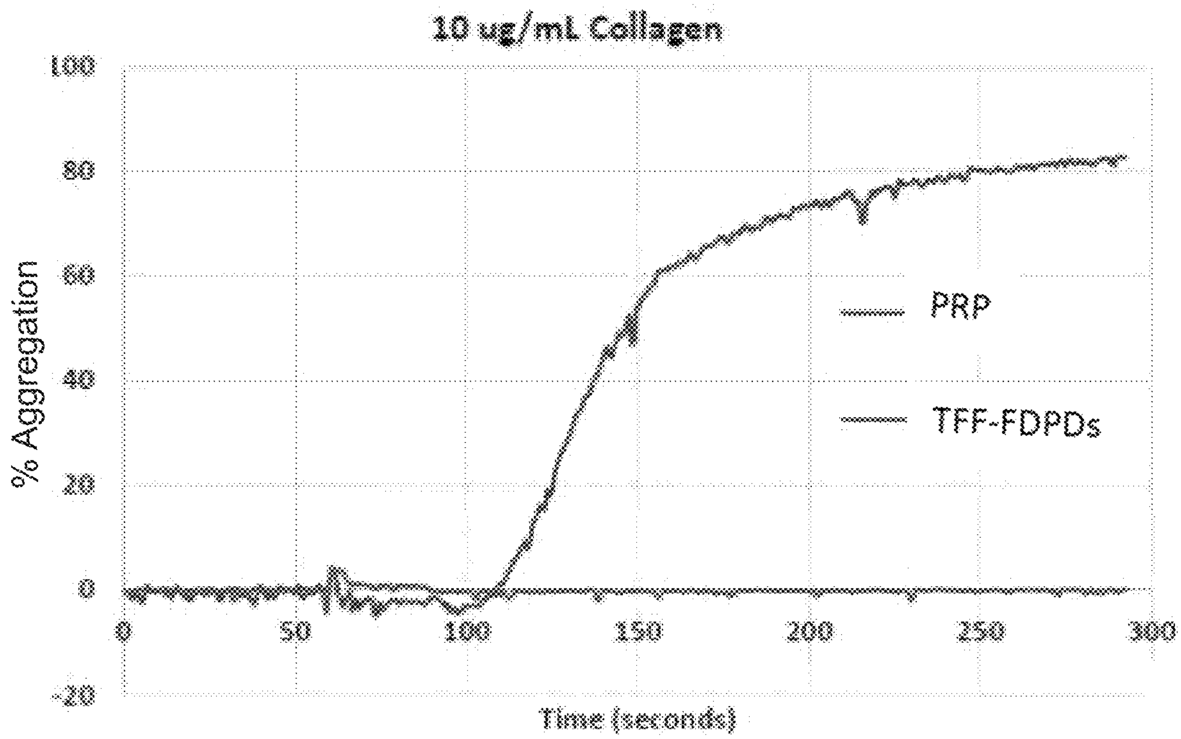
FIG. 34D shows the comparison of aggregation of thrombosomes and PRP in the presence of 10 μg/ml collagen.
Figure 34E:
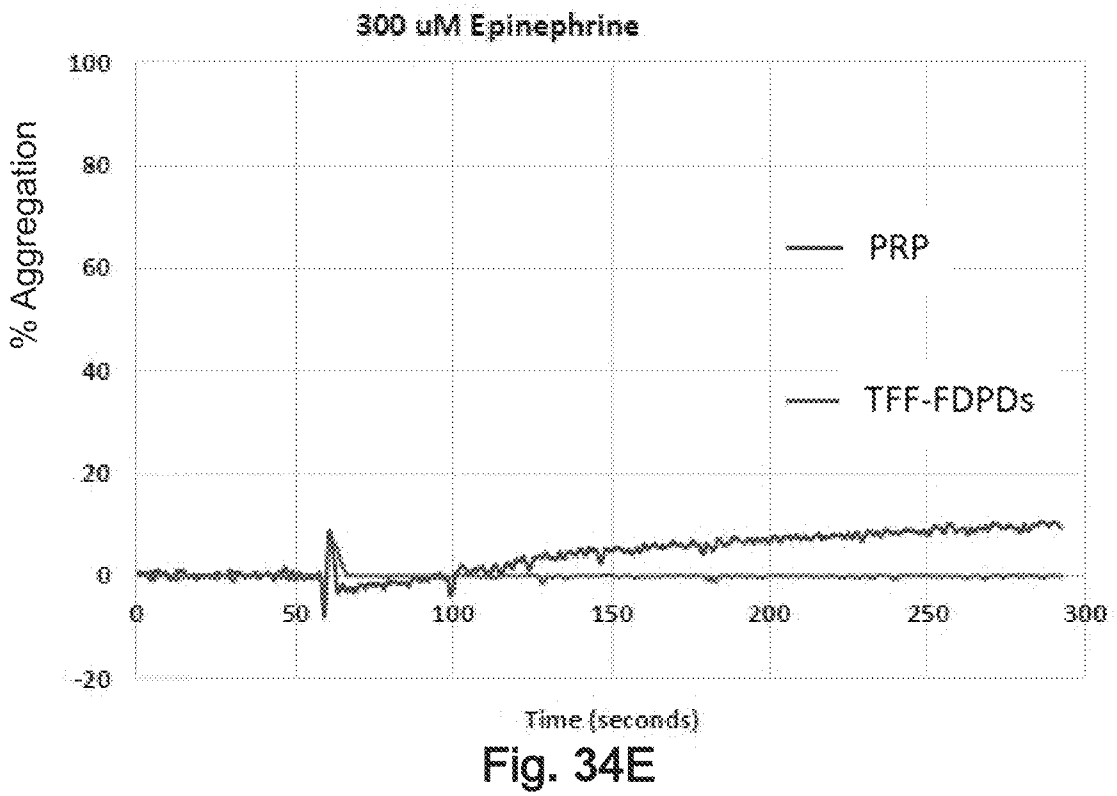
FIG. 34E shows the comparison of aggregation of thrombosomes and PRP in the presence of 300 μM epinephrine.
Figure 34F:
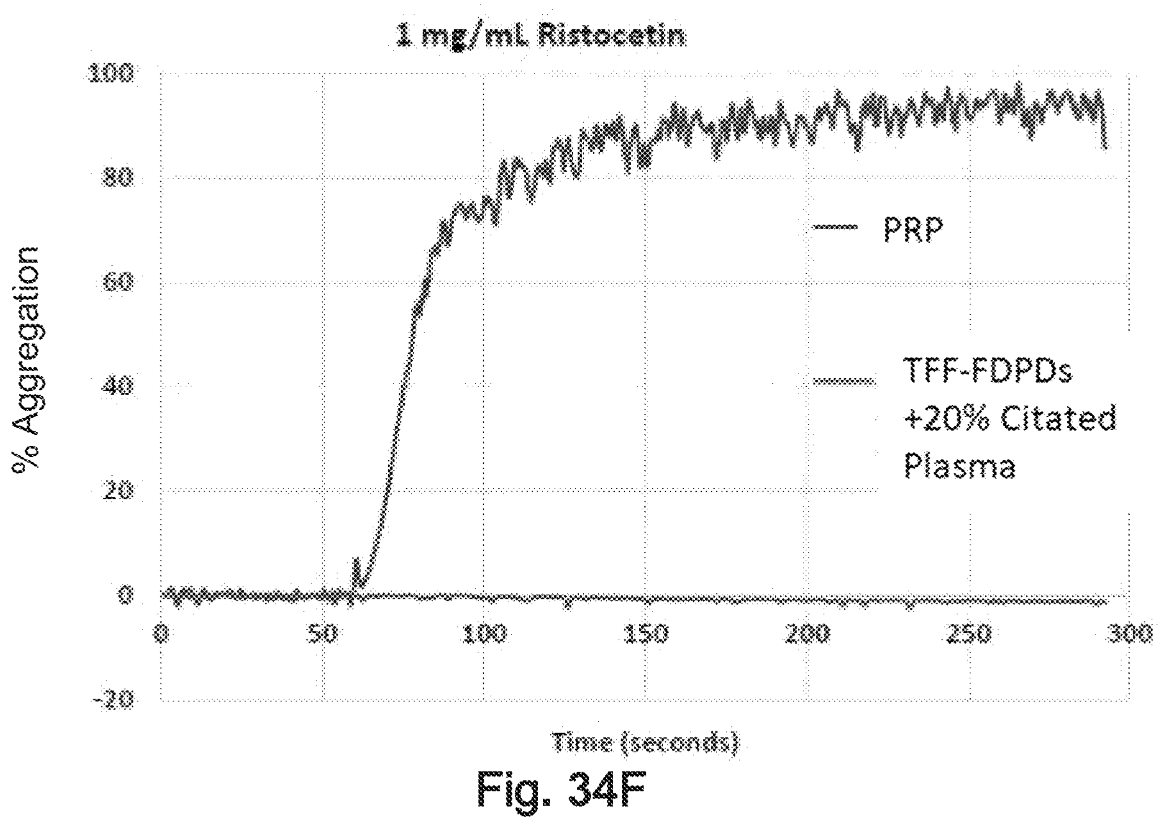
FIG. 34F shows the comparison of aggregation of thrombosomes and PRP in the presence of 1 mg/ml ristocetin.
Figure 34G:
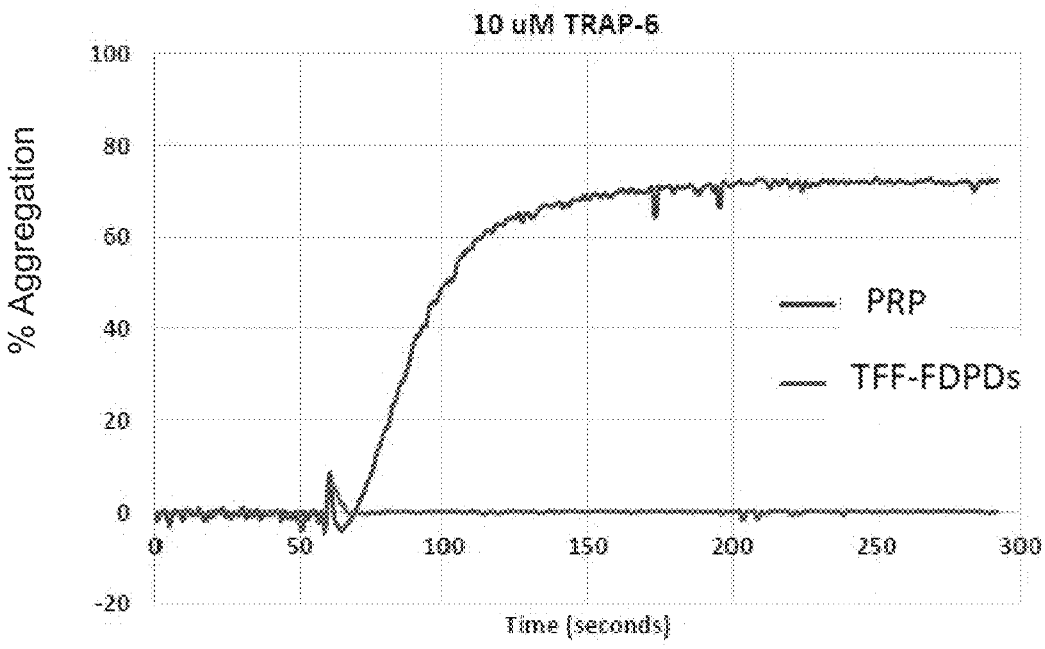
FIG. 34G shows the comparison of aggregation of thrombosomes and PRP in the presence of 10 μM TRAP-6.
Figure 34H:
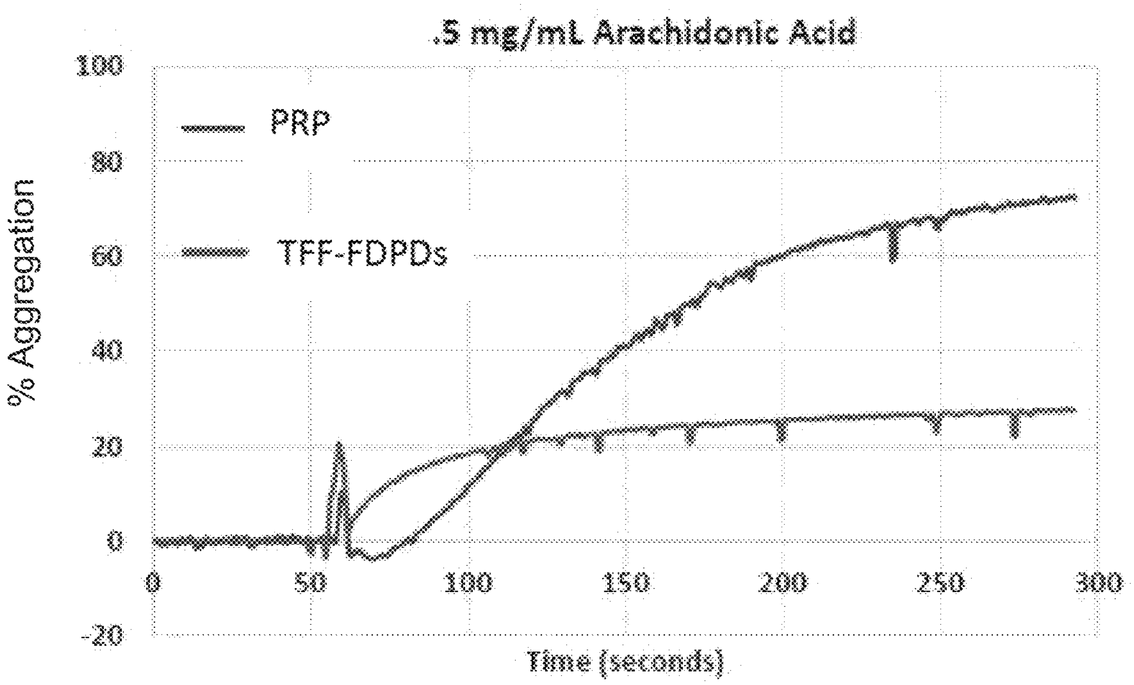
FIG. 34H shows the comparison of aggregation of thrombosomes and PRP in the presence of 5 mg/ml arachidonic acid.

Agonists' functionality was confirmed by performing LTA on fresh PRP (FIG. 34B). ADP, arachidonic acid, collagen, epinephrine, ristocetin and TRAP-6 caused normal aggregation profiles and magnitudes that are representative of a strong aggregation response in PRP. The aggregation response from epinephrine in PRP was reduced, however epinephrine was still able to elicit an aggregation response that was above baseline aggregation. The negative control of buffer in PRP indicated that the PRP was not activated prior to agonists additions. Visual inspection of the PRP samples after the aggregation tests indicated that no cell lysis had occurred and platelet aggregates were visually observed in the aggregation cuvettes for all agonists, indicating that all aggregations responses were from platelet aggregation. The aggregation percentage of freeze-dried platelet derivatives and fresh PRP observed in the presence of the aforementioned agonists have been captured in Table 30.

TABLE 30

| Agonist | Freeze-dried platelet derivatives Aggregation (n = 3) | PRP Aggregation (n = 2) |
|---|---|---|
| 20 μM ADP | 1% | 66% |
| 0.5 mg/mL Arachidonic Acid | 28%* | 73% |
| 10 μg/mL Collagen | 2% | 83% |
| 300 μM Epinephrine | 1% | 11% |
| 1 mg/mL Ristocetin | 0% | 98% |
| 10 μM TRAP-6 | 1% | 73% |
| 25 μL Buffer | 1% | 2% |

*Due to lysis of freeze-dried platelet derivatives and not aggregation

Example 18. Freeze-Dried Platelet Derivatives are Maximally Activated—Binding of Annexin V to Freeze-Dried Platelet Derivatives in the Presence of TRAP Freeze-dried platelet derivatives, prepared using the TFF process as described on Example 1 and treated with TRAP-6, were tested for the presence of phosphatidylserine (PS), indicative of an activated platelet, on the surface of the freeze-dried platelet derivatives. The presence of PS was assessed by analysis of Annexin V (AV) binding to the freeze-dried platelet derivatives.

One 30 mL vial of freeze-dried platelet derivatives composition prepared using the TFF process as described in the Example 1 was rehydrated using 30 mL of cell culture grade water (Corning Cat #25-055-CI). After water was added to the vial, the vial was incubated for 10 minutes at room temperature. Gentle swirling of the vial was performed every 2 minutes during the 10-minute period to promote full dissolution of the cake. Once the freeze-dried platelet derivatives were fully rehydrated, two 475 μL aliquots were transferred to two separate 1.7 mL microcentrifuge tubes. Twenty-five microliters of HEPES Modified Tryode's Albumin buffer (HMTA) (Cellphire RGT-004) was added to the sample in the first tube to generate freeze-dried platelet derivatives without TRAP-6. Twenty-five microliters of 400 μM Thrombin Receptor Activating Peptide 6 (TRAP-6) (Sigma Aldrich Cat #T1573-5MG) was added to the second tube to generate freeze-dried platelet derivatives with TRAP-6. The final concentration of TRAP-6 during incubation was 20 μM. Both tubes were inverted 5 times to mix and incubated at room temperature for 10 minutes.

After incubation with HMTA buffer or TRAP-6, the samples were further diluted 1:20 by adding 10 μL of the freeze-dried platelet derivatives sample to 190 μL HMTA. These diluted samples of freeze-dried platelet derivatives incubated with HMTA and freeze-dried platelet derivatives incubated with TRAP-6 were both stained in 1.7 mL microcentrifuge tubes as follows: unstained control samples were generated by combining 10 μL of freeze-dried platelet derivatives and 20 μL HMTA; calcium free control samples were generated by combining 10 μL of freeze-dried platelet derivatives, 5 μL of Annexin V-ACP (BD Pharmingen Cat

#550475), and 15 μL HMTA; Annexin V (AV) stained test samples were generated by combining 10 μL of freeze-dried platelet derivatives, 5 μL of AV-ACP, and 15 μL HMTA supplemented with 9 mM CaCl2 (Cellphire RGT-012 Lot #LAB-0047-21). The final concentration of $CaCl_2$ in the AV-stained test samples was 3 mM. All stained samples for both freeze-dried platelet derivatives incubated with HMTA and freeze-dried platelet derivatives incubated with TRAP-6 were generated in triplicate. The samples were incubated at room temperature, protected from light, for 20 minutes.

After incubation, 500 μL of HEPES buffered saline (HBS) (Cellphire RGT-017) was added to all unstained control and calcium free control samples. Five hundred microliters of HBS supplemented with 3 mM CaCl2 was added to the AV-stained test samples. One hundred microliters from each sample was transferred to an individual well in a 96 well plate, and the samples were analyzed using an Agilent Quanteon flow cytometer.

TRAP-6 activity was confirmed by measuring CD62P expression in human apheresis platelets with and without exposure to TRAP-6. Two 475 μL aliquots of apheresis platelets were transferred to two separate 1.7 mL microcentrifuge tubes. Twenty-five microliters of HMTA buffer was added to the sample in the first tube to generate apheresis platelets without TRAP-6. Twenty-five microliters of 400 μM TRAP-6 was added to the second tube to generate freeze-dried platelet derivatives with TRAP-6. The final concentration of TRAP-6 during incubation was 20 μM. Both tubes were inverted 5 times to mix and incubated at room temperature for 10 minutes.

After incubation with HMTA buffer or TRAP-6, the samples were further diluted 1:20 by adding 10 μL of apheresis platelets to 190 μL HMTA. These diluted samples of apheresis platelets incubated with HMTA and apheresis platelets incubated with TRAP-6 were both stained in 1.7 mL microcentrifuge tubes as follows: unstained control samples were generated by combining 10 μL of apheresis platelets and 20 μL HMTA; Anti-CD62P stained test samples were generated by combining 10 μL of apheresis platelets, 5 μL of anti-CD62P-PE antibody (BD Pharmingen Cat #550561 Lot #6322976), and 15 μL HMTA. All stained samples for both apheresis platelets incubated with HMTA and apheresis platelets incubated with TRAP-6 were generated in triplicate. The samples were incubated at room temperature, protected from light, for 20 minutes.

After incubation, 500 μL of phosphate buffered saline (PBS) (Corning Cat #21-040-CV1) was added to all samples. One hundred microliters from each sample was transferred to an individual well in a 96 well plate, and the samples were analyzed using an Agilent Quanteon flow cytometer.

Figure 35A:
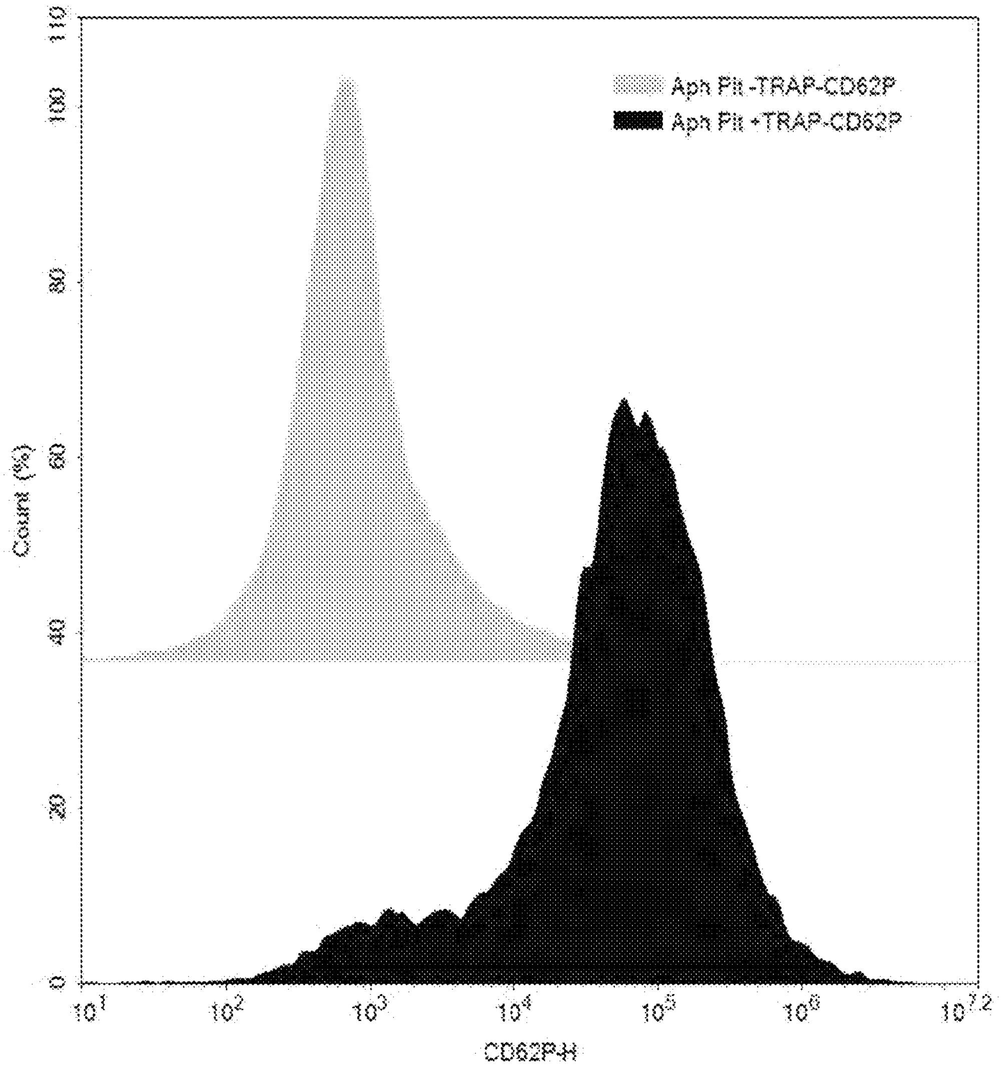
FIG. 35A shows that TRAP-6 peptide is capable of promoting platelet activation by observing expression of CD62P on the apheresis platelets.
Figure 35B:
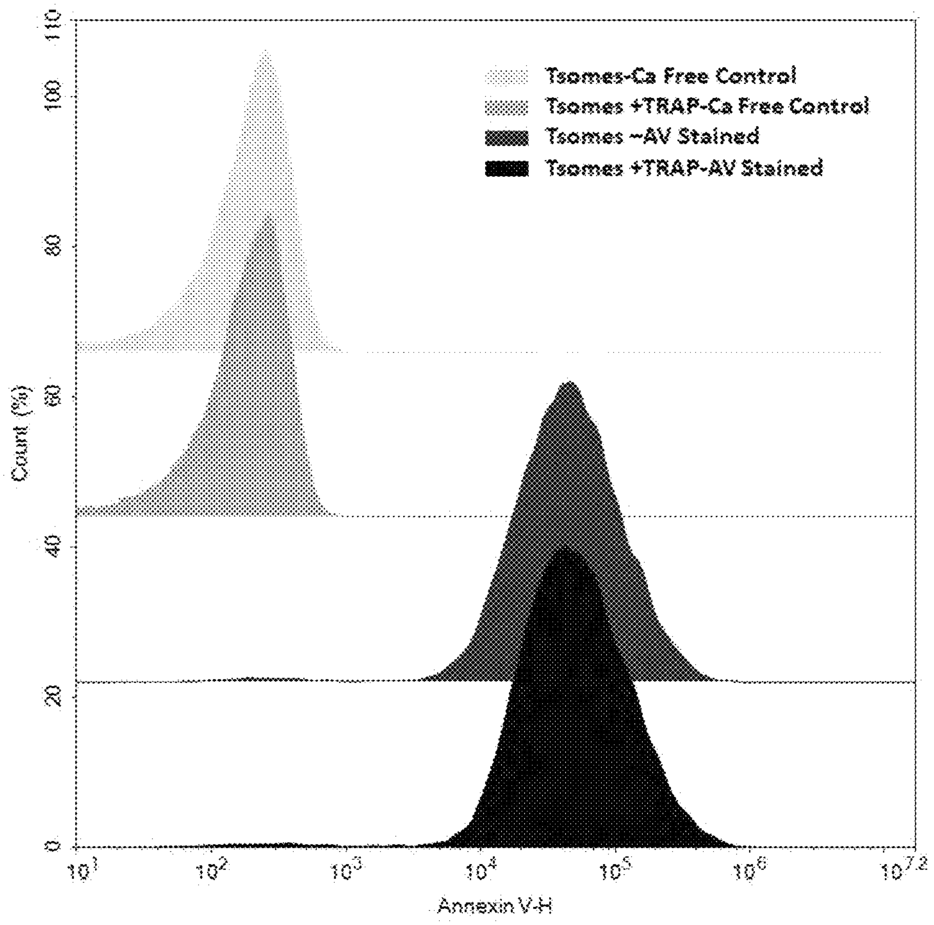
FIG. 35B shows that TRAP-6 peptide is not able to increase the expression of CD62P on thrombosomes.

Freeze-dried platelet derivatives manufactured using the TFF process were incubated with either TRAP-6 or buffer and stained with Annexin V (AV) to determine the relative presence of phosphatidylserine (PS). Apheresis platelets were used to confirm TRAP-6 activity (FIG. 35A, and Table 31), and increased expression of CD62P after the exposure to TRAP-6 confirms that TRAP-6 is capable of promoting platelet expression. PS expression on the exterior membrane leaflet is a hallmark of platelet activation and increases in membrane expression of PS result in greater amounts of AV binding. Unstained samples and samples stained with AV but without the addition of calcium were analyzed on the flow cytometer as negative controls. Unstained samples generated little to no fluorescent signal, indicating that freeze-dried platelet derivatives were not auto fluorescent at the wavelength selected to measure AV (FIG. 35B). The calcium free control samples also generated little to no fluorescent signal. Since AV binding to PS is dependent on the presence of calcium ions, a lack of signal from the calcium free control samples demonstrates that the AV-ACP conjugate was not associating with the freeze-dried platelet derivatives membrane in a nonspecific manner. All samples stained with AV in the presence of calcium provided a strong fluorescent signal that was, on average, approximately 695 times brighter than the unstained controls. This result indicates that all freeze-dried platelet derivatives samples were expressing, or comprised, PS. Incubating the freeze-dried platelet derivatives with TRAP-6 did not cause a notable increase in AV binding as measured by mean fluorescent intensity (MFI) (FIG. 35B). The average MFI values for freeze-dried platelet derivatives incubated with buffer and freeze-dried platelet derivatives incubated with TRAP-6 were 68,179 and 68,783, respectively (Table 32).

TABLE 31

Apheresis Platelet CD62P MFI

| Sample Type | −TRAP | +TRAP |
|---|---|---|
| Unstained | 100 | 107 |
| CD62P Stained | 2,351 | 126,598 |

TABLE 32

Freeze-dried platelet derivatives Annexin V MFIs

| Sample Type | −TRAP | +TRAP |
|---|---|---|
| Unstained | 98 | 99 |
| Calcium Free Control | 203 | 198 |
| AV Stained | 68,179 | 68,783 |

Freeze-dried platelet derivatives, manufactured using the TFF process as described in Example 1, were shown to contain phosphatidylserine (PS) on the membrane as evident by the binding of Annexin V (AV) to the freeze-dried platelet derivatives. The binding of AV to activated platelets is a calcium dependent binding and therefore the calcium ion dependency of AV binding to the rehydrated freeze-dried platelet derivatives provide further support that the AV conjugate was not associating with the membrane of the freeze-dried platelet derivatives in a nonspecific manner.

While TRAP-6 was shown to activate apheresis platelets, as evident by increased CD62P expression, and increased the binding of AV to the activated platelet, it was not the case for the freeze-dried platelet derivatives. The freeze-dried platelet derivatives with or without a TRAP-6 incubation exhibited same high level of AV binding, and indicate that TRAP-6 does not promote further surface expression of PS for freeze-dried platelet derivatives, likely because the freeze-dried platelet derivatives are maximally activated during the lyophilization and/or rehydration process, and further stimulation/activation is not possible.

Example 19. Presence of Thrombospondin (TSP1) on the Surface of the Freeze-Dried Platelet Derivatives Thrombospondin (TSP1), a glycoprotein typically found to coat external membranes of activated platelets, was found to coat freeze-dried platelet derivatives without activation. The presence of TSP1 was detected by fluorescence of anti-Thrombospondin-1 (TSP-1) antibody.

Fresh platelet rich plasma (PRP) was isolated by centrifuging whole blood collected in acid citrate dextrose (ACD) at 180 g for 10 minutes. Isolated PRP was centrifuged again at 823 g for an additional 10 minutes. The plasma was then removed and discarded, and the platelet pellet was resuspended in HEPES Modified Tyrode's Albumin (HMTA) buffer. An aliquot of the resulting washed platelet sample was activated by incubated the platelets at room temperature for 10 minutes in the presence of 2 mM GPRP peptide (BaChem Cat #H-1998.0025), 2 mM $CaCl_2$, 0.5 U/mL thrombin (EDM Millipore Cat #605190-1000U), and 0.5 μg/mL collagen (ChronoPar Cat #385). A separate aliquot of washed platelets was set aside to be used as a resting negative control.

All samples of freeze-dried platelet derivatives were manufactured using the TFF process as described in Example 1. The freeze-dried platelet derivatives studied in this example were baked freeze-dried platelet derivatives which were heated after lyophilization at 80° C. for 24 hours. All vials were rehydrated using the appropriate amount of cell culture grade water. After water was added, the vials were incubated for 10 minutes at room temperature. Gentle swirling of the vials was performed every 2 minutes during the 10-minute period to promote full dissolution of the cake. Once rehydrated, samples of freeze-dried platelet derivatives from each vial, along with samples from both the resting and activated fresh washed platelet aliquots, were diluted 1:500 in triplicate using phosphate buffered saline (PBS) (Corning Cat #21-040-CV). The diluted samples were analyzed on the Quanteon flow cytometer and the concentrations of the platelets and freeze-dried platelet derivatives were determined. Based on these concentrations, an aliquot of each freeze-dried platelet derivatives or fresh platelet sample was diluted to a concentration of 100,000 freeze-dried platelet derivatives per microliter.

Stained samples from each vial of freeze-dried platelet derivatives and the resting and activated fresh platelets were generated by adding 10 μL of diluted freeze-dried platelet derivatives or platelets to 20 μL of HMTA containing 4 μg/mL of anti-Thrombospondin-1 (TSP-1) antibody (Santa Cruz Biotech Cat #sc-59887 AF594). Unstained control samples were generated by adding 10 μL of diluted freeze-dried platelet derivatives or platelets to 20 μL of HMTA. All The samples were incubated at room temperature, protected from light, for 20 minutes. After incubation, 500 μL of PBS was added to all samples. One hundred microliters from each sample were transferred to an individual well in a 96 well plate, and the samples were analyzed using an Agilent Quanteon flow cytometer.

Figure 36:
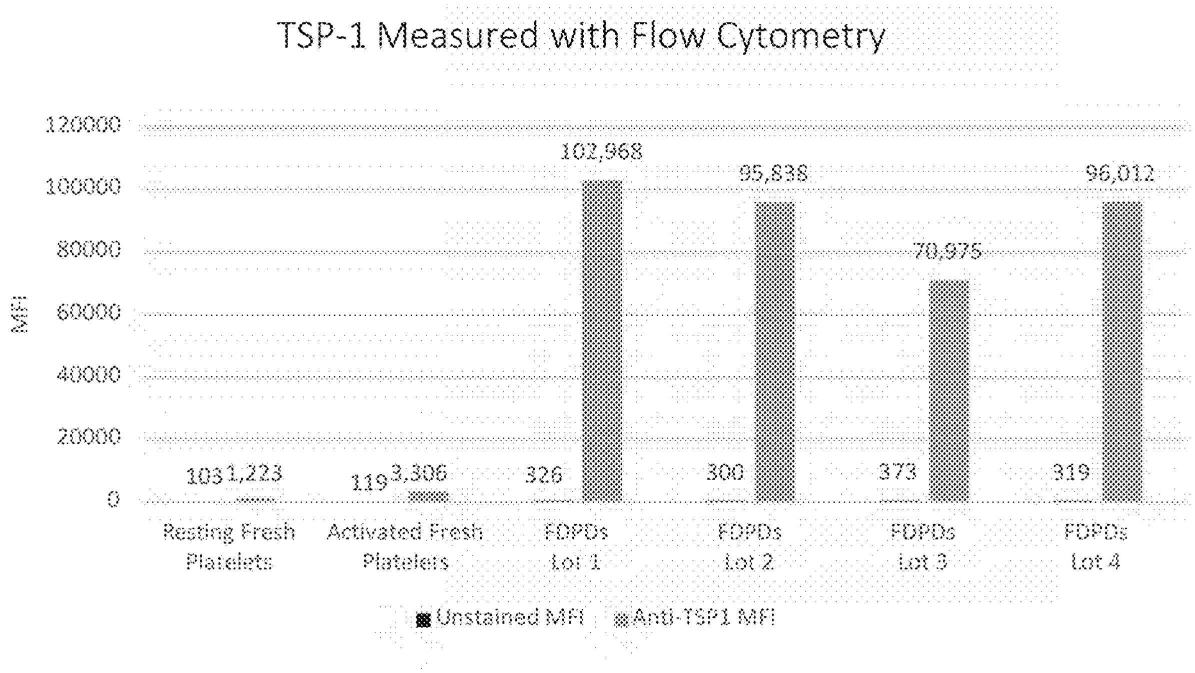
FIG. 36 shows the measurement of thrombospondin (TSP-1) by flow cytometry in terms of mean fluorescent intensity (MFI) in resting fresh platelets, activated fresh platelets, and different lots of thrombosomes.

Unstained samples of fresh platelets and freeze-dried platelet derivatives generated little to no fluorescent signal, indicating that the samples were not auto fluorescent at the wavelength selected to measure TSP-1 expression or presence. Binding of the anti-TSP-1 antibody to fresh platelets increased slightly after activation with collagen and thrombin as shown by an increase in mean fluorescent intensity (MFI) when analyzed using flow cytometry (1,223 vs 3,306). Expression or presence of TSP-1 on freeze-dried platelet derivatives samples varied from lot to lot with an average MFI value of 91,448 (FIG. 36). For all freeze-dried platelet derivatives samples tested, the fluorescent signal was significantly higher than the signal generated by either resting or fresh platelets, indicating high amounts of TSP-1 may be bound to the surface of rehydrated freeze-dried platelet derivatives. This data suggests that the freeze-dried platelet derivatives without the requirement of an activation step exhibit properties which in certain embodiments and applications are superior to activated platelet properties.

Example 20. Presence of Von Willebrand Factor (vWF) on the Surface of the Freeze-Dried Platelet Derivatives Fresh platelet rich plasma (PRP) was isolated by centrifuging whole blood collected in acid citrate dextrose (ACD) at 180 g for 10 minutes. Isolated PRP was centrifuged again at 823 g for an additional 10 minutes. The plasma was then removed and discarded, and the platelet pellet was resuspended in HEPES Modified Tyrode's Albumin (HMTA) buffer. An aliquot of the resulting washed platelet sample was activated by incubating the platelets at room temperature for 10 minutes in the presence of 2 mM GPRP peptide (BaChem Cat #H-1998.0025), 2 mM $CaCl_2$)), 0.5 U/mL thrombin (EDM Millipore Cat #605190-1000U), and 0.5 μg/mL collagen (ChronoPar Cat #385). A separate aliquot of washed platelets was set aside to be used as a resting negative control. All samples of freeze-dried platelet derivatives were prepared using the TFF process as described in the Example 1. The freeze-dried platelet derivatives studied in this example were baked freeze-dried platelet derivatives which were heated after lyophilization at 80° C. for 24 hours. All vials were rehydrated using the appropriate amount of cell culture grade water (Corning Cat #25-055-CI). After water was added, the vials were incubated for 10 minutes at room temperature. Gentle swirling of the vials was performed every 2 minutes during the 10-minute period to promote full dissolution of the cake. Once rehydrated, samples of freeze-dried platelet derivatives from each vial, along with samples from both the resting and activated fresh washed platelet aliquots, were diluted 1:500 in triplicate using phosphate buffered saline (PBS). The diluted samples were analyzed on the Quanteon flow cytometer and the concentrations were determined. Based on these concentrations, an aliquot of each freeze-dried platelet derivatives or fresh platelet sample was diluted to a concentration of 100,000 freeze-dried platelet derivatives per microliter.

Prior to staining, the anti-Von Willebrand Factor antibody (Novus Biologicals Cat #NBP2-54379PE) was diluted by a factor of 10. Stained samples from each vial of freeze-dried platelet derivatives and the resting and activated fresh platelets were generated by adding 10 μL of diluted freeze-dried platelet derivatives or platelets to 10 μL of diluted antibody and 10 μL of HMTA. Unstained control samples were generated by adding 10 μL of diluted freeze-dried platelet derivatives or platelets to 20 μL of HMTA. All The samples were incubated at room temperature, protected from light, for 20 minutes. After incubation, 500 μL of PBS was added to all samples. One hundred microliters from each sample was transferred to an individual well in a 96 well plate, and the samples were analyzed using an Agilent Quanteon flow cytometer.

Figure 37:
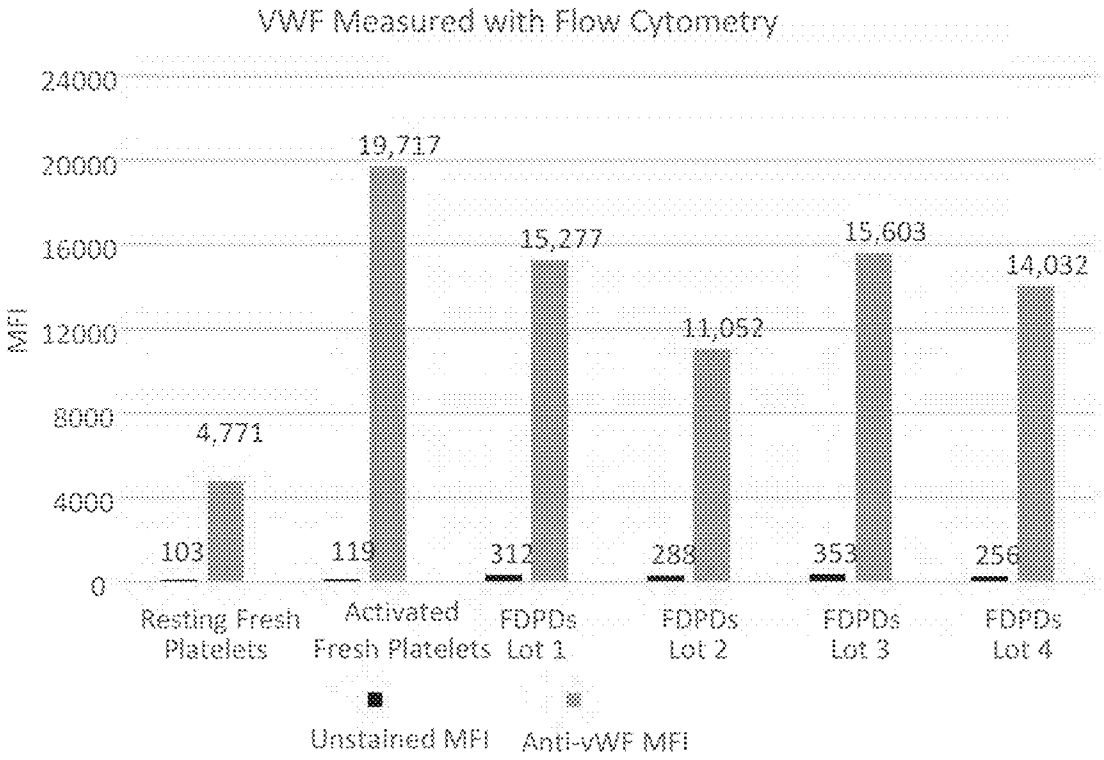
FIG. 37 shows the measurement of von Willebrand factor (vWF) by flow cytometry in terms of mean fluorescent intensity (MFI) in resting fresh platelets, activated fresh platelets, and different lots of thrombosomes.

Unstained samples of fresh platelets and freeze-dried platelet derivatives generated little to no fluorescent signal, indicating that the samples were not auto fluorescent at the wavelength selected to measure vWF expression or presence. Binding of the anti-vWF antibody to fresh platelets increased after activation with collagen and thrombin as shown by an increase in mean fluorescent intensity (MFI) when analyzed using flow cytometry (4,771 vs 19,717). Expression or presence of vWF on freeze-dried platelet derivatives samples varied from lot to lot with an average MFI value of 13,991 (FIG. 37). For all freeze-dried platelet derivatives samples tested, the fluorescent signal fell between the signals generated by resting and activated platelets. This suggests that vWF is present on the surface of rehydrated freeze-dried platelet derivatives, and that the amount of vWF present is greater than that seen on resting platelets. The data suggests that even in the absence of any activation, the freeze-dried platelet derivatives exhibit properties that is superior to resting platelets and similar to the activated platelets.

Example 21. Lyophilized Fixed Platelet and Freeze-Dried Platelet Derivatives Flow Cytometry The presence of von Willebrand factor, Thrombospondin-1, and fibrinogen, which can be desired properties for some uses of platelet derivatives, were analyzed by respective antibody binding and the MFI (mean fluorescence intensity) assay for lyophilized fixed platelets and freeze-dried platelet derivatives.

Method

All samples of freeze-dried platelet derivatives were prepared using the TFF process as described in Example 1. All vials of freeze-dried platelet derivatives were rehydrated using the appropriate amount of cell culture grade water. After water was added, the vials were incubated for 10 minutes at room temperature. Gentle swirling of the vials was performed every 2 minutes during the 10-minute period to promote full dissolution of the cake. Fixed lyophilized platelets (Chrono-Log Corp Cat #299-9-) were rehydrated using Tris buffered saline (TBS) (Chrono-Log Corp Cat #299-5) according to the manufacturer's instruction. Once rehydrated, samples of freeze-dried platelet derivatives from each vial, along with a sample of the lyophilized fixed platelets, were diluted 1:500 in triplicate using phosphate buffered saline (PBS) (Corning Cat #21-040-CV). The diluted samples were analyzed on the Quanteon flow cytometer and the concentrations were determined. Based on these concentrations, an aliquot of each freeze-dried platelet derivatives or fresh platelet sample was diluted to a concentration of 100,000 freeze-dried platelet derivatives per microliter. Prior to staining, the anti-VWF antibody was diluted 1:10 (part to whole) in HMTA and the anti-TSP-1 antibody was diluted 1:5 (part to whole) in HMTA. Single stained samples from each vial of freeze-dried platelet derivatives or fixed lyophilized platelets were generated by combining $10^6$ total cells diluted in HEPES Modified Tyrode's Albumin (HMTA) buffer (Boston Bioproducts, Inc. Cat #C-9234C) with one of the following: 2 μL anti-CD42b antibody (Milli Mark Cat #FCMAB196P), 10 μL anti-von Willebrand Factor antibody (Novus Biologicals CAT #NBP2-54379PE), 3 μL anti-Thrombospondin-1 (TSP-1) antibody (Santa Cruz Biotech Cat #sc-59887 AF594), or 5 μL anti-fibrinogen antibody (BioCytex Cat #5009-F100T). All The samples were incubated at room temperature, protected from light, for 20 minutes. After incubation, 500 μL of PBS was added to all samples. One hundred microliters from each sample was transferred to an individual well in a 96 well plate, and the samples were analyzed using an Agilent Quanteon flow cytometer.

Results

Figure 38A:
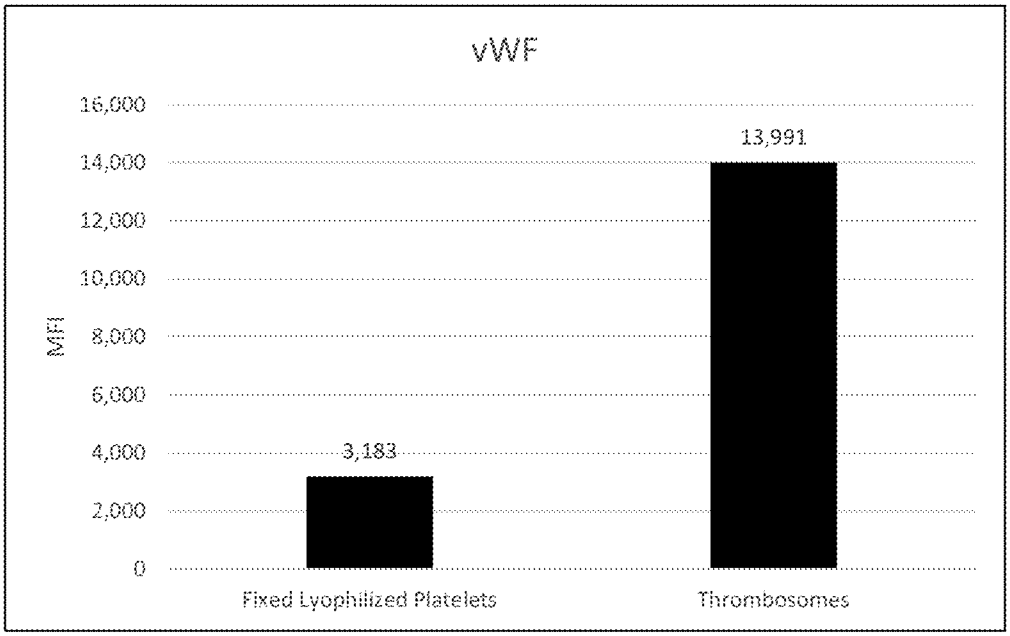
FIG. 38A shows the measurement of vWF by flow cytometry in terms of mean fluorescent intensity (MFI) in fixed lyophilized platelets, and thrombosomes.
Figure 38B:
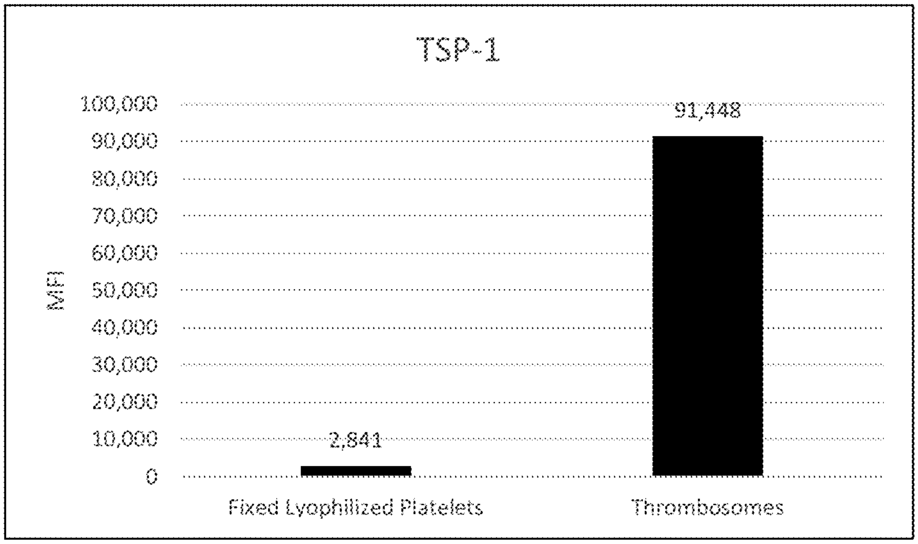
FIG. 38B shows the measurement of TSP by flow cytometry in terms of mean fluorescent intensity (MFI) in fixed lyophilized platelets, and thrombosomes.
Figure 38C:
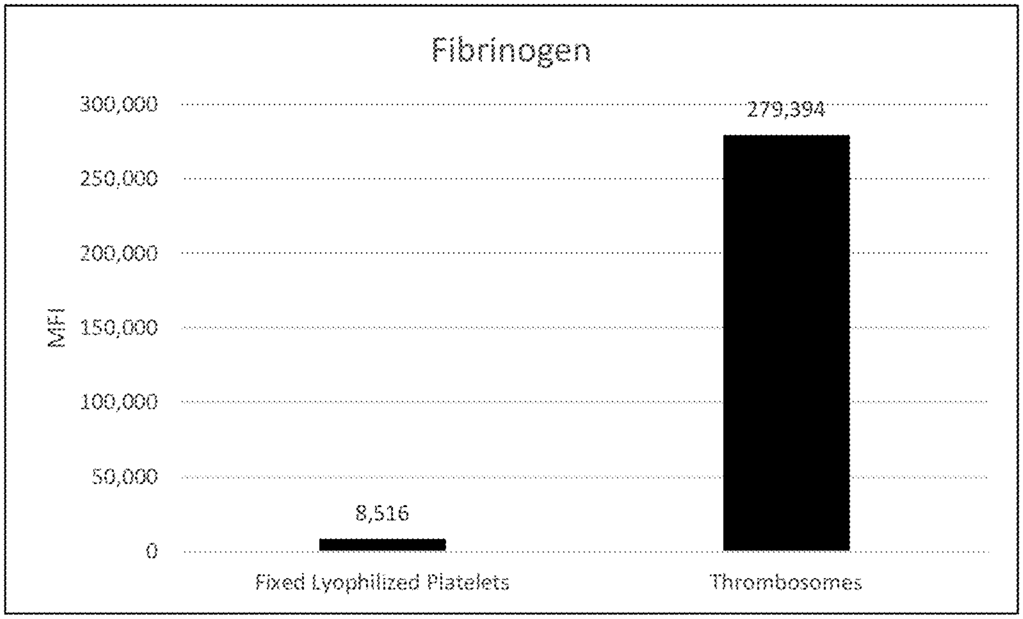
FIG. 38C shows the measurement of fibrinogen by flow cytometry in terms of mean fluorescent intensity (MFI) in fixed lyophilized platelets, and thrombosomes.

The resulting MFI values from these experiments are shown in FIGS. 38A-38C The data suggests that the addition of the fixation step appears to reduce the amount of pro-adhesive molecules that bind to the cell membrane during the lyophilization and/or rehydration process. Specifically, this experiment demonstrated the freeze-dried platelet derivative surface contains greater quantities of von Willebrand factor, Thrombospondin-1, and fibrinogen as compared to that of the fixed human platelets.

Example 22. Freeze-Dried Platelet Derivatives—Compromised Membrane

Membrane integrity of freeze-dried platelet derivatives, either heated at 80° C. for 24 hours (baked freeze-dried platelet derivatives) or not heated (unbaked freeze-dried platelet derivatives) after lyophilization, was tested. The baked and unbaked Freeze-dried platelet derivatives of the standard formulation were analyzed by forward scatter against pre-lyophilization material and by the use of an antibody against a stable intracellular antigen, β-tubulin, to determine if freeze-dried platelet derivatives were permeable to IgGs (150 kDa). Forward scatter is a flow cytometry measurement of laser scatter along the path of the laser. Forward scatter (FSC) is commonly used as an indication of cell size as larger cells will produce more scattered light. However, forward scatter also can indicate the membrane integrity of the sample via optical density (i.e., light transmission); a cell with less cytosolic material and a porous membrane would transmit more light (have a lower FSC) than the same cell if intact, despite being the same size.

The freeze-dried platelet derivatives of Example 1 were studied to determine if freeze-dried platelet derivatives were permeable to IgGs (150 kDa) by the use of an antibody against a stable intracellular antigen, β-tubulin. Fresh platelets, unbaked freeze-dried platelet derivatives, and baked freeze-dried platelet derivatives were fixed and stained with anti-β tubulin IgG with and without cell permeabilization. Fresh platelets showed a dramatic increase in IgG binding with permeabilization, whereas both baked and unbaked freeze-dried platelet derivatives showed no change in response to permeabilization (Table 33). Results from fresh platelets and freeze-dried platelet derivatives that were fixed and then either permeabilized with 0.2% Triton-X 100 or not permeabilized and then stained with anti-β tubulin IgG conjugated to the fluorophore AF594. Unstained samples are included for background fluorescence.

TABLE 33

| Sample | Mean FSC-H | AF594 MFI |
|---|---|---|
| Platelets Unstained | 120,301 | 115 |
| Platelets | 118,782 | 636 |
| Permeabilized Platelets | 49,062 | 9,009 |
| Unbaked Freeze-dried platelet derivatives Unstained | 23,140 | 75 |
| Unbaked Freeze-dried platelet derivatives | 23,280 | 546 |
| Permeabilized Unbaked Freeze-dried platelet derivatives | 7,069 | 562 |
| Baked Freeze-dried platelet derivatives Unstained | 49,740 | 362 |
| Baked Freeze-dried platelet derivatives | 49,587 | 2,720 |
| Permeabilized Baked Freeze-dried platelet derivatives | 27,527 | 2,523 |

The IgG binding studies suggest that the membrane integrity of freeze-dried platelet derivatives is severely impaired such that large molecules can pass through the cell membrane. Of additional note, permeabilization induced decreases in forward scatter value, corroborating the proposed relationship between membrane integrity and optical density for particles of the same size.

Additionally, the mean intensity of forward light scattering of freeze-dried platelet derivatives prepared by TFF method as described in Example 1 was compared to in-date human platelet apheresis units. The method is as described below.

All samples of freeze-dried platelet derivatives were manufactured using the TFF process. All vials were rehydrated using the appropriate amount of cell culture grade water (Corning Cat #25-055-CI). After water was added, the vials were incubated for 10 minutes at room temperature. Gentle swirling of the vials was performed every 2 minutes during the 10-minute period to promote full dissolution of the cake. Once rehydrated, samples of freeze-dried platelet derivatives from each vial, along with samples from both in-date human platelet apheresis units, were diluted 1:500 in triplicate using phosphate buffered saline (PBS) (Corning Cat #21-040-CV). The diluted samples were acquired on the Quanteon flow cytometer and the concentrations were determined. Based on these concentrations, an aliquot of each freeze-dried platelet derivatives or apheresis platelet sample was diluted to a concentration of 100,000 freeze-dried platelet derivatives per microliter in HEPES Modified Tyrode's Albumin (HMTA) buffer (Cellphire RGT-004).

Unstained samples of freeze-dried platelet derivatives and human apheresis platelets containing $10^6$ total cells in HMTA were diluted with 500 μL of PB. One hundred microliters from each sample were transferred to an individual well in a 96 well plate, and the samples were analyzed using an Agilent Quanteon flow cytometer.

Figure 39:
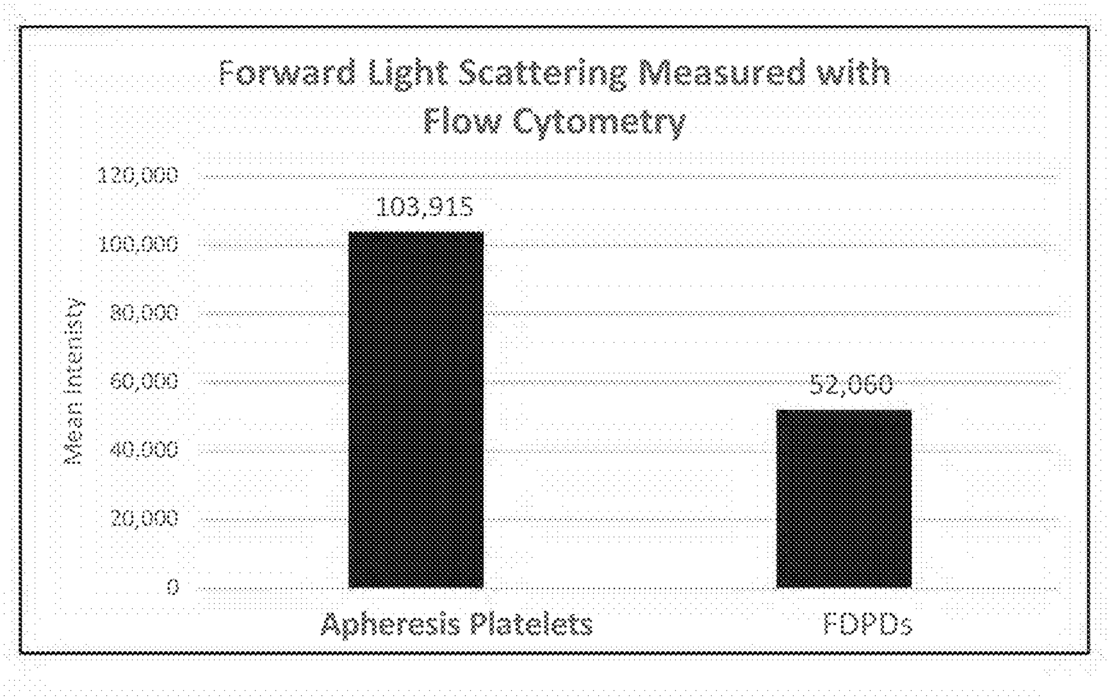
FIG. 39 shows the forward scatter (FSC) measured by flow cytometry of apheresis platelets, and thrombosomes.

The mean intensity is depicted in FIG. 39. It can be observed that the mean intensity of forward light scattering measured with flow cytometry is distinctly lower (about 50%) for freeze-dried platelet derivatives as compared to the apheresis plasma. Therefore, corroborating with the previous result of Table 33 that a cell with less cytosolic material and a porous membrane would transmit more light (have a lower FSC) than the same cell if intact, despite being the same size.

The overall results suggest that membrane integrity is substantially degraded in freeze-dried platelet derivatives; the platelet intracellular contents have been released (e.g. LDH) and large molecules can enter the cellular cytosol (e.g. anti β-tubulin IgG). The plasma membrane of freeze-dried platelet derivatives is likely damaged by the drying (sublimation) or rehydration processes as freezing in cryopreserved platelets appears to be insufficient to induce severe membrane dysfunction. These results also imply that signal transduction from the outside of the cell is not possible in freeze-dried platelet derivatives, which is corroborated by lack of aggregation response (as observed in Example 17). Baking, although it produced an increase in optical density, did not appear to improve membrane integrity significantly (e.g., IgG β-tubulin binding). The results discussed in the present example thus show that the platelet derivatives as disclosed herein have a compromised plasma membrane.

Example 23. Freeze-Dried Platelet Derivate Clinical Trial, A Dose and Impact on Bleeding Study Freeze-dried platelet derivatives at low, medium and high doses, are compared to liquid stored platelets (LSP) in their effectiveness to cease or decrease bleeding. Freeze-dried platelet derivatives have a short circulation time and are not expected to increase the platelet count immediately post infusion. As such, clinical presentation of the patient is used to evaluate bleeding during the treatment phase and guide the treatment scheme rather than only platelet count.

The Study

A prospective, multicenter, randomized, open-label, Phase 2, parallel, dose ranging, multidose trial enrolls patients into three freeze-dried platelet derivatives dose groups and one control liquid stored platelets (LSP) group in order to evaluate, in a dose-escalation manner, the impact on bleeding, and the preliminary effect on coagulation measures of increasing doses of allogeneic freeze-dried platelet derivatives. Freeze-dried platelet derivatives are prepared according to Example 1. The freeze-dried platelet derivatives in dried form with components of the mixture in which platelets were freeze-dried to form the freeze-dried platelet derivates (platelet derivative composition in the form of a powder), were resuspended in water and delivered in one of three doses indicated herein in Table 34.

The patients, 160 total selected, are: 18 years and older, female or male, that meet the following inclusion criteria:

1. Adults (≥18 years) with total circulating platelets (TCP) as defined by both (a) and (b):
   a. a count of between 10,000 and 70,000 platelets/μL blood, inclusive
   b. any one or more of (i-iii):
   i. confirmed diagnosis of hematologic malignancy, myeloproliferative disorder, myelodysplastic syndrome, or aplasia
   ii. undergoing chemotherapy, immunotherapy, radiation therapy or hematopoietic stem cell transplantation
   iii. refractory to platelet transfusion defined as two 1-hour corrected count increment (CCI) of <5000 on consecutive transfusions of LSP (Sacher, 2003)
2. WHO Bleeding Score of 2 excluding cutaneous bleeding
3. All patients provide informed consent directly or through a legally authorized representative, comply with treatment and monitoring, and all women of childbearing potential test negative for pregnancy.

A maximum of 6 doses of the freeze-dried platelet derivatives are allowed to be administered in a 72-hour period to treat enrolled bleeding patients. The study evaluates the safety and potential efficacy of three different doses of freeze-dried platelet derivatives v/s control. Freeze-dried platelet derivatives Low Dose, Medium Dose, High Dose, or control (LSP) are listed in Table 34. The medium dose is higher than the low dose, and the high dose is higher than the medium dose.

TABLE 34

| Trial-Arm Description | Freeze-dried platelet derivative particles/kg (TGPU) |
|---|---|
| Low<br>Medium<br>High | Dosage between $1.0 \times 10^7$ to $1.0 \times 10^{11}$/kg of the subject or 250 to 5000 TGPU per kg of the subject |
| Control | One unit of room temperature irradiated, leukocyte reduced apheresis platelets or whole blood derived pooled platelet concentrate equivalent (4-6 units) |

N/A = not applicable;
NOD = non-obese diabetic;
SCID = severe combined immunodeficiency;
TGPU = thrombin generating potency unit.

The specific outcomes analyzed are tabulated below in Table 35.

TABLE 35

| Efficacy Endpoint | Time Frame (Evaluated at) |
|---|---|
| Primary Outcome Measures | |
| Cessation or decrease in bleeding at primary bleeding site, based upon the most severe bleeding location at Day | 24 hours post initial infusion. |

TABLE 35-continued

| Efficacy Endpoint | Time Frame (Evaluated at) |
|---|---|
| 1 baseline taken within 12 hours prior to infusion, as evidenced by ordinal change in WHO (World Health Organization) Bleeding Score . | |
| Secondary Outcome Measures | |
| Number of days alive and without WHO (World Health Organization) Grade 2a or greater bleeding through initial 7 days after first freeze-dried platelet derivative composition or LSP Infusion | 7 days after first freeze-dried platelet derivatives or LSP infusion. |
| 30-day mortality post first infusion of freeze-dried platelet derivative composition or post first infusion of LSP as control | 30 days post first infusion (+/−2 days). |
| Cessation or decrease in each additional bleeding site (other than primary bleeding site), as evidenced by ordinal change in WHO (World Health Organization) Bleeding Score after first infusion of freeze-dried platelet derivative composition or LSP infusion as control. | 12, 24, 48, 72 hours and Day 7 post first infusion of freeze-dried platelet derivatives or LSP infusion as control. Also evaluate at Days 4-6 if patient is hospitalized at that time. |
| Number, timing, type and reason for administration of all blood products including platelets and freeze-dried platelet derivative composition during the initial 7 days after first freeze-dried platelet derivative composition or LSP infusion. | 7 days after first freeze-dried platelet derivative composition or LSP infusion |
| Platelet count | measured at 12, 24, 48, 72 hours and Day 7 of first infusion of freeze-dried platelet derivative composition or LSP. Also evaluate at Day 4-6 if patient is hospitalized at that time. |
| Measures of hematology including: Prothrombin Fragment 1 + 2; thrombin generation assay (TGA); Thrombopoietin; activated Protein C, tissue plasminogen activator (TPA), and plasminogen activator inhibitor (PAI) per schedule of assessments | From baseline through last study visit (up to 30 days (+/−2 days). |
| Measures of coagulation including: prothrombin time (PT); international normalized ratio (INR); fibrinogen; D-dimer; activated partial thromboplastin time (aPTT); and thromboelastography (TEG) or rotational thromboelastometry (ROTEM) per schedule of assessments. | From baseline through last study visit (up to 30 days (+/−2 days). |
| Changes in markers of endothelial cell injury/repair from preinfusion baseline through 72 hours after first infusion, including: Syndecan-1, hyaluronan, thrombomodulin, vascular endothelial growth factor (VEGF), interleukin 6, sVE cadherin per schedule of assessments. | From baseline through last study visit (up to 30 days (+/−2 days). |
| Other Outcome Measures | |
| Safety: Serious Adverse Events (SAEs) | From baseline through last study visit (up to 30 days (+/−2 days)) |
| Safety: Adverse Events (SAEs) | From baseline through last study visit (up to 30 days (+/−2 days)) |
| Safety: Unanticipated problems involving risk to human subjects | From baseline through last study visit (up to 30 days (+/−2 days)) |

Patients with the Following Criteria are Excluded from the Study:

Patient Exclusion Criteria:

1. Any disorder or condition related to thrombosis, embolism, vascular occlusion, or ischemia (except when a prior history of central line thrombosis has resolved), including but not limited to: past history or current diagnosis of arterial or venous thromboembolic disease including acute coronary syndrome, peripheral vascular disease, and retinal arterial or venous thrombosis, MI, stent placement, valve replacement and/or repair, sinusoidal obstruction syndrome (veno-occlusive disease) or cytokine storm syndrome associated with CAR-T cell therapy
2. Refusal to accept blood products
3. Liver enzyme blood levels greater than 3× the upper limit of normal (ULN)
4. Blood creatinine level greater than 3×ULN
5. Received platelet inhibitor drugs, cyclooxygenase-2 (COX-2) inhibitors, or nonsteroidal anti-inflammatory drugs within 5 days prior to infusion
6. Currently receiving anticoagulant therapy or antiplatelet therapy
7. Receipt of any pro-coagulant agents other than tranexamic acid (TXA) [e.g., desmopressin (DDAVP), recombinant Factor VIIa or prothrombin complex concentrates (PCC)] within 48 hours of first infusion, or with known hypercoagulable state
8. WHO Bleeding Score of 2 solely due to cutaneous bleeding such as petechia, ecchymosis, or bruising
9. Receiving L-asparaginase as part of a current cycle of treatment
10. Known inherited or acquired bleeding disorder including, but not limited to: acquired storage pool deficiency or paraproteinemia with platelet inhibition
11. Known inherited or acquired prothrombotic disorders, including antiphospholipid syndrome (Those with lupus anticoagulant or positive antiphospholipid serology without thrombosis are NOT excluded.)
12. Anuria
13. On dialysis
14. Receipt of an investigational drug within 1 month before first infusion, other than for treatment of their underlying disease
15. Females pregnant or nursing or unwilling to use contraception during and for 30 days after taking the study product (females). Evidence of effective birth control may be used, at the discretion of the physician
16. Acute or chronic medical disorder that, in the opinion of the Investigator, would impair the ability of the patient to receive or respond to study treatment
17. Prior participation in this study with successful infusion of the investigational or control product
18. Currently enrolled in other trials not related to their primary disease process or involving platelet transfusions, platelet growth factors, or other pro-coagulant agents Patients who signed the informed consent form and met the inclusion criteria but not the exclusion criteria are treated by administration of freeze-dried platelet derivative compositions according to one of the three active arms of the study or the control arm as provided in Table 34. The outcomes listed immediately above are analyzed at the timepoints indicated above for each outcome to assess the safety and efficacy of the freeze-dried platelet derivative compositions at the three different doses for the listed outcome s/indications.

Example 24. Characterization of Different Lots of FDPD Compositions

Different lots of freeze-dried platelet derivative (FDPD) compositions were produced using the TFF method provided in Example 1. Flow cytometry studies were performed on the FPD compositions using the method provided in Example 6.

TABLE 36

| | Lot | | | | | | | |
|---|---|---|---|---|---|---|---|---|
| Properties | 1 Fill size-10 ml | 2 Fill size-10 ml | 3 Fill size-10 ml | 4 Fill size-30 ml | 5 Fill size-30 ml | 6 Fill size-30 ml | 7 Fill size-10 ml | 8 Fill size-30 ml |
| Post Lyo Count (x10^6/μL) | 2.0 | 1.7 | 1.6 | 2.3 | 1.9 | 1.7 | 1.6 | 1.6 |
| CD41+ (%) | 72 | 67 | 72 | 68 | 80 | 68 | 80 | 71 |
| CD41+ <0.5 μm (%) | 0 | 0 | 0 | 0 | 0 | 0 | 0 | 0 |
| CD41+ 0.5 μm-2.5 μm (%) | 99 | 98 | 99 | 99 | 99 | 99 | 99 | 99 |
| CD41+ >2.5 μm (%) | 1 | 1 | 1 | 0 | 1 | 1 | 0 | 1 |
| CD62+ 0.5 μm-2.5 μm (%) | 83 | 83 | 76 | 77 | 83 | 75 | 84 | 81 |
| AV+ 0.5 μm-2.5 μm (%) | 100 | 100 | 100 | 100 | 100 | 99 | 99 | 100 |
| Thrombin Agg (%) | 62 | 67 | 62 | 57 | 60 | 77 | 61 | 66 |
| TGA (TGPU/10^6 Cells) | 1.6 | 1.8 | 1.8 | 1.6 | 1.6 | 1.7 | 1.6 | 1.6 |
| TGA (nM) | 55.4 | 61.7 | 65.3 | 59.7 | 51.7 | 57.7 | 45.3 | 53.2 |
| Residual Moisture (%) | 0.4 | 0.4 | 0.4 | 1.0 | 0.1 | 1.1 | 0.3 | 1.0 |

Table 36 provides the properties of the platelet derivatives of different lots that were produced by the method provided in Example 1. It can be appreciated that the platelet derivatives are positive for cell surface markers such as CD 41, CD 62, and Annexin V, and the positive particles are between the size range of 0.5 to 2.5 μm. It can be observed that in the particles larger than 2.5 μm or smaller than 0.5 μm the cell surface markers are not observed.

Example 25. FDPDs Increase Survival Rate of NOD/SCID Mice in the Presence of Clopidogrel and Aspirin Mice treated with anti-platelet agents clopidogrel and aspirin, were further treated with human FDPDs, varying in count, to assess the effect of the FDPDs on hemostasis.

Human FDPDs were prepared according to the method as described in Example 1. The FDPD were rehydrated with sterile water equivalent to fill volume prior to lyophilization. Mice (n=12) were treated with clopidogrel at 5 mg/kg and aspirin at 3 mg/kg for 3 days. The mice were then anesthetized, the tail was snipped off at 1 mm diameter and submerged in warm saline water. Animals were syringe injected, into a vein or artery, with saline or $1.6\times10^9$/kg, $4\times10^9$/kg or $6.5\times10^9$/kg of FDPDs of equal volume (804). FIG. 40 shows an increase in the number of animals that stopped bleeding when administered FDPDs in comparison to saline. The lower dose ($1.6\times10^9$/kg) did not show any change in bleed time and is not included in graph. The two higher doses ($4\times10^9$/kg and $6.5\times10^9$/kg of FDPDs) showed an increase in the number of animals that stopped bleeding, thus returning to normal hemostasis, in comparison to saline administration.

Example 26. Light Transmission Aggregometry (LTA) to Confirm Inhibitory Effect of Prasugrel and Aspirin on Patient Platelets Evaluation of platelet aggregation was conducted on platelets obtained from patient blood on a regimen of prasugrel and aspirin. Whole blood from a patient on a regimen of prasugrel and aspirin was collected in 3.2% sodium citrate tubes (BD #363083). Platelet rich plasma (PRP) was generated by centrifugation of whole blood for 10 minutes at a relative centrifugal force (RCF) of 180×g and removal of the top PRP layer. The remainder of the tube was centrifuged for 10 minutes at a RCF of 1800×g and the top platelet poor plasma (PPP) layer was removed. The PRP was adjusted to 200,000 platelets/μL with PPP.

Light Transmission aggregometry was performed on the PAP-8E aggregometer (Bio/Data Corporation) following the manufacture's recommendations. A 225 μL PRP sample was placed in test tubes (Bio/Data Corporation #101521) with a stir bar (Bio/Data Corporation #105990) and warmed at 37° C. for 5 minutes prior to adding 25 μL of the agonist. The final concentrations for the agonists in the PRP sample were: 0.5 mM for arachidonic acid (AA) (Chronolog Corporation #390), 10 uM for ADP (Chronolog Corporation #384), and 40 μM for TRAP-6 (Millipore Sigma #T1573). TRAP-6 was used as the positive control in the LTA test. FIG. 41 confirms that patient's platelet aggregation activity is inhibited by prasugrel and aspirin.

Example 27. FDPDs Contribute to an Increase of Endogenous CD41/CD62P Expression in the Presence of Dual Antiplatelet Therapy (DAPT), In-Vitro Experiment Analysis of endogenous CD41/CD62P expression was conducted on donor blood treated, in-vitro, with ticagrelor and aspirin. The effect of FDPDs, varying in dose, on CD41/CD62P expression was assessed.

Human FDPDs were prepared according to the method as described in Example 1. The FDPDs were rehydrated with sterile water equivalent to the fill volume prior to lyophilization.

Whole blood was collected in 3.2% sodium citrate tubes (BD #363083). Blood was either treated with dual anti-platelet therapy (DAPT) consisting of a final concentration of 100 μM aspirin (Cayman chemical #70260) plus 1 μg/mL ticagrelor (Sigma #SML2482) or left untreated (NT). Blood was incubated for 10 minutes on a rocker. Next, samples were treated with FDPDs at 10, 20, and 50 k/μL (k/μL=$10^3$ FDPDs/μL) and incubated for 10 minutes on the rocker. Following the treatments, blood samples were fixed in a 1:1 ratio with ThromboFix (Beckman Coulter #6607130) and incubated for 1 hour at room temperature. The fixed whole blood (5 μL) was combined with 5 μL of anti-CD41-PE (Beckman Coulter #IM1416U), 5 μL anti-CD62P-PECy5 (BD #551142), and 85 μL HMTA buffer. The stained sample was incubated for 20 minutes at room temperature. After incubation 5 μL of stained blood was then diluted in 95 μL of PBS and analyzed on the Acea NovoCyte Quanteon flow cytometer (Agilent).

Figure 42:
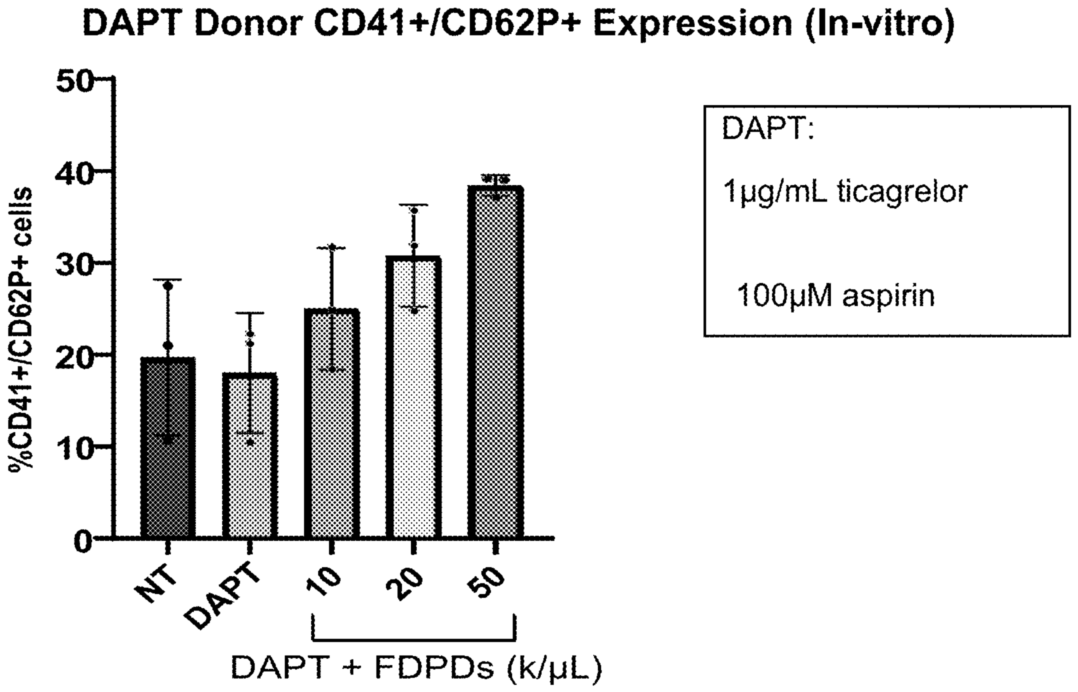
FIG. 42 is a bar plot of % CD41+/CD62P+ Expression (In-vitro) by DAPT donor platelets vs variable count of FDPDs. Donor blood is treated, ex-vivo, with ticagrelor and aspirin.

Data analysis was performed using NovoExpress® software (Agilent) by first gating on all endogenous CD41-positive events, followed by all endogenous CD62P-positive events, and then graphed as a percentage of total double-positive events (FIG. 42). Three independent experiments are graphed with error bars representing standard deviation.

FIG. 42 shows FDPDs dose dependent increase in the percent CD41/CD62P positive events of donor blood treated in vitro with ticagrelor and aspirin. This dose dependent response supports the ability of FDPDs to improve coagulation response (reflected by the increasing endogenous positivity of CD41/CD62P) in the presence of DAPT.

Example 28. FDPDs Contribute to an Increase of Endogenous CD41/CD62P Expression in the Presence of Dual Antiplatelet Therapy (DAPT), Ex-Vivo Experiment Analysis of endogenous CD41/CD62P expression was conducted on blood obtained from patients taking prasugrel and aspirin, and further treated with varying doses of FDPDs. Human FDPDs were prepared according to the method as described in Example 1. The FDPDs were rehydrated with sterile water equivalent to the fill volume prior to lyophilization.

Whole blood from a donor on a regimen of prasugrel and aspirin was collected in 3.2% sodium citrate tubes (BD #363083). Blood was aliquoted to microcentrifuge tubes, treated with FDPD concentrations of 10, 20, and 50 k/μL (k/μL=$10^3$ FDPDs/uL), and incubated for 10 minutes on the rocker. Following the treatments, blood samples were fixed in a 1:1 ratio with ThromboFix (Beckman Coulter #6607130) and incubated for 1 hour at room temperature. The fixed whole blood (5 μL) was then stained by adding 5 μL of anti-CD41-PE (Beckman Coulter #IM1416U), 5 μL anti-CD62P-PECy5 (BD #551142), and 85 μL HMTA buffer. The stained blood was incubated for 20 minutes at room temperature and 5 μL of stained blood was then diluted in 95 μL of PBS and analyzed on the Acea NovoCyte Quanteon flow cytometer (Agilent).

Figure 43:
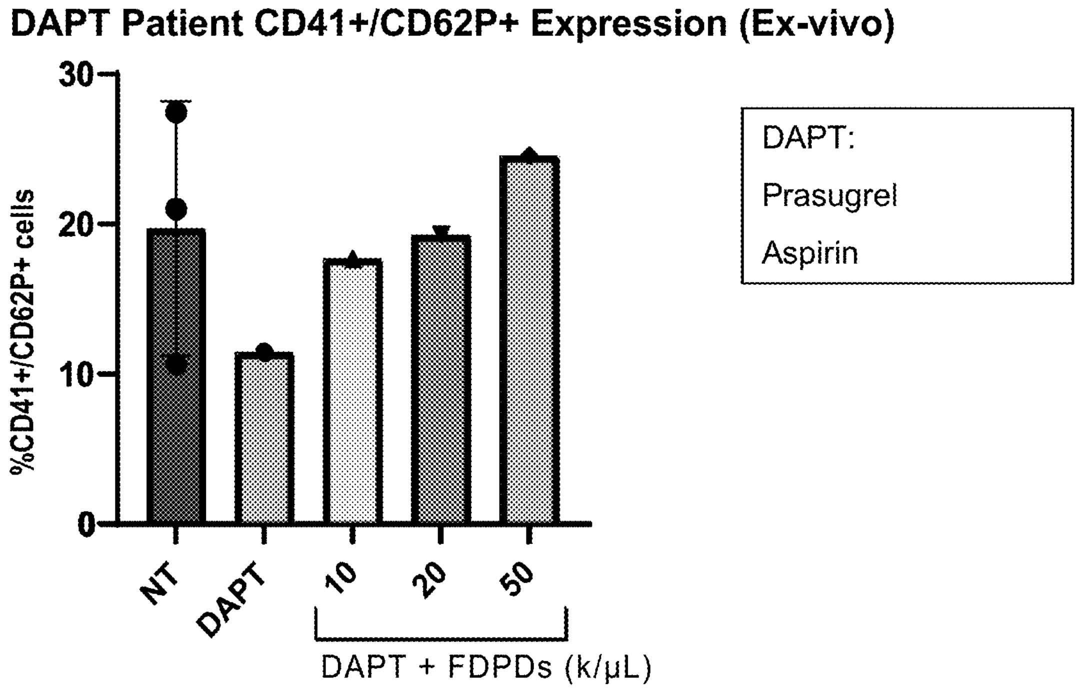
FIG. 43 is a bar plot of % CD41+/CD62P+ Expression (Ex-vivo) by DAPT donor platelets vs variable count of FDPDs. The DAPT platelets are obtained from patients treated with prasugrel and aspirin.

Data analysis was performed in NovoExpress® software (Agilent) by gating on all endogenous CD41 positive followed by all endogenous CD62P positive events and then graphed as a percentage of total double-positive events (FIG. 43). The no treatment (NT) group is from three separate in vitro experiments and is graphed next to the DAPT donor results for comparison.

FIG. 43 shows a FDPDs dose dependent increase in the percent CD41/CD62P positive events in ex-vivo analysis of patient on regimen of prasugrel and aspirin.

The replication of the dose dependent response in the ex vivo experiment (FIG. 43) further supports the ability of FDPDs to improve coagulation response (reflected by the increasing endogenous positivity of CD41/CD62P) in the presence of DAPT.

Example 29: FDPDs Increase Release of PF4 in the Presence of Dual Antiplatelet Therapy, In-Vitro Experiment Analysis of PF4 release was conducted on donor blood treated in-vitro, with ticagrelor and aspirin, and further treated with varying doses of FDPDs.

Human FDPDs were prepared according to the method as described in Example 1. The FDPDs were rehydrated with sterile water equivalent to the fill volume prior to lyophilization.

Whole blood from healthy donors was collected in 3.2% sodium citrate tubes (BD #363083). Blood was either treated with dual anti-platelet therapy (DAPT) consisting of a final concentration of 100 uM aspirin (Cayman chemical #70260) plus 1 μg/mL ticagrelor (Sigma #SML2482) or left untreated (NT). Blood was incubated for 10 minutes on a rocker. Blood was then aliquoted to microcentrifuge tubes and treated with FDPDs at concentrations of 10, 20, 50 k/μL (k/μL=$10^3$ FDPDs/4) and incubated for 10 minutes on the rocker. Following treatment, blood was centrifuged at a RCF of 1800×g for 10 minutes, and the top layer of platelet poor plasma (PPP) was collected into fresh microcentrifuge tubes.

Figure 44:
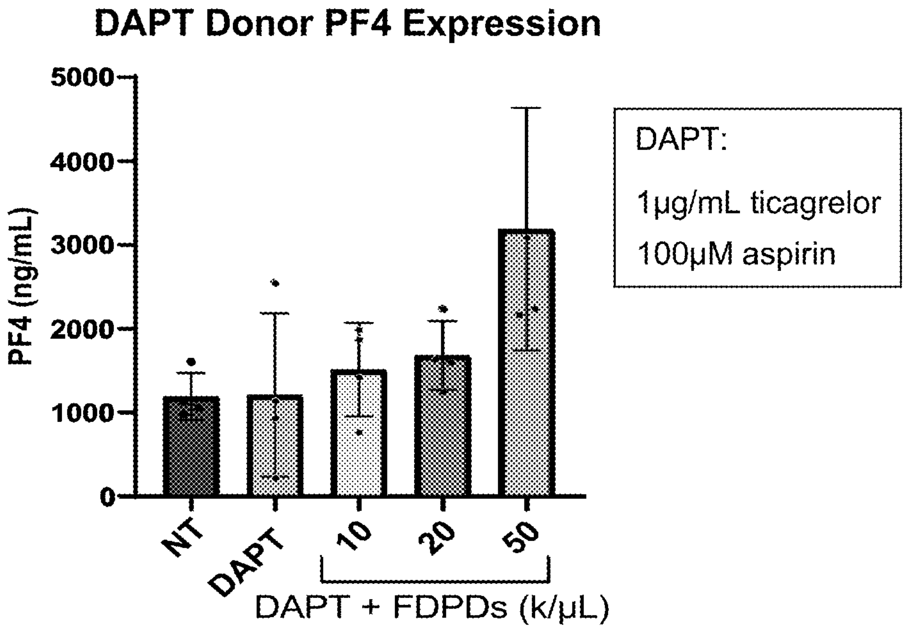
FIG. 44 is a bar plot of PF4 expression (In-vitro) by DAPT donor platelets vs variable count of FDPDs. Donor blood is treated, ex-vivo, with ticagrelor and aspirin.

The PPP samples were then diluted 1:500 in Calibrator Diluent (supplied by kit) and run according to manufacturer's instructions using the R&D Systems, Human CXCL4/PF4 Quantikine ELISA kit. Absorbance was read at 450 nm using a Tecan plate reader. Data was analyzed using GraphPad Prism. FIG. 44 shows that FDPDs increase the release of PF4 (an indicator of platelet activation) in the presence of ticagrelor and aspirin in-vitro.

Example 30: FDPDs Increase Release of PF4 in the Presence of Dual Antiplatelet Therapy, Ex-Vivo Experiment Analysis of PF4 release was conducted on blood obtained from patients taking prasugrel and aspirin, and further treated with varying doses of FDPDs. Human FDPDs were prepared according to the method as described in Example 1. The FDPDs were rehydrated with sterile water equivalent to the fill volume prior to lyophilization.

Whole blood from a patient on a regimen of prasugrel and aspirin and a healthy donor taking no antiplatelet medications was collected in 3.2% sodium citrate tubes (BD #363083). Blood was then aliquoted to microcentrifuge tubes and treated with FDPDs at concentrations of 10, 20, 50 k/μL (k/μL=$10^3$ FDPDs/μL) and incubated for 10 minutes on the rocker. Following treatment, blood was centrifuged at a RCF of 1800×g for 10 minutes, and the top layer of platelet poor plasma (PPP) was collected into fresh microcentrifuge tubes.

Figure 45:
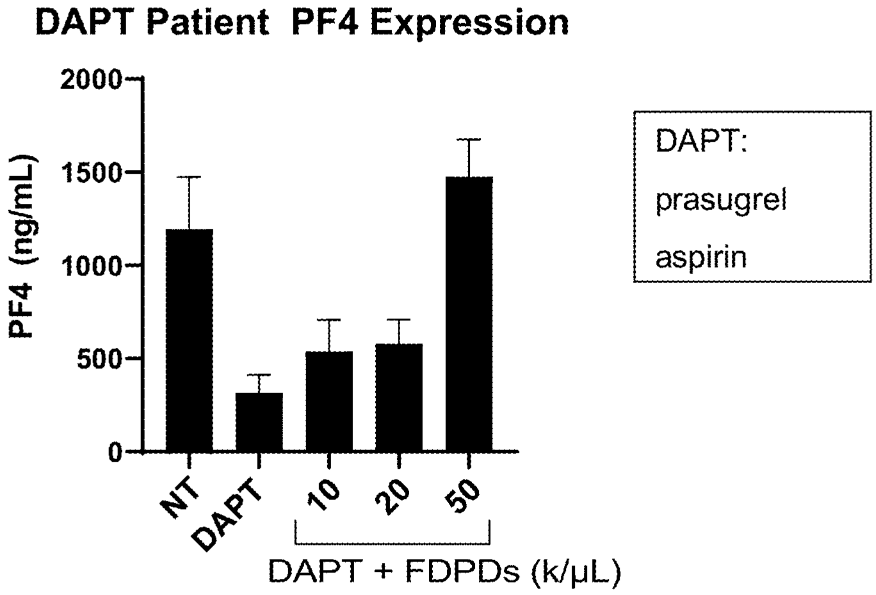
FIG. 45 is a bar plot of PF4 expression (Ex-vivo) by DAPT donor platelets vs variable count of FDPDs. The DAPT platelets are obtained from patients treated with prasugrel and aspirin.

The PPP samples were diluted 1:500 in Calibrator Diluent (supplied by kit) and run according to manufacturer's instructions using the R&D Systems, Human CXCL4/PF4 Quantikine ELISA kit. Absorbance was read at 450 nm using a Tecan plate reader. Data was analyzed using GraphPad Prism. FIG. 45 shows that FDPDs increase the release of PF4 (an indicator of platelet activation) in the presence of prasugrel and aspirin ex vivo.

Example 31. FDPDs Affect Thrombin Generation in the Presence of Dual Antiplatelet Therapy (DAPT), In-Vitro Experiment Analysis of thrombin generation by Platelet Rich Plasma (PRP), obtained from donor blood treated in-vitro, with ticagrelor and aspirin, and further treated with varying doses of FDPDs, was performed.

Human FDPDs were prepared according to the method as described in Example 1. The FDPDs were rehydrated with sterile water equivalent to the fill volume prior to lyophilization.

Whole blood from healthy donors taking no antiplatelet medications was collected in 3.2% sodium citrate tubes (BD #363083). Blood was either treated with dual anti-platelet therapy (DAPT) consisting of a final concentration of 100 μM aspirin (Cayman chemical #70260) plus 1 μg/mL ticagrelor (Sigma #SML2482) or left untreated (NT). Blood was incubated for 10 minutes on a rocker. Platelet rich plasma (PRP) was generated by centrifugation of whole blood for 10 minutes at a RCF of 180×g and removal of the top PRP layer. The remainder of the tube was centrifuged for 10 minutes at a RCF of 1800 ×g and the top platelet poor plasma (PPP) layer was removed. The PRP was adjusted to 200,000 platelets/μL with PPP.

Thrombin Calibrator reagent (Stago #86192) was prepared according to manufacturer's guidelines 20 μL of the thrombin calibrator reagent was added to each calibration well, and 20 μL of PBS was added to each Thrombin Generation well. PRP was aliquoted into microcentrifuge tubes and treated with FDPDs at 2 and 20 k/μL (k=$10^3$ FDPD/μL). Samples were diluted 1:10 in Octaplas® and a multichannel pipette was used to add 80 μL of the diluted sample to each of the assay wells in an assay plate (calibration and thrombin generator wells).

Figure 46A:
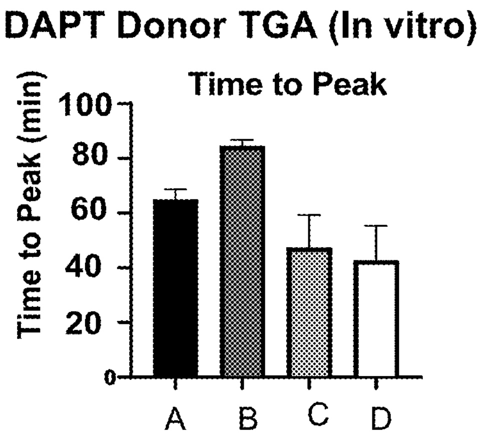
FIG. 46A is a Thrombin Generation Assay (TGA) bar plot of time to peak thrombin production by DAPT donor (in-vitro) platelets vs variable count of FDPDs. Donor blood is treated, in-vitro, with ticagrelor and aspirin.
Figure 46B:
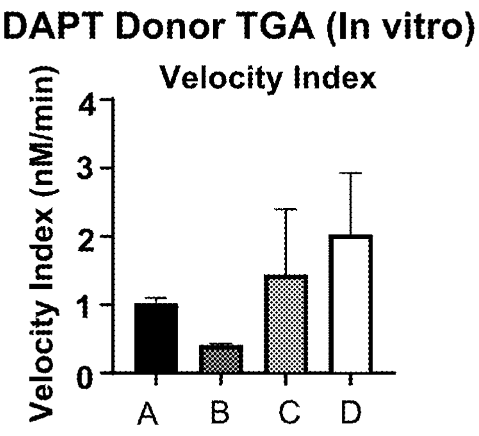
FIG. 46B is a Thrombin Generation Assay (TGA) bar plot of velocity index of thrombin production by DAPT donor (in-vitro) platelets vs variable count of FDPDs. Donor blood is treated, in-vitro, with ticagrelor and aspirin.

The assay plate was inserted into a Thrombinoscope (Stago) connected to a computer with CAT software running. The assay plate was incubated at 37° C. for 10 min. During plate incubation Fluo-substrate and Fluo-buffer (Stago #86197) were combined according to manufacturer's guidelines to obtain FluCa buffer. ADP (Chronolog #384) and PGE1 (Cayman #13010) were added to FluCa buffer. ADP was added to FluCa buffer to obtain a final concentration of 1 μM of ADP in assay wells and PGE1 was added to FluCa buffer to obtain a final concentration of 20 nM of PGE1 in the assay wells. After incubation 20 μL FluCa solution was injected into each well. Thrombin Generation was read for 180 min at 40 second intervals. Data analysis was performed in GraphPad Prism. FIGS. 46A and 46B show a reduced time to peak and increased velocity index of thrombin production with the addition of FDPDs to the PRP obtained from donor blood treated with ticagrelor and aspirin.

Example 39. FDPDs Affect Thrombin Generation in the Presence of Dual Antiplatelet Therapy (DAPT), Ex-Vivo Experiment Analysis of thrombin generation by Platelet Rich Plasma (PRP) obtained from blood of patients on a regiment of prasugrel and aspirin and further treated with varying doses of FDPDs, was performed. Human FDPDs were prepared according to the method as described in Example 1. The FDPDs were rehydrated with sterile water equivalent to the fill volume prior to lyophilization.

Whole blood from a patient on a regimen of prasugrel and aspirin and a healthy donor taking no antiplatelet medications was collected in 3.2% sodium citrate tubes (BD #363083). Platelet rich plasma (PRP) was generated by centrifugation of whole blood for 10 minutes at a RCF of 180×g and removal of the top PRP layer. The remainder of the tube was centrifuged for 10 minutes at a RCF of 1800×g and the top platelet poor plasma (PPP) layer was removed. The PRP was adjusted to 200,000 platelets/μL with PPP.

Thrombin Calibrator reagent (Stago #86192) was prepared according to manufacturer's guidelines. 20 μL of the thrombin calibrator reagent was added to each calibration well, and 20 μL of PBS was added to each Thrombin Generation well. PRP was aliquoted into microcentrifuge tubes and treated with FDPDs at 2 and 20 k/μL (k=$10^3$ FDPD/μL). Samples were diluted 1:10 in Octaplas® and a multichannel pipette was used to add 80 μL of the diluted sample to each of the assay wells of an assay plate (calibration and thrombin generator wells).

Figure 47A:
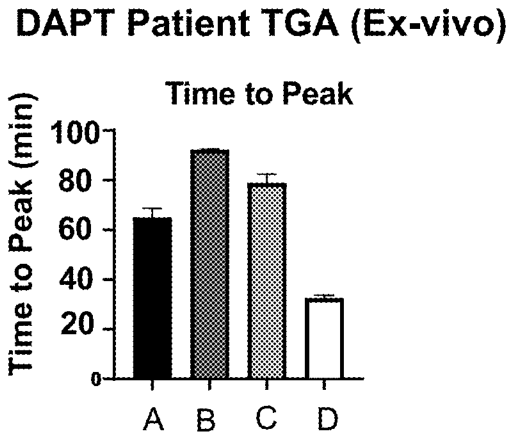
FIG. 47A is a Thrombin Generation Assay (TGA) bar plot of time to peak thrombin production by DAPT donor (ex-vivo) platelets vs variable count of FDPDs. The DAPT platelets are obtained from patients treated with prasugrel and aspirin.
Figure 47B:
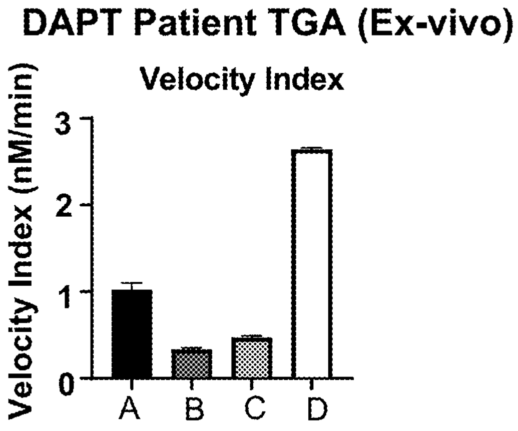
FIG. 47B is a Thrombin Generation Assay (TGA) bar plot of the velocity index of thrombin production by DAPT donor (ex-vivo) platelets vs variable count of FDPDs. The DAPT platelets are obtained from patients treated with prasugrel and aspirin.

The assay plate was inserted into Thrombinoscope (Stago) connected to a computer with CAT software running. The assay plate was incubated at 37° C. for 10 min. During plate incubation Fluo-substrate and Fluo-buffer (Stago #86197) were combined according to manufacturer's guidelines to obtain FluCa buffer. ADP (Chronolog #384) and PGE1 (Cayman #13010) were added to FluCa buffer. ADP was added to FluCa buffer to obtain a final concentration of 1 μM of ADP in assay wells and PGE1 was added to FluCa buffer to obtain a final concentration of 20 nM of PGE1 in the assay wells. After plate incubation, 20 μL FluCa solution was injected into each well. Thrombin generation was read for 180 min at 40 second intervals. Data analysis was performed in GraphPad Prism. FIGS. 47A and 48B show a reduced time to peak and increased velocity index of thrombin production with the addition of FDPDs to the PRP obtained from patient blood on a regimen of prasugrel and aspirin.

The disclosed embodiments, examples and experiments are not intended to limit the scope of the disclosure or to represent that the experiments below are all or the only experiments performed. Efforts have been made to ensure accuracy with respect to numbers used (e.g., amounts, temperature, etc.) but some experimental errors and deviations should be accounted for. It should be understood that variations in the methods as described may be made without changing the fundamental aspects that the experiments are meant to illustrate.

Those skilled in the art can devise many modifications and other embodiments within the scope and spirit of the present disclosure. Indeed, variations in the materials, methods, drawings, experiments, examples, and embodiments described may be made by skilled artisans without changing the fundamental aspects of the present disclosure. Any of the disclosed embodiments can be used in combination with any other disclosed embodiment.

In some instances, some concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

What is claimed is:

1. A method for restoring hemostasis in a subject, wherein said method comprising:

rehydrating a platelet derivative composition in the form of a powder to form a rehydrated platelet derivative composition; and administering intravenously an effective amount of platelet derivatives in the rehydrated platelet derivative composition to the subject, wherein the platelet derivatives in the rehydrated platelet derivative composition:

have a CD41 percent positivity of at least 70% when measured using flow cytometry, have a phosphatidylserine percent positivity of at least 70%, when measured using Annexin V binding in flow cytometry, have a concentration of at least $6{,}000\times10^3$ platelet derivatives/μl, are capable of generating thrombin in an in vitro thrombin formation assay, and are capable of producing an occlusion by attaining a pressure of 80 kPa in less than 14 minutes when used at a concentration of about $70\times10^3$ platelet derivatives/μL in platelet-reduced citrated whole blood in an in vitro total thrombus-formation analysis system (T-TAS), and wherein less than 3.5% of the platelet derivatives are microparticles.

2. The method of claim 1, wherein the platelet derivatives have a CD41 percent positivity of at least 80%, when measured using flow cytometry, and have a phosphatidylserine percent positivity of at least 80%, when measured using Annexin V binding in flow cytometry.

3. The method of claim 1, wherein the microparticles are present in an amount in the range of 0.1% to 3% when measured using scattering intensity in flow cytometry.

4. The method of claim 1, wherein the rehydrated platelet derivative composition comprises trehalose, polysucrose, one or more salts, and a buffer, and wherein the trehalose is present in an amount in the range of 50 mM to 200 mM, and the polysucrose is present in the range of 3% w/v to 10% w/v.

5. The method of claim 3, wherein the platelet derivatives when analyzed using flow cytometry for the binding of anti-thrombospondin (TSP) antibody in the absence of an agonist, exhibit at least 10-fold higher mean fluorescent intensity (MFI) as compared to the MFI of binding of the anti-TSP antibody to resting platelets in the absence of the agonist.

6. The method of claim 5, wherein the platelet derivatives in the rehydrated platelet derivative composition have less than 2% crosslinking of platelet membranes via proteins and/or lipids present on the platelet membranes, and wherein the platelet derivatives in the rehydrated platelet derivative composition are capable of generating thrombin in the in vitro thrombin formation assay such that the platelet derivatives when present at a concentration of at least $4.8\times10^3$ particles/μL generate a thrombin peak height (TPH) of at least 25 nM in the presence of a reagent containing tissue factor and phospholipids.

7. The method of claim 4, wherein at least 90% of the platelet derivatives are in the diameter range of 0.5 μm to 2.5 μm.

8. The method of claim 7, wherein the microparticles are present in an amount in the range of 0.1% to 3% when measured using scattering intensity in flow cytometry, wherein the platelet derivatives have a phosphatidylserine percent positivity of at least 90% when measured using Annexin V binding in flow cytometry, wherein the platelet derivatives have a CD41 percent positivity of at least 95%, when measured using flow cytometry.

9. The method of claim 8, wherein the platelet derivatives when analyzed using flow cytometry for the binding of anti-thrombospondin (TSP) antibody in the absence of an agonist, exhibit at least 10-fold higher mean fluorescent intensity (MFI) as compared to the MFI of binding of the anti-TSP antibody to resting platelets in the absence of the agonist.

10. The method of claim 9, wherein the platelet derivatives when analyzed using flow cytometry for the binding of anti-von Willebrand factor (vWF) antibody in the absence of an agonist, exhibit at least 2-fold higher mean fluorescent intensity (MFI) as compared to the MFI of binding of the anti-vWF antibody to the resting platelets in the absence of the agonist.

11. The method of claim 10, wherein the platelet derivatives in the rehydrated platelet derivative composition are present in a concentration in the range of $6{,}000\times10^3$ to $11{,}000\times10^3$ platelet derivatives/μl of the rehydrated platelet derivative composition.

12. The method of claim 11, wherein the platelet derivative composition is in a vial, and the volume of the rehydrated platelet derivative composition in the vial after the rehydrating is 10-20 ml.

13. The method of claim 10, wherein the platelet derivatives in the rehydrated platelet derivative composition are in a vial and are present in a concentration in the range of $10{,}000\times10^3$ to $20{,}000\times10^3$ platelet derivatives/μl of the rehydrated platelet derivative composition.

14. The method of claim 13, wherein the platelet derivative composition is in a vial, and the volume of the rehydrated platelet derivative composition in the vial after the rehydrating is 10-20 ml.

15. The method of claim 10, wherein the platelet derivative composition in the form of the powder is in a vial, wherein the method further comprises selecting the vial from a plurality of vials comprising the platelet derivative composition from at least 2 different lots in separate vials, wherein each lot comprises platelet derivatives from different subjects, wherein the rehydrated platelet derivative composition comprises plasma protein in a concentration in a range of 5%-50%, and wherein the percent of plasma protein in the powder from any two vials chosen from different lots, differs by less than an absolute 20% plasma protein in the powder.

16. The method of claim 15, wherein the percent of microparticles in the powder from any two vials chosen from different lots, differs by less than an absolute 2% microparticles in the powder.

* * * * *